United States Patent
De Giorgi et al.

(10) Patent No.: US 12,385,104 B2
(45) Date of Patent: Aug. 12, 2025

(54) METHODS AND COMPOSITIONS FOR DETECTING TRANSFUSION-TRANSMITTED PATHOGENS

(71) Applicant: The United States of America, as represented by the Secretary, Dept. of Health and Human Services, Bethesda, MD (US)

(72) Inventors: Valeria De Giorgi, Bethesda, MD (US); Robert D. Allison, Bethesda, MD (US); Harvey J. Alter, Bethesda, MD (US)

(73) Assignee: The United States of America, as represented by the Secretary, Department of Health Human Services, Bethesda, MD (US)

( * ) Notice: Subject to any disclaimer, the term of this patent is extended or adjusted under 35 U.S.C. 154(b) by 1056 days.

(21) Appl. No.: 17/425,228

(22) PCT Filed: Jan. 31, 2020

(86) PCT No.: PCT/US2020/016262
§ 371 (c)(1),
(2) Date: Jul. 22, 2021

(87) PCT Pub. No.: WO2020/160502
PCT Pub. Date: Aug. 6, 2020

(65) Prior Publication Data
US 2022/0119898 A1 Apr. 21, 2022

Related U.S. Application Data

(60) Provisional application No. 62/799,482, filed on Jan. 31, 2019.

(51) Int. Cl.
*C12Q 1/70* (2006.01)
*C12Q 1/6876* (2018.01)
*C12Q 1/6888* (2018.01)

(52) U.S. Cl.
CPC .......... *C12Q 1/701* (2013.01); *C12Q 1/6876* (2013.01); *C12Q 1/6888* (2013.01); *C12Q 1/702* (2013.01); *C12Q 1/703* (2013.01); *C12Q 1/705* (2013.01); *C12Q 1/706* (2013.01); *C12Q 1/707* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 6,582,908 B2 * | 6/2003 | Fodor | ................... | C07H 21/00 506/30 |
| 10,100,374 B2 * | 10/2018 | Leying | ................ | C12Q 1/6823 |
| 2004/0166494 A1 * | 8/2004 | Green | .................... | B82Y 30/00 435/6.19 |
| 2006/0110744 A1 * | 5/2006 | Sampas | ................ | C12Q 1/6883 435/6.14 |
| 2011/0033854 A1 * | 2/2011 | Drmanac | ............. | B01J 19/0046 435/6.12 |
| 2012/0088904 A1 | 4/2012 | Bartels et al. | | |
| 2013/0157258 A1 | 6/2013 | Bartels et al. | | |
| 2013/0267429 A1 * | 10/2013 | Gardner | ............... | C12Q 1/6876 506/8 |
| 2018/0340215 A1 * | 11/2018 | Metsky | ................ | C12Q 1/6816 |

FOREIGN PATENT DOCUMENTS

| | | | |
|---|---|---|---|
| CN | 106011309 | * 10/2016 | |
| WO | WO-2007130519 A2 * | 11/2007 | ............... C12Q 1/70 |
| WO | WO 2009/087685 | 7/2009 | |
| WO | WO 2012/002594 | 1/2012 | |

OTHER PUBLICATIONS

Chen et al., "Using a Pan-Viral Microarray Assay (Virochip) to Screen Clinical Samples for Viral Pathogens," *Journal of Visualized Experiments*, 50:e2536, 2011 (4 pages).

De Giorgi et al., "A microarray-based pathogen chip for simultaneous molecular detection of transfusion-transmitted infectious agents," *Journal of Translational Medicine*, 17:156, 2019 (9 pages).

Grigorenko et al., "Highly Multiplex Real-Time PCR-Based Screening for Blood-Borne Pathogens on an OpenArray Platform," *The Journal of Molecular Diagnostics*, vol. 19, No. 4, pp. 549-560, 2017.

Kourout et al., "Multiplex detection and identification of viral, bacterial, and protozoan pathogens in human blood and plasma using a high-density resequencing pathogen microarray platform," *Transfusion*, vol. 56, pp. 1537-1547, 2016.

Kurn et al., "Novel Isothermal, Linear Nucleic Acid Amplification Systems for Highly Multiplexed Applications," *Clinical Chemistry*, vol. 51, No. 10, pp. 1973-1981, 2005.

Urisman et al., "E-Predict: a computational strategy for species identification based on observed DNA microarray hybridization patterns," *Genome Biology*, 6:R78, 2005 (14 pages).

Wapner et al., Chromosomal Microarray versus Karyotyping for Prenatal Diagnosis, *The New England Journal of Medicine*, vol. 367, No. 23, pp. 2175-2184, 2012.

* cited by examiner

*Primary Examiner* — Carla J Myers
(74) *Attorney, Agent, or Firm* — Klarquist Sparkman, LLP

(57) ABSTRACT

Probe sets capable of detecting pathogen nucleic acids in a sample are described. The probe set can be provided on a solid support, such as a microarray. Methods of detecting pathogen nucleic acids in a sample using the probe set are also provided. In some examples, the probes and methods are capable of detecting one or more RNA viruses, one or more DNA viruses, one or more bacterial nucleic acids, and/or one or more protozoan nucleic acids in a sample.

24 Claims, 3 Drawing Sheets
Specification includes a Sequence Listing.

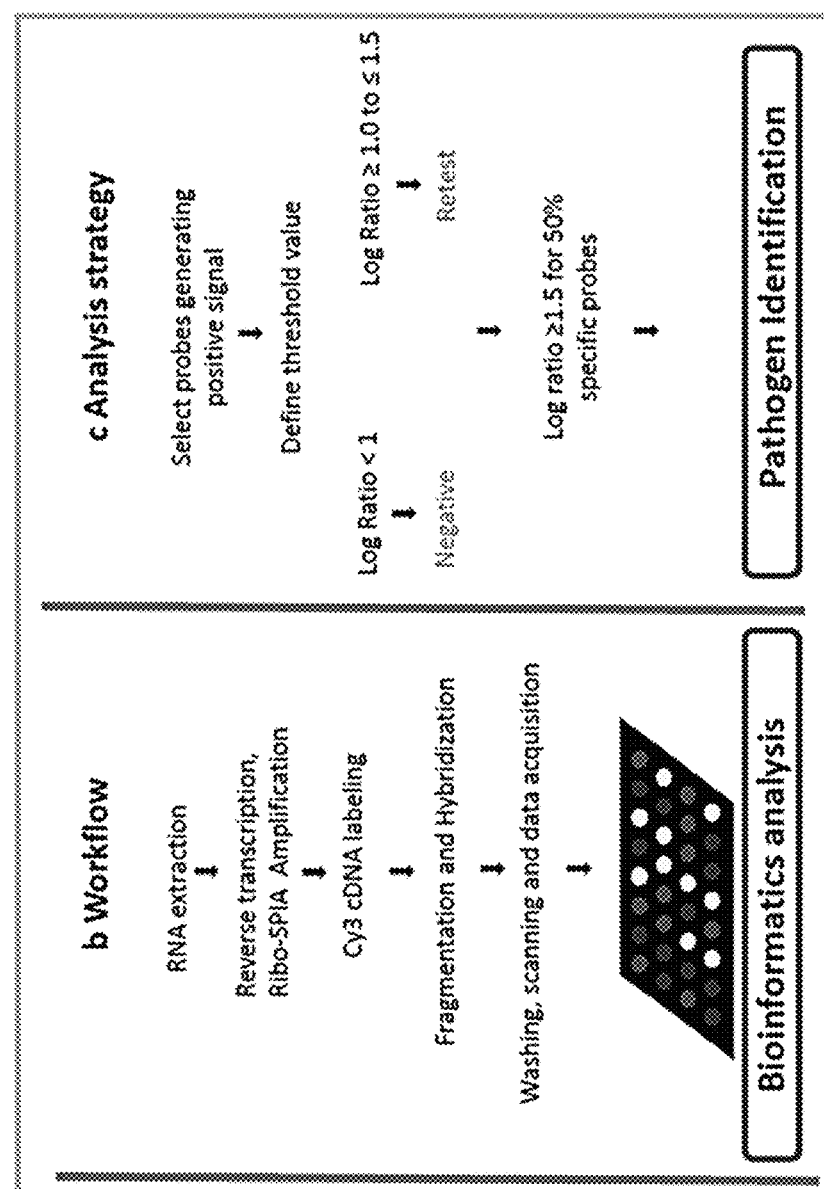

ID NOs: 1-1300, 1391-1570, and 1691-
METHODS AND COMPOSITIONS FOR DETECTING TRANSFUSION-TRANSMITTED PATHOGENS

CROSS REFERENCE TO RELATED APPLICATIONS

This application is the U.S. National Stage of International Application No. PCT/US2020/016262, filed Jan. 31, 2020, which was published in English under PCT Article 21 (2), which in turn claims the benefit of U.S. Provisional Application No. 62/799,482, filed Jan. 31, 2019, which is incorporated herein by reference in its entirety.

ACKNOWLEDGMENT OF GOVERNMENT SUPPORT

This invention was made with Government support under project number Z01 CL002068-28 by the National Institutes of Health, Clinical Center. The Government has certain rights in the invention.

FIELD

This disclosure relates to compositions and methods for detecting pathogens in a sample, particularly probes and microarrays and methods of their use.

BACKGROUND

Each year millions of blood donations are collected globally and millions of blood components are transfused to patients. Though screening of these blood units using serologic and nucleic acid testing (NAT) has greatly reduced the risk of some transfusion-transmitted infections (TTIs), the vast majority of bloodborne agents are not screened (Alter et al., *Semin. Hematol.* 44:32-41, 2007; Glynn et al., *Transfusion* 53:438-454, 2013; Leveton et al., *Transfusion* 36:919-927, 1996). The U.S. Food and Drug Administration-licensed methods for infectious disease screening of donor blood include: 1) nucleic acid testing (NAT) for Hepatitis B virus (HBV), Hepatitis C virus (HCV), HIV-1 and -2, *Babesia*, West Nile virus (WNV) and Zika virus (ZIKV); and 2) immunoassays for HBV, HCV, HIV-1 and -2, cytomegalovirus (CMV), human T-cell lymphotropic virus I and II (HTLV), *Treponema pallidum* (syphilis), and *Trypanosoma cruzi* (Chagas). HTLV, syphilis, and Chagas antibody testing fail to detect these pathogens during a window period and Chagas is screened only once on samples from first-time blood donors (Duncan et al., *Exp. Rev. Mol. Diagn.* 16:83-95, 2016).

The American Association of Blood Banks Transfusion-Transmitted Diseases Committee produced a list of over 30 pathogens of concern for transmission via blood that included bacteria, parasites, prions and viruses (Stramer et al., *Transfusion* 49:1S-29S, 2009). Only prions cannot be detected by currently available technology. Nearly all the other agents currently require individual qPCR or serologic testing and it is logistically impractical and cost prohibitive to test all known and potential agents individually (Stramer *ISBT Science Series* 9:30-37, 2014; Atrey et al., *Transfusion* 51:1855-1871, 2011).

Multiplex PCR-based devices for testing blood-borne pathogens are limited. FDA-approved blood donor screening assays that use transcription-mediated amplification for multiplex detection of HBV, HCV, and HIV 1 and 2 include the cobas TaqScreen MPX Test (Roche Molecular Systems, Inc.) and the Procleix Ultrio Plus (Gen-Probe, Inc.) (Duncan et al., *Exp. Rev. Mol. Diagn.* 16:83-95, 2016).

SUMMARY

A multiplex assay capable of detecting many, most, or all known pathogens of concern in a single small blood sample with high sensitivity and specificity could significantly increase the safety of the blood supply. Further, to counter emerging pathogens, the platform should be adaptable for rapid addition and validation of probes to detect new agents. Microarray-based technology offers the advantage of multiplex detection in a miniaturized format with high adaptability.

Disclosed herein are probe sets that include probes with at least 90% identity (such as at least 90%, at least 95%, at least 98%, or at least 99% identity) with the nucleic acid sequences of SEQ ID NOs: 1-1300, 1391-1570, and 1691-1769, or subsets thereof. In some examples, the probe set includes probes with the nucleic acid sequences of SEQ ID NOs: 1-1300, 1391-1570, and 1691-1769, or a subset thereof. In some embodiments, the probe set includes one or more probes (such as 30 or more probes) for one or more RNA viruses, such as one or more of Chikungunya virus, Dengue virus type 1, Dengue virus type 2, Dengue virus type 3, Dengue virus type 4, Hepatitis A virus, Hepatitis C virus type 1, Hepatitis C virus type 2, Hepatitis C virus type 3, Hepatitis E virus, Human immunodeficiency virus type 1, Human immunodeficiency virus type 2, Human T-lymphotropic virus type I, Human T-lymphotropic virus type II, West Nile virus, and Zika virus.

In other embodiments, the probe set includes one or more probes for one or more DNA viruses, such as one or more of cytomegalovirus (CMV, also known as HHV-5), Epstein Barr virus (EBV, also known as HHV-4, for example subtype B95-8 and/or AG876)), human herpes virus 8 (HHV-8), Hepatitis B virus (such as one or more of Hepatitis B virus subtype adw, subtype ayw, subtype adr, and subtype ayr), human parvovirus B19, and human papillomavirus (HPV, such as one or more of type 6, 11, 16, and 18). In some embodiments, the probe set includes probes with at least 90% identity (such as at least 90%, at least 95%, at least 98%, or at least 99% identity) with the nucleic acid sequences of SEQ ID NOs: 1770-2647, or a subset thereof. In some examples, the probe set includes probes with the nucleic acid sequences of SEQ ID NOs: 1770-2647, or a subset thereof.

Further disclosed are probe sets that include one or more probes for one or more bacterial or protozoan pathogens, such as one or more of *Treponema pallidum*, *Ehrlichia chaffeensis*, *Ehrlichia ewingii*, *Ehrlichia muris*, *Borrelia burgdorferi*, *Coxiella burnetii*, *Trypanosoma brucei*, *Trypanosoma cruzi Leishmania major*, *Babesia microti*, *Plasmodium falciparum*, and *Plasmodium vivax*. In some embodiments, the probe set includes probes with at least 90% identity (such as at least 90%, at least 95%, at least 98%, or at least 99% identity) with the nucleic acid sequences of SEQ ID NOs: 2648-3207, or a subset thereof. In some examples, the probe set includes probes with the nucleic acid sequences of SEQ ID NOs: 2648-3207, or a subset thereof.

In some embodiments, the disclosed probe sets include at least one negative control probe and/or at least one positive control probe. In some examples the negative control probe is a probe with at least 90% identity (such as at least 90%, at least 95%, at least 98%, or at least 99% identity) with the nucleic acid sequences of any one of SEQ ID NOs: 1571-

1690. In other examples the control probe is a probe with at least 90% identity (such as at least 90%, at least 95%, at least 98%, or at least 99% identity) with the nucleic acid sequences of any one of SEQ ID NOs: 3208-3628.

In one non-limiting embodiment, the probe set is a set of probes including each of SEQ ID NOs: 1-1769. In another non-limiting embodiment, the probe set is a set of probes including each of SEQ ID NOs: 1770-2647 and 3208-3628, each of SEQ ID NOs: 2648-3628, or each of SEQ ID NOs: 1770-3628. In a further non-limiting embodiment, the microarray includes probes including each of SEQ ID NOs: 1-3628.

Also disclosed are microarrays that include a probe set described herein, for example, wherein the probes are covalently linked to a solid support. In one non-limiting example, the microarray includes probes with at least 90% identity (such as at least 90%, at least 95%, at least 98%, at least 99%, or at least 100% identity) with the nucleic acid sequences of SEQ ID NOs: 1-1300, 1391-1570, and 1691-1769, or subsets thereof. In another non-limiting example, the microarray includes probes with at least 90% identity (such as at least 90%, at least 95%, at least 98%, at least 99%, or at least 100% identity) with the nucleic acid sequences of SEQ ID NOs: 1770-2647, or subsets thereof. In a further non-limiting example, the microarray includes probes with at least 90% identity (such as at least 90%, at least 95%, at least 98%, at least 99%, or at least 100% identity) with the nucleic acid sequences of SEQ ID NOs: 2648-3207, or subsets thereof. In yet another non-limiting embodiment, the microarray includes probes with at least 90% identity (such as at least 90%, at least 95%, at least 98%, at least 99%, or at least 100% identity) with the nucleic acid sequences of SEQ ID NOs: 1770-3207, or subsets thereof. The microarray may further include negative and/or positive control probes. In one non-limiting embodiment, the microarray includes probes including each of SEQ ID NOs: 1-1769. In other non-limiting embodiments, the microarray includes probes including each of SEQ ID NOs: 1770-2647 and 3208-3628, each of SEQ ID NOs: 2648-3628, each of SEQ ID NOs: 1770-3628. In a further non-limiting embodiment, the microarray includes probes including each of SEQ ID NOs: 1-3628.

Disclosed herein are methods of detecting one or more pathogen nucleic acids in a sample. In some examples, the methods include detecting nucleic acids from one or more RNA viruses, such as one or more of Chikungunya virus, Dengue virus type 1, Dengue virus type 2, Dengue virus type 3, Dengue virus type 4, Hepatitis A virus, Hepatitis C virus type 1, Hepatitis C virus type 2, Hepatitis C virus type 3, Hepatitis E virus, Human immunodeficiency virus type 1, Human immunodeficiency virus type 2, Human T-lymphotropic virus type I, Human T-lymphotropic virus type II, West Nile virus, and Zika virus in a sample. In other examples, the methods include detecting nucleic acids from one or more DNA viruses, such as one or more of cytomegalovirus, Epstein Barr virus, human herpes virus 8, Hepatitis B virus, human parvovirus B19, and human papillomavirus.

Also disclosed are methods of detecting one or more bacterial and/or protozoan nucleic acids in a sample. In some examples, the methods include detecting nucleic acids from one or more of *Treponema pallidum*, *Ehrlichia chaffeensis*, *Ehrlichia ewingii*, *Ehrlichia muris*, *Borrelia burgdorferi*, *Coxiella burnetii*, *Trypanosoma brucei*, *Trypanosoma cruzi*, *Leishmania major*, *Babesia microti*, *Plasmodium falciparum*, and *Plasmodium vivax*.

In some examples, the methods include contacting a sample with a disclosed probe set or microarray under conditions sufficient to allow hybridization of pathogen nucleic acids present in the sample to the probes of the probe set or microarray and measuring hybridization of the sample to one or more of the probes, thereby detecting one or more nucleic acids in the sample. The sample may be a blood, serum, or plasma sample, or nucleic acids (such as RNA or cDNA) isolated from the sample. In particular examples, the sample is a blood donation sample or nucleic acids isolated from a blood donation sample. In particular examples, nucleic acids (such as RNA or cDNA) from the sample are labeled prior to contacting the probe set or microarray with the nucleic acids. In one example, the method includes preparing cDNA from the sample and labeling the cDNA. In some examples, the method does not include amplifying RNA from the sample prior to preparing the cDNA.

The foregoing and other features of the disclosure will become more apparent from the following detailed description, which proceeds with reference to the accompanying figures.

BRIEF DESCRIPTION OF THE DRAWINGS

FIGS. 1A-1C are a series of panels showing pathogen chip design (FIG. 1A), sample preparation work flow (FIG. 1B), and analysis strategy (FIG. 1C) for pathogen detection microarrays.

FIG. 2A shows SPIA amplification vs. standard (STD) method. cDNA concentration after amplification for four representative viral RNAs is shown. Starting RNA concentration was <10 ng/µl each. FIG. 2B shows Pathogen chip assay performance 1. Bars are the mean of Cy3 signal for the Chikungunya and West Nile probes hybridized to test samples positive for CHIKV and WNV and a negative plasma sample. Only probes specific to target showed a specific hybridization signal. No signal was detected for negative plasma. FIG. 2C shows Pathogen chip assay performance 2. Detection responses of four representative samples (Dengue-4) were measured over a dilution series from 10,000 to 10 genomic copies per sample. Bars are the mean of Cy3 signals for all probes to the indicated viruses hybridized to test samples.

SEQUENCE LISTING

Figure 2A:
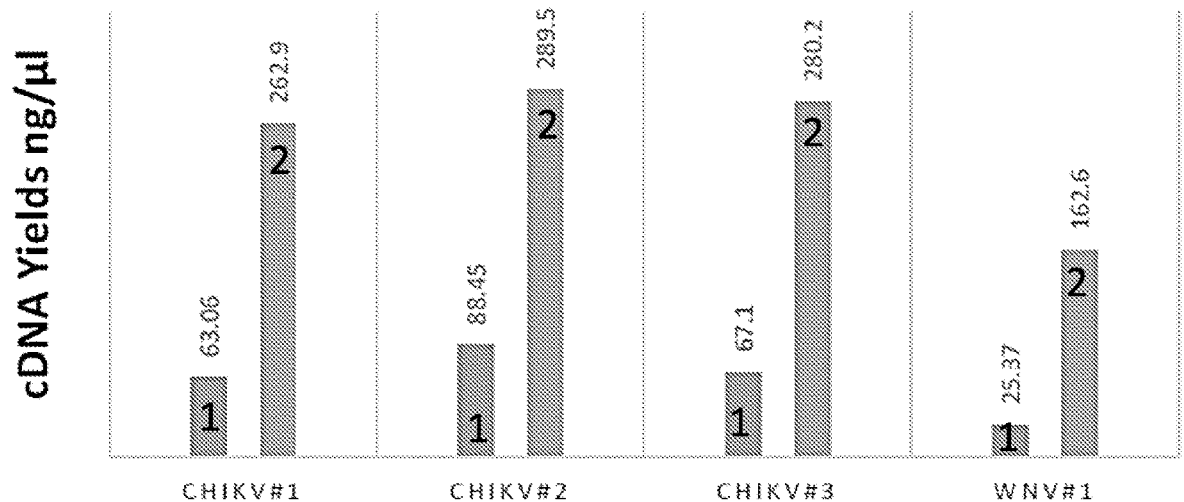
FIGS. 2A-2C are a series of graphs showing amplification method and Pathogen Chip assay performance assessed using positive control viral RNAs.

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Jul. 22, 2021, and is 676,876 bytes, which is incorporated by reference herein.

In the accompanying sequence listing:
SEQ ID NOs: 1-110 are Hepatitis C virus genotype 1 probes
SEQ ID NOs: 111-210 are Hepatitis C virus genotype 2 probes
SEQ ID NOs: 211-310 are Hepatitis C virus genotype 3 probes SEQ ID NOs: 311-400 are Human Immunodeficiency virus 1 probes
SEQ ID NOs: 401-510 are Human Immunodeficiency virus 2 probes
SEQ ID NOs: 511-570 are Human T-lymphotropic virus I probes
SEQ ID NOs: 571-660 are Human T-lymphotropic virus II probes
SEQ ID NOs: 661-760 are West Nile virus NY99 probes
SEQ ID NOs: 761-870 are West Nile virus 956 probes
SEQ ID NOs: 871-900 are Chikungunya virus probes
SEQ ID NOs: 901-1000 are Dengue virus 1 probes
SEQ ID NOs: 1001-1100 are Dengue virus 2 probes
SEQ ID NOs: 1101-1199 are Dengue virus 3 probes
SEQ ID NOs: 1200-1300 are Dengue virus 4 probes
SEQ ID NOs: 1301-1390 are GB virus C/Hepatitis G virus probes
SEQ ID NOs: 1391-1500 are Hepatitis A virus probes
SEQ ID NOs: 1501-1570 are Hepatitis E virus probes
SEQ ID NOs: 1571-1580 are White clover cryptic virus 1 probes
SEQ ID NOs: 1581-1620 are Broad bean wilt virus 1 probes
SEQ ID NOs: 1621-1690 are Lettuce necrotic yellows virus probes
SEQ ID NOs: 1691-1700 are Zika virus isolate Brazil-ZKV2015 probes
SEQ ID NOs: 1701-1710 are Zika virus strain PRV-ABC59 probes
SEQ ID NOs: 1711-1720 are Zika virus isolate Z1106033 probes
SEQ ID NOs: 1721-1730 are Zika virus isolate SSABR1 probes
SEQ ID NOs: 1731-1769 are Zika virus strain ZikaSPH2015 probes
SEQ ID NOs: 1770-1852 are Cytomegalovirus probes
SEQ ID NOs: 1853-1917 are Epstein Barr virus B95-8 probes
SEQ ID NOs: 1918-2023 are Epstein Barr virus AG876 probes
SEQ ID NOs: 2024-2108 are Human herpesvirus 8 probes
SEQ ID NOs: 2109-2192 are Human papillomavirus subtype 6b probes
SEQ ID NOs: 2193-2271 are Human papillomavirus subtype 11 probes
SEQ ID NOs: 2272-2342 are Human papillomavirus subtype 16 probes
SEQ ID NOs: 2343-2419 are Human papillomavirus subtype 18 probes
SEQ ID NOs: 2420-2470 are Hepatitis B virus subtype adw probes
SEQ ID NOs: 2471-2520 are Hepatitis B virus subtype ayw probes
SEQ ID NOs: 2521-2556 are Hepatitis B virus subtype adr probes
SEQ ID NOs: 2557-2602 are Hepatitis B virus subtype ayr probes
SEQ ID NOs: 2603-2647 are Human parvovirus B19 probes
SEQ ID NOs: 2648-2751 are *Treponema pallidum* probes
SEQ ID NOs: 2752-2852 are *Ehrlichia chaffeensis* probes
SEQ ID NOs: 2853-2861 are *Ehrlichia ewingii* probes
SEQ ID NOs: 2862-2922 are *Ehrlichia muris* probes
SEQ ID NOs: 2923-3001 are *Borrelia burgdorferi* probes
SEQ ID NOs: 3002-3085 are *Coxiella burnetii* probes
SEQ ID NOs: 3086-3097 are *Trypanosoma brucei* probes
SEQ ID NO: 3098 is a *Trypanosoma cruzi* probe
SEQ ID NOs: 3099-3113 are *Leishmania major* probes
SEQ ID NOs: 3114-3154 are *Babesia microti* probes
SEQ ID NOs: 3155-3185 are *Plasmodium falciparum* probes
SEQ ID NOs: 3186-3207 are *Plasmodium vivax* probes
SEQ ID NOs: 3208-3301 are human ACTB probes
SEQ ID NOs: 3302-3385 are human ARL1 probes
SEQ ID NOs: 3386-3519 are human CCDN1 probes
SEQ ID NOs: 3520-3557 are *Aedes albopictus* densovirus 2 probes
SEQ ID NOs: 3558-3598 are Maize streak virus probes
SEQ ID NOs: 3599-3628 are Tomato pseudo-curly top virus probes

DETAILED DESCRIPTION

Disclosed herein are customized sets of probes, including microarray-based pathogen chips, for simultaneous detection of nucleic acids from RNA viruses, DNA viruses, and/or bacteria or protozoan pathogens in blood samples (such as human plasma) that are designed to have the flexibility to expand to detect emerging agents in a relatively short time frame. The presence of multiple probes per target represents an advantage in comparison to traditional NAT or EIA assays since the pathogen(s) can be detected even in the case of failure of one of the probes due to mutation (Petrik *Vox Sanguinis* 80:1-11, 2001). The flexibility and high-throughput capability of microarrays hold great potential for pathogen detection and identification, but historically have had limitations in detecting the presence of the low viral levels (Chen et al., *J. Vis. Exp.* 50:e2536, 2011; Wang et al., *Proc. Natl. Acad. Sci. USA* 99:15687-15692, 2002; Eckburg et al., *Clin. Infect. Dis.* 43:e71-e76, 2006). Disclosed herein are probe sets and microarray assays that include: 1) a platform design that simultaneously detects and distinguishes multiple pathogens and closely related strains or subtypes; and 2) a combination of amplification and labeling protocols to detect multiple targets present at low levels in a sample.

I. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, Proteomics and Informatics*, 3$^{rd}$ Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Array or Microarray: An arrangement of nucleic acids (such as DNA or RNA) or proteins (such as antibodies) in assigned locations on a matrix or substrate. In some examples, the nucleic acid molecules or proteins are attached covalently to the matrix or substrate.

*Babesia*: A tick-borne protozoan parasite that infects vertebrate red blood cells. In humans, *Babesia* species may cause asymptomatic infection or babesiosis, characterized by flu-like symptoms. Most cases of transmission between humans are attributed to a tick vector; however, it may also be transmitted through blood transfusion or organ donation. The most common pathogenic species in humans are *Babesia divergens* and *Babesia* microti. *Babesia* sequences are publicly available, and include GenBank Accession Nos. ASM107745v2 (*Babesia divergens*) and ASM69194v2 and ASM165006v1 (*Babesia microti*), which are incorporated by reference in their entirety as present in GenBank on Jan. 30, 2020.

*Borrelia*: A genus of tick-borne spirochete bacteria that cause Lyme disease. The major species of *Borrelia* that cause Lyme disease include *Borrelia burgdorferi*, *Borrelia afzelii*, *Borrelia garinii*, and *Borrelia mayonii*. *Borrelia* has been identified in blood stored for donation, though there is currently no evidence of Lyme disease linked to blood transfusion. *Borrelia* sequences are publicly available, and include GenBank Accession Nos. ASM868v2 (*Borrelia burgdorferi*), ASM30473v1 (*Borrelia afzelii*), ASM192254v1 (*Borrelia garinii*), and ASM194566v1 (*Borrelia mayonii*), which are incorporated by reference in their entirety as present in GenBank on Jan. 30, 2020).

Chikungunya virus (CHIKV): A positive-sense single-stranded RNA virus of the alphavirus genus in the family Togaviridae. This virus is primarily transmitted by *Aedes* mosquitoes, particularly *A. albopictus* and *A. aegypti*. The symptoms of CHIKV infection include rash, high fever and joint pain. CHIKV was first isolated in Tanzania in 1952 and re-emerged in Kenya in 2004. The evolution and spread of this virus into new geographic areas, and the disease severity resulting from CHIKV infection, present a serious public health concern. CHIKV sequences are publicly available, and include GenBank Accession No. NC_004162 (gi|27754751)), which is incorporated by reference in its entirety as present in GenBank on Jan. 30, 2019.

*Coxiella burnetii*: A Gram-negative bacteria that causes Q fever. Symptoms are typically flu-like and may be mild or severe, and a small percentage of infected individuals develop chronic Q fever. The bacteria infects livestock (such as cows, sheep, and goats) and is transmitted to humans by contact with feces, urine, milk, or other products from an infected animal, typically by breathing dust contaminated with the bacteria. *Coxiella burnetii* sequences are publicly available, and includes GenBank Accession No. ASM776v2, which is incorporated by reference in its entirety as present in GenBank on Jan. 30, 2020.

Cytomegalovirus (CMV): Also known as human herpesvirus 5. A common virus that infects up to 50% of adults by the age of 40. Most people show no symptoms of infection or only mild symptoms; however, babies born with congenital CMV infection may have long-term health problems. CMV is transmitted by body fluids, including blood transfusions. CMV sequences are publicly available, and include GenBank Accession No. NC_006273, which is incorporated by reference in its entirety as present in GenBank on Jan. 30, 2020.

Dengue virus (DEN): An RNA virus of the family Flaviviridae, genus *Flavivirus*. There are four serotypes of dengue virus, referred to as DEN1, DEN2, DEN3 and DEN4. All four serotypes can cause the full spectrum of dengue disease. Infection with one serotype can produce lifelong immunity to that serotype. However, severe complications can occur upon subsequent infection by a different serotype. Dengue virus is primarily transmitted by *Aedes* mosquitoes, particularly *A. aegypti*. Symptoms of dengue virus infection include fever, headache, muscle and joint pain and a skin rash similar to measles. In a small percentage of cases, the infection develops into a life-threatening dengue hemorrhagic fever, typically resulting in bleeding, low platelet levels and blood plasma leakage, or into dengue shock syndrome, characterized by dangerously low blood pressure. DEN sequences are publicly available, and include GenBank Accession Nos. NC_001477 (gi|9626685) (DEN1), NC_001474 (gi|158976983) (DEN2), NC_001475 (gi|163644368) (DEN3), and NC_002640 (gi|12084822) (DEN4), which are incorporated by reference in their entirety as present in GenBank on Jan. 30, 2019.

Epstein-Barr virus (EBV): Also known as human herpesvirus 4. EBV is a common virus that is spread primarily through saliva, though it can also be spread by sexual contact, blood transfusion, and organ transplantation. EBV causes infectious mononucleosis, characterized by fatigue, fever, swollen lymph nodes, and sore throat; however, EBV infection may also be asymptomatic. EBV sequences are publicly available, and include GenBank Accession Nos. AJ278309 (EBV strain B95-8), DQ279927 (EBV strain AG876), and NC_009334, all of which are incorporated by reference in their entirety as present in GenBank on Jan. 30, 2020.

*Ehrlichia*: A genus of tick-borne bacteria that causes ehrlichiosis. In some cases, *Ehrlichia* has been transmitted through blood transfusion or organ transplantation. Symptoms can include rash, fever, headache, muscle aches, nausea, vomiting, and diarrhea. Severe, late stage illness can include neural damage, respiratory failure, and organ failure. Disease causing species include *Ehrlichia chaffeensis*, *Ehrlichia ewingii*, and *Ehrlichia muris*. *Ehrlichia* sequences are publicly available, and include GenBank Accession Nos. NC_007799 (*E. chaffeensis*) and NC_023063 (*E. muris*), which are incorporated by reference in their entirety as present in GenBank on Jan. 30, 2020.

Hepatitis A virus (HAV): A single-stranded RNA virus in the order Picornavirales, family Picornaviridae. The virus is transmitted through fecal-oral and blood routes. HAV causes symptoms such as nausea, vomiting, diarrhea, jaundice, fever, and abdominal pain and typically lasts about 8 weeks. Acute liver failure may occur in some cases. HAV sequences are publicly available, and include GenBank Accession No. NC_001489 (gi|9626732), which is incorporated by reference in its entirety as present in GenBank on Jan. 30, 2019.

Hepatitis B virus (HBV): A DNA virus of the Hepadnaviridae family. HBV is transmitted through blood or bodily fluids and new infections are frequently asymptomatic in healthy adults.

Immunosuppressed adults and children less than 5 years of age more commonly exhibit symptoms, including flu-like symptoms and jaundice. HBV sequences are publicly available and include GenBank Accession Nos. AY518556 (subtype adw), NC_003977 (subtype ayw), AY123041 (subtype adr), and X04615 (subtype ayr), all of which are incorporated by reference in their entirety as present in GenBank on Jan. 30, 2020.

Hepatitis C virus (HCV): A single-stranded positive sense RNA virus of the family Flaviviridae. HCV is transmitted primarily through blood and acute infection typically causes mild or no symptoms. However, chronic infection frequently leads to liver disease, including cirrhosis, liver failure, and/or hepatocellular carcinoma. HCV type 1 sequences are publicly available, and include GenBank Accession No. NC_004102 (gi|22129792). HCV type 2 sequences are also publicly available, and include GenBank Accession No. NC_009823 (gi|157781212). HCV type 3 sequences are also publicly available, and include GenBank Accession No. NC_009824 (gi|157781216). Each of these sequences are incorporated by reference in their entirety as present in GenBank on Jan. 30, 2019.

Hepatitis E virus (HEV): A single-stranded positive sense RNA virus that is currently classified in the Hepeviridae family, genus *Orthohepevirus*. HEV causes liver inflammation, and is typically an acute and self-limiting infection. However, it can cause chronic hepatitis in individuals with weakened immune systems, particularly organ transplant recipients. HEV sequences are publicly available, and include GenBank Accession No. NC_001434 (gi|9626440), which is incorporated by reference in its entirety as present in GenBank on Jan. 30, 2019.

Human Immunodeficiency virus (HIV): A single-stranded positive-sense RNA virus (retrovirus) that causes HIV infection and acquired immunodeficiency syndrome (AIDS). HIV is transmitted by blood or sexual contact. HIV type 1 sequences are publicly available, and include GenBank Accession No. NC_001802 (gi|9629357). HIV type 2 sequences are also publicly available and include GenBank Accession No. NC_001722 (gi|9628880). Each sequence is incorporated by reference in their entirety as present in GenBank on Jan. 30, 2019.

Human Herpesvirus 8 (HHV-8): Also known as Kaposi sarcoma-associated herpesvirus. HHV-8 is associated with Kaposi sarcoma and other cancers, including some lymphomas. It is transmitted through bodily fluids, including blood, saliva, and sexual contact. HHV-8 sequences are publicly available and include GenBank Accession No. NC_009333, which is incorporated by reference in its entirety as present in GenBank on Jan. 30, 2020.

Human parvovirus: A single-stranded DNA virus of the Parvoviridae family. Parvovirus B19 is the only parvovirus known to infect humans. B19 primarily causes disease in children, and causes what is sometimes called "fifth disease," a mild rash. Parvovirus B19 can be transmitted via respiratory secretions or through blood or blood products. Human parvovirus B19 sequences are publicly available and include GenBank Accession No. NC_000883, which is incorporated by reference in its entirety as present in GenBank on Jan. 30, 2020.

Human papillomavirus (HPV): A DNA virus of the family Papillomaviridae. HPV is a common sexually transmitted virus that can cause warts and cancers, including cervical cancer and head and neck cancer, in some individuals. HPV DNA can be detected in the blood in some cases; however, it is not clear whether it can be transmitted by blood transfusion. There are over 100 known types of HPV to date. HPV sequences are publicly available, and include GenBank Accession Nos. HG793809 (type 6), HE574701 (type 11), NC_001526 (type 16), and NC_001357 (type 18), each of which are incorporated by reference in their entirety as present in GenBank on Jan. 30, 2020.

Human T-lymphotropic virus (HTLV): A group of positive-sense RNA retroviruses that are implicated in cancer (for example, T-cell lymphomas) and myelopathy. HTLV type I sequences are publicly available, and include GenBank Accession Nos. AF033817 and NC_001436 (gi|9626453). HTLV type II sequences are also publicly available and include GenBank Accession No. NC_001488 (gi|9626726). Each sequence is incorporated by reference in their entirety as present in GenBank on Jan. 30, 2019.

*Leishmania major*: A trypanosomatid parasite transmitted by sand flies. *L. major* causes cutaneous leishmaniosis. *L. major* sequences are publicly available, and include GenBank Accession No. ASM272v2, incorporated by reference in its entirety as present in GenBank on Jan. 30, 2020.

*Plasmodium*: A genus of mosquito-transmitted protozoan parasites that causes malaria in humans. The two major malaria causing *Plasmodium* species in humans are *P. falciparum* and *P. vivax*. *P. falciparum* is also associated with Burkitt's lymphoma. *Plasmodium* can be transmitted by blood transfusion, causing transfusion-transmitted malaria. *Plasmodium* sequences are publicly available and include GenBank Accession No. ASM276v2 (*P. falciparum*) and ASM241v2 (*P. vivax*), which are incorporated by reference in their entirety as present in GenBank on Jan. 30, 2020.

Probe: A probe typically comprises an isolated nucleic acid (for example, at least 10 or more nucleotides in length, such as 10-60, 15-50, 20-40, 20-50, 25-50, or 30-60 nucleotides in length). In some examples, a probe includes a detectable label, while in other examples a probe does not include a detectable label.

Sample (or biological sample): A biological specimen containing nucleic acids (for example, DNA, RNA, and/or mRNA), proteins, or combinations thereof, obtained from a subject. Examples include, but are not limited to, peripheral blood, serum, plasma, urine, saliva, tissue biopsy, fine needle aspirate, surgical specimen, and autopsy material. In some examples, a sample includes blood, serum, or plasma.

Subject: A living multi-cellular vertebrate organism, a category that includes human and non-human mammals. In one example, a subject is a blood donor.

*Treponema*: A genus of spirochete bacteria. The major pathogenic species in humans is *Treponema pallidum*, of which subspecies *T. pallidum pallidum* causes syphilis. The bacteria is transmitted primarily by sexual contact. Nucleic acid sequences for *T. pallidum pallidum* are publicly available and include GenBank Accession Nos. NC_016844 and NC_00919, which are incorporated by reference in their entirety as present in GenBank on Jan. 30, 2020.

*Trypanosoma*: A genus of protozoan parasites transmitted by blood-feeding insects. *T. brucei* is transmitted by infected tsetse flies and causes sleeping sickness (trypanosomiasis) in humans. There are two types of trypanosomiasis: East African trypanosomiasis, caused by *Trypanosoma brucei rhodesiense* and West African trypanosomiasis, caused by *Trypanosoma brucei gambiense*. *Trypanosoma brucei brucei* infects primarily cattle, and does not normally infect humans. *T. cruzi* causes Chagas disease and is transmitted by triatomine bugs. *Trypanosoma* sequences are publicly available and include GenBank Accession Nos. ASM21029v1 (*T. brucei* gambiense), and ASM20906v1 (*T. cruzi*), each of which are incorporated by reference in their entirety as present in GenBank on Jan. 30, 2020.

West Nile virus (WNV): A member of the virus family Flaviviridae and the genus *Flavivirus*. WNV was first isolated from a woman in the West Nile district of Uganda in 1937. The virus was later identified in birds in the Nile delta region in 1953. Human infections attributable to WNV have been reported in many countries for over 50 years. In 1999, a WNV circulating in Israel and Tunisia was imported into New York, producing a large and dramatic outbreak that spread throughout the continental United States in the following years. Human infection is most often the result of bites from infected mosquitoes, but may also be transmitted through contact with other infected animals, their blood or other tissues. Infection with WNV is asymptomatic in about 80% of infected people, but about 20% develop West Nile fever. Symptoms include fever, headache, fatigue, body aches, nausea, vomiting, swollen lymph glands and in some cases, a skin rash. Approximately 1 in 150 of infected individuals develop severe, neuroinvasive disease, such as encephalitis, meningitis, or poliomyelitis. WNV sequences are publicly available, and include GenBank Accession Nos. NC_009942 (gi|158516887) (NY99, lineage 1) and NC_001563 (gi|11528013) (956, lineage 2), which are incorporated by reference in their entirety as present in GenBank on Jan. 30, 2019.

Zika virus (ZKV or ZIKV): A member of the virus family Flaviviridae and the genus *Flavivirus*. ZIKV is spread by the daytime-active mosquitoes *Aedes aegypti* and *A. albopictus*. This virus was first isolated from a Rhesus macaque from the Zika Forest of Uganda in 1947. Since the 1950s, ZIKV has been known to occur within a narrow equatorial belt from Africa to Asia. The virus spread eastward across the Pacific Ocean in 2013-2014, resulting in ZIKV outbreaks in Oceania to French Polynesia, New Caledonia, the Cook islands, and Easter Island. In 2015, ZKV spread to Mexico, Central America, the Caribbean and South America, where ZKV has reached pandemic levels. Infection by ZIKV generally causes either no symptoms or mild symptoms, including mild headache, maculopapular rash, fever, malaise, conjunctivitis and joint pain. However, ZKV infection has been linked to the birth of microcephalic infants following maternal infection. Reports have also indicated that ZIKV has the potential for human blood-borne and sexual transmission. ZIKV sequences are publicly available, and include GenBank Accession Nos. KU497555 (gi|985578255) (isolate Brazil-ZK2015), KU501215 (gi|984874581) (strain PRV-ABC59), KU312312 (gi|973447404) (isolate Z1106033), KU707826 (gi|992324757) (isolate SSABR1), and KU321639 (strain ZikaSPH2015), which are incorporated by reference in their entirety as present in GenBank on Jan. 30, 2019.

II. Probes and Microarrays

Disclosed herein is a nucleic acid probe set capable of detecting nucleic acid molecules from one or more RNA viruses, including Chikungunya virus (CHIKV), Dengue virus types 1, 2, 3, or 4, (DEN1, DEN2, DEN3, DEN4), Hepatitis A virus (HAV), Hepatitis C virus (HCV) types 1, 2, or 3, Hepatitis E virus (HEV), Human Immunodeficiency virus (HIV) types 1 or 2, Human T-lymphotropic virus (HTLV) types I or II, West Nile virus (WNV), and Zika virus (ZKV). In some embodiments, the probe set includes 30 or more probes for one or more of the viruses (such as 30 or more, 50 or more, 60 or more, 70 or more, 80 or more, 90 or more, 100 or more, 110 or more, or 120 or more), for example 30-120 probes, 50-100 probes, or 70-110 probes for one or more of CHIKV, DEN1, DEN2, DEN3, DEN4, HAV, HCV type 1, HCV type 2, HCV type 3, HEV, HIV type 1, HIV type 2, HTLV type 1, HTLV type 2, WNV, and ZIKV.

In some embodiments, the probe set includes nucleic acid probes that are at least 80%, at least 90%, at least 95%, at least 96%, at least 97%, at least 98%, at least 99%, or 100% identical to the nucleic acid sequences of SEQ ID NOs: 1-1300, 1391-1570, and 1691-1769. In other embodiments, the probe set includes a subset of the probes of SEQ ID NOs: 1-1300, 1391-1570, and 1691-1769, such as at least 10%, at least 20%, at least 30%, at least 40%, at least 50%, at least 60%, at least 70%, at least 80%, at least 90%, at least 95%, at least 96%, at least 97%, at least 98%, at least 99%, or at least 99.9% of the probes of SEQ ID NOs: 1-1300, 1391-1570, and 1691-1769. In some examples, the subset includes at least one probe for each of CHIKV, DEN1, DEN2, DEN3, DEN4, HAV, HCV type 1, HCV type 2, HCV type 3, HEV, HIV type 1, HIV type 2, HTLV type 1, HTLV type 2, WNV, and ZKV, such as at least 1, at least 2, at least 5, at least 10, at least 20, at least 30, or more probes for each virus. In some examples, the subset includes at least 40 probes (such as at least 50, at least 60, at least 70, at least 80, at least 90, at least 100, or at least 110 probes) for one or more of CHIKV, DEN1, DEN2, DEN3, DEN4, HAV, HCV type 1, HCV type 2, HCV type 3, HEV, HIV type 1, HIV type 2, HTLV type 1, HTLV type 2, WNV, and ZKV.

In one non-limiting example, the probe set includes or consists of each of the probes of SEQ ID NOs: 1-1769. In another non-limiting example, the probe set includes or consists of each of the probes of SEQ ID NOs: 1-1300, 1391-1570, and 1691-1769. In another example, the probe set includes or consists of each of the probes of SEQ ID NOs: 1-1300 and 1391-1769. In other embodiments, the probe set includes a subset of the probes of SEQ ID NOs: 1-1300, 1391-1570, and 1691-1769 or a subset of the probes of SEQ ID NOs: 1-1300 and 1391-1769.

Also disclosed herein is a nucleic acid probe set capable of detecting nucleic acid molecules from one or more DNA viruses, including one or more of cytomegalovirus, Epstein Barr virus (e.g., one or more of EBV subtype B95-8 and EBV subtype AG876), human herpes virus 8, Hepatitis B virus (e.g., one or more of HBV subtypes adw, ayw, adr, and ayr), human parvovirus B19, and human papillomavirus (e.g., one or more of HPV types 6, 11, 16, and 18). In some embodiments, the probe set includes 10 or more probes for one or more of the viruses (such as 15 or more, 20 or more, 30 or more, 50 or more, 60 or more, 70 or more, 80 or more, 90 or more, 100 or more, 110 or more, or 120 or more), for example 10-50 probes, 30-120 probes, 50-100 probes, or 70-110 probes for one or more of cytomegalovirus, Epstein Barr virus, human herpes virus 8, Hepatitis B virus, human parvovirus B19, and human papillomavirus.

In some embodiments, the probe set includes nucleic acid probes that are at least 80%, at least 90%, at least 95%, at least 96%, at least 97%, at least 98%, at least 99%, or 100% identical to the nucleic acid sequences of SEQ ID NOs: 1770-2647. In other embodiments, the probe set includes a subset of the probes of SEQ ID NOs: 1770-2647, such as at least 10%, at least 20%, at least 30%, at least 40%, at least 50%, at least 60%, at least 70%, at least 80%, at least 90%, at least 95%, at least 96%, at least 97%, at least 98%, at least 99%, or at least 99.9% of the probes of SEQ ID NOs: 1770-2647. In some examples, the subset includes at least one probe for each of CMV, EBV subtype B95-8, EBV subtype AG876, human herpes virus 8, Hepatitis B virus subtype adw, Hepatitis B virus subtype ayw, Hepatitis B virus subtype adr, Hepatitis B virus subtype ayr, human parvovirus B19, HPV type 6, HPV type 11, HPV type 16, and HPV type 18, such as at least 1, at least 2, at least 5, at least 10, at least 20, at least 30, or more probes for each virus. In some examples, the subset includes at least 10 probes (such as at least 20, at least 30, at least 40, at least 50, at least 60, at least 70, at least 80, at least 90, at least 100, or at least 110 probes) for one or more of CMV, EBV subtype B95-8, EBV subtype AG876, human herpes virus 8, Hepatitis B virus subtype adw, Hepatitis B virus subtype ayw, Hepatitis B virus subtype adr, Hepatitis B virus subtype ayr, human parvovirus B19, HPV type 6, HPV type 11, HPV type 16, and HPV type 18. In one non-limiting example, the probe set includes or consists of each of the probes of SEQ ID NOs: 1770-2647.

Further disclosed herein is a nucleic acid probe set capable of detecting nucleic acid molecules from one or more bacterial and/or protozoan pathogens, including one or more of *Treponema pallidum, Ehrlichia chaffeensis, Ehrlichia ewingii, Ehrlichia muris, Borrelia burgdorferi, Coxiella burnetii, Trypanosoma brucei, Trypanosoma cruzi, Leishmania major, Babesia microti, Plasmodium falciparum*, and *Plasmodium vivax*. In some embodiments, the probe set includes 10 or more probes for one or more of the viruses (such as 10 or more, 20 or more, 30 or more, 50 or more, 60 or more, 70 or more, 80 or more, 90 or more, 100 or more, 110 or more, or 120 or more), for example 30-120 probes, 50-100 probes, or 70-110 probes for one or more of *Treponema pallidum, Ehrlichia chaffeensis, Ehrlichia ewingii, Ehrlichia muris, Borrelia burgdorferi, Coxiella burnetii, Trypanosoma brucei, Leishmania major, Babesia microti, Plasmodium falciparum*, and *Plasmodium vivax*

In some embodiments, the probe set includes nucleic acid probes that are at least 80%, at least 90%, at least 95%, at least 96%, at least 97%, at least 98%, at least 99%, or 100% identical to the nucleic acid sequences of SEQ ID NOs: 2648-3207. In other embodiments, the probe set includes a subset of the probes of SEQ ID NOs: 2648-3207, such as at least 10%, at least 20%, at least 30%, at least 40%, at least 50%, at least 60%, at least 70%, at least 80%, at least 90%, at least 95%, at least 96%, at least 97%, at least 98%, at least 99%, or at least 99.9% of the probes of SEQ ID NOs: 2648-3207. In some examples, the subset includes at least one probe for each of *Treponema pallidum, Ehrlichia chaffeensis, Ehrlichia ewingii, Ehrlichia muris, Borrelia burgdorferi, Coxiella burnetii, Trypanosoma brucei, Trypanosoma cruzi, Leishmania major, Babesia microti, Plasmodium falciparum*, and *Plasmodium vivax*, such as at least 1, at least 2, at least 5, at least 10, at least 20, at least 30, or more probes for each pathogen. In some examples, the subset includes at least 10 probes (such as at least 20, at least 30, at least 50, at least 60, at least 70, at least 80, at least 90, at least 100, or at least 110 probes) for one or more of *Treponema pallidum, Ehrlichia chaffeensis, Ehrlichia ewingii, Ehrlichia muris, Borrelia burgdorferi, Coxiella burnetii, Trypanosoma brucei, Leishmania major, Babesia microti, Plasmodium falciparum*, and *Plasmodium vivax*. In one non-limiting example, the probe set includes or consists of each of the probes of SEQ ID NOs: 2648-3207.

In further embodiments, one or more of the disclosed probe sets are combined. Thus, some embodiments, the probe set includes probes for detecting at least one RNA virus, at least one DNA virus, at least one bacterial pathogen, at least one protozoan pathogen, or combinations of two or more thereof. In one example, a probe set includes probes capable of detecting nucleic acid molecules from one or more DNA viruses and one or more bacterial and/or protozoan pathogens. In one non-limiting example, a probe set includes probes including or consisting of each of the probes of SEQ ID NOs: 1770-3207. In another example, a probe set includes probes capable of detecting nucleic acid molecules from one or more RNA viruses, one or more DNA viruses, and one or more bacterial and/or protozoan pathogens. In a non-limiting example, the probe set includes probes including or consisting of each of the probes of SEQ ID NOs: 1-1300, SEQ ID NOs: 1391-1570, SEQ ID NOs: 1691-1769, and SEQ ID NOs: 1770-3207.

In additional embodiments, a disclosed probe set further includes one or more control probes, such as one or more positive and/or negative control probes. For testing for validity of the run, intra-array reproducibility control and normalization. positive control probes may include one or more of: 1) one or more reference probes for intensity normalization, 2) one or more internal standards of known concentrations, and 3) one or more probes that are homologous to an internal control included in the hybridization mix. In some embodiments, positive control probes include one or more (such as 1, 10, 25, 50, 96, or more) ERCC probes (External RNA Controls Consortium) and one or more (such as 1, 10, 25, 50, 96, 250, 500, 900, or more) biological replicates targeting human genome sequences (for example, to define possible host contaminant).

Negative control probes may include one or more probes for a virus that is known not to be present in human or mammalian subjects. In some non-limiting examples, negative control probes are specific for a plant virus. In other examples, negative control probes can be a structural negative probe, such as a sequence that forms a hairpin and does not hybridize with nucleic acids from any species.

In some examples, the probe set includes at least 10, at least 20, at least 30, at least 40, at least 50, at least 60, at least 70, at least 80, at least 90, at least 100, at least 110, or at least 120 control probes. In some examples, the control probes are for one or more one or more different negative control viruses (such as 1, 2, 3, 4, 5, or more negative control viruses). In some examples, the probe set includes at least 10, at least 20, at least 30, at least 40, at least 50, at least 60, at least 70, at least 80, at least 90, at least 100, at least 110, at least 120, or more negative control probes. In some examples, the negative control probes are probes for one or more of White clover cryptic virus 1 (e.g. SEQ ID NOs: 1571-1580), Broad bean wilt virus 1 (e.g., SEQ ID NOs: 1582-1620), Lettuce necrotic yellows virus (e.g., SEQ ID NOs: 1621-1690), *Aedes albopictus* densovirus 2 (e.g., SEQ ID NOs: 3520-3557), Maize streak virus (e.g., SEQ ID NOs: 3558-3598), and/or Tomato pseudo-curly top virus (e.g., SEQ ID NOs: 3599-3628). In additional examples, the probe set includes at least 10, at least 20, at least 30, at least 40, at least 50, at least 60, at least 70, at least 80, at least 90, at least 100, at least 110, at least 120, or more positive control probes. In some examples, the positive control probes are probes for one or more housekeeping genes, such as one of more of ACTB (e.g., SEQ ID NOs: 3208-3301), ARL1 (e.g., SEQ ID NOs: 3302-3385), and/or CCDN1 (e.g., SEQ ID NOs: 3386-3519).

In some embodiments, the disclosed probes are between 30 and 80 nucleotides in length (for example 30-50, 40-60, 50-70, or 60-80 nucleotides in length). In some examples, the probes are 30, 35, 40, 45, 50, 55, 60, 65, 70, 75, or 80 nucleotides in length and are capable of hybridizing to the disclosed pathogen (e.g., viral, bacterial, or protozoan) nucleic acid molecules. In some examples, the probes are 60 nucleotides in length. In some examples, each of the probes in the probe set has a Tm between about 72-89° C., such as about 74-88° C., about 75-85° C., or about 76-82° C. In one specific example, each of the probes in the probe set has a Tm between 74.4 and 87.8° C. Tm ranges for exemplary RNA virus probes are shown in Table 1.

In other embodiments the disclosed probe sets, or a subset thereof, are linked to a solid support. In some examples, the disclosed probe sets, or a subset thereof, are included on a microarray. In other examples, the solid support is a bead or plurality of beads, a microplate, column, or microfluidic device.

In some embodiments, the microarray is a solid support or substrate including the probe set (or subset thereof) covalently linked to the support or substrate. Within an array, each arrayed probe is addressable, in that its location can be reliably and consistently determined within at least two dimensions of the array. Addressable arrays usually are computer readable, in that a computer can be programmed to correlate a particular address on the array with information about the sample at that position (such as hybridization or binding data, including for instance signal intensity).

The microarray can include any of the probe sets described above, individually, or in combination. In some embodiments, the microarray includes nucleic acid probes that are at least 80%, at least 90%, at least 95%, at least 96%, at least 97%, at least 98%, at least 99%, or 100% identical to the nucleic acid sequences of SEQ ID NOs: 1-1300, 1391-1570, and 1691-1769. In another embodiment, the microarray includes or consists of nucleic acid probes that are at least 80%, at least 90%, at least 95%, at least 96%, at least 97%, at least 98%, at least 99%, or 100% identical to the nucleic acid sequences of SEQ ID NOs: 1-1300 and 1391-1769. In one non-limiting example, the microarray includes or consists of each of the probes of SEQ ID NOs: 1-1769. In another non-limiting example, the microarray includes or consists of each of the probes of SEQ ID NOs: 1-1300, 1391-1570, and 1691-1769. In a further non-limiting example, the microarray includes or consists of each of the probes of SEQ ID NOs: 1-1300 and 1391-1769.

In another embodiment, the microarray includes nucleic acid probes that are at least 80%, at least 90%, at least 95%, at least 96%, at least 97%, at least 98%, at least 99%, or 100% identical to the nucleic acid sequences of SEQ ID NOs: 1770-2647. In one non-limiting example, the microarray includes or consists of each of the probes of SEQ ID NOs: 1770-2647. In another non-limiting example, the microarray includes or consists of each of the probes of SEQ ID NOs: 1170-2647 and 3250-3628.

In another embodiment, the microarray includes nucleic acid probes that are at least 80%, at least 90%, at least 95%, at least 96%, at least 97%, at least 98%, at least 99%, or 100% identical to the nucleic acid sequences of SEQ ID NOs: 2648-3207. In one non-limiting example, the microarray includes or consists of each of the probes of SEQ ID NOs: 2648-3207. In another non-limiting example, the microarray includes or consists of each of the probes of SEQ ID NOs: 2648-3519.

In a further embodiment, the microarray includes nucleic acid probes that are at least 80%, at least 90%, at least 95%, at least 96%, at least 97%, at least 98%, at least 99%, or 100% identical to the nucleic acid sequences of SEQ ID NOs: 1770-3207. In one non-limiting example, the microarray includes or consists of each of the probes of SEQ ID NOs: 1770-3207. In a further non-limiting example, the microarray includes or consists of each of the probes of SEQ ID NOs: 1770-3628.

In other embodiments, the microarray includes a subset of the probes of SEQ ID NOs: 1-1300, 1391-1570, and 1691-1769, such as at least 10%, at least 20%, at least 30%, at least 40%, at least 50%, at least 60%, at least 70%, at least 80%, at least 90%, at least 95%, at least 96%, at least 97%, at least 98%, at least 99%, or at least 99.9% of the probes of SEQ ID NOs: 1-1300, 1391-1570, and 1691-1769. In some examples, the microarray includes at least one probe for each of CHIKV, DEN1, DEN2, DEN3, DEN4, HAV, HCV type 1, HCV type 2, HCV type 3, HEV, HIV type 1, HIV type 2, HTLV type 1, HTLV type 2, WNV, and ZKV, such as at least 1, at least 2, at least 5, at least 10, at least 20, at least 30, or more probes for each virus. In some examples, the microarray includes at least 40 probes (such as at least 50, at least 60, at least 70, at least 80, at least 90, at least 100, or at least 110 probes) for one or more of CHIKV, DEN1, DEN2, DEN3, DEN4, HAV, HCV type 1, HCV type 2, HCV type 3, HEV, HIV type 1, HIV type 2, HTLV type 1, HTLV type 2, WNV, and ZKV.

In other embodiments, the microarray includes a subset of the probes of SEQ ID NOs: 1770-2647, such as at least 10%, at least 20%, at least 30%, at least 40%, at least 50%, at least 60%, at least 70%, at least 80%, at least 90%, at least 95%, at least 96%, at least 97%, at least 98%, at least 99%, or at least 99.9% of the probes of SEQ ID NOs: 1770-2647. In some examples, the microarray includes at least one probe for each of CMV, EBV subtype B95-8, EBV subtype AG876, human herpes virus 8, Hepatitis B virus subtype adw, Hepatitis B virus subtype ayw, Hepatitis B virus subtype adr, Hepatitis B virus subtype ayr, human parvovirus B19, HPV type 6, HPV type 11, HPV type 16, and HPV type 18, such as at least 1, at least 2, at least 5, at least 10, at least 20, at least 30, or more probes for each virus. In some examples, the microarray includes at least 20 probes (such as at least 40, at least 50, at least 60, at least 70, at least 80, at least 90, at least 100, or at least 110 probes) for one or more of CMV, EBV subtype B95-8, EBV subtype AG876, human herpes virus 8, Hepatitis B virus subtype adw, Hepatitis B virus subtype ayw, Hepatitis B virus subtype adr, Hepatitis B virus subtype ayr, human parvovirus B19, HPV type 6, HPV type 11, HPV type 16, and HPV type 18.

In other embodiments, the microarray includes a subset of the probes of SEQ ID NOs: 2648-3207, such as at least 10%, at least 20%, at least 30%, at least 40%, at least 50%, at least 60%, at least 70%, at least 80%, at least 90%, at least 95%, at least 96%, at least 97%, at least 98%, at least 99%, or at least 99.9% of the probes of SEQ ID NOs: 2648-3207. In some examples, the microarray includes at least one probe for each of *Treponema pallidum, Ehrlichia chaffeensis, Ehrlichia ewingii, Ehrlichia muris, Borrelia burgdorferi, Coxiella burnetii, Trypanosoma brucei, Trypanosoma cruzi, Leishmania major, Babesia microti, Plasmodium falciparum,* and *Plasmodium vivax,* such as at least 1, at least 2, at least 5, at least 10, at least 20, at least 30, or more probes for each virus. In some examples, the microarray includes at least 10 probes (such as at least 30, at least 30, at least 40, at least 50, at least 60, at least 70, at least 80, at least 90, at least 100, or at least 110 probes) for one or more of *Treponema pallidum, Ehrlichia chaffeensis, Ehrlichia ewingii, Ehrlichia muris, Borrelia burgdorferi, Coxiella burnetii, Trypanosoma brucei, Leishmania major, Babesia microti, Plasmodium falciparum,* and *Plasmodium vivax.*

In additional embodiments, the microarray includes one or more control probes, such as one or more positive and/or negative control probes. In some examples, the microarray includes at least 10, at least 20, at least 30, at least 40, at least 50, at least 60, at least 70, at least 80, at least 90, at least 100, at least 110, or at least 120 negative control probes. In some examples, the microarray includes one or more negative control probes selected from SEQ ID NOs: 1571-1580, SEQ ID NOs: 1582-1620, SEQ ID NOs: 1621-1690, and SEQ ID NOs: 3520-3628. In additional examples, the microarray includes at least 10, at least 20, at least 30, at least 40, at least 50, at least 60, at least 70, at least 80, at least 90, at least 100, at least 110, or at least 120 positive control probes. In some examples, the microarray includes one or more positive control probes selected from SEQ ID NOs: 3208-3519.

The solid support or substrate of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, ethyleneacrylic acid, thylene methacrylic acid, and blends of copolymers thereof).

A wide variety of array formats can be employed in accordance with the present disclosure. One example includes a two-dimensional pattern of discrete cells (such as 4096 squares in a 64 by 64 array). Other array formats including, but not limited to slot (rectangular) and circular arrays are equally suitable for use. In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, and the like. For example, membranes can be affixed to glass slides. The particular format is, in and of itself, unimportant. All that is necessary is that the solid support can be affixed thereto without affecting the functional behavior of the solid support or any biopolymer absorbed thereon, and that the format (such as the slide) is stable to any materials into which the device is introduced (such as clinical samples and hybridization solutions).

The arrays of the present disclosure can be prepared by a variety of approaches. In one example, oligonucleotides (e.g., probes) are synthesized separately and then attached to a solid support (see U.S. Pat. No. 6,013,789). In another example, probes are synthesized directly onto the support to provide the desired array (see U.S. Pat. No. 5,554,501). Suitable methods for covalently coupling oligonucleotides to a solid support and for directly synthesizing oligonucleotides on the support are known; a summary of suitable methods can be found in Matson et al., Anal. Biochem. 217:306-10, 1994. In one example, the oligonucleotides are synthesized onto the support using conventional chemical techniques for preparing oligonucleotides on solid supports (such as PCT applications WO 85/01051 and WO 89/10977, or U.S. Pat. No. 5,554,501).

The oligonucleotides can be bound to the support or substrate by either the 3' end of the oligonucleotide or by the 5' end of the oligonucleotide. In one example, the oligonucleotides are bound to the solid support by the 3' end. In general, the internal complementarity of an oligonucleotide probe in the region of the 3' end and the 5' end determines binding to the support.

III. Methods of Detecting Viral Nucleic Acids

Disclosed herein are methods of detecting one or more pathogen nucleic acids (such as one or more viral, bacterial, and/or protozoan nucleic acids) in a sample from a subject. In some embodiments, the methods include preparing or isolating nucleic acids (such as DNA, RNA, or cDNA) from a sample, labeling the nucleic acids, and contacting the probe set, or a microarray including the probe set, with the labeled nucleic acids under conditions sufficient to allow pathogen nucleic acids present in the sample to hybridize with one or more of the probes. The presence and/or identity of pathogen nucleic acids in the sample is determined by detecting hybridization. In one example, hybridization is detected by measuring presence of labeled nucleic acid at an addressable location in an array.

In particular embodiments, the methods include detecting one or more nucleic acids from RNA viruses in a sample, including one or more of CHIKV, DEN1, DEN2, DEN3, DEN4, HAV, HCV type 1, HCV type 2, HCV type 3, HEV, HIV type 1, HIV type 2, HTLV type I, HTLV type II, WNV, and ZKV. In other embodiments, the methods include detecting one or more nucleic acids from DNA viruses, including one or more of CMV, EBV subtype B95-8, EBV subtype AG876, human herpes virus 8, Hepatitis B virus subtype adw, Hepatitis B virus subtype ayw, Hepatitis B virus subtype adr, Hepatitis B virus subtype ayr, human parvovirus B19, HPV type 6, HPV type 11, HPV type 16, and HPV type 18. In still other embodiments, the methods include detecting one or more nucleic acids from bacteria and/or protozoans, including one or more of *Treponema pallidum, Ehrlichia chaffeensis, Ehrlichia ewingii, Ehrlichia muris, Borrelia burgdorferi, Coxiella burnetii, Trypanosoma brucei, Trypanosoma cruzi, Leishmania major, Babesia microti, Plasmodium falciparum*, and *Plasmodium vivax*. In further embodiments, the methods include detecting nucleic acids from at least one RNA virus, DNA virus, bacteria, and protozoan, such as at least one of the RNA viruses, DNA viruses, bacteria, and protozoans disclosed herein, or any combination thereof.

Exemplary samples include peripheral blood, serum, plasma, cerebrospinal fluid, urine, saliva, feces, mucus, nasal wash, tissue biopsy, fine needle aspirate, surgical specimen, placenta, autopsy material, semen, vaginal fluid or tissue, and environmental samples. In particular examples, the sample is a blood sample, such as plasma. In non-limiting examples, the sample is blood or plasma from a blood donor. Thus, in some examples, the methods disclosed herein are used to screen donated blood for one or more pathogens potentially present and/or transmitted through blood transfusions.

In some embodiments, the methods include isolating nucleic acids (such as RNA, cDNA, or a combination thereof) from the sample and contacting the probe set or microarray with the isolated nucleic acids. Methods of isolating RNA (e.g., viral RNA) from a sample are known and include commercially available kits, such as QIAGEN® RNeasy® mini-columns, MASTERPURE® Complete DNA and RNA Purification Kit (EPICENTRE® Madison, Wis.), Paraffin Block RNA Isolation Kit (Ambion, Inc.), and RNA Stat-60 (Tel-Test). cDNA is then prepared from the isolated RNA, and optionally labeled. In some examples, the methods include amplifying RNA prior to cDNA preparation and labeling, for example, using Quick Amp WT labeling kit (Agilent). Other methods of amplifying RNA include commercially available kits such as Ovation® RNA Amplification kit (Nugen), Arcturus™ RiboAmp™ HS kit (ThermoFisher), and Complete Whole Transcriptome Amplification Kit (WTA2, Sigma-Aldrich).

In some embodiments, the methods do not include isolating and/or amplifying RNA from a sample prior to labeling. In some examples, the methods include generating amplified cDNA from a sample, followed by labeling the cDNA (for example with a fluorescent label, such as Cy™3 dye). In one non-limiting example, amplified cDNA is prepared from the sample using single-primer isothermal amplification (for example, Ribo-SPIA® amplification, NuGen) prior to labeling. Methods of labeling cDNA are known and include commercially available kits, such as Genomic DNA Enzymatic Labeling Kit (Agilent). In some examples, the methods generate amplified and labeled cDNA from about 250 pg of target viral RNA (such as about 500 pg, about 750 pg, about 1 ng, about 2 ng, or more of target viral RNA).

In other examples, the methods include isolating DNA from the sample and contacting the probe set or microarray with the isolated DNA. Methods of isolating DNA (such as viral DNA, bacterial DNA, or protozoan DNA) from a sample are known and include commercially available kits. In some examples, the methods include isolating viral DNA from a sample using a viral nucleic acid isolation kit. In one non-limiting example, the viral DNA is isolated using Dynabeads™ SILANE viral NA kit (Invitrogen). In other examples, bacterial or protozoan DNA is isolated from a sample using a DNA isolation kit. In one non-limiting example, bacterial or protozoan DNA is isolated using QIAamp® DNA Blood Mini kit (Qiagen). One of ordinary skill in the art can select appropriate methods or kits to isolate pathogen DNA from samples, for example, blood or plasma samples.

The sample (such as nucleic acids isolated and/or amplified from a sample) can be labeled with any suitable label. Generally, the label will be selected based on the intended use of the sample or the desired readout. In some examples, the sample or nucleic acids from the sample is labelled with a fluorescent or chemiluminescent compound. In other examples, the label is an enzyme, a fluorophore, or a radioactive isotope. In one specific non-limiting example, the label is Cy™3 or Cy™ 5.

Fluorophores suitable for use with the methods disclosed herein, include, but are not limited to, 6-carboxyfluorescein (FAM), tetrachlorofluorescein (TET), tetramethylrhodamine (TMR), hexachlorofluorescein (HEX), JOE, ROX, CAL Fluor™ dye, Pulsar™ dye, Quasar™ dye, Texas Red™ dye, Cy™3 dye and Cy™5 dye. Other examples of fluorophores that can be used with the methods provided herein include 4-acetamido-4'-isothiocyanatostilbene-2,2'disulfonic acid; acridine and derivatives such as acridine and acridine isothiocyanate, 5-(2'-aminoethyl)amino-naphthalene-1-sulfonic acid (EDANS), 4-amino-N-[3-vinylsulfonyl)phenyl]-naphthalimide-3,5 disulfonate (Lucifer Yellow VS), N-(4-anilino-1-naphthyl)-maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethyl-amino] naphthalene-1-sulfonyl chloride (DNS, dansyl chloride); 4-(4'-dimethyl-aminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red™ dye); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other fluorophores that can be used include thiol-reactive europium chelates that emit at approximately 617 nm (Heyduk and Heyduk, *Analyt. Biochem.* 248:216-27, 1997; *J. Biol. Chem.* 274:3315-22, 1999). Other fluorophores that can be used include cyanine, merocyanine, styryl, and oxonyl compounds, such as those disclosed in U.S. Pat. Nos. 5,627,027; 5,486,616; 5,569,587; and 5,569,766, and in published PCT application no. US98/00475, each of which is incorporated herein by reference. Specific examples of fluorophores disclosed in one or more of these patent documents include Cy™3 and Cy™5, for instance, and substituted versions of these fluorophores. Additional fluorophores that can be used include GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al., herein incorporated by reference) and derivatives thereof. Other fluorophores are commercially available from known sources.

The methods include contacting the sample (such as labeled nucleic acids from a sample) with a probe set disclosed herein (or subset thereof), or a microarray including the probe set (or subset thereof), under conditions sufficient to allow hybridization of pathogen nucleic acids present in the sample to one or more probes and detecting presence of pathogen nucleic acids hybridized to the probe set or microarray.

Presence of one or more pathogen nucleic acids in the sample can be detected using any suitable means. For example, detection of hybridization can be accomplished by detecting nucleic acid molecules (such as RNA) using nucleic acid amplification methods (such as real-time RT-PCR) or array analysis. In a specific embodiment of the microarray technique, labeled cDNA prepared from a sample is applied to an array including a probe set disclosed herein. Labeled cDNA from the sample can hybridize specifically to one or more probes on the array. After washing to remove non-specifically bound probes, the chip is scanned by confocal laser microscopy or by another detection method, such as a CCD camera. Quantitation of hybridization of sample to each arrayed element allows for assessment of corresponding RNA abundance (e.g., if cDNA is analyzed). Microarray analysis can be performed by commercially available equipment, following manufacturer's protocols, such as are supplied with Affymetrix GeneChip® technology (Affymetrix, Santa Clara, CA), or Agilent's microarray technology (Agilent Technologies, Santa Clara, CA).

In some examples, a sample is determined to contain nucleic acids from a particular pathogen by detecting hybridization between the sample (nucleic acid) and one or more probes of the pathogen-specific probe set. In some examples, a sample is determined to be positive for a pathogen when the log ratio between the signal intensity mean for the pathogen-specific probe set and the mean of a control group probe set is ≥1.5. In other examples, a sample is determined to be negative for a pathogen when the log ratio between the signal intensity mean for the pathogen-specific probe set and the mean of a control group probe set is <1. In further examples, the sample is determined to be borderline for the pathogen when the log ratio between the signal intensity mean for the pathogen-specific probe set and the mean of a control group probe set is ≥1.0 to ≤1.5. In some examples, a sample that is determined to be borderline for one or more pathogens is retested (for example, retested with the assay disclosed herein and/or tested using a virus-specific nucleic acid based test). In other examples, a sample that is determined to be borderline is discarded (e.g., not administered to a subject). In additional examples, a sample is determined to be positive for a particular pathogen when ≥50% of the individual probes for the particular pathogen have a log ratio of >1.5. In some examples, a sample is determined to be positive for a particular pathogen when ≥50% of the individual probes for the particular pathogen have a log ratio of >1.5 and the log ratio between the signal intensity mean for the pathogen-specific probe set and the mean of a control group probe set is ≥1.5.

EXAMPLES

The following examples are provided to illustrate certain particular features and/or embodiments. These examples should not be construed to limit the disclosure to the particular features or embodiments described.

Example 1

Materials and Methods

Microarray-Based Platform Design

Selection of transfusion-transmitted RNA viruses: Sequences of 16 RNA viruses of concern for transmission to blood recipients (released by AABB Transfusion-Transmitted Diseases Committee (Stramer et al., *Transfusion* 49:1S-29S, 2009)) were downloaded from GenBank at NCBI (available on the World Wide Web at ncbi.nlm.nih.gov/genbank).

The complete genome for each RNA virus was uploaded in FASTA format using Agilent eArray software (available on the World Wide Web at earray.chem.agilent.com/earray/, Agilent Technologies Inc., Santa Clara, CA). Design settings were chosen to select 60-mer sense probes with 3' bias from each viral gene, according to the base composition methodology, which considers fusion temperature, GC % and cross-hybridization potential for probes. To get the best quality level probes for viral genome detection the "best probe" (BP) was selected. The probes were checked for vector and low complexity masking. Entire viral genome sequences were covered to the extent possible with all available Agilent-designed probes. The microarray was supplemented with additional predesigned GE (gene expression) array probes for 906 genes from the human genome (replicated 10 times), ERCC probes (replicated 45 times) and probes covering plant virus sequences (negative control). The selected probes and their characteristics are provided in Table 1.

Oligonucleotide probe selection and methodology: Oligonucleotide probes were synthesized in situ from 3'-end base by base with Agilent SurePrint inkjet technology according to the manufacturer's protocol (Wolber et al., *Meth. Enzymol.* 410:28-57, 2006). The microarrays were manufactured with 60-mer oligonucleotides synthesized in 15,000 features on eight replicate arrays per slide.

Sample collection and processing: Specimens positive for CHIKV, DENV1-4, HIV1-2, WNV strain NY99, and ZIKV were prepared, validated, and supplied by the FDA Center for Biologics Evaluation and Research (CBER) (Dong et al., *J. Appl. Microbiol.* 120:1119-1129, 2016).

HCV genotypes 1a, 2a, and 3, and HEV RNA-positive plasma were purchased from Sera Care (Sera Care, Milford, MA). All positive specimens were diluted in negative plasma (Basematrix diluent, Sera Care) to create a range of concentrations. HAV RNA was obtained from Dr. Patrizia Farci, (National Institutes of Health, Bethesda, MD). HTLV types I and II NATtrol (Nucleic Acid Testing Control) were purchased from ZeptoMetrix (ZeptoMetrix, Buffalo, NY) (Table 2).

TABLE 1

Selected viral probes

| Product | Virus | Target ID | BP Start | SEQ ID NO: | Probe Length |
|---------|-------|-----------|----------|------------|--------------|
| 5 UTR | Hepatitis C genotype 1 | gi\|22129792:1-341 | 243 | 1 | 60 |
| 5 UTR | Hepatitis C genotype 1 | gi\|22129792:1-341 | 194 | 2 | 60 |
| 5 UTR | Hepatitis C genotype 1 | gi\|22129792:1-341 | 193 | 3 | 60 |
| 5 UTR | Hepatitis C genotype 1 | gi\|22129792:1-341 | 173 | 4 | 60 |
| 5 UTR | Hepatitis C genotype 1 | gi\|22129792:1-341 | 172 | 5 | 60 |

TABLE 1-continued

| Selected viral probes | | | | | |
|---|---|---|---|---|---|
| 5 UTR | Hepatitis C genotype 1 | gi\|22129792:1-341 | 171 | 6 | 60 |
| 5 UTR | Hepatitis C genotype 1 | gi\|22129792:1-341 | 170 | 7 | 60 |
| 5 UTR | Hepatitis C genotype 1 | gi\|22129792:1-341 | 169 | 8 | 60 |
| 5 UTR | Hepatitis C genotype 1 | gi\|22129792:1-341 | 168 | 9 | 60 |
| 5 UTR | Hepatitis C genotype 1 | gi\|22129792:1-341 | 167 | 10 | 60 |
| core protein | Hepatitis C genotype 1 | gi\|22129792:342-914 | 488 | 11 | 60 |
| core protein | Hepatitis C genotype 1 | gi\|22129792:342-914 | 487 | 12 | 60 |
| core protein | Hepatitis C genotype 1 | gi\|22129792:342-914 | 486 | 13 | 60 |
| core protein | Hepatitis C genotype 1 | gi\|22129792:342-914 | 485 | 14 | 60 |
| core protein | Hepatitis C genotype 1 | gi\|22129792:342-914 | 484 | 15 | 60 |
| core protein | Hepatitis C genotype 1 | gi\|22129792:342-914 | 483 | 16 | 60 |
| core protein | Hepatitis C genotype 1 | gi\|22129792:342-914 | 482 | 17 | 60 |
| core protein | Hepatitis C genotype 1 | gi\|22129792:342-914 | 481 | 18 | 60 |
| core protein | Hepatitis C genotype 1 | gi\|22129792:342-914 | 480 | 19 | 60 |
| core protein | Hepatitis C genotype 1 | gi\|22129792:342-914 | 479 | 20 | 60 |
| E1 protein | Hepatitis C genotype 1 | gi\|22129792:915-1494 | 342 | 21 | 60 |
| E1 protein | Hepatitis C genotype 1 | gi\|22129792:915-1494 | 341 | 22 | 60 |
| E1 protein | Hepatitis C genotype 1 | gi\|22129792:915-1494 | 340 | 23 | 60 |
| E1 protein | Hepatitis C genotype 1 | gi\|22129792:915-1494 | 339 | 24 | 60 |
| E1 protein | Hepatitis C genotype 1 | gi\|22129792:915-1494 | 504 | 25 | 60 |
| E1 protein | Hepatitis C genotype 1 | gi\|22129792:915-1494 | 503 | 26 | 60 |
| E1 protein | Hepatitis C genotype 1 | gi\|22129792:915-1494 | 502 | 27 | 60 |
| E1 protein | Hepatitis C genotype 1 | gi\|22129792:915-1494 | 501 | 28 | 60 |
| E1 protein | Hepatitis C genotype 1 | gi\|22129792:915-1494 | 500 | 29 | 60 |
| E1 protein | Hepatitis C genotype 1 | gi\|22129792:915-1494 | 379 | 30 | 60 |
| E2 protein | Hepatitis C genotype 1 | gi\|22129792:1491-2579 | 703 | 31 | 60 |
| E2 protein | Hepatitis C genotype 1 | gi\|22129792:1491-2579 | 702 | 32 | 60 |
| E2 protein | Hepatitis C genotype 1 | gi\|22129792:1491-2579 | 701 | 33 | 60 |
| E2 protein | Hepatitis C genotype 1 | gi\|22129792:1491-2579 | 700 | 34 | 60 |
| E2 protein | Hepatitis C genotype 1 | gi\|22129792:1491-2579 | 699 | 35 | 60 |
| E2 protein | Hepatitis C genotype 1 | gi\|22129792:1491-2579 | 697 | 36 | 60 |
| E2 protein | Hepatitis C genotype 1 | gi\|22129792:1491-2579 | 696 | 37 | 60 |
| E2 protein | Hepatitis C genotype 1 | gi\|22129792:1491-2579 | 695 | 38 | 60 |
| E2 protein | Hepatitis C genotype 1 | gi\|22129792:1491-2579 | 694 | 39 | 60 |
| E2 protein | Hepatitis C genotype 1 | gi\|22129792:1491-2579 | 693 | 40 | 60 |
| p7 protein | Hepatitis C genotype 1 | gi\|22129792:2580-2768 | 56 | 41 | 60 |
| p7 protein | Hepatitis C genotype 1 | gi\|22129792:2580-2768 | 55 | 42 | 60 |
| p7 protein | Hepatitis C genotype 1 | gi\|22129792:2580-2768 | 54 | 43 | 60 |
| p7 protein | Hepatitis C genotype 1 | gi\|22129792:2580-2768 | 53 | 44 | 60 |

TABLE 1-continued

| Selected viral probes | | | | | |
|---|---|---|---|---|---|
| p7 protein | Hepatitis C genotype 1 | gi\|22129792:2580-2768 | 52 | 45 | 60 |
| p7 protein | Hepatitis C genotype 1 | gi\|22129792:2580-2768 | 51 | 46 | 60 |
| p7 protein | Hepatitis C genotype 1 | gi\|22129792:2580-2768 | 50 | 47 | 60 |
| p7 protein | Hepatitis C genotype 1 | gi\|22129792:2580-2768 | 49 | 48 | 60 |
| p7 protein | Hepatitis C genotype 1 | gi\|22129792:2580-2768 | 48 | 49 | 60 |
| p7 protein | Hepatitis C genotype 1 | gi\|22129792:2769-3419 | 47 | 50 | 60 |
| NS2 protein | Hepatitis C genotype 1 | gi\|22129792:2580-2768 | 366 | 51 | 60 |
| NS2 protein | Hepatitis C genotype 1 | gi\|22129792:2769-3419 | 194 | 52 | 60 |
| NS2 protein | Hepatitis C genotype 1 | gi\|22129792:2769-3419 | 193 | 53 | 60 |
| NS2 protein | Hepatitis C genotype 1 | gi\|22129792:2769-3419 | 192 | 54 | 60 |
| NS2 protein | Hepatitis C genotype 1 | gi\|22129792:2769-3419 | 191 | 55 | 60 |
| NS2 protein | Hepatitis C genotype 1 | gi\|22129792:2769-3419 | 190 | 56 | 60 |
| NS2 protein | Hepatitis C genotype 1 | gi\|22129792:2769-3419 | 189 | 57 | 60 |
| NS2 protein | Hepatitis C genotype 1 | gi\|22129792:2769-3419 | 188 | 58 | 60 |
| NS2 protein | Hepatitis C genotype 1 | gi\|22129792:2769-3419 | 187 | 59 | 60 |
| NS2 protein | Hepatitis C genotype 1 | gi\|22129792:2769-3419 | 186 | 60 | 60 |
| NS3 protease/helicase | Hepatitis C genotype 1 | gi\|22129792:3420-5312 | 1812 | 61 | 60 |
| NS3 protease/helicase | Hepatitis C genotype 1 | gi\|22129792:3420-5312 | 1620 | 62 | 60 |
| NS3 protease/helicase | Hepatitis C genotype 1 | gi\|22129792:3420-5312 | 849 | 63 | 60 |
| NS3 protease/helicase | Hepatitis C genotype 1 | gi\|22129792:3420-5312 | 1744 | 64 | 60 |
| NS3 protease/helicase | Hepatitis C genotype 1 | gi\|22129792:3420-5312 | 1497 | 65 | 60 |
| NS3 protease/helicase | Hepatitis C genotype 1 | gi\|22129792:3420-5312 | 1294 | 66 | 60 |
| NS3 protease/helicase | Hepatitis C genotype 1 | gi\|22129792:3420-5312 | 1234 | 67 | 60 |
| NS3 protease/helicase | Hepatitis C genotype 1 | gi\|22129792:5313-5474 | 1092 | 68 | 60 |
| NS3 protease/helicase | Hepatitis C genotype 1 | gi\|22129792:3420-5312 | 1020 | 69 | 60 |
| NS3 protease/helicase | Hepatitis C genotype 1 | gi\|22129792:3420-5312 | 765 | 70 | 60 |
| NS4A protein | Hepatitis C genotype 1 | gi\|22129792:3420-5312 | 103 | 71 | 60 |
| NS4A protein | Hepatitis C genotype 1 | gi\|22129792:5313-5474 | 102 | 72 | 60 |
| NS4A protein | Hepatitis C genotype 1 | gi\|22129792:5313-5474 | 101 | 73 | 60 |
| NS4A protein | Hepatitis C genotype 1 | gi\|22129792:5313-5474 | 100 | 74 | 60 |
| NS4A protein | Hepatitis C genotype 1 | gi\|22129792:5313-5474 | 99 | 75 | 60 |
| NS4A protein | Hepatitis C genotype 1 | gi\|22129792:5313-5474 | 98 | 76 | 60 |
| NS4A protein | Hepatitis C genotype 1 | gi\|22129792:5313-5474 | 97 | 77 | 60 |
| NS4A protein | Hepatitis C genotype 1 | gi\|22129792:5313-5474 | 96 | 78 | 60 |
| NS4A protein | Hepatitis C genotype 1 | gi\|22129792:5313-5474 | 95 | 79 | 60 |
| NS4A protein | Hepatitis C genotype 1 | gi\|22129792:5313-5474 | 94 | 80 | 60 |
| NS4B protein | Hepatitis C genotype 1 | gi\|22129792:5475-6257 | 133 | 81 | 60 |
| NS4B protein | Hepatitis C genotype 1 | gi\|22129792:5475-6257 | 723 | 82 | 60 |
| NS4B protein | Hepatitis C genotype 1 | gi\|22129792:5475-6257 | 702 | 83 | 60 |

TABLE 1-continued

| Selected viral probes | | | | | |
|---|---|---|---|---|---|
| NS4B protein | Hepatitis C genotype 1 | gi|22129792:5475-6257 | 456 | 84 | 60 |
| NS4B protein | Hepatitis C genotype 1 | gi|22129792:5475-6257 | 416 | 85 | 60 |
| NS4B protein | Hepatitis C genotype 1 | gi|22129792:5475-6257 | 226 | 86 | 60 |
| NS4B protein | Hepatitis C genotype 1 | gi|22129792:5475-6257 | 204 | 87 | 60 |
| NS4B protein | Hepatitis C genotype 1 | gi|22129792:5475-6257 | 182 | 88 | 60 |
| NS4B protein | Hepatitis C genotype 1 | gi|22129792:5475-6257 | 162 | 89 | 60 |
| NS4B protein | Hepatitis C genotype 1 | gi|22129792:5475-6257 | 113 | 90 | 60 |
| NS5A protein | Hepatitis C genotype 1 | gi|22129792:6258-7601 | 402 | 91 | 60 |
| NS5A protein | Hepatitis C genotype 1 | gi|22129792:6258-7601 | 1138 | 92 | 60 |
| NS5A protein | Hepatitis C genotype 1 | gi|22129792:6258-7601 | 1078 | 93 | 60 |
| NS5A protein | Hepatitis C genotype 1 | gi|22129792:6258-7601 | 974 | 94 | 60 |
| NS5A protein | Hepatitis C genotype 1 | gi|22129792:6258-7601 | 826 | 95 | 60 |
| NS5A protein | Hepatitis C genotype 1 | gi|22129792:6258-7601 | 578 | 96 | 60 |
| NS5A protein | Hepatitis C genotype 1 | gi|22129792:6258-7601 | 515 | 97 | 60 |
| NS5A protein | Hepatitis C genotype 1 | gi|22129792:6258-7601 | 342 | 98 | 60 |
| NS5A protein | Hepatitis C genotype 1 | gi|22129792:6258-7601 | 214 | 99 | 60 |
| NS5A protein | Hepatitis C genotype 1 | gi|22129792:6258-7601 | 154 | 100 | 60 |
| NS5B RNA-dependent RNA polymerase | Hepatitis C genotype 1 | gi|22129792:7602-9374 | 1560 | 101 | 60 |
| NS5B RNA-dependent RNA polymerase | Hepatitis C genotype 1 | gi|22129792:7602-9374 | 1559 | 102 | 60 |
| NS5B RNA-dependent RNA polymerase | Hepatitis C genotype 1 | gi|22129792:7602-9374 | 1558 | 103 | 60 |
| NS5B RNA-dependent RNA polymerase | Hepatitis C genotype 1 | gi|22129792:7602-9374 | 1557 | 104 | 60 |
| NS5B RNA-dependent RNA polymerase | Hepatitis C genotype 1 | gi|22129792:7602-9374 | 1556 | 105 | 60 |
| NS5B RNA-dependent RNA polymerase | Hepatitis C genotype 1 | gi|22129792:7602-9374 | 1391 | 106 | 60 |
| NS5B RNA-dependent RNA polymerase | Hepatitis C genotype 1 | gi|22129792:7602-9374 | 1284 | 107 | 60 |
| NS5B RNA-dependent RNA polymerase | Hepatitis C genotype 1 | gi|22129792:7602-9374 | 1283 | 108 | 60 |
| NS5B RNA-dependent RNA polymerase | Hepatitis C genotype 1 | gi|22129792:7602-9374 | 1232 | 109 | 60 |
| NS5B RNA-dependent RNA polymerase | Hepatitis C genotype 1 | gi|22129792:7602-9374 | 1231 | 110 | 60 |
| 5 UTR | Hepatitis C genotype 2 | gi|157781212:1-321 | 242 | 111 | 60 |
| 5 UTR | Hepatitis C genotype 2 | gi|157781212:1-321 | 172 | 112 | 60 |
| 5 UTR | Hepatitis C genotype 2 | gi|157781212:1-321 | 171 | 113 | 60 |
| 5 UTR | Hepatitis C genotype 2 | gi|157781212:1-321 | 170 | 114 | 60 |
| 5 UTR | Hepatitis C genotype 2 | gi|157781212:1-321 | 169 | 115 | 60 |
| 5 UTR | Hepatitis C genotype 2 | gi|157781212:1-321 | 168 | 116 | 60 |
| 5 UTR | Hepatitis C genotype 2 | gi|157781212:1-321 | 167 | 117 | 60 |

TABLE 1-continued

| Selected viral probes | | | | | |
|---|---|---|---|---|---|
| 5 UTR | Hepatitis C genotype 2 | gi\|157781212:1-321 | 166 | 118 | 60 |
| 5 UTR | Hepatitis C genotype 2 | gi\|157781212:1-321 | 163 | 119 | 60 |
| 5 UTR | Hepatitis C genotype 2 | gi\|157781212:1-321 | 162 | 120 | 60 |
| core protein | Hepatitis C genotype 2 | gi\|157781212:322-906 | 36 | 121 | 60 |
| core protein | Hepatitis C genotype 2 | gi\|157781212:322-906 | 35 | 122 | 60 |
| core protein | Hepatitis C genotype 2 | gi\|157781212:322-906 | 34 | 123 | 60 |
| core protein | Hepatitis C genotype 2 | gi\|157781212:322-906 | 33 | 124 | 60 |
| core protein | Hepatitis C genotype 2 | gi\|157781212:322-906 | 32 | 125 | 60 |
| core protein | Hepatitis C genotype 2 | gi\|157781212:322-906 | 31 | 126 | 60 |
| core protein | Hepatitis C genotype 2 | gi\|157781212:322-906 | 30 | 127 | 60 |
| core protein | Hepatitis C genotype 2 | gi\|157781212:322-906 | 29 | 128 | 60 |
| core protein | Hepatitis C genotype 2 | gi\|157781212:322-906 | 28 | 129 | 60 |
| core protein | Hepatitis C genotype 2 | gi\|157781212:322-906 | 13 | 130 | 60 |
| E1 protein | Hepatitis C genotype 2 | gi\|157781212:921-1498 | 495 | 131 | 60 |
| E1 protein | Hepatitis C genotype 2 | gi\|157781212:921-1498 | 459 | 132 | 60 |
| E1 protein | Hepatitis C genotype 2 | gi\|157781212:921-1498 | 439 | 133 | 60 |
| E1 protein | Hepatitis C genotype 2 | gi\|157781212:921-1498 | 419 | 134 | 60 |
| E1 protein | Hepatitis C genotype 2 | gi\|157781212:921-1498 | 362 | 135 | 60 |
| E1 protein | Hepatitis C genotype 2 | gi\|157781212:921-1498 | 342 | 136 | 60 |
| E1 protein | Hepatitis C genotype 2 | gi\|157781212:921-1498 | 322 | 137 | 60 |
| E1 protein | Hepatitis C genotype 2 | gi\|157781212:921-1498 | 296 | 138 | 60 |
| E1 protein | Hepatitis C genotype 2 | gi\|157781212:921-1498 | 276 | 139 | 60 |
| E1 protein | Hepatitis C genotype 2 | gi\|157781212:1492-2540 | 24 | 140 | 60 |
| E2/NS1 protein | Hepatitis C genotype 2 | gi\|157781212:921-1498 | 944 | 141 | 60 |
| E2/NS1 protein | Hepatitis C genotype 2 | gi\|157781212:1492-2540 | 943 | 142 | 60 |
| E2/NS1 protein | Hepatitis C genotype 2 | gi\|157781212:1492-2540 | 941 | 143 | 60 |
| E2/NS1 protein | Hepatitis C genotype 2 | gi\|157781212:1492-2540 | 940 | 144 | 60 |
| E2/NS1 protein | Hepatitis C genotype 2 | gi\|157781212:1492-2540 | 939 | 145 | 60 |
| E2/NS1 protein | Hepatitis C genotype 2 | gi\|157781212:1492-2540 | 726 | 146 | 60 |
| E2/NS1 protein | Hepatitis C genotype 2 | gi\|157781212:1492-2540 | 725 | 147 | 60 |
| E2/NS1 protein | Hepatitis C genotype 2 | gi\|157781212:1492-2540 | 724 | 148 | 60 |
| E2/NS1 protein | Hepatitis C genotype 2 | gi\|157781212:1492-2540 | 723 | 149 | 60 |
| E2/NS1 protein | Hepatitis C genotype 2 | gi\|157781212:1492-2540 | 722 | 150 | 60 |
| NS2 protein | Hepatitis C genotype 2 | gi\|157781212:2777-3368 | 524 | 151 | 60 |
| NS2 protein | Hepatitis C genotype 2 | gi\|157781212:2777-3368 | 484 | 152 | 60 |
| NS2 protein | Hepatitis C genotype 2 | gi\|157781212:2777-3368 | 409 | 153 | 60 |
| NS2 protein | Hepatitis C genotype 2 | gi\|157781212:2777-3368 | 369 | 154 | 60 |
| NS2 protein | Hepatitis C genotype 2 | gi\|157781212:2777-3368 | 281 | 155 | 60 |
| NS2 protein | Hepatitis C genotype 2 | gi\|157781212:2777-3368 | 239 | 156 | 60 |

TABLE 1-continued

| Selected viral probes | | | | | |
|---|---|---|---|---|---|
| NS2 protein | Hepatitis C genotype 2 | gi\|157781212:2777-3368 | 199 | 157 | 60 |
| NS2 protein | Hepatitis C genotype 2 | gi\|157781212:3512-4759 | 101 | 158 | 60 |
| NS2 protein | Hepatitis C genotype 2 | gi\|157781212:2777-3368 | 61 | 159 | 60 |
| NS2 protein | Hepatitis C genotype 2 | gi\|157781212:2777-3368 | 21 | 160 | 60 |
| NS3 protease/ helicase | Hepatitis C genotype 2 | gi\|157781212:2777-3368 | 992 | 161 | 60 |
| NS3 protease/ helicase | Hepatitis C genotype 2 | gi\|157781212:3512-4759 | 991 | 162 | 60 |
| NS3 protease/ helicase | Hepatitis C genotype 2 | gi\|157781212:3512-4759 | 990 | 163 | 60 |
| NS3 protease/ helicase | Hepatitis C genotype 2 | gi\|157781212:3512-4759 | 989 | 164 | 60 |
| NS3 protease/ helicase | Hepatitis C genotype 2 | gi\|157781212:3512-4759 | 988 | 165 | 60 |
| NS3 protease/ helicase | Hepatitis C genotype 2 | gi\|157781212:3512-4759 | 987 | 166 | 60 |
| NS3 protease/ helicase | Hepatitis C genotype 2 | gi\|157781212:3512-4759 | 986 | 167 | 60 |
| NS3 protease/ helicase | Hepatitis C genotype 2 | gi\|157781212:3512-4759 | 985 | 168 | 60 |
| NS3 protease/ helicase | Hepatitis C genotype 2 | gi\|157781212:3512-4759 | 984 | 169 | 60 |
| NS3 protease/ helicase | Hepatitis C genotype 2 | gi\|157781212:3512-4759 | 983 | 170 | 60 |
| NS4A protein | Hepatitis C genotype 2 | gi\|157781212:5324-5501 | 119 | 171 | 60 |
| NS4A protein | Hepatitis C genotype 2 | gi\|157781212:5324-5501 | 118 | 172 | 60 |
| NS4A protein | Hepatitis C genotype 2 | gi\|157781212:5324-5501 | 117 | 173 | 60 |
| NS4A protein | Hepatitis C genotype 2 | gi\|157781212:5324-5501 | 116 | 174 | 60 |
| NS4A protein | Hepatitis C genotype 2 | gi\|157781212:5324-5501 | 115 | 175 | 60 |
| NS4A protein | Hepatitis C genotype 2 | gi\|157781212:5324-5501 | 114 | 176 | 60 |
| NS4A protein | Hepatitis C genotype 2 | gi\|157781212:5324-5501 | 113 | 177 | 60 |
| NS4A protein | Hepatitis C genotype 2 | gi\|157781212:5324-5501 | 112 | 178 | 60 |
| NS4A protein | Hepatitis C genotype 2 | gi\|157781212:5324-5501 | 111 | 179 | 60 |
| NS4A protein | Hepatitis C genotype 2 | gi\|157781212:5324-5501 | 110 | 180 | 60 |
| NS4B protein | Hepatitis C genotype 2 | gi\|157781212:5531-6115 | 88 | 181 | 60 |
| NS4B protein | Hepatitis C genotype 2 | gi\|157781212:5531-6115 | 87 | 182 | 60 |
| NS4B protein | Hepatitis C genotype 2 | gi\|157781212:5531-6115 | 13 | 183 | 60 |
| NS4B protein | Hepatitis C genotype 2 | gi\|157781212:5531-6115 | 12 | 184 | 60 |
| NS4B protein | Hepatitis C genotype 2 | gi\|157781212:5531-6115 | 8 | 185 | 60 |
| NS4B protein | Hepatitis C genotype 2 | gi\|157781212:5531-6115 | 7 | 186 | 60 |
| NS4B protein | Hepatitis C genotype 2 | gi\|157781212:5531-6115 | 6 | 187 | 60 |
| NS4B protein | Hepatitis C genotype 2 | gi\|157781212:5531-6115 | 5 | 188 | 60 |
| NS4B protein | Hepatitis C genotype 2 | gi\|157781212:5531-6115 | 4 | 189 | 60 |
| NS4B protein | Hepatitis C genotype 2 | gi\|157781212:5531-6115 | 3 | 190 | 60 |
| NS5A protein | Hepatitis C genotype 2 | gi\|157781212:6266-7670 | 54 | 191 | 60 |
| NS5A protein | Hepatitis C genotype 2 | gi\|157781212:6266-7670 | 46 | 192 | 60 |
| NS5A protein | Hepatitis C genotype 2 | gi\|157781212:6266-7670 | 45 | 193 | 60 |
| NS5A protein | Hepatitis C genotype 2 | gi\|157781212:6266-7670 | 43 | 194 | 60 |
| NS5A protein | Hepatitis C genotype 2 | gi\|157781212:6266-7670 | 42 | 195 | 60 |

TABLE 1-continued

| Selected viral probes | | | | | |
|---|---|---|---|---|---|
| NS5A protein | Hepatitis C genotype 2 | gi|157781212:6266-7670 | 41 | 196 | 60 |
| NS5A protein | Hepatitis C genotype 2 | gi|157781212:6266-7670 | 40 | 197 | 60 |
| NS5A protein | Hepatitis C genotype 2 | gi|157781212:6266-7670 | 39 | 198 | 60 |
| NS5A protein | Hepatitis C genotype 2 | gi|157781212:6266-7670 | 38 | 199 | 60 |
| NS5A protein | Hepatitis C genotype 2 | gi|157781212:6266-7670 | 37 | 200 | 60 |
| NS5B RNA-dependent RNA polymerase | Hepatitis C genotype 2 | gi|157781212:7664-9212 | 1389 | 201 | 60 |
| NS5B RNA-dependent RNA polymerase | Hepatitis C genotype 2 | gi|157781212:7664-9212 | 1388 | 202 | 60 |
| NS5B RNA-dependent RNA polymerase | Hepatitis C genotype 2 | gi|157781212:7664-9212 | 1387 | 203 | 60 |
| NS5B RNA-dependent RNA polymerase | Hepatitis C genotype 2 | gi|157781212:7664-9212 | 1386 | 204 | 60 |
| NS5B RNA-dependent RNA polymerase | Hepatitis C genotype 2 | gi|157781212:7664-9212 | 1385 | 205 | 60 |
| NS5B RNA-dependent RNA polymerase | Hepatitis C genotype 2 | gi|157781212:7664-9212 | 1384 | 206 | 60 |
| NS5B RNA-dependent RNA polymerase | Hepatitis C genotype 2 | gi|157781212:7664-9212 | 1383 | 207 | 60 |
| NS5B RNA-dependent RNA polymerase | Hepatitis C genotype 2 | gi|157781212:7664-9212 | 1382 | 208 | 60 |
| NS5B RNA-dependent RNA polymerase | Hepatitis C genotype 2 | gi|157781212:7664-9212 | 1381 | 209 | 60 |
| NS5B RNA-dependent RNA polymerase | Hepatitis C genotype 2 | gi|157781212:7664-9212 | 1380 | 210 | 60 |
| 5 UTR | Hepatitis C genotype 3 | gi|157781216:1-339 | 245 | 211 | 60 |
| 5 UTR | Hepatitis C genotype 3 | gi|157781216:1-339 | 244 | 212 | 60 |
| 5 UTR | Hepatitis C genotype 3 | gi|157781216:1-339 | 242 | 213 | 60 |
| 5 UTR | Hepatitis C genotype 3 | gi|157781216:1-339 | 241 | 214 | 60 |
| 5 UTR | Hepatitis C genotype 3 | gi|157781216:1-339 | 192 | 215 | 60 |
| 5 UTR | Hepatitis C genotype 3 | gi|157781216:1-339 | 191 | 216 | 60 |
| 5 UTR | Hepatitis C genotype 3 | gi|157781216:1-339 | 170 | 217 | 60 |
| 5 UTR | Hepatitis C genotype 3 | gi|157781216:1-339 | 169 | 218 | 60 |
| 5 UTR | Hepatitis C genotype 3 | gi|157781216:1-339 | 168 | 219 | 60 |
| 5 UTR | Hepatitis C genotype 3 | gi|157781216:1-339 | 167 | 220 | 60 |
| Core protein | Hepatitis C genotype 3 | gi|157781216:340-912 | 486 | 221 | 60 |
| Core protein | Hepatitis C genotype 3 | gi|157781216:340-912 | 485 | 222 | 60 |
| Core protein | Hepatitis C genotype 3 | gi|157781216:340-912 | 484 | 223 | 60 |
| Core protein | Hepatitis C genotype 3 | gi|157781216:340-912 | 483 | 224 | 60 |
| Core protein | Hepatitis C genotype 3 | gi|157781216:340-912 | 514 | 225 | 60 |
| Core protein | Hepatitis C genotype 3 | gi|157781216:340-912 | 513 | 226 | 60 |
| Core protein | Hepatitis C genotype 3 | gi|157781216:340-912 | 512 | 227 | 60 |
| Core protein | Hepatitis C genotype 3 | gi|157781216:340-912 | 502 | 228 | 60 |
| Core protein | Hepatitis C genotype 3 | gi|157781216:340-912 | 501 | 229 | 60 |

TABLE 1-continued

| Selected viral probes | | | | | |
|---|---|---|---|---|---|
| Core protein | Hepatitis C genotype 3 | gi\|157781216:913-1488 | 499 | 230 | 60 |
| E1 protein | Hepatitis C genotype 3 | gi\|157781216:340-912 | 37 | 231 | 60 |
| E1 protein | Hepatitis C genotype 3 | gi\|157781216:913-1488 | 36 | 232 | 60 |
| E1 protein | Hepatitis C genotype 3 | gi\|157781216:913-1488 | 35 | 233 | 60 |
| E1 protein | Hepatitis C genotype 3 | gi\|157781216:913-1488 | 34 | 234 | 60 |
| E1 protein | Hepatitis C genotype 3 | gi\|157781216:913-1488 | 33 | 235 | 60 |
| E1 protein | Hepatitis C genotype 3 | gi\|157781216:913-1488 | 32 | 236 | 60 |
| E1 protein | Hepatitis C genotype 3 | gi\|157781216:913-1488 | 31 | 237 | 60 |
| E1 protein | Hepatitis C genotype 3 | gi\|157781216:913-1488 | 30 | 238 | 60 |
| E1 protein | Hepatitis C genotype 3 | gi\|157781216:913-1488 | 29 | 239 | 60 |
| E1 protein | Hepatitis C genotype 3 | gi\|157781216:913-1488 | 28 | 240 | 60 |
| E2/NS1 protein | Hepatitis C genotype 3 | gi\|157781216:1489-2544 | 925 | 241 | 60 |
| E2/NS1 protein | Hepatitis C genotype 3 | gi\|157781216:1489-2544 | 737 | 242 | 60 |
| E2/NS1 protein | Hepatitis C genotype 3 | gi\|157781216:1489-2544 | 736 | 243 | 60 |
| E2/NS1 protein | Hepatitis C genotype 3 | gi\|157781216:1489-2544 | 735 | 244 | 60 |
| E2/NS1 protein | Hepatitis C genotype 3 | gi\|157781216:1489-2544 | 734 | 245 | 60 |
| E2/NS1 protein | Hepatitis C genotype 3 | gi\|157781216:1489-2544 | 733 | 246 | 60 |
| E2/NS1 protein | Hepatitis C genotype 3 | gi\|157781216:1489-2544 | 732 | 247 | 60 |
| E2/NS1 protein | Hepatitis C genotype 3 | gi\|157781216:2545-3375 | 731 | 248 | 60 |
| E2/NS1 protein | Hepatitis C genotype 3 | gi\|157781216:1489-2544 | 730 | 249 | 60 |
| E2/NS1 protein | Hepatitis C genotype 3 | gi\|157781216:1489-2544 | 729 | 250 | 60 |
| NS2 | Hepatitis C genotype 3 | gi\|157781216:1489-2544 | 724 | 251 | 60 |
| NS2 | Hepatitis C genotype 3 | gi\|157781216:2545-3375 | 710 | 252 | 60 |
| NS2 | Hepatitis C genotype 3 | gi\|157781216:2545-3375 | 708 | 253 | 60 |
| NS2 | Hepatitis C genotype 3 | gi\|157781216:2545-3375 | 707 | 254 | 60 |
| NS2 | Hepatitis C genotype 3 | gi\|157781216:2545-3375 | 706 | 255 | 60 |
| NS2 | Hepatitis C genotype 3 | gi\|157781216:2545-3375 | 705 | 256 | 60 |
| NS2 | Hepatitis C genotype 3 | gi\|157781216:2545-3375 | 704 | 257 | 60 |
| NS2 | Hepatitis C genotype 3 | gi\|157781216:2545-3375 | 703 | 258 | 60 |
| NS2 | Hepatitis C genotype 3 | gi\|157781216:2545-3375 | 702 | 259 | 60 |
| NS2 | Hepatitis C genotype 3 | gi\|157781216:2545-3375 | 701 | 260 | 60 |
| NS3 protease/ helicase | Hepatitis C genotype 3 | gi\|157781216:3376-5328 | 1684 | 261 | 60 |
| NS3 protease/ helicase | Hepatitis C genotype 3 | gi\|157781216:3376-5328 | 1682 | 262 | 60 |
| NS3 protease/ helicase | Hepatitis C genotype 3 | gi\|157781216:3376-5328 | 1677 | 263 | 60 |
| NS3 protease/ helicase | Hepatitis C genotype 3 | gi\|157781216:3376-5328 | 1676 | 264 | 60 |
| NS3 protease/ helicase | Hepatitis C genotype 3 | gi\|157781216:3376-5328 | 1674 | 265 | 60 |
| NS3 protease/ helicase | Hepatitis C genotype 3 | gi\|157781216:3376-5328 | 1673 | 266 | 60 |
| NS3 protease/ helicase | Hepatitis C genotype 3 | gi\|157781216:3376-5328 | 1671 | 267 | 60 |
| NS3 protease/ helicase | Hepatitis C genotype 3 | gi\|157781216:3376-5328 | 1645 | 268 | 60 |

TABLE 1-continued

| Selected viral probes | | | | | |
|---|---|---|---|---|---|
| NS3 protease/helicase | Hepatitis C genotype 3 | gi\|157781216:3376-5328 | 1644 | 269 | 60 |
| NS3 protease/helicase | Hepatitis C genotype 3 | gi\|157781216:3376-5328 | 1643 | 270 | 60 |
| NS4A protein | Hepatitis C genotype 3 | gi\|157781216:5329-5490 | 103 | 271 | 60 |
| NS4A protein | Hepatitis C genotype 3 | gi\|157781216:5329-5490 | 102 | 272 | 60 |
| NS4A protein | Hepatitis C genotype 3 | gi\|157781216:5329-5490 | 101 | 273 | 60 |
| NS4A protein | Hepatitis C genotype 3 | gi\|157781216:5329-5490 | 100 | 274 | 60 |
| NS4A protein | Hepatitis C genotype 3 | gi\|157781216:5329-5490 | 99 | 275 | 60 |
| NS4A protein | Hepatitis C genotype 3 | gi\|157781216:5329-5490 | 98 | 276 | 60 |
| NS4A protein | Hepatitis C genotype 3 | gi\|157781216:5329-5490 | 97 | 277 | 60 |
| NS4A protein | Hepatitis C genotype 3 | gi\|157781216:5329-5490 | 96 | 278 | 60 |
| NS4A protein | Hepatitis C genotype 3 | gi\|157781216:5329-5490 | 95 | 279 | 60 |
| NS4A protein | Hepatitis C genotype 3 | gi\|157781216:5329-5490 | 94 | 280 | 60 |
| NS4B protein | Hepatitis C genotype 3 | gi\|157781216:5491-6273 | 237 | 281 | 60 |
| NS4B protein | Hepatitis C genotype 3 | gi\|157781216:5491-6273 | 236 | 282 | 60 |
| NS4B protein | Hepatitis C genotype 3 | gi\|157781216:5491-6273 | 133 | 283 | 60 |
| NS4B protein | Hepatitis C genotype 3 | gi\|157781216:5491-6273 | 132 | 284 | 60 |
| NS4B protein | Hepatitis C genotype 3 | gi\|157781216:5491-6273 | 130 | 285 | 60 |
| NS4B protein | Hepatitis C genotype 3 | gi\|157781216:5491-6273 | 129 | 286 | 60 |
| NS4B protein | Hepatitis C genotype 3 | gi\|157781216:5491-6273 | 118 | 287 | 60 |
| NS4B protein | Hepatitis C genotype 3 | gi\|157781216:5491-6273 | 117 | 288 | 60 |
| NS4B protein | Hepatitis C genotype 3 | gi\|157781216:5491-6273 | 116 | 289 | 60 |
| NS4B protein | Hepatitis C genotype 3 | gi\|157781216:5491-6273 | 115 | 290 | 60 |
| NS5A protein | Hepatitis C genotype 3 | gi\|157781216:6274-7629 | 513 | 291 | 60 |
| NS5A protein | Hepatitis C genotype 3 | gi\|157781216:6274-7629 | 512 | 292 | 60 |
| NS5A protein | Hepatitis C genotype 3 | gi\|157781216:6274-7629 | 511 | 293 | 60 |
| NS5A protein | Hepatitis C genotype 3 | gi\|157781216:6274-7629 | 510 | 294 | 60 |
| NS5A protein | Hepatitis C genotype 3 | gi\|157781216:6274-7629 | 509 | 295 | 60 |
| NS5A protein | Hepatitis C genotype 3 | gi\|157781216:6274-7629 | 508 | 296 | 60 |
| NS5A protein | Hepatitis C genotype 3 | gi\|157781216:6274-7629 | 507 | 297 | 60 |
| NS5A protein | Hepatitis C genotype 3 | gi\|157781216:6274-7629 | 506 | 298 | 60 |
| NS5A protein | Hepatitis C genotype 3 | gi\|157781216:6274-7629 | 505 | 299 | 60 |
| NS5A protein | Hepatitis C genotype 3 | gi\|157781216:6274-7629 | 504 | 300 | 60 |
| NS5B RNA-dependent RNA polymerase | Hepatitis C genotype 3 | gi\|157781216:7630-9402 | 1548 | 301 | 60 |
| NS5B RNA-dependent RNA polymerase | Hepatitis C genotype 3 | gi\|157781216:7630-9402 | 1373 | 302 | 60 |
| NS5B RNA-dependent RNA polymerase | Hepatitis C genotype 3 | gi\|157781216:7630-9402 | 1350 | 303 | 60 |
| NS5B RNA-dependent RNA polymerase | Hepatitis C genotype 3 | gi\|157781216:7630-9402 | 1330 | 304 | 60 |

TABLE 1-continued

| Selected viral probes | | | | | |
|---|---|---|---|---|---|
| NS5B RNA-dependent RNA polymerase | Hepatitis C genotype 3 | gi\|157781216:7630-9402 | 1283 | 305 | 60 |
| NS5B RNA-dependent RNA polymerase | Hepatitis C genotype 3 | gi\|157781216:7630-9402 | 1262 | 306 | 60 |
| NS5B RNA-dependent RNA polymerase | Hepatitis C genotype 3 | gi\|157781216:7630-9402 | 672 | 307 | 60 |
| NS5B RNA-dependent RNA polymerase | Hepatitis C genotype 3 | gi\|157781216:7630-9402 | 526 | 308 | 60 |
| NS5B RNA-dependent RNA polymerase | Hepatitis C genotype 3 | gi\|157781216:7630-9402 | 147 | 309 | 60 |
| NS5B RNA-dependent RNA polymerase | Hepatitis C genotype 3 | gi\|157781216:7630-9402 | 99 | 310 | 60 |
| Gag-Pol | HIV 1 | gi\|9629357:336-4642 | 4241 | 311 | 60 |
| Gag-Pol | HIV 1 | gi\|9629357:336-4642 | 4164 | 312 | 60 |
| Gag-Pol | HIV 1 | gi\|9629357:336-4642 | 4104 | 313 | 60 |
| Gag-Pol | HIV 1 | gi\|9629357:336-4642 | 4013 | 314 | 60 |
| Gag-Pol | HIV 1 | gi\|9629357:336-4642 | 3953 | 315 | 60 |
| Gag-Pol | HIV 1 | gi\|9629357:336-4642 | 3858 | 316 | 60 |
| Gag-Pol | HIV 1 | gi\|9629357:336-4642 | 3762 | 317 | 60 |
| Gag-Pol | HIV 1 | gi\|9629357:336-4642 | 3702 | 318 | 60 |
| Gag-Pol | HIV 1 | gi\|9629357:336-4642 | 3642 | 319 | 60 |
| Gag-Pol | HIV 1 | gi\|9629357:336-1838 | 3582 | 320 | 60 |
| gag | HIV 1 | gi\|9629357:336-4642 | 1295 | 321 | 60 |
| gag | HIV 1 | gi\|9629357:336-1838 | 1235 | 322 | 60 |
| gag | HIV 1 | gi\|9629357:336-1838 | 1162 | 323 | 60 |
| gag | HIV 1 | gi\|9629357:336-1838 | 1102 | 324 | 60 |
| gag | HIV 1 | gi\|9629357:336-1838 | 959 | 325 | 60 |
| gag | HIV 1 | gi\|9629357:336-1838 | 899 | 326 | 60 |
| gag | HIV 1 | gi\|9629357:336-1838 | 837 | 327 | 60 |
| gag | HIV 1 | gi\|9629357:336-1838 | 750 | 328 | 60 |
| gag | HIV 1 | gi\|9629357:336-1838 | 690 | 329 | 60 |
| gag | HIV 1 | gi\|9629357:336-1838 | 601 | 330 | 60 |
| Vif | HIV 1 | gi\|9629357:4587-5165 | 466 | 331 | 60 |
| Vif | HIV 1 | gi\|9629357:4587-5165 | 426 | 332 | 60 |
| Vif | HIV 1 | gi\|9629357:4587-5165 | 386 | 333 | 60 |
| Vif | HIV 1 | gi\|9629357:4587-5165 | 346 | 334 | 60 |
| Vif | HIV 1 | gi\|9629357:4587-5165 | 304 | 335 | 60 |
| Vif | HIV 1 | gi\|9629357:4587-5165 | 264 | 336 | 60 |
| Vif | HIV 1 | gi\|9629357:4587-5165 | 224 | 337 | 60 |
| Vif | HIV 1 | gi\|9629357:5105-5396 | 184 | 338 | 60 |
| Vif | HIV 1 | gi\|9629357:4587-5165 | 144 | 339 | 60 |
| Vif | HIV 1 | gi\|9629357:4587-5165 | 104 | 340 | 60 |
| vpr | HIV 1 | gi\|9629357:4587-5165 | 215 | 341 | 60 |
| vpr | HIV 1 | gi\|9629357:5105-5396 | 195 | 342 | 60 |
| vpr | HIV 1 | gi\|9629357:5105-5396 | 175 | 343 | 60 |
| vpr | HIV 1 | gi\|9629357:5105-5396 | 155 | 344 | 60 |
| vpr | HIV 1 | gi\|9629357:5105-5396 | 135 | 345 | 60 |
| vpr | HIV 1 | gi\|9629357:5105-5396 | 109 | 346 | 60 |
| vpr | HIV 1 | gi\|9629357:5105-5396 | 89 | 347 | 60 |
| vpr | HIV 1 | gi\|9629357:5105-5396 | 69 | 348 | 60 |
| vpr | HIV 1 | gi\|9629357:5105-5396 | 49 | 349 | 60 |
| vpr | HIV 1 | gi\|9629357:5105-5396 | 29 | 350 | 60 |
| tat | HIV 1 | gi\|9629357:5377-7970 | 2504 | 351 | 60 |
| tat | HIV 1 | gi\|9629357:5377-7970 | 2377 | 352 | 60 |
| tat | HIV 1 | gi\|9629357:5377-7970 | 2310 | 353 | 60 |
| tat | HIV 1 | gi\|9629357:5377-7970 | 2250 | 354 | 60 |
| tat | HIV 1 | gi\|9629357:5377-7970 | 2190 | 355 | 60 |
| tat | HIV 1 | gi\|9629357:5377-7970 | 2023 | 356 | 60 |
| tat | HIV 1 | gi\|9629357:5377-7970 | 1903 | 357 | 60 |
| tat | HIV 1 | gi\|9629357:5377-7970 | 1771 | 358 | 60 |
| tat | HIV 1 | gi\|9629357:5377-7970 | 1711 | 359 | 60 |
| tat | HIV 1 | gi\|9629357:5377-7970 | 1651 | 360 | 60 |
| rev | HIV 1 | gi\|9629357:5516-8199 | 2625 | 361 | 60 |
| rev | HIV 1 | gi\|9629357:5516-8199 | 2551 | 362 | 60 |
| rev | HIV 1 | gi\|9629357:5516-8199 | 2454 | 363 | 60 |
| rev | HIV 1 | gi\|9629357:5516-8199 | 2365 | 364 | 60 |
| rev | HIV 1 | gi\|9629357:5516-8199 | 2238 | 365 | 60 |
| rev | HIV 1 | gi\|9629357:5516-8199 | 2171 | 366 | 60 |
| rev | HIV 1 | gi\|9629357:5516-8199 | 2111 | 367 | 60 |
| rev | HIV 1 | gi\|9629357:5516-8199 | 2051 | 368 | 60 |
| rev | HIV 1 | gi\|9629357:5516-8199 | 1884 | 369 | 60 |
| rev | HIV 1 | gi\|9629357:5516-8199 | 1764 | 370 | 60 |

TABLE 1-continued

| Selected viral probes | | | | | |
|---|---|---|---|---|---|
| vpu | HIV 1 | gi\|9629357:5608-5856 | 136 | 371 | 60 |
| vpu | HIV 1 | gi\|9629357:5608-5856 | 189 | 372 | 60 |
| vpu | HIV 1 | gi\|9629357:5608-5856 | 188 | 373 | 60 |
| vpu | HIV 1 | gi\|9629357:5608-5856 | 186 | 374 | 60 |
| vpu | HIV 1 | gi\|9629357:5608-5856 | 184 | 375 | 60 |
| vpu | HIV 1 | gi\|9629357:5608-5856 | 183 | 376 | 60 |
| vpu | HIV 1 | gi\|9629357:5608-5856 | 182 | 377 | 60 |
| vpu | HIV 1 | gi\|9629357:5608-5856 | 181 | 378 | 60 |
| vpu | HIV 1 | gi\|9629357:5608-5856 | 180 | 379 | 60 |
| vpu | HIV 1 | gi\|9629357:5608-5856 | 179 | 380 | 60 |
| asp | HIV 1 | gi\|9629357:6919-7488 | 478 | 381 | 60 |
| asp | HIV 1 | gi\|9629357:6919-7488 | 361 | 382 | 60 |
| asp | HIV 1 | gi\|9629357:6919-7488 | 315 | 383 | 60 |
| asp | HIV 1 | gi\|9629357:6919-7488 | 212 | 384 | 60 |
| asp | HIV 1 | gi\|9629357:6919-7488 | 182 | 385 | 60 |
| asp | HIV 1 | gi\|9629357:6919-7488 | 152 | 386 | 60 |
| asp | HIV 1 | gi\|9629357:6919-7488 | 122 | 387 | 60 |
| asp | HIV 1 | gi\|9629357:6919-7488 | 92 | 388 | 60 |
| asp | HIV 1 | gi\|9629357:6919-7488 | 62 | 389 | 60 |
| asp | HIV 1 | gi\|9629357:6919-7488 | 32 | 390 | 60 |
| nef | HIV 1 | gi\|9629357:8343-8963 | 443 | 391 | 60 |
| nef | HIV 1 | gi\|9629357:8343-8963 | 423 | 392 | 60 |
| nef | HIV 1 | gi\|9629357:8343-8963 | 402 | 393 | 60 |
| nef | HIV 1 | gi\|9629357:8343-8963 | 322 | 394 | 60 |
| nef | HIV 1 | gi\|9629357:8343-8963 | 302 | 395 | 60 |
| nef | HIV 1 | gi\|9629357:8343-8963 | 274 | 396 | 60 |
| nef | HIV 1 | gi\|9629357:8343-8963 | 254 | 397 | 60 |
| nef | HIV 1 | gi\|9629357:8343-8963 | 234 | 398 | 60 |
| nef | HIV 1 | gi\|9629357:8343-8963 | 214 | 399 | 60 |
| nef | HIV 1 | gi\|9629357:8343-8963 | 105 | 400 | 60 |
| 5' LTR | HIV 2 | gi\|9628880:1-855 | 701 | 401 | 60 |
| 5' LTR | HIV 2 | gi\|9628880:1-855 | 513 | 402 | 60 |
| 5' LTR | HIV 2 | gi\|9628880:1-855 | 384 | 403 | 60 |
| 5' LTR | HIV 2 | gi\|9628880:1-855 | 354 | 404 | 60 |
| 5' LTR | HIV 2 | gi\|9628880:1-855 | 324 | 405 | 60 |
| 5' LTR | HIV 2 | gi\|9628880:1-855 | 209 | 406 | 60 |
| 5' LTR | HIV 2 | gi\|9628880:1-855 | 141 | 407 | 60 |
| 5' LTR | HIV 2 | gi\|9628880:1-855 | 68 | 408 | 60 |
| 5' LTR | HIV 2 | gi\|9628880:1-855 | 38 | 409 | 60 |
| 5' LTR | HIV 2 | gi\|9628880:1-855 | 8 | 410 | 60 |
| gag polyprotein | HIV 2 | gi\|9628880:1103-2668 | 1137 | 411 | 60 |
| gag polyprotein | HIV 2 | gi\|9628880:1103-2668 | 990 | 412 | 60 |
| gag polyprotein | HIV 2 | gi\|9628880:1103-2668 | 930 | 413 | 60 |
| gag polyprotein | HIV 2 | gi\|9628880:1103-2668 | 870 | 414 | 60 |
| gag polyprotein | HIV 2 | gi\|9628880:1103-2668 | 810 | 415 | 60 |
| gag polyprotein | HIV 2 | gi\|9628880:1103-2668 | 750 | 416 | 60 |
| gag polyprotein | HIV 2 | gi\|9628880:1103-2668 | 606 | 417 | 60 |
| gag polyprotein | HIV 2 | gi\|9628880:1103-2668 | 546 | 418 | 60 |
| gag polyprotein | HIV 2 | gi\|9628880:1103-2668 | 473 | 419 | 60 |
| gag polyprotein | HIV 2 | gi\|9628880:1103-2668 | 348 | 420 | 60 |
| gag-pol | HIV 2 | gi\|9628880:1103-5754 | 4593 | 421 | 60 |
| gag-pol | HIV 2 | gi\|9628880:1103-5754 | 4533 | 422 | 60 |
| gag-pol | HIV 2 | gi\|9628880:1103-5754 | 4473 | 423 | 60 |
| gag-pol | HIV 2 | gi\|9628880:1103-5754 | 4388 | 424 | 60 |
| gag-pol | HIV 2 | gi\|9628880:1103-5754 | 4273 | 425 | 60 |
| gag-pol | HIV 2 | gi\|9628880:1103-5754 | 4173 | 426 | 60 |
| gag-pol | HIV 2 | gi\|9628880:1103-5754 | 4096 | 427 | 60 |
| gag-pol | HIV 2 | gi\|9628880:1103-5754 | 4036 | 428 | 60 |
| gag-pol | HIV 2 | gi\|9628880:1103-5754 | 3950 | 429 | 60 |
| gag-pol | HIV 2 | gi\|9628880:1103-5754 | 3889 | 430 | 60 |
| gp2-vif protein | HIV 2 | gi\|9628880:5423-6070 | 440 | 431 | 60 |
| gp2-vif protein | HIV 2 | gi\|9628880:5423-6070 | 388 | 432 | 60 |
| gp2-vif protein | HIV 2 | gi\|9628880:5423-6070 | 338 | 433 | 60 |
| gp2-vif protein | HIV 2 | gi\|9628880:5423-6070 | 308 | 434 | 60 |

TABLE 1-continued

| Selected viral probes | | | | | |
|---|---|---|---|---|---|
| gp2-vif protein | HIV 2 | gi\|9628880:5423-6070 | 277 | 435 | 60 |
| gp2-vif protein | HIV 2 | gi\|9628880:5423-6070 | 247 | 436 | 60 |
| gp2-vif protein | HIV 2 | gi\|9628880:5423-6070 | 217 | 437 | 60 |
| gp2-vif protein | HIV 2 | gi\|9628880:5423-6070 | 185 | 438 | 60 |
| gp2-vif protein | HIV 2 | gi\|9628880:5423-6070 | 155 | 439 | 60 |
| gp2-vif protein | HIV 2 | gi\|9628880:5423-6070 | 58 | 440 | 60 |
| gp3-vpx Protein | HIV 2 | gi\|9628880:5898-6239 | 223 | 441 | 60 |
| gp3-vpx Protein | HIV 2 | gi\|9628880:5898-6239 | 222 | 442 | 60 |
| gp3-vpx Protein | HIV 2 | gi\|9628880:5898-6239 | 221 | 443 | 60 |
| gp3-vpx Protein | HIV 2 | gi\|9628880:5898-6239 | 220 | 444 | 60 |
| gp3-vpx Protein | HIV 2 | gi\|9628880:5898-6239 | 219 | 445 | 60 |
| gp3-vpx Protein | HIV 2 | gi\|9628880:5898-6239 | 217 | 446 | 60 |
| gp3-vpx Protein | HIV 2 | gi\|9628880:5898-6239 | 216 | 447 | 60 |
| gp3-vpx Protein | HIV 2 | gi\|9628880:5898-6239 | 215 | 448 | 60 |
| gp3-vpx Protein | HIV 2 | gi\|9628880:5898-6239 | 214 | 449 | 60 |
| gp3-vpx Protein | HIV 2 | gi\|9628880:5898-6239 | 213 | 450 | 60 |
| gp4-vpr protein | HIV 2 | gi\|9628880:6239-6502 | 151 | 451 | 60 |
| gp4-vpr protein | HIV 2 | gi\|9628880:6239-6502 | 150 | 452 | 60 |
| gp4-vpr protein | HIV 2 | gi\|9628880:6239-6502 | 149 | 453 | 60 |
| gp4-vpr protein | HIV 2 | gi\|9628880:6239-6502 | 148 | 454 | 60 |
| gp4-vpr protein | HIV 2 | gi\|9628880:6239-6502 | 147 | 455 | 60 |
| gp4-vpr protein | HIV 2 | gi\|9628880:6239-6502 | 146 | 456 | 60 |
| gp4-vpr protein | HIV 2 | gi\|9628880:6239-6502 | 145 | 457 | 60 |
| gp4-vpr protein | HIV 2 | gi\|9628880:6239-6502 | 144 | 458 | 60 |
| gp4-vpr protein | HIV 2 | gi\|9628880:6239-6502 | 143 | 459 | 60 |
| gp4-vpr protein | HIV 2 | gi\|9628880:6239-6502 | 142 | 460 | 60 |
| gp5-tat protein | HIV 2 | gi\|9628880:6402-8957 | 2383 | 461 | 60 |
| gp5-tat protein | HIV 2 | gi\|9628880:6402-8957 | 2314 | 462 | 60 |
| gp5-tat protein | HIV 2 | gi\|9628880:6402-8957 | 2192 | 463 | 60 |
| gp5-tat protein | HIV 2 | gi\|9628880:6402-8957 | 2131 | 464 | 60 |
| gp5-tat protein | HIV 2 | gi\|9628880:6402-8957 | 2047 | 465 | 60 |
| gp5-tat protein | HIV 2 | gi\|9628880:6402-8957 | 1938 | 466 | 60 |
| gp5-tat protein | HIV 2 | gi\|9628880:6402-8957 | 1762 | 467 | 60 |
| gp5-tat protein | HIV 2 | gi\|9628880:6402-8957 | 1702 | 468 | 60 |
| gp5-tat protein | HIV 2 | gi\|9628880:6402-8957 | 1579 | 469 | 60 |
| gp5-tat protein | HIV 2 | gi\|9628880:6402-8957 | 1519 | 470 | 60 |
| gp6-rev protein | HIV 2 | gi\|9628880:6628-9102 | 2355 | 471 | 60 |
| gp6-rev protein | HIV 2 | gi\|9628880:6628-9102 | 2157 | 472 | 60 |
| gp6-rev protein | HIV 2 | gi\|9628880:6628-9102 | 2088 | 473 | 60 |

TABLE 1-continued

Selected viral probes

| | | | | | |
|---|---|---|---|---|---|
| gp6-rev protein | HIV 2 | gi\|9628880:6628-9102 | 1966 | 474 | 60 |
| gp6-rev protein | HIV 2 | gi\|9628880:6628-9102 | 1905 | 475 | 60 |
| gp6-rev protein | HIV 2 | gi\|9628880:6628-9102 | 1821 | 476 | 60 |
| gp6-rev protein | HIV 2 | gi\|9628880:6628-9102 | 1712 | 477 | 60 |
| gp6-rev protein | HIV 2 | gi\|9628880:6628-9102 | 1536 | 478 | 60 |
| gp6-rev protein | HIV 2 | gi\|9628880:6628-9102 | 1476 | 479 | 60 |
| gp6-rev protein | HIV 2 | gi\|9628880:6628-9102 | 1353 | 480 | 60 |
| gp7-env protein | HIV 2 | gi\|9628880:6704-9286 | 2279 | 481 | 60 |
| gp7-env protein | HIV 2 | gi\|9628880:6704-9286 | 2081 | 482 | 60 |
| gp7-env protein | HIV 2 | gi\|9628880:6704-9286 | 2012 | 483 | 60 |
| gp7-env protein | HIV 2 | gi\|9628880:6704-9286 | 1890 | 484 | 60 |
| gp7-env protein | HIV 2 | gi\|9628880:6704-9286 | 1829 | 485 | 60 |
| gp7-env protein | HIV 2 | gi\|9628880:6704-9286 | 1745 | 486 | 60 |
| gp7-env protein | HIV 2 | gi\|9628880:6704-9286 | 1636 | 487 | 60 |
| gp7-env protein | HIV 2 | gi\|9628880:6704-9286 | 1460 | 488 | 60 |
| gp7-env protein | HIV 2 | gi\|9628880:6704-9286 | 1400 | 489 | 60 |
| gp7-env protein | HIV 2 | gi\|9628880:6704-9286 | 1277 | 490 | 60 |
| gp8-nef protein | HIV 2 | gi\|9628880:9120-9893 | 709 | 491 | 60 |
| gp8-nef protein | HIV 2 | gi\|9628880:9120-9893 | 594 | 492 | 60 |
| gp8-nef protein | HIV 2 | gi\|9628880:9120-9893 | 526 | 493 | 60 |
| gp8-nef protein | HIV 2 | gi\|9628880:9120-9893 | 453 | 494 | 60 |
| gp8-nef protein | HIV 2 | gi\|9628880:9120-9893 | 423 | 495 | 60 |
| gp8-nef protein | HIV 2 | gi\|9628880:9120-9893 | 393 | 496 | 60 |
| gp8-nef protein | HIV 2 | gi\|9628880:9120-9893 | 359 | 497 | 60 |
| gp8-nef protein | HIV 2 | gi\|9628880:9120-9893 | 308 | 498 | 60 |
| gp8-nef protein | HIV 2 | gi\|9628880:9120-9893 | 278 | 499 | 60 |
| gp8-nef protein | HIV 2 | gi\|9628880:9120-9893 | 248 | 500 | 60 |
| 3 LTR | HIV 2 | | 701 | 501 | 60 |
| 3 LTR | HIV 2 | | 513 | 502 | 60 |
| 3 LTR | HIV 2 | | 384 | 503 | 60 |
| 3 LTR | HIV 2 | | 354 | 504 | 60 |
| 3 LTR | HIV 2 | | 324 | 505 | 60 |
| 3 LTR | HIV 2 | | 209 | 506 | 60 |
| 3 LTR | HIV 2 | | 141 | 507 | 60 |
| 3 LTR | HIV 2 | | 68 | 508 | 60 |
| 3 LTR | HIV 2 | | 38 | 509 | 60 |
| 3 LTR | HIV 2 | | 8 | 510 | 60 |
| gag | HTLV 1 | gb\|AF033817.1\|:450-1739 | 927 | 511 | 60 |
| gag | HTLV 1 | gb\|AF033817.1\|:450-1739 | 926 | 512 | 60 |
| gag | HTLV 1 | gb\|AF033817.1\|:450-1739 | 925 | 513 | 60 |
| gag | HTLV 1 | gb\|AF033817.1\|:450-1739 | 924 | 514 | 60 |
| gag | HTLV 1 | gb\|AF033817.1\|:450-1739 | 923 | 515 | 60 |
| gag | HTLV 1 | gb\|AF033817.1\|:450-1739 | 922 | 516 | 60 |
| gag | HTLV 1 | gb\|AF033817.1\|:450-1739 | 921 | 517 | 60 |
| gag | HTLV 1 | gb\|AF033817.1\|:450-1739 | 917 | 518 | 60 |
| gag | HTLV 1 | gb\|AF033817.1\|:450-1739 | 916 | 519 | 60 |
| gag | HTLV 1 | gb\|AF033817.1\|:450-1739 | 915 | 520 | 60 |
| pro | HTLV 1 | gb\|AF033817.1\|:1718-2404 | 609 | 521 | 60 |
| pro | HTLV 1 | gb\|AF033817.1\|:1718-2404 | 608 | 522 | 60 |
| pro | HTLV 1 | gb\|AF033817.1\|:1718-2404 | 607 | 523 | 60 |
| pro | HTLV 1 | gb\|AF033817.1\|:1718-2404 | 606 | 524 | 60 |

TABLE 1-continued

| | | Selected viral probes | | | |
|---|---|---|---|---|---|
| pro | HTLV 1 | gb|AF033817.1|:1718-2404 | 605 | 525 | 60 |
| pro | HTLV 1 | gb|AF033817.1|:1718-2404 | 604 | 526 | 60 |
| pro | HTLV 1 | gb|AF033817.1|:1718-2404 | 603 | 527 | 60 |
| pro | HTLV 1 | gb|AF033817.1|:1718-2404 | 602 | 528 | 60 |
| pro | HTLV 1 | gb|AF033817.1|:1718-2404 | 583 | 529 | 60 |
| pro | HTLV 1 | gb|AF033817.1|:1718-2404 | 582 | 530 | 60 |
| Pol | HTLV 1 | gi|9626453:2245-4836 | 2376 | 531 | 60 |
| Pol | HTLV 1 | gi|9626453:2245-4836 | 2262 | 532 | 60 |
| Pol | HTLV 1 | gi|9626453:2245-4836 | 2202 | 533 | 60 |
| Pol | HTLV 1 | gi|9626453:2245-4836 | 2051 | 534 | 60 |
| Pol | HTLV 1 | gi|9626453:2245-4836 | 1984 | 535 | 60 |
| Pol | HTLV 1 | gi|9626453:2245-4836 | 1914 | 536 | 60 |
| Pol | HTLV 1 | gi|9626453:2245-4836 | 1475 | 537 | 60 |
| Pol | HTLV 1 | gi|9626453:2245-4836 | 1333 | 538 | 60 |
| Pol | HTLV 1 | gi|9626453:2245-4836 | 1242 | 539 | 60 |
| Pol | HTLV 1 | gi|9626453:2245-4836 | 1182 | 540 | 60 |
| rex | HTLV 1 | gi|9626453:4773-8008 | 3128 | 541 | 60 |
| rex | HTLV 1 | gi|9626453:4773-8008 | 3068 | 542 | 60 |
| rex | HTLV 1 | gi|9626453:4773-8008 | 2975 | 543 | 60 |
| rex | HTLV 1 | gi|9626453:4773-8008 | 2758 | 544 | 60 |
| rex | HTLV 1 | gi|9626453:4773-8008 | 2160 | 545 | 60 |
| rex | HTLV 1 | gi|9626453:4773-8008 | 1489 | 546 | 60 |
| rex | HTLV 1 | gi|9626453:4773-8008 | 1251 | 547 | 60 |
| rex | HTLV 1 | gi|9626453:4773-8008 | 1146 | 548 | 60 |
| rex | HTLV 1 | gi|9626453:4773-8008 | 1086 | 549 | 60 |
| rex | HTLV 1 | gi|9626453:4773-8008 | 721 | 550 | 60 |
| tax | HTLV 1 | gi|9626453:4829-8008 | 3072 | 551 | 60 |
| tax | HTLV 1 | gi|9626453:4829-8008 | 3012 | 552 | 60 |
| tax | HTLV 1 | gi|9626453:4829-8008 | 2919 | 553 | 60 |
| tax | HTLV 1 | gi|9626453:4829-8008 | 2702 | 554 | 60 |
| tax | HTLV 1 | gi|9626453:4829-8008 | 2104 | 555 | 60 |
| tax | HTLV 1 | gi|9626453:4829-8008 | 1433 | 556 | 60 |
| tax | HTLV 1 | gi|9626453:4829-8008 | 1195 | 557 | 60 |
| tax | HTLV 1 | gi|9626453:4829-8008 | 1090 | 558 | 60 |
| tax | HTLV 1 | gi|9626453:4829-8008 | 1030 | 559 | 60 |
| tax | HTLV 1 | gi|9626453:4829-8008 | 665 | 560 | 60 |
| env | HTLV 1 | gi|9626453:4829-6295 | 1192 | 561 | 60 |
| env | HTLV 1 | gi|9626453:4829-6295 | 1152 | 562 | 60 |
| env | HTLV 1 | gi|9626453:4829-6295 | 1085 | 563 | 60 |
| env | HTLV 1 | gi|9626453:4829-6295 | 1045 | 564 | 60 |
| env | HTLV 1 | gi|9626453:4829-6295 | 662 | 565 | 60 |
| env | HTLV 1 | gi|9626453:4829-6295 | 621 | 566 | 60 |
| env | HTLV 1 | gi|9626453:4829-6295 | 454 | 567 | 60 |
| env | HTLV 1 | gi|9626453:4829-6295 | 388 | 568 | 60 |
| env | HTLV 1 | gi|9626453:4829-6295 | 297 | 569 | 60 |
| env | HTLV 1 | gi|9626453:4829-6295 | 257 | 570 | 60 |
| 5' LTR | HTLV 2 | gi|9626726:1-763 | 262 | 571 | 60 |
| 5' LTR | HTLV 2 | gi|9626726:1-763 | 261 | 572 | 60 |
| 5' LTR | HTLV 2 | gi|9626726:1-763 | 260 | 573 | 60 |
| 5' LTR | HTLV 2 | gi|9626726:1-763 | 258 | 574 | 60 |
| 5' LTR | HTLV 2 | gi|9626726:1-763 | 257 | 575 | 60 |
| 5' LTR | HTLV 2 | gi|9626726:1-763 | 256 | 576 | 60 |
| 5' LTR | HTLV 2 | gi|9626726:1-763 | 255 | 577 | 60 |
| 5' LTR | HTLV 2 | gi|9626726:1-763 | 254 | 578 | 60 |
| 5' LTR | HTLV 2 | gi|9626726:1-763 | 253 | 579 | 60 |
| 5' LTR | HTLV 2 | gi|9626726:1-763 | 251 | 580 | 60 |
| gp1-tax protein | HTLV 2 | gi|9626726:6-119 | 52 | 581 | 60 |
| gp1-tax protein | HTLV 2 | gi|9626726:6-119 | 51 | 582 | 60 |
| gp1-tax protein | HTLV 2 | gi|9626726:6-119 | 50 | 583 | 60 |
| gp1-tax protein | HTLV 2 | gi|9626726:6-119 | 48 | 584 | 60 |
| gp1-tax protein | HTLV 2 | gi|9626726:6-119 | 44 | 585 | 60 |
| gp1-tax protein | HTLV 2 | gi|9626726:6-119 | 43 | 586 | 60 |
| gp1-tax protein | HTLV 2 | gi|9626726:6-119 | 42 | 587 | 60 |
| gp1-tax protein | HTLV 2 | gi|9626726:6-119 | 41 | 588 | 60 |
| gp1-tax protein | HTLV 2 | gi|9626726:6-119 | 40 | 589 | 60 |
| gp1-tax protein | HTLV 2 | gi|9626726:6-119 | 39 | 590 | 60 |
| gs1 | HTLV 2 | gi|9626726:316-8751 | 8136 | 591 | 60 |
| gs1 | HTLV 2 | gi|9626726:316-8751 | 7844 | 592 | 60 |
| gs1 | HTLV 2 | gi|9626726:316-8751 | 7700 | 593 | 60 |
| gs1 | HTLV 2 | gi|9626726:316-8751 | 7607 | 594 | 60 |
| gs1 | HTLV 2 | gi|9626726:316-8751 | 7467 | 595 | 60 |
| gs1 | HTLV 2 | gi|9626726:316-8751 | 6864 | 596 | 60 |
| gs1 | HTLV 2 | gi|9626726:316-8751 | 6510 | 597 | 60 |
| gs1 | HTLV 2 | gi|9626726:316-8751 | 6302 | 598 | 60 |
| gs1 | HTLV 2 | gi|9626726:316-8751 | 6038 | 599 | 60 |
| gs1 | HTLV 2 | gi|9626726:316-8751 | 5942 | 600 | 60 |
| Gag-Pro-Pol | HTLV 2 | gi|9626726:807-5187 | 4170 | 601 | 60 |
| Gag-Pro-Pol | HTLV 2 | gi|9626726:807-5187 | 4051 | 602 | 60 |

TABLE 1-continued

| Selected viral probes | | | | | |
|---|---|---|---|---|---|
| Gag-Pro-Pol | HTLV 2 | gi\|9626726:807-5187 | 3988 | 603 | 60 |
| Gag-Pro-Pol | HTLV 2 | gi\|9626726:807-5187 | 3878 | 604 | 60 |
| Gag-Pro-Pol | HTLV 2 | gi\|9626726:807-5187 | 3759 | 605 | 60 |
| Gag-Pro-Pol | HTLV 2 | gi\|9626726:807-5187 | 3580 | 606 | 60 |
| Gag-Pro-Pol | HTLV 2 | gi\|9626726:807-5187 | 3276 | 607 | 60 |
| Gag-Pro-Pol | HTLV 2 | gi\|9626726:807-5187 | 2797 | 608 | 60 |
| Gag-Pro-Pol | HTLV 2 | gi\|9626726:807-5187 | 2698 | 609 | 60 |
| Gag-Pro-Pol | HTLV 2 | gi\|9626726:807-5187 | 2471 | 610 | 60 |
| gp2-gag polyprotein | HTLV 2 | gi\|9626726:807-2108 | 927 | 611 | 60 |
| gp2-gag polyprotein | HTLV 2 | gi\|9626726:807-2108 | 924 | 612 | 60 |
| gp2-gag polyprotein | HTLV 2 | gi\|9626726:807-2108 | 923 | 613 | 60 |
| gp2-gag polyprotein | HTLV 2 | gi\|9626726:807-2108 | 910 | 614 | 60 |
| gp2-gag polyprotein | HTLV 2 | gi\|9626726:807-2108 | 909 | 615 | 60 |
| gp2-gag polyprotein | HTLV 2 | gi\|9626726:807-2108 | 908 | 616 | 60 |
| gp2-gag polyprotein | HTLV 2 | gi\|9626726:807-2108 | 904 | 617 | 60 |
| gp2-gag polyprotein | HTLV 2 | gi\|9626726:807-2108 | 903 | 618 | 60 |
| gp2-gag polyprotein | HTLV 2 | gi\|9626726:807-2108 | 902 | 619 | 60 |
| gp2-gag polyprotein | HTLV 2 | gi\|9626726:807-2108 | 901 | 620 | 60 |
| gp4-rex 26 kD protein | HTLV 2 | gi\|9626726:5121-7663 | 2053 | 621 | 60 |
| gp4-rex 26 kD protein | HTLV 2 | gi\|9626726:5121-7663 | 2003 | 622 | 60 |
| gp4-rex 26 kD protein | HTLV 2 | gi\|9626726:5121-7663 | 1705 | 623 | 60 |
| gp4-rex 26 kD protein | HTLV 2 | gi\|9626726:5121-7663 | 1488 | 624 | 60 |
| gp4-rex 26 kD protein | HTLV 2 | gi\|9626726:5121-7663 | 1219 | 625 | 60 |
| gp4-rex 26 kD protein | HTLV 2 | gi\|9626726:5121-7663 | 1132 | 626 | 60 |
| gp4-rex 26 kD protein | HTLV 2 | gi\|9626726:5121-7663 | 1092 | 627 | 60 |
| gp4-rex 26 kD protein | HTLV 2 | gi\|9626726:5121-7663 | 680 | 628 | 60 |
| gp4-rex 26 kD protein | HTLV 2 | gi\|9626726:5121-7663 | 455 | 629 | 60 |
| gp4-rex 26 kD protein | HTLV 2 | gi\|9626726:5121-7663 | 293 | 630 | 60 |
| gp5-tax protein | HTLV 2 | gi\|9626726:5180-8205 | 2967 | 631 | 60 |
| gp5-tax protein | HTLV 2 | gi\|9626726:5180-8205 | 2836 | 632 | 60 |
| gp5-tax protein | HTLV 2 | gi\|9626726:5180-8205 | 2743 | 633 | 60 |
| gp5-tax protein | HTLV 2 | gi\|9626726:5180-8205 | 2603 | 634 | 60 |
| gp5-tax protein | HTLV 2 | gi\|9626726:5180-8205 | 2000 | 635 | 60 |
| gp5-tax protein | HTLV 2 | gi\|9626726:5180-8205 | 1646 | 636 | 60 |
| gp5-tax protein | HTLV 2 | gi\|9626726:5180-8205 | 1438 | 637 | 60 |
| gp5-tax protein | HTLV 2 | gi\|9626726:5180-8205 | 1174 | 638 | 60 |
| gp5-tax protein | HTLV 2 | gi\|9626726:5180-8205 | 1078 | 639 | 60 |
| gp5-tax protein | HTLV 2 | gi\|9626726:5180-8205 | 624 | 640 | 60 |
| gp6-env peptide | HTLV 2 | gi\|9626726:5180-6640 | 1402 | 641 | 60 |
| gp6-env peptide | HTLV 2 | gi\|9626726:5180-6640 | 1160 | 642 | 60 |
| gp6-env peptide | HTLV 2 | gi\|9626726:5180-6640 | 1073 | 643 | 60 |
| gp6-env peptide | HTLV 2 | gi\|9626726:5180-6640 | 1033 | 644 | 60 |
| gp6-env peptide | HTLV 2 | gi\|9626726:5180-6640 | 621 | 645 | 60 |
| gp6-env peptide | HTLV 2 | gi\|9626726:5180-6640 | 599 | 646 | 60 |
| gp6-env peptide | HTLV 2 | gi\|9626726:5180-6640 | 396 | 647 | 60 |
| gp6-env peptide | HTLV 2 | gi\|9626726:5180-6640 | 375 | 648 | 60 |
| gp6-env peptide | HTLV 2 | gi\|9626726:5180-6640 | 234 | 649 | 60 |
| gp6-env peptide | HTLV 2 | gi\|9626726:5180-6640 | 6 | 650 | 60 |
| 3 LTR | HTLV 2 | gi\|9626726:8190-8952 | 262 | 651 | 60 |
| 3 LTR | HTLV 2 | gi\|9626726:8190-8952 | 261 | 652 | 60 |
| 3 LTR | HTLV 2 | gi\|9626726:8190-8952 | 260 | 653 | 60 |
| 3 LTR | HTLV 2 | gi\|9626726:8190-8952 | 258 | 654 | 60 |
| 3 LTR | HTLV 2 | gi\|9626726:8190-8952 | 257 | 655 | 60 |
| 3 LTR | HTLV 2 | gi\|9626726:8190-8952 | 256 | 656 | 60 |
| 3 LTR | HTLV 2 | gi\|9626726:8190-8952 | 255 | 657 | 60 |
| 3 LTR | HTLV 2 | gi\|9626726:8190-8952 | 254 | 658 | 60 |
| 3 LTR | HTLV 2 | gi\|9626726:8190-8952 | 253 | 659 | 60 |
| 3 LTR | HTLV 2 | gi\|9626726:8190-8952 | 251 | 660 | 60 |

TABLE 1-continued

| Selected viral probes | | | | | |
|---|---|---|---|---|---|
| anchored capsid protein C | WNV NY99 | gi\|158516887:97-465 | 299 | 661 | 60 |
| anchored capsid protein C | WNV NY99 | gi\|158516887:97-465 | 298 | 662 | 60 |
| anchored capsid protein C | WNV NY99 | gi\|158516887:97-465 | 297 | 663 | 60 |
| anchored capsid protein C | WNV NY99 | gi\|158516887:97-465 | 296 | 664 | 60 |
| anchored capsid protein C | WNV NY99 | gi\|158516887:97-465 | 295 | 665 | 60 |
| anchored capsid protein C | WNV NY99 | gi\|158516887:97-465 | 294 | 666 | 60 |
| anchored capsid protein C | WNV NY99 | gi\|158516887:97-465 | 286 | 667 | 60 |
| anchored capsid protein C | WNV NY99 | gi\|158516887:97-465 | 282 | 668 | 60 |
| anchored capsid protein C | WNV NY99 | gi\|158516887:97-465 | 281 | 669 | 60 |
| anchored capsid protein C | WNV NY99 | gi\|158516887:97-465 | 279 | 670 | 60 |
| membrane glycoprotein precursor prM | WNV NY99 | gi\|158516887:466-966 | 355 | 671 | 60 |
| membrane glycoprotein precursor prM | WNV NY99 | gi\|158516887:466-966 | 354 | 672 | 60 |
| membrane glycoprotein precursor prM | WNV NY99 | gi\|158516887:466-966 | 353 | 673 | 60 |
| membrane glycoprotein precursor prM | WNV NY99 | gi\|158516887:466-966 | 352 | 674 | 60 |
| membrane glycoprotein precursor prM | WNV NY99 | gi\|158516887:466-966 | 351 | 675 | 60 |
| membrane glycoprotein precursor prM | WNV NY99 | gi\|158516887:466-966 | 350 | 676 | 60 |
| membrane glycoprotein precursor prM | WNV NY99 | gi\|158516887:466-966 | 349 | 677 | 60 |
| membrane glycoprotein precursor prM | WNV NY99 | gi\|158516887:466-966 | 348 | 678 | 60 |
| membrane glycoprotein precursor prM | WNV NY99 | gi\|158516887:466-966 | 347 | 679 | 60 |
| membrane glycoprotein precursor prM | WNV NY99 | gi\|158516887:466-966 | 346 | 680 | 60 |
| envelope protein E | WNV NY99 | gi\|158516887:967-2469 | 1168 | 681 | 60 |
| envelope protein E | WNV NY99 | gi\|158516887:967-2469 | 880 | 682 | 60 |
| envelope protein E | WNV NY99 | gi\|158516887:967-2469 | 850 | 683 | 60 |
| envelope protein E | WNV NY99 | gi\|158516887:967-2469 | 820 | 684 | 60 |
| envelope protein E | WNV NY99 | gi\|158516887:967-2469 | 788 | 685 | 60 |
| envelope protein E | WNV NY99 | gi\|158516887:967-2469 | 595 | 686 | 60 |
| envelope protein E | WNV NY99 | gi\|158516887:967-2469 | 393 | 687 | 60 |
| envelope protein E | WNV NY99 | gi\|158516887:967-2469 | 363 | 688 | 60 |
| envelope protein E | WNV NY99 | gi\|158516887:967-2469 | 319 | 689 | 60 |
| envelope protein E | WNV NY99 | gi\|158516887:967-2469 | 90 | 690 | 60 |
| nonstructural protein NS1 | WNV NY99 | gi\|158516887:2470-3525 | 971 | 691 | 60 |
| nonstructural protein NS1 | WNV NY99 | gi\|158516887:2470-3525 | 598 | 692 | 60 |
| nonstructural protein NS1 | WNV NY99 | gi\|158516887:2470-3525 | 566 | 693 | 60 |
| nonstructural protein NS1 | WNV NY99 | gi\|158516887:2470-3525 | 517 | 694 | 60 |

TABLE 1-continued

| Selected viral probes | | | | | |
|---|---|---|---|---|---|
| nonstructural protein NS1 | WNV NY99 | gi\|158516887:2470-3525 | 426 | 695 | 60 |
| nonstructural protein NS1 | WNV NY99 | gi\|158516887:2470-3525 | 357 | 696 | 60 |
| nonstructural protein NS1 | WNV NY99 | gi\|158516887:2470-3525 | 325 | 697 | 60 |
| nonstructural protein NS1 | WNV NY99 | gi\|158516887:2470-3525 | 130 | 698 | 60 |
| nonstructural protein NS1 | WNV NY99 | gi\|158516887:2470-3525 | 97 | 699 | 60 |
| nonstructural protein NS1 | WNV NY99 | gi\|158516887:2470-3525 | 54 | 700 | 60 |
| nonstructural protein NS2A | WNV NY99 | gi\|158516887:3526-4218 | 584 | 701 | 60 |
| nonstructural protein NS2A | WNV NY99 | gi\|158516887:3526-4218 | 501 | 702 | 60 |
| nonstructural protein NS2A | WNV NY99 | gi\|158516887:3526-4218 | 413 | 703 | 60 |
| nonstructural protein NS2A | WNV NY99 | gi\|158516887:3526-4218 | 393 | 704 | 60 |
| nonstructural protein NS2A | WNV NY99 | gi\|158516887:3526-4218 | 313 | 705 | 60 |
| nonstructural protein NS2A | WNV NY99 | gi\|158516887:3526-4218 | 293 | 706 | 60 |
| nonstructural protein NS2A | WNV NY99 | gi\|158516887:3526-4218 | 265 | 707 | 60 |
| nonstructural protein NS2A | WNV NY99 | gi\|158516887:3526-4218 | 243 | 708 | 60 |
| nonstructural protein NS2A | WNV NY99 | gi\|158516887:3526-4218 | 147 | 709 | 60 |
| nonstructural protein NS2A | WNV NY99 | gi\|158516887:3526-4218 | 106 | 710 | 60 |
| nonstructural protein NS2B | WNV NY99 | gi\|158516887:4219-4611 | 334 | 711 | 60 |
| nonstructural protein NS2B | WNV NY99 | gi\|158516887:4219-4611 | 249 | 712 | 60 |
| nonstructural protein NS2B | WNV NY99 | gi\|158516887:4219-4611 | 246 | 713 | 60 |
| nonstructural protein NS2B | WNV NY99 | gi\|158516887:4219-4611 | 245 | 714 | 60 |
| nonstructural protein NS2B | WNV NY99 | gi\|158516887:4219-4611 | 242 | 715 | 60 |
| nonstructural protein NS2B | WNV NY99 | gi\|158516887:4219-4611 | 240 | 716 | 60 |
| nonstructural protein NS2B | WNV NY99 | gi\|158516887:4219-4611 | 239 | 717 | 60 |
| nonstructural protein NS2B | WNV NY99 | gi\|158516887:4219-4611 | 238 | 718 | 60 |
| nonstructural protein NS2B | WNV NY99 | gi\|158516887:4219-4611 | 237 | 719 | 60 |
| nonstructural protein NS2B | WNV NY99 | gi\|158516887:4219-4611 | 236 | 720 | 60 |
| nonstructural protein NS3 | WNV NY99 | gi\|158516887:4612-6468 | 1721 | 721 | 60 |
| nonstructural protein NS3 | WNV NY99 | gi\|158516887:4612-6468 | 1591 | 722 | 60 |
| nonstructural protein NS3 | WNV NY99 | gi\|158516887:4612-6468 | 1512 | 723 | 60 |
| nonstructural protein NS3 | WNV NY99 | gi\|158516887:4612-6468 | 1217 | 724 | 60 |
| nonstructural protein NS3 | WNV NY99 | gi\|158516887:4612-6468 | 1157 | 725 | 60 |
| nonstructural protein NS3 | WNV NY99 | gi\|158516887:4612-6468 | 1097 | 726 | 60 |
| nonstructural protein NS3 | WNV NY99 | gi\|158516887:4612-6468 | 960 | 727 | 60 |
| nonstructural protein NS3 | WNV NY99 | gi\|158516887:4612-6468 | 757 | 728 | 60 |
| nonstructural protein NS3 | WNV NY99 | gi\|158516887:4612-6468 | 600 | 729 | 60 |
| nonstructural protein NS3 | WNV NY99 | gi\|158516887:4612-6468 | 428 | 730 | 60 |
| nonstructural protein NS4A | WNV NY99 | gi\|158516887:6469-6834 | 160 | 731 | 60 |
| nonstructural protein NS4A | WNV NY99 | gi\|158516887:6469-6834 | 159 | 732 | 60 |
| nonstructural protein NS4A | WNV NY99 | gi\|158516887:6469-6834 | 158 | 733 | 60 |

TABLE 1-continued

| Selected viral probes | | | | | |
|---|---|---|---|---|---|
| nonstructural protein NS4A | WNV NY99 | gi|158516887:6469-6834 | 157 | 734 | 60 |
| nonstructural protein NS4A | WNV NY99 | gi|158516887:6469-6834 | 156 | 735 | 60 |
| nonstructural protein NS4A | WNV NY99 | gi|158516887:6469-6834 | 155 | 736 | 60 |
| nonstructural protein NS4A | WNV NY99 | gi|158516887:6469-6834 | 154 | 737 | 60 |
| nonstructural protein NS4A | WNV NY99 | gi|158516887:6469-6834 | 153 | 738 | 60 |
| nonstructural protein NS4A | WNV NY99 | gi|158516887:6469-6834 | 152 | 739 | 60 |
| nonstructural protein NS4A | WNV NY99 | gi|158516887:6469-6834 | 151 | 740 | 60 |
| nonstructural protein NS4B | WNV NY99 | gi|158516887:6916-7680 | 703 | 741 | 60 |
| nonstructural protein NS4B | WNV NY99 | gi|158516887:6916-7680 | 683 | 742 | 60 |
| nonstructural protein NS4B | WNV NY99 | gi|158516887:6916-7680 | 506 | 743 | 60 |
| nonstructural protein NS4B | WNV NY99 | gi|158516887:6916-7680 | 480 | 744 | 60 |
| nonstructural protein NS4B | WNV NY99 | gi|158516887:6916-7680 | 185 | 745 | 60 |
| nonstructural protein NS4B | WNV NY99 | gi|158516887:6916-7680 | 165 | 746 | 60 |
| nonstructural protein NS4B | WNV NY99 | gi|158516887:6916-7680 | 140 | 747 | 60 |
| nonstructural protein NS4B | WNV NY99 | gi|158516887:6916-7680 | 48 | 748 | 60 |
| nonstructural protein NS4B | WNV NY99 | gi|158516887:6916-7680 | 28 | 749 | 60 |
| nonstructural protein NS4B | WNV NY99 | gi|158516887:6916-7680 | 8 | 750 | 60 |
| nonstructural protein NS5 | WNV NY99 | gi|158516887:7681-10395 | 2656 | 751 | 60 |
| nonstructural protein NS6 | WNV NY99 | gi|158516887:7681-10395 | 2596 | 752 | 60 |
| nonstructural protein NS7 | WNV NY99 | gi|158516887:7681-10395 | 2480 | 753 | 60 |
| nonstructural protein NS8 | WNV NY99 | gi|158516887:7681-10395 | 2161 | 754 | 60 |
| nonstructural protein NS9 | WNV NY99 | gi|158516887:7681-10395 | 2101 | 755 | 60 |
| nonstructural protein NS10 | WNV NY99 | gi|158516887:7681-10395 | 1353 | 756 | 60 |
| nonstructural protein NS11 | WNV NY99 | gi|158516887:7681-10395 | 1255 | 757 | 60 |
| nonstructural protein NS12 | WNV NY99 | gi|158516887:7681-10395 | 1195 | 758 | 60 |
| nonstructural protein NS13 | WNV NY99 | gi|158516887:7681-10395 | 720 | 759 | 60 |
| nonstructural protein NS14 | WNV NY99 | gi|158516887:7681-10395 | 365 | 760 | 60 |
| anchored capsid protein C | WNV 956 | gi|11528013:97-465 | 256 | 761 | 60 |
| anchored capsid protein C | WNV 956 | gi|11528013:97-465 | 254 | 762 | 60 |
| anchored capsid protein C | WNV 956 | gi|11528013:97-465 | 253 | 763 | 60 |
| anchored capsid protein C | WNV 956 | gi|11528013:97-465 | 249 | 764 | 60 |
| anchored capsid protein C | WNV 956 | gi|11528013:97-465 | 232 | 765 | 60 |
| anchored capsid protein C | WNV 956 | gi|11528013:97-465 | 231 | 766 | 60 |
| anchored capsid protein C | WNV 956 | gi|11528013:97-465 | 230 | 767 | 60 |
| anchored capsid protein C | WNV 956 | gi|11528013:97-465 | 229 | 768 | 60 |
| anchored capsid protein C | WNV 956 | gi|11528013:97-465 | 228 | 769 | 60 |
| anchored capsid protein C | WNV 956 | gi|11528013:97-465 | 227 | 770 | 60 |
| membrane glycoprotein precursor prM | WNV 956 | gi|11528013:466-966 | 417 | 771 | 60 |

TABLE 1-continued

| Selected viral probes | | | | | |
|---|---|---|---|---|---|
| membrane glycoprotein precursor prM | WNV 956 | gi\|11528013:466-966 | 335 | 772 | 60 |
| membrane glycoprotein precursor prM | WNV 956 | gi\|11528013:466-966 | 334 | 773 | 60 |
| membrane glycoprotein precursor prM | WNV 956 | gi\|11528013:466-966 | 333 | 774 | 60 |
| membrane glycoprotein precursor prM | WNV 956 | gi\|11528013:466-966 | 332 | 775 | 60 |
| membrane glycoprotein precursor prM | WNV 956 | gi\|11528013:466-966 | 331 | 776 | 60 |
| membrane glycoprotein precursor prM | WNV 956 | gi\|11528013:466-966 | 330 | 777 | 60 |
| membrane glycoprotein precursor prM | WNV 956 | gi\|11528013:466-966 | 329 | 778 | 60 |
| membrane glycoprotein precursor prM | WNV 956 | gi\|11528013:466-966 | 327 | 779 | 60 |
| membrane glycoprotein precursor prM | WNV 956 | gi\|11528013:466-966 | 320 | 780 | 60 |
| membrane glycoprotein M | WNV 956 | gi\|11528013:742-966 | 141 | 781 | 60 |
| membrane glycoprotein M | WNV 956 | gi\|11528013:742-966 | 59 | 782 | 60 |
| membrane glycoprotein M | WNV 956 | gi\|11528013:742-966 | 58 | 783 | 60 |
| membrane glycoprotein M | WNV 956 | gi\|11528013:742-966 | 57 | 784 | 60 |
| membrane glycoprotein M | WNV 956 | gi\|11528013:742-966 | 56 | 785 | 60 |
| membrane glycoprotein M | WNV 956 | gi\|11528013:742-966 | 55 | 786 | 60 |
| membrane glycoprotein M | WNV 956 | gi\|11528013:742-966 | 54 | 787 | 60 |
| membrane glycoprotein M | WNV 956 | gi\|11528013:742-966 | 53 | 788 | 60 |
| membrane glycoprotein M | WNV 956 | gi\|11528013:742-966 | 51 | 789 | 60 |
| membrane glycoprotein M | WNV 956 | gi\|11528013:742-966 | 44 | 790 | 60 |
| envelope protein E | WNV 956 | gi\|11528013:967-2457 | 1312 | 791 | 60 |
| envelope protein E | WNV 956 | gi\|11528013:967-2457 | 885 | 792 | 60 |
| envelope protein E | WNV 956 | gi\|11528013:967-2457 | 813 | 793 | 60 |
| envelope protein E | WNV 956 | gi\|11528013:967-2457 | 698 | 794 | 60 |
| envelope protein E | WNV 956 | gi\|11528013:967-2457 | 597 | 795 | 60 |
| envelope protein E | WNV 956 | gi\|11528013:967-2457 | 483 | 796 | 60 |
| envelope protein E | WNV 956 | gi\|11528013:967-2457 | 397 | 797 | 60 |
| envelope protein E | WNV 956 | gi\|11528013:967-2457 | 337 | 798 | 60 |
| envelope protein E | WNV 956 | gi\|11528013:967-2457 | 123 | 799 | 60 |
| envelope protein E | WNV 956 | gi\|11528013:967-2457 | 63 | 800 | 60 |
| nonstructural protein NS1 | WNV 956 | gi\|11528013:2458-3513 | 829 | 801 | 60 |
| nonstructural protein NS1 | WNV 956 | gi\|11528013:2458-3513 | 827 | 802 | 60 |
| nonstructural protein NS1 | WNV 956 | gi\|11528013:2458-3513 | 826 | 803 | 60 |
| nonstructural protein NS1 | WNV 956 | gi\|11528013:2458-3513 | 825 | 804 | 60 |

TABLE 1-continued

Selected viral probes

| | | | | | |
|---|---|---|---|---|---|
| nonstructural protein NS1 | WNV 956 | gi\|11528013:2458-3513 | 824 | 805 | 60 |
| nonstructural protein NS1 | WNV 956 | gi\|11528013:2458-3513 | 823 | 806 | 60 |
| nonstructural protein NS1 | WNV 956 | gi\|11528013:2458-3513 | 822 | 807 | 60 |
| nonstructural protein NS1 | WNV 956 | gi\|11528013:2458-3513 | 821 | 808 | 60 |
| nonstructural protein NS1 | WNV 956 | gi\|11528013:2458-3513 | 820 | 809 | 60 |
| nonstructural protein NS1 | WNV 956 | gi\|11528013:2458-3513 | 819 | 810 | 60 |
| nonstructural protein NS2A | WNV 956 | gi\|11528013:3514-4206 | 556 | 811 | 60 |
| nonstructural protein NS2A | WNV 956 | gi\|11528013:3514-4206 | 536 | 812 | 60 |
| nonstructural protein NS2A | WNV 956 | gi\|11528013:3514-4206 | 516 | 813 | 60 |
| nonstructural protein NS2A | WNV 956 | gi\|11528013:3514-4206 | 496 | 814 | 60 |
| nonstructural protein NS2A | WNV 956 | gi\|11528013:3514-4206 | 476 | 815 | 60 |
| nonstructural protein NS2A | WNV 956 | gi\|11528013:3514-4206 | 401 | 816 | 60 |
| nonstructural protein NS2A | WNV 956 | gi\|11528013:3514-4206 | 345 | 817 | 60 |
| nonstructural protein NS2A | WNV 956 | gi\|11528013:3514-4206 | 325 | 818 | 60 |
| nonstructural protein NS2A | WNV 956 | gi\|11528013:3514-4206 | 305 | 819 | 60 |
| nonstructural protein NS2A | WNV 956 | gi\|11528013:3514-4206 | 279 | 820 | 60 |
| nonstructural protein NS2B | WNV 956 | gi\|11528013:4207-4599 | 249 | 821 | 60 |
| nonstructural protein NS2B | WNV 956 | gi\|11528013:4207-4599 | 248 | 822 | 60 |
| nonstructural protein NS2B | WNV 956 | gi\|11528013:4207-4599 | 247 | 823 | 60 |
| nonstructural protein NS2B | WNV 956 | gi\|11528013:4207-4599 | 246 | 824 | 60 |
| nonstructural protein NS2B | WNV 956 | gi\|11528013:4207-4599 | 245 | 825 | 60 |
| nonstructural protein NS2B | WNV 956 | gi\|11528013:4207-4599 | 244 | 826 | 60 |
| nonstructural protein NS2B | WNV 956 | gi\|11528013:4207-4599 | 243 | 827 | 60 |
| nonstructural protein NS2B | WNV 956 | gi\|11528013:4207-4599 | 242 | 828 | 60 |
| nonstructural protein NS2B | WNV 956 | gi\|11528013:4207-4599 | 241 | 829 | 60 |
| nonstructural protein NS2B | WNV 956 | gi\|11528013:4207-4599 | 240 | 830 | 60 |
| nonstructural protein NS3 | WNV 956 | gi\|11528013:4600-6456 | 1798 | 831 | 60 |
| nonstructural protein NS3 | WNV 956 | gi\|11528013:4600-6456 | 1729 | 832 | 60 |
| nonstructural protein NS3 | WNV 956 | gi\|11528013:4600-6456 | 1668 | 833 | 60 |
| nonstructural protein NS3 | WNV 956 | gi\|11528013:4600-6456 | 1597 | 834 | 60 |
| nonstructural protein NS3 | WNV 956 | gi\|11528013:4600-6456 | 1437 | 835 | 60 |
| nonstructural protein NS3 | WNV 956 | gi\|11528013:4600-6456 | 1212 | 836 | 60 |
| nonstructural protein NS3 | WNV 956 | gi\|11528013:4600-6456 | 1150 | 837 | 60 |
| nonstructural protein NS3 | WNV 956 | gi\|11528013:4600-6456 | 1073 | 838 | 60 |
| nonstructural protein NS3 | WNV 956 | gi\|11528013:4600-6456 | 1013 | 839 | 60 |
| nonstructural protein NS3 | WNV 956 | gi\|11528013:4600-6456 | 809 | 840 | 60 |
| nonstructural protein NS4A | WNV 956 | gi\|11528013:6457-6834 | 206 | 841 | 60 |
| nonstructural protein NS4A | WNV 956 | gi\|11528013:6457-6834 | 205 | 842 | 60 |
| nonstructural protein NS4A | WNV 956 | gi\|11528013:6457-6834 | 204 | 843 | 60 |

TABLE 1-continued

| Selected viral probes | | | | | |
|---|---|---|---|---|---|
| nonstructural protein NS4A | WNV 956 | gi\|11528013:6457-6834 | 203 | 844 | 60 |
| nonstructural protein NS4A | WNV 956 | gi\|11528013:6457-6834 | 202 | 845 | 60 |
| nonstructural protein NS4A | WNV 956 | gi\|11528013:6457-6834 | 201 | 846 | 60 |
| nonstructural protein NS4A | WNV 956 | gi\|11528013:6457-6834 | 200 | 847 | 60 |
| nonstructural protein NS4A | WNV 956 | gi\|11528013:6457-6834 | 199 | 848 | 60 |
| nonstructural protein NS4A | WNV 956 | gi\|11528013:6457-6834 | 198 | 849 | 60 |
| nonstructural protein NS4A | WNV 956 | gi\|11528013:6457-6834 | 197 | 850 | 60 |
| nonstructural protein NS4B | WNV 956 | gi\|11528013:6904-7671 | 517 | 851 | 60 |
| nonstructural protein NS4B | WNV 956 | gi\|11528013:6904-7671 | 513 | 852 | 60 |
| nonstructural protein NS4B | WNV 956 | gi\|11528013:6904-7671 | 512 | 853 | 60 |
| nonstructural protein NS4B | WNV 956 | gi\|11528013:6904-7671 | 511 | 854 | 60 |
| nonstructural protein NS4B | WNV 956 | gi\|11528013:6904-7671 | 510 | 855 | 60 |
| nonstructural protein NS4B | WNV 956 | gi\|11528013:6904-7671 | 509 | 856 | 60 |
| nonstructural protein NS4B | WNV 956 | gi\|11528013:6904-7671 | 508 | 857 | 60 |
| nonstructural protein NS4B | WNV 956 | gi\|11528013:6904-7671 | 507 | 858 | 60 |
| nonstructural protein NS4B | WNV 956 | gi\|11528013:6904-7671 | 506 | 859 | 60 |
| nonstructural protein NS4B | WNV 956 | gi\|11528013:6904-7671 | 505 | 860 | 60 |
| nonstructural protein NS5 | WNV 956 | gi\|11528013:7672-10386 | 2656 | 861 | 60 |
| nonstructural protein NS5 | WNV 956 | gi\|11528013:7672-10386 | 2596 | 862 | 60 |
| nonstructural protein NS5 | WNV 956 | gi\|11528013:7672-10386 | 2495 | 863 | 60 |
| nonstructural protein NS5 | WNV 956 | gi\|11528013:7672-10386 | 2116 | 864 | 60 |
| nonstructural protein NS5 | WNV 956 | gi\|11528013:7672-10386 | 2048 | 865 | 60 |
| nonstructural protein NS5 | WNV 956 | gi\|11528013:7672-10386 | 1908 | 866 | 60 |
| nonstructural protein NS5 | WNV 956 | gi\|11528013:7672-10386 | 1555 | 867 | 60 |
| nonstructural protein NS5 | WNV 956 | gi\|11528013:7672-10386 | 1354 | 868 | 60 |
| nonstructural protein NS5 | WNV 956 | gi\|11528013:7672-10386 | 1241 | 869 | 60 |
| nonstructural protein NS5 | WNV 956 | gi\|11528013:7672-10386 | 1170 | 870 | 60 |
| gp1-nonstructural polyprotein | Chikungunya | gi\|27754751:77-7501 | 7323 | 871 | 60 |
| gp1-nonstructural polyprotein | Chikungunya | gi\|27754751:77-7501 | 7262 | 872 | 60 |
| gp1-nonstructural polyprotein | Chikungunya | gi\|27754751:77-7501 | 7166 | 873 | 60 |
| gp1-nonstructural polyprotein | Chikungunya | gi\|27754751:77-7501 | 7088 | 874 | 60 |
| gp1-nonstructural polyprotein | Chikungunya | gi\|27754751:77-7501 | 7016 | 875 | 60 |
| gp1-nonstructural polyprotein | Chikungunya | gi\|27754751:77-7501 | 6874 | 876 | 60 |
| gp1-nonstructural polyprotein | Chikungunya | gi\|27754751:77-7501 | 6745 | 877 | 60 |
| gp1-nonstructural polyprotein | Chikungunya | gi\|27754751:77-7501 | 6685 | 878 | 60 |

TABLE 1-continued

| Selected viral probes | | | | | |
|---|---|---|---|---|---|
| gp1-nonstructural polyprotein | Chikungunya | gi\|27754751:77-7501 | 6617 | 879 | 60 |
| gp1-nonstructural polyprotein | Chikungunya | gi\|27754751:77-7501 | 6468 | 880 | 60 |
| gp2-structural polyprotein | Chikungunya | gi\|27754751:7567-11313 | 3441 | 881 | 60 |
| gp2-structural polyprotein | Chikungunya | gi\|27754751:7567-11313 | 3376 | 882 | 60 |
| gp2-structural polyprotein | Chikungunya | gi\|27754751:7567-11313 | 3109 | 883 | 60 |
| gp2-structural polyprotein | Chikungunya | gi\|27754751:7567-11313 | 2945 | 884 | 60 |
| gp2-structural polyprotein | Chikungunya | gi\|27754751:7567-11313 | 2815 | 885 | 60 |
| gp2-structural polyprotein | Chikungunya | gi\|27754751:7567-11313 | 2750 | 886 | 60 |
| gp2-structural polyprotein | Chikungunya | gi\|27754751:7567-11313 | 2552 | 887 | 60 |
| gp2-structural polyprotein | Chikungunya | gi\|27754751:7567-11313 | 2359 | 888 | 60 |
| gp2-structural polyprotein | Chikungunya | gi\|27754751:7567-11313 | 2052 | 889 | 60 |
| gp2-structural polyprotein | Chikungunya | gi\|27754751:7567-11313 | 1733 | 890 | 60 |
| gp3-truncated polyprotein | Chikungunya | gi\|27754751:7567-10040 | 2359 | 891 | 60 |
| gp3-truncated polyprotein | Chikungunya | gi\|27754751:7567-10040 | 2052 | 892 | 60 |
| gp3-truncated polyprotein | Chikungunya | gi\|27754751:7567-10040 | 1733 | 893 | 60 |
| gp3-truncated polyprotein | Chikungunya | gi\|27754751:7567-10040 | 1631 | 894 | 60 |
| gp3-truncated polyprotein | Chikungunya | gi\|27754751:7567-10040 | 1568 | 895 | 60 |
| gp3-truncated polyprotein | Chikungunya | gi\|27754751:7567-10040 | 1294 | 896 | 60 |
| gp3-truncated polyprotein | Chikungunya | gi\|27754751:7567-10040 | 1224 | 897 | 60 |
| gp3-truncated polyprotein | Chikungunya | gi\|27754751:7567-10040 | 1134 | 898 | 60 |
| gp3-truncated polyprotein | Chikungunya | gi\|27754751:7567-10040 | 988 | 899 | 60 |
| gp3-truncated polyprotein | Chikungunya | gi\|27754751:7567-10040 | 899 | 900 | 60 |
| anchored capsid protein C | DEN 1 | gi\|9626685:95-436 | 266 | 901 | 60 |
| anchored capsid protein C | DEN 1 | gi\|9626685:95-436 | 236 | 902 | 60 |
| anchored capsid protein C | DEN 1 | gi\|9626685:95-436 | 216 | 903 | 60 |
| anchored capsid protein C | DEN 1 | gi\|9626685:95-436 | 193 | 904 | 60 |
| anchored capsid protein C | DEN 1 | gi\|9626685:95-436 | 165 | 905 | 60 |
| anchored capsid protein C | DEN 1 | gi\|9626685:95-436 | 145 | 906 | 60 |
| anchored capsid protein C | DEN 1 | gi\|9626685:95-436 | 125 | 907 | 60 |
| anchored capsid protein C | DEN 1 | gi\|9626685:95-436 | 105 | 908 | 60 |
| anchored capsid protein C | DEN 1 | gi\|9626685:95-436 | 81 | 909 | 60 |
| anchored capsid protein C | DEN 1 | gi\|9626685:95-436 | 57 | 910 | 60 |
| membrane glycoprotein precursor M | DEN 1 | gi\|9626685:437-934 | 439 | 911 | 60 |
| membrane glycoprotein precursor M | DEN 1 | gi\|9626685:437-934 | 438 | 912 | 60 |
| membrane glycoprotein precursor M | DEN 1 | gi\|9626685:437-934 | 437 | 913 | 60 |
| membrane glycoprotein precursor M | DEN 1 | gi\|9626685:437-934 | 436 | 914 | 60 |

TABLE 1-continued

| Selected viral probes | | | | | |
|---|---|---|---|---|---|
| membrane glycoprotein precursor M | DEN 1 | gi\|9626685:437-934 | 435 | 915 | 60 |
| membrane glycoprotein precursor M | DEN 1 | gi\|9626685:437-934 | 434 | 916 | 60 |
| membrane glycoprotein precursor M | DEN 1 | gi\|9626685:437-934 | 433 | 917 | 60 |
| membrane glycoprotein precursor M | DEN 1 | gi\|9626685:437-934 | 432 | 918 | 60 |
| membrane glycoprotein precursor M | DEN 1 | gi\|9626685:437-934 | 431 | 919 | 60 |
| membrane glycoprotein precursor M | DEN 1 | gi\|9626685:437-934 | 430 | 920 | 60 |
| envelope protein E | DEN 1 | gi\|9626685:935-2419 | 1381 | 921 | 60 |
| envelope protein E | DEN 1 | gi\|9626685:935-2419 | 1319 | 922 | 60 |
| envelope protein E | DEN 1 | gi\|9626685:935-2419 | 1163 | 923 | 60 |
| envelope protein E | DEN 1 | gi\|9626685:935-2419 | 1082 | 924 | 60 |
| envelope protein E | DEN 1 | gi\|9626685:935-2419 | 954 | 925 | 60 |
| envelope protein E | DEN 1 | gi\|9626685:935-2419 | 892 | 926 | 60 |
| envelope protein E | DEN 1 | gi\|9626685:935-2419 | 820 | 927 | 60 |
| envelope protein E | DEN 1 | gi\|9626685:935-2419 | 734 | 928 | 60 |
| envelope protein E | DEN 1 | gi\|9626685:935-2419 | 674 | 929 | 60 |
| envelope protein E | DEN 1 | gi\|9626685:935-2419 | 550 | 930 | 60 |
| nonstructural protein NS1 | DEN 1 | gi\|9626685:2420-3475 | 997 | 931 | 60 |
| nonstructural protein NS1 | DEN 1 | gi\|9626685:2420-3475 | 897 | 932 | 60 |
| nonstructural protein NS1 | DEN 1 | gi\|9626685:2420-3475 | 837 | 933 | 60 |
| nonstructural protein NS1 | DEN 1 | gi\|9626685:2420-3475 | 777 | 934 | 60 |
| nonstructural protein NS1 | DEN 1 | gi\|9626685:2420-3475 | 717 | 935 | 60 |
| nonstructural protein NS1 | DEN 1 | gi\|9626685:2420-3475 | 656 | 936 | 60 |
| nonstructural protein NS1 | DEN 1 | gi\|9626685:2420-3475 | 596 | 937 | 60 |
| nonstructural protein NS1 | DEN 1 | gi\|9626685:2420-3475 | 496 | 938 | 60 |
| nonstructural protein NS1 | DEN 1 | gi\|9626685:2420-3475 | 436 | 939 | 60 |
| nonstructural protein NS1 | DEN 1 | gi\|9626685:2420-3475 | 359 | 940 | 60 |
| nonstructural protein NS2A | DEN 1 | gi\|9626685:3476-4129 | 592 | 941 | 60 |
| nonstructural protein NS2A | DEN 1 | gi\|9626685:3476-4129 | 517 | 942 | 60 |
| nonstructural protein NS2A | DEN 1 | gi\|9626685:3476-4129 | 477 | 943 | 60 |
| nonstructural protein NS2A | DEN 1 | gi\|9626685:3476-4129 | 437 | 944 | 60 |
| nonstructural protein NS2A | DEN 1 | gi\|9626685:3476-4129 | 397 | 945 | 60 |
| nonstructural protein NS2A | DEN 1 | gi\|9626685:3476-4129 | 357 | 946 | 60 |
| nonstructural protein NS2A | DEN 1 | gi\|9626685:3476-4129 | 309 | 947 | 60 |
| nonstructural protein NS2A | DEN 1 | gi\|9626685:3476-4129 | 269 | 948 | 60 |
| nonstructural protein NS2A | DEN 1 | gi\|9626685:3476-4129 | 131 | 949 | 60 |
| nonstructural protein NS2A | DEN 1 | gi\|9626685:3476-4129 | 86 | 950 | 60 |

TABLE 1-continued

| | | Selected viral probes | | | |
|---|---|---|---|---|---|
| nonstructural protein NS2B | DEN 1 | gi\|9626685:4130-4519 | 331 | 951 | 60 |
| nonstructural protein NS2B | DEN 1 | gi\|9626685:4130-4519 | 330 | 952 | 60 |
| nonstructural protein NS2B | DEN 1 | gi\|9626685:4130-4519 | 329 | 953 | 60 |
| nonstructural protein NS2B | DEN 1 | gi\|9626685:4130-4519 | 328 | 954 | 60 |
| nonstructural protein NS2B | DEN 1 | gi\|9626685:4130-4519 | 327 | 955 | 60 |
| nonstructural protein NS2B | DEN 1 | gi\|9626685:4130-4519 | 326 | 956 | 60 |
| nonstructural protein NS2B | DEN 1 | gi\|9626685:4130-4519 | 325 | 957 | 60 |
| nonstructural protein NS2B | DEN 1 | gi\|9626685:4130-4519 | 324 | 958 | 60 |
| nonstructural protein NS2B | DEN 1 | gi\|9626685:4130-4519 | 323 | 959 | 60 |
| nonstructural protein NS2B | DEN 1 | gi\|9626685:4130-4519 | 321 | 960 | 60 |
| nonstructural protein NS3 | DEN 1 | gi\|9626685:4520-6376 | 1475 | 961 | 60 |
| nonstructural protein NS3 | DEN 1 | gi\|9626685:4520-6376 | 1415 | 962 | 60 |
| nonstructural protein NS3 | DEN 1 | gi\|9626685:4520-6376 | 1213 | 963 | 60 |
| nonstructural protein NS3 | DEN 1 | gi\|9626685:4520-6376 | 1153 | 964 | 60 |
| nonstructural protein NS3 | DEN 1 | gi\|9626685:4520-6376 | 1093 | 965 | 60 |
| nonstructural protein NS3 | DEN 1 | gi\|9626685:4520-6376 | 1033 | 966 | 60 |
| nonstructural protein NS3 | DEN 1 | gi\|9626685:4520-6376 | 973 | 967 | 60 |
| nonstructural protein NS3 | DEN 1 | gi\|9626685:4520-6376 | 845 | 968 | 60 |
| nonstructural protein NS3 | DEN 1 | gi\|9626685:4520-6376 | 785 | 969 | 60 |
| nonstructural protein NS3 | DEN 1 | gi\|9626685:4520-6376 | 725 | 970 | 60 |
| nonstructural protein NS4A | DEN 1 | gi\|9626685:6377-6757 | 302 | 971 | 60 |
| nonstructural protein NS4A | DEN 1 | gi\|9626685:6377-6757 | 231 | 972 | 60 |
| nonstructural protein NS4A | DEN 1 | gi\|9626685:6377-6757 | 208 | 973 | 60 |
| nonstructural protein NS4A | DEN 1 | gi\|9626685:6377-6757 | 154 | 974 | 60 |
| nonstructural protein NS4A | DEN 1 | gi\|9626685:6377-6757 | 134 | 975 | 60 |
| nonstructural protein NS4A | DEN 1 | gi\|9626685:6377-6757 | 113 | 976 | 60 |
| nonstructural protein NS4A | DEN 1 | gi\|9626685:6377-6757 | 86 | 977 | 60 |
| nonstructural protein NS4A | DEN 1 | gi\|9626685:6377-6757 | 66 | 978 | 60 |
| nonstructural protein NS4A | DEN 1 | gi\|9626685:6377-6757 | 23 | 979 | 60 |
| nonstructural protein NS4A | DEN 1 | gi\|9626685:6377-6757 | 3 | 980 | 60 |
| nonstructural protein NS4B | DEN 1 | gi\|9626685:6827-7573 | 685 | 981 | 60 |
| nonstructural protein NS4B | DEN 1 | gi\|9626685:6827-7573 | 634 | 982 | 60 |
| nonstructural protein NS4B | DEN 1 | gi\|9626685:6827-7573 | 506 | 983 | 60 |
| nonstructural protein NS4B | DEN 1 | gi\|9626685:6827-7573 | 466 | 984 | 60 |
| nonstructural protein NS4B | DEN 1 | gi\|9626685:6827-7573 | 424 | 985 | 60 |
| nonstructural protein NS4B | DEN 1 | gi\|9626685:6827-7573 | 383 | 986 | 60 |
| nonstructural protein NS4B | DEN 1 | gi\|9626685:6827-7573 | 336 | 987 | 60 |
| nonstructural protein NS4B | DEN 1 | gi\|9626685:6827-7573 | 224 | 988 | 60 |
| nonstructural protein NS4B | DEN 1 | gi\|9626685:6827-7573 | 184 | 989 | 60 |

TABLE 1-continued

| Selected viral probes | | | | | |
|---|---|---|---|---|---|
| nonstructural protein NS4B | DEN 1 | gi\|9626685:6827-7573 | 144 | 990 | 60 |
| nonstructural protein NS5 | DEN 1 | gi\|9626685:7574-10270 | 2637 | 991 | 60 |
| nonstructural protein NS5 | DEN 1 | gi\|9626685:7574-10270 | 2577 | 992 | 60 |
| nonstructural protein NS5 | DEN 1 | gi\|9626685:7574-10270 | 2508 | 993 | 60 |
| nonstructural protein NS5 | DEN 1 | gi\|9626685:7574-10270 | 2425 | 994 | 60 |
| nonstructural protein NS5 | DEN 1 | gi\|9626685:7574-10270 | 2276 | 995 | 60 |
| nonstructural protein NS5 | DEN 1 | gi\|9626685:7574-10270 | 2102 | 996 | 60 |
| nonstructural protein NS5 | DEN 1 | gi\|9626685:7574-10270 | 2042 | 997 | 60 |
| nonstructural protein NS5 | DEN 1 | gi\|9626685:7574-10270 | 1982 | 998 | 60 |
| nonstructural protein NS5 | DEN 1 | gi\|9626685:7574-10270 | 1919 | 999 | 60 |
| nonstructural protein NS5 | DEN 1 | gi\|9626685:7574-10270 | 1857 | 1000 | 60 |
| anchored capsid protein C | DEN 2 | gi\|158976983:97-438 | 281 | 1001 | 60 |
| anchored capsid protein C | DEN 2 | gi\|158976983:97-438 | 280 | 1002 | 60 |
| anchored capsid protein C | DEN 2 | gi\|158976983:97-438 | 279 | 1003 | 60 |
| anchored capsid protein C | DEN 2 | gi\|158976983:97-438 | 278 | 1004 | 60 |
| anchored capsid protein C | DEN 2 | gi\|158976983:97-438 | 277 | 1005 | 60 |
| anchored capsid protein C | DEN 2 | gi\|158976983:97-438 | 276 | 1006 | 60 |
| anchored capsid protein C | DEN 2 | gi\|158976983:97-438 | 275 | 1007 | 60 |
| anchored capsid protein C | DEN 2 | gi\|158976983:97-438 | 274 | 1008 | 60 |
| anchored capsid protein C | DEN 2 | gi\|158976983:97-438 | 273 | 1009 | 60 |
| anchored capsid protein C | DEN 2 | gi\|158976983:97-438 | 272 | 1010 | 60 |
| membrane glycoprotein precursor M | DEN 2 | gi\|158976983:439-936 | 439 | 1011 | 60 |
| membrane glycoprotein precursor M | DEN 2 | gi\|158976983:439-936 | 419 | 1012 | 60 |
| membrane glycoprotein precursor M | DEN 2 | gi\|158976983:439-936 | 366 | 1013 | 60 |
| membrane glycoprotein precursor M | DEN 2 | gi\|158976983:439-936 | 334 | 1014 | 60 |
| membrane glycoprotein precursor M | DEN 2 | gi\|158976983:439-936 | 314 | 1015 | 60 |
| membrane glycoprotein precursor M | DEN 2 | gi\|158976983:439-936 | 254 | 1016 | 60 |
| membrane glycoprotein precursor M | DEN 2 | gi\|158976983:439-936 | 229 | 1017 | 60 |
| membrane glycoprotein precursor M | DEN 2 | gi\|158976983:439-936 | 60 | 1018 | 60 |
| membrane glycoprotein precursor M | DEN 2 | gi\|158976983:439-936 | 40 | 1019 | 60 |
| membrane glycoprotein precursor M | DEN 2 | gi\|158976983:439-936 | 20 | 1020 | 60 |
| envelope protein E | DEN 2 | gi\|158976983:937-2421 | 1422 | 1021 | 60 |
| envelope protein E | DEN 2 | gi\|158976983:937-2421 | 1362 | 1022 | 60 |
| envelope protein E | DEN 2 | gi\|158976983:937-2421 | 1286 | 1023 | 60 |

TABLE 1-continued

Selected viral probes

| | | | | | |
|---|---|---|---|---|---|
| envelope protein E | DEN 2 | gi\|158976983:937-2421 | 1186 | 1024 | 60 |
| envelope protein E | DEN 2 | gi\|158976983:937-2421 | 1126 | 1025 | 60 |
| envelope protein E | DEN 2 | gi\|158976983:937-2421 | 1066 | 1026 | 60 |
| envelope protein E | DEN 2 | gi\|158976983:937-2421 | 1006 | 1027 | 60 |
| envelope protein E | DEN 2 | gi\|158976983:937-2421 | 946 | 1028 | 60 |
| envelope protein E | DEN 2 | gi\|158976983:937-2421 | 886 | 1029 | 60 |
| envelope protein E | DEN 2 | gi\|158976983:937-2421 | 826 | 1030 | 60 |
| nonstructural protein NS1 | DEN 2 | gi\|158976983:2422-3477 | 997 | 1031 | 60 |
| nonstructural protein NS1 | DEN 2 | gi\|158976983:2422-3477 | 916 | 1032 | 60 |
| nonstructural protein NS1 | DEN 2 | gi\|158976983:2422-3477 | 827 | 1033 | 60 |
| nonstructural protein NS1 | DEN 2 | gi\|158976983:2422-3477 | 767 | 1034 | 60 |
| nonstructural protein NS1 | DEN 2 | gi\|158976983:2422-3477 | 707 | 1035 | 60 |
| nonstructural protein NS1 | DEN 2 | gi\|158976983:2422-3477 | 647 | 1036 | 60 |
| nonstructural protein NS1 | DEN 2 | gi\|158976983:2422-3477 | 587 | 1037 | 60 |
| nonstructural protein NS1 | DEN 2 | gi\|158976983:2422-3477 | 520 | 1038 | 60 |
| nonstructural protein NS1 | DEN 2 | gi\|158976983:2422-3477 | 460 | 1039 | 60 |
| nonstructural protein NS1 | DEN 2 | gi\|158976983:2422-3477 | 362 | 1040 | 60 |
| nonstructural protein NS2A | DEN 2 | gi\|158976983:3478-4131 | 550 | 1041 | 60 |
| nonstructural protein NS2A | DEN 2 | gi\|158976983:3478-4131 | 508 | 1042 | 60 |
| nonstructural protein NS2A | DEN 2 | gi\|158976983:3478-4131 | 468 | 1043 | 60 |
| nonstructural protein NS2A | DEN 2 | gi\|158976983:3478-4131 | 428 | 1044 | 60 |
| nonstructural protein NS2A | DEN 2 | gi\|158976983:3478-4131 | 388 | 1045 | 60 |
| nonstructural protein NS2A | DEN 2 | gi\|158976983:3478-4131 | 346 | 1046 | 60 |
| nonstructural protein NS2A | DEN 2 | gi\|158976983:3478-4131 | 306 | 1047 | 60 |
| nonstructural protein NS2A | DEN 2 | gi\|158976983:3478-4131 | 266 | 1048 | 60 |
| nonstructural protein NS2A | DEN 2 | gi\|158976983:3478-4131 | 219 | 1049 | 60 |
| nonstructural protein NS2A | DEN 2 | gi\|158976983:3478-4131 | 119 | 1050 | 60 |
| nonstructural protein NS2B | DEN 2 | gi\|158976983:4132-4521 | 328 | 1051 | 60 |
| nonstructural protein NS2B | DEN 2 | gi\|158976983:4132-4521 | 327 | 1052 | 60 |
| nonstructural protein NS2B | DEN 2 | gi\|158976983:4132-4521 | 326 | 1053 | 60 |
| nonstructural protein NS2B | DEN 2 | gi\|158976983:4132-4521 | 325 | 1054 | 60 |
| nonstructural protein NS2B | DEN 2 | gi\|158976983:4132-4521 | 324 | 1055 | 60 |
| nonstructural protein NS2B | DEN 2 | gi\|158976983:4132-4521 | 306 | 1056 | 60 |
| nonstructural protein NS2B | DEN 2 | gi\|158976983:4132-4521 | 298 | 1057 | 60 |
| nonstructural protein NS2B | DEN 2 | gi\|158976983:4132-4521 | 297 | 1058 | 60 |
| nonstructural protein NS2B | DEN 2 | gi\|158976983:4132-4521 | 296 | 1059 | 60 |
| nonstructural protein NS2B | DEN 2 | gi\|158976983:4132-4521 | 295 | 1060 | 60 |
| nonstructural protein NS3 | DEN 2 | gi\|158976983:4522-6375 | 1795 | 1061 | 60 |
| nonstructural protein NS3 | DEN 2 | gi\|158976983:4522-6375 | 1735 | 1062 | 60 |

TABLE 1-continued

Selected viral probes

| | | | | | |
|---|---|---|---|---|---|
| nonstructural protein NS3 | DEN 2 | gi\|158976983:4522-6375 | 1675 | 1063 | 60 |
| nonstructural protein NS3 | DEN 2 | gi\|158976983:4522-6375 | 1590 | 1064 | 60 |
| nonstructural protein NS3 | DEN 2 | gi\|158976983:4522-6375 | 1509 | 1065 | 60 |
| nonstructural protein NS3 | DEN 2 | gi\|158976983:4522-6375 | 1449 | 1066 | 60 |
| nonstructural protein NS3 | DEN 2 | gi\|158976983:4522-6375 | 1389 | 1067 | 60 |
| nonstructural protein NS3 | DEN 2 | gi\|158976983:4522-6375 | 1246 | 1068 | 60 |
| nonstructural protein NS3 | DEN 2 | gi\|158976983:4522-6375 | 1186 | 1069 | 60 |
| nonstructural protein NS3 | DEN 2 | gi\|158976983:4522-6375 | 1126 | 1070 | 60 |
| nonstructural protein NS4A | DEN 2 | gi\|158976983:6376-6756 | 312 | 1071 | 60 |
| nonstructural protein NS4A | DEN 2 | gi\|158976983:6376-6756 | 311 | 1072 | 60 |
| nonstructural protein NS4A | DEN 2 | gi\|158976983:6376-6756 | 310 | 1073 | 60 |
| nonstructural protein NS4A | DEN 2 | gi\|158976983:6376-6756 | 309 | 1074 | 60 |
| nonstructural protein NS4A | DEN 2 | gi\|158976983:6376-6756 | 308 | 1075 | 60 |
| nonstructural protein NS4A | DEN 2 | gi\|158976983:6376-6756 | 307 | 1076 | 60 |
| nonstructural protein NS4A | DEN 2 | gi\|158976983:6376-6756 | 306 | 1077 | 60 |
| nonstructural protein NS4A | DEN 2 | gi\|158976983:6376-6756 | 305 | 1078 | 60 |
| nonstructural protein NS4A | DEN 2 | gi\|158976983:6376-6756 | 304 | 1079 | 60 |
| nonstructural protein NS4A | DEN 2 | gi\|158976983:6376-6756 | 303 | 1080 | 60 |
| nonstructural protein NS4B | DEN 2 | gi\|158976983:6826-7569 | 682 | 1081 | 60 |
| nonstructural protein NS4B | DEN 2 | gi\|158976983:6826-7569 | 632 | 1082 | 60 |
| nonstructural protein NS4B | DEN 2 | gi\|158976983:6826-7569 | 532 | 1083 | 60 |
| nonstructural protein NS4B | DEN 2 | gi\|158976983:6826-7569 | 491 | 1084 | 60 |
| nonstructural protein NS4B | DEN 2 | gi\|158976983:6826-7569 | 451 | 1085 | 60 |
| nonstructural protein NS4B | DEN 2 | gi\|158976983:6826-7569 | 332 | 1086 | 60 |
| nonstructural protein NS4B | DEN 2 | gi\|158976983:6826-7569 | 287 | 1087 | 60 |
| nonstructural protein NS4B | DEN 2 | gi\|158976983:6826-7569 | 168 | 1088 | 60 |
| nonstructural protein NS4B | DEN 2 | gi\|158976983:6826-7569 | 128 | 1089 | 60 |
| nonstructural protein NS4B | DEN 2 | gi\|158976983:6826-7569 | 6 | 1090 | 60 |
| RNA-dependent RNA pol. NS5 | DEN 2 | gi\|158976983:7570-10269 | 2641 | 1091 | 60 |
| RNA-dependent RNA pol. NS5 | DEN 2 | gi\|158976983:7570-10269 | 2581 | 1092 | 60 |
| RNA-dependent RNA pol. NS5 | DEN 2 | gi\|158976983:7570-10269 | 2505 | 1093 | 60 |
| RNA-dependent RNA pol. NS5 | DEN 2 | gi\|158976983:7570-10269 | 2440 | 1094 | 60 |
| RNA-dependent RNA pol. NS5 | DEN 2 | gi\|158976983:7570-10269 | 2379 | 1095 | 60 |
| RNA-dependent RNA pol. NS5 | DEN 2 | gi\|158976983:7570-10269 | 2152 | 1096 | 60 |
| RNA-dependent RNA pol. NS5 | DEN 2 | gi\|158976983:7570-10269 | 2092 | 1097 | 60 |

TABLE 1-continued

| Selected viral probes | | | | | |
|---|---|---|---|---|---|
| RNA-dependent RNA pol. NS5 | DEN 2 | gi\|158976983:7570-10269 | 2032 | 1098 | 60 |
| RNA-dependent RNA pol. NS5 | DEN 2 | gi\|158976983:7570-10269 | 1969 | 1099 | 60 |
| RNA-dependent RNA pol. NS5 | DEN 2 | gi\|158976983:7570-10269 | 1894 | 1100 | 60 |
| anchored capsid protein C | DEN 3 | gi\|163644368:95-436 | 283 | 1101 | 60 |
| anchored capsid protein C | DEN 3 | gi\|163644368:95-436 | 282 | 1102 | 60 |
| anchored capsid protein C | DEN 3 | gi\|163644368:95-436 | 281 | 1103 | 60 |
| anchored capsid protein C | DEN 3 | gi\|163644368:95-436 | 280 | 1104 | 60 |
| anchored capsid protein C | DEN 3 | gi\|163644368:95-436 | 279 | 1105 | 60 |
| anchored capsid protein C | DEN 3 | gi\|163644368:95-436 | 278 | 1106 | 60 |
| anchored capsid protein C | DEN 3 | gi\|163644368:95-436 | 277 | 1107 | 60 |
| anchored capsid protein C | DEN 3 | gi\|163644368:95-436 | 276 | 1108 | 60 |
| anchored capsid protein C | DEN 3 | gi\|163644368:95-436 | 275 | 1109 | 60 |
| anchored capsid protein C | DEN 3 | gi\|163644368:95-436 | 274 | 1110 | 60 |
| membrane glycoprotein precursor M | DEN 3 | gi\|163644368:437-934 | 439 | 1111 | 60 |
| membrane glycoprotein precursor M | DEN 3 | gi\|163644368:437-934 | 438 | 1112 | 60 |
| membrane glycoprotein precursor M | DEN 3 | gi\|163644368:437-934 | 437 | 1113 | 60 |
| membrane glycoprotein precursor M | DEN 3 | gi\|163644368:437-934 | 436 | 1114 | 60 |
| membrane glycoprotein precursor M | DEN 3 | gi\|163644368:437-934 | 435 | 1115 | 60 |
| membrane glycoprotein precursor M | DEN 3 | gi\|163644368:437-934 | 434 | 1116 | 60 |
| membrane glycoprotein precursor M | DEN 3 | gi\|163644368:437-934 | 432 | 1117 | 60 |
| membrane glycoprotein precursor M | DEN 3 | gi\|163644368:437-934 | 431 | 1118 | 60 |
| membrane glycoprotein precursor M | DEN 3 | gi\|163644368:437-934 | 430 | 1119 | 60 |
| membrane glycoprotein precursor M | DEN 3 | gi\|163644368:437-934 | 429 | 1120 | 60 |
| envelope protein E | DEN 3 | gi\|163644368:935-2413 | 1420 | 1121 | 60 |
| envelope protein E | DEN 3 | gi\|163644368:935-2413 | 1359 | 1122 | 60 |
| envelope protein E | DEN 3 | gi\|163644368:935-2413 | 1296 | 1123 | 60 |
| envelope protein E | DEN 3 | gi\|163644368:935-2413 | 1137 | 1124 | 60 |
| envelope protein E | DEN 3 | gi\|163644368:935-2413 | 1077 | 1125 | 60 |
| envelope protein E | DEN 3 | gi\|163644368:935-2413 | 994 | 1126 | 60 |
| envelope protein E | DEN 3 | gi\|163644368:935-2413 | 926 | 1127 | 60 |
| envelope protein E | DEN 3 | gi\|163644368:935-2413 | 866 | 1128 | 60 |

TABLE 1-continued

| Selected viral probes | | | | | |
|---|---|---|---|---|---|
| envelope protein E | DEN 3 | gi\|163644368:935-2413 | 805 | 1129 | 60 |
| envelope protein E | DEN 3 | gi\|163644368:935-2413 | 719 | 1130 | 60 |
| nonstructural protein NS1 | DEN 3 | gi\|163644368:2414-3469 | 997 | 1131 | 60 |
| nonstructural protein NS1 | DEN 3 | gi\|163644368:2414-3469 | 879 | 1132 | 60 |
| nonstructural protein NS1 | DEN 3 | gi\|163644368:2414-3469 | 816 | 1133 | 60 |
| nonstructural protein NS1 | DEN 3 | gi\|163644368:2414-3469 | 711 | 1134 | 60 |
| nonstructural protein NS1 | DEN 3 | gi\|163644368:2414-3469 | 651 | 1135 | 60 |
| nonstructural protein NS1 | DEN 3 | gi\|163644368:2414-3469 | 591 | 1136 | 60 |
| nonstructural protein NS1 | DEN 3 | gi\|163644368:2414-3469 | 492 | 1137 | 60 |
| nonstructural protein NS1 | DEN 3 | gi\|163644368:2414-3469 | 380 | 1138 | 60 |
| nonstructural protein NS1 | DEN 3 | gi\|163644368:2414-3469 | 320 | 1139 | 60 |
| nonstructural protein NS1 | DEN 3 | gi\|163644368:2414-3469 | 256 | 1140 | 60 |
| nonstructural protein NS2A | DEN 3 | gi\|163644368:3470-4123 | 592 | 1141 | 60 |
| nonstructural protein NS2A | DEN 3 | gi\|163644368:3470-4123 | 511 | 1142 | 60 |
| nonstructural protein NS2A | DEN 3 | gi\|163644368:3470-4123 | 463 | 1143 | 60 |
| nonstructural protein NS2A | DEN 3 | gi\|163644368:3470-4123 | 423 | 1144 | 60 |
| nonstructural protein NS2A | DEN 3 | gi\|163644368:3470-4123 | 383 | 1145 | 60 |
| nonstructural protein NS2A | DEN 3 | gi\|163644368:3470-4123 | 301 | 1146 | 60 |
| nonstructural protein NS2A | DEN 3 | gi\|163644368:3470-4123 | 260 | 1147 | 60 |
| nonstructural protein NS2A | DEN 3 | gi\|163644368:3470-4123 | 220 | 1148 | 60 |
| nonstructural protein NS2A | DEN 3 | gi\|163644368:3470-4123 | 117 | 1149 | 60 |
| nonstructural protein NS2A | DEN 3 | gi\|163644368:3470-4123 | 76 | 1150 | 60 |
| nonstructural protein NS2B | DEN 3 | gi\|163644368:4124-4513 | 325 | 1151 | 60 |
| nonstructural protein NS2B | DEN 3 | gi\|163644368:4124-4513 | 324 | 1152 | 60 |
| nonstructural protein NS2B | DEN 3 | gi\|163644368:4124-4513 | 323 | 1153 | 60 |
| nonstructural protein NS2B | DEN 3 | gi\|163644368:4124-4513 | 322 | 1154 | 60 |
| nonstructural protein NS2B | DEN 3 | gi\|163644368:4124-4513 | 321 | 1155 | 60 |
| nonstructural protein NS2B | DEN 3 | gi\|163644368:4124-4513 | 319 | 1156 | 60 |
| nonstructural protein NS2B | DEN 3 | gi\|163644368:4124-4513 | 318 | 1157 | 60 |
| nonstructural protein NS2B | DEN 3 | gi\|163644368:4124-4513 | 317 | 1158 | 60 |
| nonstructural protein NS2B | DEN 3 | gi\|163644368:4124-4513 | 313 | 1159 | 60 |
| nonstructural protein NS2B | DEN 3 | gi\|163644368:4124-4513 | 312 | 1160 | 60 |
| nonstructural protein NS3 | DEN 3 | gi\|163644368:4514-6370 | 1767 | 1161 | 60 |
| nonstructural protein NS3 | DEN 3 | gi\|163644368:4514-6370 | 1698 | 1162 | 60 |
| nonstructural protein NS3 | DEN 3 | gi\|163644368:4514-6370 | 1638 | 1163 | 60 |
| nonstructural protein NS3 | DEN 3 | gi\|163644368:4514-6370 | 1493 | 1164 | 60 |
| nonstructural protein NS3 | DEN 3 | gi\|163644368:4514-6370 | 1402 | 1165 | 60 |
| nonstructural protein NS3 | DEN 3 | gi\|163644368:4514-6370 | 1260 | 1166 | 60 |
| nonstructural protein NS3 | DEN 3 | gi\|163644368:4514-6370 | 1200 | 1167 | 60 |

TABLE 1-continued

| Selected viral probes | | | | | |
|---|---|---|---|---|---|
| nonstructural protein NS3 | DEN 3 | gi\|163644368:4514-6370 | 1137 | 1168 | 60 |
| nonstructural protein NS3 | DEN 3 | gi\|163644368:4514-6370 | 1077 | 1169 | 60 |
| nonstructural protein NS3 | DEN 3 | gi\|163644368:4514-6370 | 1016 | 1170 | 60 |
| nonstructural protein NS4A | DEN 3 | gi\|163644368:6371-6751 | 322 | 1171 | 60 |
| nonstructural protein NS4A | DEN 3 | gi\|163644368:6371-6751 | 321 | 1172 | 60 |
| nonstructural protein NS4A | DEN 3 | gi\|163644368:6371-6751 | 320 | 1173 | 60 |
| nonstructural protein NS4A | DEN 3 | gi\|163644368:6371-6751 | 319 | 1174 | 60 |
| nonstructural protein NS4A | DEN 3 | gi\|163644368:6371-6751 | 318 | 1175 | 60 |
| nonstructural protein NS4A | DEN 3 | gi\|163644368:6371-6751 | 317 | 1176 | 60 |
| nonstructural protein NS4A | DEN 3 | gi\|163644368:6371-6751 | 316 | 1177 | 60 |
| nonstructural protein NS4A | DEN 3 | gi\|163644368:6371-6751 | 315 | 1178 | 60 |
| nonstructural protein NS4A | DEN 3 | gi\|163644368:6371-6751 | 314 | 1179 | 60 |
| nonstructural protein NS4A | DEN 3 | gi\|163644368:6371-6751 | 313 | 1180 | 60 |
| nonstructural protein NS4B | DEN 3 | gi\|163644368:6821-7564 | 685 | 1181 | 60 |
| nonstructural protein NS4B | DEN 3 | gi\|163644368:6821-7564 | 621 | 1182 | 60 |
| nonstructural protein NS4B | DEN 3 | gi\|163644368:6821-7564 | 559 | 1183 | 60 |
| nonstructural protein NS4B | DEN 3 | gi\|163644368:6821-7564 | 492 | 1184 | 60 |
| nonstructural protein NS4B | DEN 3 | gi\|163644368:6821-7564 | 426 | 1185 | 60 |
| nonstructural protein NS4B | DEN 3 | gi\|163644368:6821-7564 | 350 | 1186 | 60 |
| nonstructural protein NS4B | DEN 3 | gi\|163644368:6821-7564 | 290 | 1187 | 60 |
| nonstructural protein NS4B | DEN 3 | gi\|163644368:6821-7564 | 208 | 1188 | 60 |
| nonstructural protein NS4B | DEN 3 | gi\|163644368:6821-7564 | 148 | 1189 | 60 |
| nonstructural protein NS4B | DEN 3 | gi\|163644368:6821-7564 | 37 | 1190 | 60 |
| nonstructural protein NS5 | DEN 3 | gi\|163644368:7565-10264 | 2626 | 1191 | 60 |
| nonstructural protein NS5 | DEN 3 | gi\|163644368:7565-10264 | 2516 | 1192 | 60 |
| nonstructural protein NS5 | DEN 3 | gi\|163644368:7565-10264 | 2456 | 1193 | 60 |
| nonstructural protein NS5 | DEN 3 | gi\|163644368:7565-10264 | 2390 | 1194 | 60 |
| nonstructural protein NS5 | DEN 3 | gi\|163644368:7565-10264 | 2300 | 1195 | 60 |
| nonstructural protein NS5 | DEN 3 | gi\|163644368:7565-10264 | 2198 | 1196 | 60 |
| nonstructural protein NS5 | DEN 3 | gi\|163644368:7565-10264 | 2137 | 1197 | 60 |
| nonstructural protein NS5 | DEN 3 | gi\|163644368:7565-10264 | 2048 | 1198 | 60 |
| nonstructural protein NS5 | DEN 3 | gi\|163644368:7565-10264 | 1963 | 1199 | 60 |
| nonstructural protein NS5 | DEN 4 | gi\|163644368:7565-10264 | 1903 | 1200 | 60 |
| anchored capsid protein C | DEN 4 | gi\|12084822:102-440 | 278 | 1201 | 60 |
| anchored capsid protein C | DEN 4 | gi\|12084822:102-440 | 277 | 1202 | 60 |
| anchored capsid protein C | DEN 4 | gi\|12084822:102-440 | 276 | 1203 | 60 |
| anchored capsid protein C | DEN 4 | gi\|12084822:102-440 | 275 | 1204 | 60 |
| anchored capsid protein C | DEN 4 | gi\|12084822:102-440 | 274 | 1205 | 60 |
| anchored capsid protein C | DEN 4 | gi\|12084822:102-440 | 273 | 1206 | 60 |

TABLE 1-continued

| Selected viral probes | | | | | |
|---|---|---|---|---|---|
| anchored capsid protein C | DEN 4 | gi\|12084822:102-440 | 272 | 1207 | 60 |
| anchored capsid protein C | DEN 4 | gi\|12084822:102-440 | 271 | 1208 | 60 |
| anchored capsid protein C | DEN 4 | gi\|12084822:102-440 | 270 | 1209 | 60 |
| anchored capsid protein C | DEN 4 | gi\|12084822:102-440 | 269 | 1210 | 60 |
| membrane glycoprotein precursor M | DEN 4 | gi\|12084822:441-938 | 422 | 1211 | 60 |
| membrane glycoprotein precursor M | DEN 4 | gi\|12084822:441-938 | 402 | 1212 | 60 |
| membrane glycoprotein precursor M | DEN 4 | gi\|12084822:441-938 | 380 | 1213 | 60 |
| membrane glycoprotein precursor M | DEN 4 | gi\|12084822:441-938 | 281 | 1214 | 60 |
| membrane glycoprotein precursor M | DEN 4 | gi\|12084822:441-938 | 259 | 1215 | 60 |
| membrane glycoprotein precursor M | DEN 4 | gi\|12084822:441-938 | 140 | 1216 | 60 |
| membrane glycoprotein precursor M | DEN 4 | gi\|12084822:441-938 | 96 | 1217 | 60 |
| membrane glycoprotein precursor M | DEN 4 | gi\|12084822:441-938 | 73 | 1218 | 60 |
| membrane glycoprotein precursor M | DEN 4 | gi\|12084822:441-938 | 50 | 1219 | 60 |
| membrane glycoprotein precursor M | DEN 4 | gi\|12084822:441-938 | 26 | 1220 | 60 |
| envelope protein E | DEN 4 | gi\|12084822:939-2423 | 1405 | 1221 | 60 |
| envelope protein E | DEN 4 | gi\|12084822:939-2423 | 1345 | 1222 | 60 |
| envelope protein E | DEN 4 | gi\|12084822:939-2423 | 1285 | 1223 | 60 |
| envelope protein E | DEN 4 | gi\|12084822:939-2423 | 1216 | 1224 | 60 |
| envelope protein E | DEN 4 | gi\|12084822:939-2423 | 1156 | 1225 | 60 |
| envelope protein E | DEN 4 | gi\|12084822:939-2423 | 1096 | 1226 | 60 |
| envelope protein E | DEN 4 | gi\|12084822:939-2423 | 1026 | 1227 | 60 |
| envelope protein E | DEN 4 | gi\|12084822:939-2423 | 966 | 1228 | 60 |
| envelope protein E | DEN 4 | gi\|12084822:939-2423 | 906 | 1229 | 60 |
| envelope protein E | DEN 4 | gi\|12084822:939-2423 | 846 | 1230 | 60 |
| non-structural protein NS1 | DEN 4 | gi\|12084822:2424-3479 | 993 | 1231 | 60 |
| non-structural protein NS1 | DEN 4 | gi\|12084822:2424-3479 | 823 | 1232 | 60 |
| non-structural protein NS1 | DEN 4 | gi\|12084822:2424-3479 | 710 | 1233 | 60 |
| non-structural protein NS1 | DEN 4 | gi\|12084822:2424-3479 | 638 | 1234 | 60 |
| non-structural protein NS1 | DEN 4 | gi\|12084822:2424-3479 | 570 | 1235 | 60 |
| non-structural protein NS1 | DEN 4 | gi\|12084822:2424-3479 | 510 | 1236 | 60 |
| non-structural protein NS1 | DEN 4 | gi\|12084822:2424-3479 | 450 | 1237 | 60 |
| non-structural protein NS1 | DEN 4 | gi\|12084822:2424-3479 | 390 | 1238 | 60 |
| non-structural protein NS1 | DEN 4 | gi\|12084822:2424-3479 | 330 | 1239 | 60 |
| non-structural protein NS1 | DEN 4 | gi\|12084822:2424-3479 | 209 | 1240 | 60 |

TABLE 1-continued

| | | Selected viral probes | | | |
|---|---|---|---|---|---|
| non-structural protein NS2A | DEN 4 | gi\|12084822:3480-4133 | 576 | 1241 | 60 |
| non-structural protein NS2A | DEN 4 | gi\|12084822:3480-4133 | 536 | 1242 | 60 |
| non-structural protein NS2A | DEN 4 | gi\|12084822:3480-4133 | 496 | 1243 | 60 |
| non-structural protein NS2A | DEN 4 | gi\|12084822:3480-4133 | 456 | 1244 | 60 |
| non-structural protein NS2A | DEN 4 | gi\|12084822:3480-4133 | 416 | 1245 | 60 |
| non-structural protein NS2A | DEN 4 | gi\|12084822:3480-4133 | 376 | 1246 | 60 |
| non-structural protein NS2A | DEN 4 | gi\|12084822:3480-4133 | 336 | 1247 | 60 |
| non-structural protein NS2A | DEN 4 | gi\|12084822:3480-4133 | 296 | 1248 | 60 |
| non-structural protein NS2A | DEN 4 | gi\|12084822:3480-4133 | 256 | 1249 | 60 |
| non-structural protein NS2A | DEN 4 | gi\|12084822:3480-4133 | 90 | 1250 | 60 |
| non-structural protein NS2B | DEN 4 | gi\|12084822:4134-4523 | 331 | 1251 | 60 |
| non-structural protein NS2B | DEN 4 | gi\|12084822:4134-4523 | 330 | 1252 | 60 |
| non-structural protein NS2B | DEN 4 | gi\|12084822:4134-4523 | 329 | 1253 | 60 |
| non-structural protein NS2B | DEN 4 | gi\|12084822:4134-4523 | 328 | 1254 | 60 |
| non-structural protein NS2B | DEN 4 | gi\|12084822:4134-4523 | 327 | 1255 | 60 |
| non-structural protein NS2B | DEN 4 | gi\|12084822:4134-4523 | 326 | 1256 | 60 |
| non-structural protein NS2B | DEN 4 | gi\|12084822:4134-4523 | 325 | 1257 | 60 |
| non-structural protein NS2B | DEN 4 | gi\|12084822:4134-4523 | 324 | 1258 | 60 |
| non-structural protein NS2B | DEN 4 | gi\|12084822:4134-4523 | 323 | 1259 | 60 |
| non-structural protein NS2B | DEN 4 | gi\|12084822:4134-4523 | 311 | 1260 | 60 |
| non-structural protein NS3 | DEN 4 | gi\|12084822:4524-6377 | 1780 | 1261 | 60 |
| non-structural protein NS3 | DEN 4 | gi\|12084822:4524-6377 | 1679 | 1262 | 60 |
| non-structural protein NS3 | DEN 4 | gi\|12084822:4524-6377 | 1591 | 1263 | 60 |
| non-structural protein NS3 | DEN 4 | gi\|12084822:4524-6377 | 1513 | 1264 | 60 |
| non-structural protein NS3 | DEN 4 | gi\|12084822:4524-6377 | 1442 | 1265 | 60 |
| non-structural protein NS3 | DEN 4 | gi\|12084822:4524-6377 | 1210 | 1266 | 60 |
| non-structural protein NS3 | DEN 4 | gi\|12084822:4524-6377 | 1150 | 1267 | 60 |
| non-structural protein NS3 | DEN 4 | gi\|12084822:4524-6377 | 1088 | 1268 | 60 |
| non-structural protein NS3 | DEN 4 | gi\|12084822:4524-6377 | 1027 | 1269 | 60 |
| non-structural protein NS3 | DEN 4 | gi\|12084822:4524-6377 | 840 | 1270 | 60 |
| non-structural protein NS4A | DEN 4 | gi\|12084822:6378-6758 | 322 | 1271 | 60 |
| non-structural protein NS4A | DEN 4 | gi\|12084822:6378-6758 | 321 | 1272 | 60 |
| non-structural protein NS4A | DEN 4 | gi\|12084822:6378-6758 | 320 | 1273 | 60 |
| non-structural protein NS4A | DEN 4 | gi\|12084822:6378-6758 | 319 | 1274 | 60 |
| non-structural protein NS4A | DEN 4 | gi\|12084822:6378-6758 | 318 | 1275 | 60 |
| non-structural protein NS4A | DEN 4 | gi\|12084822:6378-6758 | 317 | 1276 | 60 |
| non-structural protein NS4A | DEN 4 | gi\|12084822:6378-6758 | 316 | 1277 | 60 |
| non-structural protein NS4A | DEN 4 | gi\|12084822:6378-6758 | 315 | 1278 | 60 |
| non-structural protein NS4A | DEN 4 | gi\|12084822:6378-6758 | 314 | 1279 | 60 |

TABLE 1-continued

| Selected viral probes | | | | | |
|---|---|---|---|---|---|
| non-structural protein NS4A | DEN 4 | gi\|12084822:6378-6758 | 313 | 1280 | 60 |
| non-structural protein NS4B | DEN 4 | gi\|12084822:6828-7562 | 657 | 1281 | 60 |
| non-structural protein NS4B | DEN 4 | gi\|12084822:6828-7562 | 536 | 1282 | 60 |
| non-structural protein NS4B | DEN 4 | gi\|12084822:6828-7562 | 506 | 1283 | 60 |
| non-structural protein NS4B | DEN 4 | gi\|12084822:6828-7562 | 475 | 1284 | 60 |
| non-structural protein NS4B | DEN 4 | gi\|12084822:6828-7562 | 445 | 1285 | 60 |
| non-structural protein NS4B | DEN 4 | gi\|12084822:6828-7562 | 414 | 1286 | 60 |
| non-structural protein NS4B | DEN 4 | gi\|12084822:6828-7562 | 326 | 1287 | 60 |
| non-structural protein NS4B | DEN 4 | gi\|12084822:6828-7562 | 296 | 1288 | 60 |
| non-structural protein NS4B | DEN 4 | gi\|12084822:6828-7562 | 37 | 1289 | 60 |
| non-structural protein NS4B | DEN 4 | gi\|12084822:6828-7562 | 7 | 1290 | 60 |
| non-structural protein NS5 | DEN 4 | gi\|12084822:7563-10262 | 2641 | 1291 | 60 |
| non-structural protein NS5 | DEN 4 | gi\|12084822:7563-10262 | 2510 | 1292 | 60 |
| non-structural protein NS5 | DEN 4 | gi\|12084822:7563-10262 | 2450 | 1293 | 60 |
| non-structural protein NS5 | DEN 4 | gi\|12084822:7563-10262 | 2379 | 1294 | 60 |
| non-structural protein NS5 | DEN 4 | gi\|12084822:7563-10262 | 2153 | 1295 | 60 |
| non-structural protein NS5 | DEN 4 | gi\|12084822:7563-10262 | 2093 | 1296 | 60 |
| non-structural protein NS5 | DEN 4 | gi\|12084822:7563-10262 | 1925 | 1297 | 60 |
| non-structural protein NS5 | DEN 4 | gi\|12084822:7563-10262 | 1865 | 1298 | 60 |
| non-structural protein NS5 | DEN 4 | gi\|12084822:7563-10262 | 1805 | 1299 | 60 |
| non-structural protein NS5 | DEN 4 | gi\|12084822:7563-10262 | 1702 | 1300 | 60 |
| polyprotein precursor | GB virus C/ Hepatitis G | gi\|9628705:459-9080 | 8205 | 1301 | 60 |
| polyprotein precursor | GB virus C/ Hepatitis G | gi\|9628705:459-9080 | 7786 | 1302 | 60 |
| polyprotein precursor | GB virus C/ Hepatitis G | gi\|9628705:459-9080 | 7305 | 1303 | 60 |
| polyprotein precursor | GB virus C/ Hepatitis G | gi\|9628705:459-9080 | 7004 | 1304 | 60 |
| polyprotein precursor | GB virus C/ Hepatitis G | gi\|9628705:459-9080 | 6890 | 1305 | 60 |
| polyprotein precursor | GB virus C/ Hepatitis G | gi\|9628705:459-9080 | 6638 | 1306 | 60 |
| polyprotein precursor | GB virus C/ Hepatitis G | gi\|9628705:459-9080 | 5864 | 1307 | 60 |
| polyprotein precursor | GB virus C/ Hepatitis G | gi\|9628705:459-9080 | 5551 | 1308 | 60 |
| polyprotein precursor | GB virus C/ Hepatitis G | gi\|9628705:459-9080 | 5488 | 1309 | 60 |
| polyprotein precursor | GB virus C/ Hepatitis G | gi\|9628705:459-9080 | 3943 | 1310 | 60 |
| putative E1 protein | GB virus C/ Hepatitis G | gi\|9628705:459-1538 | 545 | 1311 | 60 |
| putative E1 protein | GB virus C/ Hepatitis G | gi\|9628705:459-1538 | 1021 | 1312 | 60 |
| putative E1 protein | GB virus C/ Hepatitis G | gi\|9628705:459-1538 | 964 | 1313 | 60 |
| putative E1 protein | GB virus C/ Hepatitis G | gi\|9628705:459-1538 | 924 | 1314 | 60 |
| putative E1 protein | GB virus C/ Hepatitis G | gi\|9628705:459-1538 | 879 | 1315 | 60 |
| putative E1 protein | GB virus C/ Hepatitis G | gi\|9628705:459-1538 | 783 | 1316 | 60 |
| putative E1 protein | GB virus C/ Hepatitis G | gi\|9628705:459-1538 | 737 | 1317 | 60 |
| putative E1 protein | GB virus C/ Hepatitis G | gi\|9628705:459-1538 | 644 | 1318 | 60 |

TABLE 1-continued

| Selected viral probes | | | | | |
|---|---|---|---|---|---|
| putative E1 protein | GB virus C/ Hepatitis G | gi|9628705:459-1538 | 601 | 1319 | 60 |
| putative E1 protein | GB virus C/ Hepatitis G | gi|9628705:459-1538 | 505 | 1320 | 60 |
| putative E2 protein | GB virus C/ Hepatitis G | gi|9628705:1539-2474 | 877 | 1321 | 60 |
| putative E2 protein | GB virus C/ Hepatitis G | gi|9628705:1539-2474 | 847 | 1322 | 60 |
| putative E2 protein | GB virus C/ Hepatitis G | gi|9628705:1539-2474 | 817 | 1323 | 60 |
| putative E2 protein | GB virus C/ Hepatitis G | gi|9628705:1539-2474 | 671 | 1324 | 60 |
| putative E2 protein | GB virus C/ Hepatitis G | gi|9628705:1539-2474 | 641 | 1325 | 60 |
| putative E2 protein | GB virus C/ Hepatitis G | gi|9628705:1539-2474 | 611 | 1326 | 60 |
| putative E2 protein | GB virus C/ Hepatitis G | gi|9628705:1539-2474 | 573 | 1327 | 60 |
| putative E2 protein | GB virus C/ Hepatitis G | gi|9628705:1539-2474 | 543 | 1328 | 60 |
| putative E2 protein | GB virus C/ Hepatitis G | gi|9628705:1539-2474 | 502 | 1329 | 60 |
| putative E2 protein | GB virus C/ Hepatitis G | gi|9628705:1539-2474 | 310 | 1330 | 60 |
| putative protein p7-NS2 | GB virus C/ Hepatitis G | gi|9628705:2475-3233 | 700 | 1331 | 60 |
| putative protein p7-NS2 | GB virus C/ Hepatitis G | gi|9628705:2475-3233 | 594 | 1332 | 60 |
| putative protein p7-NS2 | GB virus C/ Hepatitis G | gi|9628705:2475-3233 | 564 | 1333 | 60 |
| putative protein p7-NS2 | GB virus C/ Hepatitis G | gi|9628705:2475-3233 | 532 | 1334 | 60 |
| putative protein p7-NS2 | GB virus C/ Hepatitis G | gi|9628705:2475-3233 | 502 | 1335 | 60 |
| putative protein p7-NS2 | GB virus C/ Hepatitis G | gi|9628705:2475-3233 | 472 | 1336 | 60 |
| putative protein p7-NS2 | GB virus C/ Hepatitis G | gi|9628705:2475-3233 | 350 | 1337 | 60 |
| putative protein p7-NS2 | GB virus C/ Hepatitis G | gi|9628705:2475-3233 | 320 | 1338 | 60 |
| putative protein p7-NS2 | GB virus C/ Hepatitis G | gi|9628705:2475-3233 | 286 | 1339 | 60 |
| putative protein p7-NS2 | GB virus C/ Hepatitis G | gi|9628705:2475-3233 | 194 | 1340 | 60 |
| NS3 proteinase/ ATPase/helicase | GB virus C/ Hepatitis G | gi|9628705:3234-5111 | 1168 | 1341 | 60 |
| NS3 proteinase/ ATPase/helicase | GB virus C/ Hepatitis G | gi|9628705:3234-5111 | 1162 | 1342 | 60 |
| NS3 proteinase/ ATPase/helicase | GB virus C/ Hepatitis G | gi|9628705:3234-5111 | 1156 | 1343 | 60 |
| NS3 proteinase/ ATPase/helicase | GB virus C/ Hepatitis G | gi|9628705:3234-5111 | 1155 | 1344 | 60 |
| NS3 proteinase/ ATPase/helicase | GB virus C/ Hepatitis G | gi|9628705:3234-5111 | 1154 | 1345 | 60 |
| NS3 proteinase/ ATPase/helicase | GB virus C/ Hepatitis G | gi|9628705:3234-5111 | 1153 | 1346 | 60 |
| NS3 proteinase/ ATPase/helicase | GB virus C/ Hepatitis G | gi|9628705:3234-5111 | 1152 | 1347 | 60 |
| NS3 proteinase/ ATPase/helicase | GB virus C/ Hepatitis G | gi|9628705:3234-5111 | 1146 | 1348 | 60 |
| NS3 proteinase/ ATPase/helicase | GB virus C/ Hepatitis G | gi|9628705:3234-5111 | 1145 | 1349 | 60 |
| NS3 proteinase/ ATPase/helicase | GB virus C/ Hepatitis G | gi|9628705:3234-5111 | 1144 | 1350 | 60 |
| putative NS4A protein | GB virus C/ Hepatitis G | gi|9628705:5112-5309 | 45 | 1351 | 60 |
| putative NS4A protein | GB virus C/ Hepatitis G | gi|9628705:5112-5309 | 44 | 1352 | 60 |

TABLE 1-continued

| Selected viral probes | | | | | |
|---|---|---|---|---|---|
| putative NS4A protein | GB virus C/ Hepatitis G | gi\|9628705:5112-5309 | 43 | 1353 | 60 |
| putative NS4A protein | GB virus C/ Hepatitis G | gi\|9628705:5112-5309 | 42 | 1354 | 60 |
| putative NS4A protein | GB virus C/ Hepatitis G | gi\|9628705:5112-5309 | 16 | 1355 | 60 |
| putative NS4A protein | GB virus C/ Hepatitis G | gi\|9628705:5112-5309 | 13 | 1356 | 60 |
| putative NS4A protein | GB virus C/ Hepatitis G | gi\|9628705:5112-5309 | 12 | 1357 | 60 |
| putative NS4A protein | GB virus C/ Hepatitis G | gi\|9628705:5112-5309 | 11 | 1358 | 60 |
| putative NS4A protein | GB virus C/ Hepatitis G | gi\|9628705:5112-5309 | 6 | 1359 | 60 |
| putative NS4A protein | GB virus C/ Hepatitis G | gi\|9628705:5112-5309 | 5 | 1360 | 60 |
| putative NS4B protein | GB virus C/ Hepatitis G | gi\|9628705:5310-6152 | 700 | 1361 | 60 |
| putative NS4B protein | GB virus C/ Hepatitis G | gi\|9628705:5310-6152 | 699 | 1362 | 60 |
| putative NS4B protein | GB virus C/ Hepatitis G | gi\|9628705:5310-6152 | 698 | 1363 | 60 |
| putative NS4B protein | GB virus C/ Hepatitis G | gi\|9628705:5310-6152 | 696 | 1364 | 60 |
| putative NS4B protein | GB virus C/ Hepatitis G | gi\|9628705:5310-6152 | 695 | 1365 | 60 |
| putative NS4B protein | GB virus C/ Hepatitis G | gi\|9628705:5310-6152 | 694 | 1366 | 60 |
| putative NS4B protein | GB virus C/ Hepatitis G | gi\|9628705:5310-6152 | 693 | 1367 | 60 |
| putative NS4B protein | GB virus C/ Hepatitis G | gi\|9628705:5310-6152 | 692 | 1368 | 60 |
| putative NS4B protein | GB virus C/ Hepatitis G | gi\|9628705:5310-6152 | 691 | 1369 | 60 |
| putative NS4B protein | GB virus C/ Hepatitis G | gi\|9628705:5310-6152 | 690 | 1370 | 60 |
| putative NS5A protein | GB virus C/ Hepatitis G | gi\|9628705:6153-7388 | 1174 | 1371 | 60 |
| putative NS5A protein | GB virus C/ Hepatitis G | gi\|9628705:6153-7388 | 1173 | 1372 | 60 |
| putative NS5A protein | GB virus C/ Hepatitis G | gi\|9628705:6153-7388 | 1155 | 1373 | 60 |
| putative NS5A protein | GB virus C/ Hepatitis G | gi\|9628705:6153-7388 | 1154 | 1374 | 60 |
| putative NS5A protein | GB virus C/ Hepatitis G | gi\|9628705:6153-7388 | 1153 | 1375 | 60 |
| putative NS5A protein | GB virus C/ Hepatitis G | gi\|9628705:6153-7388 | 944 | 1376 | 60 |
| putative NS5A protein | GB virus C/ Hepatitis G | gi\|9628705:6153-7388 | 941 | 1377 | 60 |
| putative NS5A protein | GB virus C/ Hepatitis G | gi\|9628705:6153-7388 | 940 | 1378 | 60 |
| putative NS5A protein | GB virus C/ Hepatitis G | gi\|9628705:6153-7388 | 939 | 1379 | 60 |
| putative NS5A protein | GB virus C/ Hepatitis G | gi\|9628705:6153-7388 | 936 | 1380 | 60 |
| putative NS5B RNA-dependent RNA pol. | GB virus C/ Hepatitis G | gi\|9628705:7389-9077 | 1275 | 1381 | 60 |
| putative NS5B RNA-dependent RNA pol. | GB virus C/ Hepatitis G | gi\|9628705:7389-9077 | 1274 | 1382 | 60 |
| putative NS5B RNA-dependent RNA pol. | GB virus C/ Hepatitis G | gi\|9628705:7389-9077 | 856 | 1383 | 60 |
| putative NS5B RNA-dependent RNA pol. | GB virus C/ Hepatitis G | gi\|9628705:7389-9077 | 375 | 1384 | 60 |
| putative NS5B RNA-dependent RNA pol. | GB virus C/ Hepatitis G | gi\|9628705:7389-9077 | 374 | 1385 | 60 |

TABLE 1-continued

| Selected viral probes | | | | | |
|---|---|---|---|---|---|
| putative NS5B RNA-dependent RNA pol. | GB virus C/ Hepatitis G | gi\|9628705:7389-9077 | 373 | 1386 | 60 |
| putative NS5B RNA-dependent RNA pol. | GB virus C/ Hepatitis G | gi\|9628705:7389-9077 | 372 | 1387 | 60 |
| putative NS5B RNA-dependent RNA pol. | GB virus C/ Hepatitis G | gi\|9628705:7389-9077 | 371 | 1388 | 60 |
| putative NS5B RNA-dependent RNA pol. | GB virus C/ Hepatitis G | gi\|9628705:7389-9077 | 74 | 1389 | 60 |
| putative NS5B RNA-dependent RNA pol. | GB virus C/ Hepatitis G | gi\|9628705:7389-9077 | 73 | 1390 | 60 |
| 1A VP4b mature peptide | Hepatitis A virus | gi\|9626732:1-805 | 738 | 1391 | 60 |
| 1A VP4b mature peptide | Hepatitis A virus | gi\|9626732:1-805 | 691 | 1392 | 60 |
| 1A VP4b mature peptide | Hepatitis A virus | gi\|9626732:1-805 | 568 | 1393 | 60 |
| 1A VP4b mature peptide | Hepatitis A virus | gi\|9626732:1-805 | 513 | 1394 | 60 |
| 1A VP4b mature peptide | Hepatitis A virus | gi\|9626732:1-805 | 466 | 1395 | 60 |
| 1A VP4b mature peptide | Hepatitis A virus | gi\|9626732:1-805 | 426 | 1396 | 60 |
| 1A VP4b mature peptide | Hepatitis A virus | gi\|9626732:1-805 | 378 | 1397 | 60 |
| 1A VP4b mature peptide | Hepatitis A virus | gi\|9626732:1-805 | 338 | 1398 | 60 |
| 1A VP4b mature peptide | Hepatitis A virus | gi\|9626732:1-805 | 286 | 1399 | 60 |
| 1A VP4b mature peptide | Hepatitis A virus | gi\|9626732:1-805 | 159 | 1400 | 60 |
| 1B VP2 mature peptide | Hepatitis A virus | gi\|9626732:804-1469 | 606 | 1401 | 60 |
| 1B VP2 mature peptide | Hepatitis A virus | gi\|9626732:804-1469 | 546 | 1402 | 60 |
| 1B VP2 mature peptide | Hepatitis A virus | gi\|9626732:804-1469 | 486 | 1403 | 60 |
| 1B VP2 mature peptide | Hepatitis A virus | gi\|9626732:804-1469 | 397 | 1404 | 60 |
| 1B VP2 mature peptide | Hepatitis A virus | gi\|9626732:804-1469 | 329 | 1405 | 60 |
| 1B VP2 mature peptide | Hepatitis A virus | gi\|9626732:804-1469 | 269 | 1406 | 60 |
| 1B VP2 mature peptide | Hepatitis A virus | gi\|9626732:804-1469 | 203 | 1407 | 60 |
| 1B VP2 mature peptide | Hepatitis A virus | gi\|9626732:804-1469 | 143 | 1408 | 60 |
| 1B VP2 mature peptide | Hepatitis A virus | gi\|9626732:804-1469 | 82 | 1409 | 60 |
| 1B VP2 mature peptide | Hepatitis A virus | gi\|9626732:804-1469 | 22 | 1410 | 60 |
| 1C VP3 mature peptide | Hepatitis A virus | gi\|9626732:1470-2207 | 679 | 1411 | 60 |
| 1C VP3 mature peptide | Hepatitis A virus | gi\|9626732:1470-2207 | 619 | 1412 | 60 |
| 1C VP3 mature peptide | Hepatitis A virus | gi\|9626732:1470-2207 | 559 | 1413 | 60 |
| 1C VP3 mature peptide | Hepatitis A virus | gi\|9626732:1470-2207 | 499 | 1414 | 60 |
| 1C VP3 mature peptide | Hepatitis A virus | gi\|9626732:1470-2207 | 439 | 1415 | 60 |
| 1C VP3 mature peptide | Hepatitis A virus | gi\|9626732:1470-2207 | 379 | 1416 | 60 |
| 1C VP3 mature peptide | Hepatitis A virus | gi\|9626732:1470-2207 | 316 | 1417 | 60 |
| 1C VP3 mature peptide | Hepatitis A virus | gi\|9626732:1470-2207 | 246 | 1418 | 60 |
| 1C VP3 mature peptide | Hepatitis A virus | gi\|9626732:1470-2207 | 185 | 1419 | 60 |

TABLE 1-continued

| Selected viral probes | | | | | |
|---|---|---|---|---|---|
| 1C VP3 mature peptide | Hepatitis A virus | gi\|9626732:1470-2207 | 125 | 1420 | 60 |
| 1D VP1 mature peptide | Hepatitis A virus | gi\|9626732:2208-3107 | 841 | 1421 | 60 |
| 1D VP1 mature peptide | Hepatitis A virus | gi\|9626732:2208-3107 | 781 | 1422 | 60 |
| 1D VP1 mature peptide | Hepatitis A virus | gi\|9626732:2208-3107 | 654 | 1423 | 60 |
| 1D VP1 mature peptide | Hepatitis A virus | gi\|9626732:2208-3107 | 594 | 1424 | 60 |
| 1D VP1 mature peptide | Hepatitis A virus | gi\|9626732:2208-3107 | 534 | 1425 | 60 |
| 1D VP1 mature peptide | Hepatitis A virus | gi\|9626732:2208-3107 | 434 | 1426 | 60 |
| 1D VP1 mature peptide | Hepatitis A virus | gi\|9626732:2208-3107 | 374 | 1427 | 60 |
| 1D VP1 mature peptide | Hepatitis A virus | gi\|9626732:2208-3107 | 314 | 1428 | 60 |
| 1D VP1 mature peptide | Hepatitis A virus | gi\|9626732:2208-3107 | 249 | 1429 | 60 |
| 1D VP1 mature peptide | Hepatitis A virus | gi\|9626732:2208-3107 | 189 | 1430 | 60 |
| 2A mature peptide | Hepatitis A virus | gi\|9626732:3108-3674 | 494 | 1431 | 60 |
| 2A mature peptide | Hepatitis A virus | gi\|9626732:3108-3674 | 452 | 1432 | 60 |
| 2A mature peptide | Hepatitis A virus | gi\|9626732:3108-3674 | 412 | 1433 | 60 |
| 2A mature peptide | Hepatitis A virus | gi\|9626732:3108-3674 | 372 | 1434 | 60 |
| 2A mature peptide | Hepatitis A virus | gi\|9626732:3108-3674 | 281 | 1435 | 60 |
| 2A mature peptide | Hepatitis A virus | gi\|9626732:3108-3674 | 179 | 1436 | 60 |
| 2A mature peptide | Hepatitis A virus | gi\|9626732:3108-3674 | 136 | 1437 | 60 |
| 2A mature peptide | Hepatitis A virus | gi\|9626732:3108-3674 | 96 | 1438 | 60 |
| 2A mature peptide | Hepatitis A virus | gi\|9626732:3108-3674 | 56 | 1439 | 60 |
| 2A mature peptide | Hepatitis A virus | gi\|9626732:3108-3674 | 16 | 1440 | 60 |
| 2B mature peptide | Hepatitis A virus | gi\|9626732:3675-3995 | 262 | 1441 | 60 |
| 2B mature peptide | Hepatitis A virus | gi\|9626732:3675-3995 | 261 | 1442 | 60 |
| 2B mature peptide | Hepatitis A virus | gi\|9626732:3675-3995 | 260 | 1443 | 60 |
| 2B mature peptide | Hepatitis A virus | gi\|9626732:3675-3995 | 258 | 1444 | 60 |
| 2B mature peptide | Hepatitis A virus | gi\|9626732:3675-3995 | 257 | 1445 | 60 |
| 2B mature peptide | Hepatitis A virus | gi\|9626732:3675-3995 | 256 | 1446 | 60 |
| 2B mature peptide | Hepatitis A virus | gi\|9626732:3675-3995 | 255 | 1447 | 60 |
| 2B mature peptide | Hepatitis A virus | gi\|9626732:3675-3995 | 254 | 1448 | 60 |
| 2B mature peptide | Hepatitis A virus | gi\|9626732:3675-3995 | 253 | 1449 | 60 |
| 2B mature peptide | Hepatitis A virus | gi\|9626732:3675-3995 | 252 | 1450 | 60 |
| 2C mature peptide | Hepatitis A virus | gi\|9626732:3996-5000 | 946 | 1451 | 60 |
| 2C mature peptide | Hepatitis A virus | gi\|9626732:3996-5000 | 882 | 1452 | 60 |
| 2C mature peptide | Hepatitis A virus | gi\|9626732:3996-5000 | 774 | 1453 | 60 |
| 2C mature peptide | Hepatitis A virus | gi\|9626732:3996-5000 | 714 | 1454 | 60 |
| 2C mature peptide | Hepatitis A virus | gi\|9626732:3996-5000 | 654 | 1455 | 60 |
| 2C mature peptide | Hepatitis A virus | gi\|9626732:3996-5000 | 594 | 1456 | 60 |
| 2C mature peptide | Hepatitis A virus | gi\|9626732:3996-5000 | 534 | 1457 | 60 |
| 2C mature peptide | Hepatitis A virus | gi\|9626732:3996-5000 | 449 | 1458 | 60 |

TABLE 1-continued

| Selected viral probes | | | | | |
|---|---|---|---|---|---|
| 2C mature peptide | Hepatitis A virus | gi\|9626732:3996-5000 | 389 | 1459 | 60 |
| 2C mature peptide | Hepatitis A virus | gi\|9626732:3996-5000 | 327 | 1460 | 60 |
| 3A mature peptide | Hepatitis A virus | gi\|9626732:5001-5222 | 92 | 1461 | 60 |
| 3A mature peptide | Hepatitis A virus | gi\|9626732:5001-5222 | 91 | 1462 | 60 |
| 3A mature peptide | Hepatitis A virus | gi\|9626732:5001-5222 | 90 | 1463 | 60 |
| 3A mature peptide | Hepatitis A virus | gi\|9626732:5001-5222 | 83 | 1464 | 60 |
| 3A mature peptide | Hepatitis A virus | gi\|9626732:5001-5222 | 82 | 1465 | 60 |
| 3A mature peptide | Hepatitis A virus | gi\|9626732:5001-5222 | 81 | 1466 | 60 |
| 3A mature peptide | Hepatitis A virus | gi\|9626732:5001-5222 | 80 | 1467 | 60 |
| 3A mature peptide | Hepatitis A virus | gi\|9626732:5001-5222 | 79 | 1468 | 60 |
| 3A mature peptide | Hepatitis A virus | gi\|9626732:5001-5222 | 78 | 1469 | 60 |
| 3A mature peptide | Hepatitis A virus | gi\|9626732:5001-5222 | 77 | 1470 | 60 |
| 3B (VPg) mature peptide | Hepatitis A virus | gi\|9626732:5001-5291 | 232 | 1471 | 60 |
| 3B (VPg) mature peptide | Hepatitis A virus | gi\|9626732:5001-5291 | 231 | 1472 | 60 |
| 3B (VPg) mature peptide | Hepatitis A virus | gi\|9626732:5001-5291 | 230 | 1473 | 60 |
| 3B (VPg) mature peptide | Hepatitis A virus | gi\|9626732:5001-5291 | 229 | 1474 | 60 |
| 3B (VPg) mature peptide | Hepatitis A virus | gi\|9626732:5001-5291 | 228 | 1475 | 60 |
| 3B (VPg) mature peptide | Hepatitis A virus | gi\|9626732:5001-5291 | 227 | 1476 | 60 |
| 3B (VPg) mature peptide | Hepatitis A virus | gi\|9626732:5001-5291 | 226 | 1477 | 60 |
| 3B (VPg) mature peptide | Hepatitis A virus | gi\|9626732:5001-5291 | 225 | 1478 | 60 |
| 3B (VPg) mature peptide | Hepatitis A virus | gi\|9626732:5001-5291 | 224 | 1479 | 60 |
| 3B (VPg) mature peptide | Hepatitis A virus | gi\|9626732:5001-5291 | 223 | 1480 | 60 |
| 3C mature peptide | Hepatitis A virus | gi\|9626732:5292-5948 | 568 | 1481 | 60 |
| 3C mature peptide | Hepatitis A virus | gi\|9626732:5292-5948 | 528 | 1482 | 60 |
| 3C mature peptide | Hepatitis A virus | gi\|9626732:5292-5948 | 444 | 1483 | 60 |
| 3C mature peptide | Hepatitis A virus | gi\|9626732:5292-5948 | 396 | 1484 | 60 |
| 3C mature peptide | Hepatitis A virus | gi\|9626732:5292-5948 | 356 | 1485 | 60 |
| 3C mature peptide | Hepatitis A virus | gi\|9626732:5292-5948 | 313 | 1486 | 60 |
| 3C mature peptide | Hepatitis A virus | gi\|9626732:5292-5948 | 270 | 1487 | 60 |
| 3C mature peptide | Hepatitis A virus | gi\|9626732:5292-5948 | 230 | 1488 | 60 |
| 3C mature peptide | Hepatitis A virus | gi\|9626732:5292-5948 | 190 | 1489 | 60 |
| 3C mature peptide | Hepatitis A virus | gi\|9626732:5292-5948 | 111 | 1490 | 60 |
| 3D mature peptide | Hepatitis A virus | gi\|9626732:5949-7415 | 1403 | 1491 | 60 |
| 3D mature peptide | Hepatitis A virus | gi\|9626732:5949-7415 | 1293 | 1492 | 60 |
| 3D mature peptide | Hepatitis A virus | gi\|9626732:5949-7415 | 1233 | 1493 | 60 |
| 3D mature peptide | Hepatitis A virus | gi\|9626732:5949-7415 | 1173 | 1494 | 60 |
| 3D mature peptide | Hepatitis A virus | gi\|9626732:5949-7415 | 1113 | 1495 | 60 |
| 3D mature peptide | Hepatitis A virus | gi\|9626732:5949-7415 | 1009 | 1496 | 60 |
| 3D mature peptide | Hepatitis A virus | gi\|9626732:5949-7415 | 900 | 1497 | 60 |

TABLE 1-continued

| Selected viral probes | | | | | |
|---|---|---|---|---|---|
| 3D mature peptide | Hepatitis A virus | gi\|9626732:5949-7415 | 837 | 1498 | 60 |
| 3D mature peptide | Hepatitis A virus | gi\|9626732:5949-7415 | 777 | 1499 | 60 |
| 3D mature peptide | Hepatitis A virus | gi\|9626732:5949-7415 | 710 | 1500 | 60 |
| ORF 1-polyprotein | Hepatitis E virus | gi\|9626440:4-5085 | 4891 | 1501 | 60 |
| ORF 1-polyprotein | Hepatitis E virus | gi\|9626440:4-5085 | 4569 | 1502 | 60 |
| ORF 1-polyprotein | Hepatitis E virus | gi\|9626440:4-5085 | 4395 | 1503 | 60 |
| ORF 1-polyprotein | Hepatitis E virus | gi\|9626440:4-5085 | 4138 | 1504 | 60 |
| ORF 1-polyprotein | Hepatitis E virus | gi\|9626440:4-5085 | 3840 | 1505 | 60 |
| ORF 1-polyprotein | Hepatitis E virus | gi\|9626440:4-5085 | 3594 | 1506 | 60 |
| ORF 1-polyprotein | Hepatitis E virus | gi\|9626440:4-5085 | 2791 | 1507 | 60 |
| ORF 1-polyprotein | Hepatitis E virus | gi\|9626440:4-5085 | 2548 | 1508 | 60 |
| ORF 1-polyprotein | Hepatitis E virus | gi\|9626440:4-5085 | 2130 | 1509 | 60 |
| ORF 1-polyprotein | Hepatitis E virus | gi\|9626440:4-5085 | 1211 | 1510 | 60 |
| Viral methyltransferase | Hepatitis E virus | gi\|9626440:100-1057 | 15 | 1511 | 60 |
| Viral methyltransferase | Hepatitis E virus | gi\|9626440:100-1057 | 899 | 1512 | 60 |
| Viral methyltransferase | Hepatitis E virus | gi\|9626440:100-1057 | 826 | 1513 | 60 |
| Viral methyltransferase | Hepatitis E virus | gi\|9626440:100-1057 | 650 | 1514 | 60 |
| Viral methyltransferase | Hepatitis E virus | gi\|9626440:100-1057 | 590 | 1515 | 60 |
| Viral methyltransferase | Hepatitis E virus | gi\|9626440:100-1057 | 526 | 1516 | 60 |
| Viral methyltransferase | Hepatitis E virus | gi\|9626440:100-1057 | 409 | 1517 | 60 |
| Viral methyltransferase | Hepatitis E virus | gi\|9626440:100-1057 | 349 | 1518 | 60 |
| Viral methyltransferase | Hepatitis E virus | gi\|9626440:100-1057 | 190 | 1519 | 60 |
| Viral methyltransferase | Hepatitis E virus | gi\|9626440:100-1057 | 115 | 1520 | 60 |
| Peptidase C41 | Hepatitis E virus | gi\|9626440:1294-1783 | 431 | 1521 | 60 |
| Peptidase C41 | Hepatitis E virus | gi\|9626440:1294-1783 | 411 | 1522 | 60 |
| Peptidase C41 | Hepatitis E virus | gi\|9626440:1294-1783 | 391 | 1523 | 60 |
| Peptidase C41 | Hepatitis E virus | gi\|9626440:1294-1783 | 371 | 1524 | 60 |
| Peptidase C41 | Hepatitis E virus | gi\|9626440:1294-1783 | 251 | 1525 | 60 |
| Peptidase C41 | Hepatitis E virus | gi\|9626440:1294-1783 | 227 | 1526 | 60 |
| Peptidase C41 | Hepatitis E virus | gi\|9626440:1294-1783 | 207 | 1527 | 60 |
| Peptidase C41 | Hepatitis E virus | gi\|9626440:1294-1783 | 126 | 1528 | 60 |
| Peptidase C41 | Hepatitis E virus | gi\|9626440:1294-1783 | 106 | 1529 | 60 |
| Peptidase C41 | Hepatitis E virus | gi\|9626440:1294-1783 | 86 | 1530 | 60 |
| Viral helicase 1 | Hepatitis E virus | gi\|9626440:2914-3562 | 590 | 1531 | 60 |
| Viral helicase 1 | Hepatitis E virus | gi\|9626440:2914-3562 | 589 | 1532 | 60 |
| Viral helicase 1 | Hepatitis E virus | gi\|9626440:2914-3562 | 586 | 1533 | 60 |
| Viral helicase 1 | Hepatitis E virus | gi\|9626440:2914-3562 | 585 | 1534 | 60 |
| Viral helicase 1 | Hepatitis E virus | gi\|9626440:2914-3562 | 583 | 1535 | 60 |
| Viral helicase 1 | Hepatitis E virus | gi\|9626440:2914-3562 | 548 | 1536 | 60 |

TABLE 1-continued

| Selected viral probes | | | | | |
|---|---|---|---|---|---|
| Viral helicase 1 | Hepatitis E virus | gi\|9626440:2914-3562 | 547 | 1537 | 60 |
| Viral helicase 1 | Hepatitis E virus | gi\|9626440:2914-3562 | 546 | 1538 | 60 |
| Viral helicase 1 | Hepatitis E virus | gi\|9626440:2914-3562 | 544 | 1539 | 60 |
| Viral helicase 1 | Hepatitis E virus | gi\|9626440:2914-3562 | 543 | 1540 | 60 |
| RNA dependent RNA pol. | Hepatitis E virus | gi\|9626440:4191-4684 | 382 | 1541 | 60 |
| RNA dependent RNA pol. | Hepatitis E virus | gi\|9626440:4191-4684 | 381 | 1542 | 60 |
| RNA dependent RNA pol. | Hepatitis E virus | gi\|9626440:4191-4684 | 380 | 1543 | 60 |
| RNA dependent RNA pol. | Hepatitis E virus | gi\|9626440:4191-4684 | 208 | 1544 | 60 |
| RNA dependent RNA pol. | Hepatitis E virus | gi\|9626440:4191-4684 | 207 | 1545 | 60 |
| RNA dependent RNA pol. | Hepatitis E virus | gi\|9626440:4191-4684 | 205 | 1546 | 60 |
| RNA dependent RNA pol. | Hepatitis E virus | gi\|9626440:4191-4684 | 204 | 1547 | 60 |
| RNA dependent RNA pol. | Hepatitis E virus | gi\|9626440:4191-4684 | 203 | 1548 | 60 |
| RNA dependent RNA pol. | Hepatitis E virus | gi\|9626440:4191-4684 | 202 | 1549 | 60 |
| RNA dependent RNA pol. | Hepatitis E virus | gi\|9626440:4191-4684 | 201 | 1550 | 60 |
| ORF 3-hypothetical protein | Hepatitis E virus | gi\|9626440:5109-5453 | 135 | 1551 | 60 |
| ORF 3-hypothetical protein | Hepatitis E virus | gi\|9626440:5109-5453 | 134 | 1552 | 60 |
| ORF 3-hypothetical protein | Hepatitis E virus | gi\|9626440:5109-5453 | 133 | 1553 | 60 |
| ORF 3-hypothetical protein | Hepatitis E virus | gi\|9626440:5109-5453 | 132 | 1554 | 60 |
| ORF 3-hypothetical protein | Hepatitis E virus | gi\|9626440:5109-5453 | 131 | 1555 | 60 |
| ORF 3-hypothetical protein | Hepatitis E virus | gi\|9626440:5109-5453 | 130 | 1556 | 60 |
| ORF 3-hypothetical protein | Hepatitis E virus | gi\|9626440:5109-5453 | 129 | 1557 | 60 |
| ORF 3-hypothetical protein | Hepatitis E virus | gi\|9626440:5109-5453 | 142 | 1558 | 60 |
| ORF 3-hypothetical protein | Hepatitis E virus | gi\|9626440:5109-5453 | 141 | 1559 | 60 |
| ORF 3-hypothetical protein | Hepatitis E virus | gi\|9626440:5109-5453 | 140 | 1560 | 60 |
| ORF 2-capsid protein | Hepatitis E virus | gi\|9626440:5123-7105 | 1661 | 1561 | 60 |
| ORF 2-capsid protein | Hepatitis E virus | gi\|9626440:5123-7105 | 1660 | 1562 | 60 |
| ORF 2-capsid protein | Hepatitis E virus | gi\|9626440:5123-7105 | 1659 | 1563 | 60 |
| ORF 2-capsid protein | Hepatitis E virus | gi\|9626440:5123-7105 | 1658 | 1564 | 60 |
| ORF 2-capsid protein | Hepatitis E virus | gi\|9626440:5123-7105 | 1657 | 1565 | 60 |
| ORF 2-capsid protein | Hepatitis E virus | gi\|9626440:5123-7105 | 1656 | 1566 | 60 |
| ORF 2-capsid protein | Hepatitis E virus | gi\|9626440:5123-7105 | 1655 | 1567 | 60 |
| ORF 2-capsid protein | Hepatitis E virus | gi\|9626440:5123-7105 | 1654 | 1568 | 60 |
| ORF 2-capsid protein | Hepatitis E virus | gi\|9626440:5123-7105 | 1653 | 1569 | 60 |
| ORF 2-capsid protein | Hepatitis E virus | gi\|9626440:5123-7105 | 1652 | 1570 | 60 |

TABLE 1-continued

| Selected viral probes | | | | | |
|---|---|---|---|---|---|
| RNA dependent RNA pol. | WCCV1 RNA1 | gi\|52220883:75-1925 | 1783 | 1571 | 60 |
| RNA dependent RNA pol. | WCCV1 RNA1 | gi\|52220883:75-1925 | 1722 | 1572 | 60 |
| RNA dependent RNA pol. | WCCV1 RNA1 | gi\|52220883:75-1925 | 1638 | 1573 | 60 |
| RNA dependent RNA pol. | WCCV1 RNA1 | gi\|52220883:75-1925 | 1410 | 1574 | 60 |
| RNA dependent RNA pol. | WCCV1 RNA1 | gi\|52220883:75-1925 | 1350 | 1575 | 60 |
| RNA dependent RNA pol. | WCCV1 RNA1 | gi\|52220883:75-1925 | 1290 | 1576 | 60 |
| RNA dependent RNA pol. | WCCV1 RNA1 | gi\|52220883:75-1925 | 1230 | 1577 | 60 |
| RNA dependent RNA pol. | WCCV1 RNA1 | gi\|52220883:75-1925 | 1170 | 1578 | 60 |
| RNA dependent RNA pol. | WCCV1 RNA1 | gi\|52220883:75-1925 | 1087 | 1579 | 60 |
| RNA dependent RNA pol. | WCCV1 RNA1 | gi\|52220883:75-1925 | 999 | 1580 | 60 |
| Putative protease cofactor | BBWV 1 RNA 1 | gi\|39163640:201-1154 | 875 | 1581 | 60 |
| putative protease cofactor | BBWV 1 RNA 1 | gi\|39163640:201-1154 | 815 | 1582 | 60 |
| putative protease cofactor | BBWV 1 RNA 1 | gi\|39163640:201-1154 | 731 | 1583 | 60 |
| putative protease cofactor | BBWV 1 RNA 1 | gi\|39163640:201-1154 | 671 | 1584 | 60 |
| putative protease cofactor | BBWV 1 RNA 1 | gi\|39163640:201-1154 | 609 | 1585 | 60 |
| putative protease cofactor | BBWV 1 RNA 1 | gi\|39163640:201-1154 | 546 | 1586 | 60 |
| putative protease cofactor | BBWV 1 RNA 1 | gi\|39163640:201-1154 | 479 | 1587 | 60 |
| putative protease cofactor | BBWV 1 RNA 1 | gi\|39163640:201-1154 | 419 | 1588 | 60 |
| putative protease cofactor | BBWV 1 RNA 1 | gi\|39163640:201-1154 | 330 | 1589 | 60 |
| putative protease cofactor | BBWV 1 RNA 1 | gi\|39163640:201-1154 | 252 | 1590 | 60 |
| NTP-binding protein | BBWV 1 RNA 1 | gi\|39163640:1155-2924 | 1694 | 1591 | 60 |
| NTP-binding protein | BBWV 1 RNA 1 | gi\|39163640:1155-2924 | 1623 | 1592 | 60 |
| NTP-binding protein | BBWV 1 RNA 1 | gi\|39163640:1155-2924 | 1553 | 1593 | 60 |
| NTP-binding protein | BBWV 1 RNA 1 | gi\|39163640:1155-2924 | 1493 | 1594 | 60 |
| NTP-binding protein | BBWV 1 RNA 1 | gi\|39163640:1155-2924 | 1431 | 1595 | 60 |
| NTP-binding protein | BBWV 1 RNA 1 | gi\|39163640:1155-2924 | 1371 | 1596 | 60 |
| NTP-binding protein | BBWV 1 RNA 1 | gi\|39163640:1155-2924 | 1310 | 1597 | 60 |
| NTP-binding protein | BBWV 1 RNA 1 | gi\|39163640:1155-2924 | 1250 | 1598 | 60 |
| NTP-binding protein | BBWV 1 RNA 1 | gi\|39163640:1155-2924 | 1113 | 1599 | 60 |
| NTP-binding protein | BBWV 1 RNA 1 | gi\|39163640:1155-2924 | 1053 | 1600 | 60 |
| cysteine protease | BBWV 1 RNA 1 | gi\|39163640:3003-3629 | 512 | 1601 | 60 |
| cysteine protease | BBWV 1 RNA 1 | gi\|39163640:3003-3629 | 466 | 1602 | 60 |
| cysteine protease | BBWV 1 RNA 1 | gi\|39163640:3003-3629 | 426 | 1603 | 60 |
| cysteine protease | BBWV 1 RNA 1 | gi\|39163640:3003-3629 | 335 | 1604 | 60 |

TABLE 1-continued

| Selected viral probes | | | | | |
|---|---|---|---|---|---|
| cysteine protease | BBWV 1 RNA 1 | gi\|39163640:3003-3629 | 295 | 1605 | 60 |
| cysteine protease | BBWV 1 RNA 1 | gi\|39163640:3003-3629 | 251 | 1606 | 60 |
| cysteine protease | BBWV 1 RNA 1 | gi\|39163640:3003-3629 | 211 | 1607 | 60 |
| cysteine protease | BBWV 1 RNA 1 | gi\|39163640:3003-3629 | 171 | 1608 | 60 |
| cysteine protease | BBWV 1 RNA 1 | gi\|39163640:3003-3629 | 131 | 1609 | 60 |
| cysteine protease | BBWV 1 RNA 1 | gi\|39163640:3003-3629 | 91 | 1610 | 60 |
| RNA-dependent RNA pol. | BBWV 1 RNA 1 | gi\|39163640:3630-5726 | 2038 | 1611 | 60 |
| RNA-dependent RNA pol. | BBWV 1 RNA 1 | gi\|39163640:3630-5726 | 1978 | 1612 | 60 |
| RNA-dependent RNA pol. | BBWV 1 RNA 1 | gi\|39163640:3630-5726 | 1918 | 1613 | 60 |
| RNA-dependent RNA pol. | BBWV 1 RNA 1 | gi\|39163640:3630-5726 | 1858 | 1614 | 60 |
| RNA-dependent RNA pol. | BBWV 1 RNA 1 | gi\|39163640:3630-5726 | 1798 | 1615 | 60 |
| RNA-dependent RNA pol. | BBWV 1 RNA 1 | gi\|39163640:3630-5726 | 1738 | 1616 | 60 |
| RNA-dependent RNA pol. | BBWV 1 RNA 1 | gi\|39163640:3630-5726 | 1678 | 1617 | 60 |
| RNA-dependent RNA pol. | BBWV 1 RNA 1 | gi\|39163640:3630-5726 | 1588 | 1618 | 60 |
| RNA-dependent RNA pol. | BBWV 1 RNA 1 | gi\|39163640:3630-5726 | 1525 | 1619 | 60 |
| RNA-dependent RNA pol. | BBWV 1 RNA 1 | gi\|39163640:3630-5726 | 1362 | 1620 | 60 |
| nucleocapsid protein | LNYV | gi\|83659771:1-1623 | 1525 | 1621 | 60 |
| nucleocapsid protein | LNYV | gi\|83659771:1-1623 | 1465 | 1622 | 60 |
| nucleocapsid protein | LNYV | gi\|83659771:1-1623 | 1398 | 1623 | 60 |
| nucleocapsid protein | LNYV | gi\|83659771:1-1623 | 1313 | 1624 | 60 |
| nucleocapsid protein | LNYV | gi\|83659771:1-1623 | 1253 | 1625 | 60 |
| nucleocapsid protein | LNYV | gi\|83659771:1-1623 | 1193 | 1626 | 60 |
| nucleocapsid protein | LNYV | gi\|83659771:1-1623 | 1125 | 1627 | 60 |
| nucleocapsid protein | LNYV | gi\|83659771:1-1623 | 1065 | 1628 | 60 |
| nucleocapsid protein | LNYV | gi\|83659771:1-1623 | 989 | 1629 | 60 |
| nucleocapsid protein | LNYV | gi\|83659771:1-1623 | 901 | 1630 | 60 |
| phospoprotein | LNYV | gi\|83659771:1631-2712 | 993 | 1631 | 60 |
| phospoprotein | LNYV | gi\|83659771:1631-2712 | 933 | 1632 | 60 |
| phospoprotein | LNYV | gi\|83659771:1631-2712 | 873 | 1633 | 60 |
| phospoprotein | LNYV | gi\|83659771:1631-2712 | 738 | 1634 | 60 |
| phospoprotein | LNYV | gi\|83659771:1631-2712 | 652 | 1635 | 60 |
| phospoprotein | LNYV | gi\|83659771:1631-2712 | 559 | 1636 | 60 |
| phospoprotein | LNYV | gi\|83659771:1631-2712 | 491 | 1637 | 60 |
| phospoprotein | LNYV | gi\|83659771:1631-2712 | 431 | 1638 | 60 |
| phospoprotein | LNYV | gi\|83659771:1631-2712 | 371 | 1639 | 60 |
| phospoprotein | LNYV | gi\|83659771:1631-2712 | 311 | 1640 | 60 |
| gene"4b | LNYV | gi\|83659771:2720-3765 | 987 | 1641 | 60 |
| gene"4b | LNYV | gi\|83659771:2720-3765 | 927 | 1642 | 60 |
| gene"4b | LNYV | gi\|83659771:2720-3765 | 867 | 1643 | 60 |
| gene"4b | LNYV | gi\|83659771:2720-3765 | 794 | 1644 | 60 |
| gene"4b | LNYV | gi\|83659771:2720-3765 | 734 | 1645 | 60 |
| gene"4b | LNYV | gi\|83659771:2720-3765 | 674 | 1646 | 60 |

TABLE 1-continued

| Selected viral probes | | | | | |
|---|---|---|---|---|---|
| gene"4b | LNYV | gi\|83659771:2720-3765 | 613 | 1647 | 60 |
| gene"4b | LNYV | gi\|83659771:2720-3765 | 553 | 1648 | 60 |
| gene"4b | LNYV | gi\|83659771:2720-3765 | 491 | 1649 | 60 |
| gene"4b | LNYV | gi\|83659771:2720-3765 | 431 | 1650 | 60 |
| matrix protein | LNYV | gi\|83659771:3773-4403 | 554 | 1651 | 60 |
| matrix protein | LNYV | gi\|83659771:3773-4403 | 514 | 1652 | 60 |
| matrix protein | LNYV | gi\|83659771:3773-4403 | 438 | 1653 | 60 |
| matrix protein | LNYV | gi\|83659771:3773-4403 | 391 | 1654 | 60 |
| matrix protein | LNYV | gi\|83659771:3773-4403 | 351 | 1655 | 60 |
| matrix protein | LNYV | gi\|83659771:3773-4403 | 308 | 1656 | 60 |
| matrix protein | LNYV | gi\|83659771:3773-4403 | 244 | 1657 | 60 |
| matrix protein | LNYV | gi\|83659771:3773-4403 | 203 | 1658 | 60 |
| matrix protein | LNYV | gi\|83659771:3773-4403 | 163 | 1659 | 60 |
| matrix protein | LNYV | gi\|83659771:3773-4403 | 51 | 1660 | 60 |
| gene G | LNYV | gi\|83659771:4412-6247 | 1777 | 1661 | 60 |
| gene G | LNYV | gi\|83659771:4412-6247 | 1717 | 1662 | 60 |
| gene G | LNYV | gi\|83659771:4412-6247 | 1657 | 1663 | 60 |
| gene G | LNYV | gi\|83659771:4412-6247 | 1597 | 1664 | 60 |
| gene G | LNYV | gi\|83659771:4412-6247 | 1531 | 1665 | 60 |
| gene G | LNYV | gi\|83659771:4412-6247 | 1448 | 1666 | 60 |
| gene G | LNYV | gi\|83659771:4412-6247 | 1365 | 1667 | 60 |
| gene G | LNYV | gi\|83659771:4412-6247 | 1236 | 1668 | 60 |
| gene G | LNYV | gi\|83659771:4412-6247 | 1160 | 1669 | 60 |
| gene G | LNYV | gi\|83659771:4412-6247 | 1100 | 1670 | 60 |
| RNA-dependent RNA pol. | LNYV | gi\|83659771:6278-12613 | 6101 | 1671 | 60 |
| RNA-dependent RNA pol. | LNYV | gi\|83659771:6278-12613 | 6041 | 1672 | 60 |
| RNA-dependent RNA pol. | LNYV | gi\|83659771:6278-12613 | 5949 | 1673 | 60 |
| RNA-dependent RNA pol. | LNYV | gi\|83659771:6278-12613 | 5887 | 1674 | 60 |
| RNA-dependent RNA pol. | LNYV | gi\|83659771:6278-12613 | 5827 | 1675 | 60 |
| RNA-dependent RNA pol. | LNYV | gi\|83659771:6278-12613 | 5767 | 1676 | 60 |
| RNA-dependent RNA pol. | LNYV | gi\|83659771:6278-12613 | 5707 | 1677 | 60 |
| RNA-dependent RNA pol. | LNYV | gi\|83659771:6278-12613 | 5573 | 1678 | 60 |
| RNA-dependent RNA pol. | LNYV | gi\|83659771:6278-12613 | 5513 | 1679 | 60 |
| RNA-dependent RNA pol. | LNYV | gi\|83659771:6278-12613 | 5423 | 1680 | 60 |
| 5' trailer RNA | LNYV | gi\|83659771:12621-12807 | 128 | 1681 | 60 |
| 5' trailer RNA | LNYV | gi\|83659771:12621-12807 | 127 | 1682 | 60 |
| 5' trailer RNA | LNYV | gi\|83659771:12621-12807 | 126 | 1683 | 60 |
| 5' trailer RNA | LNYV | gi\|83659771:12621-12807 | 125 | 1684 | 60 |
| 5' trailer RNA | LNYV | gi\|83659771:12621-12807 | 124 | 1685 | 60 |
| 5' trailer RNA | LNYV | gi\|83659771:12621-12807 | 123 | 1686 | 60 |
| 5' trailer RNA | LNYV | gi\|83659771:12621-12807 | 115 | 1687 | 60 |
| 5' trailer RNA | LNYV | gi\|83659771:12621-12807 | 114 | 1688 | 60 |
| 5' trailer RNA | LNYV | gi\|83659771:12621-12807 | 113 | 1689 | 60 |
| 5' trailer RNA | LNYV | gi\|83659771:12621-12807 | 112 | 1690 | 60 |
| NS5 protein | Zika Brazil-ZKV2015 | gi\|985578255\|gb\|KU497555.1\| | 10296 | 1691 | 60 |
| NS5 protein | Zika Brazil-ZKV2015 | gi\|985578255\|gb\|KU497555.1\| | 10235 | 1692 | 60 |
| NS5 protein | Zika Brazil-ZKV2015 | gi\|985578255\|gb\|KU497555.1\| | 10162 | 1693 | 60 |
| NS5 protein | Zika Brazil-ZKV2015 | gi\|985578255\|gb\|KU497555.1\| | 9922 | 1694 | 60 |
| NS5 protein | Zika Brazil-ZKV2015 | gi\|985578255\|gb\|KU497555.1\| | 9714 | 1695 | 60 |
| NS5 protein | Zika Brazil-ZKV2015 | gi\|985578255\|gb\|KU497555.1\| | 9654 | 1696 | 60 |
| NS5 protein | Zika Brazil-ZKV2015 | gi\|985578255\|gb\|KU497555.1\| | 9510 | 1697 | 60 |

TABLE 1-continued

| \multicolumn{5}{c}{Selected viral probes} | | | | |
|---|---|---|---|---|
| NS5 protein | Zika Brazil-ZKV2015 | gi\|985578255\|gb\|KU497555.1\| | 9444 | 1698 | 60 |
| NS5 protein | Zika Brazil-ZKV2015 | gi\|985578255\|gb\|KU497555.1\| | 9383 | 1699 | 60 |
| NS5 protein | Zika Brazil-ZKV2015 | gi\|985578255\|gb\|KU497555.1\| | 9288 | 1700 | 60 |
| NS5 protein | Zika PRVABC59 | gi\|984874581\|gb\|KU501215.1\| | 10340 | 1701 | 60 |
| NS5 protein | Zika PRVABC59 | gi\|984874581\|gb\|KU501215.1\| | 10277 | 1702 | 60 |
| NS5 protein | Zika PRVABC59 | gi\|984874581\|gb\|KU501215.1\| | 10168 | 1703 | 60 |
| NS5 protein | Zika PRVABC59 | gi\|984874581\|gb\|KU501215.1\| | 9928 | 1704 | 60 |
| NS5 protein | Zika PRVABC59 | gi\|984874581\|gb\|KU501215.1\| | 9720 | 1705 | 60 |
| NS5 protein | Zika PRVABC59 | gi\|984874581\|gb\|KU501215.1\| | 9660 | 1706 | 60 |
| NS5 protein | Zika PRVABC59 | gi\|984874581\|gb\|KU501215.1\| | 9516 | 1707 | 60 |
| NS5 protein | Zika PRVABC59 | gi\|984874581\|gb\|KU501215.1\| | 9450 | 1708 | 60 |
| NS5 protein | Zika PRVABC59 | gi\|984874581\|gb\|KU501215.1\| | 9389 | 1709 | 60 |
| NS5 protein | Zika PRVABC59 | gi\|984874581\|gb\|KU501215.1\| | 9295 | 1710 | 60 |
| NS5 protein | Zika Z1106033 | gi\|973447404\|gb\|KU312312.1\| | 10274 | 1711 | 60 |
| NS5 protein | Zika Z1106033 | gi\|973447404\|gb\|KU312312.1\| | 10211 | 1712 | 60 |
| NS5 protein | Zika Z1106033 | gi\|973447404\|gb\|KU312312.1\| | 10102 | 1713 | 60 |
| NS5 protein | Zika Z1106033 | gi\|973447404\|gb\|KU312312.1\| | 9862 | 1714 | 60 |
| NS5 protein | Zika Z1106033 | gi\|973447404\|gb\|KU312312.1\| | 9654 | 1715 | 60 |
| NS5 protein | Zika Z1106033 | gi\|973447404\|gb\|KU312312.1\| | 9594 | 1716 | 60 |
| NS5 protein | Zika Z1106033 | gi\|973447404\|gb\|KU312312.1\| | 9450 | 1717 | 60 |
| NS5 protein | Zika Z1106033 | gi\|973447404\|gb\|KU312312.1\| | 9384 | 1718 | 60 |
| NS5 protein | Zika Z1106033 | gi\|973447404\|gb\|KU312312.1\| | 9323 | 1719 | 60 |
| NS5 protein | Zika Z1106033 | gi\|973447404\|gb\|KU312312.1\| | 9229 | 1720 | 60 |
| NS5 protein | Zika SSABR1 | gi\|992324757\|gb\|KU707826.1\| | 10274 | 1721 | 60 |
| NS5 protein | Zika SSABR1 | gi\|992324757\|gb\|KU707826.1\| | 10139 | 1722 | 60 |
| NS5 protein | Zika SSABR1 | gi\|992324757\|gb\|KU707826.1\| | 9900 | 1723 | 60 |
| NS5 protein | Zika SSABR1 | gi\|992324757\|gb\|KU707826.1\| | 9692 | 1724 | 60 |
| NS5 protein | Zika SSABR1 | gi\|992324757\|gb\|KU707826.1\| | 9632 | 1725 | 60 |
| NS5 protein | Zika SSABR1 | gi\|992324757\|gb\|KU707826.1\| | 9488 | 1726 | 60 |
| NS5 protein | Zika SSABR1 | gi\|992324757\|gb\|KU707826.1\| | 9422 | 1727 | 60 |
| NS5 protein | Zika SSABR1 | gi\|992324757\|gb\|KU707826.1\| | 9361 | 1728 | 60 |
| NS5 protein | Zika SSABR1 | gi\|992324757\|gb\|KU707826.1\| | 9296 | 1729 | 60 |
| NS5 protein | Zika SSABR1 | gi\|992324757\|gb\|KU707826.1\| | 9190 | 1730 | 60 |
| 5UTR | ZikaSPH2015 | gb\|KU321639.1\|:1-105 | 46 | 1731 | 60 |
| 5UTR | ZikaSPH2015 | gb\|KU321639.1\|:1-105 | 37 | 1732 | 60 |
| capsid | ZikaSPH2015 | gb\|KU321639.1\|:106-480 | 232 | 1733 | 60 |
| capsid | ZikaSPH2015 | gb\|KU321639.1\|:106-480 | 216 | 1734 | 60 |
| propeptide | ZikaSPH2015 | gb\|KU321639.1\|:478-750 | 100 | 1735 | 60 |
| propeptide | ZikaSPH2015 | gb\|KU321639.1\|:478-750 | 91 | 1736 | 60 |
| membrane protein | ZikaSPH2015 | gb\|KU321639.1\|:751-975 | 162 | 1737 | 60 |
| membrane protein | ZikaSPH2015 | gb\|KU321639.1\|:751-975 | 148 | 1738 | 60 |
| envelope protein | ZikaSPH2015 | gb\|KU321639.1\|:976-2490 | 1442 | 1739 | 60 |
| envelope protein | ZikaSPH2015 | gb\|KU321639.1\|:976-2490 | 1322 | 1740 | 60 |
| envelope protein | ZikaSPH2015 | gb\|KU321639.1\|:976-2490 | 1069 | 1741 | 60 |
| envelope protein | ZikaSPH2015 | gb\|KU321639.1\|:976-2490 | 556 | 1742 | 60 |
| envelope protein | ZikaSPH2015 | gb\|KU321639.1\|:976-2490 | 318 | 1743 | 60 |
| NS1 protein | ZikaSPH2015 | gb\|KU321639.1\|:2491-3576 | 1023 | 1744 | 60 |
| NS1 protein | ZikaSPH2015 | gb\|KU321639.1\|:2491-3576 | 648 | 1745 | 60 |
| NS1 protein | ZikaSPH2015 | gb\|KU321639.1\|:2491-3576 | 479 | 1746 | 60 |
| NS1 protein | ZikaSPH2015 | gb\|KU321639.1\|:2491-3576 | 221 | 1747 | 60 |
| NS2A protein | ZikaSPH2015 | gb\|KU321639.1\|:3577-4230 | 507 | 1748 | 60 |
| NS2A protein | ZikaSPH2015 | gb\|KU321639.1\|:3577-4230 | 503 | 1749 | 60 |
| NS2A protein | ZikaSPH2015 | gb\|KU321639.1\|:3577-4230 | 204 | 1750 | 60 |
| NS2B protein | ZikaSPH2015 | gb\|KU321639.1\|:4231-4662 | 146 | 1751 | 60 |
| NS2B protein | ZikaSPH2015 | gb\|KU321639.1\|:4231-4662 | 141 | 1752 | 60 |
| NS2B protein | ZikaSPH2015 | gb\|KU321639.1\|:4231-4662 | 136 | 1753 | 60 |
| NS3 protein | ZikaSPH2015 | gb\|KU321639.1\|:4663-6471 | 1618 | 1754 | 60 |
| NS3 protein | ZikaSPH2015 | gb\|KU321639.1\|:4663-6471 | 1415 | 1755 | 60 |
| NS3 protein | ZikaSPH2015 | gb\|KU321639.1\|:4663-6471 | 1013 | 1756 | 60 |
| NS3 protein | ZikaSPH2015 | gb\|KU321639.1\|:4663-6471 | 679 | 1757 | 60 |
| NS4A protein | ZikaSPH2015 | gb\|KU321639.1\|:6472-6912 | 196 | 1758 | 60 |
| NS4A protein | ZikaSPH2015 | gb\|KU321639.1\|:6472-6912 | 238 | 1759 | 60 |
| NS4A protein | ZikaSPH2015 | gb\|KU321639.1\|:6472-6912 | 59 | 1760 | 60 |
| NS4B protein | ZikaSPH2015 | gb\|KU321639.1\|:6913-8418 | 1395 | 1761 | 60 |
| NS4B protein | ZikaSPH2015 | gb\|KU321639.1\|:6913-8418 | 688 | 1762 | 60 |
| NS4B protein | ZikaSPH2015 | gb\|KU321639.1\|:6913-8418 | 425 | 1763 | 60 |
| NS4B protein | ZikaSPH2015 | gb\|KU321639.1\|:6913-8418 | 1 | 1764 | 60 |
| NS5 protein | ZikaSPH2015 | gb\|KU321639.1\|:8419-10374 | 1883 | 1765 | 60 |

TABLE 1-continued

| Selected viral probes | | | | | | | |
|---|---|---|---|---|---|---|---|
| NS5 protein | ZikaSPH2015 | gb\|KU321639.1\|:8419-10374 | 1241 | 1766 | 60 | | |
| NS5 protein | ZikaSPH2015 | gb\|KU321639.1\|:8419-10374 | 785 | 1767 | 60 | | |
| 3UTR | ZikaSPH2015 | gb\|KU321639.1\|:10378-10676 | 239 | 1768 | 60 | | |
| 3UTR | ZikaSPH2015 | gb\|KU321639.1\|:10378-10676 | 230 | 1769 | 60 | | |

| Product | End Distance | Tm | X-Hyb Pot | % G | % C | % A | % T | % GC | PolyX |
|---|---|---|---|---|---|---|---|---|---|
| 5 UTR | 99 | 85.97 | 0 | 36.67 | 18.33 | 20 | 25 | 55 | 3 |
| 5 UTR | 148 | 86.4 | 0 | 26.67 | 28.33 | 20 | 25 | 55 | 5 |
| 5 UTR | 149 | 86.4 | 0 | 25 | 30 | 20 | 25 | 55 | 5 |
| 5 UTR | 169 | 86.33 | 0 | 28.33 | 26.67 | 20 | 25 | 55 | 3 |
| 5 UTR | 170 | 85.49 | 0 | 28.33 | 25 | 21.67 | 25 | 53.33 | 3 |
| 5 UTR | 171 | 84.8 | 0 | 28.33 | 25 | 21.67 | 25 | 53.33 | 3 |
| 5 UTR | 172 | 84.8 | 0 | 28.33 | 25 | 21.67 | 25 | 53.33 | 3 |
| 5 UTR | 173 | 85.38 | 0 | 26.67 | 26.67 | 21.67 | 25 | 53.33 | 3 |
| 5 UTR | 174 | 86.09 | 0 | 26.67 | 28.33 | 21.67 | 23.33 | 55 | 3 |
| 5 UTR | 175 | 86.62 | 0 | 26.67 | 28.33 | 23.33 | 21.67 | 55 | 3 |
| core protein | 86 | 83.62 | 0 | 16.67 | 33.33 | 13.33 | 36.67 | 50 | 3 |
| core protein | 87 | 83.16 | 0 | 16.67 | 33.33 | 15 | 35 | 50 | 3 |
| core protein | 88 | 83.16 | 0 | 18.33 | 31.67 | 15 | 35 | 50 | 3 |
| core protein | 89 | 83.23 | 0 | 18.33 | 31.67 | 15 | 35 | 50 | 3 |
| core protein | 90 | 82.5 | 0 | 20 | 30 | 15 | 35 | 50 | 3 |
| core protein | 91 | 83.08 | 0 | 18.33 | 31.67 | 15 | 35 | 50 | 3 |
| core protein | 92 | 83.48 | 0 | 20 | 31.67 | 15 | 33.33 | 51.67 | 3 |
| core protein | 93 | 83.48 | 0 | 21.67 | 30 | 15 | 33.33 | 51.67 | 3 |
| core protein | 94 | 83.47 | 0 | 21.67 | 30 | 15 | 33.33 | 51.67 | 3 |
| core protein | 95 | 83.15 | 0 | 21.67 | 28.33 | 16.67 | 33.33 | 50 | 3 |
| E1 protein | 239 | 81.42 | 0 | 25 | 20 | 25 | 30 | 45 | 3 |
| E1 protein | 240 | 81.39 | 0 | 25 | 20 | 25 | 30 | 45 | 3 |
| E1 protein | 241 | 80.98 | 0 | 25 | 20 | 25 | 30 | 45 | 3 |
| E1 protein | 242 | 80.98 | 0 | 23.33 | 21.67 | 25 | 30 | 45 | 3 |
| E1 protein | 77 | 86.03 | 0 | 35 | 20 | 15 | 30 | 55 | 4 |
| E1 protein | 78 | 84.91 | 0 | 35 | 18.33 | 15 | 31.67 | 53.33 | 4 |
| E1 protein | 79 | 84.78 | 0 | 33.33 | 18.33 | 16.67 | 31.67 | 51.67 | 4 |
| E1 protein | 80 | 84.88 | 0 | 33.33 | 20 | 16.67 | 30 | 53.33 | 4 |
| E1 protein | 81 | 85.73 | 0 | 35 | 20 | 16.67 | 28.33 | 55 | 4 |
| E1 protein | 202 | 85.79 | 0 | 35 | 20 | 20 | 25 | 55 | 4 |
| E2 protein | 387 | 80.23 | 0 | 25 | 20 | 28.33 | 26.67 | 45 | 4 |
| E2 protein | 388 | 80.23 | 0 | 23.33 | 21.67 | 28.33 | 26.67 | 45 | 4 |
| E2 protein | 389 | 80.33 | 0 | 23.33 | 21.67 | 28.33 | 26.67 | 45 | 4 |
| E2 protein | 390 | 79.75 | 0 | 21.67 | 23.33 | 28.33 | 26.67 | 45 | 4 |
| E2 protein | 391 | 80.57 | 0 | 23.33 | 21.67 | 28.33 | 26.67 | 45 | 4 |
| E2 protein | 393 | 80.57 | 0 | 23.33 | 21.67 | 28.33 | 26.67 | 45 | 3 |
| E2 protein | 394 | 79.86 | 0 | 21.67 | 21.67 | 28.33 | 28.33 | 43.33 | 3 |
| E2 protein | 395 | 79.16 | 0 | 20 | 21.67 | 28.33 | 30 | 41.67 | 3 |
| E2 protein | 396 | 79.16 | 0 | 18.33 | 23.33 | 28.33 | 30 | 41.67 | 3 |
| E2 protein | 397 | 79.61 | 0 | 20 | 23.33 | 26.67 | 30 | 43.33 | 3 |
| p7 protein | 134 | 85.66 | 0 | 33.33 | 21.67 | 6.67 | 38.33 | 55 | 3 |
| p7 protein | 135 | 85.02 | 0 | 31.67 | 23.33 | 6.67 | 38.33 | 55 | 3 |
| p7 protein | 136 | 84.74 | 0 | 31.67 | 21.67 | 6.67 | 40 | 53.33 | 3 |
| p7 protein | 137 | 84.15 | 0 | 33.33 | 20 | 6.67 | 40 | 53.33 | 3 |
| p7 protein | 138 | 84.01 | 0 | 35 | 18.33 | 6.67 | 40 | 53.33 | 3 |
| p7 protein | 139 | 84.59 | 0 | 33.33 | 20 | 6.67 | 40 | 53.33 | 3 |
| p7 protein | 140 | 84.59 | 0 | 33.33 | 20 | 8.33 | 38.33 | 53.33 | 3 |
| p7 protein | 141 | 84 | 0 | 31.67 | 21.67 | 8.33 | 38.33 | 53.33 | 3 |
| p7 protein | 142 | 84.14 | 0 | 31.67 | 21.67 | 8.33 | 38.33 | 53.33 | 3 |
| p7 protein | 143 | 84.72 | 0 | 30 | 23.33 | 8.33 | 38.33 | 53.33 | 3 |
| NS2 protein | 286 | 81.87 | 0 | 23.33 | 21.67 | 26.67 | 28.33 | 45 | 4 |
| NS2 protein | 458 | 80.3 | 0 | 16.67 | 28.33 | 21.67 | 33.33 | 45 | 3 |
| NS2 protein | 459 | 79.57 | 0 | 15 | 28.33 | 23.33 | 33.33 | 43.33 | 3 |
| NS2 protein | 460 | 79.57 | 0 | 13.33 | 30 | 23.33 | 33.33 | 43.33 | 3 |
| NS2 protein | 461 | 79.55 | 0 | 13.33 | 30 | 23.33 | 33.33 | 43.33 | 3 |
| NS2 protein | 462 | 78.99 | 0 | 15 | 28.33 | 23.33 | 33.33 | 43.33 | 3 |
| NS2 protein | 463 | 79.66 | 0 | 15 | 28.33 | 23.33 | 33.33 | 43.33 | 3 |
| NS2 protein | 464 | 79.92 | 0 | 15 | 30 | 23.33 | 31.67 | 45 | 3 |
| NS2 protein | 465 | 80.63 | 0 | 16.67 | 28.33 | 23.33 | 31.67 | 45 | 3 |
| NS2 protein | 466 | 81.42 | 0 | 16.67 | 28.33 | 21.67 | 33.33 | 45 | 3 |
| NS3 protease/helicase | 82 | 81.47 | 0 | 15 | 30 | 33.33 | 21.67 | 45 | 3 |
| NS3 protease/helicase | 274 | 80.84 | 0 | 18.33 | 26.67 | 28.33 | 26.67 | 45 | 4 |
| NS3 protease/helicase | 1045 | 81.99 | 0 | 20 | 25 | 26.67 | 28.33 | 45 | 3 |
| NS3 protease/helicase | 150 | 85.74 | 0 | 18.33 | 35 | 25 | 21.67 | 53.33 | 4 |
| NS3 protease/helicase | 397 | 85.21 | 0 | 26.67 | 28.33 | 25 | 20 | 55 | 3 |

TABLE 1-continued

| Selected viral probes | | | | | | | | | |
|---|---|---|---|---|---|---|---|---|---|
| NS3 protease/helicase | 600 | 82.34 | 0 | 15 | 35 | 25 | 25 | 50 | 3 |
| NS3 protease/helicase | 660 | 83.78 | 0 | 25 | 26.67 | 20 | 28.33 | 51.67 | 3 |
| NS3 protease/helicase | 802 | 86.5 | 0 | 25 | 30 | 23.33 | 21.67 | 55 | 3 |
| NS3 protease/helicase | 874 | 85.78 | 0 | 21.67 | 33.33 | 21.67 | 23.33 | 55 | 5 |
| NS3 protease/helicase | 1129 | 85.24 | 0 | 20 | 35 | 25 | 20 | 55 | 4 |
| NS4A protein | 60 | 82.67 | 0 | 31.67 | 20 | 26.67 | 21.67 | 51.67 | 3 |
| NS4A protein | 61 | 82.67 | 0 | 33.33 | 18.33 | 26.67 | 21.67 | 51.67 | 3 |
| NS4A protein | 62 | 83 | 0 | 31.67 | 18.33 | 28.33 | 21.67 | 50 | 3 |
| NS4A protein | 63 | 82.48 | 0 | 31.67 | 18.33 | 30 | 20 | 50 | 3 |
| NS4A protein | 64 | 82.45 | 0 | 31.67 | 18.33 | 30 | 20 | 50 | 3 |
| NS4A protein | 65 | 82.74 | 0 | 33.33 | 18.33 | 28.33 | 20 | 51.67 | 3 |
| NS4A protein | 66 | 83.4 | 0 | 33.33 | 18.33 | 28.33 | 20 | 51.67 | 3 |
| NS4A protein | 67 | 84.1 | 0 | 33.33 | 20 | 26.67 | 20 | 53.33 | 3 |
| NS4A protein | 68 | 84.37 | 0 | 33.33 | 21.67 | 25 | 20 | 55 | 3 |
| NS4A protein | 69 | 84.1 | 0 | 31.67 | 21.67 | 25 | 21.67 | 53.33 | 3 |
| NS4B protein | 651 | 81.1 | 0 | 26.67 | 18.33 | 28.33 | 26.67 | 45 | 3 |
| NS4B protein | 61 | 85.12 | 0 | 26.67 | 28.33 | 23.33 | 21.67 | 55 | 3 |
| NS4B protein | 82 | 85.36 | 0 | 23.33 | 31.67 | 25 | 20 | 55 | 3 |
| NS4B protein | 328 | 85.9 | 0 | 28.33 | 26.67 | 21.67 | 23.33 | 55 | 4 |
| NS4B protein | 368 | 86.89 | 0 | 35 | 20 | 20 | 25 | 55 | 3 |
| NS4B protein | 558 | 85.23 | 0 | 16.67 | 35 | 23.33 | 25 | 51.67 | 4 |
| NS4B protein | 580 | 86.8 | 0 | 21.67 | 33.33 | 18.33 | 26.67 | 55 | 4 |
| NS4B protein | 602 | 86.58 | 0 | 25 | 30 | 18.33 | 26.67 | 55 | 4 |
| NS4B protein | 622 | 84.77 | 0 | 28.33 | 25 | 21.67 | 25 | 53.33 | 3 |
| NS4B protein | 671 | 84.31 | 0 | 26.67 | 25 | 26.67 | 21.67 | 51.67 | 3 |
| NS5A protein | 943 | 82.2 | 0 | 16.67 | 28.33 | 28.33 | 26.67 | 45 | 5 |
| NS5A protein | 207 | 85.98 | 0 | 20 | 35 | 23.33 | 21.67 | 55 | 3 |
| NS5A protein | 267 | 86.55 | 0 | 20 | 35 | 23.33 | 21.67 | 55 | 4 |
| NS5A protein | 371 | 85.27 | 0 | 26.67 | 28.33 | 26.67 | 18.33 | 55 | 5 |
| NS5A protein | 519 | 85.49 | 0 | 36.67 | 18.33 | 23.33 | 21.67 | 55 | 3 |
| NS5A protein | 767 | 85.27 | 0 | 23.33 | 31.67 | 25 | 20 | 55 | 3 |
| NS5A protein | 830 | 85.03 | 0 | 30 | 25 | 23.33 | 21.67 | 55 | 4 |
| NS5A protein | 1003 | 84.8 | 0 | 38.33 | 16.67 | 25 | 20 | 55 | 5 |
| NS5A protein | 1131 | 85.18 | 0 | 31.67 | 23.33 | 23.33 | 21.67 | 55 | 4 |
| NS5A protein | 1191 | 84.43 | 0 | 26.67 | 25 | 28.33 | 20 | 51.67 | 5 |
| NS5B RNA-dependent RNA polymerase | 214 | 81.13 | 0 | 18.33 | 26.67 | 35 | 20 | 45 | 3 |
| NS5B RNA-dependent RNA polymerase | 215 | 80 | 0 | 18.33 | 25 | 35 | 21.67 | 43.33 | 3 |
| NS5B RNA-dependent RNA polymerase | 216 | 79.91 | 0 | 16.67 | 25 | 36.67 | 21.67 | 41.67 | 3 |
| NS5B RNA-dependent RNA polymerase | 217 | 80.32 | 0 | 16.67 | 26.67 | 35 | 21.67 | 43.33 | 3 |
| NS5B RNA-dependent RNA polymerase | 218 | 81.05 | 0 | 16.67 | 28.33 | 35 | 20 | 45 | 3 |
| NS5B RNA-dependent RNA polymerase | 383 | 81.64 | 0 | 15 | 30 | 30 | 25 | 45 | 4 |
| NS5B RNA-dependent RNA polymerase | 490 | 80.87 | 0 | 21.67 | 23.33 | 23.33 | 31.67 | 45 | 3 |
| NS5B RNA-dependent RNA polymerase | 491 | 81.12 | 0 | 21.67 | 23.33 | 23.33 | 31.67 | 45 | 3 |
| NS5B RNA-dependent RNA polymerase | 542 | 81.8 | 0 | 20 | 25 | 25 | 30 | 45 | 5 |
| NS5B RNA-dependent RNA polymerase | 543 | 82.09 | 0 | 20 | 25 | 25 | 30 | 45 | 5 |
| 5 UTR | 80 | 86.27 | 0 | 36.67 | 18.33 | 20 | 25 | 55 | 3 |
| 5 UTR | 150 | 86.34 | 0 | 26.67 | 28.33 | 18.33 | 26.67 | 55 | 3 |
| 5 UTR | 151 | 85.5 | 0 | 26.67 | 26.67 | 20 | 26.67 | 53.33 | 3 |
| 5 UTR | 152 | 84.8 | 0 | 26.67 | 26.67 | 20 | 26.67 | 53.33 | 3 |
| 5 UTR | 153 | 84.8 | 0 | 26.67 | 26.67 | 20 | 26.67 | 53.33 | 3 |
| 5 UTR | 154 | 85.38 | 0 | 25 | 28.33 | 20 | 26.67 | 53.33 | 3 |
| 5 UTR | 155 | 86.1 | 0 | 25 | 30 | 20 | 25 | 55 | 3 |
| 5 UTR | 156 | 86.64 | 0 | 25 | 30 | 21.67 | 23.33 | 55 | 3 |

TABLE 1-continued

| Selected viral probes | | | | | | | | | |
|---|---|---|---|---|---|---|---|---|---|
| 5 UTR | 159 | 85.77 | 0 | 25 | 30 | 21.67 | 23.33 | 55 | 3 |
| 5 UTR | 160 | 85.03 | 0 | 26.67 | 28.33 | 21.67 | 23.33 | 55 | 3 |
| core protein | 550 | 82 | 0 | 15 | 30 | 43.33 | 11.67 | 45 | 5 |
| core protein | 551 | 81.31 | 0 | 13.33 | 30 | 45 | 11.67 | 43.33 | 5 |
| core protein | 552 | 80.33 | 0 | 11.67 | 30 | 45 | 13.33 | 41.67 | 5 |
| core protein | 553 | 79.71 | 0 | 11.67 | 30 | 45 | 13.33 | 41.67 | 5 |
| core protein | 554 | 80.36 | 0 | 11.67 | 30 | 45 | 13.33 | 41.67 | 5 |
| core protein | 555 | 80.76 | 0 | 11.67 | 30 | 45 | 13.33 | 41.67 | 5 |
| core protein | 556 | 80.73 | 0 | 11.67 | 30 | 46.67 | 11.67 | 41.67 | 5 |
| core protein | 557 | 80.23 | 0 | 11.67 | 30 | 48.33 | 10 | 41.67 | 5 |
| core protein | 558 | 80.17 | 0 | 10 | 30 | 50 | 10 | 40 | 5 |
| core protein | 573 | 80.76 | 0 | 13.33 | 30 | 46.67 | 10 | 43.33 | 5 |
| E1 protein | 84 | 85.82 | 0 | 30 | 25 | 13.33 | 31.67 | 55 | 3 |
| E1 protein | 120 | 86.52 | 0 | 31.67 | 23.33 | 15 | 30 | 55 | 4 |
| E1 protein | 140 | 85.78 | 0 | 31.67 | 23.33 | 16.67 | 28.33 | 55 | 4 |
| E1 protein | 160 | 85.1 | 0 | 30 | 25 | 18.33 | 26.67 | 55 | 4 |
| E1 protein | 217 | 86.77 | 0 | 28.33 | 26.67 | 23.33 | 21.67 | 55 | 3 |
| E1 protein | 237 | 84.8 | 0 | 26.67 | 26.67 | 25 | 21.67 | 53.33 | 3 |
| E1 protein | 257 | 85.97 | 0 | 21.67 | 33.33 | 23.33 | 21.67 | 55 | 3 |
| E1 protein | 283 | 85.94 | 0 | 20 | 35 | 18.33 | 26.67 | 55 | 3 |
| E1 protein | 303 | 86.01 | 0 | 20 | 33.33 | 21.67 | 25 | 53.33 | 3 |
| E1 protein | 555 | 85.87 | 0 | 23.33 | 31.67 | 23.33 | 21.67 | 55 | 2 |
| E2/NS1 protein | 106 | 81.03 | 0 | 15 | 30 | 30 | 25 | 45 | 4 |
| E2/NS1 protein | 107 | 81 | 0 | 15 | 28.33 | 31.67 | 25 | 43.33 | 4 |
| E2/NS1 protein | 109 | 79.92 | 0 | 13.33 | 30 | 33.33 | 23.33 | 43.33 | 4 |
| E2/NS1 protein | 110 | 80.58 | 0 | 13.33 | 30 | 33.33 | 23.33 | 43.33 | 4 |
| E2/NS1 protein | 111 | 81.11 | 0 | 13.33 | 30 | 35 | 21.67 | 43.33 | 4 |
| E2/NS1 protein | 324 | 80.66 | 0 | 28.33 | 16.67 | 30 | 25 | 45 | 4 |
| E2/NS1 protein | 325 | 80.1 | 0 | 28.33 | 16.67 | 30 | 25 | 45 | 4 |
| E2/NS1 protein | 326 | 79.81 | 0 | 26.67 | 16.67 | 31.67 | 25 | 43.33 | 4 |
| E2/NS1 protein | 327 | 79.81 | 0 | 26.67 | 16.67 | 31.67 | 25 | 43.33 | 4 |
| E2/NS1 protein | 328 | 79.81 | 0 | 26.67 | 16.67 | 31.67 | 25 | 43.33 | 4 |
| NS2 protein | 69 | 86.42 | 0 | 33.33 | 21.67 | 16.67 | 28.33 | 55 | 4 |
| NS2 protein | 109 | 83.87 | 0 | 33.33 | 20 | 23.33 | 23.33 | 53.33 | 4 |
| NS2 protein | 184 | 85.33 | 0 | 23.33 | 31.67 | 18.33 | 26.67 | 55 | 4 |
| NS2 protein | 224 | 85.13 | 0 | 28.33 | 26.67 | 21.67 | 23.33 | 55 | 3 |
| NS2 protein | 312 | 86.25 | 0 | 30 | 25 | 18.33 | 26.67 | 55 | 4 |
| NS2 protein | 354 | 86.42 | 0 | 28.33 | 26.67 | 16.67 | 28.33 | 55 | 4 |
| NS2 protein | 394 | 86.1 | 0 | 30 | 25 | 16.67 | 28.33 | 55 | 3 |
| NS2 protein | 492 | 85.79 | 0 | 36.67 | 18.33 | 13.33 | 31.67 | 55 | 5 |
| NS2 protein | 532 | 83.84 | 0 | 23.33 | 26.67 | 13.33 | 36.67 | 50 | 5 |
| NS2 protein | 572 | 85.42 | 0 | 25 | 30 | 18.33 | 26.67 | 55 | 5 |
| NS3 protease/helicase | 257 | 80.97 | 0 | 25 | 20 | 35 | 20 | 45 | 5 |
| NS3 protease/helicase | 258 | 79.98 | 0 | 23.33 | 20 | 35 | 21.67 | 43.33 | 5 |
| NS3 protease/helicase | 259 | 79.94 | 0 | 23.33 | 18.33 | 35 | 23.33 | 41.67 | 5 |
| NS3 protease/helicase | 260 | 79.58 | 0 | 23.33 | 20 | 35 | 21.67 | 43.33 | 5 |
| NS3 protease/helicase | 261 | 79.13 | 0 | 23.33 | 18.33 | 35 | 23.33 | 41.67 | 5 |
| NS3 protease/helicase | 262 | 79.21 | 0 | 23.33 | 18.33 | 35 | 23.33 | 41.67 | 5 |
| NS3 protease/helicase | 263 | 79.3 | 0 | 23.33 | 18.33 | 33.33 | 25 | 41.67 | 5 |
| NS3 protease/helicase | 264 | 78.66 | 0 | 21.67 | 20 | 33.33 | 25 | 41.67 | 5 |
| NS3 protease/helicase | 265 | 79.21 | 0 | 21.67 | 20 | 33.33 | 25 | 41.67 | 5 |
| NS3 protease/helicase | 266 | 79.51 | 0 | 21.67 | 21.67 | 31.67 | 25 | 43.33 | 5 |
| NS4A protein | 60 | 84.4 | 0 | 35 | 18.33 | 21.67 | 25 | 53.33 | 4 |
| NS4A protein | 61 | 84.4 | 0 | 36.67 | 16.67 | 21.67 | 25 | 53.33 | 4 |
| NS4A protein | 62 | 84.65 | 0 | 38.33 | 16.67 | 21.67 | 23.33 | 55 | 4 |
| NS4A protein | 63 | 84.55 | 0 | 38.33 | 16.67 | 21.67 | 23.33 | 55 | 4 |
| NS4A protein | 64 | 84.5 | 0 | 36.67 | 18.33 | 21.67 | 23.33 | 55 | 4 |
| NS4A protein | 65 | 84.65 | 0 | 36.67 | 18.33 | 21.67 | 23.33 | 55 | 4 |

TABLE 1-continued

| Selected viral probes | | | | | | | | | |
|---|---|---|---|---|---|---|---|---|---|
| NS4A protein | 66 | 84.5 | 0 | 36.67 | 18.33 | 21.67 | 23.33 | 55 | 4 |
| NS4A protein | 67 | 84.64 | 0 | 36.67 | 18.33 | 21.67 | 23.33 | 55 | 4 |
| NS4A protein | 68 | 84.45 | 0 | 35 | 18.33 | 21.67 | 25 | 53.33 | 4 |
| NS4A protein | 69 | 84.41 | 0 | 33.33 | 18.33 | 21.67 | 26.67 | 51.67 | 4 |
| NS4B protein | 498 | 81.45 | 0 | 20 | 25 | 33.33 | 21.67 | 45 | 3 |
| NS4B protein | 499 | 81.54 | 0 | 20 | 25 | 33.33 | 21.67 | 45 | 3 |
| NS4B protein | 573 | 81.76 | 0 | 16.67 | 28.33 | 36.67 | 18.33 | 45 | 3 |
| NS4B protein | 574 | 81.76 | 0 | 15 | 30 | 36.67 | 18.33 | 45 | 3 |
| NS4B protein | 578 | 82.24 | 0 | 15 | 30 | 38.33 | 16.67 | 45 | 3 |
| NS4B protein | 579 | 81.73 | 0 | 15 | 30 | 38.33 | 16.67 | 45 | 3 |
| NS4B protein | 580 | 81.06 | 0 | 16.67 | 28.33 | 38.33 | 16.67 | 45 | 3 |
| NS4B protein | 581 | 80.87 | 0 | 16.67 | 26.67 | 38.33 | 18.33 | 43.33 | 3 |
| NS4B protein | 582 | 80.8 | 0 | 16.67 | 26.67 | 38.33 | 18.33 | 43.33 | 3 |
| NS4B protein | 583 | 81.64 | 0 | 18.33 | 26.67 | 36.67 | 18.33 | 45 | 3 |
| NS5A protein | 1352 | 82.47 | 0 | 15 | 30 | 26.67 | 28.33 | 45 | 5 |
| NS5A protein | 1360 | 80.77 | 0 | 13.33 | 30 | 31.67 | 25 | 43.33 | 5 |
| NS5A protein | 1361 | 80.86 | 0 | 13.33 | 30 | 31.67 | 25 | 43.33 | 5 |
| NS5A protein | 1363 | 80.94 | 0 | 13.33 | 30 | 33.33 | 23.33 | 43.33 | 5 |
| NS5A protein | 1364 | 80.21 | 0 | 13.33 | 30 | 33.33 | 23.33 | 43.33 | 5 |
| NS5A protein | 1365 | 80.37 | 0 | 13.33 | 30 | 33.33 | 23.33 | 43.33 | 5 |
| NS5A protein | 1366 | 80.16 | 0 | 11.67 | 30 | 33.33 | 25 | 41.67 | 5 |
| NS5A protein | 1367 | 79.46 | 0 | 11.67 | 28.33 | 33.33 | 26.67 | 40 | 5 |
| NS5A protein | 1368 | 78.76 | 0 | 11.67 | 26.67 | 33.33 | 28.33 | 38.33 | 5 |
| NS5A protein | 1369 | 78.05 | 0 | 13.33 | 25 | 33.33 | 28.33 | 38.33 | 5 |
| NS5B RNA-dependent RNA polymerase | 161 | 82.16 | 0 | 16.67 | 28.33 | 26.67 | 28.33 | 45 | 5 |
| NS5B RNA-dependent RNA polymerase | 162 | 81.45 | 0 | 16.67 | 28.33 | 26.67 | 28.33 | 45 | 5 |
| NS5B RNA-dependent RNA polymerase | 163 | 81.29 | 0 | 16.67 | 26.67 | 28.33 | 28.33 | 43.33 | 5 |
| NS5B RNA-dependent RNA polymerase | 164 | 81.01 | 0 | 16.67 | 26.67 | 26.67 | 30 | 43.33 | 5 |
| NS5B RNA-dependent RNA polymerase | 165 | 80.66 | 0 | 16.67 | 28.33 | 25 | 30 | 45 | 5 |
| NS5B RNA-dependent RNA polymerase | 166 | 80.8 | 0 | 16.67 | 28.33 | 25 | 30 | 45 | 5 |
| NS5B RNA-dependent RNA polymerase | 167 | 81.11 | 0 | 16.67 | 26.67 | 26.67 | 30 | 43.33 | 5 |
| NS5B RNA-dependent RNA polymerase | 168 | 80.73 | 0 | 16.67 | 28.33 | 25 | 30 | 45 | 5 |
| NS5B RNA-dependent RNA polymerase | 169 | 80.73 | 0 | 16.67 | 28.33 | 25 | 30 | 45 | 5 |
| NS5B RNA-dependent RNA polymerase | 170 | 80.73 | 0 | 16.67 | 28.33 | 25 | 30 | 45 | 5 |
| 5 UTR | 95 | 86.03 | 0 | 35 | 20 | 16.67 | 28.33 | 55 | 3 |
| 5 UTR | 96 | 86.01 | 0 | 35 | 20 | 18.33 | 26.67 | 55 | 3 |
| 5 UTR | 98 | 85.18 | 0 | 36.67 | 18.33 | 20 | 25 | 55 | 3 |
| 5 UTR | 99 | 85.09 | 0 | 36.67 | 18.33 | 20 | 25 | 55 | 3 |
| 5 UTR | 148 | 86.22 | 0 | 23.33 | 31.67 | 23.33 | 21.67 | 55 | 5 |
| 5 UTR | 149 | 86.22 | 0 | 21.67 | 33.33 | 23.33 | 21.67 | 55 | 5 |
| 5 UTR | 170 | 86.32 | 0 | 28.33 | 26.67 | 21.67 | 23.33 | 55 | 4 |
| 5 UTR | 171 | 85.62 | 0 | 28.33 | 26.67 | 21.67 | 23.33 | 55 | 4 |
| 5 UTR | 172 | 85.62 | 0 | 28.33 | 26.67 | 21.67 | 23.33 | 55 | 4 |
| 5 UTR | 173 | 86.2 | 0 | 26.67 | 28.33 | 21.67 | 23.33 | 55 | 4 |
| Core protein | 88 | 82.34 | 0 | 16.67 | 28.33 | 15 | 40 | 45 | 4 |
| Core protein | 89 | 82.06 | 0 | 16.67 | 28.33 | 15 | 40 | 45 | 4 |
| Core protein | 90 | 81.52 | 0 | 16.67 | 28.33 | 16.67 | 38.33 | 45 | 4 |
| Core protein | 91 | 81.43 | 0 | 16.67 | 28.33 | 16.67 | 38.33 | 45 | 4 |
| Core protein | 60 | 80.8 | 0 | 11.67 | 31.67 | 11.67 | 45 | 43.33 | 4 |
| Core protein | 61 | 80.29 | 0 | 11.67 | 31.67 | 11.67 | 45 | 43.33 | 4 |
| Core protein | 62 | 80.37 | 0 | 11.67 | 31.67 | 11.67 | 45 | 43.33 | 4 |
| Core protein | 72 | 80.32 | 0 | 11.67 | 30 | 10 | 48.33 | 41.67 | 4 |
| Core protein | 73 | 80.39 | 0 | 13.33 | 30 | 10 | 46.67 | 43.33 | 4 |
| Core protein | 75 | 81.25 | 0 | 16.67 | 28.33 | 8.33 | 46.67 | 45 | 4 |
| E1 protein | 540 | 81.72 | 0 | 21.67 | 23.33 | 28.33 | 26.67 | 45 | 2 |
| E1 protein | 541 | 80.93 | 0 | 21.67 | 23.33 | 26.67 | 28.33 | 45 | 2 |
| E1 protein | 542 | 80.8 | 0 | 21.67 | 21.67 | 26.67 | 30 | 43.33 | 2 |
| E1 protein | 543 | 80.36 | 0 | 21.67 | 23.33 | 25 | 30 | 45 | 2 |

TABLE 1-continued

| Selected viral probes | | | | | | | | | |
|---|---|---|---|---|---|---|---|---|---|
| E1 protein | 544 | 80.92 | 0 | 21.67 | 23.33 | 25 | 30 | 45 | 2 |
| E1 protein | 545 | 80.83 | 0 | 21.67 | 23.33 | 23.33 | 31.67 | 45 | 2 |
| E1 protein | 546 | 80.12 | 0 | 23.33 | 21.67 | 23.33 | 31.67 | 45 | 2 |
| E1 protein | 547 | 80.69 | 0 | 21.67 | 23.33 | 23.33 | 31.67 | 45 | 2 |
| E1 protein | 548 | 80.76 | 0 | 21.67 | 23.33 | 25 | 30 | 45 | 2 |
| E1 protein | 549 | 80.44 | 0 | 21.67 | 21.67 | 25 | 31.67 | 43.33 | 2 |
| E2/NS1 protein | 132 | 81.65 | 0 | 16.67 | 28.33 | 28.33 | 26.67 | 45 | 4 |
| E2/NS1 protein | 320 | 81.74 | 0 | 31.67 | 13.33 | 20 | 35 | 45 | 3 |
| E2/NS1 protein | 321 | 81.07 | 0 | 31.67 | 13.33 | 20 | 35 | 45 | 3 |
| E2/NS1 protein | 322 | 81.08 | 0 | 31.67 | 13.33 | 20 | 35 | 45 | 3 |
| E2/NS1 protein | 323 | 80.65 | 0 | 31.67 | 11.67 | 20 | 36.67 | 43.33 | 3 |
| E2/NS1 protein | 324 | 80.08 | 0 | 31.67 | 11.67 | 20 | 36.67 | 43.33 | 3 |
| E2/NS1 protein | 325 | 79.81 | 0 | 31.67 | 10 | 21.67 | 36.67 | 41.67 | 3 |
| E2/NS1 protein | 326 | 79.81 | 0 | 31.67 | 10 | 21.67 | 36.67 | 41.67 | 3 |
| E2/NS1 protein | 327 | 80.59 | 0 | 31.67 | 10 | 21.67 | 36.67 | 41.67 | 3 |
| E2/NS1 protein | 328 | 80.31 | 0 | 31.67 | 10 | 21.67 | 36.67 | 41.67 | 3 |
| NS2 | 108 | 81.33 | 0 | 23.33 | 21.67 | 30 | 25 | 45 | 4 |
| NS2 | 122 | 81.32 | 0 | 18.33 | 26.67 | 30 | 25 | 45 | 3 |
| NS2 | 124 | 80.65 | 0 | 20 | 25 | 31.67 | 23.33 | 45 | 3 |
| NS2 | 125 | 80.51 | 0 | 20 | 23.33 | 33.33 | 23.33 | 43.33 | 3 |
| NS2 | 126 | 80 | 0 | 20 | 23.33 | 33.33 | 23.33 | 43.33 | 3 |
| NS2 | 127 | 80.1 | 0 | 20 | 23.33 | 33.33 | 23.33 | 43.33 | 3 |
| NS2 | 128 | 80.54 | 0 | 20 | 23.33 | 33.33 | 23.33 | 43.33 | 3 |
| NS2 | 129 | 80.09 | 0 | 20 | 25 | 31.67 | 23.33 | 45 | 3 |
| NS2 | 130 | 80.47 | 0 | 20 | 23.33 | 31.67 | 25 | 43.33 | 3 |
| NS2 | 131 | 80.09 | 0 | 21.67 | 23.33 | 31.67 | 23.33 | 45 | 3 |
| NS3 protease/helicase | 270 | 80.7 | 0 | 16.67 | 28.33 | 28.33 | 26.67 | 45 | 3 |
| NS3 protease/helicase | 272 | 80.77 | 0 | 16.67 | 28.33 | 30 | 25 | 45 | 3 |
| NS3 protease/helicase | 277 | 80.89 | 0 | 16.67 | 28.33 | 30 | 25 | 45 | 3 |
| NS3 protease/helicase | 278 | 80.89 | 0 | 16.67 | 28.33 | 28.33 | 26.67 | 45 | 3 |
| NS3 protease/helicase | 280 | 80.24 | 0 | 15 | 30 | 30 | 25 | 45 | 3 |
| NS3 protease/helicase | 281 | 80.24 | 0 | 16.67 | 28.33 | 30 | 25 | 45 | 3 |
| NS3 protease/helicase | 283 | 80.98 | 0 | 18.33 | 26.67 | 30 | 25 | 45 | 3 |
| NS3 protease/helicase | 309 | 80.9 | 0 | 20 | 25 | 23.33 | 31.67 | 45 | 4 |
| NS3 protease/helicase | 310 | 80.39 | 0 | 20 | 25 | 21.67 | 33.33 | 45 | 4 |
| NS3 protease/helicase | 311 | 80.33 | 0 | 20 | 23.33 | 23.33 | 33.33 | 43.33 | 4 |
| NS4A protein | 60 | 81.66 | 0 | 28.33 | 20 | 31.67 | 20 | 48.33 | 3 |
| NS4A protein | 61 | 81.66 | 0 | 30 | 18.33 | 31.67 | 20 | 48.33 | 3 |
| NS4A protein | 62 | 81.97 | 0 | 28.33 | 18.33 | 33.33 | 20 | 46.67 | 3 |
| NS4A protein | 63 | 81.46 | 0 | 28.33 | 18.33 | 35 | 18.33 | 46.67 | 3 |
| NS4A protein | 64 | 81.53 | 0 | 26.67 | 20 | 35 | 18.33 | 46.67 | 3 |
| NS4A protein | 65 | 81.96 | 0 | 28.33 | 20 | 33.33 | 18.33 | 48.33 | 3 |
| NS4A protein | 66 | 81.96 | 0 | 28.33 | 20 | 33.33 | 18.33 | 48.33 | 3 |
| NS4A protein | 67 | 82.6 | 0 | 28.33 | 20 | 33.33 | 18.33 | 48.33 | 3 |
| NS4A protein | 68 | 82.63 | 0 | 28.33 | 20 | 33.33 | 18.33 | 48.33 | 3 |
| NS4A protein | 69 | 81.96 | 0 | 28.33 | 20 | 33.33 | 18.33 | 48.33 | 3 |
| NS4B protein | 547 | 81.84 | 0 | 15 | 30 | 25 | 30 | 45 | 6 |
| NS4B protein | 548 | 81.84 | 0 | 15 | 30 | 23.33 | 31.67 | 45 | 6 |
| NS4B protein | 651 | 81.96 | 0 | 26.67 | 18.33 | 26.67 | 28.33 | 45 | 4 |
| NS4B protein | 652 | 82.25 | 0 | 26.67 | 18.33 | 26.67 | 28.33 | 45 | 4 |
| NS4B protein | 654 | 81.23 | 0 | 26.67 | 18.33 | 28.33 | 26.67 | 45 | 4 |
| NS4B protein | 655 | 81.95 | 0 | 28.33 | 16.67 | 28.33 | 26.67 | 45 | 4 |
| NS4B protein | 666 | 82.5 | 0 | 25 | 20 | 28.33 | 26.67 | 45 | 4 |
| NS4B protein | 667 | 81.99 | 0 | 25 | 20 | 30 | 25 | 45 | 4 |
| NS4B protein | 668 | 81.65 | 0 | 23.33 | 20 | 30 | 26.67 | 43.33 | 4 |
| NS4B protein | 669 | 81.37 | 0 | 25 | 20 | 28.33 | 26.67 | 45 | 4 |
| NS5A protein | 844 | 80.76 | 0 | 20 | 25 | 23.33 | 31.67 | 45 | 4 |
| NS5A protein | 845 | 80.32 | 0 | 20 | 25 | 23.33 | 31.67 | 45 | 4 |

TABLE 1-continued

| Selected viral probes | | | | | | | | |
|---|---|---|---|---|---|---|---|---|
| NS5A protein | 846 | 80.22 | 0 | 20 | 25 | 23.33 | 31.67 | 45 | 4 |
| NS5A protein | 847 | 80.15 | 0 | 20 | 25 | 25 | 30 | 45 | 4 |
| NS5A protein | 848 | 80.05 | 0 | 20 | 25 | 25 | 30 | 45 | 4 |
| NS5A protein | 849 | 80.05 | 0 | 20 | 25 | 26.67 | 28.33 | 45 | 4 |
| NS5A protein | 850 | 79.39 | 0 | 21.67 | 23.33 | 26.67 | 28.33 | 45 | 3 |
| NS5A protein | 851 | 79.19 | 0 | 21.67 | 21.67 | 26.67 | 30 | 43.33 | 3 |
| NS5A protein | 852 | 78.49 | 0 | 21.67 | 20 | 26.67 | 31.67 | 41.67 | 3 |
| NS5A protein | 853 | 78.59 | 0 | 23.33 | 18.33 | 26.67 | 31.67 | 41.67 | 3 |
| NS5B RNA-dependent RNA polymerase | 226 | 82.27 | 0 | 20 | 25 | 30 | 25 | 45 | 4 |
| NS5B RNA-dependent RNA polymerase | 401 | 81.84 | 0 | 16.67 | 28.33 | 28.33 | 26.67 | 45 | 3 |
| NS5B RNA-dependent RNA polymerase | 424 | 79.41 | 0 | 16.67 | 26.67 | 26.67 | 30 | 43.33 | 3 |
| NS5B RNA-dependent RNA polymerase | 444 | 81.36 | 0 | 20 | 25 | 23.33 | 31.67 | 45 | 4 |
| NS5B RNA-dependent RNA polymerase | 491 | 80.71 | 0 | 13.33 | 30 | 23.33 | 33.33 | 43.33 | 5 |
| NS5B RNA-dependent RNA polymerase | 512 | 80.85 | 0 | 18.33 | 26.67 | 25 | 30 | 45 | 5 |
| NS5B RNA-dependent RNA polymerase | 1102 | 80.76 | 0 | 26.67 | 18.33 | 35 | 20 | 45 | 3 |
| NS5B RNA-dependent RNA polymerase | 1248 | 79.68 | 0 | 25 | 18.33 | 28.33 | 28.33 | 43.33 | 3 |
| NS5B RNA-dependent RNA polymerase | 1627 | 80.61 | 0 | 23.33 | 21.67 | 33.33 | 21.67 | 45 | 3 |
| NS5B RNA-dependent RNA polymerase | 1675 | 79.91 | 0 | 20 | 25 | 28.33 | 26.67 | 45 | 2 |
| Gag-Pol | 67 | 80.21 | 0 | 35 | 8.33 | 33.33 | 23.33 | 43.33 | 4 |
| Gag-Pol | 144 | 77.82 | 0 | 28.33 | 11.67 | 40 | 20 | 40 | 4 |
| Gag-Pol | 204 | 80.91 | 0 | 23.33 | 20 | 33.33 | 23.33 | 43.33 | 4 |
| Gag-Pol | 295 | 79.33 | 0 | 28.33 | 13.33 | 43.33 | 15 | 41.67 | 6 |
| Gag-Pol | 355 | 78.04 | 0 | 21.67 | 15 | 40 | 23.33 | 36.67 | 6 |
| Gag-Pol | 450 | 74.91 | 0 | 18.33 | 16.67 | 43.33 | 21.67 | 35 | 4 |
| Gag-Pol | 546 | 81.58 | 0 | 23.33 | 21.67 | 33.33 | 21.67 | 45 | 5 |
| Gag-Pol | 606 | 77.74 | 0 | 21.67 | 15 | 38.33 | 25 | 36.67 | 4 |
| Gag-Pol | 666 | 77.52 | 0 | 26.67 | 11.67 | 36.67 | 25 | 38.33 | 4 |
| Gag-Pol | 726 | 79.82 | 0 | 25 | 18.33 | 35 | 21.67 | 43.33 | 2 |
| gag | 209 | 81.78 | 0 | 26.67 | 18.33 | 26.67 | 28.33 | 45 | 6 |
| gag | 269 | 80.24 | 0 | 31.67 | 11.67 | 38.33 | 18.33 | 43.33 | 3 |
| gag | 342 | 82.47 | 0 | 28.33 | 16.67 | 33.33 | 21.67 | 45 | 3 |
| gag | 402 | 78.85 | 0 | 20 | 18.33 | 43.33 | 18.33 | 38.33 | 4 |
| gag | 545 | 79.58 | 0 | 21.67 | 20 | 31.67 | 26.67 | 41.67 | 4 |
| gag | 605 | 78.28 | 0 | 21.67 | 16.67 | 43.33 | 18.33 | 38.33 | 6 |
| gag | 667 | 80.04 | 0 | 21.67 | 23.33 | 36.67 | 18.33 | 45 | 3 |
| gag | 754 | 75.62 | 0 | 18.33 | 16.67 | 40 | 25 | 35 | 4 |
| gag | 814 | 80.67 | 0 | 26.67 | 18.33 | 38.33 | 16.67 | 45 | 4 |
| gag | 903 | 81.87 | 0 | 28.33 | 16.67 | 36.67 | 18.33 | 45 | 4 |
| Vif | 114 | 78.8 | 0 | 21.67 | 20 | 40 | 18.33 | 41.67 | 6 |
| Vif | 154 | 77.98 | 0 | 13.33 | 25 | 43.33 | 18.33 | 38.33 | 6 |
| Vif | 194 | 78.39 | 0 | 23.33 | 18.33 | 33.33 | 25 | 41.67 | 3 |
| Vif | 234 | 77.97 | 0 | 21.67 | 18.33 | 31.67 | 28.33 | 40 | 3 |
| Vif | 276 | 75.46 | 0 | 13.33 | 21.67 | 28.33 | 36.67 | 35 | 5 |
| Vif | 316 | 78.46 | 0 | 20 | 20 | 45 | 15 | 40 | 5 |
| Vif | 356 | 79.26 | 0 | 33.33 | 10 | 38.33 | 18.33 | 43.33 | 5 |
| Vif | 396 | 78.73 | 0 | 28.33 | 13.33 | 33.33 | 25 | 41.67 | 4 |
| Vif | 436 | 77.87 | 0 | 20 | 20 | 38.33 | 21.67 | 40 | 4 |
| Vif | 476 | 77.27 | 0 | 21.67 | 18.33 | 35 | 25 | 40 | 4 |
| vpr | 78 | 81.1 | 0 | 30 | 15 | 35 | 20 | 45 | 3 |
| vpr | 98 | 79.56 | 0 | 21.67 | 20 | 26.67 | 31.67 | 41.67 | 4 |
| vpr | 118 | 78.61 | 0 | 18.33 | 20 | 30 | 31.67 | 38.33 | 4 |
| vpr | 138 | 79.69 | 0 | 21.67 | 18.33 | 31.67 | 28.33 | 40 | 3 |
| vpr | 158 | 78.79 | 0 | 26.67 | 13.33 | 33.33 | 26.67 | 40 | 4 |
| vpr | 184 | 81.7 | 0 | 28.33 | 16.67 | 26.67 | 28.33 | 45 | 4 |
| vpr | 204 | 78.58 | 0 | 20 | 20 | 25 | 35 | 40 | 4 |
| vpr | 224 | 79.94 | 0 | 28.33 | 15 | 26.67 | 30 | 43.33 | 4 |
| vpr | 244 | 77.34 | 0 | 26.67 | 13.33 | 31.67 | 28.33 | 40 | 4 |
| vpr | 264 | 79.95 | 0 | 28.33 | 16.67 | 38.33 | 16.67 | 45 | 4 |

TABLE 1-continued

| | | Selected viral probes | | | | | | |
|---|---|---|---|---|---|---|---|---|
| tat | 91 | 80.29 | 0 | 18.33 | 26.67 | 30 | 25 | 45 | 3 |
| tat | 218 | 77.17 | 0 | 28.33 | 6.67 | 33.33 | 31.67 | 35 | 3 |
| tat | 285 | 76.51 | 0 | 15 | 20 | 48.33 | 16.67 | 35 | 4 |
| tat | 345 | 79.94 | 0 | 26.67 | 15 | 38.33 | 20 | 41.67 | 3 |
| tat | 405 | 80.08 | 0 | 21.67 | 21.67 | 26.67 | 30 | 43.33 | 4 |
| tat | 572 | 82.24 | 0 | 28.33 | 16.67 | 28.33 | 26.67 | 45 | 3 |
| tat | 692 | 81.72 | 0 | 35 | 10 | 30 | 25 | 45 | 6 |
| tat | 824 | 79.96 | 0 | 30 | 15 | 35 | 20 | 45 | 3 |
| tat | 884 | 77.23 | 0 | 25 | 13.33 | 35 | 26.67 | 38.33 | 3 |
| tat | 944 | 77.7 | 0 | 16.67 | 18.33 | 45 | 20 | 35 | 4 |
| rev | 60 | 78.01 | 0 | 25 | 16.67 | 35 | 23.33 | 41.67 | 3 |
| rev | 134 | 80.4 | 0 | 23.33 | 21.67 | 23.33 | 31.67 | 45 | 2 |
| rev | 231 | 80.23 | 0 | 31.67 | 13.33 | 38.33 | 16.67 | 45 | 2 |
| rev | 320 | 80.29 | 0 | 18.33 | 26.67 | 30 | 25 | 45 | 3 |
| rev | 447 | 77.17 | 0 | 28.33 | 6.67 | 33.33 | 31.67 | 35 | 3 |
| rev | 514 | 76.51 | 0 | 15 | 20 | 48.33 | 16.67 | 35 | 4 |
| rev | 574 | 79.94 | 0 | 26.67 | 15 | 38.33 | 20 | 41.67 | 3 |
| rev | 634 | 80.08 | 0 | 21.67 | 21.67 | 26.67 | 30 | 43.33 | 4 |
| rev | 801 | 82.24 | 0 | 28.33 | 16.67 | 28.33 | 26.67 | 45 | 3 |
| rev | 921 | 81.72 | 0 | 35 | 10 | 30 | 25 | 45 | 6 |
| vpu | 114 | 78.38 | 0 | 30 | 11.67 | 41.67 | 16.67 | 41.67 | 3 |
| vpu | 61 | 85.51 | 0 | 40 | 13.33 | 18.33 | 28.33 | 53.33 | 5 |
| vpu | 62 | 85.89 | 0 | 40 | 15 | 16.67 | 28.33 | 55 | 5 |
| vpu | 64 | 86.58 | 0 | 40 | 15 | 18.33 | 26.67 | 55 | 5 |
| vpu | 66 | 86.64 | 0 | 40 | 15 | 18.33 | 26.67 | 55 | 5 |
| vpu | 67 | 86.64 | 0 | 40 | 15 | 20 | 25 | 55 | 5 |
| vpu | 68 | 85.92 | 0 | 40 | 15 | 18.33 | 26.67 | 55 | 5 |
| vpu | 69 | 85.79 | 0 | 38.33 | 15 | 20 | 26.67 | 53.33 | 5 |
| vpu | 70 | 85.81 | 0 | 38.33 | 15 | 21.67 | 25 | 53.33 | 5 |
| vpu | 71 | 85.37 | 0 | 38.33 | 15 | 21.67 | 25 | 53.33 | 5 |
| asp | 93 | 82.24 | 0 | 28.33 | 16.67 | 28.33 | 26.67 | 45 | 3 |
| asp | 210 | 81.72 | 0 | 35 | 10 | 30 | 25 | 45 | 6 |
| asp | 256 | 80.7 | 0 | 26.67 | 16.67 | 41.67 | 15 | 43.33 | 5 |
| asp | 359 | 80.63 | 0 | 30 | 15 | 35 | 20 | 45 | 2 |
| asp | 389 | 76.87 | 0 | 21.67 | 13.33 | 38.33 | 26.67 | 35 | 3 |
| asp | 419 | 79.95 | 0 | 18.33 | 23.33 | 30 | 28.33 | 41.67 | 4 |
| asp | 449 | 80.68 | 0 | 21.67 | 20 | 38.33 | 20 | 41.67 | 4 |
| asp | 479 | 78.34 | 0 | 16.67 | 20 | 46.67 | 16.67 | 36.67 | 4 |
| asp | 509 | 79.23 | 0 | 16.67 | 23.33 | 43.33 | 16.67 | 40 | 4 |
| asp | 539 | 77.8 | 0 | 25 | 13.33 | 36.67 | 25 | 38.33 | 3 |
| nef | 179 | 80.47 | 0 | 25 | 20 | 38.33 | 16.67 | 45 | 3 |
| nef | 199 | 79.2 | 0 | 28.33 | 15 | 41.67 | 15 | 43.33 | 3 |
| nef | 220 | 79.81 | 0 | 23.33 | 20 | 31.67 | 25 | 43.33 | 3 |
| nef | 300 | 79.39 | 0 | 16.67 | 28.33 | 28.33 | 26.67 | 45 | 3 |
| nef | 320 | 80.05 | 0 | 15 | 28.33 | 33.33 | 23.33 | 43.33 | 3 |
| nef | 348 | 80.65 | 0 | 26.67 | 16.67 | 40 | 16.67 | 43.33 | 6 |
| nef | 368 | 79.99 | 0 | 23.33 | 18.33 | 35 | 23.33 | 41.67 | 6 |
| nef | 388 | 80.05 | 0 | 26.67 | 15 | 35 | 23.33 | 41.67 | 6 |
| nef | 408 | 78.88 | 0 | 16.67 | 25 | 28.33 | 30 | 41.67 | 5 |
| nef | 517 | 81.69 | 0 | 21.67 | 23.33 | 38.33 | 16.67 | 45 | 5 |
| 5' LTR | 155 | 79.1 | 0 | 18.33 | 25 | 25 | 31.67 | 43.33 | 3 |
| 5' LTR | 343 | 79.71 | 0 | 20 | 23.33 | 21.67 | 35 | 43.33 | 3 |
| 5' LTR | 472 | 79.15 | 0 | 25 | 18.33 | 41.67 | 15 | 43.33 | 3 |
| 5' LTR | 502 | 77.55 | 0 | 21.67 | 16.67 | 45 | 16.67 | 38.33 | 3 |
| 5' LTR | 532 | 79.96 | 0 | 28.33 | 13.33 | 43.33 | 15 | 41.67 | 4 |
| 5' LTR | 647 | 81.97 | 0 | 28.33 | 16.67 | 33.33 | 21.67 | 45 | 4 |
| 5' LTR | 715 | 80.36 | 0 | 26.67 | 18.33 | 36.67 | 18.33 | 45 | 2 |
| 5' LTR | 788 | 78.77 | 0 | 23.33 | 18.33 | 33.33 | 25 | 41.67 | 3 |
| 5' LTR | 818 | 75.67 | 0 | 20 | 16.67 | 43.33 | 20 | 36.67 | 5 |
| 5' LTR | 848 | 75.56 | 0 | 26.67 | 11.67 | 41.67 | 20 | 38.33 | 5 |
| gag polyprotein | 430 | 82.46 | 0 | 30 | 15 | 38.33 | 16.67 | 45 | 3 |
| gag polyprotein | 577 | 80.03 | 0 | 25 | 20 | 36.67 | 18.33 | 45 | 4 |
| gag polyprotein | 637 | 81.88 | 0 | 16.67 | 28.33 | 41.67 | 13.33 | 45 | 6 |
| gag polyprotein | 697 | 81.02 | 0 | 21.67 | 21.67 | 40 | 16.67 | 43.33 | 4 |
| gag polyprotein | 757 | 79.55 | 0 | 21.67 | 20 | 41.67 | 16.67 | 41.67 | 4 |
| gag polyprotein | 817 | 80.48 | 0 | 23.33 | 21.67 | 36.67 | 18.33 | 45 | 4 |
| gag polyprotein | 961 | 80.93 | 0 | 25 | 20 | 38.33 | 16.67 | 45 | 3 |
| gag polyprotein | 1021 | 79.57 | 0 | 20 | 20 | 31.67 | 28.33 | 40 | 3 |
| gag polyprotein | 1094 | 81.5 | 0 | 31.67 | 13.33 | 33.33 | 21.67 | 45 | 4 |

TABLE 1-continued

| Selected viral probes | | | | | | | | |
|---|---|---|---|---|---|---|---|---|
| gag polyprotein | 1219 | 80.48 | 0 | 20 | 25 | 45 | 10 | 45 | 4 |
| gag-pol | 60 | 77.83 | 0 | 20 | 21.67 | 35 | 23.33 | 41.67 | 4 |
| gag-pol | 120 | 79.05 | 0 | 18.33 | 23.33 | 35 | 23.33 | 41.67 | 5 |
| gag-pol | 180 | 79.42 | 0 | 23.33 | 20 | 36.67 | 20 | 43.33 | 5 |
| gag-pol | 265 | 80.72 | 0 | 23.33 | 21.67 | 33.33 | 21.67 | 45 | 4 |
| gag-pol | 380 | 78.61 | 0 | 28.33 | 15 | 43.33 | 13.33 | 43.33 | 4 |
| gag-pol | 480 | 80.85 | 0 | 28.33 | 16.67 | 33.33 | 21.67 | 45 | 3 |
| gag-pol | 557 | 76.38 | 0 | 11.67 | 23.33 | 50 | 15 | 35 | 3 |
| gag-pol | 617 | 79.46 | 0 | 30 | 11.67 | 33.33 | 25 | 41.67 | 4 |
| gag-pol | 703 | 76.51 | 0 | 23.33 | 15 | 45 | 16.67 | 38.33 | 3 |
| gag-pol | 764 | 81.32 | 0 | 26.67 | 18.33 | 31.67 | 23.33 | 45 | 3 |
| gp2-vif protein | 209 | 79 | 0 | 18.33 | 25 | 40 | 16.67 | 43.33 | 4 |
| gp2-vif protein | 261 | 80.96 | 0 | 13.33 | 30 | 31.67 | 25 | 43.33 | 4 |
| gp2-vif protein | 311 | 80.06 | 0 | 28.33 | 13.33 | 30 | 28.33 | 41.67 | 4 |
| gp2-vif protein | 341 | 78.94 | 0 | 18.33 | 21.67 | 28.33 | 31.67 | 40 | 3 |
| gp2-vif protein | 372 | 80.21 | 0 | 18.33 | 25 | 35 | 21.67 | 43.33 | 4 |
| gp2-vif protein | 402 | 79.16 | 0 | 18.33 | 23.33 | 31.67 | 26.67 | 41.67 | 4 |
| gp2-vif protein | 432 | 80.3 | 0 | 20 | 23.33 | 33.33 | 23.33 | 43.33 | 5 |
| gp2-vif protein | 464 | 78.01 | 0 | 21.67 | 16.67 | 46.67 | 15 | 38.33 | 5 |
| gp2-vif protein | 494 | 79.25 | 0 | 21.67 | 20 | 38.33 | 20 | 41.67 | 5 |
| gp2-vif protein | 591 | 80.18 | 0 | 26.67 | 18.33 | 38.33 | 16.67 | 45 | 4 |
| gp3-vpx Protein | 120 | 81.55 | 0 | 30 | 15 | 31.67 | 23.33 | 45 | 6 |
| gp3-vpx Protein | 121 | 81.42 | 0 | 28.33 | 15 | 33.33 | 23.33 | 43.33 | 6 |
| gp3-vpx Protein | 122 | 81.16 | 0 | 28.33 | 15 | 33.33 | 23.33 | 43.33 | 6 |
| gp3-vpx Protein | 123 | 80.71 | 0 | 28.33 | 16.67 | 31.67 | 23.33 | 45 | 6 |
| gp3-vpx Protein | 124 | 81.28 | 0 | 28.33 | 16.67 | 31.67 | 23.33 | 45 | 6 |
| gp3-vpx Protein | 126 | 81.53 | 0 | 28.33 | 16.67 | 30 | 25 | 45 | 6 |
| gp3-vpx Protein | 127 | 81.6 | 0 | 28.33 | 16.67 | 30 | 25 | 45 | 6 |
| gp3-vpx Protein | 128 | 81.7 | 0 | 28.33 | 16.67 | 28.33 | 26.67 | 45 | 6 |
| gp3-vpx Protein | 129 | 80.99 | 0 | 26.67 | 16.67 | 28.33 | 28.33 | 43.33 | 5 |
| gp3-vpx Protein | 130 | 80.29 | 0 | 25 | 16.67 | 28.33 | 30 | 41.67 | 5 |
| gp4-vpr protein | 114 | 81.27 | 0 | 18.33 | 26.67 | 38.33 | 16.67 | 45 | 4 |
| gp4-vpr protein | 115 | 80.99 | 0 | 18.33 | 26.67 | 36.67 | 18.33 | 45 | 4 |
| gp4-vpr protein | 116 | 80.45 | 0 | 18.33 | 26.67 | 36.67 | 18.33 | 45 | 4 |
| gp4-vpr protein | 117 | 80.03 | 0 | 18.33 | 25 | 36.67 | 20 | 43.33 | 4 |
| gp4-vpr protein | 118 | 80.37 | 0 | 18.33 | 26.67 | 35 | 20 | 45 | 4 |
| gp4-vpr protein | 119 | 80.45 | 0 | 18.33 | 26.67 | 36.67 | 18.33 | 45 | 4 |
| gp4-vpr protein | 120 | 79.46 | 0 | 18.33 | 25 | 36.67 | 20 | 43.33 | 4 |
| gp4-vpr protein | 121 | 78.83 | 0 | 18.33 | 25 | 36.67 | 20 | 43.33 | 4 |
| gp4-vpr protein | 122 | 79.54 | 0 | 20 | 23.33 | 36.67 | 20 | 43.33 | 4 |
| gp4-vpr protein | 123 | 80.24 | 0 | 21.67 | 23.33 | 35 | 20 | 45 | 3 |
| gp5-tat protein | 174 | 79.14 | 0 | 21.67 | 20 | 23.33 | 35 | 41.67 | 6 |
| gp5-tat protein | 243 | 75.32 | 0 | 25 | 10 | 35 | 30 | 35 | 3 |
| gp5-tat protein | 365 | 76.3 | 0 | 16.67 | 18.33 | 48.33 | 16.67 | 35 | 4 |

TABLE 1-continued

| Selected viral probes | | | | | | | | | |
|---|---|---|---|---|---|---|---|---|---|
| gp5-tat protein | 426 | 80.93 | 0 | 26.67 | 18.33 | 33.33 | 21.67 | 45 | 5 |
| gp5-tat protein | 510 | 81.51 | 0 | 26.67 | 18.33 | 31.67 | 23.33 | 45 | 4 |
| gp5-tat protein | 619 | 82.14 | 0 | 26.67 | 18.33 | 38.33 | 16.67 | 45 | 3 |
| gp5-tat protein | 795 | 81.1 | 0 | 16.67 | 28.33 | 35 | 20 | 45 | 3 |
| gp5-tat protein | 855 | 78.13 | 0 | 25 | 16.67 | 35 | 23.33 | 41.67 | 3 |
| gp5-tat protein | 978 | 81.02 | 0 | 33.33 | 11.67 | 30 | 25 | 45 | 5 |
| gp5-tat protein | 1038 | 77.77 | 0 | 15 | 21.67 | 45 | 18.33 | 36.67 | 3 |
| gp6-rev protein | 121 | 80.43 | 0 | 16.67 | 28.33 | 28.33 | 26.67 | 45 | 3 |
| gp6-rev protein | 319 | 79.14 | 0 | 21.67 | 20 | 23.33 | 35 | 41.67 | 6 |
| gp6-rev protein | 388 | 75.32 | 0 | 25 | 10 | 35 | 30 | 35 | 3 |
| gp6-rev protein | 510 | 76.3 | 0 | 16.67 | 18.33 | 48.33 | 16.67 | 35 | 4 |
| gp6-rev protein | 571 | 80.93 | 0 | 26.67 | 18.33 | 33.33 | 21.67 | 45 | 5 |
| gp6-rev protein | 655 | 81.51 | 0 | 26.67 | 18.33 | 31.67 | 23.33 | 45 | 4 |
| gp6-rev protein | 764 | 82.14 | 0 | 26.67 | 18.33 | 38.33 | 16.67 | 45 | 3 |
| gp6-rev protein | 940 | 81.1 | 0 | 16.67 | 28.33 | 35 | 20 | 45 | 3 |
| gp6-rev protein | 1000 | 78.13 | 0 | 25 | 16.67 | 35 | 23.33 | 41.67 | 3 |
| gp6-rev protein | 1123 | 81.02 | 0 | 33.33 | 11.67 | 30 | 25 | 45 | 5 |
| gp7-env protein | 305 | 80.43 | 0 | 16.67 | 28.33 | 28.33 | 26.67 | 45 | 3 |
| gp7-env protein | 503 | 79.14 | 0 | 21.67 | 20 | 23.33 | 35 | 41.67 | 6 |
| gp7-env protein | 572 | 75.32 | 0 | 25 | 10 | 35 | 30 | 35 | 3 |
| gp7-env protein | 694 | 76.3 | 0 | 16.67 | 18.33 | 48.33 | 16.67 | 35 | 4 |
| gp7-env protein | 755 | 80.93 | 0 | 26.67 | 18.33 | 33.33 | 21.67 | 45 | 5 |
| gp7-env protein | 839 | 81.51 | 0 | 26.67 | 18.33 | 31.67 | 23.33 | 45 | 4 |
| gp7-env protein | 948 | 82.14 | 0 | 26.67 | 18.33 | 38.33 | 16.67 | 45 | 3 |
| gp7-env protein | 1124 | 81.1 | 0 | 16.67 | 28.33 | 35 | 20 | 45 | 3 |
| gp7-env protein | 1184 | 78.13 | 0 | 25 | 16.67 | 35 | 23.33 | 41.67 | 3 |
| gp7-env protein | 1307 | 81.02 | 0 | 33.33 | 11.67 | 30 | 25 | 45 | 5 |
| gp8-nef protein | 66 | 79.96 | 0 | 28.33 | 13.33 | 43.33 | 15 | 41.67 | 4 |
| gp8-nef protein | 181 | 81.97 | 0 | 28.33 | 16.67 | 33.33 | 21.67 | 45 | 4 |
| gp8-nef protein | 249 | 80.36 | 0 | 26.67 | 18.33 | 36.67 | 18.33 | 45 | 2 |
| gp8-nef protein | 322 | 78.77 | 0 | 23.33 | 18.33 | 33.33 | 25 | 41.67 | 3 |
| gp8-nef protein | 352 | 75.67 | 0 | 20 | 16.67 | 43.33 | 20 | 36.67 | 5 |
| gp8-nef protein | 382 | 75.56 | 0 | 26.67 | 11.67 | 41.67 | 20 | 38.33 | 5 |
| gp8-nef protein | 416 | 77.69 | 0 | 28.33 | 10 | 40 | 21.67 | 38.33 | 5 |
| gp8-nef protein | 467 | 76.63 | 0 | 18.33 | 18.33 | 40 | 23.33 | 36.67 | 4 |
| gp8-nef protein | 497 | 79.73 | 0 | 23.33 | 20 | 35 | 21.67 | 43.33 | 3 |
| gp8-nef protein | 527 | 77.26 | 0 | 26.67 | 11.67 | 31.67 | 30 | 38.33 | 4 |
| 3 LTR | 155 | 79.1 | 0 | 18.33 | 25 | 25 | 31.67 | 43.33 | 3 |
| 3 LTR | 343 | 79.71 | 0 | 20 | 23.33 | 21.67 | 35 | 43.33 | 3 |
| 3 LTR | 472 | 79.15 | 0 | 25 | 18.33 | 41.67 | 15 | 43.33 | 3 |
| 3 LTR | 502 | 77.55 | 0 | 21.67 | 16.67 | 45 | 16.67 | 38.33 | 3 |

TABLE 1-continued

| Selected viral probes | | | | | | | | |
|---|---|---|---|---|---|---|---|---|
| 3 LTR | 532 | 79.96 | 0 | 28.33 | 13.33 | 43.33 | 15 | 41.67 | 4 |
| 3 LTR | 647 | 81.97 | 0 | 28.33 | 16.67 | 33.33 | 21.67 | 45 | 4 |
| 3 LTR | 715 | 80.36 | 0 | 26.67 | 18.33 | 36.67 | 18.33 | 45 | 2 |
| 3 LTR | 788 | 78.77 | 0 | 23.33 | 18.33 | 33.33 | 25 | 41.67 | 3 |
| 3 LTR | 818 | 75.67 | 0 | 20 | 16.67 | 43.33 | 20 | 36.67 | 5 |
| 3 LTR | 848 | 75.56 | 0 | 26.67 | 11.67 | 41.67 | 20 | 38.33 | 5 |
| gag | 364 | 81.2 | 0 | 21.67 | 23.33 | 35 | 20 | 45 | 5 |
| gag | 365 | 81.2 | 0 | 21.67 | 23.33 | 36.67 | 18.33 | 45 | 5 |
| gag | 366 | 80.69 | 0 | 21.67 | 23.33 | 38.33 | 16.67 | 45 | 5 |
| gag | 367 | 80.69 | 0 | 20 | 25 | 38.33 | 16.67 | 45 | 5 |
| gag | 368 | 81.23 | 0 | 20 | 25 | 40 | 15 | 45 | 5 |
| gag | 369 | 81.51 | 0 | 20 | 25 | 40 | 15 | 45 | 5 |
| gag | 370 | 81.54 | 0 | 20 | 25 | 41.67 | 13.33 | 45 | 5 |
| gag | 374 | 81.41 | 0 | 18.33 | 26.67 | 40 | 15 | 45 | 5 |
| gag | 375 | 81.36 | 0 | 16.67 | 26.67 | 41.67 | 15 | 43.33 | 5 |
| gag | 376 | 81.36 | 0 | 16.67 | 26.67 | 40 | 16.67 | 43.33 | 5 |
| pro | 79 | 81.5 | 0 | 16.67 | 28.33 | 35 | 20 | 45 | 6 |
| pro | 80 | 81.38 | 0 | 15 | 28.33 | 36.67 | 20 | 43.33 | 6 |
| pro | 81 | 80.97 | 0 | 16.67 | 28.33 | 36.67 | 18.33 | 45 | 6 |
| pro | 82 | 80.97 | 0 | 18.33 | 26.67 | 36.67 | 18.33 | 45 | 6 |
| pro | 83 | 81.28 | 0 | 18.33 | 25 | 38.33 | 18.33 | 43.33 | 6 |
| pro | 84 | 80.99 | 0 | 18.33 | 26.67 | 36.67 | 18.33 | 45 | 6 |
| pro | 85 | 80.99 | 0 | 16.67 | 28.33 | 36.67 | 18.33 | 45 | 6 |
| pro | 86 | 81.71 | 0 | 18.33 | 26.67 | 36.67 | 18.33 | 45 | 6 |
| pro | 105 | 81.26 | 0 | 16.67 | 28.33 | 38.33 | 16.67 | 45 | 6 |
| pro | 106 | 81.26 | 0 | 15 | 30 | 38.33 | 16.67 | 45 | 6 |
| Pol | 217 | 81.86 | 0 | 20 | 25 | 28.33 | 26.67 | 45 | 3 |
| Pol | 331 | 81.66 | 0 | 13.33 | 30 | 38.33 | 18.33 | 43.33 | 4 |
| Pol | 391 | 77.91 | 0 | 11.67 | 28.33 | 31.67 | 28.33 | 40 | 3 |
| Pol | 542 | 79.82 | 0 | 11.67 | 30 | 31.67 | 26.67 | 41.67 | 3 |
| Pol | 609 | 81.28 | 0 | 18.33 | 26.67 | 30 | 25 | 45 | 3 |
| Pol | 679 | 80.45 | 0 | 18.33 | 26.67 | 26.67 | 28.33 | 45 | 4 |
| Pol | 1118 | 79.19 | 0 | 11.67 | 30 | 25 | 33.33 | 41.67 | 3 |
| Pol | 1260 | 81.34 | 0 | 15 | 30 | 26.67 | 28.33 | 45 | 5 |
| Pol | 1351 | 81.27 | 0 | 16.67 | 28.33 | 21.67 | 33.33 | 45 | 4 |
| Pol | 1411 | 79.74 | 0 | 16.67 | 25 | 33.33 | 25 | 41.67 | 5 |
| rex | 109 | 81.24 | 0 | 18.33 | 26.67 | 35 | 20 | 45 | 5 |
| rex | 169 | 76.49 | 0 | 6.67 | 30 | 26.67 | 36.67 | 36.67 | 4 |
| rex | 262 | 77.12 | 0 | 6.67 | 30 | 30 | 33.33 | 36.67 | 3 |
| rex | 479 | 81.27 | 0 | 15 | 30 | 26.67 | 28.33 | 45 | 4 |
| rex | 1077 | 80.71 | 0 | 18.33 | 26.67 | 21.67 | 33.33 | 45 | 4 |
| rex | 1748 | 78.44 | 0 | 8.33 | 30 | 35 | 26.67 | 38.33 | 3 |
| rex | 1986 | 77.3 | 0 | 11.67 | 28.33 | 30 | 30 | 40 | 6 |
| rex | 2091 | 82.63 | 0 | 18.33 | 26.67 | 36.67 | 18.33 | 45 | 5 |
| rex | 2151 | 78.28 | 0 | 16.67 | 21.67 | 40 | 21.67 | 38.33 | 3 |
| rex | 2516 | 81.15 | 0 | 16.67 | 28.33 | 20 | 35 | 45 | 2 |
| tax | 109 | 81.24 | 0 | 18.33 | 26.67 | 35 | 20 | 45 | 5 |
| tax | 169 | 76.49 | 0 | 6.67 | 30 | 26.67 | 36.67 | 36.67 | 4 |
| tax | 262 | 77.12 | 0 | 6.67 | 30 | 30 | 33.33 | 36.67 | 3 |
| tax | 479 | 81.27 | 0 | 15 | 30 | 26.67 | 28.33 | 45 | 4 |
| tax | 1077 | 80.71 | 0 | 18.33 | 26.67 | 21.67 | 33.33 | 45 | 4 |
| tax | 1748 | 78.44 | 0 | 8.33 | 30 | 35 | 26.67 | 38.33 | 3 |
| tax | 1986 | 77.3 | 0 | 11.67 | 28.33 | 30 | 30 | 40 | 6 |
| tax | 2091 | 82.63 | 0 | 18.33 | 26.67 | 36.67 | 18.33 | 45 | 5 |
| tax | 2151 | 78.28 | 0 | 16.67 | 21.67 | 40 | 21.67 | 38.33 | 3 |
| tax | 2516 | 81.15 | 0 | 16.67 | 28.33 | 20 | 35 | 45 | 2 |
| env | 276 | 75.75 | 0 | 13.33 | 23.33 | 33.33 | 30 | 36.67 | 4 |
| env | 316 | 79.9 | 0 | 25 | 16.67 | 31.67 | 26.67 | 41.67 | 4 |
| env | 383 | 82.22 | 0 | 16.67 | 28.33 | 40 | 15 | 45 | 5 |
| env | 423 | 76.35 | 0 | 15 | 20 | 45 | 20 | 35 | 5 |
| env | 806 | 80.64 | 0 | 16.67 | 28.33 | 20 | 35 | 45 | 2 |
| env | 847 | 77.56 | 0 | 10 | 26.67 | 31.67 | 31.67 | 36.67 | 4 |
| env | 1014 | 80.5 | 0 | 15 | 30 | 18.33 | 36.67 | 45 | 5 |
| env | 1080 | 78.82 | 0 | 13.33 | 25 | 33.33 | 28.33 | 38.33 | 4 |
| env | 1171 | 80.15 | 0 | 13.33 | 30 | 23.33 | 33.33 | 43.33 | 4 |
| env | 1211 | 80.16 | 0 | 20 | 23.33 | 31.67 | 25 | 43.33 | 5 |
| 5' LTR | 502 | 80.91 | 0 | 28.33 | 16.67 | 36.67 | 18.33 | 45 | 4 |
| 5' LTR | 503 | 80.27 | 0 | 26.67 | 18.33 | 36.67 | 18.33 | 45 | 4 |
| 5' LTR | 504 | 80.93 | 0 | 26.67 | 18.33 | 36.67 | 18.33 | 45 | 4 |
| 5' LTR | 506 | 81 | 0 | 28.33 | 16.67 | 36.67 | 18.33 | 45 | 4 |
| 5' LTR | 507 | 80.3 | 0 | 26.67 | 16.67 | 36.67 | 20 | 43.33 | 4 |
| 5' LTR | 508 | 80.17 | 0 | 25 | 16.67 | 36.67 | 21.67 | 41.67 | 4 |
| 5' LTR | 509 | 79.64 | 0 | 25 | 16.67 | 38.33 | 20 | 41.67 | 4 |
| 5' LTR | 510 | 78.94 | 0 | 23.33 | 16.67 | 40 | 20 | 40 | 4 |
| 5' LTR | 511 | 78.88 | 0 | 21.67 | 16.67 | 41.67 | 20 | 38.33 | 4 |
| 5' LTR | 513 | 77.51 | 0 | 20 | 16.67 | 41.67 | 21.67 | 36.67 | 4 |
| gp1-tax protein | 63 | 83.12 | 0 | 15 | 33.33 | 26.67 | 25 | 48.33 | 6 |
| gp1-tax protein | 64 | 83.12 | 0 | 15 | 33.33 | 28.33 | 23.33 | 48.33 | 5 |

TABLE 1-continued

| Selected viral probes | | | | | | | | |
|---|---|---|---|---|---|---|---|---|
| gp1-tax protein | 65 | 83.12 | 0 | 15 | 33.33 | 30 | 21.67 | 48.33 | 5 |
| gp1-tax protein | 67 | 83.24 | 0 | 15 | 35 | 31.67 | 18.33 | 50 | 5 |
| gp1-tax protein | 71 | 83.33 | 0 | 16.67 | 35 | 33.33 | 15 | 51.67 | 4 |
| gp1-tax protein | 72 | 83.33 | 0 | 16.67 | 35 | 33.33 | 15 | 51.67 | 4 |
| gp1-tax protein | 73 | 83.05 | 0 | 16.67 | 33.33 | 33.33 | 16.67 | 50 | 4 |
| gp1-tax protein | 74 | 83 | 0 | 16.67 | 31.67 | 35 | 16.67 | 48.33 | 4 |
| gp1-tax protein | 75 | 82.67 | 0 | 16.67 | 33.33 | 35 | 15 | 50 | 4 |
| gp1-tax protein | 76 | 83.07 | 0 | 16.67 | 31.67 | 35 | 16.67 | 48.33 | 4 |
| gs1 | 301 | 80.91 | 0 | 28.33 | 16.67 | 36.67 | 18.33 | 45 | 4 |
| gs1 | 593 | 80.6 | 0 | 23.33 | 21.67 | 30 | 25 | 45 | 4 |
| gs1 | 737 | 78.82 | 0 | 10 | 30 | 30 | 30 | 40 | 5 |
| gs1 | 830 | 80.73 | 0 | 13.33 | 30 | 30 | 26.67 | 43.33 | 4 |
| gs1 | 970 | 80.42 | 0 | 20 | 25 | 35 | 20 | 45 | 4 |
| gs1 | 1573 | 80.03 | 0 | 13.33 | 30 | 30 | 26.67 | 43.33 | 3 |
| gs1 | 1927 | 80.81 | 0 | 13.33 | 30 | 43.33 | 13.33 | 43.33 | 4 |
| gs1 | 2135 | 81.49 | 0 | 15 | 30 | 31.67 | 23.33 | 45 | 4 |
| gs1 | 2399 | 81.19 | 0 | 16.67 | 28.33 | 30 | 25 | 45 | 2 |
| gs1 | 2495 | 81.23 | 0 | 20 | 25 | 36.67 | 18.33 | 45 | 4 |
| Gag-Pro-Pol | 212 | 82.08 | 0 | 20 | 25 | 28.33 | 26.67 | 45 | 4 |
| Gag-Pro-Pol | 331 | 81.97 | 0 | 18.33 | 26.67 | 33.33 | 21.67 | 45 | 4 |
| Gag-Pro-Pol | 394 | 77.04 | 0 | 8.33 | 30 | 36.67 | 25 | 38.33 | 4 |
| Gag-Pro-Pol | 504 | 78.39 | 0 | 11.67 | 30 | 30 | 28.33 | 41.67 | 4 |
| Gag-Pro-Pol | 623 | 81.77 | 0 | 20 | 25 | 30 | 25 | 45 | 5 |
| Gag-Pro-Pol | 802 | 81.24 | 0 | 15 | 30 | 31.67 | 23.33 | 45 | 3 |
| Gag-Pro-Pol | 1106 | 80.47 | 0 | 13.33 | 30 | 26.67 | 30 | 43.33 | 4 |
| Gag-Pro-Pol | 1585 | 79.64 | 0 | 15 | 30 | 30 | 25 | 45 | 3 |
| Gag-Pro-Pol | 1684 | 81.71 | 0 | 16.67 | 28.33 | 28.33 | 26.67 | 45 | 4 |
| Gag-Pro-Pol | 1911 | 80.7 | 0 | 20 | 25 | 31.67 | 23.33 | 45 | 3 |
| gp2-gag polyprotein | 376 | 81.37 | 0 | 15 | 30 | 43.33 | 11.67 | 45 | 6 |
| gp2-gag polyprotein | 379 | 82.65 | 0 | 15 | 30 | 43.33 | 11.67 | 45 | 6 |
| gp2-gag polyprotein | 380 | 82.37 | 0 | 15 | 30 | 41.67 | 13.33 | 45 | 6 |
| gp2-gag polyprotein | 393 | 80.15 | 0 | 11.67 | 30 | 38.33 | 20 | 41.67 | 6 |
| gp2-gag polyprotein | 394 | 79.59 | 0 | 11.67 | 30 | 38.33 | 20 | 41.67 | 6 |
| gp2-gag polyprotein | 395 | 79.44 | 0 | 11.67 | 30 | 38.33 | 20 | 41.67 | 6 |
| gp2-gag polyprotein | 399 | 80.74 | 0 | 13.33 | 30 | 36.67 | 20 | 43.33 | 6 |
| gp2-gag polyprotein | 400 | 81.46 | 0 | 13.33 | 30 | 36.67 | 20 | 43.33 | 6 |
| gp2-gag polyprotein | 401 | 81.46 | 0 | 13.33 | 30 | 38.33 | 18.33 | 43.33 | 6 |
| gp2-gag polyprotein | 402 | 81.02 | 0 | 13.33 | 30 | 40 | 16.67 | 43.33 | 6 |
| gp4-rex 26 kD protein | 491 | 78.63 | 0 | 10 | 30 | 30 | 30 | 40 | 6 |
| gp4-rex 26 kD protein | 541 | 80.11 | 0 | 13.33 | 30 | 30 | 26.67 | 43.33 | 6 |
| gp4-rex 26 kD protein | 839 | 80.81 | 0 | 13.33 | 30 | 43.33 | 13.33 | 43.33 | 4 |
| gp4-rex 26 kD protein | 1056 | 79.23 | 0 | 11.67 | 30 | 31.67 | 26.67 | 41.67 | 3 |
| gp4-rex 26 kD protein | 1325 | 80.73 | 0 | 20 | 23.33 | 28.33 | 28.33 | 43.33 | 3 |
| gp4-rex 26 kD protein | 1412 | 81.46 | 0 | 18.33 | 25 | 38.33 | 18.33 | 43.33 | 5 |
| gp4-rex 26 kD protein | 1452 | 79.8 | 0 | 13.33 | 30 | 38.33 | 18.33 | 43.33 | 5 |
| gp4-rex 26 kD protein | 1864 | 80.7 | 0 | 20 | 25 | 26.67 | 28.33 | 45 | 3 |
| gp4-rex 26 kD protein | 2089 | 80.18 | 0 | 15 | 28.33 | 28.33 | 28.33 | 43.33 | 3 |
| gp4-rex 26 kD protein | 2251 | 80.81 | 0 | 18.33 | 26.67 | 35 | 20 | 45 | 6 |
| gp5-tax protein | 60 | 78.34 | 0 | 20 | 20 | 33.33 | 26.67 | 40 | 4 |
| gp5-tax protein | 191 | 78.82 | 0 | 10 | 30 | 30 | 30 | 40 | 5 |
| gp5-tax protein | 284 | 80.73 | 0 | 13.33 | 30 | 30 | 26.67 | 43.33 | 4 |
| gp5-tax protein | 424 | 80.42 | 0 | 20 | 25 | 35 | 20 | 45 | 4 |
| gp5-tax protein | 1027 | 80.03 | 0 | 13.33 | 30 | 30 | 26.67 | 43.33 | 3 |
| gp5-tax protein | 1381 | 80.81 | 0 | 13.33 | 30 | 43.33 | 13.33 | 43.33 | 4 |
| gp5-tax protein | 1589 | 81.49 | 0 | 15 | 30 | 31.67 | 23.33 | 45 | 4 |
| gp5-tax protein | 1853 | 81.19 | 0 | 16.67 | 28.33 | 30 | 25 | 45 | 2 |
| gp5-tax protein | 1949 | 81.23 | 0 | 20 | 25 | 36.67 | 18.33 | 45 | 4 |
| gp5-tax protein | 2403 | 80.99 | 0 | 20 | 25 | 25 | 30 | 45 | 3 |

TABLE 1-continued

| Selected viral probes | | | | | | | | |
|---|---|---|---|---|---|---|---|---|
| gp6-env peptide | 60 | 79.45 | 0 | 11.67 | 30 | 38.33 | 20 | 41.67 | 4 |
| gp6-env peptide | 302 | 80.73 | 0 | 20 | 23.33 | 28.33 | 28.33 | 43.33 | 3 |
| gp6-env peptide | 389 | 81.46 | 0 | 18.33 | 25 | 38.33 | 18.33 | 43.33 | 5 |
| gp6-env peptide | 429 | 79.8 | 0 | 13.33 | 30 | 38.33 | 18.33 | 43.33 | 5 |
| gp6-env peptide | 841 | 80.7 | 0 | 20 | 25 | 26.67 | 28.33 | 45 | 3 |
| gp6-env peptide | 863 | 80.06 | 0 | 13.33 | 30 | 33.33 | 23.33 | 43.33 | 3 |
| gp6-env peptide | 1066 | 80.18 | 0 | 15 | 28.33 | 28.33 | 28.33 | 43.33 | 3 |
| gp6-env peptide | 1087 | 80.45 | 0 | 20 | 25 | 28.33 | 26.67 | 45 | 3 |
| gp6-env peptide | 1228 | 80.81 | 0 | 18.33 | 26.67 | 35 | 20 | 45 | 6 |
| gp6-env peptide | 1456 | 79.38 | 0 | 11.67 | 30 | 21.67 | 36.67 | 41.67 | 4 |
| 3 LTR | 502 | 80.91 | 0 | 28.33 | 16.67 | 36.67 | 18.33 | 45 | 4 |
| 3 LTR | 503 | 80.27 | 0 | 26.67 | 18.33 | 36.67 | 18.33 | 45 | 4 |
| 3 LTR | 504 | 80.93 | 0 | 26.67 | 18.33 | 36.67 | 18.33 | 45 | 4 |
| 3 LTR | 506 | 81 | 0 | 28.33 | 16.67 | 36.67 | 18.33 | 45 | 4 |
| 3 LTR | 507 | 80.3 | 0 | 26.67 | 16.67 | 36.67 | 20 | 43.33 | 4 |
| 3 LTR | 508 | 80.17 | 0 | 25 | 16.67 | 36.67 | 21.67 | 41.67 | 4 |
| 3 LTR | 509 | 79.64 | 0 | 25 | 16.67 | 38.33 | 20 | 41.67 | 4 |
| 3 LTR | 510 | 78.94 | 0 | 23.33 | 16.67 | 40 | 20 | 40 | 4 |
| 3 LTR | 511 | 78.88 | 0 | 21.67 | 16.67 | 41.67 | 20 | 38.33 | 4 |
| 3 LTR | 513 | 77.51 | 0 | 20 | 16.67 | 41.67 | 21.67 | 36.67 | 4 |
| anchored capsid protein C | 71 | 81.86 | 0 | 26.67 | 18.33 | 41.67 | 13.33 | 45 | 4 |
| anchored capsid protein C | 72 | 81.77 | 0 | 26.67 | 18.33 | 40 | 15 | 45 | 4 |
| anchored capsid protein C | 73 | 81.13 | 0 | 26.67 | 18.33 | 40 | 15 | 45 | 4 |
| anchored capsid protein C | 74 | 81.13 | 0 | 28.33 | 16.67 | 40 | 15 | 45 | 4 |
| anchored capsid protein C | 75 | 80.86 | 0 | 26.67 | 16.67 | 41.67 | 15 | 43.33 | 4 |
| anchored capsid protein C | 76 | 80.86 | 0 | 28.33 | 15 | 41.67 | 15 | 43.33 | 4 |
| anchored capsid protein C | 84 | 81.58 | 0 | 28.33 | 15 | 43.33 | 13.33 | 43.33 | 4 |
| anchored capsid protein C | 88 | 81.3 | 0 | 26.67 | 16.67 | 43.33 | 13.33 | 43.33 | 4 |
| anchored capsid protein C | 89 | 81.38 | 0 | 26.67 | 18.33 | 43.33 | 11.67 | 45 | 4 |
| anchored capsid protein C | 91 | 82.19 | 0 | 28.33 | 16.67 | 41.67 | 13.33 | 45 | 4 |
| membrane glycoprotein precursor prM | 147 | 81.75 | 0 | 28.33 | 16.67 | 30 | 25 | 45 | 5 |
| membrane glycoprotein precursor prM | 148 | 81.23 | 0 | 28.33 | 16.67 | 30 | 25 | 45 | 5 |
| membrane glycoprotein precursor prM | 149 | 80.51 | 0 | 28.33 | 16.67 | 30 | 25 | 45 | 5 |
| membrane glycoprotein precursor prM | 150 | 80.31 | 0 | 26.67 | 16.67 | 31.67 | 25 | 43.33 | 5 |
| membrane glycoprotein precursor prM | 151 | 80.31 | 0 | 25 | 18.33 | 31.67 | 25 | 43.33 | 5 |
| membrane glycoprotein precursor prM | 152 | 80.51 | 0 | 25 | 20 | 31.67 | 23.33 | 45 | 5 |
| membrane glycoprotein precursor prM | 153 | 80.66 | 0 | 25 | 20 | 31.67 | 23.33 | 45 | 5 |
| membrane glycoprotein precursor prM | 154 | 81.23 | 0 | 25 | 20 | 31.67 | 23.33 | 45 | 5 |
| membrane glycoprotein precursor prM | 155 | 81.23 | 0 | 25 | 20 | 33.33 | 21.67 | 45 | 5 |
| membrane glycoprotein precursor prM | 156 | 80.53 | 0 | 25 | 18.33 | 35 | 21.67 | 43.33 | 5 |
| envelope protein E | 336 | 82.12 | 0 | 20 | 25 | 36.67 | 18.33 | 45 | 3 |
| envelope protein E | 624 | 81.25 | 0 | 26.67 | 16.67 | 26.67 | 30 | 43.33 | 3 |
| envelope protein E | 654 | 79.31 | 0 | 31.67 | 10 | 35 | 23.33 | 41.67 | 5 |
| envelope protein E | 684 | 80.21 | 0 | 28.33 | 13.33 | 30 | 28.33 | 41.67 | 4 |

TABLE 1-continued

| Selected viral probes | | | | | | | | | |
|---|---|---|---|---|---|---|---|---|---|
| envelope protein E | 716 | 82.63 | 0 | 23.33 | 21.67 | 25 | 30 | 45 | 4 |
| envelope protein E | 909 | 81.01 | 0 | 26.67 | 18.33 | 25 | 30 | 45 | 3 |
| envelope protein E | 1111 | 79.43 | 0 | 25 | 18.33 | 31.67 | 25 | 43.33 | 5 |
| envelope protein E | 1141 | 78.97 | 0 | 21.67 | 20 | 40 | 18.33 | 41.67 | 3 |
| envelope protein E | 1185 | 82.37 | 0 | 20 | 25 | 31.67 | 23.33 | 45 | 3 |
| envelope protein E | 1414 | 79.7 | 0 | 26.67 | 18.33 | 31.67 | 23.33 | 45 | 2 |
| nonstructural protein NS1 | 86 | 81.31 | 0 | 30 | 15 | 36.67 | 18.33 | 45 | 4 |
| nonstructural protein NS1 | 459 | 82.08 | 0 | 33.33 | 11.67 | 30 | 25 | 45 | 3 |
| nonstructural protein NS1 | 491 | 81.68 | 0 | 23.33 | 21.67 | 31.67 | 23.33 | 45 | 3 |
| nonstructural protein NS1 | 540 | 80.7 | 0 | 25 | 20 | 36.67 | 18.33 | 45 | 2 |
| nonstructural protein NS1 | 631 | 81.55 | 0 | 30 | 15 | 23.33 | 31.67 | 45 | 4 |
| nonstructural protein NS1 | 700 | 81.52 | 0 | 21.67 | 21.67 | 28.33 | 28.33 | 43.33 | 4 |
| nonstructural protein NS1 | 732 | 79.8 | 0 | 28.33 | 13.33 | 33.33 | 25 | 41.67 | 5 |
| nonstructural protein NS1 | 927 | 80.43 | 0 | 26.67 | 18.33 | 31.67 | 23.33 | 45 | 3 |
| nonstructural protein NS1 | 960 | 80.83 | 0 | 18.33 | 25 | 40 | 16.67 | 43.33 | 3 |
| nonstructural protein NS1 | 1003 | 80.82 | 0 | 26.67 | 18.33 | 30 | 25 | 45 | 3 |
| nonstructural protein NS2A | 110 | 80.91 | 0 | 20 | 25 | 33.33 | 21.67 | 45 | 6 |
| nonstructural protein NS2A | 193 | 81.59 | 0 | 31.67 | 13.33 | 23.33 | 31.67 | 45 | 2 |
| nonstructural protein NS2A | 281 | 81.21 | 0 | 21.67 | 23.33 | 30 | 25 | 45 | 3 |
| nonstructural protein NS2A | 301 | 81.07 | 0 | 25 | 20 | 28.33 | 26.67 | 45 | 2 |
| nonstructural protein NS2A | 381 | 81.95 | 0 | 21.67 | 20 | 18.33 | 40 | 41.67 | 4 |
| nonstructural protein NS2A | 401 | 81.59 | 0 | 26.67 | 16.67 | 21.67 | 35 | 43.33 | 4 |
| nonstructural protein NS2A | 429 | 80.89 | 0 | 26.67 | 16.67 | 26.67 | 30 | 43.33 | 4 |
| nonstructural protein NS2A | 451 | 81.2 | 0 | 23.33 | 21.67 | 30 | 25 | 45 | 3 |
| nonstructural protein NS2A | 547 | 81.37 | 0 | 25 | 20 | 21.67 | 33.33 | 45 | 5 |
| nonstructural protein NS2A | 588 | 80.63 | 0 | 26.67 | 18.33 | 16.67 | 38.33 | 45 | 5 |
| nonstructural protein NS2B | 60 | 80.85 | 0 | 20 | 25 | 28.33 | 26.67 | 45 | 4 |
| nonstructural protein NS2B | 145 | 81.64 | 0 | 25 | 20 | 31.67 | 23.33 | 45 | 3 |
| nonstructural protein NS2B | 148 | 81.54 | 0 | 25 | 20 | 31.67 | 23.33 | 45 | 3 |
| nonstructural protein NS2B | 149 | 81.54 | 0 | 25 | 20 | 33.33 | 21.67 | 45 | 3 |
| nonstructural protein NS2B | 152 | 81.58 | 0 | 25 | 20 | 31.67 | 23.33 | 45 | 3 |
| nonstructural protein NS2B | 154 | 81.58 | 0 | 26.67 | 18.33 | 30 | 25 | 45 | 3 |
| nonstructural protein NS2B | 155 | 81.11 | 0 | 26.67 | 18.33 | 31.67 | 23.33 | 45 | 3 |
| nonstructural protein NS2B | 156 | 80.29 | 0 | 28.33 | 16.67 | 31.67 | 23.33 | 45 | 3 |
| nonstructural protein NS2B | 157 | 80.67 | 0 | 26.67 | 16.67 | 31.67 | 25 | 43.33 | 3 |
| nonstructural protein NS2B | 158 | 80.7 | 0 | 26.67 | 16.67 | 31.67 | 25 | 43.33 | 3 |
| nonstructural protein NS3 | 137 | 80.84 | 0 | 30 | 15 | 38.33 | 16.67 | 45 | 3 |
| nonstructural protein NS3 | 267 | 81.55 | 0 | 26.67 | 18.33 | 28.33 | 26.67 | 45 | 6 |
| nonstructural protein NS3 | 346 | 80.83 | 0 | 25 | 20 | 33.33 | 21.67 | 45 | 4 |

TABLE 1-continued

| Selected viral probes | | | | | | | | |
|---|---|---|---|---|---|---|---|---|
| nonstructural protein NS3 | 641 | 81.63 | 0 | 26.67 | 18.33 | 33.33 | 21.67 | 45 | 5 |
| nonstructural protein NS3 | 701 | 79.88 | 0 | 28.33 | 15 | 36.67 | 20 | 43.33 | 4 |
| nonstructural protein NS3 | 761 | 81.94 | 0 | 26.67 | 18.33 | 31.67 | 23.33 | 45 | 4 |
| nonstructural protein NS3 | 898 | 81.24 | 0 | 15 | 30 | 30 | 25 | 45 | 3 |
| nonstructural protein NS3 | 1101 | 81.77 | 0 | 23.33 | 21.67 | 25 | 30 | 45 | 3 |
| nonstructural protein NS3 | 1258 | 80.94 | 0 | 23.33 | 21.67 | 43.33 | 11.67 | 45 | 3 |
| nonstructural protein NS3 | 1430 | 82.18 | 0 | 26.67 | 18.33 | 28.33 | 26.67 | 45 | 3 |
| nonstructural protein NS4A | 207 | 81.11 | 0 | 23.33 | 21.67 | 18.33 | 36.67 | 45 | 3 |
| nonstructural protein NS4A | 208 | 81.05 | 0 | 21.67 | 21.67 | 20 | 36.67 | 43.33 | 3 |
| nonstructural protein NS4A | 209 | 80.67 | 0 | 21.67 | 23.33 | 18.33 | 36.67 | 45 | 3 |
| nonstructural protein NS4A | 210 | 80.32 | 0 | 21.67 | 21.67 | 20 | 36.67 | 43.33 | 3 |
| nonstructural protein NS4A | 211 | 80.23 | 0 | 21.67 | 21.67 | 20 | 36.67 | 43.33 | 3 |
| nonstructural protein NS4A | 212 | 80.69 | 0 | 21.67 | 21.67 | 21.67 | 35 | 43.33 | 3 |
| nonstructural protein NS4A | 213 | 80.32 | 0 | 21.67 | 23.33 | 20 | 35 | 45 | 3 |
| nonstructural protein NS4A | 214 | 80.69 | 0 | 21.67 | 21.67 | 20 | 36.67 | 43.33 | 3 |
| nonstructural protein NS4A | 215 | 80.26 | 0 | 21.67 | 21.67 | 20 | 36.67 | 43.33 | 3 |
| nonstructural protein NS4A | 216 | 79.62 | 0 | 21.67 | 21.67 | 20 | 36.67 | 43.33 | 3 |
| nonstructural protein NS4B | 63 | 76.76 | 0 | 15 | 20 | 43.33 | 21.67 | 35 | 5 |
| nonstructural protein NS4B | 83 | 80.89 | 0 | 23.33 | 20 | 30 | 26.67 | 43.33 | 5 |
| nonstructural protein NS4B | 260 | 80.89 | 0 | 30 | 15 | 26.67 | 28.33 | 45 | 3 |
| nonstructural protein NS4B | 286 | 81.85 | 0 | 21.67 | 23.33 | 35 | 20 | 45 | 3 |
| nonstructural protein NS4B | 581 | 79.07 | 0 | 11.67 | 30 | 35 | 23.33 | 41.67 | 3 |
| nonstructural protein NS4B | 601 | 78.17 | 0 | 11.67 | 26.67 | 35 | 26.67 | 38.33 | 3 |
| nonstructural protein NS4B | 626 | 81.65 | 0 | 15 | 30 | 31.67 | 23.33 | 45 | 3 |
| nonstructural protein NS4B | 718 | 80.6 | 0 | 31.67 | 11.67 | 26.67 | 30 | 43.33 | 3 |
| nonstructural protein NS4B | 738 | 79.4 | 0 | 30 | 10 | 35 | 25 | 40 | 3 |
| nonstructural protein NS4B | 758 | 80.52 | 0 | 33.33 | 10 | 31.67 | 25 | 43.33 | 3 |
| nonstructural protein NS5 | 60 | 77.17 | 0 | 23.33 | 16.67 | 36.67 | 23.33 | 40 | 3 |
| nonstructural protein NS6 | 120 | 80.17 | 0 | 26.67 | 18.33 | 36.67 | 18.33 | 45 | 4 |
| nonstructural protein NS7 | 236 | 81.19 | 0 | 26.67 | 18.33 | 40 | 15 | 45 | 4 |
| nonstructural protein NS8 | 555 | 81.66 | 0 | 31.67 | 13.33 | 31.67 | 23.33 | 45 | 3 |
| nonstructural protein NS9 | 615 | 81.92 | 0 | 21.67 | 23.33 | 25 | 30 | 45 | 4 |
| nonstructural protein NS10 | 1363 | 81.34 | 0 | 28.33 | 15 | 41.67 | 15 | 43.33 | 6 |
| nonstructural protein NS11 | 1461 | 82.15 | 0 | 33.33 | 11.67 | 35 | 20 | 45 | 4 |
| nonstructural protein NS12 | 1521 | 81.38 | 0 | 30 | 15 | 33.33 | 21.67 | 45 | 3 |
| nonstructural protein NS13 | 1996 | 80.61 | 0 | 28.33 | 16.67 | 41.67 | 13.33 | 45 | 6 |
| nonstructural protein NS14 | 2351 | 81.09 | 0 | 28.33 | 16.67 | 25 | 30 | 45 | 2 |
| anchored capsid protein C | 114 | 82.17 | 0 | 20 | 25 | 46.67 | 8.33 | 45 | 4 |
| anchored capsid protein C | 116 | 82.17 | 0 | 20 | 25 | 46.67 | 8.33 | 45 | 4 |

TABLE 1-continued

| Selected viral probes | | | | | | | | | |
|---|---|---|---|---|---|---|---|---|---|
| anchored capsid protein C | 117 | 82.17 | 0 | 20 | 25 | 46.67 | 8.33 | 45 | 4 |
| anchored capsid protein C | 121 | 82.23 | 0 | 18.33 | 26.67 | 41.67 | 13.33 | 45 | 4 |
| anchored capsid protein C | 138 | 80.98 | 0 | 20 | 25 | 33.33 | 21.67 | 45 | 3 |
| anchored capsid protein C | 139 | 80.13 | 0 | 20 | 23.33 | 35 | 21.67 | 43.33 | 3 |
| anchored capsid protein C | 140 | 79.56 | 0 | 18.33 | 25 | 35 | 21.67 | 43.33 | 3 |
| anchored capsid protein C | 141 | 79.71 | 0 | 20 | 23.33 | 35 | 21.67 | 43.33 | 3 |
| anchored capsid protein C | 142 | 80 | 0 | 20 | 21.67 | 36.67 | 21.67 | 41.67 | 3 |
| anchored capsid protein C | 143 | 80.14 | 0 | 20 | 23.33 | 35 | 21.67 | 43.33 | 3 |
| membrane glycoprotein precursor prM | 85 | 82.64 | 0 | 25 | 20 | 25 | 30 | 45 | 3 |
| membrane glycoprotein precursor prM | 167 | 80.7 | 0 | 25 | 20 | 40 | 15 | 45 | 4 |
| membrane glycoprotein precursor prM | 168 | 80.01 | 0 | 25 | 18.33 | 40 | 16.67 | 43.33 | 4 |
| membrane glycoprotein precursor prM | 169 | 80.01 | 0 | 26.67 | 16.67 | 40 | 16.67 | 43.33 | 4 |
| membrane glycoprotein precursor prM | 170 | 80.7 | 0 | 28.33 | 16.67 | 38.33 | 16.67 | 45 | 4 |
| membrane glycoprotein precursor prM | 171 | 81.21 | 0 | 28.33 | 16.67 | 36.67 | 18.33 | 45 | 4 |
| membrane glycoprotein precursor prM | 172 | 80.8 | 0 | 28.33 | 16.67 | 35 | 20 | 45 | 4 |
| membrane glycoprotein precursor prM | 173 | 80.8 | 0 | 26.67 | 18.33 | 35 | 20 | 45 | 4 |
| membrane glycoprotein precursor prM | 175 | 81.55 | 0 | 26.67 | 18.33 | 35 | 20 | 45 | 4 |
| membrane glycoprotein precursor prM | 182 | 81.69 | 0 | 28.33 | 16.67 | 38.33 | 16.67 | 45 | 4 |
| membrane glycoprotein M | 85 | 82.64 | 0 | 25 | 20 | 25 | 30 | 45 | 3 |
| membrane glycoprotein M | 167 | 80.7 | 0 | 25 | 20 | 40 | 15 | 45 | 4 |
| membrane glycoprotein M | 168 | 80.01 | 0 | 25 | 18.33 | 40 | 16.67 | 43.33 | 4 |
| membrane glycoprotein M | 169 | 80.01 | 0 | 26.67 | 16.67 | 40 | 16.67 | 43.33 | 4 |
| membrane glycoprotein M | 170 | 80.7 | 0 | 28.33 | 16.67 | 38.33 | 16.67 | 45 | 4 |
| membrane glycoprotein M | 171 | 81.21 | 0 | 28.33 | 16.67 | 36.67 | 18.33 | 45 | 4 |
| membrane glycoprotein M | 172 | 80.8 | 0 | 28.33 | 16.67 | 35 | 20 | 45 | 4 |
| membrane glycoprotein M | 173 | 80.8 | 0 | 26.67 | 18.33 | 35 | 20 | 45 | 4 |
| membrane glycoprotein M | 175 | 81.55 | 0 | 26.67 | 18.33 | 35 | 20 | 45 | 4 |
| membrane glycoprotein M | 182 | 81.69 | 0 | 28.33 | 16.67 | 38.33 | 16.67 | 45 | 4 |
| envelope protein E | 180 | 81.01 | 0 | 25 | 20 | 25 | 30 | 45 | 4 |
| envelope protein E | 607 | 81.26 | 0 | 21.67 | 23.33 | 31.67 | 23.33 | 45 | 4 |
| envelope protein E | 679 | 81.49 | 0 | 31.67 | 13.33 | 33.33 | 21.67 | 45 | 3 |
| envelope protein E | 794 | 82 | 0 | 23.33 | 21.67 | 30 | 25 | 45 | 3 |
| envelope protein E | 895 | 81.01 | 0 | 26.67 | 18.33 | 21.67 | 33.33 | 45 | 3 |
| envelope protein E | 1009 | 81.24 | 0 | 25 | 20 | 28.33 | 26.67 | 45 | 3 |

TABLE 1-continued

| Selected viral probes | | | | | | | | |
|---|---|---|---|---|---|---|---|---|
| envelope protein E | 1095 | 81.7 | 0 | 23.33 | 21.67 | 28.33 | 26.67 | 45 | 4 |
| envelope protein E | 1155 | 81.72 | 0 | 23.33 | 21.67 | 33.33 | 21.67 | 45 | 3 |
| envelope protein E | 1369 | 82.3 | 0 | 25 | 20 | 31.67 | 23.33 | 45 | 4 |
| envelope protein E | 1429 | 80.88 | 0 | 25 | 18.33 | 33.33 | 23.33 | 43.33 | 4 |
| nonstructural protein NS1 | 228 | 81.52 | 0 | 21.67 | 23.33 | 31.67 | 23.33 | 45 | 3 |
| nonstructural protein NS1 | 230 | 80.95 | 0 | 21.67 | 23.33 | 33.33 | 21.67 | 45 | 3 |
| nonstructural protein NS1 | 231 | 80.85 | 0 | 23.33 | 21.67 | 33.33 | 21.67 | 45 | 3 |
| nonstructural protein NS1 | 232 | 80.95 | 0 | 23.33 | 21.67 | 31.67 | 23.33 | 45 | 3 |
| nonstructural protein NS1 | 233 | 80.26 | 0 | 21.67 | 21.67 | 31.67 | 25 | 43.33 | 3 |
| nonstructural protein NS1 | 234 | 80.1 | 0 | 20 | 21.67 | 33.33 | 25 | 41.67 | 3 |
| nonstructural protein NS1 | 235 | 79.64 | 0 | 21.67 | 21.67 | 33.33 | 23.33 | 43.33 | 3 |
| nonstructural protein NS1 | 236 | 79.35 | 0 | 20 | 21.67 | 35 | 23.33 | 41.67 | 3 |
| nonstructural protein NS1 | 237 | 78.71 | 0 | 21.67 | 20 | 35 | 23.33 | 41.67 | 3 |
| nonstructural protein NS1 | 238 | 79.27 | 0 | 21.67 | 20 | 35 | 23.33 | 41.67 | 3 |
| nonstructural protein NS2A | 138 | 80.91 | 0 | 20 | 23.33 | 40 | 16.67 | 43.33 | 6 |
| nonstructural protein NS2A | 158 | 80.41 | 0 | 26.67 | 15 | 41.67 | 16.67 | 41.67 | 6 |
| nonstructural protein NS2A | 178 | 79 | 0 | 26.67 | 13.33 | 33.33 | 26.67 | 40 | 6 |
| nonstructural protein NS2A | 198 | 78.54 | 0 | 25 | 13.33 | 26.67 | 35 | 38.33 | 4 |
| nonstructural protein NS2A | 218 | 79.47 | 0 | 20 | 20 | 25 | 35 | 40 | 4 |
| nonstructural protein NS2A | 293 | 80.68 | 0 | 16.67 | 28.33 | 25 | 30 | 45 | 3 |
| nonstructural protein NS2A | 349 | 81.37 | 0 | 25 | 20 | 25 | 30 | 45 | 4 |
| nonstructural protein NS2A | 369 | 81.68 | 0 | 21.67 | 23.33 | 23.33 | 31.67 | 45 | 3 |
| nonstructural protein NS2A | 389 | 81.52 | 0 | 20 | 23.33 | 23.33 | 33.33 | 43.33 | 4 |
| nonstructural protein NS2A | 415 | 82.2 | 0 | 25 | 20 | 23.33 | 31.67 | 45 | 5 |
| nonstructural protein NS2B | 145 | 82.27 | 0 | 26.67 | 18.33 | 30 | 25 | 45 | 4 |
| nonstructural protein NS2B | 146 | 81.44 | 0 | 28.33 | 16.67 | 30 | 25 | 45 | 4 |
| nonstructural protein NS2B | 147 | 81.44 | 0 | 28.33 | 16.67 | 30 | 25 | 45 | 4 |
| nonstructural protein NS2B | 148 | 81.83 | 0 | 26.67 | 16.67 | 30 | 26.67 | 43.33 | 4 |
| nonstructural protein NS2B | 149 | 81.83 | 0 | 26.67 | 16.67 | 31.67 | 25 | 43.33 | 4 |
| nonstructural protein NS2B | 150 | 81.44 | 0 | 28.33 | 16.67 | 30 | 25 | 45 | 4 |
| nonstructural protein NS2B | 151 | 81.25 | 0 | 26.67 | 16.67 | 30 | 26.67 | 43.33 | 4 |
| nonstructural protein NS2B | 152 | 81.16 | 0 | 25 | 16.67 | 31.67 | 26.67 | 41.67 | 4 |
| nonstructural protein NS2B | 153 | 81.48 | 0 | 26.67 | 16.67 | 30 | 26.67 | 43.33 | 4 |
| nonstructural protein NS2B | 154 | 81.99 | 0 | 26.67 | 16.67 | 30 | 26.67 | 43.33 | 4 |
| nonstructural protein NS3 | 60 | 80.56 | 0 | 21.67 | 21.67 | 33.33 | 23.33 | 43.33 | 4 |
| nonstructural protein NS3 | 129 | 80.67 | 0 | 30 | 15 | 36.67 | 18.33 | 45 | 3 |
| nonstructural protein NS3 | 190 | 81.8 | 0 | 21.67 | 23.33 | 31.67 | 23.33 | 45 | 3 |
| nonstructural protein NS3 | 261 | 81.8 | 0 | 20 | 25 | 26.67 | 28.33 | 45 | 3 |
| nonstructural protein NS3 | 421 | 81.85 | 0 | 21.67 | 23.33 | 31.67 | 23.33 | 45 | 3 |

TABLE 1-continued

| Selected viral probes | | | | | | | | | |
|---|---|---|---|---|---|---|---|---|---|
| nonstructural protein NS3 | 646 | 81.8 | 0 | 23.33 | 21.67 | 33.33 | 21.67 | 45 | 4 |
| nonstructural protein NS3 | 708 | 80.26 | 0 | 25 | 20 | 36.67 | 18.33 | 45 | 4 |
| nonstructural protein NS3 | 785 | 81.88 | 0 | 26.67 | 18.33 | 25 | 30 | 45 | 4 |
| nonstructural protein NS3 | 845 | 80.16 | 0 | 28.33 | 16.67 | 35 | 20 | 45 | 3 |
| nonstructural protein NS3 | 1049 | 81.46 | 0 | 15 | 30 | 30 | 25 | 45 | 4 |
| nonstructural protein NS4A | 173 | 80.63 | 0 | 33.33 | 11.67 | 28.33 | 26.67 | 45 | 3 |
| nonstructural protein NS4A | 174 | 80.57 | 0 | 31.67 | 11.67 | 28.33 | 28.33 | 43.33 | 3 |
| nonstructural protein NS4A | 175 | 80.16 | 0 | 31.67 | 11.67 | 26.67 | 30 | 43.33 | 4 |
| nonstructural protein NS4A | 176 | 79.45 | 0 | 30 | 11.67 | 26.67 | 31.67 | 41.67 | 5 |
| nonstructural protein NS4A | 177 | 79.39 | 0 | 28.33 | 11.67 | 26.67 | 33.33 | 40 | 6 |
| nonstructural protein NS4A | 178 | 79.81 | 0 | 30 | 11.67 | 25 | 33.33 | 41.67 | 6 |
| nonstructural protein NS4A | 179 | 80.32 | 0 | 30 | 11.67 | 25 | 33.33 | 41.67 | 6 |
| nonstructural protein NS4A | 180 | 80.02 | 0 | 31.67 | 11.67 | 25 | 31.67 | 43.33 | 6 |
| nonstructural protein NS4A | 181 | 80.49 | 0 | 31.67 | 10 | 25 | 33.33 | 41.67 | 6 |
| nonstructural protein NS4A | 182 | 80.65 | 0 | 33.33 | 10 | 25 | 31.67 | 43.33 | 6 |
| nonstructural protein NS4B | 252 | 81.84 | 0 | 25 | 20 | 26.67 | 28.33 | 45 | 3 |
| nonstructural protein NS4B | 256 | 80.86 | 0 | 26.67 | 18.33 | 28.33 | 26.67 | 45 | 6 |
| nonstructural protein NS4B | 257 | 80.6 | 0 | 26.67 | 16.67 | 30 | 26.67 | 43.33 | 6 |
| nonstructural protein NS4B | 258 | 80.69 | 0 | 26.67 | 16.67 | 30 | 26.67 | 43.33 | 6 |
| nonstructural protein NS4B | 259 | 81.56 | 0 | 28.33 | 16.67 | 30 | 25 | 45 | 6 |
| nonstructural protein NS4B | 260 | 82.07 | 0 | 28.33 | 16.67 | 28.33 | 26.67 | 45 | 6 |
| nonstructural protein NS4B | 261 | 81.53 | 0 | 28.33 | 16.67 | 28.33 | 26.67 | 45 | 6 |
| nonstructural protein NS4B | 262 | 81.63 | 0 | 28.33 | 16.67 | 28.33 | 26.67 | 45 | 6 |
| nonstructural protein NS4B | 263 | 81.53 | 0 | 28.33 | 16.67 | 28.33 | 26.67 | 45 | 6 |
| nonstructural protein NS4B | 264 | 80.96 | 0 | 28.33 | 16.67 | 28.33 | 26.67 | 45 | 6 |
| nonstructural protein NS5 | 60 | 79.85 | 0 | 30 | 15 | 26.67 | 28.33 | 45 | 4 |
| nonstructural protein NS5 | 120 | 78.8 | 0 | 28.33 | 13.33 | 33.33 | 25 | 41.67 | 4 |
| nonstructural protein NS5 | 221 | 81.04 | 0 | 31.67 | 13.33 | 31.67 | 23.33 | 45 | 3 |
| nonstructural protein NS5 | 600 | 81.29 | 0 | 21.67 | 23.33 | 28.33 | 26.67 | 45 | 3 |
| nonstructural protein NS5 | 668 | 81.48 | 0 | 18.33 | 26.67 | 35 | 20 | 45 | 3 |
| nonstructural protein NS5 | 808 | 81.66 | 0 | 31.67 | 13.33 | 35 | 20 | 45 | 5 |
| nonstructural protein NS5 | 1161 | 81.68 | 0 | 28.33 | 16.67 | 33.33 | 21.67 | 45 | 3 |
| nonstructural protein NS5 | 1362 | 81.41 | 0 | 30 | 15 | 40 | 15 | 45 | 3 |
| nonstructural protein NS5 | 1475 | 82.03 | 0 | 28.33 | 16.67 | 35 | 20 | 45 | 4 |
| nonstructural protein NS5 | 1546 | 81.44 | 0 | 26.67 | 18.33 | 33.33 | 21.67 | 45 | 4 |
| gp1-nonstructural polyprotein | 103 | 81.63 | 0 | 20 | 25 | 26.67 | 28.33 | 45 | 3 |
| gp1-nonstructural polyprotein | 164 | 80.48 | 0 | 33.33 | 11.67 | 33.33 | 21.67 | 45 | 3 |

TABLE 1-continued

| Selected viral probes | | | | | | | | | |
|---|---|---|---|---|---|---|---|---|---|
| gp1-nonstructural polyprotein | 260 | 81.9 | 0 | 28.33 | 16.67 | 38.33 | 16.67 | 45 | 5 |
| gp1-nonstructural polyprotein | 338 | 81.53 | 0 | 25 | 20 | 26.67 | 28.33 | 45 | 4 |
| gp1-nonstructural polyprotein | 410 | 81.53 | 0 | 30 | 15 | 33.33 | 21.67 | 45 | 2 |
| gp1-nonstructural polyprotein | 552 | 80.19 | 0 | 13.33 | 30 | 28.33 | 28.33 | 43.33 | 3 |
| gp1-nonstructural polyprotein | 681 | 80.36 | 0 | 30 | 15 | 21.67 | 33.33 | 45 | 4 |
| gp1-nonstructural polyprotein | 741 | 80.26 | 0 | 20 | 21.67 | 28.33 | 30 | 41.67 | 4 |
| gp1-nonstructural polyprotein | 809 | 81.32 | 0 | 18.33 | 26.67 | 26.67 | 28.33 | 45 | 3 |
| gp1-nonstructural polyprotein | 958 | 80.67 | 0 | 26.67 | 18.33 | 36.67 | 18.33 | 45 | 3 |
| gp2-structural polyprotein | 307 | 80.44 | 0 | 25 | 20 | 28.33 | 26.67 | 45 | 3 |
| gp2-structural polyprotein | 372 | 82.09 | 0 | 25 | 20 | 33.33 | 21.67 | 45 | 3 |
| gp2-structural polyprotein | 639 | 81.49 | 0 | 21.67 | 23.33 | 30 | 25 | 45 | 4 |
| gp2-structural polyprotein | 803 | 81.59 | 0 | 21.67 | 23.33 | 30 | 25 | 45 | 4 |
| gp2-structural polyprotein | 933 | 81.13 | 0 | 15 | 30 | 31.67 | 23.33 | 45 | 3 |
| gp2-structural polyprotein | 998 | 82.28 | 0 | 21.67 | 23.33 | 35 | 20 | 45 | 4 |
| gp2-structural polyprotein | 1196 | 81.58 | 0 | 16.67 | 28.33 | 28.33 | 26.67 | 45 | 4 |
| gp2-structural polyprotein | 1389 | 82.61 | 0 | 21.67 | 23.33 | 21.67 | 33.33 | 45 | 6 |
| gp2-structural polyprotein | 1696 | 80.13 | 0 | 21.67 | 23.33 | 18.33 | 36.67 | 45 | 3 |
| gp2-structural polyprotein | 2015 | 82.38 | 0 | 21.67 | 23.33 | 33.33 | 21.67 | 45 | 5 |
| gp3-truncated polyprotein | 116 | 82.61 | 0 | 21.67 | 23.33 | 21.67 | 33.33 | 45 | 6 |
| gp3-truncated polyprotein | 423 | 80.13 | 0 | 21.67 | 23.33 | 18.33 | 36.67 | 45 | 3 |
| gp3-truncated polyprotein | 742 | 82.38 | 0 | 21.67 | 23.33 | 33.33 | 21.67 | 45 | 5 |
| gp3-truncated polyprotein | 844 | 82.49 | 0 | 21.67 | 23.33 | 33.33 | 21.67 | 45 | 5 |
| gp3-truncated polyprotein | 907 | 75.74 | 0 | 25 | 10 | 38.33 | 26.67 | 35 | 3 |
| gp3-truncated polyprotein | 1181 | 79.99 | 0 | 28.33 | 16.67 | 33.33 | 21.67 | 45 | 3 |
| gp3-truncated polyprotein | 1251 | 81.55 | 0 | 20 | 25 | 31.67 | 23.33 | 45 | 3 |
| gp3-truncated polyprotein | 1341 | 81.89 | 0 | 28.33 | 16.67 | 33.33 | 21.67 | 45 | 3 |
| gp3-truncated polyprotein | 1487 | 80.92 | 0 | 16.67 | 28.33 | 33.33 | 21.67 | 45 | 3 |
| gp3-truncated polyprotein | 1576 | 80.51 | 0 | 20 | 25 | 30 | 25 | 45 | 3 |
| anchored capsid protein C | 77 | 80.16 | 0 | 21.67 | 21.67 | 35 | 21.67 | 43.33 | 4 |
| anchored capsid protein C | 107 | 77.96 | 0 | 25 | 11.67 | 41.67 | 21.67 | 36.67 | 4 |
| anchored capsid protein C | 127 | 78.45 | 0 | 25 | 13.33 | 40 | 21.67 | 38.33 | 4 |
| anchored capsid protein C | 150 | 81.44 | 0 | 31.67 | 13.33 | 26.67 | 28.33 | 45 | 4 |
| anchored capsid protein C | 178 | 80.98 | 0 | 21.67 | 21.67 | 31.67 | 25 | 43.33 | 4 |
| anchored capsid protein C | 198 | 78.55 | 0 | 16.67 | 23.33 | 28.33 | 31.67 | 40 | 4 |
| anchored capsid protein C | 218 | 78.65 | 0 | 16.67 | 23.33 | 28.33 | 31.67 | 40 | 4 |

TABLE 1-continued

| Selected viral probes | | | | | | | | |
|---|---|---|---|---|---|---|---|---|
| anchored capsid protein C | 238 | 80.84 | 0 | 25 | 18.33 | 26.67 | 30 | 43.33 | 4 |
| anchored capsid protein C | 262 | 82.4 | 0 | 26.67 | 18.33 | 31.67 | 23.33 | 45 | 4 |
| anchored capsid protein C | 286 | 81.07 | 0 | 25 | 20 | 28.33 | 26.67 | 45 | 4 |
| membrane glycoprotein precursor M | 60 | 81.61 | 0 | 18.33 | 26.67 | 23.33 | 31.67 | 45 | 5 |
| membrane glycoprotein precursor M | 61 | 80.88 | 0 | 18.33 | 25 | 25 | 31.67 | 43.33 | 5 |
| membrane glycoprotein precursor M | 62 | 80.15 | 0 | 18.33 | 25 | 25 | 31.67 | 43.33 | 5 |
| membrane glycoprotein precursor M | 63 | 79.96 | 0 | 16.67 | 25 | 26.67 | 31.67 | 41.67 | 5 |
| membrane glycoprotein precursor M | 64 | 79.82 | 0 | 15 | 25 | 28.33 | 31.67 | 40 | 5 |
| membrane glycoprotein precursor M | 65 | 79.89 | 0 | 16.67 | 25 | 28.33 | 30 | 41.67 | 5 |
| membrane glycoprotein precursor M | 66 | 80.09 | 0 | 18.33 | 25 | 26.67 | 30 | 43.33 | 5 |
| membrane glycoprotein precursor M | 67 | 79.82 | 0 | 18.33 | 23.33 | 28.33 | 30 | 41.67 | 5 |
| membrane glycoprotein precursor M | 68 | 79.49 | 0 | 18.33 | 21.67 | 28.33 | 31.67 | 40 | 5 |
| membrane glycoprotein precursor M | 69 | 79.49 | 0 | 18.33 | 21.67 | 30 | 30 | 40 | 5 |
| envelope protein E | 105 | 80.9 | 0 | 21.67 | 23.33 | 26.67 | 28.33 | 45 | 3 |
| envelope protein E | 167 | 81.01 | 0 | 33.33 | 11.67 | 21.67 | 33.33 | 45 | 4 |
| envelope protein E | 323 | 81.49 | 0 | 30 | 15 | 35 | 20 | 45 | 4 |
| envelope protein E | 404 | 81.47 | 0 | 26.67 | 18.33 | 33.33 | 21.67 | 45 | 5 |
| envelope protein E | 532 | 80.95 | 0 | 20 | 25 | 31.67 | 23.33 | 45 | 4 |
| envelope protein E | 594 | 81.36 | 0 | 28.33 | 16.67 | 31.67 | 23.33 | 45 | 3 |
| envelope protein E | 666 | 77.48 | 0 | 20 | 15 | 41.67 | 23.33 | 35 | 5 |
| envelope protein E | 752 | 81.12 | 0 | 26.67 | 18.33 | 40 | 15 | 45 | 6 |
| envelope protein E | 812 | 79.51 | 0 | 20 | 23.33 | 35 | 21.67 | 43.33 | 3 |
| envelope protein E | 936 | 77.28 | 0 | 25 | 11.67 | 35 | 28.33 | 36.67 | 6 |
| nonstructural protein NS1 | 60 | 80.02 | 0 | 26.67 | 16.67 | 38.33 | 18.33 | 43.33 | 3 |
| nonstructural protein NS1 | 160 | 81.26 | 0 | 20 | 25 | 35 | 20 | 45 | 3 |
| nonstructural protein NS1 | 220 | 80.04 | 0 | 28.33 | 15 | 26.67 | 30 | 43.33 | 3 |
| nonstructural protein NS1 | 280 | 80.92 | 0 | 23.33 | 18.33 | 30 | 28.33 | 41.67 | 4 |
| nonstructural protein NS1 | 340 | 78.4 | 0 | 20 | 21.67 | 40 | 18.33 | 41.67 | 3 |
| nonstructural protein NS1 | 401 | 81.84 | 0 | 21.67 | 23.33 | 35 | 20 | 45 | 4 |
| nonstructural protein NS1 | 461 | 79.88 | 0 | 30 | 15 | 35 | 20 | 45 | 4 |
| nonstructural protein NS1 | 561 | 81.72 | 0 | 21.67 | 23.33 | 28.33 | 26.67 | 45 | 3 |
| nonstructural protein NS1 | 621 | 79.19 | 0 | 25 | 13.33 | 36.67 | 25 | 38.33 | 4 |
| nonstructural protein NS1 | 698 | 81.74 | 0 | 16.67 | 28.33 | 40 | 15 | 45 | 4 |
| nonstructural protein NS2A | 63 | 78.19 | 0 | 18.33 | 20 | 36.67 | 25 | 38.33 | 4 |

TABLE 1-continued

| Selected viral probes | | | | | | | | | |
|---|---|---|---|---|---|---|---|---|---|
| nonstructural protein NS2A | 138 | 79.52 | 0 | 10 | 30 | 25 | 35 | 40 | 6 |
| nonstructural protein NS2A | 178 | 78.48 | 0 | 16.67 | 23.33 | 25 | 35 | 40 | 3 |
| nonstructural protein NS2A | 218 | 79.02 | 0 | 16.67 | 21.67 | 25 | 36.67 | 38.33 | 5 |
| nonstructural protein NS2A | 258 | 78.42 | 0 | 18.33 | 20 | 23.33 | 38.33 | 38.33 | 4 |
| nonstructural protein NS2A | 298 | 80.78 | 0 | 31.67 | 13.33 | 28.33 | 26.67 | 45 | 4 |
| nonstructural protein NS2A | 346 | 79.96 | 0 | 25 | 18.33 | 25 | 31.67 | 43.33 | 3 |
| nonstructural protein NS2A | 386 | 77.34 | 0 | 21.67 | 18.33 | 23.33 | 36.67 | 40 | 3 |
| nonstructural protein NS2A | 524 | 80.68 | 0 | 28.33 | 16.67 | 30 | 25 | 45 | 3 |
| nonstructural protein NS2A | 569 | 80.86 | 0 | 23.33 | 20 | 28.33 | 28.33 | 43.33 | 5 |
| nonstructural protein NS2B | 60 | 80.85 | 0 | 23.33 | 20 | 31.67 | 25 | 43.33 | 5 |
| nonstructural protein NS2B | 61 | 81.14 | 0 | 23.33 | 21.67 | 30 | 25 | 45 | 5 |
| nonstructural protein NS2B | 62 | 81.59 | 0 | 21.67 | 21.67 | 31.67 | 25 | 43.33 | 5 |
| nonstructural protein NS2B | 63 | 80.89 | 0 | 21.67 | 21.67 | 30 | 26.67 | 43.33 | 5 |
| nonstructural protein NS2B | 64 | 80.81 | 0 | 20 | 21.67 | 31.67 | 26.67 | 41.67 | 5 |
| nonstructural protein NS2B | 65 | 80.02 | 0 | 20 | 21.67 | 30 | 28.33 | 41.67 | 5 |
| nonstructural protein NS2B | 66 | 80.02 | 0 | 21.67 | 20 | 30 | 28.33 | 41.67 | 5 |
| nonstructural protein NS2B | 67 | 80.72 | 0 | 23.33 | 20 | 28.33 | 28.33 | 43.33 | 5 |
| nonstructural protein NS2B | 68 | 81.42 | 0 | 25 | 20 | 26.67 | 28.33 | 45 | 5 |
| nonstructural protein NS2B | 70 | 82.09 | 0 | 25 | 20 | 26.67 | 28.33 | 45 | 5 |
| nonstructural protein NS3 | 383 | 80.94 | 0 | 15 | 30 | 35 | 20 | 45 | 5 |
| nonstructural protein NS3 | 443 | 80.76 | 0 | 23.33 | 21.67 | 35 | 20 | 45 | 3 |
| nonstructural protein NS3 | 645 | 81.42 | 0 | 23.33 | 21.67 | 35 | 20 | 45 | 3 |
| nonstructural protein NS3 | 705 | 77.27 | 0 | 18.33 | 18.33 | 46.67 | 16.67 | 36.67 | 6 |
| nonstructural protein NS3 | 765 | 80.34 | 0 | 26.67 | 15 | 38.33 | 20 | 41.67 | 3 |
| nonstructural protein NS3 | 825 | 81.37 | 0 | 23.33 | 21.67 | 25 | 30 | 45 | 4 |
| nonstructural protein NS3 | 885 | 80.25 | 0 | 21.67 | 21.67 | 36.67 | 20 | 43.33 | 3 |
| nonstructural protein NS3 | 1013 | 81.43 | 0 | 21.67 | 23.33 | 30 | 25 | 45 | 4 |
| nonstructural protein NS3 | 1073 | 80.31 | 0 | 16.67 | 28.33 | 21.67 | 33.33 | 45 | 3 |
| nonstructural protein NS3 | 1133 | 80.39 | 0 | 30 | 15 | 36.67 | 18.33 | 45 | 3 |
| nonstructural protein NS4A | 80 | 80.8 | 0 | 21.67 | 23.33 | 18.33 | 36.67 | 45 | 4 |
| nonstructural protein NS4A | 151 | 81.8 | 0 | 21.67 | 23.33 | 25 | 30 | 45 | 5 |
| nonstructural protein NS4A | 174 | 81.34 | 0 | 23.33 | 21.67 | 23.33 | 31.67 | 45 | 5 |
| nonstructural protein NS4A | 228 | 80.81 | 0 | 28.33 | 16.67 | 21.67 | 33.33 | 45 | 3 |
| nonstructural protein NS4A | 248 | 80.32 | 0 | 21.67 | 21.67 | 31.67 | 25 | 43.33 | 3 |
| nonstructural protein NS4A | 269 | 80.12 | 0 | 18.33 | 26.67 | 40 | 15 | 45 | 4 |
| nonstructural protein NS4A | 296 | 80.09 | 0 | 21.67 | 21.67 | 38.33 | 18.33 | 43.33 | 4 |
| nonstructural protein NS4A | 316 | 80.57 | 0 | 25 | 20 | 33.33 | 21.67 | 45 | 4 |
| nonstructural protein NS4A | 359 | 81.64 | 0 | 20 | 25 | 38.33 | 16.67 | 45 | 3 |
| nonstructural protein NS4A | 379 | 78.87 | 0 | 20 | 21.67 | 36.67 | 21.67 | 41.67 | 3 |

TABLE 1-continued

| Selected viral probes | | | | | | | | |
|---|---|---|---|---|---|---|---|---|
| nonstructural protein NS4B | 63 | 79.97 | 0 | 30 | 15 | 26.67 | 28.33 | 45 | 4 |
| nonstructural protein NS4B | 114 | 80.33 | 0 | 23.33 | 18.33 | 31.67 | 26.67 | 41.67 | 5 |
| nonstructural protein NS4B | 242 | 81.11 | 0 | 18.33 | 25 | 28.33 | 28.33 | 43.33 | 3 |
| nonstructural protein NS4B | 282 | 79.24 | 0 | 23.33 | 15 | 31.67 | 30 | 38.33 | 5 |
| nonstructural protein NS4B | 324 | 80.65 | 0 | 23.33 | 20 | 30 | 26.67 | 43.33 | 5 |
| nonstructural protein NS4B | 365 | 79.43 | 0 | 20 | 21.67 | 48.33 | 10 | 41.67 | 6 |
| nonstructural protein NS4B | 412 | 81.34 | 0 | 23.33 | 21.67 | 30 | 25 | 45 | 4 |
| nonstructural protein NS4B | 524 | 79.92 | 0 | 26.67 | 16.67 | 31.67 | 25 | 43.33 | 3 |
| nonstructural protein NS4B | 564 | 80.18 | 0 | 21.67 | 21.67 | 31.67 | 25 | 43.33 | 3 |
| nonstructural protein NS4B | 604 | 79.98 | 0 | 13.33 | 28.33 | 38.33 | 20 | 41.67 | 4 |
| nonstructural protein NS5 | 61 | 80.76 | 0 | 25 | 20 | 36.67 | 18.33 | 45 | 5 |
| nonstructural protein NS5 | 121 | 79.62 | 0 | 21.67 | 20 | 38.33 | 20 | 41.67 | 3 |
| nonstructural protein NS5 | 190 | 80.76 | 0 | 26.67 | 18.33 | 35 | 20 | 45 | 5 |
| nonstructural protein NS5 | 273 | 81.21 | 0 | 33.33 | 11.67 | 31.67 | 23.33 | 45 | 4 |
| nonstructural protein NS5 | 422 | 81.23 | 0 | 26.67 | 18.33 | 28.33 | 26.67 | 45 | 3 |
| nonstructural protein NS5 | 596 | 82.36 | 0 | 21.67 | 23.33 | 26.67 | 28.33 | 45 | 3 |
| nonstructural protein NS5 | 656 | 79.94 | 0 | 28.33 | 13.33 | 43.33 | 15 | 41.67 | 4 |
| nonstructural protein NS5 | 716 | 80.73 | 0 | 25 | 18.33 | 31.67 | 25 | 43.33 | 3 |
| nonstructural protein NS5 | 779 | 82.27 | 0 | 26.67 | 18.33 | 40 | 15 | 45 | 6 |
| nonstructural protein NS5 | 841 | 81.36 | 0 | 21.67 | 23.33 | 35 | 20 | 45 | 4 |
| anchored capsid protein C | 62 | 80.98 | 0 | 26.67 | 18.33 | 28.33 | 26.67 | 45 | 2 |
| anchored capsid protein C | 63 | 80.25 | 0 | 25 | 18.33 | 30 | 26.67 | 43.33 | 2 |
| anchored capsid protein C | 64 | 80.25 | 0 | 23.33 | 20 | 30 | 26.67 | 43.33 | 2 |
| anchored capsid protein C | 65 | 80.78 | 0 | 23.33 | 20 | 31.67 | 25 | 43.33 | 2 |
| anchored capsid protein C | 66 | 80.38 | 0 | 23.33 | 20 | 31.67 | 25 | 43.33 | 2 |
| anchored capsid protein C | 67 | 80.28 | 0 | 23.33 | 20 | 31.67 | 25 | 43.33 | 2 |
| anchored capsid protein C | 68 | 80.28 | 0 | 23.33 | 20 | 31.67 | 25 | 43.33 | 2 |
| anchored capsid protein C | 69 | 80.28 | 0 | 21.67 | 21.67 | 31.67 | 25 | 43.33 | 2 |
| anchored capsid protein C | 70 | 80.62 | 0 | 23.33 | 21.67 | 30 | 25 | 45 | 2 |
| anchored capsid protein C | 71 | 80.99 | 0 | 23.33 | 20 | 30 | 26.67 | 43.33 | 2 |
| membrane glycoprotein precursor M | 60 | 80.14 | 0 | 11.67 | 30 | 28.33 | 30 | 41.67 | 4 |
| membrane glycoprotein precursor M | 80 | 80.21 | 0 | 16.67 | 26.67 | 31.67 | 25 | 43.33 | 4 |
| membrane glycoprotein precursor M | 133 | 82.19 | 0 | 21.67 | 23.33 | 30 | 25 | 45 | 3 |
| membrane glycoprotein precursor M | 165 | 81.49 | 0 | 25 | 20 | 33.33 | 21.67 | 45 | 4 |
| membrane glycoprotein precursor M | 185 | 81.32 | 0 | 26.67 | 18.33 | 38.33 | 16.67 | 45 | 4 |
| membrane glycoprotein precursor M | 245 | 81.44 | 0 | 30 | 15 | 38.33 | 16.67 | 45 | 6 |

TABLE 1-continued

Selected viral probes

| | | | | | | | | |
|---|---|---|---|---|---|---|---|---|
| membrane glycoprotein precursor M | 270 | 81.21 | 0 | 28.33 | 16.67 | 36.67 | 18.33 | 45 | 6 |
| membrane glycoprotein precursor M | 439 | 81.29 | 0 | 26.67 | 18.33 | 30 | 25 | 45 | 4 |
| membrane glycoprotein precursor M | 459 | 79.83 | 0 | 30 | 13.33 | 38.33 | 18.33 | 43.33 | 4 |
| membrane glycoprotein precursor M | 479 | 80.03 | 0 | 23.33 | 18.33 | 41.67 | 16.67 | 41.67 | 4 |
| envelope protein E | 64 | 81.37 | 0 | 31.67 | 13.33 | 21.67 | 33.33 | 45 | 3 |
| envelope protein E | 124 | 78.25 | 0 | 18.33 | 21.67 | 35 | 25 | 40 | 4 |
| envelope protein E | 200 | 81.06 | 0 | 20 | 25 | 26.67 | 28.33 | 45 | 3 |
| envelope protein E | 300 | 82.18 | 0 | 30 | 15 | 31.67 | 23.33 | 45 | 6 |
| envelope protein E | 360 | 80.89 | 0 | 26.67 | 18.33 | 36.67 | 18.33 | 45 | 3 |
| envelope protein E | 420 | 80.32 | 0 | 20 | 25 | 40 | 15 | 45 | 5 |
| envelope protein E | 480 | 77.43 | 0 | 21.67 | 16.67 | 31.67 | 30 | 38.33 | 6 |
| envelope protein E | 540 | 80.4 | 0 | 25 | 20 | 35 | 20 | 45 | 4 |
| envelope protein E | 600 | 77.18 | 0 | 25 | 11.67 | 40 | 23.33 | 36.67 | 3 |
| envelope protein E | 660 | 81.36 | 0 | 20 | 25 | 35 | 20 | 45 | 3 |
| nonstructural protein NS1 | 60 | 80.06 | 0 | 25 | 16.67 | 36.67 | 21.67 | 41.67 | 3 |
| nonstructural protein NS1 | 141 | 81.62 | 0 | 20 | 25 | 33.33 | 21.67 | 45 | 3 |
| nonstructural protein NS1 | 230 | 80.58 | 0 | 31.67 | 13.33 | 30 | 25 | 45 | 3 |
| nonstructural protein NS1 | 290 | 80.38 | 0 | 23.33 | 21.67 | 36.67 | 18.33 | 45 | 3 |
| nonstructural protein NS1 | 350 | 79.7 | 0 | 20 | 21.67 | 35 | 23.33 | 41.67 | 3 |
| nonstructural protein NS1 | 410 | 81.28 | 0 | 18.33 | 26.67 | 33.33 | 21.67 | 45 | 5 |
| nonstructural protein NS1 | 470 | 79.06 | 0 | 26.67 | 15 | 36.67 | 21.67 | 41.67 | 3 |
| nonstructural protein NS1 | 537 | 81.45 | 0 | 20 | 25 | 38.33 | 16.67 | 45 | 4 |
| nonstructural protein NS1 | 597 | 76.37 | 0 | 21.67 | 13.33 | 38.33 | 26.67 | 35 | 4 |
| nonstructural protein NS1 | 695 | 80.24 | 0 | 15 | 30 | 31.67 | 23.33 | 45 | 5 |
| nonstructural protein NS2A | 105 | 79.5 | 0 | 15 | 25 | 38.33 | 21.67 | 40 | 6 |
| nonstructural protein NS2A | 147 | 82.33 | 0 | 15 | 30 | 30 | 25 | 45 | 6 |
| nonstructural protein NS2A | 187 | 80.48 | 0 | 26.67 | 15 | 35 | 23.33 | 41.67 | 4 |
| nonstructural protein NS2A | 227 | 80.44 | 0 | 20 | 21.67 | 30 | 28.33 | 41.67 | 3 |
| nonstructural protein NS2A | 267 | 78.32 | 0 | 26.67 | 13.33 | 35 | 25 | 40 | 4 |
| nonstructural protein NS2A | 309 | 81.33 | 0 | 23.33 | 21.67 | 26.67 | 28.33 | 45 | 3 |
| nonstructural protein NS2A | 349 | 79.47 | 0 | 16.67 | 28.33 | 30 | 25 | 45 | 3 |
| nonstructural protein NS2A | 389 | 77.78 | 0 | 23.33 | 18.33 | 31.67 | 26.67 | 41.67 | 3 |
| nonstructural protein NS2A | 436 | 81.39 | 0 | 15 | 30 | 23.33 | 31.67 | 45 | 4 |
| nonstructural protein NS2A | 536 | 80.56 | 0 | 31.67 | 13.33 | 26.67 | 28.33 | 45 | 3 |
| nonstructural protein NS2B | 63 | 81.92 | 0 | 23.33 | 21.67 | 33.33 | 21.67 | 45 | 3 |
| nonstructural protein NS2B | 64 | 81.92 | 0 | 23.33 | 21.67 | 31.67 | 23.33 | 45 | 4 |
| nonstructural protein NS2B | 65 | 81.41 | 0 | 23.33 | 21.67 | 30 | 25 | 45 | 5 |

TABLE 1-continued

| Selected viral probes | | | | | | | | | |
|---|---|---|---|---|---|---|---|---|---|
| nonstructural protein NS2B | 66 | 81.34 | 0 | 23.33 | 21.67 | 30 | 25 | 45 | 5 |
| nonstructural protein NS2B | 67 | 81.85 | 0 | 23.33 | 21.67 | 30 | 25 | 45 | 5 |
| nonstructural protein NS2B | 85 | 81.85 | 0 | 21.67 | 23.33 | 25 | 30 | 45 | 5 |
| nonstructural protein NS2B | 93 | 81.68 | 0 | 21.67 | 23.33 | 28.33 | 26.67 | 45 | 5 |
| nonstructural protein NS2B | 94 | 80.89 | 0 | 21.67 | 23.33 | 26.67 | 28.33 | 45 | 5 |
| nonstructural protein NS2B | 95 | 80.04 | 0 | 21.67 | 21.67 | 26.67 | 30 | 43.33 | 5 |
| nonstructural protein NS2B | 96 | 79.95 | 0 | 20 | 21.67 | 28.33 | 30 | 41.67 | 5 |
| nonstructural protein NS3 | 60 | 80.58 | 0 | 25 | 18.33 | 35 | 21.67 | 43.33 | 4 |
| nonstructural protein NS3 | 120 | 80.15 | 0 | 31.67 | 10 | 40 | 18.33 | 41.67 | 4 |
| nonstructural protein NS3 | 180 | 79.61 | 0 | 28.33 | 13.33 | 40 | 18.33 | 41.67 | 4 |
| nonstructural protein NS3 | 265 | 79.93 | 0 | 26.67 | 18.33 | 31.67 | 23.33 | 45 | 4 |
| nonstructural protein NS3 | 346 | 82.18 | 0 | 26.67 | 18.33 | 31.67 | 23.33 | 45 | 4 |
| nonstructural protein NS3 | 406 | 81.01 | 0 | 21.67 | 23.33 | 40 | 15 | 45 | 4 |
| nonstructural protein NS3 | 466 | 77.78 | 0 | 21.67 | 15 | 45 | 18.33 | 36.67 | 6 |
| nonstructural protein NS3 | 609 | 81.33 | 0 | 21.67 | 23.33 | 35 | 20 | 45 | 4 |
| nonstructural protein NS3 | 669 | 80.44 | 0 | 25 | 18.33 | 31.67 | 25 | 43.33 | 3 |
| nonstructural protein NS3 | 729 | 76.54 | 0 | 25 | 11.67 | 40 | 23.33 | 36.67 | 5 |
| nonstructural protein NS4A | 70 | 76.19 | 0 | 16.67 | 18.33 | 26.67 | 38.33 | 35 | 6 |
| nonstructural protein NS4A | 71 | 76.49 | 0 | 18.33 | 18.33 | 25 | 38.33 | 36.67 | 6 |
| nonstructural protein NS4A | 72 | 76.83 | 0 | 16.67 | 18.33 | 25 | 40 | 35 | 6 |
| nonstructural protein NS4A | 73 | 76.49 | 0 | 16.67 | 20 | 25 | 38.33 | 36.67 | 6 |
| nonstructural protein NS4A | 74 | 76.29 | 0 | 16.67 | 18.33 | 26.67 | 38.33 | 35 | 6 |
| nonstructural protein NS4A | 75 | 76.29 | 0 | 16.67 | 18.33 | 26.67 | 38.33 | 35 | 6 |
| nonstructural protein NS4A | 76 | 76.77 | 0 | 16.67 | 18.33 | 26.67 | 38.33 | 35 | 6 |
| nonstructural protein NS4A | 77 | 76.54 | 0 | 16.67 | 20 | 25 | 38.33 | 36.67 | 6 |
| nonstructural protein NS4A | 78 | 77.15 | 0 | 15 | 21.67 | 25 | 38.33 | 36.67 | 6 |
| nonstructural protein NS4A | 79 | 77.52 | 0 | 16.67 | 21.67 | 23.33 | 38.33 | 38.33 | 6 |
| nonstructural protein NS4B | 63 | 79.89 | 0 | 18.33 | 23.33 | 31.67 | 26.67 | 41.67 | 4 |
| nonstructural protein NS4B | 113 | 80.07 | 0 | 28.33 | 15 | 23.33 | 33.33 | 43.33 | 5 |
| nonstructural protein NS4B | 213 | 80.39 | 0 | 28.33 | 16.67 | 23.33 | 31.67 | 45 | 3 |
| nonstructural protein NS4B | 254 | 80.55 | 0 | 25 | 18.33 | 28.33 | 28.33 | 43.33 | 4 |
| nonstructural protein NS4B | 294 | 78.5 | 0 | 20 | 18.33 | 36.67 | 25 | 38.33 | 4 |
| nonstructural protein NS4B | 413 | 81.51 | 0 | 18.33 | 25 | 31.67 | 25 | 43.33 | 4 |
| nonstructural protein NS4B | 458 | 79.87 | 0 | 15 | 28.33 | 25 | 31.67 | 43.33 | 4 |
| nonstructural protein NS4B | 577 | 80.18 | 0 | 16.67 | 25 | 33.33 | 25 | 41.67 | 4 |
| nonstructural protein NS4B | 617 | 78.77 | 0 | 18.33 | 20 | 33.33 | 28.33 | 38.33 | 4 |
| nonstructural protein NS4B | 739 | 81.65 | 0 | 26.67 | 18.33 | 36.67 | 18.33 | 45 | 6 |
| RNA-dependent RNA pol. NS5 | 60 | 79.36 | 0 | 30 | 13.33 | 38.33 | 18.33 | 43.33 | 4 |

TABLE 1-continued

Selected viral probes

| | | | | | | | | |
|---|---|---|---|---|---|---|---|---|
| RNA-dependent RNA pol. NS5 | 120 | 76.91 | 0 | 15 | 20 | 46.67 | 18.33 | 35 | 3 |
| RNA-dependent RNA pol. NS5 | 196 | 81.55 | 0 | 28.33 | 16.67 | 33.33 | 21.67 | 45 | 4 |
| RNA-dependent RNA pol. NS5 | 261 | 81.5 | 0 | 28.33 | 16.67 | 38.33 | 16.67 | 45 | 4 |
| RNA-dependent RNA pol. NS5 | 322 | 81.11 | 0 | 23.33 | 21.67 | 35 | 20 | 45 | 3 |
| RNA-dependent RNA pol. NS5 | 549 | 81.62 | 0 | 26.67 | 18.33 | 31.67 | 23.33 | 45 | 3 |
| RNA-dependent RNA pol. NS5 | 609 | 80.4 | 0 | 21.67 | 21.67 | 28.33 | 28.33 | 43.33 | 3 |
| RNA-dependent RNA pol. NS5 | 669 | 77.57 | 0 | 20 | 16.67 | 43.33 | 20 | 36.67 | 3 |
| RNA-dependent RNA pol. NS5 | 732 | 81.46 | 0 | 30 | 15 | 28.33 | 26.67 | 45 | 3 |
| RNA-dependent RNA pol. NS5 | 807 | 81.59 | 0 | 25 | 20 | 36.67 | 18.33 | 45 | 4 |
| anchored capsid protein C | 60 | 82.23 | 0 | 18.33 | 26.67 | 31.67 | 23.33 | 45 | 5 |
| anchored capsid protein C | 61 | 81.79 | 0 | 18.33 | 26.67 | 33.33 | 21.67 | 45 | 5 |
| anchored capsid protein C | 62 | 80.67 | 0 | 18.33 | 25 | 33.33 | 23.33 | 43.33 | 5 |
| anchored capsid protein C | 63 | 80.51 | 0 | 16.67 | 25 | 35 | 23.33 | 41.67 | 5 |
| anchored capsid protein C | 64 | 80.64 | 0 | 16.67 | 26.67 | 35 | 21.67 | 43.33 | 5 |
| anchored capsid protein C | 65 | 81.05 | 0 | 18.33 | 26.67 | 35 | 20 | 45 | 5 |
| anchored capsid protein C | 66 | 81.36 | 0 | 18.33 | 25 | 36.67 | 20 | 43.33 | 5 |
| anchored capsid protein C | 67 | 80.89 | 0 | 20 | 25 | 35 | 20 | 45 | 5 |
| anchored capsid protein C | 68 | 80.55 | 0 | 20 | 23.33 | 35 | 21.67 | 43.33 | 5 |
| anchored capsid protein C | 69 | 80.55 | 0 | 18.33 | 25 | 35 | 21.67 | 43.33 | 5 |
| membrane glycoprotein precursor M | 60 | 80.72 | 0 | 16.67 | 26.67 | 25 | 31.67 | 43.33 | 4 |
| membrane glycoprotein precursor M | 61 | 80.2 | 0 | 16.67 | 26.67 | 23.33 | 33.33 | 43.33 | 4 |
| membrane glycoprotein precursor M | 62 | 80.13 | 0 | 16.67 | 26.67 | 23.33 | 33.33 | 43.33 | 4 |
| membrane glycoprotein precursor M | 63 | 80.23 | 0 | 16.67 | 26.67 | 23.33 | 33.33 | 43.33 | 4 |
| membrane glycoprotein precursor M | 64 | 80.23 | 0 | 15 | 28.33 | 23.33 | 33.33 | 43.33 | 4 |
| membrane glycoprotein precursor M | 65 | 81.12 | 0 | 16.67 | 28.33 | 23.33 | 31.67 | 45 | 4 |
| membrane glycoprotein precursor M | 67 | 81.05 | 0 | 18.33 | 26.67 | 23.33 | 31.67 | 45 | 4 |
| membrane glycoprotein precursor M | 68 | 80.73 | 0 | 18.33 | 25 | 23.33 | 33.33 | 43.33 | 4 |
| membrane glycoprotein precursor M | 69 | 80.73 | 0 | 18.33 | 25 | 25 | 31.67 | 43.33 | 4 |
| membrane glycoprotein precursor M | 70 | 80.35 | 0 | 18.33 | 26.67 | 23.33 | 31.67 | 45 | 4 |

TABLE 1-continued

| Selected viral probes | | | | | | | | |
|---|---|---|---|---|---|---|---|---|
| envelope protein E | 60 | 79.96 | 0 | 21.67 | 20 | 25 | 33.33 | 41.67 | 4 |
| envelope protein E | 121 | 77.5 | 0 | 21.67 | 15 | 35 | 28.33 | 36.67 | 6 |
| envelope protein E | 184 | 81.88 | 0 | 26.67 | 18.33 | 23.33 | 31.67 | 45 | 3 |
| envelope protein E | 343 | 81.88 | 0 | 30 | 15 | 36.67 | 18.33 | 45 | 4 |
| envelope protein E | 403 | 80.4 | 0 | 30 | 15 | 28.33 | 26.67 | 45 | 4 |
| envelope protein E | 486 | 81.55 | 0 | 23.33 | 21.67 | 35 | 20 | 45 | 4 |
| envelope protein E | 554 | 80.83 | 0 | 28.33 | 16.67 | 38.33 | 16.67 | 45 | 4 |
| envelope protein E | 614 | 80.1 | 0 | 28.33 | 13.33 | 33.33 | 25 | 41.67 | 4 |
| envelope protein E | 675 | 81.01 | 0 | 25 | 20 | 35 | 20 | 45 | 4 |
| envelope protein E | 761 | 82.39 | 0 | 26.67 | 18.33 | 38.33 | 16.67 | 45 | 6 |
| nonstructural protein NS1 | 60 | 78.87 | 0 | 25 | 16.67 | 38.33 | 20 | 41.67 | 3 |
| nonstructural protein NS1 | 178 | 81.3 | 0 | 28.33 | 16.67 | 35 | 20 | 45 | 3 |
| nonstructural protein NS1 | 241 | 81.09 | 0 | 26.67 | 18.33 | 31.67 | 23.33 | 45 | 3 |
| nonstructural protein NS1 | 346 | 79.82 | 0 | 18.33 | 26.67 | 35 | 20 | 45 | 3 |
| nonstructural protein NS1 | 406 | 81.24 | 0 | 20 | 25 | 33.33 | 21.67 | 45 | 5 |
| nonstructural protein NS1 | 466 | 80.52 | 0 | 26.67 | 16.67 | 40 | 16.67 | 43.33 | 5 |
| nonstructural protein NS1 | 565 | 81.04 | 0 | 18.33 | 26.67 | 35 | 20 | 45 | 3 |
| nonstructural protein NS1 | 677 | 82.15 | 0 | 16.67 | 28.33 | 35 | 20 | 45 | 4 |
| nonstructural protein NS1 | 737 | 80.86 | 0 | 26.67 | 16.67 | 41.67 | 15 | 43.33 | 5 |
| nonstructural protein NS1 | 801 | 81.32 | 0 | 30 | 15 | 33.33 | 21.67 | 45 | 4 |
| nonstructural protein NS2A | 63 | 79.26 | 0 | 16.67 | 25 | 26.67 | 31.67 | 41.67 | 5 |
| nonstructural protein NS2A | 144 | 82.49 | 0 | 25 | 20 | 25 | 30 | 45 | 4 |
| nonstructural protein NS2A | 192 | 82.44 | 0 | 21.67 | 23.33 | 25 | 30 | 45 | 5 |
| nonstructural protein NS2A | 232 | 78.41 | 0 | 15 | 21.67 | 30 | 33.33 | 36.67 | 5 |
| nonstructural protein NS2A | 272 | 80.03 | 0 | 21.67 | 21.67 | 30 | 26.67 | 43.33 | 4 |
| nonstructural protein NS2A | 354 | 81.71 | 0 | 26.67 | 16.67 | 28.33 | 28.33 | 43.33 | 3 |
| nonstructural protein NS2A | 395 | 76.4 | 0 | 25 | 10 | 28.33 | 36.67 | 35 | 5 |
| nonstructural protein NS2A | 435 | 78.21 | 0 | 13.33 | 23.33 | 25 | 38.33 | 36.67 | 5 |
| nonstructural protein NS2A | 538 | 81.23 | 0 | 21.67 | 23.33 | 30 | 25 | 45 | 3 |
| nonstructural protein NS2A | 579 | 80.06 | 0 | 21.67 | 18.33 | 23.33 | 36.67 | 40 | 4 |
| nonstructural protein NS2B | 66 | 81.62 | 0 | 13.33 | 30 | 30 | 26.67 | 43.33 | 5 |
| nonstructural protein NS2B | 67 | 81.05 | 0 | 13.33 | 30 | 30 | 26.67 | 43.33 | 5 |
| nonstructural protein NS2B | 68 | 81.76 | 0 | 15 | 28.33 | 30 | 26.67 | 43.33 | 5 |
| nonstructural protein NS2B | 69 | 82.46 | 0 | 16.67 | 28.33 | 28.33 | 26.67 | 45 | 5 |
| nonstructural protein NS2B | 70 | 82.91 | 0 | 16.67 | 28.33 | 28.33 | 26.67 | 45 | 5 |
| nonstructural protein NS2B | 72 | 82.81 | 0 | 16.67 | 28.33 | 26.67 | 28.33 | 45 | 5 |
| nonstructural protein NS2B | 73 | 82.78 | 0 | 16.67 | 28.33 | 26.67 | 28.33 | 45 | 5 |
| nonstructural protein NS2B | 74 | 82.5 | 0 | 16.67 | 28.33 | 25 | 30 | 45 | 5 |
| nonstructural protein NS2B | 78 | 81.4 | 0 | 18.33 | 26.67 | 23.33 | 31.67 | 45 | 5 |

TABLE 1-continued

| Selected viral probes | | | | | | | | | |
|---|---|---|---|---|---|---|---|---|---|
| nonstructural protein NS2B | 79 | 80.7 | 0 | 16.67 | 26.67 | 25 | 31.67 | 43.33 | 5 |
| nonstructural protein NS3 | 91 | 81.61 | 0 | 21.67 | 23.33 | 30 | 25 | 45 | 6 |
| nonstructural protein NS3 | 160 | 79.32 | 0 | 28.33 | 10 | 40 | 21.67 | 38.33 | 4 |
| nonstructural protein NS3 | 220 | 77.1 | 0 | 21.67 | 15 | 41.67 | 21.67 | 36.67 | 4 |
| nonstructural protein NS3 | 365 | 80.49 | 0 | 21.67 | 23.33 | 38.33 | 16.67 | 45 | 3 |
| nonstructural protein NS3 | 456 | 81.65 | 0 | 20 | 25 | 36.67 | 18.33 | 45 | 3 |
| nonstructural protein NS3 | 598 | 80.54 | 0 | 25 | 20 | 36.67 | 18.33 | 45 | 3 |
| nonstructural protein NS3 | 658 | 80.82 | 0 | 28.33 | 15 | 30 | 26.67 | 43.33 | 5 |
| nonstructural protein NS3 | 721 | 75.78 | 0 | 20 | 15 | 43.33 | 21.67 | 35 | 6 |
| nonstructural protein NS3 | 781 | 81.42 | 0 | 25 | 18.33 | 33.33 | 23.33 | 43.33 | 6 |
| nonstructural protein NS3 | 842 | 82.06 | 0 | 23.33 | 21.67 | 35 | 20 | 45 | 4 |
| nonstructural protein NS4A | 60 | 79.18 | 0 | 25 | 16.67 | 30 | 28.33 | 41.67 | 6 |
| nonstructural protein NS4A | 61 | 79.47 | 0 | 26.67 | 16.67 | 28.33 | 28.33 | 43.33 | 6 |
| nonstructural protein NS4A | 62 | 80.12 | 0 | 25 | 18.33 | 28.33 | 28.33 | 43.33 | 6 |
| nonstructural protein NS4A | 63 | 80.12 | 0 | 25 | 18.33 | 26.67 | 30 | 43.33 | 6 |
| nonstructural protein NS4A | 64 | 80.19 | 0 | 25 | 18.33 | 26.67 | 30 | 43.33 | 6 |
| nonstructural protein NS4A | 65 | 80.4 | 0 | 25 | 20 | 25 | 30 | 45 | 6 |
| nonstructural protein NS4A | 66 | 80.4 | 0 | 26.67 | 18.33 | 25 | 30 | 45 | 6 |
| nonstructural protein NS4A | 67 | 81.04 | 0 | 25 | 20 | 25 | 30 | 45 | 6 |
| nonstructural protein NS4A | 68 | 81.45 | 0 | 25 | 20 | 23.33 | 31.67 | 45 | 6 |
| nonstructural protein NS4A | 69 | 81.42 | 0 | 25 | 20 | 23.33 | 31.67 | 45 | 6 |
| nonstructural protein NS4B | 60 | 78.06 | 0 | 25 | 11.67 | 31.67 | 31.67 | 36.67 | 5 |
| nonstructural protein NS4B | 124 | 81.1 | 0 | 23.33 | 21.67 | 26.67 | 28.33 | 45 | 5 |
| nonstructural protein NS4B | 186 | 81.35 | 0 | 21.67 | 23.33 | 30 | 25 | 45 | 3 |
| nonstructural protein NS4B | 253 | 82.36 | 0 | 23.33 | 21.67 | 25 | 30 | 45 | 5 |
| nonstructural protein NS4B | 319 | 75.02 | 0 | 21.67 | 13.33 | 36.67 | 28.33 | 35 | 3 |
| nonstructural protein NS4B | 395 | 82.01 | 0 | 23.33 | 21.67 | 36.67 | 18.33 | 45 | 4 |
| nonstructural protein NS4B | 455 | 80.53 | 0 | 16.67 | 28.33 | 26.67 | 28.33 | 45 | 4 |
| nonstructural protein NS4B | 537 | 82.23 | 0 | 28.33 | 16.67 | 33.33 | 21.67 | 45 | 5 |
| nonstructural protein NS4B | 597 | 79.33 | 0 | 18.33 | 25 | 33.33 | 23.33 | 43.33 | 3 |
| nonstructural protein NS4B | 708 | 80.91 | 0 | 28.33 | 16.67 | 21.67 | 33.33 | 45 | 3 |
| nonstructural protein NS5 | 75 | 80.29 | 0 | 30 | 15 | 35 | 20 | 45 | 2 |
| nonstructural protein NS5 | 185 | 80.9 | 0 | 25 | 20 | 31.67 | 23.33 | 45 | 3 |
| nonstructural protein NS5 | 245 | 78.2 | 0 | 20 | 18.33 | 40 | 21.67 | 38.33 | 4 |
| nonstructural protein NS5 | 311 | 81.46 | 0 | 25 | 20 | 26.67 | 28.33 | 45 | 3 |
| nonstructural protein NS5 | 401 | 81.03 | 0 | 16.67 | 28.33 | 31.67 | 23.33 | 45 | 2 |
| nonstructural protein NS5 | 503 | 81.02 | 0 | 28.33 | 16.67 | 38.33 | 16.67 | 45 | 3 |
| nonstructural protein NS5 | 564 | 81.38 | 0 | 26.67 | 18.33 | 30 | 25 | 45 | 4 |
| nonstructural protein NS5 | 653 | 82.17 | 0 | 28.33 | 16.67 | 35 | 20 | 45 | 3 |

TABLE 1-continued

| Selected viral probes | | | | | | | | | |
|---|---|---|---|---|---|---|---|---|---|
| nonstructural protein NS5 | 738 | 81.85 | 0 | 30 | 15 | 31.67 | 23.33 | 45 | 5 |
| nonstructural protein NS5 | 798 | 80.9 | 0 | 26.67 | 18.33 | 40 | 15 | 45 | 4 |
| anchored capsid protein C | 62 | 81.5 | 0 | 25 | 20 | 30 | 25 | 45 | 5 |
| anchored capsid protein C | 63 | 80.77 | 0 | 23.33 | 20 | 31.67 | 25 | 43.33 | 5 |
| anchored capsid protein C | 64 | 80.77 | 0 | 21.67 | 21.67 | 31.67 | 25 | 43.33 | 5 |
| anchored capsid protein C | 65 | 81.31 | 0 | 21.67 | 21.67 | 33.33 | 23.33 | 43.33 | 5 |
| anchored capsid protein C | 66 | 81.31 | 0 | 21.67 | 21.67 | 33.33 | 23.33 | 43.33 | 5 |
| anchored capsid protein C | 67 | 81.62 | 0 | 23.33 | 21.67 | 31.67 | 23.33 | 45 | 5 |
| anchored capsid protein C | 68 | 81.61 | 0 | 23.33 | 21.67 | 31.67 | 23.33 | 45 | 5 |
| anchored capsid protein C | 69 | 80.97 | 0 | 21.67 | 23.33 | 31.67 | 23.33 | 45 | 5 |
| anchored capsid protein C | 70 | 81.12 | 0 | 23.33 | 21.67 | 31.67 | 23.33 | 45 | 5 |
| anchored capsid protein C | 71 | 81.5 | 0 | 23.33 | 20 | 31.67 | 25 | 43.33 | 5 |
| membrane glycoprotein precursor M | 77 | 79.82 | 0 | 23.33 | 20 | 25 | 31.67 | 43.33 | 3 |
| membrane glycoprotein precursor M | 97 | 81.54 | 0 | 26.67 | 18.33 | 25 | 30 | 45 | 3 |
| membrane glycoprotein precursor M | 119 | 81.97 | 0 | 25 | 20 | 26.67 | 28.33 | 45 | 3 |
| membrane glycoprotein precursor M | 218 | 80.6 | 0 | 26.67 | 18.33 | 33.33 | 21.67 | 45 | 3 |
| membrane glycoprotein precursor M | 240 | 81.5 | 0 | 26.67 | 18.33 | 38.33 | 16.67 | 45 | 3 |
| membrane glycoprotein precursor M | 359 | 81.47 | 0 | 16.67 | 28.33 | 30 | 25 | 45 | 5 |
| membrane glycoprotein precursor M | 403 | 81.3 | 0 | 25 | 20 | 28.33 | 26.67 | 45 | 3 |
| membrane glycoprotein precursor M | 426 | 80.83 | 0 | 25 | 18.33 | 33.33 | 23.33 | 43.33 | 4 |
| membrane glycoprotein precursor M | 449 | 81.32 | 0 | 25 | 20 | 35 | 20 | 45 | 5 |
| membrane glycoprotein precursor M | 473 | 80.95 | 0 | 23.33 | 21.67 | 35 | 20 | 45 | 5 |
| envelope protein E | 81 | 81.58 | 0 | 25 | 20 | 26.67 | 28.33 | 45 | 3 |
| envelope protein E | 141 | 80.03 | 0 | 33.33 | 11.67 | 21.67 | 33.33 | 45 | 3 |
| envelope protein E | 201 | 80.98 | 0 | 25 | 16.67 | 25 | 33.33 | 41.67 | 5 |
| envelope protein E | 270 | 82.36 | 0 | 28.33 | 16.67 | 26.67 | 28.33 | 45 | 4 |
| envelope protein E | 330 | 81.57 | 0 | 25 | 20 | 28.33 | 26.67 | 45 | 3 |
| envelope protein E | 390 | 80.71 | 0 | 25 | 20 | 33.33 | 21.67 | 45 | 6 |
| envelope protein E | 460 | 82.09 | 0 | 21.67 | 23.33 | 33.33 | 21.67 | 45 | 5 |
| envelope protein E | 520 | 80.11 | 0 | 30 | 15 | 33.33 | 21.67 | 45 | 4 |
| envelope protein E | 580 | 80.85 | 0 | 26.67 | 15 | 38.33 | 20 | 41.67 | 4 |
| envelope protein E | 640 | 78.53 | 0 | 26.67 | 13.33 | 35 | 25 | 40 | 3 |
| non-structural protein NS1 | 64 | 80.92 | 0 | 31.67 | 13.33 | 36.67 | 18.33 | 45 | 5 |
| non-structural protein NS1 | 234 | 81.36 | 0 | 25 | 20 | 35 | 20 | 45 | 4 |

TABLE 1-continued

| Selected viral probes | | | | | | | | | |
|---|---|---|---|---|---|---|---|---|---|
| non-structural protein NS1 | 347 | 82.19 | 0 | 16.67 | 28.33 | 30 | 25 | 45 | 5 |
| non-structural protein NS1 | 419 | 81.84 | 0 | 21.67 | 23.33 | 33.33 | 21.67 | 45 | 4 |
| non-structural protein NS1 | 487 | 81.23 | 0 | 26.67 | 18.33 | 33.33 | 21.67 | 45 | 6 |
| non-structural protein NS1 | 547 | 80.05 | 0 | 26.67 | 15 | 35 | 23.33 | 41.67 | 3 |
| non-structural protein NS1 | 607 | 80.03 | 0 | 26.67 | 16.67 | 30 | 26.67 | 43.33 | 3 |
| non-structural protein NS1 | 667 | 81.13 | 0 | 20 | 25 | 35 | 20 | 45 | 5 |
| non-structural protein NS1 | 727 | 79.15 | 0 | 20 | 18.33 | 45 | 16.67 | 38.33 | 5 |
| non-structural protein NS1 | 848 | 80.26 | 0 | 25 | 20 | 33.33 | 21.67 | 45 | 3 |
| non-structural protein NS2A | 79 | 80.84 | 0 | 16.67 | 28.33 | 31.67 | 23.33 | 45 | 3 |
| non-structural protein NS2A | 119 | 80.42 | 0 | 20 | 23.33 | 33.33 | 23.33 | 43.33 | 5 |
| non-structural protein NS2A | 159 | 82.34 | 0 | 23.33 | 21.67 | 16.67 | 38.33 | 45 | 3 |
| non-structural protein NS2A | 199 | 80.91 | 0 | 25 | 16.67 | 23.33 | 35 | 41.67 | 3 |
| non-structural protein NS2A | 239 | 79.77 | 0 | 15 | 26.67 | 30 | 28.33 | 41.67 | 3 |
| non-structural protein NS2A | 279 | 77.78 | 0 | 18.33 | 18.33 | 38.33 | 25 | 36.67 | 5 |
| non-structural protein NS2A | 319 | 77.31 | 0 | 16.67 | 20 | 28.33 | 35 | 36.67 | 4 |
| non-structural protein NS2A | 359 | 81.43 | 0 | 21.67 | 23.33 | 33.33 | 21.67 | 45 | 3 |
| non-structural protein NS2A | 399 | 78.89 | 0 | 25 | 15 | 31.67 | 28.33 | 40 | 5 |
| non-structural protein NS2A | 565 | 80.72 | 0 | 23.33 | 21.67 | 21.67 | 33.33 | 45 | 3 |
| non-structural protein NS2B | 60 | 80.94 | 0 | 20 | 23.33 | 35 | 21.67 | 43.33 | 4 |
| non-structural protein NS2B | 61 | 81.23 | 0 | 20 | 25 | 33.33 | 21.67 | 45 | 4 |
| non-structural protein NS2B | 62 | 81.69 | 0 | 18.33 | 25 | 35 | 21.67 | 43.33 | 4 |
| non-structural protein NS2B | 63 | 81.4 | 0 | 18.33 | 25 | 33.33 | 23.33 | 43.33 | 4 |
| non-structural protein NS2B | 64 | 81.46 | 0 | 18.33 | 26.67 | 31.67 | 23.33 | 45 | 4 |
| non-structural protein NS2B | 65 | 81.36 | 0 | 18.33 | 26.67 | 30 | 25 | 45 | 4 |
| non-structural protein NS2B | 66 | 81.29 | 0 | 18.33 | 26.67 | 30 | 25 | 45 | 4 |
| non-structural protein NS2B | 67 | 81.2 | 0 | 18.33 | 26.67 | 28.33 | 26.67 | 45 | 4 |
| non-structural protein NS2B | 68 | 81.2 | 0 | 20 | 25 | 28.33 | 26.67 | 45 | 4 |
| non-structural protein NS2B | 80 | 81.14 | 0 | 18.33 | 26.67 | 25 | 30 | 45 | 4 |
| non-structural protein NS3 | 75 | 81.8 | 0 | 28.33 | 16.67 | 25 | 30 | 45 | 4 |
| non-structural protein NS3 | 176 | 78.8 | 0 | 30 | 10 | 40 | 20 | 40 | 4 |
| non-structural protein NS3 | 264 | 80.87 | 0 | 33.33 | 11.67 | 28.33 | 26.67 | 45 | 4 |
| non-structural protein NS3 | 342 | 82.25 | 0 | 25 | 20 | 31.67 | 23.33 | 45 | 6 |
| non-structural protein NS3 | 413 | 81.19 | 0 | 20 | 25 | 35 | 20 | 45 | 3 |
| non-structural protein NS3 | 645 | 81.26 | 0 | 30 | 15 | 28.33 | 26.67 | 45 | 5 |
| non-structural protein NS3 | 705 | 79.28 | 0 | 23.33 | 20 | 38.33 | 18.33 | 43.33 | 5 |
| non-structural protein NS3 | 767 | 78.17 | 0 | 25 | 11.67 | 41.67 | 21.67 | 36.67 | 4 |
| non-structural protein NS3 | 828 | 81.6 | 0 | 28.33 | 16.67 | 30 | 25 | 45 | 4 |
| non-structural protein NS3 | 1015 | 80.76 | 0 | 25 | 20 | 26.67 | 28.33 | 45 | 3 |
| non-structural protein NS4A | 60 | 76.92 | 0 | 18.33 | 18.33 | 35 | 28.33 | 36.67 | 6 |

TABLE 1-continued

| Selected viral probes | | | | | | | | |
|---|---|---|---|---|---|---|---|---|
| non-structural protein NS4A | 61 | 76.3 | 0 | 16.67 | 20 | 35 | 28.33 | 36.67 | 6 |
| non-structural protein NS4A | 62 | 76.92 | 0 | 15 | 21.67 | 35 | 28.33 | 36.67 | 6 |
| non-structural protein NS4A | 63 | 77.77 | 0 | 16.67 | 21.67 | 33.33 | 28.33 | 38.33 | 6 |
| non-structural protein NS4A | 64 | 78.47 | 0 | 18.33 | 21.67 | 31.67 | 28.33 | 40 | 6 |
| non-structural protein NS4A | 65 | 78.69 | 0 | 18.33 | 23.33 | 30 | 28.33 | 41.67 | 6 |
| non-structural protein NS4A | 66 | 79.4 | 0 | 20 | 21.67 | 30 | 28.33 | 41.67 | 6 |
| non-structural protein NS4A | 67 | 79.82 | 0 | 20 | 21.67 | 30 | 28.33 | 41.67 | 6 |
| non-structural protein NS4A | 68 | 79.54 | 0 | 20 | 21.67 | 28.33 | 30 | 41.67 | 6 |
| non-structural protein NS4A | 69 | 79.51 | 0 | 20 | 21.67 | 28.33 | 30 | 41.67 | 6 |
| non-structural protein NS4B | 79 | 81.5 | 0 | 26.67 | 18.33 | 26.67 | 28.33 | 45 | 5 |
| non-structural protein NS4B | 200 | 81.85 | 0 | 23.33 | 21.67 | 25 | 30 | 45 | 3 |
| non-structural protein NS4B | 230 | 80.7 | 0 | 25 | 20 | 21.67 | 33.33 | 45 | 3 |
| non-structural protein NS4B | 261 | 79.88 | 0 | 23.33 | 18.33 | 31.67 | 26.67 | 41.67 | 4 |
| non-structural protein NS4B | 291 | 76.31 | 0 | 18.33 | 18.33 | 40 | 23.33 | 36.67 | 4 |
| non-structural protein NS4B | 322 | 76.94 | 0 | 18.33 | 20 | 41.67 | 20 | 38.33 | 5 |
| non-structural protein NS4B | 410 | 81.05 | 0 | 21.67 | 21.67 | 33.33 | 23.33 | 43.33 | 4 |
| non-structural protein NS4B | 440 | 78.06 | 0 | 13.33 | 25 | 31.67 | 30 | 38.33 | 4 |
| non-structural protein NS4B | 699 | 81.8 | 0 | 21.67 | 23.33 | 30 | 25 | 45 | 5 |
| non-structural protein NS4B | 729 | 78.65 | 0 | 23.33 | 13.33 | 41.67 | 21.67 | 36.67 | 6 |
| non-structural protein NS5 | 60 | 79.06 | 0 | 28.33 | 15 | 31.67 | 25 | 43.33 | 4 |
| non-structural protein NS5 | 191 | 80.9 | 0 | 26.67 | 18.33 | 23.33 | 31.67 | 45 | 4 |
| non-structural protein NS5 | 251 | 79.7 | 0 | 23.33 | 20 | 35 | 21.67 | 43.33 | 3 |
| non-structural protein NS5 | 322 | 81.8 | 0 | 18.33 | 26.67 | 35 | 20 | 45 | 3 |
| non-structural protein NS5 | 548 | 81.03 | 0 | 28.33 | 16.67 | 30 | 25 | 45 | 3 |
| non-structural protein NS5 | 608 | 81.4 | 0 | 20 | 25 | 28.33 | 26.67 | 45 | 5 |
| non-structural protein NS5 | 776 | 80.94 | 0 | 35 | 8.33 | 36.67 | 20 | 43.33 | 3 |
| non-structural protein NS5 | 836 | 80.84 | 0 | 26.67 | 16.67 | 43.33 | 13.33 | 43.33 | 4 |
| non-structural protein NS5 | 896 | 80.34 | 0 | 18.33 | 25 | 33.33 | 23.33 | 43.33 | 3 |
| non-structural protein NS5 | 999 | 81.94 | 0 | 18.33 | 26.67 | 36.67 | 18.33 | 45 | 4 |
| polyprotein precursor | 418 | 81.82 | 0 | 20 | 25 | 28.33 | 26.67 | 45 | 3 |
| polyprotein precursor | 837 | 81.13 | 0 | 26.67 | 18.33 | 28.33 | 26.67 | 45 | 5 |
| polyprotein precursor | 1318 | 81.07 | 0 | 23.33 | 21.67 | 26.67 | 28.33 | 45 | 5 |
| polyprotein precursor | 1619 | 80.79 | 0 | 25 | 20 | 23.33 | 31.67 | 45 | 3 |
| polyprotein precursor | 1733 | 81.81 | 0 | 25 | 20 | 23.33 | 31.67 | 45 | 3 |
| polyprotein precursor | 1985 | 81.93 | 0 | 20 | 25 | 26.67 | 28.33 | 45 | 4 |
| polyprotein precursor | 2759 | 81.52 | 0 | 21.67 | 23.33 | 28.33 | 26.67 | 45 | 3 |
| polyprotein precursor | 3072 | 81.18 | 0 | 21.67 | 23.33 | 25 | 30 | 45 | 3 |
| polyprotein precursor | 3135 | 81.21 | 0 | 18.33 | 26.67 | 23.33 | 31.67 | 45 | 2 |
| polyprotein precursor | 4680 | 80.5 | 0 | 30 | 15 | 26.67 | 28.33 | 45 | 4 |

TABLE 1-continued

| Selected viral probes | | | | | | | | | |
|---|---|---|---|---|---|---|---|---|---|
| putative E1 protein | 536 | 80.9 | 0 | 26.67 | 18.33 | 25 | 30 | 45 | 3 |
| putative E1 protein | 60 | 85.53 | 0 | 33.33 | 21.67 | 18.33 | 26.67 | 55 | 3 |
| putative E1 protein | 117 | 86.53 | 0 | 28.33 | 26.67 | 10 | 35 | 55 | 4 |
| putative E1 protein | 157 | 85.28 | 0 | 23.33 | 31.67 | 20 | 25 | 55 | 5 |
| putative E1 protein | 202 | 86.76 | 0 | 28.33 | 26.67 | 25 | 20 | 55 | 4 |
| putative E1 protein | 298 | 86.37 | 0 | 38.33 | 16.67 | 16.67 | 28.33 | 55 | 5 |
| putative E1 protein | 344 | 86.91 | 0 | 30 | 25 | 15 | 30 | 55 | 5 |
| putative E1 protein | 437 | 86.26 | 0 | 35 | 20 | 16.67 | 28.33 | 55 | 3 |
| putative E1 protein | 480 | 87.8 | 0 | 28.33 | 26.67 | 15 | 30 | 55 | 5 |
| putative E1 protein | 576 | 80.9 | 0 | 28.33 | 18.33 | 28.33 | 25 | 46.67 | 4 |
| putative E2 protein | 60 | 86.63 | 0 | 33.33 | 21.67 | 15 | 30 | 55 | 4 |
| putative E2 protein | 90 | 84.02 | 0 | 30 | 20 | 20 | 30 | 50 | 4 |
| putative E2 protein | 120 | 84.81 | 0 | 33.33 | 20 | 15 | 31.67 | 53.33 | 3 |
| putative E2 protein | 266 | 86.43 | 0 | 31.67 | 23.33 | 15 | 30 | 55 | 3 |
| putative E2 protein | 296 | 82.71 | 0 | 30 | 18.33 | 15 | 36.67 | 48.33 | 3 |
| putative E2 protein | 326 | 87.29 | 0 | 23.33 | 31.67 | 11.67 | 33.33 | 55 | 5 |
| putative E2 protein | 364 | 86.06 | 0 | 30 | 25 | 20 | 25 | 55 | 3 |
| putative E2 protein | 394 | 85.42 | 0 | 30 | 23.33 | 15 | 31.67 | 53.33 | 3 |
| putative E2 protein | 435 | 86.32 | 0 | 33.33 | 21.67 | 15 | 30 | 55 | 4 |
| putative E2 protein | 627 | 85.74 | 0 | 23.33 | 31.67 | 25 | 20 | 55 | 3 |
| putative protein p7-NS2 | 60 | 85.27 | 0 | 26.67 | 28.33 | 13.33 | 31.67 | 55 | 3 |
| putative protein p7-NS2 | 166 | 85.18 | 0 | 28.33 | 26.67 | 18.33 | 26.67 | 55 | 3 |
| putative protein p7-NS2 | 196 | 84.7 | 0 | 26.67 | 26.67 | 20 | 26.67 | 53.33 | 3 |
| putative protein p7-NS2 | 228 | 87.2 | 0 | 33.33 | 21.67 | 16.67 | 28.33 | 55 | 5 |
| putative protein p7-NS2 | 258 | 82.78 | 0 | 31.67 | 16.67 | 16.67 | 35 | 48.33 | 5 |
| putative protein p7-NS2 | 288 | 85.07 | 0 | 28.33 | 25 | 20 | 26.67 | 53.33 | 3 |
| putative protein p7-NS2 | 410 | 86.51 | 0 | 35 | 20 | 8.33 | 36.67 | 55 | 3 |
| putative protein p7-NS2 | 440 | 86.19 | 0 | 33.33 | 21.67 | 8.33 | 36.67 | 55 | 3 |
| putative protein p7-NS2 | 474 | 86.96 | 0 | 33.33 | 21.67 | 11.67 | 33.33 | 55 | 3 |
| putative protein p7-NS2 | 566 | 85.08 | 0 | 38.33 | 16.67 | 25 | 20 | 55 | 4 |
| NS3 proteinase/ ATPase/helicase | 711 | 80.5 | 0 | 30 | 15 | 26.67 | 28.33 | 45 | 4 |
| NS3 proteinase/ ATPase/helicase | 717 | 80.82 | 0 | 30 | 15 | 25 | 30 | 45 | 4 |
| NS3 proteinase/ ATPase/helicase | 723 | 80.66 | 0 | 28.33 | 16.67 | 28.33 | 26.67 | 45 | 4 |
| NS3 proteinase/ ATPase/helicase | 724 | 80.66 | 0 | 26.67 | 18.33 | 28.33 | 26.67 | 45 | 4 |
| NS3 proteinase/ ATPase/helicase | 725 | 80.56 | 0 | 26.67 | 18.33 | 28.33 | 26.67 | 45 | 4 |
| NS3 proteinase/ ATPase/helicase | 726 | 79.99 | 0 | 26.67 | 18.33 | 28.33 | 26.67 | 45 | 4 |

TABLE 1-continued

| Selected viral probes | | | | | | | | | |
|---|---|---|---|---|---|---|---|---|---|
| NS3 proteinase/ ATPase/helicase | 727 | 80.56 | 0 | 26.67 | 18.33 | 28.33 | 26.67 | 45 | 4 |
| NS3 proteinase/ ATPase/helicase | 733 | 80.43 | 0 | 30 | 15 | 28.33 | 26.67 | 45 | 6 |
| NS3 proteinase/ ATPase/helicase | 734 | 79.79 | 0 | 28.33 | 16.67 | 28.33 | 26.67 | 45 | 6 |
| NS3 proteinase/ ATPase/helicase | 735 | 80.52 | 0 | 28.33 | 16.67 | 28.33 | 26.67 | 45 | 6 |
| putative NS4A protein | 154 | 85.13 | 0 | 36.67 | 18.33 | 23.33 | 21.67 | 55 | 3 |
| putative NS4A protein | 155 | 84.45 | 0 | 36.67 | 18.33 | 23.33 | 21.67 | 55 | 3 |
| putative NS4A protein | 156 | 84.45 | 0 | 36.67 | 18.33 | 23.33 | 21.67 | 55 | 3 |
| putative NS4A protein | 157 | 85.11 | 0 | 36.67 | 18.33 | 23.33 | 21.67 | 55 | 3 |
| putative NS4A protein | 183 | 85.51 | 0 | 31.67 | 23.33 | 20 | 25 | 55 | 6 |
| putative NS4A protein | 186 | 84.95 | 0 | 31.67 | 23.33 | 20 | 25 | 55 | 6 |
| putative NS4A protein | 187 | 84.28 | 0 | 31.67 | 23.33 | 20 | 25 | 55 | 6 |
| putative NS4A protein | 188 | 84.95 | 0 | 31.67 | 23.33 | 20 | 25 | 55 | 6 |
| putative NS4A protein | 193 | 85.09 | 0 | 31.67 | 23.33 | 20 | 25 | 55 | 6 |
| putative NS4A protein | 194 | 85.03 | 0 | 31.67 | 23.33 | 20 | 25 | 55 | 6 |
| putative NS4B protein | 144 | 81.18 | 0 | 21.67 | 23.33 | 25 | 30 | 45 | 3 |
| putative NS4B protein | 145 | 80.68 | 0 | 21.67 | 23.33 | 25 | 30 | 45 | 3 |
| putative NS4B protein | 146 | 80.77 | 0 | 21.67 | 23.33 | 25 | 30 | 45 | 3 |
| putative NS4B protein | 148 | 81.51 | 0 | 21.67 | 23.33 | 26.67 | 28.33 | 45 | 3 |
| putative NS4B protein | 149 | 80.72 | 0 | 21.67 | 23.33 | 26.67 | 28.33 | 45 | 3 |
| putative NS4B protein | 150 | 80.02 | 0 | 20 | 23.33 | 26.67 | 30 | 43.33 | 3 |
| putative NS4B protein | 151 | 80.1 | 0 | 20 | 23.33 | 26.67 | 30 | 43.33 | 3 |
| putative NS4B protein | 152 | 80.8 | 0 | 20 | 25 | 25 | 30 | 45 | 3 |
| putative NS4B protein | 153 | 80.8 | 0 | 20 | 25 | 25 | 30 | 45 | 3 |
| putative NS4B protein | 154 | 80.39 | 0 | 20 | 23.33 | 25 | 31.67 | 43.33 | 3 |
| putative NS5A protein | 63 | 81.64 | 0 | 30 | 15 | 28.33 | 26.67 | 45 | 3 |
| putative NS5A protein | 64 | 81.57 | 0 | 28.33 | 16.67 | 28.33 | 26.67 | 45 | 3 |
| putative NS5A protein | 82 | 82.61 | 0 | 33.33 | 11.67 | 23.33 | 31.67 | 45 | 3 |
| putative NS5A protein | 83 | 82.19 | 0 | 33.33 | 11.67 | 21.67 | 33.33 | 45 | 3 |
| putative NS5A protein | 84 | 82.12 | 0 | 31.67 | 13.33 | 21.67 | 33.33 | 45 | 3 |
| putative NS5A protein | 293 | 81.93 | 0 | 20 | 25 | 26.67 | 28.33 | 45 | 4 |
| putative NS5A protein | 296 | 81.15 | 0 | 21.67 | 23.33 | 26.67 | 28.33 | 45 | 4 |
| putative NS5A protein | 297 | 80.48 | 0 | 21.67 | 23.33 | 26.67 | 28.33 | 45 | 4 |
| putative NS5A protein | 298 | 81.04 | 0 | 23.33 | 21.67 | 26.67 | 28.33 | 45 | 4 |
| putative NS5A protein | 301 | 80.92 | 0 | 25 | 20 | 26.67 | 28.33 | 45 | 4 |
| putative NS5B RNA- dependent RNA pol. | 415 | 81.82 | 0 | 20 | 25 | 28.33 | 26.67 | 45 | 3 |

TABLE 1-continued

| Selected viral probes | | | | | | | | |
|---|---|---|---|---|---|---|---|---|
| putative NS5B RNA-dependent RNA pol. | 416 | 81.85 | 0 | 20 | 25 | 28.33 | 26.67 | 45 | 3 |
| putative NS5B RNA-dependent RNA pol. | 834 | 81.13 | 0 | 26.67 | 18.33 | 28.33 | 26.67 | 45 | 5 |
| putative NS5B RNA-dependent RNA pol. | 1315 | 81.07 | 0 | 23.33 | 21.67 | 26.67 | 28.33 | 45 | 5 |
| putative NS5B RNA-dependent RNA pol. | 1316 | 80.37 | 0 | 23.33 | 21.67 | 25 | 30 | 45 | 5 |
| putative NS5B RNA-dependent RNA pol. | 1317 | 80.28 | 0 | 21.67 | 21.67 | 26.67 | 30 | 43.33 | 5 |
| putative NS5B RNA-dependent RNA pol. | 1318 | 80.32 | 0 | 23.33 | 21.67 | 25 | 30 | 45 | 5 |
| putative NS5B RNA-dependent RNA pol. | 1319 | 80.76 | 0 | 23.33 | 21.67 | 25 | 30 | 45 | 5 |
| putative NS5B RNA-dependent RNA pol. | 1616 | 80.79 | 0 | 25 | 20 | 23.33 | 31.67 | 45 | 3 |
| putative NS5B RNA-dependent RNA pol. | 1617 | 80.23 | 0 | 25 | 20 | 23.33 | 31.67 | 45 | 3 |
| 1A VP4b mature peptide | 68 | 81.03 | 0 | 23.33 | 21.67 | 23.33 | 31.67 | 45 | 4 |
| 1A VP4b mature peptide | 115 | 75.84 | 0 | 18.33 | 16.67 | 30 | 35 | 35 | 5 |
| 1A VP4b mature peptide | 238 | 80.5 | 0 | 21.67 | 21.67 | 23.33 | 33.33 | 43.33 | 3 |
| 1A VP4b mature peptide | 293 | 81.47 | 0 | 26.67 | 18.33 | 20 | 35 | 45 | 3 |
| 1A VP4b mature peptide | 340 | 80.79 | 0 | 21.67 | 21.67 | 31.67 | 25 | 43.33 | 5 |
| 1A VP4b mature peptide | 380 | 80.48 | 0 | 33.33 | 11.67 | 26.67 | 28.33 | 45 | 3 |
| 1A VP4b mature peptide | 428 | 80.46 | 0 | 25 | 20 | 28.33 | 26.67 | 45 | 4 |
| 1A VP4b mature peptide | 468 | 80.54 | 0 | 21.67 | 23.33 | 20 | 35 | 45 | 4 |
| 1A VP4b mature peptide | 520 | 81.35 | 0 | 30 | 15 | 28.33 | 26.67 | 45 | 4 |
| 1A VP4b mature peptide | 647 | 77.38 | 0 | 16.67 | 21.67 | 21.67 | 40 | 38.33 | 5 |
| 1B VP2 mature peptide | 61 | 76.15 | 0 | 16.67 | 18.33 | 26.67 | 38.33 | 35 | 4 |
| 1B VP2 mature peptide | 121 | 75.88 | 0 | 20 | 15 | 33.33 | 31.67 | 35 | 3 |
| 1B VP2 mature peptide | 181 | 77.16 | 0 | 15 | 20 | 33.33 | 31.67 | 35 | 3 |
| 1B VP2 mature peptide | 270 | 76.51 | 0 | 18.33 | 16.67 | 25 | 40 | 35 | 3 |
| 1B VP2 mature peptide | 338 | 80.84 | 0 | 21.67 | 23.33 | 25 | 30 | 45 | 6 |
| 1B VP2 mature peptide | 398 | 79.36 | 0 | 25 | 13.33 | 30 | 31.67 | 38.33 | 3 |
| 1B VP2 mature peptide | 464 | 77.13 | 0 | 20 | 15 | 28.33 | 36.67 | 35 | 4 |
| 1B VP2 mature peptide | 524 | 77.9 | 0 | 20 | 16.67 | 33.33 | 30 | 36.67 | 5 |
| 1B VP2 mature peptide | 585 | 81.32 | 0 | 21.67 | 23.33 | 23.33 | 31.67 | 45 | 3 |
| 1B VP2 mature peptide | 645 | 78.29 | 0 | 21.67 | 16.67 | 23.33 | 38.33 | 38.33 | 4 |
| 1C VP3 mature peptide | 60 | 77.07 | 0 | 15 | 20 | 26.67 | 38.33 | 35 | 4 |

TABLE 1-continued

| Selected viral probes | | | | | | | | | |
|---|---|---|---|---|---|---|---|---|---|
| 1C VP3 mature peptide | 120 | 77.83 | 0 | 15 | 23.33 | 23.33 | 38.33 | 38.33 | 3 |
| 1C VP3 mature peptide | 180 | 80.34 | 0 | 25 | 16.67 | 31.67 | 26.67 | 41.67 | 3 |
| 1C VP3 mature peptide | 240 | 79.49 | 0 | 20 | 21.67 | 23.33 | 35 | 41.67 | 3 |
| 1C VP3 mature peptide | 300 | 79.56 | 0 | 21.67 | 20 | 33.33 | 25 | 41.67 | 3 |
| 1C VP3 mature peptide | 360 | 77.2 | 0 | 23.33 | 13.33 | 21.67 | 41.67 | 36.67 | 4 |
| 1C VP3 mature peptide | 423 | 77.17 | 0 | 20 | 15 | 21.67 | 43.33 | 35 | 5 |
| 1C VP3 mature peptide | 493 | 76.77 | 0 | 11.67 | 23.33 | 35 | 30 | 35 | 6 |
| 1C VP3 mature peptide | 554 | 76.13 | 0 | 15 | 20 | 28.33 | 36.67 | 35 | 3 |
| 1C VP3 mature peptide | 614 | 78.67 | 0 | 21.67 | 18.33 | 25 | 35 | 40 | 4 |
| 1D VP1 mature peptide | 60 | 78.57 | 0 | 31.67 | 11.67 | 33.33 | 23.33 | 43.33 | 4 |
| 1D VP1 mature peptide | 120 | 79.89 | 0 | 18.33 | 21.67 | 35 | 25 | 40 | 3 |
| 1D VP1 mature peptide | 247 | 76.59 | 0 | 20 | 15 | 31.67 | 33.33 | 35 | 3 |
| 1D VP1 mature peptide | 307 | 77.15 | 0 | 23.33 | 13.33 | 21.67 | 41.67 | 36.67 | 3 |
| 1D VP1 mature peptide | 367 | 79.08 | 0 | 21.67 | 18.33 | 36.67 | 23.33 | 40 | 4 |
| 1D VP1 mature peptide | 467 | 80.54 | 0 | 26.67 | 18.33 | 23.33 | 31.67 | 45 | 2 |
| 1D VP1 mature peptide | 527 | 78.63 | 0 | 23.33 | 16.67 | 25 | 35 | 40 | 5 |
| 1D VP1 mature peptide | 587 | 78.77 | 0 | 10 | 30 | 25 | 35 | 40 | 3 |
| 1D VP1 mature peptide | 652 | 76.68 | 0 | 15 | 20 | 26.67 | 38.33 | 35 | 4 |
| 1D VP1 mature peptide | 712 | 77.66 | 0 | 16.67 | 21.67 | 36.67 | 25 | 38.33 | 3 |
| 2A mature peptide | 74 | 75.99 | 0 | 25 | 10 | 35 | 30 | 35 | 4 |
| 2A mature peptide | 116 | 77.96 | 0 | 18.33 | 16.67 | 30 | 35 | 35 | 4 |
| 2A mature peptide | 156 | 77.7 | 0 | 20 | 16.67 | 30 | 33.33 | 36.67 | 4 |
| 2A mature peptide | 196 | 77.49 | 0 | 21.67 | 13.33 | 36.67 | 28.33 | 35 | 3 |
| 2A mature peptide | 287 | 77.59 | 0 | 33.33 | 6.67 | 35 | 25 | 40 | 3 |
| 2A mature peptide | 389 | 80.03 | 0 | 30 | 13.33 | 20 | 36.67 | 43.33 | 4 |
| 2A mature peptide | 432 | 76.63 | 0 | 21.67 | 13.33 | 30 | 35 | 35 | 6 |
| 2A mature peptide | 472 | 79.08 | 0 | 13.33 | 25 | 30 | 31.67 | 38.33 | 6 |
| 2A mature peptide | 512 | 78.94 | 0 | 18.33 | 21.67 | 40 | 20 | 40 | 5 |
| 2A mature peptide | 552 | 77.38 | 0 | 25 | 13.33 | 43.33 | 18.33 | 38.33 | 3 |
| 2B mature peptide | 60 | 79.54 | 0 | 26.67 | 15 | 33.33 | 25 | 41.67 | 3 |
| 2B mature peptide | 61 | 79.47 | 0 | 25 | 15 | 35 | 25 | 40 | 3 |
| 2B mature peptide | 62 | 78.97 | 0 | 25 | 15 | 35 | 25 | 40 | 3 |
| 2B mature peptide | 64 | 78.64 | 0 | 25 | 15 | 36.67 | 23.33 | 40 | 4 |
| 2B mature peptide | 65 | 79.2 | 0 | 25 | 15 | 36.67 | 23.33 | 40 | 4 |
| 2B mature peptide | 66 | 79.2 | 0 | 25 | 15 | 35 | 25 | 40 | 4 |
| 2B mature peptide | 67 | 78.5 | 0 | 23.33 | 15 | 35 | 26.67 | 38.33 | 4 |
| 2B mature peptide | 68 | 78.43 | 0 | 21.67 | 15 | 35 | 28.33 | 36.67 | 4 |
| 2B mature peptide | 69 | 78.43 | 0 | 21.67 | 15 | 33.33 | 30 | 36.67 | 4 |
| 2B mature peptide | 70 | 78.71 | 0 | 21.67 | 15 | 31.67 | 31.67 | 36.67 | 5 |

TABLE 1-continued

| Selected viral probes | | | | | | | | |
|---|---|---|---|---|---|---|---|---|
| 2C mature peptide | 60 | 76.89 | 0 | 23.33 | 13.33 | 36.67 | 26.67 | 36.67 | 4 |
| 2C mature peptide | 124 | 76.33 | 0 | 25 | 10 | 21.67 | 43.33 | 35 | 3 |
| 2C mature peptide | 232 | 77.11 | 0 | 11.67 | 23.33 | 33.33 | 31.67 | 35 | 5 |
| 2C mature peptide | 292 | 77.41 | 0 | 16.67 | 18.33 | 40 | 25 | 35 | 5 |
| 2C mature peptide | 352 | 77.62 | 0 | 20 | 18.33 | 25 | 36.67 | 38.33 | 5 |
| 2C mature peptide | 412 | 78.68 | 0 | 26.67 | 13.33 | 31.67 | 28.33 | 40 | 5 |
| 2C mature peptide | 472 | 77.56 | 0 | 25 | 11.67 | 28.33 | 35 | 36.67 | 3 |
| 2C mature peptide | 557 | 78.01 | 0 | 18.33 | 16.67 | 35 | 30 | 35 | 4 |
| 2C mature peptide | 617 | 80.04 | 0 | 35 | 6.67 | 31.67 | 26.67 | 41.67 | 5 |
| 2C mature peptide | 679 | 75.26 | 0 | 20 | 15 | 40 | 25 | 35 | 5 |
| 3A mature peptide | 131 | 81.75 | 0 | 26.67 | 18.33 | 18.33 | 36.67 | 45 | 4 |
| 3A mature peptide | 132 | 81.63 | 0 | 25 | 18.33 | 18.33 | 38.33 | 43.33 | 5 |
| 3A mature peptide | 133 | 81.68 | 0 | 25 | 20 | 18.33 | 36.67 | 45 | 5 |
| 3A mature peptide | 140 | 81.4 | 0 | 26.67 | 18.33 | 18.33 | 36.67 | 45 | 5 |
| 3A mature peptide | 141 | 81.28 | 0 | 25 | 18.33 | 18.33 | 38.33 | 43.33 | 5 |
| 3A mature peptide | 142 | 81.25 | 0 | 25 | 18.33 | 20 | 36.67 | 43.33 | 5 |
| 3A mature peptide | 143 | 80.74 | 0 | 25 | 18.33 | 21.67 | 35 | 43.33 | 5 |
| 3A mature peptide | 144 | 80.68 | 0 | 23.33 | 18.33 | 23.33 | 35 | 41.67 | 5 |
| 3A mature peptide | 145 | 79.89 | 0 | 23.33 | 18.33 | 21.67 | 36.67 | 41.67 | 5 |
| 3A mature peptide | 146 | 79.1 | 0 | 23.33 | 18.33 | 21.67 | 36.67 | 41.67 | 5 |
| 3B (VPg) mature peptide | 60 | 77.74 | 0 | 21.67 | 18.33 | 36.67 | 23.33 | 40 | 3 |
| 3B (VPg) mature peptide | 61 | 78.06 | 0 | 20 | 18.33 | 36.67 | 25 | 38.33 | 3 |
| 3B (VPg) mature peptide | 62 | 77.53 | 0 | 20 | 18.33 | 36.67 | 25 | 38.33 | 3 |
| 3B (VPg) mature peptide | 63 | 77.19 | 0 | 20 | 16.67 | 36.67 | 26.67 | 36.67 | 3 |
| 3B (VPg) mature peptide | 64 | 76.75 | 0 | 20 | 16.67 | 38.33 | 25 | 36.67 | 3 |
| 3B (VPg) mature peptide | 65 | 76.4 | 0 | 20 | 15 | 38.33 | 26.67 | 35 | 3 |
| 3B (VPg) mature peptide | 66 | 76.59 | 0 | 21.67 | 15 | 38.33 | 25 | 36.67 | 3 |
| 3B (VPg) mature peptide | 67 | 77.29 | 0 | 23.33 | 15 | 36.67 | 25 | 38.33 | 3 |
| 3B (VPg) mature peptide | 68 | 77.59 | 0 | 25 | 15 | 35 | 25 | 40 | 3 |
| 3B (VPg) mature peptide | 69 | 78.22 | 0 | 25 | 15 | 35 | 25 | 40 | 4 |
| 3C mature peptide | 90 | 77.51 | 0 | 20 | 15 | 30 | 35 | 35 | 4 |
| 3C mature peptide | 130 | 79.93 | 0 | 23.33 | 18.33 | 30 | 28.33 | 41.67 | 3 |
| 3C mature peptide | 214 | 81.56 | 0 | 33.33 | 11.67 | 31.67 | 23.33 | 45 | 4 |
| 3C mature peptide | 262 | 77.18 | 0 | 23.33 | 15 | 41.67 | 20 | 38.33 | 5 |
| 3C mature peptide | 302 | 79.04 | 0 | 23.33 | 18.33 | 33.33 | 25 | 41.67 | 4 |
| 3C mature peptide | 345 | 81.22 | 0 | 26.67 | 16.67 | 33.33 | 23.33 | 43.33 | 4 |
| 3C mature peptide | 388 | 75.69 | 0 | 18.33 | 16.67 | 31.67 | 33.33 | 35 | 4 |
| 3C mature peptide | 428 | 78.44 | 0 | 25 | 15 | 21.67 | 38.33 | 40 | 3 |
| 3C mature peptide | 468 | 76.48 | 0 | 20 | 15 | 23.33 | 41.67 | 35 | 3 |

TABLE 1-continued

| Selected viral probes | | | | | | | | |
|---|---|---|---|---|---|---|---|---|
| 3C mature peptide | 547 | 78.48 | 0 | 23.33 | 13.33 | 26.67 | 36.67 | 36.67 | 3 |
| 3D mature peptide | 65 | 75.79 | 0 | 23.33 | 11.67 | 26.67 | 38.33 | 35 | 4 |
| 3D mature peptide | 175 | 77.16 | 0 | 23.33 | 11.67 | 28.33 | 36.67 | 35 | 4 |
| 3D mature peptide | 235 | 77.77 | 0 | 23.33 | 11.67 | 36.67 | 28.33 | 35 | 6 |
| 3D mature peptide | 295 | 76.15 | 0 | 20 | 15 | 30 | 35 | 35 | 4 |
| 3D mature peptide | 355 | 80.71 | 0 | 20 | 23.33 | 33.33 | 23.33 | 43.33 | 3 |
| 3D mature peptide | 459 | 75.3 | 0 | 23.33 | 11.67 | 21.67 | 43.33 | 35 | 4 |
| 3D mature peptide | 568 | 76.5 | 0 | 15 | 20 | 25 | 40 | 35 | 3 |
| 3D mature peptide | 631 | 75.91 | 0 | 15 | 20 | 23.33 | 41.67 | 35 | 3 |
| 3D mature peptide | 691 | 80.51 | 0 | 20 | 23.33 | 28.33 | 28.33 | 43.33 | 4 |
| 3D mature peptide | 758 | 75.88 | 0 | 21.67 | 13.33 | 18.33 | 46.67 | 35 | 4 |
| ORF 1-polyprotein | 192 | 81.49 | 0 | 25 | 20 | 16.67 | 38.33 | 45 | 3 |
| ORF 1-polyprotein | 514 | 81.26 | 0 | 20 | 25 | 23.33 | 31.67 | 45 | 3 |
| ORF 1-polyprotein | 688 | 81.52 | 0 | 28.33 | 16.67 | 20 | 35 | 45 | 5 |
| ORF 1-polyprotein | 945 | 81.1 | 0 | 23.33 | 21.67 | 31.67 | 23.33 | 45 | 5 |
| ORF 1-polyprotein | 1243 | 81.02 | 0 | 25 | 20 | 25 | 30 | 45 | 4 |
| ORF 1-polyprotein | 1489 | 82.77 | 0 | 20 | 25 | 21.67 | 33.33 | 45 | 5 |
| ORF 1-polyprotein | 2292 | 81.07 | 0 | 20 | 25 | 30 | 25 | 45 | 3 |
| ORF 1-polyprotein | 2535 | 81.77 | 0 | 21.67 | 23.33 | 28.33 | 26.67 | 45 | 3 |
| ORF 1-polyprotein | 2953 | 79.59 | 0 | 18.33 | 26.67 | 20 | 35 | 45 | 4 |
| ORF 1-polyprotein | 3872 | 80.53 | 0 | 21.67 | 23.33 | 25 | 30 | 45 | 3 |
| Viral methyltransferase | 944 | 80.72 | 0 | 13.33 | 30 | 23.33 | 33.33 | 43.33 | 4 |
| Viral methyltransferase | 60 | 84.17 | 0 | 18.33 | 31.67 | 21.67 | 28.33 | 50 | 4 |
| Viral methyltransferase | 133 | 85.34 | 0 | 23.33 | 31.67 | 15 | 30 | 55 | 3 |
| Viral methyltransferase | 309 | 85.66 | 0 | 25 | 30 | 13.33 | 31.67 | 55 | 3 |
| Viral methyltransferase | 369 | 83.02 | 0 | 20 | 30 | 28.33 | 21.67 | 50 | 3 |
| Viral methyltransferase | 433 | 86.2 | 0 | 35 | 20 | 18.33 | 26.67 | 55 | 3 |
| Viral methyltransferase | 550 | 86.55 | 0 | 26.67 | 28.33 | 16.67 | 28.33 | 55 | 3 |
| Viral methyltransferase | 610 | 85.53 | 0 | 23.33 | 31.67 | 11.67 | 33.33 | 55 | 4 |
| Viral methyltransferase | 769 | 86.83 | 0 | 23.33 | 31.67 | 18.33 | 26.67 | 55 | 3 |
| Viral methyltransferase | 844 | 87.13 | 0 | 26.67 | 28.33 | 16.67 | 28.33 | 55 | 3 |
| Peptidase C41 | 60 | 85.09 | 0 | 28.33 | 25 | 18.33 | 28.33 | 53.33 | 4 |
| Peptidase C41 | 80 | 83.94 | 0 | 28.33 | 23.33 | 21.67 | 26.67 | 51.67 | 4 |
| Peptidase C41 | 100 | 84.32 | 0 | 26.67 | 25 | 20 | 28.33 | 51.67 | 4 |
| Peptidase C41 | 120 | 85.83 | 0 | 25 | 30 | 21.67 | 23.33 | 55 | 4 |
| Peptidase C41 | 240 | 85.25 | 0 | 20 | 35 | 18.33 | 26.67 | 55 | 3 |
| Peptidase C41 | 264 | 85.6 | 0 | 23.33 | 31.67 | 18.33 | 26.67 | 55 | 4 |
| Peptidase C41 | 284 | 84.24 | 0 | 30 | 25 | 20 | 25 | 55 | 4 |
| Peptidase C41 | 365 | 86.97 | 0 | 30 | 25 | 20 | 25 | 55 | 4 |

TABLE 1-continued

| Selected viral probes | | | | | | | | |
|---|---|---|---|---|---|---|---|---|
| Peptidase C41 | 385 | 84.04 | 0 | 30 | 20 | 16.67 | 33.33 | 50 | 4 |
| Peptidase C41 | 405 | 83.26 | 0 | 33.33 | 16.67 | 18.33 | 31.67 | 50 | 4 |
| Viral helicase 1 | 60 | 86.01 | 0 | 25 | 30 | 21.67 | 23.33 | 55 | 2 |
| Viral helicase 1 | 61 | 86.57 | 0 | 25 | 30 | 21.67 | 23.33 | 55 | 2 |
| Viral helicase 1 | 64 | 86.38 | 0 | 23.33 | 31.67 | 20 | 25 | 55 | 3 |
| Viral helicase 1 | 65 | 86.38 | 0 | 25 | 30 | 20 | 25 | 55 | 3 |
| Viral helicase 1 | 67 | 86.95 | 0 | 23.33 | 31.67 | 18.33 | 26.67 | 55 | 3 |
| Viral helicase 1 | 102 | 86.17 | 0 | 25 | 30 | 16.67 | 28.33 | 55 | 3 |
| Viral helicase 1 | 103 | 86.05 | 0 | 23.33 | 30 | 18.33 | 28.33 | 53.33 | 3 |
| Viral helicase 1 | 104 | 86.14 | 0 | 23.33 | 31.67 | 18.33 | 26.67 | 55 | 3 |
| Viral helicase 1 | 106 | 86.75 | 0 | 21.67 | 33.33 | 20 | 25 | 55 | 3 |
| Viral helicase 1 | 107 | 86.47 | 0 | 21.67 | 33.33 | 20 | 25 | 55 | 3 |
| RNA dependent RNA pol. | 113 | 81.26 | 0 | 20 | 25 | 23.33 | 31.67 | 45 | 3 |
| RNA dependent RNA pol. | 114 | 80.83 | 0 | 20 | 25 | 23.33 | 31.67 | 45 | 3 |
| RNA dependent RNA pol. | 115 | 80.85 | 0 | 20 | 25 | 23.33 | 31.67 | 45 | 3 |
| RNA dependent RNA pol. | 287 | 81.52 | 0 | 28.33 | 16.67 | 20 | 35 | 45 | 5 |
| RNA dependent RNA pol. | 288 | 81.52 | 0 | 28.33 | 16.67 | 21.67 | 33.33 | 45 | 5 |
| RNA dependent RNA pol. | 290 | 80.94 | 0 | 28.33 | 16.67 | 20 | 35 | 45 | 5 |
| RNA dependent RNA pol. | 291 | 80.23 | 0 | 26.67 | 16.67 | 20 | 36.67 | 43.33 | 5 |
| RNA dependent RNA pol. | 292 | 80.1 | 0 | 25 | 16.67 | 20 | 38.33 | 41.67 | 5 |
| RNA dependent RNA pol. | 293 | 79.73 | 0 | 26.67 | 16.67 | 20 | 36.67 | 43.33 | 5 |
| RNA dependent RNA pol. | 294 | 80.02 | 0 | 25 | 16.67 | 21.67 | 36.67 | 41.67 | 5 |
| ORF 3-hypothetical protein | 211 | 85.04 | 0 | 18.33 | 35 | 20 | 26.67 | 53.33 | 4 |
| ORF 3-hypothetical protein | 212 | 84.93 | 0 | 18.33 | 33.33 | 20 | 28.33 | 51.67 | 4 |
| ORF 3-hypothetical protein | 213 | 85.04 | 0 | 20 | 33.33 | 18.33 | 28.33 | 53.33 | 4 |
| ORF 3-hypothetical protein | 214 | 85.22 | 0 | 21.67 | 33.33 | 16.67 | 28.33 | 55 | 4 |
| ORF 3-hypothetical protein | 215 | 85.04 | 0 | 21.67 | 31.67 | 16.67 | 30 | 53.33 | 4 |
| ORF 3-hypothetical protein | 216 | 85.04 | 0 | 23.33 | 30 | 16.67 | 30 | 53.33 | 4 |
| ORF 3-hypothetical protein | 217 | 85.75 | 0 | 25 | 30 | 15 | 30 | 55 | 4 |
| ORF 3-hypothetical protein | 204 | 85.2 | 0 | 15 | 40 | 20 | 25 | 55 | 4 |
| ORF 3-hypothetical protein | 205 | 85.22 | 0 | 15 | 40 | 20 | 25 | 55 | 4 |
| ORF 3-hypothetical protein | 206 | 85.92 | 0 | 16.67 | 38.33 | 20 | 25 | 55 | 4 |
| ORF 2-capsid protein | 323 | 80.69 | 0 | 20 | 25 | 30 | 25 | 45 | 3 |
| ORF 2-capsid protein | 324 | 80.56 | 0 | 18.33 | 25 | 31.67 | 25 | 43.33 | 3 |

TABLE 1-continued

| Selected viral probes | | | | | | | | | |
|---|---|---|---|---|---|---|---|---|---|
| ORF 2-capsid protein | 325 | 80.31 | 0 | 18.33 | 25 | 31.67 | 25 | 43.33 | 3 |
| ORF 2-capsid protein | 326 | 80.37 | 0 | 18.33 | 26.67 | 30 | 25 | 45 | 3 |
| ORF 2-capsid protein | 327 | 80.47 | 0 | 18.33 | 26.67 | 30 | 25 | 45 | 3 |
| ORF 2-capsid protein | 328 | 80.12 | 0 | 16.67 | 26.67 | 30 | 26.67 | 43.33 | 3 |
| ORF 2-capsid protein | 329 | 79.78 | 0 | 16.67 | 28.33 | 28.33 | 26.67 | 45 | 3 |
| ORF 2-capsid protein | 330 | 80.15 | 0 | 15 | 28.33 | 30 | 26.67 | 43.33 | 3 |
| ORF 2-capsid protein | 331 | 79.86 | 0 | 15 | 28.33 | 30 | 26.67 | 43.33 | 3 |
| ORF 2-capsid protein | 332 | 79.5 | 0 | 16.67 | 28.33 | 30 | 25 | 45 | 3 |
| RNA dependent RNA pol. | 69 | 81.65 | 0 | 20 | 25 | 31.67 | 23.33 | 45 | 3 |
| RNA dependent RNA pol. | 130 | 80.78 | 0 | 11.67 | 30 | 31.67 | 26.67 | 41.67 | 4 |
| RNA dependent RNA pol. | 214 | 80.92 | 0 | 23.33 | 21.67 | 20 | 35 | 45 | 3 |
| RNA dependent RNA pol. | 442 | 80.83 | 0 | 20 | 25 | 28.33 | 26.67 | 45 | 3 |
| RNA dependent RNA pol. | 502 | 76.41 | 0 | 11.67 | 23.33 | 35 | 30 | 35 | 3 |
| RNA dependent RNA pol. | 562 | 77.91 | 0 | 16.67 | 21.67 | 28.33 | 33.33 | 38.33 | 3 |
| RNA dependent RNA pol. | 622 | 80.63 | 0 | 13.33 | 30 | 20 | 36.67 | 43.33 | 3 |
| RNA dependent RNA pol. | 682 | 79.55 | 0 | 15 | 26.67 | 23.33 | 35 | 41.67 | 3 |
| RNA dependent RNA pol. | 765 | 81.34 | 0 | 20 | 25 | 23.33 | 31.67 | 45 | 5 |
| RNA dependent RNA pol. | 853 | 80.88 | 0 | 15 | 30 | 26.67 | 28.33 | 45 | 4 |
| Putative protease cofactor | 80 | 81.54 | 0 | 26.67 | 18.33 | 18.33 | 36.67 | 45 | 5 |
| putative protease cofactor | 140 | 81.22 | 0 | 25 | 20 | 21.67 | 33.33 | 45 | 4 |
| putative protease cofactor | 224 | 80.72 | 0 | 20 | 25 | 15 | 40 | 45 | 3 |
| putative protease cofactor | 284 | 81.98 | 0 | 26.67 | 16.67 | 20 | 36.67 | 43.33 | 3 |
| putative protease cofactor | 346 | 83.3 | 0 | 30 | 15 | 30 | 25 | 45 | 6 |
| putative protease cofactor | 409 | 82.71 | 0 | 23.33 | 21.67 | 18.33 | 36.67 | 45 | 5 |
| putative protease cofactor | 476 | 81.05 | 0 | 20 | 25 | 21.67 | 33.33 | 45 | 3 |
| putative protease cofactor | 536 | 79.88 | 0 | 20 | 21.67 | 28.33 | 30 | 41.67 | 3 |
| putative protease cofactor | 625 | 81.68 | 0 | 28.33 | 16.67 | 26.67 | 28.33 | 45 | 4 |
| putative protease cofactor | 703 | 81.33 | 0 | 20 | 25 | 23.33 | 31.67 | 45 | 2 |
| NTP-binding protein | 77 | 81.2 | 0 | 25 | 20 | 15 | 40 | 45 | 4 |
| NTP-binding protein | 148 | 82.13 | 0 | 25 | 20 | 15 | 40 | 45 | 4 |
| NTP-binding protein | 218 | 81.07 | 0 | 25 | 20 | 30 | 25 | 45 | 3 |
| NTP-binding protein | 278 | 80.23 | 0 | 28.33 | 15 | 25 | 31.67 | 43.33 | 5 |
| NTP-binding protein | 340 | 80.25 | 0 | 28.33 | 16.67 | 31.67 | 23.33 | 45 | 5 |
| NTP-binding protein | 400 | 79.53 | 0 | 28.33 | 11.67 | 30 | 30 | 40 | 4 |

TABLE 1-continued

| Selected viral probes | | | | | | | | |
|---|---|---|---|---|---|---|---|---|
| NTP-binding protein | 461 | 82.34 | 0 | 21.67 | 23.33 | 28.33 | 26.67 | 45 | 5 |
| NTP-binding protein | 521 | 79.93 | 0 | 20 | 21.67 | 33.33 | 25 | 41.67 | 3 |
| NTP-binding protein | 658 | 80.52 | 0 | 21.67 | 21.67 | 26.67 | 30 | 43.33 | 3 |
| NTP-binding protein | 718 | 81.13 | 0 | 23.33 | 21.67 | 28.33 | 26.67 | 45 | 4 |
| cysteine protease | 116 | 80.72 | 0 | 35 | 8.33 | 28.33 | 28.33 | 43.33 | 3 |
| cysteine protease | 162 | 80.95 | 0 | 28.33 | 15 | 26.67 | 30 | 43.33 | 2 |
| cysteine protease | 202 | 79.43 | 0 | 23.33 | 18.33 | 28.33 | 30 | 41.67 | 4 |
| cysteine protease | 293 | 79.61 | 0 | 20 | 20 | 30 | 30 | 40 | 3 |
| cysteine protease | 333 | 78.88 | 0 | 15 | 23.33 | 26.67 | 35 | 38.33 | 4 |
| cysteine protease | 377 | 81.6 | 0 | 21.67 | 23.33 | 25 | 30 | 45 | 4 |
| cysteine protease | 417 | 80.36 | 0 | 15 | 26.67 | 28.33 | 30 | 41.67 | 4 |
| cysteine protease | 457 | 77.1 | 0 | 25 | 10 | 33.33 | 31.67 | 35 | 3 |
| cysteine protease | 497 | 79.67 | 0 | 30 | 13.33 | 31.67 | 25 | 43.33 | 3 |
| cysteine protease | 537 | 78.55 | 0 | 25 | 15 | 28.33 | 31.67 | 40 | 6 |
| RNA-dependent RNA pol. | 60 | 79.2 | 0 | 21.67 | 16.67 | 26.67 | 35 | 38.33 | 5 |
| RNA-dependent RNA pol. | 120 | 79.34 | 0 | 23.33 | 16.67 | 25 | 35 | 40 | 3 |
| RNA-dependent RNA pol. | 180 | 77.5 | 0 | 16.67 | 18.33 | 28.33 | 36.67 | 35 | 4 |
| RNA-dependent RNA pol. | 240 | 79.94 | 0 | 25 | 16.67 | 36.67 | 21.67 | 41.67 | 5 |
| RNA-dependent RNA pol. | 300 | 80.36 | 0 | 25 | 18.33 | 26.67 | 30 | 43.33 | 5 |
| RNA-dependent RNA pol. | 360 | 78.03 | 0 | 20 | 16.67 | 36.67 | 26.67 | 36.67 | 4 |
| RNA-dependent RNA pol. | 420 | 80.67 | 0 | 25 | 16.67 | 35 | 23.33 | 41.67 | 4 |
| RNA-dependent RNA pol. | 510 | 81.16 | 0 | 25 | 20 | 26.67 | 28.33 | 45 | 3 |
| RNA-dependent RNA pol. | 573 | 81.41 | 0 | 25 | 20 | 33.33 | 21.67 | 45 | 4 |
| RNA-dependent RNA pol. | 736 | 81.66 | 0 | 31.67 | 11.67 | 31.67 | 25 | 43.33 | 4 |
| nucleocapsid protein | 99 | 77.34 | 0 | 20 | 15 | 36.67 | 28.33 | 35 | 3 |
| nucleocapsid protein | 159 | 79.32 | 0 | 31.67 | 10 | 30 | 28.33 | 41.67 | 3 |
| nucleocapsid protein | 226 | 82.08 | 0 | 18.33 | 26.67 | 31.67 | 23.33 | 45 | 5 |
| nucleocapsid protein | 311 | 80.47 | 0 | 23.33 | 21.67 | 26.67 | 28.33 | 45 | 2 |
| nucleocapsid protein | 371 | 76.59 | 0 | 20 | 16.67 | 35 | 28.33 | 36.67 | 4 |
| nucleocapsid protein | 431 | 79.43 | 0 | 31.67 | 13.33 | 33.33 | 21.67 | 45 | 3 |
| nucleocapsid protein | 499 | 80.41 | 0 | 31.67 | 13.33 | 28.33 | 26.67 | 45 | 3 |
| nucleocapsid protein | 559 | 81.55 | 0 | 15 | 30 | 23.33 | 31.67 | 45 | 3 |
| nucleocapsid protein | 635 | 81.41 | 0 | 26.67 | 18.33 | 28.33 | 26.67 | 45 | 4 |
| nucleocapsid protein | 723 | 81.28 | 0 | 23.33 | 21.67 | 25 | 30 | 45 | 3 |

TABLE 1-continued

| Selected viral probes | | | | | | | | | |
|---|---|---|---|---|---|---|---|---|---|
| phospoprotein | 90 | 74.7 | 0 | 23.33 | 11.67 | 31.67 | 33.33 | 35 | 3 |
| phospoprotein | 150 | 78.41 | 0 | 25 | 15 | 31.67 | 28.33 | 40 | 2 |
| phospoprotein | 210 | 79.22 | 0 | 25 | 15 | 31.67 | 28.33 | 40 | 4 |
| phospoprotein | 345 | 81.57 | 0 | 20 | 25 | 41.67 | 13.33 | 45 | 4 |
| phospoprotein | 431 | 81.09 | 0 | 23.33 | 21.67 | 31.67 | 23.33 | 45 | 3 |
| phospoprotein | 524 | 80.06 | 0 | 25 | 20 | 28.33 | 26.67 | 45 | 3 |
| phospoprotein | 592 | 78.34 | 0 | 30 | 10 | 40 | 20 | 40 | 5 |
| phospoprotein | 652 | 80.68 | 0 | 26.67 | 16.67 | 36.67 | 20 | 43.33 | 3 |
| phospoprotein | 712 | 77.31 | 0 | 20 | 16.67 | 23.33 | 40 | 36.67 | 3 |
| phospoprotein | 772 | 80.9 | 0 | 25 | 20 | 26.67 | 28.33 | 45 | 2 |
| gene"4b | 60 | 80.04 | 0 | 26.67 | 13.33 | 28.33 | 31.67 | 40 | 4 |
| gene"4b | 120 | 80.91 | 0 | 28.33 | 16.67 | 23.33 | 31.67 | 45 | 3 |
| gene"4b | 180 | 79.39 | 0 | 30 | 13.33 | 40 | 16.67 | 43.33 | 3 |
| gene"4b | 253 | 81.24 | 0 | 25 | 20 | 43.33 | 11.67 | 45 | 3 |
| gene"4b | 313 | 78.57 | 0 | 21.67 | 18.33 | 35 | 25 | 40 | 3 |
| gene"4b | 373 | 74.79 | 0 | 16.67 | 18.33 | 31.67 | 33.33 | 35 | 3 |
| gene"4b | 434 | 80.65 | 0 | 31.67 | 13.33 | 30 | 25 | 45 | 4 |
| gene"4b | 494 | 79.78 | 0 | 23.33 | 20 | 23.33 | 33.33 | 43.33 | 3 |
| gene"4b | 556 | 80.43 | 0 | 30 | 15 | 30 | 25 | 45 | 4 |
| gene"4b | 616 | 81.19 | 0 | 21.67 | 23.33 | 30 | 25 | 45 | 3 |
| matrix protein | 78 | 77.42 | 0 | 23.33 | 13.33 | 30 | 33.33 | 36.67 | 5 |
| matrix protein | 118 | 80.98 | 0 | 25 | 18.33 | 31.67 | 25 | 43.33 | 5 |
| matrix protein | 194 | 78.92 | 0 | 28.33 | 15 | 31.67 | 25 | 43.33 | 3 |
| matrix protein | 241 | 76.19 | 0 | 23.33 | 11.67 | 38.33 | 26.67 | 35 | 3 |
| matrix protein | 281 | 79.78 | 0 | 25 | 18.33 | 28.33 | 28.33 | 43.33 | 4 |
| matrix protein | 324 | 80.81 | 0 | 23.33 | 21.67 | 20 | 35 | 45 | 4 |
| matrix protein | 388 | 80.6 | 0 | 23.33 | 21.67 | 30 | 25 | 45 | 4 |
| matrix protein | 429 | 75.23 | 0 | 20 | 15 | 33.33 | 31.67 | 35 | 4 |
| matrix protein | 469 | 79.2 | 0 | 21.67 | 18.33 | 18.33 | 41.67 | 40 | 4 |
| matrix protein | 581 | 81.35 | 0 | 21.67 | 23.33 | 31.67 | 23.33 | 45 | 3 |
| gene G | 60 | 78.09 | 0 | 26.67 | 11.67 | 38.33 | 23.33 | 38.33 | 4 |
| gene G | 120 | 78.28 | 0 | 25 | 15 | 26.67 | 33.33 | 40 | 2 |
| gene G | 180 | 79.75 | 0 | 18.33 | 25 | 36.67 | 20 | 43.33 | 2 |
| gene G | 240 | 79.25 | 0 | 21.67 | 16.67 | 46.67 | 15 | 38.33 | 4 |
| gene G | 306 | 81.5 | 0 | 23.33 | 21.67 | 21.67 | 33.33 | 45 | 3 |
| gene G | 389 | 81.56 | 0 | 25 | 20 | 30 | 25 | 45 | 4 |
| gene G | 472 | 80.43 | 0 | 26.67 | 18.33 | 38.33 | 16.67 | 45 | 3 |
| gene G | 601 | 81.23 | 0 | 25 | 20 | 30 | 25 | 45 | 4 |
| gene G | 677 | 80.45 | 0 | 35 | 8.33 | 30 | 26.67 | 43.33 | 3 |
| gene G | 737 | 79.98 | 0 | 21.67 | 20 | 26.67 | 31.67 | 41.67 | 3 |
| RNA-dependent RNA pol. | 236 | 75.47 | 0 | 18.33 | 16.67 | 31.67 | 33.33 | 35 | 3 |
| RNA-dependent RNA pol. | 296 | 80.36 | 0 | 21.67 | 21.67 | 20 | 36.67 | 43.33 | 3 |
| RNA-dependent RNA pol. | 388 | 81.57 | 0 | 31.67 | 13.33 | 20 | 35 | 45 | 5 |
| RNA-dependent RNA pol. | 450 | 80.33 | 0 | 26.67 | 18.33 | 33.33 | 21.67 | 45 | 3 |
| RNA-dependent RNA pol. | 510 | 78.62 | 0 | 26.67 | 16.67 | 30 | 26.67 | 43.33 | 4 |
| RNA-dependent RNA pol. | 570 | 77.84 | 0 | 16.67 | 21.67 | 31.67 | 30 | 38.33 | 4 |
| RNA-dependent RNA pol. | 630 | 78.97 | 0 | 21.67 | 18.33 | 36.67 | 23.33 | 40 | 3 |
| RNA-dependent RNA pol. | 764 | 81.66 | 0 | 28.33 | 16.67 | 36.67 | 18.33 | 45 | 3 |
| RNA-dependent RNA pol. | 824 | 77.97 | 0 | 30 | 10 | 28.33 | 31.67 | 40 | 5 |
| RNA-dependent RNA pol. | 914 | 79.84 | 0 | 28.33 | 15 | 35 | 21.67 | 43.33 | 3 |
| 5' trailer RNA | 60 | 77.75 | 0 | 25 | 11.67 | 18.33 | 45 | 36.67 | 5 |
| 5' trailer RNA | 61 | 77.33 | 0 | 25 | 13.33 | 18.33 | 43.33 | 38.33 | 5 |
| 5' trailer RNA | 62 | 77 | 0 | 23.33 | 13.33 | 18.33 | 45 | 36.67 | 5 |
| 5' trailer RNA | 63 | 76.39 | 0 | 23.33 | 13.33 | 18.33 | 45 | 36.67 | 5 |
| 5' trailer RNA | 64 | 76.82 | 0 | 23.33 | 11.67 | 20 | 45 | 35 | 5 |
| 5' trailer RNA | 65 | 76.05 | 0 | 23.33 | 11.67 | 20 | 45 | 35 | 5 |
| 5' trailer RNA | 73 | 75.88 | 0 | 23.33 | 11.67 | 21.67 | 43.33 | 35 | 5 |
| 5' trailer RNA | 74 | 76.29 | 0 | 23.33 | 11.67 | 23.33 | 41.67 | 35 | 5 |

TABLE 1-continued

| Selected viral probes | | | | | | | | | |
|---|---|---|---|---|---|---|---|---|---|
| 5' trailer RNA | 75 | 76.29 | 0 | 23.33 | 11.67 | 25 | 40 | 35 | 5 |
| 5' trailer RNA | 76 | 76.39 | 0 | 25 | 11.67 | 25 | 38.33 | 36.67 | 5 |
| NS5 protein | 498 | 80.74 | 0 | 23.33 | 21.67 | 33.33 | 21.67 | 45 | 4 |
| NS5 protein | 559 | 81.87 | 0 | 25 | 20 | 35 | 20 | 45 | 5 |
| NS5 protein | 632 | 80.62 | 0 | 30 | 15 | 28.33 | 26.67 | 45 | 5 |
| NS5 protein | 872 | 82.48 | 0 | 20 | 25 | 28.33 | 26.67 | 45 | 4 |
| NS5 protein | 1080 | 81.39 | 0 | 28.33 | 16.67 | 40 | 15 | 45 | 4 |
| NS5 protein | 1140 | 81.31 | 0 | 26.67 | 16.67 | 23.33 | 33.33 | 43.33 | 3 |
| NS5 protein | 1284 | 81.05 | 0 | 31.67 | 13.33 | 28.33 | 26.67 | 45 | 2 |
| NS5 protein | 1350 | 81.53 | 0 | 23.33 | 21.67 | 31.67 | 23.33 | 45 | 5 |
| NS5 protein | 1411 | 78.37 | 0 | 23.33 | 15 | 43.33 | 18.33 | 38.33 | 5 |
| NS5 protein | 1506 | 81.82 | 0 | 25 | 20 | 36.67 | 18.33 | 45 | 3 |
| NS5 protein | 336 | 81.2 | 0 | 26.67 | 18.33 | 26.67 | 28.33 | 45 | 3 |
| NS5 protein | 399 | 81.27 | 0 | 25 | 20 | 33.33 | 21.67 | 45 | 4 |
| NS5 protein | 508 | 80.62 | 0 | 30 | 15 | 28.33 | 26.67 | 45 | 5 |
| NS5 protein | 748 | 82.48 | 0 | 20 | 25 | 28.33 | 26.67 | 45 | 4 |
| NS5 protein | 956 | 81.39 | 0 | 28.33 | 16.67 | 40 | 15 | 45 | 4 |
| NS5 protein | 1016 | 81.31 | 0 | 26.67 | 16.67 | 23.33 | 33.33 | 43.33 | 3 |
| NS5 protein | 1160 | 81.05 | 0 | 31.67 | 13.33 | 28.33 | 26.67 | 45 | 2 |
| NS5 protein | 1226 | 81.53 | 0 | 23.33 | 21.67 | 31.67 | 23.33 | 45 | 5 |
| NS5 protein | 1287 | 78.37 | 0 | 23.33 | 15 | 43.33 | 18.33 | 38.33 | 5 |
| NS5 protein | 1381 | 81.05 | 0 | 26.67 | 18.33 | 36.67 | 18.33 | 45 | 3 |
| NS5 protein | 101 | 81.2 | 0 | 26.67 | 18.33 | 26.67 | 28.33 | 45 | 3 |
| NS5 protein | 164 | 81.27 | 0 | 25 | 20 | 33.33 | 21.67 | 45 | 4 |
| NS5 protein | 273 | 80.62 | 0 | 30 | 15 | 28.33 | 26.67 | 45 | 5 |
| NS5 protein | 513 | 82.48 | 0 | 20 | 25 | 28.33 | 26.67 | 45 | 4 |
| NS5 protein | 721 | 81.39 | 0 | 28.33 | 16.67 | 40 | 15 | 45 | 4 |
| NS5 protein | 781 | 81.31 | 0 | 26.67 | 16.67 | 23.33 | 33.33 | 43.33 | 3 |
| NS5 protein | 925 | 81.05 | 0 | 31.67 | 13.33 | 28.33 | 26.67 | 45 | 2 |
| NS5 protein | 991 | 81.53 | 0 | 23.33 | 21.67 | 31.67 | 23.33 | 45 | 5 |
| NS5 protein | 1052 | 78.37 | 0 | 23.33 | 15 | 43.33 | 18.33 | 38.33 | 5 |
| NS5 protein | 1146 | 81.05 | 0 | 26.67 | 18.33 | 36.67 | 18.33 | 45 | 3 |
| NS5 protein | 375 | 80.74 | 0 | 23.33 | 21.67 | 33.33 | 21.67 | 45 | 4 |
| NS5 protein | 510 | 80.62 | 0 | 28.33 | 16.67 | 30 | 25 | 45 | 5 |
| NS5 protein | 749 | 82.48 | 0 | 20 | 25 | 28.33 | 26.67 | 45 | 4 |
| NS5 protein | 957 | 81.39 | 0 | 28.33 | 16.67 | 40 | 15 | 45 | 4 |
| NS5 protein | 1017 | 81.31 | 0 | 26.67 | 16.67 | 23.33 | 33.33 | 43.33 | 3 |
| NS5 protein | 1161 | 81.05 | 0 | 31.67 | 13.33 | 28.33 | 26.67 | 45 | 2 |
| NS5 protein | 1227 | 81.53 | 0 | 23.33 | 21.67 | 31.67 | 23.33 | 45 | 5 |
| NS5 protein | 1288 | 78.37 | 0 | 23.33 | 15 | 43.33 | 18.33 | 38.33 | 5 |
| NS5 protein | 1353 | 82.74 | 0 | 21.67 | 23.33 | 38.33 | 16.67 | 45 | 5 |
| NS5 protein | 1459 | 80.12 | 0 | 30 | 15 | 31.67 | 23.33 | 45 | 2 |
| 5UTR | 60 | 78.39 | 0 | 25 | 15 | 30 | 30 | 40 | 4 |
| 5UTR | 69 | 78.43 | 0 | 26.67 | 11.67 | 35 | 26.67 | 38.33 | 4 |
| capsid | 144 | 77.34 | 0 | 21.67 | 13.33 | 41.67 | 23.33 | 35 | 3 |
| capsid | 160 | 79.12 | 0 | 28.33 | 11.67 | 41.67 | 18.33 | 40 | 6 |
| propeptide | 174 | 80.99 | 0 | 23.33 | 21.67 | 28.33 | 26.67 | 45 | 3 |
| propeptide | 183 | 78.98 | 0 | 23.33 | 16.67 | 31.67 | 28.33 | 40 | 2 |
| membrane protein | 64 | 81.94 | 0 | 20 | 25 | 31.67 | 23.33 | 45 | 5 |
| membrane protein | 78 | 80.99 | 0 | 25 | 20 | 26.67 | 28.33 | 45 | 5 |
| envelope protein | 74 | 80.57 | 0 | 25 | 20 | 16.67 | 38.33 | 45 | 5 |
| envelope protein | 194 | 81.61 | 0 | 26.67 | 15 | 26.67 | 31.67 | 41.67 | 5 |
| envelope protein | 447 | 80.6 | 0 | 21.67 | 23.33 | 33.33 | 21.67 | 45 | 4 |
| envelope protein | 960 | 79.05 | 0 | 23.33 | 18.33 | 23.33 | 35 | 41.67 | 4 |
| envelope protein | 1198 | 82.15 | 0 | 26.67 | 18.33 | 28.33 | 26.67 | 45 | 5 |
| NS1 protein | 64 | 79.96 | 0 | 21.67 | 21.67 | 31.67 | 25 | 43.33 | 2 |
| NS1 protein | 439 | 80.43 | 0 | 26.67 | 16.67 | 38.33 | 18.33 | 43.33 | 4 |
| NS1 protein | 608 | 77.05 | 0 | 26.67 | 13.33 | 26.67 | 33.33 | 40 | 3 |
| NS1 protein | 866 | 81.68 | 0 | 28.33 | 16.67 | 31.67 | 23.33 | 45 | 5 |
| NS2A protein | 148 | 80.85 | 0 | 25 | 20 | 28.33 | 26.67 | 45 | 4 |
| NS2A protein | 152 | 80.03 | 0 | 25 | 18.33 | 28.33 | 28.33 | 43.33 | 4 |
| NS2A protein | 451 | 80.55 | 0 | 23.33 | 21.67 | 25 | 30 | 45 | 3 |
| NS2B protein | 287 | 81.46 | 0 | 28.33 | 16.67 | 40 | 15 | 45 | 5 |
| NS2B protein | 292 | 80.68 | 0 | 28.33 | 15 | 40 | 16.67 | 43.33 | 5 |
| NS2B protein | 297 | 81.32 | 0 | 30 | 15 | 36.67 | 18.33 | 45 | 5 |
| NS3 protein | 192 | 81.23 | 0 | 26.67 | 18.33 | 36.67 | 18.33 | 45 | 3 |
| NS3 protein | 395 | 80.79 | 0 | 15 | 30 | 28.33 | 26.67 | 45 | 3 |
| NS3 protein | 797 | 82.73 | 0 | 28.33 | 16.67 | 28.33 | 26.67 | 45 | 5 |
| NS3 protein | 1131 | 81.83 | 0 | 18.33 | 26.67 | 33.33 | 21.67 | 45 | 3 |
| NS4A protein | 246 | 81.88 | 0 | 33.33 | 11.67 | 23.33 | 31.67 | 45 | 5 |
| NS4A protein | 204 | 87.21 | 0 | 33.33 | 21.67 | 18.33 | 26.67 | 55 | 4 |

TABLE 1-continued

Selected viral probes

| | | | | | | | | | |
|---|---|---|---|---|---|---|---|---|---|
| NS4A protein | 383 | 86.35 | 0 | 28.33 | 26.67 | 28.33 | 16.67 | 55 | 3 |
| NS4B protein | 112 | 80.14 | 0 | 23.33 | 21.67 | 33.33 | 21.67 | 45 | 5 |
| NS4B protein | 819 | 80.74 | 0 | 23.33 | 21.67 | 28.33 | 26.67 | 45 | 3 |
| NS4B protein | 1082 | 80.52 | 0 | 26.67 | 16.67 | 33.33 | 23.33 | 43.33 | 3 |
| NS4B protein | 1506 | 80.98 | 0 | 31.67 | 13.33 | 38.33 | 16.67 | 45 | 3 |
| NS5 protein | 74 | 80.74 | 0 | 23.33 | 21.67 | 33.33 | 21.67 | 45 | 4 |
| NS5 protein | 716 | 81.31 | 0 | 26.67 | 16.67 | 23.33 | 33.33 | 43.33 | 3 |
| NS5 protein | 1172 | 79.51 | 0 | 30 | 15 | 35 | 20 | 45 | 3 |
| 3UTR | 61 | 84.45 | 0 | 40 | 15 | 25 | 20 | 55 | 4 |
| 3UTR | 70 | 84.24 | 0 | 33.33 | 21.67 | 23.33 | 21.67 | 55 | 4 |

WCCV - White clover cryptic virus;
BBWV - Broad bean wilt virus;
LNYV - Lettuce necrotic yellows virus

TABLE 2

Viral pathogens used in testing the Pathogen Chip

| Virus | Type/Strain | Source | References |
|---|---|---|---|
| CHIKV | R91064 | FDA/CBER Lot Release Panels* | |
| HAV | SD11 | Dr. Farci Lab | |
| HCV | Genotype 1b | Sera Care (Sera Care, Milford, MA) | |
| HCV | Genotype 2a | Sera Care (Sera Care, Milford, MA) | |
| HCV | Genotype 3 | Sera Care (Sera Care, Milford, MA) | |
| HEV | Genotype 3a | WHO Standard | |
| HIV-1 | Group M, Subtype B | FDA/CBER Lot Release Panels | 1, 2 |
| HIV-2 | Subtype B | FDA/CBER Lot Release Panels | 3 |
| DENGUE | Serotype 1, 2, 3 and 4 | Aedes albopictus C6/36 cell culture | 4 |
| HTLV-I | | ZeptoMetrix | |
| HTLV-II | | ZeptoMetrix | |
| WEST NILE | NY99 | Cell culture | 5 |
| ZIKA | PRVABC62 | FDA/CBER Lot Release Panels | |
| ZIKA | FSS13025 | FDA/CBER Lot Release Panels | |

*The FDA Center for Biologics Evaluation and Research (CBER), Division of Emerging and Transfusion Transmitted Diseases produces and makes available to blood donor screening test manufacturers panels which are sets of vialed human plasma containing virus particles that are carefully quantified for evaluating virus detection devices. Each set has several vials each one a different virus concentration and some with virus-free plasma. These panels are also used to test each new lot of a licensed blood donor screening device for release to the public, hence they are called Lot Release Panels. There are separate panels prepared for each type of virus.
1 Davis et al., J Virol Methods, 107: 37-44 (2003)
2 Lee et al., J Virol Methods, 137: 287-291 (2006)
3 Lee et al., J Virol Methods, 137: 287-291 (2005).
4 Dong et al., J Appl Microbiol, 120: 1119-1129 (2016).
5 Grinev et al., J Virol Methods, 154: 27-40 (2008).

Nucleic acids from positive plasma and from NATtrol were extracted using the Dynabeads™ SILANE Viral NA Kit (ThermoFisher Scientific, Waltham, MA) according to the manufacturer's protocol.

cDNA from random-primed, reverse-transcribed total RNA was performed with the Ovation® Pico WTA System (NuGEN, San Carlos, CA) using the manufacturer's recommended protocols and input amounts. For this study, the Agilent SureTag® Labeling Kit was used for generating Cy™3 dye labeled cDNA targets. Labeled cDNA was purified with SureTag® Kit spin columns and specific activities (degree of labeling) were calculated for use in hybridization reactions. A master mix containing 10× blocking agent and 2× GE hybridization buffer HI-RPM, was added to 3-5 µg of labeled cDNA, denatured, and hybridized to arrays under 8-chamber gasket slides at 65° C. with 20-rpm rotation for 24 hours in an Agilent hybridization oven. Arrays were processed using wash procedure A and scanned on an Agilent SureScan® G4900DA microarray scanner using 5-µm resolution.

Microarray-based platform data analysis: After scanning, microarray images were analyzed using Agilent Feature Extraction software (Agilent Technologies, Inc., Santa Clara, CA) with default protocols and settings. Average pixel intensity and subtraction of local background for each feature was calculated. Images were manually examined to note any arrays affected by high background, scratches, or other technical artifacts. Probe sets associated with low signal intensity or bad quality features were considered unreliable and excluded from the analysis. Feature intensities for Cy™3 dye channels were imported into the Partek™ Genomics Suite™ software (Partek Inc., St. Louis, MO, USA).

First, microarray analysis was performed by ranking the highest signal intensity probes by the mean of the set of probes defining each pathogen on the platform. Next, an experimental threshold was defined as a log ratio of signal intensity mean for the set of probes defining each pathogen and the mean of the Agilent control probes set. The threshold was applied to all the arrays tested to define the final parameters for test validation.

RT-qPCR Validation

Altona RT-qPCR: CHIKV, DENV 1-4 and ZIKV positive specimens were quantified using the Altona RealStar RT-qPCR kit (Altona Diagnostic GmbH, Hamburg, Germany) according to the manufacturer's instructions. The positive control and the internal control were provided by the manufacturer. Serial dilutions of CHIKV (ATCC VR-3246SD), DENV (ATCC VR-3231SD), and ZIKV (ATCC VR-1843DQ) quantitative genomic RNA (specification range: $1\times10^5$-$1\times10^6$ copies/4) obtained from ATCC (American Type Culture Collection Manassas, VA) were prepared to generate a standard curve for copy number quantification.

Primer Design (Genesig) RT-qPCR: HAV (target/5' NCR), HCV (5'UTR), HEV (ORF2), HIV-1 (target/POL), HIV-2 (target/POL), HTLVI (target/POL), HTLVII (target/POL), and WNV (5'UTR) positive specimens were quantified using the Primer Design Genesig kit (Primerdesign Ltd, United Kingdom) according to the manufacturer's protocol (OneStep RT-qPCR protocol). Each kit contained a positive control template for the PCR set up and for copy number determination (generated serial dilutions for the standard curve).

The RT-qPCR assays were performed on a ViiA7 Applied Biosystems real-time PCR system (Thermo Fisher Scientific Inc., Waltham, MA, USA). Each sample was tested in duplicate and the mean $C_q$ value was calculated.

Example 2

Microarray Design, Specificity, and Validation

Microarray design: The pathogen chip design strategy was to cover all high priority blood-borne RNA viruses (retroviruses and both positive- and negative-strand RNA viruses) using multiple probes to independent targets sites in the genome of each species. In total, 1,769 unique viral oligonucleotides derived from 16 distinct viral genomes (Table 1) were included that allowed discrimination of pathogens at the level of species, subtypes and genotypes. The microarray was supplemented with an additional number of predesigned GE array probes for 906 genes from the human genome, 84 ERCC probes and 120 probes specific for plant viruses representing negative controls (Table 3).

TABLE 3

Probe distribution on pathogen chip

| Probe group type | Number of targets | Number of probes | Purpose |
|---|---|---|---|
| All spot | 1010 | 14,716 | RNA pathogens coverage and internal controls |
| Pathogen Specific (not replicated) | 17 | 1,769 | Probes intensity analysis of pathogen specific genes |
| Internal Control (replicated 10 times) | 902 | 902 | Agilent requirement for probes normalization |
| ERCC probes (replicated 45 times) | 84 | 84 | Determination of intra-probe variance |
| Negative Control (not replicated) | 3 | 120 | Determination of probes cross reactivity |

The design included multiple gene targets for each pathogen genome in order to select the best probes for the final platform design. The design strategy was to balance the number of probes for each pathogen with a final count of 90-110 probes each. Probes selected in the final design generated a more intense signal and produced higher percentage coverage of the specific genome across the different experiments (FIG. 1A).

Figure 2B:
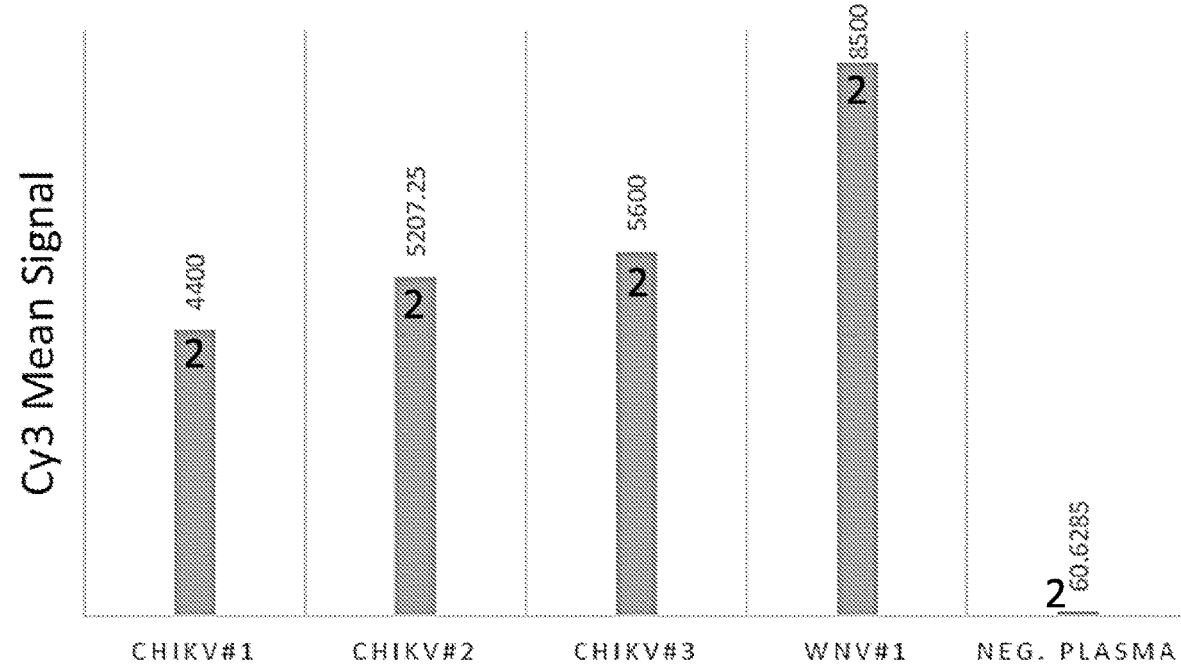
Figure 2C:
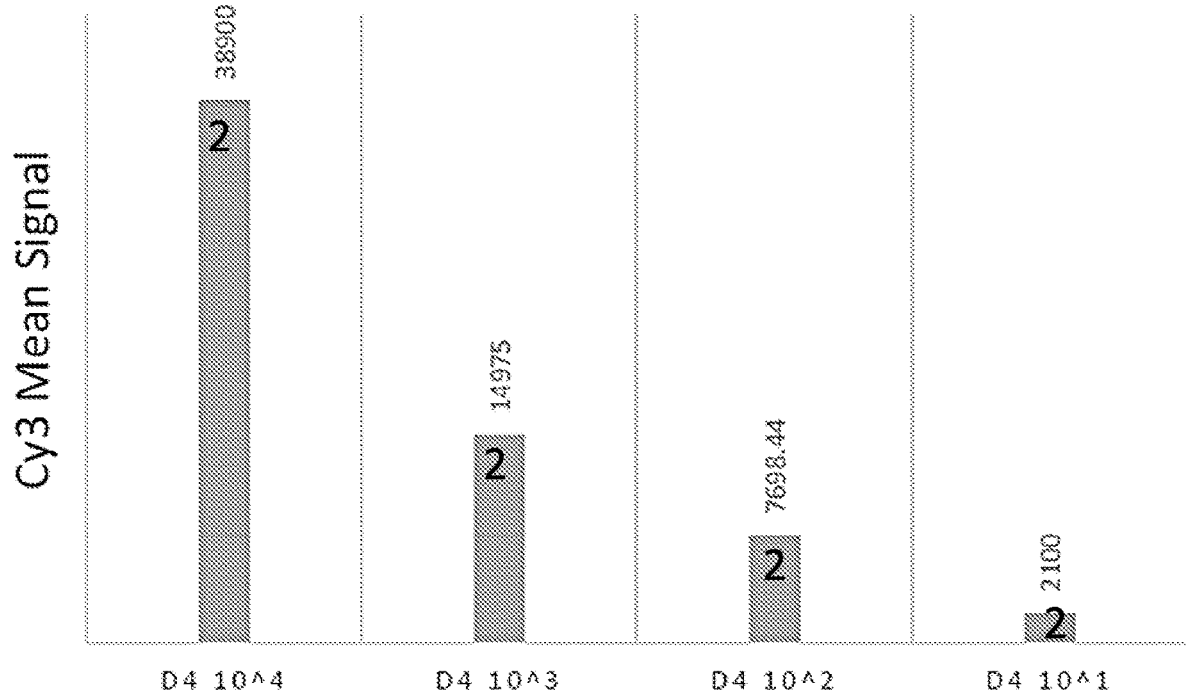

Microarray specificity: One of the challenges impacting the sensitivity of microarray based multi-pathogen nucleic acid detection in blood specimens is the relatively small concentration of target nucleic acids compared to a high background concentration of human DNA. A novel workflow was designed, combining two different applications (Agilent and Nugen), that had not been previously combined, to address this challenge. Typically, the Agilent amplification WT kit (Oligo dT) is used to amplify total RNA, with a minimum nucleic acid requirement of 25 nanograms, and produces a cRNA final product that is labelled with Cy3 fluorophore. The workflow was modified using a method that generates amplified cDNA from as little as 500 picograms of target viral RNA. One single-primer isothermal amplification using Nugen Ribo-SPIA technology was combined with the Agilent Genomic DNA Enzymatic Labeling Kit for generating Cy3 labeled cDNA. This kit was not previously developed for single color RNA probes and produces 300% the amplified product compared to the standard methodology (FIG. 1B, FIG. 2A). Nearly all samples were detected on the platform and all probes generated a strong signal specific for each positive plasma specimen analyzed. No specific signal was produced by negative control plasma (FIG. 2B). Random non-specific intensity signal was produced in only a few arrays. This indicated that the generation of cDNA instead of amplified RNA followed by Cy3 labelling and hybridization based on a DNA application was successful (FIG. 2C).

Analysis strategies: Quality of signals generated by probes for each species was assessed according to two experimental criteria: 1) defining a threshold able to distinguish a true signal from its background; and 2) defining true positives only when 50% of probes generated a signal above the set threshold. These two levels of data analysis were needed to detect positive probes in the presence of multi-pathogen testing at the same time and at different concentrations.

The threshold was defined as the log ratio between the signal intensity mean for each pathogen specific probe set and the mean of the Agilent control group probe set. After comparing the results of the same set of probes across different arrays and selecting the probes showing an inter-array reproducibility, an experimental threshold value was defined as follows: Log Ratio <1 negative; Log Ratio ≥1.0 to ≤1.5 borderline; Log Ratio ≥1.5 positive.

Data analysis at the individual probe level was also performed to assess if the tested samples were false positives. Only when at least 50% of specific probes had Log Ratio >1.5 was the test considered valid (FIG. 1C).

For nearly all borderline results, only 20-25% of the specific probes showed mean intensity in the correct range, so the test was defined negative. For positive results (Log Ratio >1.5) more than 50% of the specific probes set were in the correct range. One example was an HCV 1a positive plasma samples test that was detected by 110 out of 110 probes at a concentration of $10^5$ copies/mL, 90 out of 110 probes at a concentration of $10^4$ copies/mL, and 70 out of 110 probes at a concentration of $10^3$ copies/mL. On average, at $10^2$ copies/mL more than 50% of the probes were generating a fluorescence signal above the set threshold.

Data from more than 168 tested samples (one or multiple targets per array) showed consistent results. The mean of the probes specific for any positive plasma sample was always at least 10-fold higher than the mean of internal control probes (background), showing a wide probe population range of intensity. As shown in Table 4 and Table 5, the Log Ratio was above 1.5 for all the pathogens tested at a concentration of $10^2$ copies/mL and there were no cross reactions with other probes across the platform.

Microarray sensitivity: HAV, CHIKV, DENV1-4, HCV Genotypes 1a, 2b, and 3, HIV-1,2 and WNV strain NY99 had $10^2$ copies/mL limits of detection. The lowest detectable level for HEV was $10^4$ copies/mL. The analytical sensitivity for each assay was determined using a concentration range based on the clinical requirement for pathogen detection. There were no false negatives or false positives when testing the positive plasma. In the presence of very low pathogen concentrations, the log ratio was at the borderline level so the results were qualified according to double level analysis (at least 50% of the probes generated a fluorescence signal above the set threshold). In the presence of negative plasma samples, the log ratio value was always negative (Table 4).

A mix of different positive plasma samples at different concentrations was simultaneously tested in a single experiment. Four different combinations were generated. The multi-pathogens-mixes were composed of 8 (CHIKV, DEN3, DEN1, HAV, HCV1a, HEV, WNV and ZIKV), 4 (CHIKV, DEN1, ZKV, WNV), 4 (DENV3, HAV HCV1a HEV) and 3 (CHIKV, DEN1, ZIKV) different pathogens, respectively at a concentration range from $10^5$ to $10^3$ copies/mL. (Table 6).

TABLE 4

Test results based on Log ratio

|        | CK    | DEN1  | DEN2  | DEN3  | DEN4  | HAV   | HCV1a | HCV2a |
|--------|-------|-------|-------|-------|-------|-------|-------|-------|
| CK     | 2.42  | −1.15 | −1.22 | −0.04 | −0.28 | −0.50 | −0.24 | −0.35 |
| DEN1   | −0.12 | 1.60  | −0.33 | 0.09  | 0.14  | −0.08 | −0.20 | −0.31 |
| DEN2   | −0.24 | −0.82 | 1.84  | −0.30 | −0.25 | −0.24 | −0.17 | −0.28 |
| DEN3   | 0.03  | −0.19 | −0.02 | 1.62  | −0.24 | −0.28 | −0.24 | −0.34 |
| DEN4   | 0.07  | −0.31 | −0.64 | 0.18  | 1.80  | −0.64 | −0.17 | −0.28 |
| HAV    | −0.06 | −0.97 | −1.24 | −0.25 | −0.34 | 2.97  | −0.21 | −0.31 |
| HCV1   | 0.46  | −0.53 | −0.55 | 0.63  | 0.56  | 0.26  | 2.91  | 2.80  |
| HCV2   | 0.47  | −0.60 | −0.72 | 0.66  | 0.31  | 0.09  | 2.16  | 2.85  |
| HCV3   | 0.39  | −0.73 | −0.77 | 0.06  | 0.06  | −0.07 | 2.63  | 2.53  |
| HEV    | 0.41  | −0.62 | −0.63 | 0.23  | 0.35  | 1.06  | −0.14 | −0.24 |
| HIV1   | 0.96  | 0.55  | 0.08  | 0.77  | 0.56  | 0.01  | 0.05  | −0.06 |
| HIV2   | −0.13 | −0.90 | −0.94 | 0.02  | −0.29 | −0.07 | −0.09 | −0.20 |
| HTLVI  | −0.57 | −1.29 | −1.43 | −0.35 | −0.55 | −0.51 | −0.06 | −0.17 |
| HTLVII | −0.21 | −1.11 | −1.19 | −0.45 | −0.40 | −0.21 | 0.19  | 0.08  |
| WNV    | 0.10  | −0.50 | −0.70 | 0.21  | −0.34 | −0.33 | −0.19 | −0.29 |
| ZKV    | −0.29 | −0.64 | −0.92 | −0.49 | −0.41 | −0.45 | 0.12  | 0.26  |

|        | HCV3  | HEV   | HIV-1 | HIV-2 | HTLVI | HTLVII | WNV   | ZKV   | NC    |
|--------|-------|-------|-------|-------|-------|--------|-------|-------|-------|
| CK     | −0.56 | −0.02 | −0.99 | −0.68 | −0.42 | −0.96  | −0.97 | −0.20 | −0.96 |
| DEN1   | −0.52 | 0.46  | −0.76 | −0.55 | −0.28 | −0.76  | −0.53 | 0.00  | −0.86 |
| DEN2   | −0.49 | −0.11 | −1.13 | −0.89 | −0.52 | −0.84  | −1.00 | −0.28 | −1.01 |
| DEN3   | −0.55 | 0.01  | −0.95 | −0.81 | −0.56 | −0.91  | −0.22 | 0.05  | −0.96 |
| DEN4   | −0.49 | −0.20 | −1.02 | −0.80 | −0.66 | −1.05  | −0.30 | −0.36 | −1.07 |
| HAV    | −0.52 | 0.35  | −0.78 | −0.47 | −0.35 | −0.71  | −1.22 | −0.04 | −0.69 |
| HCV1   | 2.59  | 0.79  | −0.30 | 0.94  | 0.44  | −0.05  | −0.43 | 0.60  | −0.37 |
| HCV2   | 1.84  | 0.76  | −0.53 | 0.65  | −0.10 | −0.37  | −0.05 | 0.50  | −0.32 |
| HCV3   | 2.32  | 0.34  | −0.28 | 0.92  | 0.02  | −0.51  | −0.68 | 0.28  | −0.46 |
| HEV    | −0.45 | 1.89  | −0.31 | −0.17 | 0.10  | −0.04  | −0.51 | 0.54  | −0.39 |
| HIV1   | −0.27 | 1.07  | 1.89  | 0.46  | −0.22 | 0.06   | 0.13  | 0.92  | 0.23  |
| HIV2   | −0.41 | 0.23  | 0.91  | 1.68  | −0.07 | −0.44  | −0.75 | 0.09  | −0.66 |
| HTLVI  | −0.38 | −0.21 | −1.08 | −0.87 | 2.67  | 0.88   | −1.47 | −0.15 | −0.99 |
| HTLVII | −0.13 | −0.09 | −0.92 | −0.59 | 0.38  | 3.30   | −1.13 | −0.10 | −0.86 |
| WNV    | −0.51 | 0.25  | −0.62 | −0.52 | −0.40 | −0.64  | 2.24  | 0.00  | −0.82 |
| ZKV    | 0.32  | 0.68  | −0.96 | −0.68 | −0.52 | −0.78  | 0.16  | 2.07  | −0.83 |

CK, Chikungunya virus;
DEN, dengue;
HAV, hepatitis A virus;
HCV, hepatitis C virus;
HEV, hepatitis E virus;
HIV, human immunodeficiency virus;
HTLV, Human T-cell lymphotropic virus;
WNV, West Nile Virus;
ZKV, Zika Virus;
NC, negative control.

TABLE 5

Multi-pathogen mix test results based on Log ratio

|         | MPM1  | MPM2  | MPM3  | MPM4  |
|---------|-------|-------|-------|-------|
| CHIKV   | 3.42  | 3.37  | 0.24  | 2.25  |
| DEN1    | 3.14  | 3.10  | 1.80  | 2.45  |
| DEN2    | 1.11  | 1.10  | −0.23 | 0.35  |
| DEN3    | 2.72  | 1.19  | 3.00  | 0.51  |
| DEN4    | 1.31  | 1.19  | 0.83  | 0.59  |
| HAV     | 1.33  | 0.12  | 2.18  | −1.13 |
| HCV-1a  | 2.53  | 0.61  | 2.72  | −0.59 |
| HCV-2a  | 2.16  | 0.66  | 2.44  | −0.65 |
| HCV-3   | 2.45  | 0.65  | 2.60  | −0.72 |
| HEV     | 1.64  | 0.67  | 1.21  | −0.71 |
| HIV-1   | 1.05  | 1.24  | 1.11  | −0.36 |
| HIV-2   | 0.13  | 0.24  | 0.17  | −0.81 |
| HTLV-I  | −0.17 | 0.06  | −0.07 | −1.37 |
| HTLV-II | −0.02 | 0.12  | −0.09 | −1.07 |
| WNV     | 1.63  | 1.65  | 0.11  | −0.03 |
| ZKV     | 3.09  | 3.04  | 0.30  | 1.98  |

MPM1 = CHIKV, HAV, HCV-1a, HEV, DEN3, DEN1, ZKV, WNV
MPM2 = CHIKV, DEN1, ZKV, WNV
MPM3 = HAV, HEV, DEN3, HCV-1a
MPM4 = CHIKV, ZKV, DEN1

TABLE 6

Pathogen Chip performance based plasma panel test results

| Pathogen    | Copies/mL | pos/total | qPCR Validation |
|-------------|-----------|-----------|-----------------|
| Chikungunya | $10^3$    | 1/1       | Y               |
| Chikungunya | $10^2$    | 4/4       | Y               |
| Dengue1     | $10^3$    | 3/3       | Y               |
| Dengue1     | $10^2$    | 2/2       | Y               |
| Dengue1     | $10^1$    | 0/1       | Y               |
| Dengue2     | $10^3$    | 3/3       | Y               |
| Dengue2     | $10^2$    | 3/3       | Y               |
| Dengue2     | $10^1$    | 0/1       | Y               |
| Dengue3     | $10^3$    | 3/3       | Y               |
| Dengue3     | $10^2$    | 3/3       | Y               |
| Dengue3     | $10^1$    | 0/1       | Y               |
| Dengue4     | $10^3$    | 3/3       | Y               |
| Dengue4     | $10^2$    | 3/3       | Y               |
| Dengue4     | $10^1$    | 0/1       | Y               |
| HAV         | $10^3$    | 2/2       | Y               |
| HAV         | $10^2$    | 2/2       | Y               |
| HCV-1a      | $10^3$    | 3/3       | Y               |
| HCV-1a      | $10^2$    | 3/3       | Y               |
| HCV-2a      | $10^2$    | 2/2       | Y               |
| HCV-3       | $10^2$    | 2/2       | Y               |
| HEV         | $10^4$    | 3/3       | Y               |

TABLE 6-continued

Pathogen Chip performance based plasma panel test results

| Pathogen | Copies/mL | pos/total | qPCR Validation |
|---|---|---|---|
| HEV | 10^3 | 0/2 | Y |
| HEV | 10^2 | 0/2 | NA |
| HIV-1 | 10^3 | 2/2 | y |
| HIV-1 | 10^2 | 2/2 | y |
| HIV-2 | 10^3 | 3/3 | y |
| HIV-2 | 10^2 | 3/3 | y |
| HTLV-I | 10^3 | 2/2 | y |
| HTLV-I | 10^2 | 2/2 | y |
| HTLV-II | 10^3 | 2/2 | y |
| HTLV-II | 10^2 | 2/2 | y |
| WNV (NY99) | 10^5 | 1/1 | y |
| WNV (NY99) | 10^4 | 1/1 | y |
| WNV (NY99) | 10^3 | 3/3 | y |
| WNV (NY99) | 10^2 | 4/4 | y |
| WNV (NY99) | 10^1 | 0/2 | NA |
| ZIKA PRVABC60 | 10^3 | 3/3 | Y |
| ZIKA PRVABC61 | 10^2 | 3/3 | Y |
| ZIKA PRVABC62 | 10^1 | 0/2 | Y |
| ZIKV FSS13025 | 10^3 | 3/3 | Y |
| ZIKV FSS13025 | 10^2 | 3/3 | Y |
| ZIKV FSS13025 | 10^1 | 0/2 | Y |
| MPM1 | 10^5-10^3 | 3/3 | y |
| MPM2 | 10^5-10^3 | 3/3 | y |
| MPM3 | 10^5-10^3 | 3/3 | y |
| MPM4 | 10^5-10^3 | 3/3 | y |

NA = not applicable

Among the 99 positive samples tested at a concentration ranking from $10^5$ to $10^2$ copies/mL, 92 out 92 samples were correctly detected. Only HEV testing resulted correct detection in 3 out of 7 positive samples (42%) at a final concentration of $10^4$ copies/mL. No specific signal was detected below this value. There were 21 positive samples that were not detected because the concentration was below the limit of detection of the platform (<$10^2$ copies/mL). In all four mix combinations all pathogens were detected without interference among the targets.

All of the samples tested (single or multiple pathogens at the same time) were performed at least 3 times each, with at least a week interval between the experiments, in order to test the reproducibility of the results. The consistency of positive results across the different arrays confirmed that the array design together with the double level analysis model performed well.

Validation of the limit of microarray data by RT-qPCR: Microarray-based pathogen chip results were confirmed by RT-qPCR of the RNA aliquots used for testing. All positive results were confirmed and the copy numbers for each pathogen were calculated to define the limit of the detection for each species on the array (Table 7).

TABLE 7

Validation of Pathogen Chip detection results

| Virus | Pathogen Chip Results | qPCR Ct Value | Virus Copy No. |
|---|---|---|---|
| CHIKV | POS | 26.9 | $3.1 \times 10^3$ |
| CHIKV | POS | 31.6 | $1.4 \times 10^2$ |
| CHIKV | POS | 31.5 | $1.6 \times 10^2$ |
| CHIKV | POS | 29.4 | $6.3 \times 10^2$ |
| CHIKV | POS | 29.7 | $5.8 \times 10^2$ |
| DENGUE-1 | POS | 31.1 | $2.3 \times 10^3$ |
| DENGUE-1 | POS | 34.4 | $3.0 \times 10^2$ |
| DENGUE-1 | NEG | 38.7 | 41 |
| DENGUE-2 | POS | 29.1 | $8.4 \times 10^3$ |
| DENGUE-2 | POS | 35.9 | $1.2 \times 10^2$ |
| DENGUE-2 | NEG | 38.9 | 18 |
| DENGUE-3 | POS | 29.3 | $7.1 \times 10^3$ |
| DENGUE-3 | POS | 32.7 | $8.4 \times 10^2$ |
| DENGUE-3 | NEG | 37.3 | 31 |
| DENGUE-4 | POS | 30.3 | $3.3 \times 10^3$ |
| DENGUE-4 | POS | 34.2 | $2.6 \times 10^2$ |
| DENGUE-4 | NEG | 37.0 | 79 |
| HAV | POS | 28.4 | $3.2 \times 10^3$ |
| HAV | POS | 39.1 | $2.8 \times 10^3$ |
| HAV | POS | 29.2 | $8.2 \times 10^2$ |
| HAV | POS | 32.2 | $1.2 \times 10^2$ |
| HCV-1a | POS | 26.2 | $4.1 \times 10^3$ |
| HCV-1a | POS | 31.4 | $1.6 \times 10^2$ |
| HCV-2a | POS | 27.4 | $3.8 \times 10^3$ |
| HCV-2a | POS | 32.1 | $1.8 \times 10^2$ |
| HCV-3 | POS | 33.1 | $1.4 \times 10^2$ |
| HEV | POS | 25.4 | $1.9 \times 10^4$ |
| HEV | NEG | 28.4 | $1.8 \times 10^3$ |
| HIV-1 | POS | 27.3 | $4.6 \times 10^3$ |
| HIV-1 | POS | 32.8 | $1.6 \times 10^2$ |
| HIV-2 | POS | 27.4 | $4.3 \times 10^3$ |
| HIV-2 | POS | 30.7 | $1.8 \times 10^2$ |
| HTLV-I | POS | 28.7 | $3.9 \times 10^3$ |
| HTLV-I | POS | 28.3 | $2.9 \times 10^2$ |
| HTLV-II | POS | 25.574 | $2.7 \times 10^3$ |
| HTLV-II | POS | 29.289 | $2.4 \times 10^2$ |
| WNV (NY99) | POS | 21.5 | $1.9 \times 10^5$ |
| WNV (NY99) | POS | 24.5 | $1.5 \times 10^4$ |
| WNV (NY99) | POS | 27.6 | $2.1 \times 10^3$ |
| WNV (NY99) | POS | 31.4 | $1.0 \times 10^2$ |
| ZIKA PRVABC60 | POS | 26.2 | $1.5 \times 10^3$ |
| ZIKA PRVABC60 | POS | 30.1 | $1.2 \times 10^2$ |
| ZIKA PRVABC60 | NEG | 31.8 | 41 |
| ZIKA FSS13025 | POS | 25.3 | $2.4 \times 10^3$ |
| ZIKA FSS13025 | POS | 29.1 | $1.3 \times 10^2$ |
| ZIKA FSS13025 | NEG | 33.0 | 17 |

Example 3

Microarray for Detection of DNA Viruses, Bacteria, and Protozoan Pathogens

A microarray for DNA viruses, bacteria, and protozoan pathogens was developed. The design included multiple gene targets for each pathogen genome in order to select the best probes for the final platform design. The design strategy was to choose the probes with the best "scores" (homology, thermodynamics, secondary structure and sequence complexity) balancing the cross-hybridization with the host genome and with other pathogens' genomes. The second design strategy was to balance the number of probes for each pathogen with a final count of 50-110 probes each. Probes selected in the final design generated a more intense signal and produced higher percentage coverage of the specific genome across the different experiments.

The final design was supplemented with predesigned DNA array probes (577 control probes, 225 replicates, and 11,620 backbone) specific for the reagents and the assay performance. These are used specifically for image orientation, to assess whether the samples are labeled, for the orientation of the platform during the scan process, and for measuring on element background. These probes form a hairpin and do not hybridize well with labeled sample of any species. In addition, 312 probes specific for three human housekeeping genes (ACTB, ARL1, CCDN1) and 109 probes specific for one Mosquito-specific virus and two plant viruses (Aedes albopictus densovirus 2, Maize streak virus, Tomato pseudo-curly top virus) were added to the design.

The microarray includes probes for cytomegalovirus (CMV; also known as HHV-5), Epstein Barr virus (EBV; also known as HHV-4), human herpesvirus 8 (HHV-8), human papilloma virus (HPV) type 6b HPV6, HPV11, HPV 16, HPV 17, hepatitis B virus (HBV) subtype adw, HBV subtype ayw, HBV subtype adr, HBV subtype ayr, and human parvovirus B19. Exemplary probes provided in Table 8 and include SEQ ID NOs: 1770-1852 (CMV), SEQ ID NOs: 1853-1917 (EBV B95-8), SEQ ID NOs: 1918-2023 (EBV AG876), SEQ ID NOs: 2024-2108 (HHV-8), SEQ ID NOs: 2109-2192 (HPV 6b), SEQ ID NOs: 2193-2271 (HPV 11), SEQ ID NOs: 2272-2342 (HPV 16), SEQ ID NOs: 2343-2419 (HPV 18), SEQ ID NOs: 2420-2470 (HBV subtype adw), SEQ ID NOs: 2471-2520 (HBV subtype ayw), SEQ ID NOs: 2521-2556 (HBV subtype adr), SEQ ID NOs: 2557-2602 (HBV subtype ayr), and SEQ ID NOs: 2603-2647 (human parvovirus B19).

The microarray also includes probes for *Treponema pallidum*, *Ehrlichia chaffeensis*, *Ehrlichia ewingii*, *Ehrlichia muris*, *Borrelia burgdorferi*, *Coxiella burnetii*, *Trypanosoma brucei*, *Trypanosoma cruzi*, *Leishmania major*, *Babesia microti*, *Plasmodium falciparum*, and *Plasmodium vivax*. Exemplary probes provided in Table 9 and include SEQ ID NOs: 2648-2751 (*Treponema pallidum*), SEQ ID NOs: 2752-2852 (*Ehrlichia chaffeensis*), SEQ ID NOs: 2853-2861 (*Ehrlichia ewingii*), SEQ ID NOs: 2862-2922 (*Ehrlichia muris*), SEQ ID NOs: 2923-3001 (*Borrelia burgdorferi*), SEQ ID NOs: 3002-3085 (*Coxiella burnetii*), SEQ ID NOs: 3086-3097 (*Trypanosoma brucei*), SEQ ID NO: 3098 (*Trypanosoma cruzi*), SEQ ID NOs: 3099-3113 (*Leishmania major*), SEQ ID NOs: 3114-3154 (*Babesia microti*), SEQ ID NOs: 3155-3185 (*Plasmodium falciparum*), and SEQ ID NOs: 3186-3207 (*Plasmodium vivax*).

Finally, the microarray includes housekeeping and negative control probes (Table 10). Exemplary probes include SEQ ID NOs: 3208-3301 (housekeeping gene ACTB), SEQ ID NOs: 3302-3385 (housekeeping gene ARL1), SEQ ID NOs: 3386-3519 (housekeeping gene CCDN1), SEQ ID NOs: 3520-3557 (*Aedes albopictus* densovirus 2), SEQ ID NO: 3558-3598 (Maize streak virus), and SEQ ID NOs: 3599-3628 (Tomato pseudo-curly top virus).

For sample analysis, viral DNA from plasma specimens was extracted with the Invitrogen Dynabeads™ SILANE viral NA kit. The kit is designed for highly predictable and consistent isolation of viral nucleic acids. Beads and buffers are optimized for sensitive isolation of viral DNA. DNA from bacteria and protozoans was extracted from whole blood with the QIAamp® DNA Blood Mini kit (Qiagen) according to the manufacturer's protocol.

SureTag® Labeling Kit (Agilent technology) was used to enzymatically label DNA from plasma and blood. A modified protocol was developed and optimized for efficient sample fragmentation, enzymatic labeling, and clean up. A master mix containing 10×aCGH blocking agent and 2×HI-RPM hybridization buffer, was added to 2.5-3 µg of labeled DNA, denatured, and hybridized to arrays under 8-chamber gasket slides at 67° C. with 20-rpm rotation for 24 hours in an Agilent hybridization oven. Arrays were processed using wash procedure A and scanned on an Agilent SureScan® G4900DA microarray scanner using 5-µm resolution.

CMV, *Trypanosoma*, Parvovirus B19, HBV, EBV (HHV-4), *Treponema*, *Babesia*, *Leishmania*, *Coxiella*, *Borrelia*, Papilloma Virus (HPV 6, 11, 16, 18), and *P. falciparum* had $10^4$-$10^3$ copies/mL limits of detection. There were no false negatives or false positives when testing the positive plasma. All the results were confirmed by RT-qPCR of the DNA aliquots used for testing. All positive results were confirmed and the copy numbers for each pathogen were calculated to define the limit of the detection for each species on the array.

TABLE 8

Exemplary DNA virus probes

| ProbeID | Start | End | SEQ ID NO: | Virus | Genomic Region | Product |
|---|---|---|---|---|---|---|
| CUST_P10000630 | 45812 | 45860 | 1770 | CMV (HHV-5) Cytomegalovirus | UL34 | protein |
| CUST_P10000631 | 45872 | 45916 | 1771 | CMV (HHV-5) Cytomegalovirus | UL34 | protein |
| CUST_P10000638 | 46336 | 46384 | 1772 | CMV (HHV-5) Cytomegalovirus | UL34 | protein |
| CUST_P10001082 | 78547 | 78591 | 1773 | CMV (HHV-5) Cytomegalovirus | UL54 | DNA rep |
| CUST_P10001099 | 79469 | 79514 | 1774 | CMV (HHV-5) Cytomegalovirus | UL54 | DNA rep |
| CUST_P10001109 | 80183 | 80227 | 1775 | CMV (HHV-5) Cytomegalovirus | UL54 | DNA rep |
| CUST_P10001111 | 80253 | 80301 | 1776 | CMV (HHV-5) Cytomegalovirus | UL54 | DNA rep |
| CUST_P10001120 | 80933 | 80979 | 1777 | CMV (HHV-5) Cytomegalovirus | UL54 | DNA rep |
| CUST_P10001123 | 81072 | 81116 | 1778 | CMV (HHV-5) Cytomegalovirus | UL54 | DNA rep |
| CUST_P10001126 | 81245 | 81289 | 1779 | CMV (HHV-5) Cytomegalovirus | UL54 | DNA rep |
| CUST_P10001131 | 81599 | 81643 | 1780 | CMV (HHV-5) Cytomegalovirus | UL54 | DNA rep |
| CUST_P10001132 | 81738 | 81782 | 1781 | CMV (HHV-5) Cytomegalovirus | UL54 | DNA rep |
| CUST_P10001140 | 82327 | 82375 | 1782 | CMV (HHV-5) Cytomegalovirus | UL55 | envelop |
| CUST_P10001146 | 82856 | 82901 | 1783 | CMV (HHV-5) Cytomegalovirus | UL55 | envelop |
| CUST_P10001152 | 83347 | 83399 | 1784 | CMV (HHV-5) Cytomegalovirus | UL55 | envelop |
| CUST_P10001154 | 83475 | 83525 | 1785 | CMV (HHV-5) Cytomegalovirus | UL55 | envelop |
| CUST_P10001155 | 83645 | 83701 | 1786 | CMV (HHV-5) Cytomegalovirus | UL55 | envelop |
| CUST_P10001156 | 83677 | 83724 | 1787 | CMV (HHV-5) Cytomegalovirus | UL55 | envelop |
| CUST_P10001158 | 83744 | 83797 | 1788 | CMV (HHV-5) Cytomegalovirus | UL55 | envelop |
| CUST_P10001160 | 83961 | 84012 | 1789 | CMV (HHV-5) Cytomegalovirus | UL55 | envelop |
| CUST_P10001161 | 83993 | 84052 | 1790 | CMV (HHV-5) Cytomegalovirus | UL55 | envelop |
| CUST_P10001162 | 84021 | 84073 | 1791 | CMV (HHV-5) Cytomegalovirus | UL55 | envelop |
| CUST_P10001164 | 84223 | 84275 | 1792 | CMV (HHV-5) Cytomegalovirus | UL55 | envelop |
| CUST_P10001165 | 84398 | 84442 | 1793 | CMV (HHV-5) Cytomegalovirus | UL55 | envelop |
| CUST_P10001169 | 84665 | 84716 | 1794 | CMV (HHV-5) Cytomegalovirus | UL55 | envelop |
| CUST_P10001175 | 85014 | 85071 | 1795 | CMV (HHV-5) Cytomegalovirus | UL56 | encapsi |
| CUST_P10001177 | 85085 | 85132 | 1796 | CMV (HHV-5) Cytomegalovirus | UL56 | encapsi |
| CUST_P10001179 | 85221 | 85272 | 1797 | CMV (HHV-5) Cytomegalovirus | UL56 | encapsi |
| CUST_P10001183 | 85645 | 85693 | 1798 | CMV (HHV-5) Cytomegalovirus | UL56 | encapsi |
| CUST_P10001189 | 86404 | 86461 | 1799 | CMV (HHV-5) Cytomegalovirus | UL56 | encapsi |

TABLE 8-continued

Exemplary DNA virus probes

| ProbeID | Start | End | SEQ ID NO: | Virus | Genomic Region | Product |
|---|---|---|---|---|---|---|
| CUST_P10001198 | 87249 | 87308 | 1800 | CMV (HHV-5) Cytomegalovirus | UL56 | encapsi |
| CUST_P10001603 | 117602 | 117650 | 1801 | CMV (HHV-5) Cytomegalovirus | UL80 | capsid |
| CUST_P10001618 | 118112 | 118156 | 1802 | CMV (HHV-5) Cytomegalovirus | UL80 | capsid |
| CUST_P10001622 | 118567 | 118615 | 1803 | CMV (HHV-5) Cytomegalovirus | UL80 | capsid |
| CUST_P10001664 | 121437 | 121483 | 1804 | CMV (HHV-5) Cytomegalovirus | UL83 | tegumen |
| CUST_P10001665 | 121470 | 121522 | 1805 | CMV (HHV-5) Cytomegalovirus | UL83 | tegumen |
| CUST_P10001666 | 121493 | 121543 | 1806 | CMV (HHV-5) Cytomegalovirus | UL83 | tegumen |
| CUST_P10001675 | 122579 | 122623 | 1807 | CMV (HHV-5) Cytomegalovirus | UL83 | tegumen |
| CUST_P10001945 | 141984 | 142028 | 1808 | CMV (HHV-5) Cytomegalovirus | UL97 | core |
| CUST_P10001948 | 142100 | 142144 | 1809 | CMV (HHV-5) Cytomegalovirus | UL97 | core |
| CUST_P10001960 | 142742 | 142789 | 1810 | CMV (HHV-5) Cytomegalovirus | UL97 | core |
| CUST_P10001965 | 143122 | 143180 | 1811 | CMV (HHV-5) Cytomegalovirus | UL97 | core |
| CUST_P10001966 | 143159 | 143203 | 1812 | CMV (HHV-5) Cytomegalovirus | UL97 | core |
| CUST_P10002353 | 170852 | 170896 | 1813 | CMV (HHV-5) Cytomegalovirus | UL122 | Beta Ge |
| CUST_P10002359 | 171207 | 171256 | 1814 | CMV (HHV-5) Cytomegalovirus | UL122 | Beta Ge |
| CUST_P10002362 | 171393 | 171444 | 1815 | CMV (HHV-5) Cytomegalovirus | UL122 | Beta Ge |
| CUST_P10002371 | 171811 | 171858 | 1816 | CMV (HHV-5) Cytomegalovirus | UL122 | Beta Ge |
| CUST_P10002377 | 172241 | 172300 | 1817 | CMV (HHV-5) Cytomegalovirus | UL122 | Beta Ge |
| CUST_P10002378 | 172286 | 172345 | 1818 | CMV (HHV-5) Cytomegalovirus | UL122 | Beta Ge |
| CUST_P10002379 | 172307 | 172366 | 1819 | CMV (HHV-5) Cytomegalovirus | UL122 | Beta Ge |
| CUST_P10002381 | 172506 | 172559 | 1820 | CMV (HHV-5) Cytomegalovirus | UL122 | Beta Ge |
| CUST_P10002382 | 172633 | 172678 | 1821 | CMV (HHV-5) Cytomegalovirus | UL122 | Beta Ge |
| CUST_P10002384 | 172987 | 173046 | 1822 | CMV (HHV-5) Cytomegalovirus | UL122 | Beta Ge |
| CUST_P10002385 | 173023 | 173082 | 1823 | CMV (HHV-5) Cytomegalovirus | UL122 | Beta Ge |
| CUST_P10002386 | 173044 | 173097 | 1824 | CMV (HHV-5) Cytomegalovirus | UL122 | Beta Ge |
| CUST_P10002389 | 173134 | 173193 | 1825 | CMV (HHV-5) Cytomegalovirus | UL122 | Beta Ge |
| CUST_P10002390 | 173156 | 173215 | 1826 | CMV (HHV-5) Cytomegalovirus | UL122 | Beta Ge |
| CUST_P10002391 | 173191 | 173239 | 1827 | CMV (HHV-5) Cytomegalovirus | UL122 | Beta Ge |
| CUST_P10002392 | 173374 | 173433 | 1828 | CMV (HHV-5) Cytomegalovirus | UL122 | Beta Ge |
| CUST_P10002393 | 173395 | 173454 | 1829 | CMV (HHV-5) Cytomegalovirus | UL122 | Beta Ge |
| CUST_P10002394 | 173432 | 173489 | 1830 | CMV (HHV-5) Cytomegalovirus | UL122 | Beta Ge |
| CUST_P10002395 | 173456 | 173514 | 1831 | CMV (HHV-5) Cytomegalovirus | UL122 | Beta Ge |
| CUST_P10002396 | 173503 | 173553 | 1832 | CMV (HHV-5) Cytomegalovirus | UL122 | Beta Ge |
| CUST_P10002397 | 173520 | 173579 | 1833 | CMV (HHV-5) Cytomegalovirus | UL122 | Beta Ge |
| CUST_P10002398 | 173555 | 173613 | 1834 | CMV (HHV-5) Cytomegalovirus | UL122 | Beta Ge |
| CUST_P10002399 | 173596 | 173649 | 1835 | CMV (HHV-5) Cytomegalovirus | UL122 | Beta Ge |
| CUST_P10002400 | 173621 | 173679 | 1836 | CMV (HHV-5) Cytomegalovirus | UL122 | Beta Ge |
| CUST_P10002401 | 173674 | 173731 | 1837 | CMV (HHV-5) Cytomegalovirus | UL122 | Beta Ge |
| CUST_P10002402 | 173693 | 173746 | 1838 | CMV (HHV-5) Cytomegalovirus | UL122 | Beta Ge |
| CUST_P10002403 | 173735 | 173780 | 1839 | CMV (HHV-5) Cytomegalovirus | UL122 | Beta Ge |
| CUST_P10002404 | 173766 | 173812 | 1840 | CMV (HHV-5) Cytomegalovirus | UL122 | Beta Ge |
| CUST_P10002406 | 174051 | 174095 | 1841 | CMV (HHV-5) Cytomegalovirus | UL122 | Beta Ge |
| CUST_P10002407 | 174065 | 174109 | 1842 | CMV (HHV-5) Cytomegalovirus | UL123 | Prot E |
| CUST_P10002408 | 174215 | 174259 | 1843 | CMV (HHV-5) Cytomegalovirus | UL123 | Prot E |
| CUST_P10002411 | 174671 | 174726 | 1844 | CMV (HHV-5) Cytomegalovirus | UL124 | Prot E |
| CUST_P10002466 | 178473 | 178527 | 1845 | CMV (HHV-5) Cytomegalovirus | UL132 | Glyco |
| CUST_P10002470 | 178801 | 178851 | 1846 | CMV (HHV-5) Cytomegalovirus | UL132 | Glyco |
| CUST_P10002471 | 178825 | 178870 | 1847 | CMV (HHV-5) Cytomegalovirus | UL132 | Glyco |
| CUST_P10002474 | 178926 | 178974 | 1848 | CMV (HHV-5) Cytomegalovirus | UL132 | Glyco |
| CUST_P10002475 | 178954 | 179000 | 1849 | CMV (HHV-5) Cytomegalovirus | UL132 | Glyco |
| CUST_P10002927 | 211545 | 211592 | 1850 | CMV (HHV-5) Cytomegalovirus | US17 | protein |
| CUST_P10002930 | 211944 | 211988 | 1851 | CMV (HHV-5) Cytomegalovirus | US17 | protein |
| CUST_P10002934 | 212083 | 212127 | 1852 | CMV (HHV-5) Cytomegalovirus | US17 | protein |
| CUST_P10003273 | 1 | 60 | 1853 | Human herpesvirus 4 (EBV), B95-8 | LMP-2A | transmembrane protein |
| CUST_P10003278 | 444 | 503 | 1854 | Human herpesvirus 4 (EBV), B95-8 | LMP-2A | transmembrane protein |
| CUST_P10003289 | 1435 | 1487 | 1855 | Human herpesvirus 4 (EBV), B95-8 | LMP-2A | transmembrane protein |
| CUST_P10003301 | 2062 | 2106 | 1856 | Human herpesvirus 4 (EBV), B95-8 | BNFR1 | tegument protein |
| CUST_P10003303 | 2221 | 2265 | 1857 | Human herpesvirus 4 (EBV), B95-8 | BNFR1 | tegument protein |
| CUST_P10003307 | 2620 | 2664 | 1858 | Human herpesvirus 4 (EBV), B95-8 | BNFR1 | tegument protein |
| CUST_P10003313 | 3104 | 3148 | 1859 | Human herpesvirus 4 (EBV), B95-8 | BNFR1 | tegument protein |
| CUST_P10003322 | 3928 | 3972 | 1860 | Human herpesvirus 4 (EBV), B95-8 | BNFR1 | tegument protein |
| CUST_P10003342 | 5201 | 5245 | 1861 | Human herpesvirus 4 (EBV), B95-8 | BNFR1 | tegument protein |
| CUST_P10003349 | 5834 | 5893 | 1862 | Human herpesvirus 4 (EBV), B95-8 | BNFR1 | tegument protein |
| CUST_P10003351 | 5931 | 5985 | 1863 | Human herpesvirus 4 (EBV), B95-8 | EBNA-1 | Nuclear antigen |

TABLE 8-continued

Exemplary DNA virus probes

| ProbeID | Start | End | SEQ ID NO: | Virus | Genomic Region | Product |
|---|---|---|---|---|---|---|
| CUST_P10003352 | 6010 | 6069 | 1864 | Human herpesvirus 4 (EBV), B95-8 | EBNA-1 | Nuclear antigen |
| CUST_P10003367 | 7289 | 7347 | 1865 | Human herpesvirus 4 (EBV), B95-8 | EBNA-1 | Nuclear antigen |
| CUST_P10003369 | 7409 | 7468 | 1866 | Human herpesvirus 4 (EBV), B95-8 | EBNA-1 | Nuclear antigen |
| CUST_P10003372 | 7520 | 7579 | 1867 | Human herpesvirus 4 (EBV), B95-8 | EBNA-1 | Nuclear antigen |
| CUST_P10003375 | 7605 | 7664 | 1868 | Human herpesvirus 4 (EBV), B95-8 | EBNA-1 | Nuclear antigen |
| CUST_P10003376 | 7635 | 7694 | 1869 | Human herpesvirus 4 (EBV), B95-8 | EBNA-1 | Nuclear antigen |
| CUST_P10003377 | 7706 | 7765 | 1870 | Human herpesvirus 4 (EBV), B95-8 | EBNA-1 | Nuclear antigen |
| CUST_P10003378 | 7731 | 7790 | 1871 | Human herpesvirus 4 (EBV), B95-8 | EBNA-1 | Nuclear antigen |
| CUST_P10003379 | 7786 | 7845 | 1872 | Human herpesvirus 4 (EBV), B95-8 | EBNA-1 | Nuclear antigen |
| CUST_P10003380 | 7821 | 7880 | 1873 | Human herpesvirus 4 (EBV), B95-8 | EBNA-1 | Nuclear antigen |
| CUST_P10003381 | 7871 | 7930 | 1874 | Human herpesvirus 4 (EBV), B95-8 | EBNA-1 | Nuclear antigen |
| CUST_P10003382 | 7901 | 7960 | 1875 | Human herpesvirus 4 (EBV), B95-8 | EBNA-1 | Nuclear antigen |
| CUST_P10003383 | 7941 | 8000 | 1876 | Human herpesvirus 4 (EBV), B95-8 | EBNA-1 | Nuclear antigen |
| CUST_P10003384 | 8000 | 8051 | 1877 | Human herpesvirus 4 (EBV), B95-8 | EBNA-1 | Nuclear antigen |
| CUST_P10003390 | 8236 | 8291 | 1878 | Human herpesvirus 4 (EBV), B95-8 | EBNA-1 | Nuclear antigen |
| CUST_P10003398 | 8631 | 8690 | 1879 | Human herpesvirus 4 (EBV), B95-8 | EBNA-1 | Nuclear antigen |
| CUST_P10003399 | 8659 | 8716 | 1880 | Human herpesvirus 4 (EBV), B95-8 | EBNA-1 | Nuclear antigen |
| CUST_P10003400 | 8690 | 8737 | 1881 | Human herpesvirus 4 (EBV), B95-8 | EBNA-1 | Nuclear antigen |
| CUST_P10003404 | 9006 | 9063 | 1882 | Human herpesvirus 4 (EBV), B95-8 | EBNA-1 | Nuclear antigen |
| CUST_P10003405 | 9052 | 9111 | 1883 | Human herpesvirus 4 (EBV), B95-8 | EBNA-1 | Nuclear antigen |
| CUST_P10003406 | 9110 | 9166 | 1884 | Human herpesvirus 4 (EBV), B95-8 | EBNA-1 | Nuclear antigen |
| CUST_P10003408 | 9301 | 9350 | 1885 | Human herpesvirus 4 (EBV), B95-8 | EBNA-1 | Nuclear antigen |
| CUST_P10003409 | 9349 | 9399 | 1886 | Human herpesvirus 4 (EBV), B95-8 | EBNA-1 | Nuclear antigen |
| CUST_P10003412 | 9759 | 9811 | 1887 | Human herpesvirus 4 (EBV), B95-8 | EBNA-1 | Nuclear antigen |
| CUST_P10003413 | 9788 | 9841 | 1888 | Human herpesvirus 4 (EBV), B95-8 | EBNA-1 | Nuclear antigen |
| CUST_P10003418 | 9961 | 10012 | 1889 | Human herpesvirus 4 (EBV), B95-8 | EBNA-1 | Nuclear antigen |
| CUST_P10003427 | 10915 | 10966 | 1890 | Human herpesvirus 4 (EBV), B95-8 | EBNA-1 | Nuclear antigen |
| CUST_P10003429 | 10994 | 11046 | 1891 | Human herpesvirus 4 (EBV), B95-8 | EBNA-1 | Nuclear antigen |
| CUST_P10003432 | 11304 | 11362 | 1892 | Human herpesvirus 4 (EBV), B95-8 | EBNA-1 | Nuclear antigen |
| CUST_P10003721 | 35383 | 35442 | 1893 | Human herpesvirus 4 (EBV), B95-8 | EBNA-1 | Nuclear antigen |
| CUST_P10003725 | 35654 | 35708 | 1894 | Human herpesvirus 4 (EBV), B95-8 | EBNA-1 | Nuclear antigen |
| CUST_P10005257 | 152676 | 152720 | 1895 | Human herpesvirus 4 (EBV), B95-8 | BALF5 | Binding Protein |
| CUST_P10005266 | 153637 | 153681 | 1896 | Human herpesvirus 4 (EBV), B95-8 | BALF5 | Binding Protein |
| CUST_P10005267 | 153658 | 153702 | 1897 | Human herpesvirus 4 (EBV), B95-8 | BALF5 | Binding Protein |
| CUST_P10005275 | 154346 | 154393 | 1898 | Human herpesvirus 4 (EBV), B95-8 | BALF5 | Binding Protein |
| CUST_P10005279 | 154462 | 154516 | 1899 | Human herpesvirus 4 (EBV), B95-8 | BALF5 | Binding Protein |
| CUST_P10005291 | 155318 | 155362 | 1900 | Human herpesvirus 4 (EBV), B95-8 | BALF5 | Binding Protein |

TABLE 8-continued

Exemplary DNA virus probes

| ProbeID | Start | End | SEQ ID NO: | Virus | Genomic Region | Product |
|---|---|---|---|---|---|---|
| CUST_P10005293 | 155583 | 155627 | 1901 | Human herpesvirus 4 (EBV), B95-8 | BALF5 | Binding Protein |
| CUST_P10005300 | 155914 | 155958 | 1902 | Human herpesvirus 4 (EBV), B95-8 | BALF5 | Binding Protein |
| CUST_P10005304 | 156254 | 156306 | 1903 | Human herpesvirus 4 (EBV), B95-8 | BALF5 | Binding Protein |
| CUST_P10005325 | 157914 | 157963 | 1904 | Human herpesvirus 4 (EBV), B95-8 | BALF4 | Binding Protein |
| CUST_P10005327 | 158072 | 158121 | 1905 | Human herpesvirus 4 (EBV), B95-8 | BALF4 | Binding Protein |
| CUST_P10005329 | 158133 | 158183 | 1906 | Human herpesvirus 4 (EBV), B95-8 | BALF4 | Binding Protein |
| CUST_P10005332 | 158230 | 158286 | 1907 | Human herpesvirus 4 (EBV), B95-8 | BALF4 | Binding Protein |
| CUST_P10005334 | 158408 | 158453 | 1908 | Human herpesvirus 4 (EBV), B95-8 | BALF4 | Binding Protein |
| CUST_P10005335 | 158572 | 158625 | 1909 | Human herpesvirus 4 (EBV), B95-8 | BALF4 | Binding Protein |
| CUST_P10005336 | 158595 | 158644 | 1910 | Human herpesvirus 4 (EBV), B95-8 | BALF4 | Binding Protein |
| CUST_P10005340 | 158865 | 158916 | 1911 | Human herpesvirus 4 (EBV), B95-8 | BALF4 | Binding Protein |
| CUST_P10005355 | 160486 | 160545 | 1912 | Human herpesvirus 4 (EBV), B95-8 | BALF4 | Binding Protein |
| CUST_P10005356 | 160515 | 160574 | 1913 | Human herpesvirus 4 (EBV), B95-8 | BALF3 | Binding Protein |
| CUST_P10005367 | 161267 | 161318 | 1914 | Human herpesvirus 4 (EBV), B95-8 | BALF3 | Binding Protein |
| CUST_P10005380 | 162040 | 162086 | 1915 | Human herpesvirus 4 (EBV), B95-8 | BALF3 | Binding Protein |
| CUST_P10005381 | 162117 | 162161 | 1916 | Human herpesvirus 4 (EBV), B95-8 | BALF3 | Binding Protein |
| CUST_P10005382 | 162322 | 162366 | 1917 | Human herpesvirus 4 (EBV), B95-8 | BALF3 | Binding Protein |
| CUST_P10005496 | 1 | 60 | 1918 | Human herpesvirus 4 (EBV), AG876 | LMP-2B | latency and B cell survival |
| CUST_P10005503 | 903 | 961 | 1919 | Human herpesvirus 4 (EBV), AG876 | LMP-2B | latency and B cell survival |
| CUST_P10005506 | 1162 | 1221 | 1920 | Human herpesvirus 4 (EBV), AG876 | LMP-2B | latency and B cell survival |
| CUST_P10005507 | 1290 | 1345 | 1921 | Human herpesvirus 4 (EBV), AG876 | LMP-2B | latency and B cell survival |
| CUST_P10005515 | 1658 | 1717 | 1922 | Human herpesvirus 4 (EBV), AG876 | LMP-2B | latency and B cell survival |
| CUST_P10005567 | 5833 | 5892 | 1923 | Human herpesvirus 4 (EBV), AG876 | EBER-1 | DNA replication |
| CUST_P10005568 | 5869 | 5928 | 1924 | Human herpesvirus 4 (EBV), AG876 | EBER-1 | DNA replication |
| CUST_P10005571 | 6014 | 6073 | 1925 | Human herpesvirus 4 (EBV), AG876 | EBER-1 | DNA replication |
| CUST_P10005581 | 6584 | 6635 | 1926 | Human herpesvirus 4 (EBV), AG876 | EBER-1 | DNA replication |
| CUST_P10005585 | 6912 | 6967 | 1927 | Human herpesvirus 4 (EBV), AG876 | EBER-1 | DNA replication |
| CUST_P10005589 | 7293 | 7348 | 1928 | Human herpesvirus 4 (EBV), AG876 | EBER-1 | DNA replication |
| CUST_P10005592 | 7417 | 7476 | 1929 | Human herpesvirus 4 (EBV), AG876 | EBER-1 | DNA replication |
| CUST_P10005593 | 7470 | 7529 | 1930 | Human herpesvirus 4 (EBV), AG876 | EBER-1 | DNA replication |
| CUST_P10005594 | 7520 | 7579 | 1931 | Human herpesvirus 4 (EBV), AG876 | EBER-1 | DNA replication |
| CUST_P10005595 | 7590 | 7649 | 1932 | Human herpesvirus 4 (EBV), AG876 | EBER-1 | DNA replication |
| CUST_P10005596 | 7615 | 7674 | 1933 | Human herpesvirus 4 (EBV), AG876 | EBER-1 | DNA replication |
| CUST_P10005597 | 7645 | 7704 | 1934 | Human herpesvirus 4 (EBV), AG876 | EBER-1 | DNA replication |
| CUST_P10005598 | 7701 | 7760 | 1935 | Human herpesvirus 4 (EBV), AG876 | EBER-1 | DNA replication |
| CUST_P10005599 | 7740 | 7799 | 1936 | Human herpesvirus 4 (EBV), AG876 | EBER-1 | DNA replication |

TABLE 8-continued

Exemplary DNA virus probes

| ProbeID | Start | End | SEQ ID NO: | Virus | Genomic Region | Product |
|---|---|---|---|---|---|---|
| CUST_P10005600 | 7770 | 7829 | 1937 | Human herpesvirus 4 (EBV), AG876 | EBER-1 | DNA replication |
| CUST_P10005601 | 7799 | 7858 | 1938 | Human herpesvirus 4 (EBV), AG876 | EBER-1 | DNA replication |
| CUST_P10005602 | 7835 | 7894 | 1939 | Human herpesvirus 4 (EBV), AG876 | EBER-1 | DNA replication |
| CUST_P10005604 | 7910 | 7969 | 1940 | Human herpesvirus 4 (EBV), AG876 | EBER-1 | DNA replication |
| CUST_P10005605 | 7940 | 7999 | 1941 | Human herpesvirus 4 (EBV), AG876 | EBER-1 | DNA replication |
| CUST_P10005606 | 7972 | 8031 | 1942 | Human herpesvirus 4 (EBV), AG876 | EBER-1 | DNA replication |
| CUST_P10005617 | 8432 | 8486 | 1943 | Human herpesvirus 4 (EBV), AG876 | EBER-1 | DNA replication |
| CUST_P10005619 | 8501 | 8560 | 1944 | Human herpesvirus 4 (EBV), AG876 | EBER-1 | DNA replication |
| CUST_P10005620 | 8536 | 8590 | 1945 | Human herpesvirus 4 (EBV), AG876 | EBER-1 | DNA replication |
| CUST_P10005622 | 8614 | 8673 | 1946 | Human herpesvirus 4 (EBV), AG876 | EBER-1 | DNA replication |
| CUST_P10005623 | 8647 | 8706 | 1947 | Human herpesvirus 4 (EBV), AG876 | EBER-1 | DNA replication |
| CUST_P10005626 | 8996 | 9052 | 1948 | Human herpesvirus 4 (EBV), AG876 | EBER-1 | DNA replication |
| CUST_P10005627 | 9041 | 9100 | 1949 | Human herpesvirus 4 (EBV), AG876 | EBER-1 | DNA replication |
| CUST_P10005628 | 9096 | 9149 | 1950 | Human herpesvirus 4 (EBV), AG876 | EBER-1 | DNA replication |
| CUST_P10005635 | 9782 | 9837 | 1951 | Human herpesvirus 4 (EBV), AG876 | BCRF1 | Early protein |
| CUST_P10005640 | 9942 | 9995 | 1952 | Human herpesvirus 4 (EBV), AG876 | BCRF1 | Early protein |
| CUST_P10005641 | 10139 | 10194 | 1953 | Human herpesvirus 4 (EBV), AG876 | BCRF1 | Early protein |
| CUST_P10005654 | 11289 | 11348 | 1954 | Human herpesvirus 4 (EBV), AG876 | BCRF1 | Early protein |
| CUST_P10005661 | 11661 | 11720 | 1955 | Human herpesvirus 4 (EBV), AG876 | IR1 | Repeat Sequence |
| CUST_P10005662 | 11765 | 11824 | 1956 | Human herpesvirus 4 (EBV), AG876 | IR1 | Repeat Sequence |
| CUST_P10005663 | 11948 | 11999 | 1957 | Human herpesvirus 4 (EBV), AG876 | IR1 | Repeat Sequence |
| CUST_P10005933 | 35619 | 35674 | 1958 | Human herpesvirus 4 (EBV), AG876 | EBNA-2 | Nuclear antigen |
| CUST_P10005934 | 35650 | 35709 | 1959 | Human herpesvirus 4 (EBV), AG876 | EBNA-2 | Nuclear antigen |
| CUST_P10005935 | 35773 | 35832 | 1960 | Human herpesvirus 4 (EBV), AG876 | EBNA-2 | Nuclear antigen |
| CUST_P10005941 | 36221 | 36277 | 1961 | Human herpesvirus 4 (EBV), AG876 | EBNA-2 | Nuclear antigen |
| CUST_P10005943 | 36301 | 36360 | 1962 | Human herpesvirus 4 (EBV), AG876 | EBNA-2 | Nuclear antigen |
| CUST_P10005961 | 37425 | 37477 | 1963 | Human herpesvirus 4 (EBV), AG876 | EBNA-2 | Nuclear antigen |
| CUST_P10005962 | 37566 | 37625 | 1964 | Human herpesvirus 4 (EBV), AG876 | EBNA-2 | Nuclear antigen |
| CUST_P10005965 | 37982 | 38041 | 1965 | Human herpesvirus 4 (EBV), AG876 | EBNA-2 | Nuclear antigen |
| CUST_P10005981 | 41069 | 41128 | 1966 | Human herpesvirus 4 (EBV), AG876 | BFLF2 | Nuclear antigen |
| CUST_P10005994 | 42062 | 42114 | 1967 | Human herpesvirus 4 (EBV), AG876 | BFLF2 | Nuclear antigen |
| CUST_P10005995 | 42170 | 42229 | 1968 | Human herpesvirus 4 (EBV), AG876 | BFLF2 | Nuclear antigen |
| CUST_P10005996 | 42338 | 42397 | 1969 | Human herpesvirus 4 (EBV), AG876 | BFLF2 | Nuclear antigen |
| CUST_P10005997 | 42368 | 42427 | 1970 | Human herpesvirus 4 (EBV), AG876 | BFLF2 | Nuclear antigen |
| CUST_P10005998 | 42421 | 42480 | 1971 | Human herpesvirus 4 (EBV), AG876 | BFLF2 | Nuclear antigen |
| CUST_P10006001 | 42542 | 42594 | 1972 | Human herpesvirus 4 (EBV), AG876 | BFLF2 | Nuclear antigen |
| CUST_P10006009 | 43272 | 43331 | 1973 | Human herpesvirus 4 (EBV), AG876 | BFLF2 | Nuclear antigen |
| CUST_P10006010 | 43296 | 43355 | 1974 | Human herpesvirus 4 (EBV), AG876 | BFLF2 | Nuclear antigen |
| CUST_P10006011 | 43322 | 43381 | 1975 | Human herpesvirus 4 (EBV), AG876 | BFLF2 | Nuclear antigen |

TABLE 8-continued

Exemplary DNA virus probes

| ProbeID | Start | End | SEQ ID NO: | Virus | Genomic Region | Product |
|---|---|---|---|---|---|---|
| CUST_P10006026 | 44210 | 44266 | 1976 | Human herpesvirus 4 (EBV), AG876 | BFLF2 | Nuclear antigen |
| CUST_P10006062 | 46628 | 46687 | 1977 | Human herpesvirus 4 (EBV), AG876 | BFLF2 | Nuclear antigen |
| CUST_P10006104 | 49867 | 49926 | 1978 | Human herpesvirus 4 (EBV), AG876 | BFLF2 | Nuclear antigen |
| CUST_P10006292 | 64392 | 64446 | 1979 | Human herpesvirus 4 (EBV), AG876 | BARF1 | Protein |
| CUST_P10006337 | 67573 | 67632 | 1980 | Human herpesvirus 4 (EBV), AG876 | BARF1 | Protein |
| CUST_P10006338 | 67734 | 67780 | 1981 | Human herpesvirus 4 (EBV), AG876 | BARF1 | Protein |
| CUST_P10006346 | 68303 | 68351 | 1982 | Human herpesvirus 4 (EBV), AG876 | BARF1 | Protein |
| CUST_P10006354 | 68922 | 68968 | 1983 | Human herpesvirus 4 (EBV), AG876 | BARF1 | Protein |
| CUST_P10006495 | 79411 | 79470 | 1984 | Human herpesvirus 4 (EBV), AG876 | EBNA-3C | Protein |
| CUST_P10006496 | 79445 | 79504 | 1985 | Human herpesvirus 4 (EBV), AG876 | EBNA-3C | Protein |
| CUST_P10006497 | 79520 | 79575 | 1986 | Human herpesvirus 4 (EBV), AG876 | EBNA-3C | Protein |
| CUST_P10006499 | 79742 | 79801 | 1987 | Human herpesvirus 4 (EBV), AG876 | EBNA-3C | Protein |
| CUST_P10006506 | 80288 | 80346 | 1988 | Human herpesvirus 4 (EBV), AG876 | EBNA-3C | Protein |
| CUST_P10006513 | 80822 | 80881 | 1989 | Human herpesvirus 4 (EBV), AG876 | EBNA-3C | Protein |
| CUST_P10006515 | 80901 | 80955 | 1990 | Human herpesvirus 4 (EBV), AG876 | EBNA-3C | Protein |
| CUST_P10006542 | 83005 | 83064 | 1991 | Human herpesvirus 4 (EBV), AG876 | EBNA-3C | Protein |
| CUST_P10006547 | 83394 | 83446 | 1992 | Human herpesvirus 4 (EBV), AG876 | EBNA-3C | Protein |
| CUST_P10006549 | 83520 | 83575 | 1993 | Human herpesvirus 4 (EBV), AG876 | EBNA-3C | Protein |
| CUST_P10006559 | 84220 | 84279 | 1994 | Human herpesvirus 4 (EBV), AG876 | EBNA-3C | Protein |
| CUST_P10006560 | 84245 | 84304 | 1995 | Human herpesvirus 4 (EBV), AG876 | EBNA-3C | Protein |
| CUST_P10006562 | 84360 | 84419 | 1996 | Human herpesvirus 4 (EBV), AG876 | EBNA-3C | Protein |
| CUST_P10006563 | 84394 | 84453 | 1997 | Human herpesvirus 4 (EBV), AG876 | EBNA-3C | Protein |
| CUST_P10006619 | 87106 | 87160 | 1998 | Human herpesvirus 4 (EBV), AG876 | EBNA-3C | Protein |
| CUST_P10006629 | 87723 | 87782 | 1999 | Human herpesvirus 4 (EBV), AG876 | EBNA-3C | Protein |
| CUST_P10006659 | 90250 | 90309 | 2000 | Human herpesvirus 4 (EBV), AG876 | EBNA-3C | Protein |
| CUST_P10006735 | 95481 | 95540 | 2001 | Human herpesvirus 4 (EBV), AG876 | EBNA-3C | Protein |
| CUST_P10006749 | 96426 | 96485 | 2002 | Human herpesvirus 4 (EBV), AG876 | EBNA-3C | Protein |
| CUST_P10006975 | 114037 | 114096 | 2003 | Human herpesvirus 4 (EBV), AG876 | BZLF1 | Transcription factor |
| CUST_P10007058 | 119518 | 119568 | 2004 | Human herpesvirus 4 (EBV), AG876 | BZLF1 | Transcription factor |
| CUST_P10007154 | 127252 | 127301 | 2005 | Human herpesvirus 4 (EBV), AG876 | BZLF1 | Transcription factor |
| CUST_P10007332 | 140366 | 140418 | 2006 | Human herpesvirus 4 (EBV), AG876 | BRRF1 | Early Protein |
| CUST_P10007342 | 141133 | 141189 | 2007 | Human herpesvirus 4 (EBV), AG876 | BRRF1 | Early Protein |
| CUST_P10007350 | 141491 | 141550 | 2008 | Human herpesvirus 4 (EBV), AG876 | BRRF1 | Early Protein |
| CUST_P10007368 | 146390 | 146444 | 2009 | Human herpesvirus 4 (EBV), AG876 | BRRF1 | Early Protein |
| CUST_P10007370 | 146461 | 146520 | 2010 | Human herpesvirus 4 (EBV), AG876 | BRRF1 | Early Protein |
| CUST_P10007371 | 146485 | 146544 | 2011 | Human herpesvirus 4 (EBV), AG876 | BRRF1 | Early Protein |
| CUST_P10007385 | 147651 | 147710 | 2012 | Human herpesvirus 4 (EBV), AG876 | BRRF1 | Early Protein |
| CUST_P10007389 | 147919 | 147978 | 2013 | Human herpesvirus 4 (EBV), AG876 | BRRF1 | Early Protein |
| CUST_P10007496 | 155451 | 155495 | 2014 | Human herpesvirus 4 (EBV), AG876 | BALF5 | Pol |
| CUST_P10007497 | 155595 | 155639 | 2015 | Human herpesvirus 4 (EBV), AG876 | BALF5 | Pol |
| CUST_P10007498 | 155833 | 155878 | 2016 | Human herpesvirus 4 (EBV), AG876 | BALF5 | Pol |
| CUST_P10007499 | 155874 | 155918 | 2017 | Human herpesvirus 4 (EBV), AG876 | BALF5 | Pol |
| CUST_P10007511 | 156741 | 156785 | 2018 | Human herpesvirus 4 (EBV), AG876 | BALF5 | Pol |
| CUST_P10007512 | 156802 | 156846 | 2019 | Human herpesvirus 4 (EBV), AG876 | BALF5 | Pol |
| CUST_P10007519 | 157248 | 157292 | 2020 | Human herpesvirus 4 (EBV), AG876 | BALF5 | Pol |
| CUST_P10007686 | 169787 | 169844 | 2021 | Human herpesvirus 4 (EBV), AG876 | BALF4 | Pol |
| CUST_P10007687 | 169910 | 169964 | 2022 | Human herpesvirus 4 (EBV), AG876 | BALF4 | Pol |
| CUST_P10007688 | 169977 | 170032 | 2023 | Human herpesvirus 4 (EBV), AG876 | BALF4 | Pol |
| CUST_P10007838 | 8641 | 8685 | 2024 | Human herpesvirus 8 (HHV-8) | UL27 | Core |
| CUST_P10007845 | 9121 | 9173 | 2025 | Human herpesvirus 8 (HHV-8) | UL27 | Core |
| CUST_P10007846 | 9136 | 9192 | 2026 | Human herpesvirus 8 (HHV-8) | UL27 | Core |
| CUST_P10007847 | 9164 | 9219 | 2027 | Human herpesvirus 8 (HHV-8) | UL27 | Core |
| CUST_P10007848 | 9291 | 9338 | 2028 | Human herpesvirus 8 (HHV-8) | UL27 | Core |
| CUST_P10007849 | 9301 | 9352 | 2029 | Human herpesvirus 8 (HHV-8) | UL27 | Core |
| CUST_P10007850 | 9325 | 9380 | 2030 | Human herpesvirus 8 (HHV-8) | UL27 | Core |
| CUST_P10007859 | 10189 | 10234 | 2031 | Human herpesvirus 8 (HHV-8) | UL27 | Core |
| CUST_P10007861 | 10387 | 10436 | 2032 | Human herpesvirus 8 (HHV-8) | UL27 | Core |
| CUST_P10007862 | 10525 | 10584 | 2033 | Human herpesvirus 8 (HHV-8) | UL27 | Core |
| CUST_P10007865 | 10694 | 10743 | 2034 | Human herpesvirus 8 (HHV-8) | UL27 | Core |
| CUST_P10007870 | 11141 | 11191 | 2035 | Human herpesvirus 8 (HHV-8) | UL27 | Core |
| CUST_P10007871 | 11189 | 11243 | 2036 | Human herpesvirus 8 (HHV-8) | UL27 | Core |
| CUST_P10007875 | 11324 | 11370 | 2037 | Human herpesvirus 8 (HHV-8) | UL30 | DNA Pol |
| CUST_P10007882 | 11596 | 11644 | 2038 | Human herpesvirus 8 (HHV-8) | UL30 | DNA Pol |
| CUST_P10007889 | 12191 | 12244 | 2039 | Human herpesvirus 8 (HHV-8) | UL30 | DNA Pol |
| CUST_P10007890 | 12231 | 12276 | 2040 | Human herpesvirus 8 (HHV-8) | UL30 | DNA Pol |
| CUST_P10007892 | 12408 | 12453 | 2041 | Human herpesvirus 8 (HHV-8) | UL30 | DNA Pol |
| CUST_P10007894 | 12597 | 12642 | 2042 | Human herpesvirus 8 (HHV-8) | UL30 | DNA Pol |
| CUST_P10007895 | 12731 | 12786 | 2043 | Human herpesvirus 8 (HHV-8) | UL30 | DNA Pol |
| CUST_P10007896 | 12803 | 12855 | 2044 | Human herpesvirus 8 (HHV-8) | UL30 | DNA Pol |

TABLE 8-continued

Exemplary DNA virus probes

| ProbeID | Start | End | SEQ ID NO: | Virus | Genomic Region | Product |
|---|---|---|---|---|---|---|
| CUST_P10007900 | 13330 | 13383 | 2045 | Human herpesvirus 8 (HHV-8) | UL30 | DNA Pol |
| CUST_P10007902 | 13405 | 13449 | 2046 | Human herpesvirus 8 (HHV-8) | UL30 | DNA Pol |
| CUST_P10007903 | 13429 | 13473 | 2047 | Human herpesvirus 8 (HHV-8) | UL30 | DNA Pol |
| CUST_P10007906 | 13774 | 13821 | 2048 | Human herpesvirus 8 (HHV-8) | UL30 | DNA Pol |
| CUST_P10007907 | 13815 | 13859 | 2049 | Human herpesvirus 8 (HHV-8) | UL30 | DNA Pol |
| CUST_P10007910 | 14391 | 14438 | 2050 | Human herpesvirus 8 (HHV-8) | UL30 | DNA Pol |
| CUST_P10007912 | 14506 | 14551 | 2051 | Human herpesvirus 8 (HHV-8) | UL30 | DNA Pol |
| CUST_P10007915 | 14605 | 14655 | 2052 | Human herpesvirus 8 (HHV-8) | UL30 | DNA Pol |
| CUST_P10007916 | 14632 | 14686 | 2053 | Human herpesvirus 8 (HHV-8) | UL30 | DNA Pol |
| CUST_P10007921 | 15015 | 15062 | 2054 | Human herpesvirus 8 (HHV-8) | UL30 | DNA Pol |
| CUST_P10007922 | 15051 | 15095 | 2055 | Human herpesvirus 8 (HHV-8) | UL30 | DNA Pol |
| CUST_P10007923 | 15187 | 15232 | 2056 | Human herpesvirus 8 (HHV-8) | UL30 | DNA Pol |
| CUST_P10007925 | 15488 | 15536 | 2057 | Human herpesvirus 8 (HHV-8) | UL30 | DNA Pol |
| CUST_P10007929 | 15833 | 15879 | 2058 | Human herpesvirus 8 (HHV-8) | UL30 | DNA Pol |
| CUST_P10007933 | 16005 | 16057 | 2059 | Human herpesvirus 8 (HHV-8) | UL30 | DNA Pol |
| CUST_P10007936 | 16274 | 16324 | 2060 | Human herpesvirus 8 (HHV-8) | UL30 | DNA Pol |
| CUST_P10007937 | 16293 | 16350 | 2061 | Human herpesvirus 8 (HHV-8) | UL30 | DNA Pol |
| CUST_P10007942 | 16565 | 16614 | 2062 | Human herpesvirus 8 (HHV-8) | UL30 | DNA Pol |
| CUST_P10007943 | 16679 | 16733 | 2063 | Human herpesvirus 8 (HHV-8) | UL30 | DNA Pol |
| CUST_P10007944 | 16760 | 16804 | 2064 | Human herpesvirus 8 (HHV-8) | UL30 | DNA Pol |
| CUST_P10007946 | 16874 | 16922 | 2065 | Human herpesvirus 8 (HHV-8) | UL30 | DNA Pol |
| CUST_P10007947 | 17007 | 17064 | 2066 | Human herpesvirus 8 (HHV-8) | UL30 | DNA Pol |
| CUST_P10008350 | 47027 | 47078 | 2067 | Human herpesvirus 8 (HHV-8) | ORF26 | Capsid |
| CUST_P10008352 | 47180 | 47235 | 2068 | Human herpesvirus 8 (HHV-8) | ORF26 | Capsid |
| CUST_P10008353 | 47205 | 47256 | 2069 | Human herpesvirus 8 (HHV-8) | ORF26 | Capsid |
| CUST_P10008354 | 47279 | 47328 | 2070 | Human herpesvirus 8 (HHV-8) | ORF26 | Capsid |
| CUST_P10008355 | 47290 | 47343 | 2071 | Human herpesvirus 8 (HHV-8) | ORF26 | Capsid |
| CUST_P10008356 | 47379 | 47429 | 2072 | Human herpesvirus 8 (HHV-8) | ORF26 | Capsid |
| CUST_P10008357 | 47404 | 47448 | 2073 | Human herpesvirus 8 (HHV-8) | ORF26 | Capsid |
| CUST_P10008358 | 47526 | 47583 | 2074 | Human herpesvirus 8 (HHV-8) | ORF26 | Capsid |
| CUST_P10008362 | 47811 | 47857 | 2075 | Human herpesvirus 8 (HHV-8) | ORF26 | Capsid |
| CUST_P10008363 | 47833 | 47889 | 2076 | Human herpesvirus 8 (HHV-8) | ORF26 | Capsid |
| CUST_P10008367 | 48249 | 48296 | 2077 | Human herpesvirus 8 (HHV-8) | ORF27 | PolyA |
| CUST_P10008370 | 48367 | 48418 | 2078 | Human herpesvirus 8 (HHV-8) | ORF27 | PolyA |
| CUST_P10008371 | 48393 | 48441 | 2079 | Human herpesvirus 8 (HHV-8) | ORF27 | PolyA |
| CUST_P10008373 | 48456 | 48500 | 2080 | Human herpesvirus 8 (HHV-8) | ORF27 | PolyA |
| CUST_P10008374 | 48487 | 48538 | 2081 | Human herpesvirus 8 (HHV-8) | ORF27 | PolyA |
| CUST_P10008376 | 48548 | 48592 | 2082 | Human herpesvirus 8 (HHV-8) | ORF27 | PolyA |
| CUST_P10008377 | 48585 | 48643 | 2083 | Human herpesvirus 8 (HHV-8) | ORF27 | PolyA |
| CUST_P10008378 | 48655 | 48702 | 2084 | Human herpesvirus 8 (HHV-8) | ORF27 | PolyA |
| CUST_P10008380 | 48859 | 48918 | 2085 | Human herpesvirus 8 (HHV-8) | ORF27 | PolyA |
| CUST_P10009322 | 112342 | 112396 | 2086 | Human herpesvirus 8 (HHV-8) | ORF73 | PolyA |
| CUST_P10009323 | 112362 | 112421 | 2087 | Human herpesvirus 8 (HHV-8) | ORF73 | PolyA |
| CUST_P10009324 | 112390 | 112439 | 2088 | Human herpesvirus 8 (HHV-8) | ORF73 | PolyA |
| CUST_P10009462 | 123077 | 123124 | 2089 | Human herpesvirus 8 (HHV-8) | ORF73 | PolyA |
| CUST_P10009466 | 123331 | 123382 | 2090 | Human herpesvirus 8 (HHV-8) | ORF73 | PolyA |
| CUST_P10009467 | 123379 | 123425 | 2091 | Human herpesvirus 8 (HHV-8) | ORF73 | PolyA |
| CUST_P10009468 | 123391 | 123441 | 2092 | Human herpesvirus 8 (HHV-8) | ORF73 | PolyA |
| CUST_P10009469 | 123537 | 123593 | 2093 | Human herpesvirus 8 (HHV-8) | ORF73 | PolyA |
| CUST_P10009470 | 123611 | 123664 | 2094 | Human herpesvirus 8 (HHV-8) | ORF73 | PolyA |
| CUST_P10009471 | 123635 | 123692 | 2095 | Human herpesvirus 8 (HHV-8) | ORF73 | PolyA |
| CUST_P10009472 | 123655 | 123714 | 2096 | Human herpesvirus 8 (HHV-8) | ORF73 | PolyA |
| CUST_P10009473 | 123682 | 123736 | 2097 | Human herpesvirus 8 (HHV-8) | ORF73 | PolyA |
| CUST_P10009474 | 123710 | 123769 | 2098 | Human herpesvirus 8 (HHV-8) | ORF73 | PolyA |
| CUST_P10009475 | 123738 | 123788 | 2099 | Human herpesvirus 8 (HHV-8) | ORF73 | PolyA |
| CUST_P10009482 | 124109 | 124164 | 2100 | Human herpesvirus 8 (HHV-8) | ORF73 | PolyA |
| CUST_P10009484 | 124384 | 124437 | 2101 | Human herpesvirus 8 (HHV-8) | ORF73 | PolyA |
| CUST_P10009486 | 124635 | 124686 | 2102 | Human herpesvirus 8 (HHV-8) | ORF73 | PolyA |
| CUST_P10009487 | 124654 | 124707 | 2103 | Human herpesvirus 8 (HHV-8) | ORF73 | PolyA |
| CUST_P10009488 | 124679 | 124723 | 2104 | Human herpesvirus 8 (HHV-8) | ORF73 | PolyA |
| CUST_P10009489 | 126493 | 126541 | 2105 | Human herpesvirus 8 (HHV-8) | ORF73 | PolyA |
| CUST_P10009493 | 126960 | 127005 | 2106 | Human herpesvirus 8 (HHV-8) | ORF73 | PolyA |
| CUST_P10009503 | 127324 | 127368 | 2107 | Human herpesvirus 8 (HHV-8) | ORF73 | PolyA |
| CUST_P10009504 | 127347 | 127395 | 2108 | Human herpesvirus 8 (HHV-8) | ORF73 | PolyA |
| CUST_P10009640 | 3 | 59 | 2109 | Human papillomavirus type 6b (HPV 6b) | E6 | Regulatory Protein |
| CUST_P10009641 | 34 | 85 | 2110 | Human papillomavirus type 6b (HPV 6b) | E6 | Regulatory Protein |
| CUST_P10009642 | 57 | 116 | 2111 | Human papillomavirus type 6b (HPV 6b) | E6 | Regulatory Protein |
| CUST_P10009644 | 148 | 207 | 2112 | Human papillomavirus type 6b (HPV 6b) | E6 | Regulatory Protein |

TABLE 8-continued

Exemplary DNA virus probes

| ProbeID | Start | End | SEQ ID NO: | Virus | Genomic Region | Product |
|---|---|---|---|---|---|---|
| CUST_P10009645 | 207 | 266 | 2113 | Human papillomavirus type 6b (HPV 6b) | E6 | Regulatory Protein |
| CUST_P10009646 | 347 | 406 | 2114 | Human papillomavirus type 6b (HPV 6b) | E6 | Regulatory Protein |
| CUST_P10009647 | 401 | 449 | 2115 | Human papillomavirus type 6b (HPV 6b) | E6 | Regulatory Protein |
| CUST_P10009648 | 527 | 582 | 2116 | Human papillomavirus type 6b (HPV 6b) | E6 | Regulatory Protein |
| CUST_P10009649 | 645 | 702 | 2117 | Human papillomavirus type 6b (HPV 6b) | E7 | Regulatory Protein |
| CUST_P10009651 | 952 | 1005 | 2118 | Human papillomavirus type 6b (HPV 6b) | E7 | Regulatory Protein |
| CUST_P10009652 | 975 | 1034 | 2119 | Human papillomavirus type 6b (HPV 6b) | E7 | Regulatory Protein |
| CUST_P10009654 | 1048 | 1099 | 2120 | Human papillomavirus type 6b (HPV 6b) | E1 | Regulatory Protein |
| CUST_P10009655 | 1079 | 1138 | 2121 | Human papillomavirus type 6b (HPV 6b) | E1 | Regulatory Protein |
| CUST_P10009656 | 1101 | 1160 | 2122 | Human papillomavirus type 6b (HPV 6b) | E1 | Regulatory Protein |
| CUST_P10009657 | 1140 | 1199 | 2123 | Human papillomavirus type 6b (HPV 6b) | E1 | Regulatory Protein |
| CUST_P10009658 | 1168 | 1221 | 2124 | Human papillomavirus type 6b (HPV 6b) | E1 | Regulatory Protein |
| CUST_P10009659 | 1204 | 1249 | 2125 | Human papillomavirus type 6b (HPV 6b) | E1 | Regulatory Protein |
| CUST_P10009660 | 1418 | 1477 | 2126 | Human papillomavirus type 6b (HPV 6b) | E1 | Regulatory Protein |
| CUST_P10009661 | 1492 | 1551 | 2127 | Human papillomavirus type 6b (HPV 6b) | E1 | Regulatory Protein |
| CUST_P10009662 | 1852 | 1908 | 2128 | Human papillomavirus type 6b (HPV 6b) | E1 | Regulatory Protein |
| CUST_P10009663 | 1899 | 1958 | 2129 | Human papillomavirus type 6b (HPV 6b) | E1 | Regulatory Protein |
| CUST_P10009664 | 2058 | 2117 | 2130 | Human papillomavirus type 6b (HPV 6b) | E1 | Regulatory Protein |
| CUST_P10009665 | 2086 | 2145 | 2131 | Human papillomavirus type 6b (HPV 6b) | E1 | Regulatory Protein |
| CUST_P10009666 | 2353 | 2412 | 2132 | Human papillomavirus type 6b (HPV 6b) | E1 | Regulatory Protein |
| CUST_P10009667 | 2463 | 2522 | 2133 | Human papillomavirus type 6b (HPV 6b) | E1 | Regulatory Protein |
| CUST_P10009668 | 2507 | 2566 | 2134 | Human papillomavirus type 6b (HPV 6b) | E1 | Regulatory Protein |
| CUST_P10009669 | 2554 | 2613 | 2135 | Human papillomavirus type 6b (HPV 6b) | E1 | Regulatory Protein |
| CUST_P10009670 | 2601 | 2660 | 2136 | Human papillomavirus type 6b (HPV 6b) | E1 | Regulatory Protein |
| CUST_P10009671 | 2686 | 2734 | 2137 | Human papillomavirus type 6b (HPV 6b) | E2 | Regulatory Protein |
| CUST_P10009672 | 2894 | 2946 | 2138 | Human papillomavirus type 6b (HPV 6b) | E2 | Regulatory Protein |
| CUST_P10009673 | 2916 | 2975 | 2139 | Human papillomavirus type 6b (HPV 6b) | E2 | Regulatory Protein |
| CUST_P10009674 | 2942 | 3001 | 2140 | Human papillomavirus type 6b (HPV 6b) | E2 | Regulatory Protein |
| CUST_P10009675 | 2963 | 3022 | 2141 | Human papillomavirus type 6b (HPV 6b) | E2 | Regulatory Protein |
| CUST_P10009676 | 3002 | 3061 | 2142 | Human papillomavirus type 6b (HPV 6b) | E2 | Regulatory Protein |
| CUST_P10009677 | 3030 | 3089 | 2143 | Human papillomavirus type 6b (HPV 6b) | E2 | Regulatory Protein |
| CUST_P10009678 | 3061 | 3120 | 2144 | Human papillomavirus type 6b (HPV 6b) | E2 | Regulatory Protein |
| CUST_P10009679 | 3091 | 3148 | 2145 | Human papillomavirus type 6b (HPV 6b) | E2 | Regulatory Protein |
| CUST_P10009680 | 3265 | 3324 | 2146 | Human papillomavirus type 6b (HPV 6b) | E2 | Regulatory Protein |
| CUST_P10009681 | 3305 | 3364 | 2147 | Human papillomavirus type 6b (HPV 6b) | E2 | Regulatory Protein |
| CUST_P10009686 | 3592 | 3651 | 2148 | Human papillomavirus type 6b (HPV 6b) | E2 | Regulatory Protein |

TABLE 8-continued

Exemplary DNA virus probes

| ProbeID | Start | End | SEQ ID NO: | Virus | Genomic Region | Product |
|---|---|---|---|---|---|---|
| CUST_P10009687 | 3614 | 3673 | 2149 | Human papillomavirus type 6b (HPV 6b) | E2 | Regulatory Protein |
| CUST_P10009689 | 3686 | 3740 | 2150 | Human papillomavirus type 6b (HPV 6b) | E2 | Regulatory Protein |
| CUST_P10009690 | 3724 | 3783 | 2151 | Human papillomavirus type 6b (HPV 6b) | E2 | Regulatory Protein |
| CUST_P10009691 | 3751 | 3810 | 2152 | Human papillomavirus type 6b (HPV 6b) | E2 | Regulatory Protein |
| CUST_P10009692 | 3937 | 3996 | 2153 | Human papillomavirus type 6b (HPV 6b) | E5 | Regulatory Protein |
| CUST_P10009693 | 4048 | 4107 | 2154 | Human papillomavirus type 6b (HPV 6b) | E5 | Regulatory Protein |
| CUST_P10009694 | 4077 | 4136 | 2155 | Human papillomavirus type 6b (HPV 6b) | E5 | Regulatory Protein |
| CUST_P10009695 | 4116 | 4175 | 2156 | Human papillomavirus type 6b (HPV 6b) | E5 | Regulatory Protein |
| CUST_P10009696 | 4140 | 4199 | 2157 | Human papillomavirus type 6b (HPV 6b) | E5 | Regulatory Protein |
| CUST_P10009697 | 4281 | 4340 | 2158 | Human papillomavirus type 6b (HPV 6b) | E5 | Regulatory Protein |
| CUST_P10009698 | 4505 | 4557 | 2159 | Human papillomavirus type 6b (HPV 6b) | L2 | Capsid |
| CUST_P10009702 | 4718 | 4773 | 2160 | Human papillomavirus type 6b (HPV 6b) | L2 | Capsid |
| CUST_P10009705 | 4804 | 4863 | 2161 | Human papillomavirus type 6b (HPV 6b) | L2 | Capsid |
| CUST_P10009706 | 4937 | 4991 | 2162 | Human papillomavirus type 6b (HPV 6b) | L2 | Capsid |
| CUST_P10009707 | 4970 | 5029 | 2163 | Human papillomavirus type 6b (HPV 6b) | L2 | Capsid |
| CUST_P10009709 | 5118 | 5175 | 2164 | Human papillomavirus type 6b (HPV 6b) | L2 | Capsid |
| CUST_P10009710 | 5237 | 5285 | 2165 | Human papillomavirus type 6b (HPV 6b) | L2 | Capsid |
| CUST_P10009711 | 5508 | 5567 | 2166 | Human papillomavirus type 6b (HPV 6b) | L2 | Capsid |
| CUST_P10009712 | 5568 | 5617 | 2167 | Human papillomavirus type 6b (HPV 6b) | L2 | Capsid |
| CUST_P10009713 | 5581 | 5640 | 2168 | Human papillomavirus type 6b (HPV 6b) | L2 | Capsid |
| CUST_P10009714 | 5611 | 5663 | 2169 | Human papillomavirus type 6b (HPV 6b) | L2 | Capsid |
| CUST_P10009715 | 5664 | 5716 | 2170 | Human papillomavirus type 6b (HPV 6b) | L2 | Capsid |
| CUST_P10009716 | 5699 | 5758 | 2171 | Human papillomavirus type 6b (HPV 6b) | L1 | PolyA |
| CUST_P10009717 | 5835 | 5893 | 2172 | Human papillomavirus type 6b (HPV 6b) | L1 | PolyA |
| CUST_P10009718 | 5882 | 5941 | 2173 | Human papillomavirus type 6b (HPV 6b) | L1 | PolyA |
| CUST_P10009719 | 5917 | 5971 | 2174 | Human papillomavirus type 6b (HPV 6b) | L1 | PolyA |
| CUST_P10009720 | 5980 | 6039 | 2175 | Human papillomavirus type 6b (HPV 6b) | L1 | PolyA |
| CUST_P10009721 | 6023 | 6077 | 2176 | Human papillomavirus type 6b (HPV 6b) | L1 | PolyA |
| CUST_P10009723 | 6106 | 6157 | 2177 | Human papillomavirus type 6b (HPV 6b) | L1 | PolyA |
| CUST_P10009724 | 6131 | 6190 | 2178 | Human papillomavirus type 6b (HPV 6b) | L1 | PolyA |
| CUST_P10009726 | 6346 | 6399 | 2179 | Human papillomavirus type 6b (HPV 6b) | L1 | PolyA |
| CUST_P10009727 | 6387 | 6446 | 2180 | Human papillomavirus type 6b (HPV 6b) | L1 | PolyA |
| CUST_P10009728 | 6426 | 6485 | 2181 | Human papillomavirus type 6b (HPV 6b) | L1 | PolyA |
| CUST_P10009729 | 6587 | 6641 | 2182 | Human papillomavirus type 6b (HPV 6b) | L1 | PolyA |
| CUST_P10009731 | 6661 | 6710 | 2183 | Human papillomavirus type 6b (HPV 6b) | L1 | PolyA |
| CUST_P10009732 | 6674 | 6727 | 2184 | Human papillomavirus type 6b (HPV 6b) | L1 | PolyA |

TABLE 8-continued

Exemplary DNA virus probes

| ProbeID | Start | End | SEQ ID NO: | Virus | Genomic Region | Product |
|---|---|---|---|---|---|---|
| CUST_P10009733 | 6713 | 6771 | 2185 | Human papillomavirus type 6b (HPV 6b) | L1 | PolyA |
| CUST_P10009734 | 6799 | 6858 | 2186 | Human papillomavirus type 6b (HPV 6b) | L1 | PolyA |
| CUST_P10009735 | 6914 | 6973 | 2187 | Human papillomavirus type 6b (HPV 6b) | L1 | PolyA |
| CUST_P10009736 | 7025 | 7070 | 2188 | Human papillomavirus type 6b (HPV 6b) | L1 | PolyA |
| CUST_P10009737 | 7146 | 7201 | 2189 | Human papillomavirus type 6b (HPV 6b) | L1 | PolyA |
| CUST_P10009739 | 7409 | 7456 | 2190 | Human papillomavirus type 6b (HPV 6b) |  | PolyA |
| CUST_P10009740 | 7560 | 7619 | 2191 | Human papillomavirus type 6b (HPV 6b) | ? | PolyA |
| CUST_P10009742 | 7703 | 7762 | 2192 | Human papillomavirus type 6b (HPV 6b) | ? | PolyA |
| CUST_P10009743 | 9 | 65 | 2193 | Human papillomavirus type 6b (HPV 11) | E6 | Regulatory Protein |
| CUST_P10009744 | 45 | 104 | 2194 | Human papillomavirus type 6b (HPV 11) | E6 | Regulatory Protein |
| CUST_P10009745 | 97 | 149 | 2195 | Human papillomavirus type 6b (HPV 11) | E6 | Regulatory Protein |
| CUST_P10009746 | 146 | 201 | 2196 | Human papillomavirus type 6b (HPV 11) | E6 | Regulatory Protein |
| CUST_P10009747 | 203 | 257 | 2197 | Human papillomavirus type 6b (HPV 11) | E6 | Regulatory Protein |
| CUST_P10009748 | 226 | 284 | 2198 | Human papillomavirus type 6b (HPV 11) | E6 | Regulatory Protein |
| CUST_P10009749 | 267 | 311 | 2199 | Human papillomavirus type 6b (HPV 11) | E6 | Regulatory Protein |
| CUST_P10009750 | 444 | 503 | 2200 | Human papillomavirus type 6b (HPV 11) | E6 | Regulatory Protein |
| CUST_P10009751 | 477 | 531 | 2201 | Human papillomavirus type 6b (HPV 11) | E6 | Regulatory Protein |
| CUST_P10009752 | 642 | 696 | 2202 | Human papillomavirus type 6b (HPV 11) | E7 | Regulatory Protein |
| CUST_P10009753 | 676 | 724 | 2203 | Human papillomavirus type 6b (HPV 11) | E7 | Regulatory Protein |
| CUST_P10009755 | 744 | 796 | 2204 | Human papillomavirus type 6b (HPV 11) | E7 | Regulatory Protein |
| CUST_P10009756 | 980 | 1039 | 2205 | Human papillomavirus type 6b (HPV 11) | E7 | Regulatory Protein |
| CUST_P10009758 | 1159 | 1212 | 2206 | Human papillomavirus type 6b (HPV 11) | E1 | Regulatory Protein |
| CUST_P10009759 | 1195 | 1242 | 2207 | Human papillomavirus type 6b (HPV 11) | E1 | Regulatory Protein |
| CUST_P10009760 | 1393 | 1452 | 2208 | Human papillomavirus type 6b (HPV 11) | E1 | Regulatory Protein |
| CUST_P10009761 | 1419 | 1478 | 2209 | Human papillomavirus type 6b (HPV 11) | E1 | Regulatory Protein |
| CUST_P10009762 | 1450 | 1509 | 2210 | Human papillomavirus type 6b (HPV 11) | E1 | Regulatory Protein |
| CUST_P10009763 | 1476 | 1535 | 2211 | Human papillomavirus type 6b (HPV 11) | E1 | Regulatory Protein |
| CUST_P10009765 | 1847 | 1899 | 2212 | Human papillomavirus type 6b (HPV 11) | E1 | Regulatory Protein |
| CUST_P10009766 | 1864 | 1923 | 2213 | Human papillomavirus type 6b (HPV 11) | E1 | Regulatory Protein |
| CUST_P10009767 | 1923 | 1982 | 2214 | Human papillomavirus type 6b (HPV 11) | E1 | Regulatory Protein |
| CUST_P10009768 | 1962 | 2017 | 2215 | Human papillomavirus type 6b (HPV 11) | E1 | Regulatory Protein |
| CUST_P10009769 | 2003 | 2062 | 2216 | Human papillomavirus type 6b (HPV 11) | E1 | Regulatory Protein |
| CUST_P10009770 | 2127 | 2186 | 2217 | Human papillomavirus type 6b (HPV 11) | E2 | Regulatory Protein |
| CUST_P10009771 | 2265 | 2316 | 2218 | Human papillomavirus type 6b (HPV 11) | E2 | Regulatory Protein |
| CUST_P10009772 | 2303 | 2362 | 2219 | Human papillomavirus type 6b (HPV 11) | E2 | Regulatory Protein |
| CUST_P10009773 | 2327 | 2384 | 2220 | Human papillomavirus type 6b (HPV 11) | E2 | Regulatory Protein |

TABLE 8-continued

Exemplary DNA virus probes

| ProbeID | Start | End | SEQ ID NO: | Virus | Genomic Region | Product |
|---|---|---|---|---|---|---|
| CUST_P10009774 | 2370 | 2420 | 2221 | Human papillomavirus type 6b (HPV 11) | E2 | Regulatory Protein |
| CUST_P10009775 | 2422 | 2481 | 2222 | Human papillomavirus type 6b (HPV 11) | E2 | Regulatory Protein |
| CUST_P10009776 | 2458 | 2517 | 2223 | Human papillomavirus type 6b (HPV 11) | E2 | Regulatory Protein |
| CUST_P10009777 | 2590 | 2649 | 2224 | Human papillomavirus type 6b (HPV 11) | E2 | Regulatory Protein |
| CUST_P10009778 | 2625 | 2684 | 2225 | Human papillomavirus type 6b (HPV 11) | E2 | Regulatory Protein |
| CUST_P10009779 | 2655 | 2708 | 2226 | Human papillomavirus type 6b (HPV 11) | E2 | Regulatory Protein |
| CUST_P10009780 | 2692 | 2740 | 2227 | Human papillomavirus type 6b (HPV 11) | E2 | Regulatory Protein |
| CUST_P10009781 | 2920 | 2979 | 2228 | Human papillomavirus type 6b (HPV 11) | E2 | Regulatory Protein |
| CUST_P10009782 | 2985 | 3035 | 2229 | Human papillomavirus type 6b (HPV 11) | E2 | Regulatory Protein |
| CUST_P10009783 | 3047 | 3106 | 2230 | Human papillomavirus type 6b (HPV 11) | E2 | Regulatory Protein |
| CUST_P10009784 | 3081 | 3140 | 2231 | Human papillomavirus type 6b (HPV 11) | E2 | Regulatory Protein |
| CUST_P10009785 | 3120 | 3176 | 2232 | Human papillomavirus type 6b (HPV 11) | E2 | Regulatory Protein |
| CUST_P10009786 | 3265 | 3324 | 2233 | Human papillomavirus type 6b (HPV 11) | E2 | Regulatory Protein |
| CUST_P10009787 | 3380 | 3424 | 2234 | Human papillomavirus type 6b (HPV 11) | E2 | Regulatory Protein |
| CUST_P10009788 | 3432 | 3476 | 2235 | Human papillomavirus type 6b (HPV 11) | E2 | Regulatory Protein |
| CUST_P10009789 | 3505 | 3560 | 2236 | Human papillomavirus type 6b (HPV 11) | E2 | Regulatory Protein |
| CUST_P10009790 | 3678 | 3735 | 2237 | Human papillomavirus type 6b (HPV 11) | E2 | Regulatory Protein |
| CUST_P10009791 | 3709 | 3768 | 2238 | Human papillomavirus type 6b (HPV 11) | E2 | Regulatory Protein |
| CUST_P10009792 | 3901 | 3960 | 2239 | Human papillomavirus type 6b (HPV 11) | E5 | Regulatory Protein |
| CUST_P10009793 | 4136 | 4195 | 2240 | Human papillomavirus type 6b (HPV 11) | E5 | Regulatory Protein |
| CUST_P10009794 | 4283 | 4342 | 2241 | Human papillomavirus type 6b (HPV 11) | E5 | Regulatory Protein |
| CUST_P10009795 | 4408 | 4458 | 2242 | Human papillomavirus type 6b (HPV 11) | E5 | Regulatory Protein |
| CUST_P10009796 | 4497 | 4556 | 2243 | Human papillomavirus type 6b (HPV 11) | L2 | Capsid |
| CUST_P10009798 | 4792 | 4851 | 2244 | Human papillomavirus type 6b (HPV 11) | L2 | Capsid |
| CUST_P10009799 | 4818 | 4875 | 2245 | Human papillomavirus type 6b (HPV 11) | L2 | Capsid |
| CUST_P10009800 | 4855 | 4912 | 2246 | Human papillomavirus type 6b (HPV 11) | L2 | Capsid |
| CUST_P10009802 | 4936 | 4993 | 2247 | Human papillomavirus type 6b (HPV 11) | L2 | Capsid |
| CUST_P10009804 | 5164 | 5223 | 2248 | Human papillomavirus type 6b (HPV 11) | L2 | Capsid |
| CUST_P10009805 | 5341 | 5397 | 2249 | Human papillomavirus type 6b (HPV 11) | L2 | Capsid |
| CUST_P10009806 | 5423 | 5480 | 2250 | Human papillomavirus type 6b (HPV 11) | L2 | Capsid |
| CUST_P10009808 | 5491 | 5548 | 2251 | Human papillomavirus type 6b (HPV 11) | L2 | Capsid |
| CUST_P10009809 | 5514 | 5566 | 2252 | Human papillomavirus type 6b (HPV 11) | L2 | Capsid |
| CUST_P10009810 | 5539 | 5586 | 2253 | Human papillomavirus type 6b (HPV 11) | L2 | Capsid |
| CUST_P10009811 | 5576 | 5622 | 2254 | Human papillomavirus type 6b (HPV 11) | L2 | Capsid |
| CUST_P10009812 | 5603 | 5651 | 2255 | Human papillomavirus type 6b (HPV 11) | L2 | Capsid |
| CUST_P10009813 | 5618 | 5670 | 2256 | Human papillomavirus type 6b (HPV 11) | L2 | Capsid |

TABLE 8-continued

Exemplary DNA virus probes

| ProbeID | Start | End | SEQ ID NO: | Virus | Genomic Region | Product |
|---|---|---|---|---|---|---|
| CUST_P10009814 | 5745 | 5800 | 2257 | Human papillomavirus type 6b (HPV 11) | L2 | Capsid |
| CUST_P10009815 | 5819 | 5875 | 2258 | Human papillomavirus type 6b (HPV 11) | L1 | PolyA |
| CUST_P10009816 | 5978 | 6034 | 2259 | Human papillomavirus type 6b (HPV 11) | L1 | PolyA |
| CUST_P10009817 | 6008 | 6059 | 2260 | Human papillomavirus type 6b (HPV 11) | L1 | PolyA |
| CUST_P10009818 | 6031 | 6075 | 2261 | Human papillomavirus type 6b (HPV 11) | L1 | PolyA |
| CUST_P10009819 | 6069 | 6113 | 2262 | Human papillomavirus type 6b (HPV 11) | L1 | PolyA |
| CUST_P10009820 | 6089 | 6139 | 2263 | Human papillomavirus type 6b (HPV 11) | L1 | PolyA |
| CUST_P10009821 | 6118 | 6177 | 2264 | Human papillomavirus type 6b (HPV 11) | L1 | PolyA |
| CUST_P10009822 | 6338 | 6390 | 2265 | Human papillomavirus type 6b (HPV 11) | L1 | PolyA |
| CUST_P10009823 | 6356 | 6415 | 2266 | Human papillomavirus type 6b (HPV 11) | L1 | PolyA |
| CUST_P10009824 | 6383 | 6442 | 2267 | Human papillomavirus type 6b (HPV 11) | L1 | PolyA |
| CUST_P10009825 | 6408 | 6467 | 2268 | Human papillomavirus type 6b (HPV 11) | L1 | PolyA |
| CUST_P10009826 | 6707 | 6757 | 2269 | Human papillomavirus type 6b (HPV 11) | L1 | PolyA |
| CUST_P10009827 | 6796 | 6855 | 2270 | Human papillomavirus type 6b (HPV 11) | L1 | PolyA |
| CUST_P10009828 | 7130 | 7187 | 2271 | Human papillomavirus type 6b (HPV 11) | L1 | PolyA |
| CUST_P10009831 | 13 | 69 | 2272 | Human papillomavirus type 6b (HPV 16) | E6 | Regulatory Protein |
| CUST_P10009832 | 54 | 113 | 2273 | Human papillomavirus type 6b (HPV 16) | E6 | Regulatory Protein |
| CUST_P10009833 | 221 | 280 | 2274 | Human papillomavirus type 6b (HPV 16) | E6 | Regulatory Protein |
| CUST_P10009834 | 355 | 414 | 2275 | Human papillomavirus type 6b (HPV 16) | E6 | Regulatory Protein |
| CUST_P10009836 | 564 | 623 | 2276 | Human papillomavirus type 6b (HPV 16) | E6 | Regulatory Protein |
| CUST_P10009837 | 704 | 758 | 2277 | Human papillomavirus type 6b (HPV 16) | E7 | Regulatory Protein |
| CUST_P10009838 | 816 | 867 | 2278 | Human papillomavirus type 6b (HPV 16) | E7 | Regulatory Protein |
| CUST_P10009839 | 969 | 1028 | 2279 | Human papillomavirus type 6b (HPV 16) | E1 | Regulatory Protein |
| CUST_P10009840 | 994 | 1053 | 2280 | Human papillomavirus type 6b (HPV 16) | E1 | Regulatory Protein |
| CUST_P10009841 | 1049 | 1098 | 2281 | Human papillomavirus type 6b (HPV 16) | E1 | Regulatory Protein |
| CUST_P10009842 | 1131 | 1190 | 2282 | Human papillomavirus type 6b (HPV 16) | E1 | Regulatory Protein |
| CUST_P10009843 | 1269 | 1316 | 2283 | Human papillomavirus type 6b (HPV 16) | E1 | Regulatory Protein |
| CUST_P10009844 | 1296 | 1346 | 2284 | Human papillomavirus type 6b (HPV 16) | E1 | Regulatory Protein |
| CUST_P10009845 | 1461 | 1520 | 2285 | Human papillomavirus type 6b (HPV 16) | E1 | Regulatory Protein |
| CUST_P10009846 | 1734 | 1793 | 2286 | Human papillomavirus type 6b (HPV 16) | E1 | Regulatory Protein |
| CUST_P10009847 | 1841 | 1900 | 2287 | Human papillomavirus type 6b (HPV 16) | E1 | Regulatory Protein |
| CUST_P10009848 | 2010 | 2069 | 2288 | Human papillomavirus type 6b (HPV 16) | E1 | Regulatory Protein |
| CUST_P10009849 | 2153 | 2212 | 2289 | Human papillomavirus type 6b (HPV 16) | E1 | Regulatory Protein |
| CUST_P10009850 | 2326 | 2385 | 2290 | Human papillomavirus type 6b (HPV 16) | E1 | Regulatory Protein |
| CUST_P10009851 | 2372 | 2431 | 2291 | Human papillomavirus type 6b (HPV 16) | E1 | Regulatory Protein |
| CUST_P10009852 | 2583 | 2642 | 2292 | Human papillomavirus type 6b (HPV 16) | E1 | Regulatory Protein |
| CUST_P10009853 | 2679 | 2732 | 2293 | Human papillomavirus type 6b (HPV 16) | E1 | Regulatory Protein |

TABLE 8-continued

Exemplary DNA virus probes

| ProbeID | Start | End | SEQ ID NO: | Virus | Genomic Region | Product |
| --- | --- | --- | --- | --- | --- | --- |
| CUST_P10009854 | 2745 | 2803 | 2294 | Human papillomavirus type 6b (HPV 16) | E1 | Regulatory Protein |
| CUST_P10009855 | 2862 | 2921 | 2295 | Human papillomavirus type 6b (HPV 16) | E2 | Regulatory Protein |
| CUST_P10009856 | 2895 | 2951 | 2296 | Human papillomavirus type 6b (HPV 16) | E2 | Regulatory Protein |
| CUST_P10009857 | 2932 | 2991 | 2297 | Human papillomavirus type 6b (HPV 16) | E2 | Regulatory Protein |
| CUST_P10009858 | 2974 | 3033 | 2298 | Human papillomavirus type 6b (HPV 16) | E2 | Regulatory Protein |
| CUST_P10009859 | 2995 | 3054 | 2299 | Human papillomavirus type 6b (HPV 16) | E2 | Regulatory Protein |
| CUST_P10009860 | 3091 | 3150 | 2300 | Human papillomavirus type 6b (HPV 16) | E2 | Regulatory Protein |
| CUST_P10009861 | 3190 | 3249 | 2301 | Human papillomavirus type 6b (HPV 16) | E2 | Regulatory Protein |
| CUST_P10009862 | 3325 | 3384 | 2302 | Human papillomavirus type 6b (HPV 16) | E2 | Regulatory Protein |
| CUST_P10009864 | 3437 | 3481 | 2303 | Human papillomavirus type 6b (HPV 16) | E2 | Regulatory Protein |
| CUST_P10009867 | 3503 | 3547 | 2304 | Human papillomavirus type 6b (HPV 16) | E2 | Regulatory Protein |
| CUST_P10009868 | 3777 | 3836 | 2305 | Human papillomavirus type 6b (HPV 16) | E2 | Regulatory Protein |
| CUST_P10009869 | 3949 | 4008 | 2306 | Human papillomavirus type 6b (HPV 16) | E5 | Regulatory Protein |
| CUST_P10009870 | 4245 | 4297 | 2307 | Human papillomavirus type 6b (HPV 16) | E5 | Regulatory Protein |
| CUST_P10009871 | 4323 | 4382 | 2308 | Human papillomavirus type 6b (HPV 16) | L2 | Capsid |
| CUST_P10009872 | 4347 | 4406 | 2309 | Human papillomavirus type 6b (HPV 16) | L2 | Capsid |
| CUST_P10009873 | 4510 | 4566 | 2310 | Human papillomavirus type 6b (HPV 16) | L2 | Capsid |
| CUST_P10009874 | 4532 | 4591 | 2311 | Human papillomavirus type 6b (HPV 16) | L2 | Capsid |
| CUST_P10009875 | 4644 | 4703 | 2312 | Human papillomavirus type 6b (HPV 16) | L2 | Capsid |
| CUST_P10009876 | 4680 | 4739 | 2313 | Human papillomavirus type 6b (HPV 16) | L2 | Capsid |
| CUST_P10009878 | 4821 | 4880 | 2314 | Human papillomavirus type 6b (HPV 16) | L2 | Capsid |
| CUST_P10009879 | 4842 | 4890 | 2315 | Human papillomavirus type 6b (HPV 16) | L2 | Capsid |
| CUST_P10009880 | 4898 | 4951 | 2316 | Human papillomavirus type 6b (HPV 16) | L2 | Capsid |
| CUST_P10009881 | 4931 | 4990 | 2317 | Human papillomavirus type 6b (HPV 16) | L2 | Capsid |
| CUST_P10009882 | 5068 | 5125 | 2318 | Human papillomavirus type 6b (HPV 16) | L2 | Capsid |
| CUST_P10009883 | 5237 | 5296 | 2319 | Human papillomavirus type 6b (HPV 16) | L2 | Capsid |
| CUST_P10009884 | 5292 | 5351 | 2320 | Human papillomavirus type 6b (HPV 16) | L2 | Capsid |
| CUST_P10009885 | 5444 | 5503 | 2321 | Human papillomavirus type 6b (HPV 16) | L2 | Capsid |
| CUST_P10009886 | 5527 | 5586 | 2322 | Human papillomavirus type 6b (HPV 16) | L2 | Capsid |
| CUST_P10009887 | 5685 | 5744 | 2323 | Human papillomavirus type 6b (HPV 16) | L2 | Capsid |
| CUST_P10009888 | 5849 | 5908 | 2324 | Human papillomavirus type 6b (HPV 16) | L1 | PolyA |
| CUST_P10009891 | 6051 | 6110 | 2325 | Human papillomavirus type 6b (HPV 16) | L1 | PolyA |
| CUST_P10009892 | 6078 | 6137 | 2326 | Human papillomavirus type 6b (HPV 16) | L1 | PolyA |
| CUST_P10009893 | 6192 | 6251 | 2327 | Human papillomavirus type 6b (HPV 16) | L1 | PolyA |
| CUST_P10009894 | 6527 | 6586 | 2328 | Human papillomavirus type 6b (HPV 16) | L1 | PolyA |
| CUST_P10009895 | 6551 | 6610 | 2329 | Human papillomavirus type 6b (HPV 16) | L1 | PolyA |
| CUST_P10009896 | 6735 | 6794 | 2330 | Human papillomavirus type 6b (HPV 16) | L1 | PolyA |

TABLE 8-continued

Exemplary DNA virus probes

| ProbeID | Start | End | SEQ ID NO: | Virus | Genomic Region | Product |
|---|---|---|---|---|---|---|
| CUST_P10009897 | 6786 | 6845 | 2331 | Human papillomavirus type 6b (HPV 16) | L1 | PolyA |
| CUST_P10009898 | 6868 | 6923 | 2332 | Human papillomavirus type 6b (HPV 16) | L1 | PolyA |
| CUST_P10009899 | 7030 | 7089 | 2333 | Human papillomavirus type 6b (HPV 16) | L1 | PolyA |
| CUST_P10009900 | 7329 | 7388 | 2334 | Human papillomavirus type 6b (HPV 16) | L1 | PolyA |
| CUST_P10009901 | 7571 | 7620 | 2335 | Human papillomavirus type 6b (HPV 16) | L1 | PolyA |
| CUST_P10009902 | 7677 | 7736 | 2336 | Human papillomavirus type 6b (HPV 16) | L1 | PolyA |
| CUST_P10009903 | 7700 | 7759 | 2337 | Human papillomavirus type 6b (HPV 16) | L1 | PolyA |
| CUST_P10009904 | 7723 | 7782 | 2338 | Human papillomavirus type 6b (HPV 16) | L1 | PolyA |
| CUST_P10009905 | 7756 | 7815 | 2339 | Human papillomavirus type 6b (HPV 16) | L1 | PolyA |
| CUST_P10009906 | 7789 | 7848 | 2340 | Human papillomavirus type 6b (HPV 16) | L1 | PolyA |
| CUST_P10009907 | 7824 | 7880 | 2341 | Human papillomavirus type 6b (HPV 16) | L1 | PolyA |
| CUST_P10009908 | 7846 | 7905 | 2342 | Human papillomavirus type 6b (HPV 16) | L1 | PolyA |
| CUST_P10009909 | 6 | 65 | 2343 | Human papillomavirus type 6b (HPV 18) | E6 | Regulatory Protein |
| CUST_P10009910 | 60 | 116 | 2344 | Human papillomavirus type 6b (HPV 18) | E6 | Regulatory Protein |
| CUST_P10009911 | 182 | 241 | 2345 | Human papillomavirus type 6b (HPV 18) | E6 | Regulatory Protein |
| CUST_P10009912 | 233 | 292 | 2346 | Human papillomavirus type 6b (HPV 18) | E6 | Regulatory Protein |
| CUST_P10009913 | 254 | 313 | 2347 | Human papillomavirus type 6b (HPV 18) | E6 | Regulatory Protein |
| CUST_P10009914 | 291 | 350 | 2348 | Human papillomavirus type 6b (HPV 18) | E6 | Regulatory Protein |
| CUST_P10009915 | 339 | 398 | 2349 | Human papillomavirus type 6b (HPV 18) | E6 | Regulatory Protein |
| CUST_P10009916 | 369 | 428 | 2350 | Human papillomavirus type 6b (HPV 18) | E6 | Regulatory Protein |
| CUST_P10009917 | 422 | 468 | 2351 | Human papillomavirus type 6b (HPV 18) | E6 | Regulatory Protein |
| CUST_P10009918 | 535 | 583 | 2352 | Human papillomavirus type 6b (HPV 18) | E6 | Regulatory Protein |
| CUST_P10009919 | 560 | 619 | 2353 | Human papillomavirus type 6b (HPV 18) | E6 | Regulatory Protein |
| CUST_P10009920 | 594 | 651 | 2354 | Human papillomavirus type 6b (HPV 18) | E7 | Regulatory Protein |
| CUST_P10009921 | 643 | 694 | 2355 | Human papillomavirus type 6b (HPV 18) | E7 | Regulatory Protein |
| CUST_P10009922 | 681 | 740 | 2356 | Human papillomavirus type 6b (HPV 18) | E7 | Regulatory Protein |
| CUST_P10009925 | 1017 | 1071 | 2357 | Human papillomavirus type 6b (HPV 18) | E1 | Regulatory Protein |
| CUST_P10009926 | 1134 | 1187 | 2358 | Human papillomavirus type 6b (HPV 18) | E1 | Regulatory Protein |
| CUST_P10009927 | 1302 | 1357 | 2359 | Human papillomavirus type 6b (HPV 18) | E1 | Regulatory Protein |
| CUST_P10009928 | 1663 | 1722 | 2360 | Human papillomavirus type 6b (HPV 18) | E1 | Regulatory Protein |
| CUST_P10009929 | 1691 | 1750 | 2361 | Human papillomavirus type 6b (HPV 18) | E1 | Regulatory Protein |
| CUST_P10009930 | 1719 | 1778 | 2362 | Human papillomavirus type 6b (HPV 18) | E1 | Regulatory Protein |
| CUST_P10009931 | 1883 | 1942 | 2363 | Human papillomavirus type 6b (HPV 18) | E1 | Regulatory Protein |
| CUST_P10009932 | 1937 | 1996 | 2364 | Human papillomavirus type 6b (HPV 18) | E1 | Regulatory Protein |
| CUST_P10009933 | 2186 | 2245 | 2365 | Human papillomavirus type 6b (HPV 18) | E1 | Regulatory Protein |
| CUST_P10009934 | 2210 | 2269 | 2366 | Human papillomavirus type 6b (HPV 18) | E1 | Regulatory Protein |
| CUST_P10009935 | 2392 | 2451 | 2367 | Human papillomavirus type 6b (HPV 18) | E1 | Regulatory Protein |

TABLE 8-continued

Exemplary DNA virus probes

| ProbeID | Start | End | SEQ ID NO: | Virus | Genomic Region | Product |
|---|---|---|---|---|---|---|
| CUST_P10009936 | 2430 | 2489 | 2368 | Human papillomavirus type 6b (HPV 18) | E1 | Regulatory Protein |
| CUST_P10009937 | 2471 | 2520 | 2369 | Human papillomavirus type 6b (HPV 18) | E1 | Regulatory Protein |
| CUST_P10009938 | 2512 | 2571 | 2370 | Human papillomavirus type 6b (HPV 18) | E1 | Regulatory Protein |
| CUST_P10009939 | 2558 | 2617 | 2371 | Human papillomavirus type 6b (HPV 18) | E1 | Regulatory Protein |
| CUST_P10009940 | 2606 | 2665 | 2372 | Human papillomavirus type 6b (HPV 18) | E1 | Regulatory Protein |
| CUST_P10009941 | 2642 | 2701 | 2373 | Human papillomavirus type 6b (HPV 18) | E1 | Regulatory Protein |
| CUST_P10009942 | 2808 | 2852 | 2374 | Human papillomavirus type 6b (HPV 18) | E1 | Regulatory Protein |
| CUST_P10009943 | 2837 | 2891 | 2375 | Human papillomavirus type 6b (HPV 18) | E2 | Regulatory Protein |
| CUST_P10009944 | 2858 | 2917 | 2376 | Human papillomavirus type 6b (HPV 18) | E2 | Regulatory Protein |
| CUST_P10009945 | 2885 | 2944 | 2377 | Human papillomavirus type 6b (HPV 18) | E2 | Regulatory Protein |
| CUST_P10009946 | 2914 | 2973 | 2378 | Human papillomavirus type 6b (HPV 18) | E2 | Regulatory Protein |
| CUST_P10009947 | 3085 | 3133 | 2379 | Human papillomavirus type 6b (HPV 18) | E2 | Regulatory Protein |
| CUST_P10009948 | 3205 | 3264 | 2380 | Human papillomavirus type 6b (HPV 18) | E2 | Regulatory Protein |
| CUST_P10009949 | 3260 | 3312 | 2381 | Human papillomavirus type 6b (HPV 18) | E2 | Regulatory Protein |
| CUST_P10009952 | 3727 | 3781 | 2382 | Human papillomavirus type 6b (HPV 18) | E2 | Regulatory Protein |
| CUST_P10009953 | 3753 | 3807 | 2383 | Human papillomavirus type 6b (HPV 18) | E4 | Regulatory Protein |
| CUST_P10009954 | 4025 | 4080 | 2384 | Human papillomavirus type 6b (HPV 18) | E5 | Regulatory Protein |
| CUST_P10009955 | 4262 | 4316 | 2385 | Human papillomavirus type 6b (HPV 18) | L2 | Capsid |
| CUST_P10009956 | 4357 | 4414 | 2386 | Human papillomavirus type 6b (HPV 18) | L2 | Capsid |
| CUST_P10009959 | 4544 | 4599 | 2387 | Human papillomavirus type 6b (HPV 18) | L2 | Capsid |
| CUST_P10009960 | 4678 | 4735 | 2388 | Human papillomavirus type 6b (HPV 18) | L2 | Capsid |
| CUST_P10009961 | 4704 | 4762 | 2389 | Human papillomavirus type 6b (HPV 18) | L2 | Capsid |
| CUST_P10009962 | 4796 | 4852 | 2390 | Human papillomavirus type 6b (HPV 18) | L2 | Capsid |
| CUST_P10009964 | 4933 | 4979 | 2391 | Human papillomavirus type 6b (HPV 18) | L2 | Capsid |
| CUST_P10009965 | 4947 | 5002 | 2392 | Human papillomavirus type 6b (HPV 18) | L2 | Capsid |
| CUST_P10009967 | 5016 | 5075 | 2393 | Human papillomavirus type 6b (HPV 18) | L2 | Capsid |
| CUST_P10009968 | 5037 | 5096 | 2394 | Human papillomavirus type 6b (HPV 18) | L2 | Capsid |
| CUST_P10009969 | 5067 | 5119 | 2395 | Human papillomavirus type 6b (HPV 18) | L2 | Capsid |
| CUST_P10009970 | 5218 | 5269 | 2396 | Human papillomavirus type 6b (HPV 18) | L2 | Capsid |
| CUST_P10009971 | 5412 | 5462 | 2397 | Human papillomavirus type 6b (HPV 18) | L2 | Capsid |
| CUST_P10009972 | 5437 | 5495 | 2398 | Human papillomavirus type 6b (HPV 18) | L2 | Capsid |
| CUST_P10009973 | 5635 | 5693 | 2399 | Human papillomavirus type 6b (HPV 18) | L2 | Capsid |
| CUST_P10009975 | 5781 | 5840 | 2400 | Human papillomavirus type 6b (HPV 18) | L1 | PolyA |
| CUST_P10009976 | 5823 | 5882 | 2401 | Human papillomavirus type 6b (HPV 18) | L1 | PolyA |
| CUST_P10009977 | 5844 | 5903 | 2402 | Human papillomavirus type 6b (HPV 18) | L1 | PolyA |
| CUST_P10009978 | 5873 | 5927 | 2403 | Human papillomavirus type 6b (HPV 18) | L1 | PolyA |
| CUST_P10009979 | 6014 | 6068 | 2404 | Human papillomavirus type 6b (HPV 18) | L1 | PolyA |

TABLE 8-continued

Exemplary DNA virus probes

| ProbeID | Start | End | SEQ ID NO: | Virus | Genomic Region | Product |
|---|---|---|---|---|---|---|
| CUST_P10009980 | 6030 | 6089 | 2405 | Human papillomavirus type 6b (HPV 18) | L1 | PolyA |
| CUST_P10009981 | 6111 | 6158 | 2406 | Human papillomavirus type 6b (HPV 18) | L1 | PolyA |
| CUST_P10009982 | 6122 | 6167 | 2407 | Human papillomavirus type 6b (HPV 18) | L1 | PolyA |
| CUST_P10009983 | 6149 | 6200 | 2408 | Human papillomavirus type 6b (HPV 18) | L1 | PolyA |
| CUST_P10009984 | 6175 | 6234 | 2409 | Human papillomavirus type 6b (HPV 18) | L1 | PolyA |
| CUST_P10009985 | 6284 | 6343 | 2410 | Human papillomavirus type 6b (HPV 18) | L1 | PolyA |
| CUST_P10009986 | 6409 | 6462 | 2411 | Human papillomavirus type 6b (HPV 18) | L1 | PolyA |
| CUST_P10009987 | 6516 | 6575 | 2412 | Human papillomavirus type 6b (HPV 18) | L1 | PolyA |
| CUST_P10009988 | 6547 | 6606 | 2413 | Human papillomavirus type 6b (HPV 18) | L1 | PolyA |
| CUST_P10009989 | 6669 | 6728 | 2414 | Human papillomavirus type 6b (HPV 18) | L1 | PolyA |
| CUST_P10009990 | 6765 | 6824 | 2415 | Human papillomavirus type 6b (HPV 18) | L1 | PolyA |
| CUST_P10009991 | 6890 | 6947 | 2416 | Human papillomavirus type 6b (HPV 18) | L1 | PolyA |
| CUST_P10009992 | 6911 | 6970 | 2417 | Human papillomavirus type 6b (HPV 18) | L1 | PolyA |
| CUST_P10009993 | 6954 | 7013 | 2418 | Human papillomavirus type 6b (HPV 18) | L1 | PolyA |
| CUST_P10009994 | 6997 | 7042 | 2419 | Human papillomavirus type 6b (HPV 18) | L1 | PolyA |
| CUST_P10010004 | 44 | 88 | 2420 | Hepatitis B virus subtype adw | S | surface protein |
| CUST_P10010005 | 78 | 126 | 2421 | Hepatitis B virus subtype adw | S | surface protein |
| CUST_P10010006 | 158 | 202 | 2422 | Hepatitis B virus subtype adw | S | surface protein |
| CUST_P10010008 | 230 | 281 | 2423 | Hepatitis B virus subtype adw | S | surface protein |
| CUST_P10010009 | 267 | 311 | 2424 | Hepatitis B virus subtype adw | S | surface protein |
| CUST_P10010010 | 328 | 372 | 2425 | Hepatitis B virus subtype adw | S | surface protein |
| CUST_P10010011 | 394 | 453 | 2426 | Hepatitis B virus subtype adw | S | surface protein |
| CUST_P10010012 | 419 | 475 | 2427 | Hepatitis B virus subtype adw | S | surface protein |
| CUST_P10010013 | 441 | 494 | 2428 | Hepatitis B virus subtype adw | S | surface protein |
| CUST_P10010015 | 600 | 647 | 2429 | Hepatitis B virus subtype adw | S | surface protein |
| CUST_P10010016 | 624 | 668 | 2430 | Hepatitis B virus subtype adw | S | surface protein |
| CUST_P10010017 | 840 | 899 | 2431 | Hepatitis B virus subtype adw | S | surface protein |
| CUST_P10010018 | 981 | 1036 | 2432 | Hepatitis B virus subtype adw | C | Core |
| CUST_P10010019 | 1040 | 1099 | 2433 | Hepatitis B virus subtype adw | C | Core |
| CUST_P10010020 | 1085 | 1144 | 2434 | Hepatitis B virus subtype adw | C | Core |
| CUST_P10010021 | 1130 | 1174 | 2435 | Hepatitis B virus subtype adw | C | Core |
| CUST_P10010022 | 1170 | 1214 | 2436 | Hepatitis B virus subtype adw | C | Core |
| CUST_P10010023 | 1216 | 1260 | 2437 | Hepatitis B virus subtype adw | C | Core |
| CUST_P10010024 | 1241 | 1285 | 2438 | Hepatitis B virus subtype adw | C | Core |
| CUST_P10010025 | 1282 | 1326 | 2439 | Hepatitis B virus subtype adw | C | Core |
| CUST_P10010026 | 1453 | 1497 | 2440 | Hepatitis B virus subtype adw | C | Core |
| CUST_P10010027 | 1560 | 1605 | 2441 | Hepatitis B virus subtype adw | C | Core |
| CUST_P10010028 | 1581 | 1625 | 2442 | Hepatitis B virus subtype adw | C | Core |
| CUST_P10010029 | 1623 | 1667 | 2443 | Hepatitis B virus subtype adw | C | Core |
| CUST_P10010030 | 1643 | 1691 | 2444 | Hepatitis B virus subtype adw | C | Core |
| CUST_P10010031 | 1679 | 1728 | 2445 | Hepatitis B virus subtype adw | C | Core |
| CUST_P10010032 | 1696 | 1743 | 2446 | Hepatitis B virus subtype adw | C | Core |
| CUST_P10010033 | 1743 | 1796 | 2447 | Hepatitis B virus subtype adw | C | Core |
| CUST_P10010034 | 1948 | 1998 | 2448 | Hepatitis B virus subtype adw | C | Core |
| CUST_P10010035 | 2054 | 2099 | 2449 | Hepatitis B virus subtype adw | C | Core |
| CUST_P10010036 | 2131 | 2190 | 2450 | Hepatitis B virus subtype adw | C | Core |
| CUST_P10010037 | 2164 | 2223 | 2451 | Hepatitis B virus subtype adw | C | Core |
| CUST_P10010038 | 2208 | 2267 | 2452 | Hepatitis B virus subtype adw | C | Core |
| CUST_P10010039 | 2238 | 2285 | 2453 | Hepatitis B virus subtype adw | C | Core |
| CUST_P10010040 | 2275 | 2321 | 2454 | Hepatitis B virus subtype adw | C | Core |
| CUST_P10010041 | 2293 | 2349 | 2455 | Hepatitis B virus subtype adw | C | Core |
| CUST_P10010042 | 2334 | 2378 | 2456 | Hepatitis B virus subtype adw | C | Core |
| CUST_P10010044 | 2416 | 2463 | 2457 | Hepatitis B virus subtype adw | C | Core |
| CUST_P10010045 | 2431 | 2490 | 2458 | Hepatitis B virus subtype adw | C | Core |
| CUST_P10010046 | 2469 | 2528 | 2459 | Hepatitis B virus subtype adw | C | Core |
| CUST_P10010047 | 2510 | 2569 | 2460 | Hepatitis B virus subtype adw | C | Core |
| CUST_P10010048 | 2539 | 2598 | 2461 | Hepatitis B virus subtype adw | C | Core |
| CUST_P10010049 | 2666 | 2725 | 2462 | Hepatitis B virus subtype adw | C | Core |
| CUST_P10010050 | 2690 | 2749 | 2463 | Hepatitis B virus subtype adw | C | Core |
| CUST_P10010051 | 2723 | 2782 | 2464 | Hepatitis B virus subtype adw | C | Core |

TABLE 8-continued

Exemplary DNA virus probes

| ProbeID | Start | End | SEQ ID NO: | Virus | Genomic Region | Product |
|---|---|---|---|---|---|---|
| CUST_P10010052 | 2868 | 2912 | 2465 | Hepatitis B virus subtype adw | C | Core |
| CUST_P10010053 | 2933 | 2980 | 2466 | Hepatitis B virus subtype adw | P | Pol |
| CUST_P10010054 | 2961 | 3007 | 2467 | Hepatitis B virus subtype adw | P | Pol |
| CUST_P10010055 | 2976 | 3020 | 2468 | Hepatitis B virus subtype adw | P | Pol |
| CUST_P10010056 | 3014 | 3058 | 2469 | Hepatitis B virus subtype adw | P | Pol |
| CUST_P10010058 | 3163 | 3207 | 2470 | Hepatitis B virus subtype adw | P | Pol |
| CUST_P10010059 | 1 | 46 | 2471 | Hepatitis B virus subtype ayw | S | surface protein |
| CUST_P10010060 | 74 | 118 | 2472 | Hepatitis B virus subtype ayw | S | surface protein |
| CUST_P10010061 | 93 | 138 | 2473 | Hepatitis B virus subtype ayw | S | surface protein |
| CUST_P10010062 | 114 | 158 | 2474 | Hepatitis B virus subtype ayw | S | surface protein |
| CUST_P10010063 | 155 | 201 | 2475 | Hepatitis B virus subtype ayw | S | surface protein |
| CUST_P10010064 | 190 | 240 | 2476 | Hepatitis B virus subtype ayw | S | surface protein |
| CUST_P10010065 | 234 | 283 | 2477 | Hepatitis B virus subtype ayw | S | surface protein |
| CUST_P10010066 | 264 | 313 | 2478 | Hepatitis B virus subtype ayw | S | surface protein |
| CUST_P10010067 | 295 | 339 | 2479 | Hepatitis B virus subtype ayw | S | surface protein |
| CUST_P10010068 | 330 | 374 | 2480 | Hepatitis B virus subtype ayw | S | surface protein |
| CUST_P10010069 | 369 | 416 | 2481 | Hepatitis B virus subtype ayw | S | surface protein |
| CUST_P10010070 | 392 | 447 | 2482 | Hepatitis B virus subtype ayw | S | surface protein |
| CUST_P10010071 | 443 | 493 | 2483 | Hepatitis B virus subtype ayw | S | surface protein |
| CUST_P10010072 | 473 | 517 | 2484 | Hepatitis B virus subtype ayw | S | surface protein |
| CUST_P10010073 | 600 | 645 | 2485 | Hepatitis B virus subtype ayw | S | surface protein |
| CUST_P10010076 | 851 | 907 | 2486 | Hepatitis B virus subtype ayw | X | x-protein |
| CUST_P10010077 | 983 | 1033 | 2487 | Hepatitis B virus subtype ayw | X | x-protein |
| CUST_P10010078 | 1028 | 1087 | 2488 | Hepatitis B virus subtype ayw | X | x-protein |
| CUST_P10010079 | 1091 | 1147 | 2489 | Hepatitis B virus subtype ayw | X | x-protein |
| CUST_P10010080 | 1161 | 1205 | 2490 | Hepatitis B virus subtype ayw | X | x-protein |
| CUST_P10010081 | 1218 | 1262 | 2491 | Hepatitis B virus subtype ayw | X | x-protein |
| CUST_P10010082 | 1265 | 1309 | 2492 | Hepatitis B virus subtype ayw | X | x-protein |
| CUST_P10010083 | 1319 | 1374 | 2493 | Hepatitis B virus subtype ayw | X | x-protein |
| CUST_P10010084 | 1384 | 1429 | 2494 | Hepatitis B virus subtype ayw | X | x-protein |
| CUST_P10010085 | 1446 | 1490 | 2495 | Hepatitis B virus subtype ayw | X | x-protein |
| CUST_P10010086 | 1476 | 1520 | 2496 | Hepatitis B virus subtype ayw | X | x-protein |
| CUST_P10010087 | 1528 | 1572 | 2497 | Hepatitis B virus subtype ayw | X | x-protein |
| CUST_P10010088 | 1552 | 1596 | 2498 | Hepatitis B virus subtype ayw | X | x-protein |
| CUST_P10010089 | 1610 | 1654 | 2499 | Hepatitis B virus subtype ayw | X | x-protein |
| CUST_P10010090 | 1636 | 1685 | 2500 | Hepatitis B virus subtype ayw | X | x-protein |
| CUST_P10010092 | 1815 | 1870 | 2501 | Hepatitis B virus subtype ayw | C | Core |
| CUST_P10010093 | 2042 | 2088 | 2502 | Hepatitis B virus subtype ayw | C | Core |
| CUST_P10010094 | 2133 | 2192 | 2503 | Hepatitis B virus subtype ayw | C | Core |
| CUST_P10010095 | 2162 | 2221 | 2504 | Hepatitis B virus subtype ayw | C | Core |
| CUST_P10010096 | 2210 | 2269 | 2505 | Hepatitis B virus subtype ayw | C | Core |
| CUST_P10010097 | 2343 | 2387 | 2506 | Hepatitis B virus subtype ayw | C | Core |
| CUST_P10010098 | 2390 | 2434 | 2507 | Hepatitis B virus subtype ayw | C | Core |
| CUST_P10010099 | 2427 | 2477 | 2508 | Hepatitis B virus subtype ayw | C | Core |
| CUST_P10010100 | 2535 | 2594 | 2509 | Hepatitis B virus subtype ayw | C | Core |
| CUST_P10010101 | 2577 | 2636 | 2510 | Hepatitis B virus subtype ayw | P | Pol |
| CUST_P10010102 | 2641 | 2700 | 2511 | Hepatitis B virus subtype ayw | P | Pol |
| CUST_P10010103 | 2698 | 2757 | 2512 | Hepatitis B virus subtype ayw | P | Pol |
| CUST_P10010104 | 2756 | 2815 | 2513 | Hepatitis B virus subtype ayw | P | Pol |
| CUST_P10010105 | 2794 | 2845 | 2514 | Hepatitis B virus subtype ayw | P | Pol |
| CUST_P10010106 | 2824 | 2872 | 2515 | Hepatitis B virus subtype ayw | P | Pol |
| CUST_P10010107 | 2856 | 2900 | 2516 | Hepatitis B virus subtype ayw | P | Pol |
| CUST_P10010108 | 2885 | 2929 | 2517 | Hepatitis B virus subtype ayw | P | Pol |
| CUST_P10010109 | 2915 | 2963 | 2518 | Hepatitis B virus subtype ayw | P | Pol |
| CUST_P10010110 | 3046 | 3090 | 2519 | Hepatitis B virus subtype ayw | P | Pol |
| CUST_P10010111 | 3121 | 3165 | 2520 | Hepatitis B virus subtype ayw | P | Pol |
| CUST_P10010112 | 8 | 55 | 2521 | Hepatitis B virus, subtype adr | P | Pol |
| CUST_P10010113 | 79 | 125 | 2522 | Hepatitis B virus, subtype adr | P | Pol |
| CUST_P10010114 | 112 | 156 | 2523 | Hepatitis B virus, subtype adr | P | Pol |
| CUST_P10010119 | 325 | 370 | 2524 | Hepatitis B virus, subtype adr | P | Pol |
| CUST_P10010122 | 451 | 497 | 2525 | Hepatitis B virus, subtype adr | P | Pol |
| CUST_P10010123 | 477 | 521 | 2526 | Hepatitis B virus, subtype adr | P | Pol |
| CUST_P10010124 | 638 | 682 | 2527 | Hepatitis B virus, subtype adr | P | Pol |
| CUST_P10010125 | 667 | 714 | 2528 | Hepatitis B virus, subtype adr | P | Pol |
| CUST_P10010126 | 705 | 754 | 2529 | Hepatitis B virus, subtype adr | P | Pol |
| CUST_P10010127 | 839 | 894 | 2530 | Hepatitis B virus, subtype adr | P | Pol |
| CUST_P10010128 | 971 | 1022 | 2531 | Hepatitis B virus, subtype adr | P | Pol |
| CUST_P10010129 | 1088 | 1145 | 2532 | Hepatitis B virus, subtype adr | P | Pol |
| CUST_P10010131 | 1160 | 1204 | 2533 | Hepatitis B virus, subtype adr | P | Pol |
| CUST_P10010132 | 1203 | 1247 | 2534 | Hepatitis B virus, subtype adr | P | Pol |
| CUST_P10010133 | 1315 | 1361 | 2535 | Hepatitis B virus, subtype adr | P | Pol |
| CUST_P10010134 | 1458 | 1502 | 2536 | Hepatitis B virus, subtype adr | P | Pol |
| CUST_P10010136 | 1556 | 1600 | 2537 | Hepatitis B virus, subtype adr | P | Pol |
| CUST_P10010137 | 1635 | 1683 | 2538 | Hepatitis B virus, subtype adr | P | Pol |
| CUST_P10010138 | 1679 | 1729 | 2539 | Hepatitis B virus, subtype adr | C | Core |

TABLE 8-continued

Exemplary DNA virus probes

| ProbeID | Start | End | SEQ ID NO: | Virus | Genomic Region | Product |
|---|---|---|---|---|---|---|
| CUST_P10010139 | 1810 | 1864 | 2540 | Hepatitis B virus, subtype adr | C | Core |
| CUST_P10010140 | 1999 | 2043 | 2541 | Hepatitis B virus, subtype adr | C | Core |
| CUST_P10010141 | 2109 | 2153 | 2542 | Hepatitis B virus, subtype adr | C | Core |
| CUST_P10010142 | 2220 | 2279 | 2543 | Hepatitis B virus, subtype adr | C | Core |
| CUST_P10010143 | 2247 | 2294 | 2544 | Hepatitis B virus, subtype adr | C | Core |
| CUST_P10010144 | 2295 | 2346 | 2545 | Hepatitis B virus, subtype adr | C | Core |
| CUST_P10010145 | 2365 | 2409 | 2546 | Hepatitis B virus, subtype adr | C | Core |
| CUST_P10010148 | 2545 | 2604 | 2547 | Hepatitis B virus, subtype adr | P | Pol |
| CUST_P10010149 | 2575 | 2634 | 2548 | Hepatitis B virus, subtype adr | P | Pol |
| CUST_P10010150 | 2618 | 2677 | 2549 | Hepatitis B virus, subtype adr | P | Pol |
| CUST_P10010151 | 2646 | 2705 | 2550 | Hepatitis B virus, subtype adr | P | Pol |
| CUST_P10010152 | 2672 | 2731 | 2551 | Hepatitis B virus, subtype adr | P | Pol |
| CUST_P10010153 | 2699 | 2758 | 2552 | Hepatitis B virus, subtype adr | P | Pol |
| CUST_P10010154 | 2735 | 2794 | 2553 | Hepatitis B virus, subtype adr | P | Pol |
| CUST_P10010156 | 2928 | 2972 | 2554 | Hepatitis B virus, subtype adr | S1 | surface protein |
| CUST_P10010157 | 2976 | 3020 | 2555 | Hepatitis B virus, subtype adr | S1 | surface protein |
| CUST_P10010158 | 3063 | 3107 | 2556 | Hepatitis B virus, subtype adr | S1 | surface protein |
| CUST_P10010159 | 42 | 86 | 2557 | Hepatitis B virus, subtype ayr | P | Pol |
| CUST_P10010160 | 79 | 126 | 2558 | Hepatitis B virus, subtype ayr | P | Pol |
| CUST_P10010161 | 133 | 177 | 2559 | Hepatitis B virus, subtype ayr | S | surface protein |
| CUST_P10010162 | 158 | 202 | 2560 | Hepatitis B virus, subtype ayr | S | surface protein |
| CUST_P10010163 | 190 | 238 | 2561 | Hepatitis B virus, subtype ayr | S | surface protein |
| CUST_P10010164 | 227 | 280 | 2562 | Hepatitis B virus, subtype ayr | S | surface protein |
| CUST_P10010165 | 272 | 316 | 2563 | Hepatitis B virus, subtype ayr | S | surface protein |
| CUST_P10010166 | 328 | 372 | 2564 | Hepatitis B virus, subtype ayr | S | surface protein |
| CUST_P10010167 | 366 | 414 | 2565 | Hepatitis B virus, subtype ayr | S | surface protein |
| CUST_P10010168 | 390 | 447 | 2566 | Hepatitis B virus, subtype ayr | S | surface protein |
| CUST_P10010169 | 452 | 500 | 2567 | Hepatitis B virus, subtype ayr | S | surface protein |
| CUST_P10010170 | 477 | 521 | 2568 | Hepatitis B virus, subtype ayr | S | surface protein |
| CUST_P10010171 | 598 | 642 | 2569 | Hepatitis B virus, subtype ayr | S | surface protein |
| CUST_P10010172 | 659 | 707 | 2570 | Hepatitis B virus, subtype ayr | S | surface protein |
| CUST_P10010173 | 839 | 898 | 2571 | Hepatitis B virus, subtype ayr | P | Pol |
| CUST_P10010174 | 971 | 1023 | 2572 | Hepatitis B virus, subtype ayr | P | Pol |
| CUST_P10010175 | 1087 | 1146 | 2573 | Hepatitis B virus, subtype ayr | P | Pol |
| CUST_P10010176 | 1116 | 1163 | 2574 | Hepatitis B virus, subtype ayr | P | Pol |
| CUST_P10010177 | 1151 | 1195 | 2575 | Hepatitis B virus, subtype ayr | P | Pol |
| CUST_P10010179 | 1318 | 1366 | 2576 | Hepatitis B virus, subtype ayr | P | Pol |
| CUST_P10010180 | 1356 | 1400 | 2577 | Hepatitis B virus, subtype ayr | X | x-protein |
| CUST_P10010181 | 1388 | 1432 | 2578 | Hepatitis B virus, subtype ayr | X | x-protein |
| CUST_P10010182 | 1419 | 1463 | 2579 | Hepatitis B virus, subtype ayr | X | x-protein |
| CUST_P10010183 | 1472 | 1516 | 2580 | Hepatitis B virus, subtype ayr | X | x-protein |
| CUST_P10010185 | 1565 | 1609 | 2581 | Hepatitis B virus, subtype ayr | X | x-protein |
| CUST_P10010187 | 1643 | 1690 | 2582 | Hepatitis B virus, subtype ayr | X | x-protein |
| CUST_P10010188 | 1675 | 1725 | 2583 | Hepatitis B virus, subtype ayr | X | x-protein |
| CUST_P10010189 | 1808 | 1856 | 2584 | Hepatitis B virus, subtype ayr | X | x-protein |
| CUST_P10010190 | 1941 | 1996 | 2585 | Hepatitis B virus, subtype ayr | C | Core |
| CUST_P10010191 | 2001 | 2045 | 2586 | Hepatitis B virus, subtype ayr | C | Core |
| CUST_P10010192 | 2111 | 2155 | 2587 | Hepatitis B virus, subtype ayr | C | Core |
| CUST_P10010193 | 2210 | 2266 | 2588 | Hepatitis B virus, subtype ayr | C | Core |
| CUST_P10010194 | 2290 | 2335 | 2589 | Hepatitis B virus, subtype ayr | C | Core |
| CUST_P10010195 | 2365 | 2409 | 2590 | Hepatitis B virus, subtype ayr | C | Core |
| CUST_P10010196 | 2410 | 2456 | 2591 | Hepatitis B virus, subtype ayr | C | Core |
| CUST_P10010197 | 2430 | 2484 | 2592 | Hepatitis B virus, subtype ayr | C | Core |
| CUST_P10010198 | 2516 | 2571 | 2593 | Hepatitis B virus, subtype ayr | C | Core |
| CUST_P10010199 | 2577 | 2636 | 2594 | Hepatitis B virus, subtype ayr | C | Core |
| CUST_P10010200 | 2629 | 2688 | 2595 | Hepatitis B virus, subtype ayr | C | Core |
| CUST_P10010201 | 2675 | 2734 | 2596 | Hepatitis B virus, subtype ayr | C | Core |
| CUST_P10010202 | 2702 | 2761 | 2597 | Hepatitis B virus, subtype ayr | C | Core |
| CUST_P10010203 | 2742 | 2801 | 2598 | Hepatitis B virus, subtype ayr | C | Core |
| CUST_P10010204 | 2890 | 2936 | 2599 | Hepatitis B virus, subtype ayr | S | surface protein |
| CUST_P10010205 | 2955 | 3001 | 2600 | Hepatitis B virus, subtype ayr | S | surface protein |
| CUST_P10010206 | 2978 | 3022 | 2601 | Hepatitis B virus, subtype ayr | S | surface protein |
| CUST_P10010207 | 3012 | 3056 | 2602 | Hepatitis B virus, subtype ayr | S | surface protein |
| CUST_P10010208 | 57 | 104 | 2603 | Human parvovirus B19 | NS | non-structural protein NS1 |
| CUST_P10010209 | 227 | 271 | 2604 | Human parvovirus B19 | NS | non-structural protein NS2 |
| CUST_P10010211 | 637 | 693 | 2605 | Human parvovirus B19 | NS | non-structural protein NS1 |
| CUST_P10010212 | 685 | 744 | 2606 | Human parvovirus B19 | NS | non-structural protein NS1 |
| CUST_P10010214 | 973 | 1032 | 2607 | Human parvovirus B19 | NS | non-structural protein NS1 |
| CUST_P10010215 | 1065 | 1124 | 2608 | Human parvovirus B19 | NS | non-structural protein NS1 |

TABLE 8-continued

Exemplary DNA virus probes

| ProbeID | Start | End | SEQ ID NO: | Virus | Genomic Region | Product |
|---|---|---|---|---|---|---|
| CUST_P10010216 | 1165 | 1210 | 2609 | Human parvovirus B19 | NS | non-structural protein NS1 |
| CUST_P10010217 | 1220 | 1279 | 2610 | Human parvovirus B19 | NS | non-structural protein NS1 |
| CUST_P10010218 | 1258 | 1317 | 2611 | Human parvovirus B19 | NS | non-structural protein NS1 |
| CUST_P10010219 | 1357 | 1416 | 2612 | Human parvovirus B19 | NS | non-structural protein NS1 |
| CUST_P10010220 | 1408 | 1467 | 2613 | Human parvovirus B19 | NS | non-structural protein NS1 |
| CUST_P10010221 | 1542 | 1601 | 2614 | Human parvovirus B19 | NS | non-structural protein NS1 |
| CUST_P10010222 | 1628 | 1687 | 2615 | Human parvovirus B19 | NS | non-structural protein NS1 |
| CUST_P10010223 | 1767 | 1812 | 2616 | Human parvovirus B19 | NS | non-structural protein NS1 |
| CUST_P10010224 | 1845 | 1902 | 2617 | Human parvovirus B19 | NS | non-structural protein NS1 |
| CUST_P10010225 | 1911 | 1970 | 2618 | Human parvovirus B19 | NS | non-structural protein NS1 |
| CUST_P10010226 | 2041 | 2096 | 2619 | Human parvovirus B19 | NS | non-structural protein NS1 |
| CUST_P10010227 | 2257 | 2301 | 2620 | Human parvovirus B19 | NS | non-structural protein NS1 |
| CUST_P10010228 | 2351 | 2399 | 2621 | Human parvovirus B19 | NS | non-structural protein NS1 |
| CUST_P10010229 | 2395 | 2446 | 2622 | Human parvovirus B19 | NS | non-structural protein NS1 |
| CUST_P10010230 | 2426 | 2478 | 2623 | Human parvovirus B19 | NS | non-structural protein NS1 |
| CUST_P10010231 | 2552 | 2607 | 2624 | Human parvovirus B19 | NS | non-structural protein NS1 |
| CUST_P10010232 | 2787 | 2846 | 2625 | Human parvovirus B19 | VP1 | minor capsid protein |
| CUST_P10010233 | 2836 | 2895 | 2626 | Human parvovirus B19 | VP1 | minor capsid protein |
| CUST_P10010234 | 2868 | 2915 | 2627 | Human parvovirus B19 | VP1 | minor capsid protein |
| CUST_P10010235 | 2914 | 2973 | 2628 | Human parvovirus B19 | VP1 | minor capsid protein |
| CUST_P10010236 | 3081 | 3140 | 2629 | Human parvovirus B19 | VP1 | minor capsid protein |
| CUST_P10010237 | 3252 | 3297 | 2630 | Human parvovirus B19 | VP1 | minor capsid protein |
| CUST_P10010238 | 3276 | 3330 | 2631 | Human parvovirus B19 | VP1 | minor capsid protein |
| CUST_P10010239 | 3422 | 3481 | 2632 | Human parvovirus B19 | VP1 | minor capsid protein |
| CUST_P10010240 | 3524 | 3583 | 2633 | Human parvovirus B19 | VP1 | minor capsid protein |
| CUST_P10010241 | 3652 | 3711 | 2634 | Human parvovirus B19 | VP1 | minor capsid protein |
| CUST_P10010242 | 3801 | 3856 | 2635 | Human parvovirus B19 | VP1 | minor capsid protein |
| CUST_P10010243 | 3826 | 3885 | 2636 | Human parvovirus B19 | VP1 | minor capsid protein |
| CUST_P10010244 | 3864 | 3923 | 2637 | Human parvovirus B19 | VP1 | minor capsid protein |
| CUST_P10010245 | 3996 | 4042 | 2638 | Human parvovirus B19 | VP1 | minor capsid protein |
| CUST_P10010246 | 4097 | 4156 | 2639 | Human parvovirus B19 | VP1 | minor capsid protein |
| CUST_P10010247 | 4334 | 4393 | 2640 | Human parvovirus B19 | VP1 | minor capsid protein |
| CUST_P10010248 | 4463 | 4522 | 2641 | Human parvovirus B19 | VP1 | minor capsid protein |
| CUST_P10010249 | 4587 | 4646 | 2642 | Human parvovirus B19 | VP1 | minor capsid protein |
| CUST_P10010250 | 4723 | 4782 | 2643 | Human parvovirus B19 | VP1 | minor capsid protein |
| CUST_P10010251 | 4820 | 4864 | 2644 | Human parvovirus B19 | VP1 | minor capsid protein |
| CUST_P10010252 | 4915 | 4960 | 2645 | Human parvovirus B19 | VP1 | minor capsid protein |

TABLE 8-continued

Exemplary DNA virus probes

| ProbeID | Start | End | SEQ ID NO: | Virus | Genomic Region | Product |
|---|---|---|---|---|---|---|
| CUST_P10010254 | 5087 | 5146 | 2646 | Human parvovirus B19 | VP2 | major capsid protein |
| CUST_P10010257 | 5492 | 5539 | 2647 | Human parvovirus B19 | VP2 | major capsid protein |

TABLE 9

Exemplary bacterial and protozoan probes

| SEQ ID NO: | ProbeID | Start | End | Pathogen | Genomic Region | Product |
|---|---|---|---|---|---|---|
| 2648 | CUST_P10011833 | 115100 | 115153 | *Treponema pallidum* | polA | Polymerase |
| 2649 | CUST_P10011835 | 115167 | 115219 | *Treponema pallidum* | polA | Polymerase |
| 2650 | CUST_P10011836 | 115187 | 115237 | *Treponema pallidum* | polA | Polymerase |
| 2651 | CUST_P10011838 | 115259 | 115314 | *Treponema pallidum* | polA | Polymerase |
| 2652 | CUST_P10011840 | 115554 | 115613 | *Treponema pallidum* | polA | Polymerase |
| 2653 | CUST_P10011841 | 115579 | 115638 | *Treponema pallidum* | polA | Polymerase |
| 2654 | CUST_P10011842 | 115605 | 115664 | *Treponema pallidum* | polA | Polymerase |
| 2655 | CUST_P10011843 | 115667 | 115716 | *Treponema pallidum* | polA | Polymerase |
| 2656 | CUST_P10011844 | 115696 | 115740 | *Treponema pallidum* | polA | Polymerase |
| 2657 | CUST_P10011845 | 115755 | 115807 | *Treponema pallidum* | polA | Polymerase |
| 2658 | CUST_P10011847 | 116076 | 116126 | *Treponema pallidum* | polA | Polymerase |
| 2659 | CUST_P10011848 | 116171 | 116223 | *Treponema pallidum* | polA | Polymerase |
| 2660 | CUST_P10011849 | 116242 | 116294 | *Treponema pallidum* | polA | Polymerase |
| 2661 | CUST_P10011850 | 116332 | 116384 | *Treponema pallidum* | polA | Polymerase |
| 2662 | CUST_P10011851 | 116352 | 116396 | *Treponema pallidum* | polA | Polymerase |
| 2663 | CUST_P10011852 | 116408 | 116459 | *Treponema pallidum* | polA | Polymerase |
| 2664 | CUST_P10011853 | 116430 | 116488 | *Treponema pallidum* | polA | Polymerase |
| 2665 | CUST_P10011854 | 116601 | 116649 | *Treponema pallidum* | polA | Polymerase |
| 2666 | CUST_P10011855 | 116623 | 116674 | *Treponema pallidum* | polA | Polymerase |
| 2667 | CUST_P10011856 | 116654 | 116713 | *Treponema pallidum* | polA | Polymerase |
| 2668 | CUST_P10011857 | 116677 | 116736 | *Treponema pallidum* | polA | Polymerase |
| 2669 | CUST_P10011858 | 116707 | 116760 | *Treponema pallidum* | polA | Polymerase |
| 2670 | CUST_P10011860 | 116852 | 116906 | *Treponema pallidum* | polA | Polymerase |
| 2671 | CUST_P10011862 | 116903 | 116962 | *Treponema pallidum* | polA | Polymerase |
| 2672 | CUST_P10011863 | 116925 | 116978 | *Treponema pallidum* | polA | Polymerase |
| 2673 | CUST_P10011864 | 116987 | 117032 | *Treponema pallidum* | polA | Polymerase |
| 2674 | CUST_P10011865 | 117028 | 117077 | *Treponema pallidum* | polA | Polymerase |
| 2675 | CUST_P10011866 | 117128 | 117176 | *Treponema pallidum* | polA | Polymerase |
| 2676 | CUST_P10011867 | 117270 | 117329 | *Treponema pallidum* | polA | Polymerase |
| 2677 | CUST_P10011868 | 117441 | 117488 | *Treponema pallidum* | polA | Polymerase |
| 2678 | CUST_P10011870 | 117516 | 117575 | *Treponema pallidum* | polA | Polymerase |
| 2679 | CUST_P10011871 | 117570 | 117620 | *Treponema pallidum* | polA | Polymerase |
| 2680 | CUST_P10011872 | 117777 | 117836 | *Treponema pallidum* | polA | Polymerase |
| 2681 | CUST_P10011873 | 117806 | 117865 | *Treponema pallidum* | polA | Polymerase |
| 2682 | CUST_P10011874 | 117873 | 117932 | *Treponema pallidum* | polA | Polymerase |
| 2683 | CUST_P10011875 | 118152 | 118211 | *Treponema pallidum* | polA | Polymerase |
| 2684 | CUST_P10011876 | 118181 | 118240 | *Treponema pallidum* | polA | Polymerase |
| 2685 | CUST_P10011877 | 118281 | 118340 | *Treponema pallidum* | polA | Polymerase |
| 2686 | CUST_P10011878 | 118302 | 118361 | *Treponema pallidum* | polA | Polymerase |
| 2687 | CUST_P10011880 | 118541 | 118600 | *Treponema pallidum* | polA | Polymerase |
| 2688 | CUST_P10011882 | 118756 | 118810 | *Treponema pallidum* | polA | Polymerase |
| 2689 | CUST_P10018873 | 622214 | 622258 | *Treponema pallidum* | TP0576 | protein |
| 2690 | CUST_P10018877 | 622589 | 622637 | *Treponema pallidum* | TP0576 | protein |
| 2691 | CUST_P10018878 | 622725 | 622775 | *Treponema pallidum* | TP0576 | protein |
| 2692 | CUST_P10018881 | 622908 | 622961 | *Treponema pallidum* | TP0576 | protein |
| 2693 | CUST_P10018882 | 622953 | 622997 | *Treponema pallidum* | TP0576 | protein |
| 2694 | CUST_P10018883 | 622978 | 623030 | *Treponema pallidum* | TP0576 | protein |
| 2695 | CUST_P10018884 | 623033 | 623087 | *Treponema pallidum* | TP0576 | protein |
| 2696 | CUST_P10018887 | 623258 | 623302 | *Treponema pallidum* | TP0576 | protein |
| 2697 | CUST_P10024966 | 1067780 | 1067830 | *Treponema pallidum* | aspS | aspartate-tRNA ligase |
| 2698 | CUST_P10024967 | 1067910 | 1067970 | *Treponema pallidum* | aspS | aspartate-tRNA ligase |
| 2699 | CUST_P10024968 | 1067940 | 1067990 | *Treponema pallidum* | aspS | aspartate-tRNA ligase |
| 2700 | CUST_P10024969 | 1068070 | 1068120 | *Treponema pallidum* | aspS | aspartate-tRNA ligase |
| 2701 | CUST_P10024970 | 1068180 | 1068230 | *Treponema pallidum* | aspS | aspartate-tRNA ligase |
| 2702 | CUST_P10024971 | 1068330 | 1068380 | *Treponema pallidum* | aspS | aspartate-tRNA ligase |
| 2703 | CUST_P10024972 | 1068410 | 1068470 | *Treponema pallidum* | aspS | aspartate-tRNA ligase |
| 2704 | CUST_P10024976 | 1068840 | 1068900 | *Treponema pallidum* | aspS | aspartate-tRNA ligase |
| 2705 | CUST_P10024981 | 1069090 | 1069140 | *Treponema pallidum* | aspS | aspartate-tRNA ligase |
| 2706 | CUST_P10024984 | 1069200 | 1069260 | *Treponema pallidum* | aspS | aspartate-tRNA ligase |

TABLE 9-continued

Exemplary bacterial and protozoan probes

| SEQ ID NO: | ProbeID | Start | End | Pathogen | Genomic Region | Product |
|---|---|---|---|---|---|---|
| 2707 | CUST_P10024986 | 1069380 | 1069420 | *Treponema pallidum* | aspS | aspartate-tRNA ligase |
| 2708 | CUST_P10024991 | 1069740 | 1069790 | *Treponema pallidum* | aspS | aspartate-tRNA ligase |
| 2709 | CUST_P10024994 | 1069890 | 1069940 | *Treponema pallidum* | aspS | aspartate-tRNA ligase |
| 2710 | CUST_P10024996 | 1070010 | 1070060 | *Treponema pallidum* | aspS | aspartate-tRNA ligase |
| 2711 | CUST_P10024997 | 1070040 | 1070080 | *Treponema pallidum* | aspS | aspartate-tRNA ligase |
| 2712 | CUST_P10024998 | 1070090 | 1070130 | *Treponema pallidum* | aspS | aspartate-tRNA ligase |
| 2713 | CUST_P10024999 | 1070140 | 1070190 | *Treponema pallidum* | aspS | aspartate-tRNA ligase |
| 2714 | CUST_P10025000 | 1070250 | 1070300 | *Treponema pallidum* | aspS | aspartate-tRNA ligase |
| 2715 | CUST_P10025003 | 1070380 | 1070430 | *Treponema pallidum* | aspS | aspartate-tRNA ligase |
| 2716 | CUST_P10025005 | 1070670 | 1070710 | *Treponema pallidum* | aspS | aspartate-tRNA ligase |
| 2717 | CUST_P10025006 | 1070800 | 1070850 | *Treponema pallidum* | TP0986 | protein |
| 2718 | CUST_P10025009 | 1071210 | 1071260 | *Treponema pallidum* | TP0986 | protein |
| 2719 | CUST_P10025010 | 1071230 | 1071290 | *Treponema pallidum* | TP0986 | protein |
| 2720 | CUST_P10025018 | 1071990 | 1072040 | *Treponema pallidum* | TP0986 | protein |
| 2721 | CUST_P10025019 | 1072210 | 1072260 | *Treponema pallidum* | TP0989 | protein |
| 2722 | CUST_P10025024 | 1072490 | 1072540 | *Treponema pallidum* | TP0989 | protein |
| 2723 | CUST_P10025027 | 1072660 | 1072710 | *Treponema pallidum* | TP0989 | protein |
| 2724 | CUST_P10025028 | 1072870 | 1072910 | *Treponema pallidum* | TP0989 | protein |
| 2725 | CUST_P10025029 | 1072990 | 1073040 | *Treponema pallidum* | TP0989 | protein |
| 2726 | CUST_P10025030 | 1073010 | 1073060 | *Treponema pallidum* | TP0989 | protein |
| 2727 | CUST_P10025044 | 1074070 | 1074120 | *Treponema pallidum* | TP0990 | protein |
| 2728 | CUST_P10025045 | 1074230 | 1074270 | *Treponema pallidum* | TP0991 | protein |
| 2729 | CUST_P10025047 | 1074310 | 1074360 | *Treponema pallidum* | TP0992 | protein |
| 2730 | CUST_P10025050 | 1074480 | 1074520 | *Treponema pallidum* | TP0993 | protein |
| 2731 | CUST_P10025051 | 1074520 | 1074560 | *Treponema pallidum* | TP0994 | protein |
| 2732 | CUST_P10025052 | 1074560 | 1074610 | *Treponema pallidum* | TP0995 | protein |
| 2733 | CUST_P10025054 | 1074620 | 1074670 | *Treponema pallidum* | TP0996 | protein |
| 2734 | CUST_P10025055 | 1074740 | 1074780 | *Treponema pallidum* | TP0997 | protein |
| 2735 | CUST_P10025056 | 1074790 | 1074830 | *Treponema pallidum* | TP0998 | protein |
| 2736 | CUST_P10025058 | 1075040 | 1075090 | *Treponema pallidum* | TP0999 | protein |
| 2737 | CUST_P10025059 | 1075150 | 1075210 | *Treponema pallidum* | TP1000 | protein |
| 2738 | CUST_P10025061 | 1075310 | 1075360 | *Treponema pallidum* | TP1001 | protein |
| 2739 | CUST_P10025062 | 1075380 | 1075430 | *Treponema pallidum* | TP1002 | protein |
| 2740 | CUST_P10025063 | 1075540 | 1075600 | *Treponema pallidum* | TP1003 | protein |
| 2741 | CUST_P10025064 | 1075600 | 1075640 | *Treponema pallidum* | TP1004 | protein |
| 2742 | CUST_P10025065 | 1075670 | 1075720 | *Treponema pallidum* | TP1005 | protein |
| 2743 | CUST_P10025067 | 1075970 | 1076030 | *Treponema pallidum* | TP1006 | protein |
| 2744 | CUST_P10025068 | 1076040 | 1076100 | *Treponema pallidum* | TP1007 | protein |
| 2745 | CUST_P10025069 | 1076170 | 1076220 | *Treponema pallidum* | TP0990 | protein |
| 2746 | CUST_P10025073 | 1076400 | 1076450 | *Treponema pallidum* | TP0991 | protein |
| 2747 | CUST_P10025084 | 1077230 | 1077280 | *Treponema pallidum* | TP0992 | protein |
| 2748 | CUST_P10025095 | 1077820 | 1077870 | *Treponema pallidum* | TP0992 | protein |
| 2749 | CUST_P10025097 | 1077980 | 1078030 | *Treponema pallidum* | TP0993 | protein |
| 2750 | CUST_P10025098 | 1078120 | 1078170 | *Treponema pallidum* | TP0993 | protein |
| 2751 | CUST_P10025104 | 1078320 | 1078370 | *Treponema pallidum* | TP0993 | protein |
| 2752 | CUST_P10025934 | 479 | 538 | *Ehrlichia chaffeensis* | ECH_RS00020 | protein |
| 2753 | CUST_P10026529 | 69254 | 69313 | *Ehrlichia chaffeensis* | argF | protein |
| 2754 | CUST_P10026957 | 118031 | 118090 | *Ehrlichia chaffeensis* | ECH_RS00525 | protein |
| 2755 | CUST_P10027106 | 133725 | 133784 | *Ehrlichia chaffeensis* | ECH_RS00595 | protein |
| 2756 | CUST_P10027296 | 155652 | 155711 | *Ehrlichia chaffeensis* | ECH_RS00695 | protein |
| 2757 | CUST_P10027314 | 158001 | 158060 | *Ehrlichia chaffeensis* | ECH_RS00710 | protein |
| 2758 | CUST_P10027972 | 235733 | 235792 | *Ehrlichia chaffeensis* | ECH_RS01035 | protein |
| 2759 | CUST_P10027973 | 235768 | 235827 | *Ehrlichia chaffeensis* | ECH_RS01035 | protein |
| 2760 | CUST_P10028360 | 279872 | 279931 | *Ehrlichia chaffeensis* | ECH_RS01185 | protein |
| 2761 | CUST_P10028636 | 313330 | 313389 | *Ehrlichia chaffeensis* | ECH_RS01325 | protein |
| 2762 | CUST_P10028976 | 353675 | 353734 | *Ehrlichia chaffeensis* | groL | chaperonin GroEL |
| 2763 | CUST_P10028977 | 353852 | 353911 | *Ehrlichia chaffeensis* | groL | chaperonin GroEL |
| 2764 | CUST_P10028978 | 354008 | 354067 | *Ehrlichia chaffeensis* | groL | chaperonin GroEL |
| 2765 | CUST_P10028979 | 354044 | 354103 | *Ehrlichia chaffeensis* | groL | chaperonin GroEL |
| 2766 | CUST_P10028980 | 354207 | 354266 | *Ehrlichia chaffeensis* | groL | chaperonin GroEL |
| 2767 | CUST_P10028981 | 354405 | 354464 | *Ehrlichia chaffeensis* | groL | chaperonin GroEL |
| 2768 | CUST_P10028982 | 354433 | 354492 | *Ehrlichia chaffeensis* | groL | chaperonin GroEL |
| 2769 | CUST_P10028983 | 354474 | 354533 | *Ehrlichia chaffeensis* | groL | chaperonin GroEL |
| 2770 | CUST_P10028984 | 354504 | 354563 | *Ehrlichia chaffeensis* | groL | chaperonin GroEL |
| 2771 | CUST_P10028985 | 354573 | 354632 | *Ehrlichia chaffeensis* | groL | chaperonin GroEL |
| 2772 | CUST_P10028986 | 354646 | 354694 | *Ehrlichia chaffeensis* | groL | chaperonin GroEL |
| 2773 | CUST_P10028987 | 354808 | 354867 | *Ehrlichia chaffeensis* | groL | chaperonin GroEL |
| 2774 | CUST_P10028988 | 354995 | 355054 | *Ehrlichia chaffeensis* | groL | chaperonin GroEL |
| 2775 | CUST_P10028989 | 355085 | 355144 | *Ehrlichia chaffeensis* | groL | chaperonin GroEL |
| 2776 | CUST_P10028990 | 355336 | 355395 | *Ehrlichia chaffeensis* | groL | chaperonin GroEL |
| 2777 | CUST_P10028991 | 355454 | 355508 | *Ehrlichia chaffeensis* | groL | chaperonin GroEL |
| 2778 | CUST_P10029114 | 369147 | 369206 | *Ehrlichia chaffeensis* | groL | chaperonin GroEL |
| 2779 | CUST_P10029290 | 392046 | 392105 | *Ehrlichia chaffeensis* | sppA | signal peptide |
| 2780 | CUST_P10029649 | 429284 | 429343 | *Ehrlichia chaffeensis* | ECH_RS01865 | Protein |

TABLE 9-continued

Exemplary bacterial and protozoan probes

| SEQ ID NO: | ProbeID | Start | End | Pathogen | Genomic Region | Product |
|---|---|---|---|---|---|---|
| 2781 | CUST_P10029666 | 431631 | 431690 | *Ehrlichia chaffeensis* | ECH_RS01866 | Protein |
| 2782 | CUST_P10029696 | 434789 | 434848 | *Ehrlichia chaffeensis* | ECH_RS01867 | Protein |
| 2783 | CUST_P10029724 | 437453 | 437512 | *Ehrlichia chaffeensis* | ECH_RS01868 | Protein |
| 2784 | CUST_P10030575 | 531280 | 531339 | *Ehrlichia chaffeensis* | ECH_RS01869 | Protein |
| 2785 | CUST_P10030591 | 532929 | 532988 | *Ehrlichia chaffeensis* | ECH_RS01870 | Protein |
| 2786 | CUST_P10030711 | 547792 | 547851 | *Ehrlichia chaffeensis* | ECH_RS01871 | Protein |
| 2787 | CUST_P10030738 | 551432 | 551491 | *Ehrlichia chaffeensis* | ECH_RS01872 | Protein |
| 2788 | CUST_P10030817 | 563329 | 563388 | *Ehrlichia chaffeensis* | ECH_RS01873 | Protein |
| 2789 | CUST_P10030998 | 588404 | 588463 | *Ehrlichia chaffeensis* | ECH_RS02440 | Protein |
| 2790 | CUST_P10031006 | 590051 | 590110 | *Ehrlichia chaffeensis* | ECH_RS02441 | Protein |
| 2791 | CUST_P10031019 | 591869 | 591928 | *Ehrlichia chaffeensis* | ECH_RS02442 | Protein |
| 2792 | CUST_P10031129 | 603725 | 603784 | *Ehrlichia chaffeensis* | ECH_RS02443 | Protein |
| 2793 | CUST_P10031152 | 607138 | 607197 | *Ehrlichia chaffeensis* | ECH_RS02444 | Protein |
| 2794 | CUST_P10031295 | 626729 | 626788 | *Ehrlichia chaffeensis* | ECH_RS02445 | Protein |
| 2795 | CUST_P10031314 | 628696 | 628755 | *Ehrlichia chaffeensis* | ECH_RS02446 | Protein |
| 2796 | CUST_P1OO3132O | 629770 | 629829 | *Ehrlichia chaffeensis* | ECH_RS02447 | Protein |
| 2797 | CUST_P10031396 | 640107 | 640166 | *Ehrlichia chaffeensis* | ECH_RS02448 | Protein |
| 2798 | CUST_P10031397 | 640131 | 640190 | *Ehrlichia chaffeensis* | ECH_RS02449 | Protein |
| 2799 | CUST_P10031498 | 651172 | 651231 | *Ehrlichia chaffeensis* | ECH_RS02450 | Protein |
| 2800 | CUST_P10031499 | 651236 | 651295 | *Ehrlichia chaffeensis* | ECH_RS02451 | Protein |
| 2801 | CUST_P10031500 | 651472 | 651531 | *Ehrlichia chaffeensis* | ECH_RS02452 | Protein |
| 2802 | CUST_P10031501 | 651648 | 651707 | *Ehrlichia chaffeensis* | ECH_RS02453 | Protein |
| 2803 | CUST_P10031502 | 651715 | 651774 | *Ehrlichia chaffeensis* | ECH_RS02454 | Protein |
| 2804 | CUST_P10031503 | 651749 | 651808 | *Ehrlichia chaffeensis* | ECH_RS02455 | Protein |
| 2805 | CUST_P10031504 | 651916 | 651975 | *Ehrlichia chaffeensis* | ECH_RS02456 | Protein |
| 2806 | CUST_P10031720 | 672910 | 672969 | *Ehrlichia chaffeensis* | ECH_RS02457 | Protein |
| 2807 | CUST_P10031846 | 688686 | 688745 | *Ehrlichia chaffeensis* | ECH_RS02458 | Protein |
| 2808 | CUST_P10031955 | 700839 | 700898 | *Ehrlichia chaffeensis* | ECH_RS02459 | Protein |
| 2809 | CUST_P10032107 | 718318 | 718377 | *Ehrlichia chaffeensis* | ECH_RS02460 | Protein |
| 2810 | CUST_P10032134 | 720951 | 721010 | *Ehrlichia chaffeensis* | ECH_RS02461 | Protein |
| 2811 | CUST_P10032155 | 723928 | 723987 | *Ehrlichia chaffeensis* | ECH_RS02462 | Protein |
| 2812 | CUST_P10032156 | 724045 | 724104 | *Ehrlichia chaffeensis* | ECH_RS02463 | Protein |
| 2813 | CUST_P10032157 | 724081 | 724140 | *Ehrlichia chaffeensis* | ECH_RS02464 | Protein |
| 2814 | CUST_P10032207 | 729136 | 729195 | *Ehrlichia chaffeensis* | ECH_RS02465 | Protein |
| 2815 | CUST_P10032413 | 753701 | 753760 | *Ehrlichia chaffeensis* | ECH_RS02466 | Protein |
| 2816 | CUST_P10032541 | 768672 | 768731 | *Ehrlichia chaffeensis* | ECH_RS02467 | Protein |
| 2817 | CUST_P10032560 | 770310 | 770369 | *Ehrlichia chaffeensis* | ECH_RS02468 | Protein |
| 2818 | CUST_P10032563 | 770754 | 770813 | *Ehrlichia chaffeensis* | ECH_RS02469 | Protein |
| 2819 | CUST_P10032708 | 789240 | 789299 | *Ehrlichia chaffeensis* | ECH_RS02470 | Protein |
| 2820 | CUST_P10032835 | 805456 | 805515 | *Ehrlichia chaffeensis* | ECH_RS02471 | Protein |
| 2821 | CUST_P10032934 | 816181 | 816240 | *Ehrlichia chaffeensis* | ECH_RS02472 | Protein |
| 2822 | CUST_P10032949 | 818626 | 818685 | *Ehrlichia chaffeensis* | ECH_RS02473 | Protein |
| 2823 | CUST_P10033029 | 827167 | 827226 | *Ehrlichia chaffeensis* | ECH_RS02474 | Protein |
| 2824 | CUST_P10033095 | 834972 | 835031 | *Ehrlichia chaffeensis* | ECH_RS02475 | Protein |
| 2825 | CUST_P10033283 | 854588 | 854647 | *Ehrlichia chaffeensis* | ECH_RS02476 | Protein |
| 2826 | CUST_P10033296 | 856372 | 856431 | *Ehrlichia chaffeensis* | ECH_RS02477 | Protein |
| 2827 | CUST_P10033303 | 858073 | 858132 | *Ehrlichia chaffeensis* | ECH_RS02478 | Protein |
| 2828 | CUST_P10033406 | 871304 | 871363 | *Ehrlichia chaffeensis* | ECH_RS02479 | Protein |
| 2829 | CUST_P10033442 | 875535 | 875594 | *Ehrlichia chaffeensis* | ECH_RS02480 | Protein |
| 2830 | CUST_P10033524 | 883572 | 883631 | *Ehrlichia chaffeensis* | ECH_RS02481 | Protein |
| 2831 | CUST_P10033559 | 887845 | 887904 | *Ehrlichia chaffeensis* | ECH_RS02482 | Protein |
| 2832 | CUST_P10033633 | 897694 | 897753 | *Ehrlichia chaffeensis* | ECH_RS02483 | Protein |
| 2833 | CUST_P10033864 | 922188 | 922247 | *Ehrlichia chaffeensis* | ECH_RS02484 | Protein |
| 2834 | CUST_P10033889 | 925077 | 925136 | *Ehrlichia chaffeensis* | ECH_RS02485 | Protein |
| 2835 | CUST_P10034084 | 946234 | 946293 | *Ehrlichia chaffeensis* | ECH_RS02486 | Protein |
| 2836 | CUST_P10034141 | 950852 | 950911 | *Ehrlichia chaffeensis* | ECH_RS02487 | Protein |
| 2837 | CUST_P10034279 | 966861 | 966920 | *Ehrlichia chaffeensis* | ECH_RS02488 | Protein |
| 2838 | CUST_P10034323 | 971540 | 971599 | *Ehrlichia chaffeensis* | ECH_RS02489 | Protein |
| 2839 | CUST_P10034725 | 1012370 | 1012430 | *Ehrlichia chaffeensis* | ECH_RS02490 | Protein |
| 2840 | CUST_P10034780 | 1018290 | 1018350 | *Ehrlichia chaffeensis* | ECH_RS02491 | Protein |
| 2841 | CUST_P10034783 | 1018550 | 1018610 | *Ehrlichia chaffeensis* | ECH_RS02492 | Protein |
| 2842 | CUST_P10034934 | 1034960 | 1035020 | *Ehrlichia chaffeensis* | ECH_RS02493 | Protein |
| 2843 | CUST_P10035002 | 1039980 | 1040040 | *Ehrlichia chaffeensis* | ECH_RS02494 | Protein |
| 2844 | CUST_P10035116 | 1053370 | 1053430 | *Ehrlichia chaffeensis* | ECH_RS02495 | Protein |
| 2845 | CUST_P10035418 | 1084080 | 1084130 | *Ehrlichia chaffeensis* | ECH_RS02496 | Protein |
| 2846 | CUST_P10035470 | 1089260 | 1089310 | *Ehrlichia chaffeensis* | ECH_RS02497 | Protein |
| 2847 | CUST_P10035547 | 1098110 | 1098170 | *Ehrlichia chaffeensis* | ECH_RS02498 | Protein |
| 2848 | CUST_P10035833 | 1129330 | 1129390 | *Ehrlichia chaffeensis* | ECH_RS02499 | Protein |
| 2849 | CUST_P10035846 | 1131120 | 1131180 | *Ehrlichia chaffeensis* | ECH_RS02500 | Protein |
| 2850 | CUST_P10036040 | 1151290 | 1151350 | *Ehrlichia chaffeensis* | ECH_RS02501 | Protein |
| 2851 | CUST_P10036201 | 1166620 | 1166680 | *Ehrlichia chaffeensis* | ECH_RS02502 | Protein |
| 2852 | CUST_P10036255 | 1172870 | 1172930 | *Ehrlichia chaffeensis* | ECH_RS02503 | Protein |
| 2853 | CUST_P10036280 | 37 | 96 | *Ehrlichia ewingii* | 16S ribosomal RNA | 16S ribosomal RNA |
| 2854 | CUST_P10036282 | 142 | 201 | *Ehrlichia ewingii* | 16S ribosomal RNA | 16S ribosomal RNA |

TABLE 9-continued

Exemplary bacterial and protozoan probes

| SEQ ID NO: | ProbeID | Start | End | Pathogen | Genomic Region | Product |
|---|---|---|---|---|---|---|
| 2855 | CUST_P10036288 | 828 | 872 | Ehrlichia ewingii | 16S ribosomal RNA | 16S ribosomal RNA |
| 2856 | CUST_P10036289 | 859 | 903 | Ehrlichia ewingii | 16S ribosomal RNA | 16S ribosomal RNA |
| 2857 | CUST_P10036290 | 885 | 938 | Ehrlichia ewingii | 16S ribosomal RNA | 16S ribosomal RNA |
| 2858 | CUST_P10036291 | 915 | 969 | Ehrlichia ewingii | 16S ribosomal RNA | 16S ribosomal RNA |
| 2859 | CUST_P10036293 | 1099 | 1144 | Ehrlichia ewingii | 16S ribosomal RNA | 16S ribosomal RNA |
| 2860 | CUST_P10036294 | 1120 | 1164 | Ehrlichia ewingii | 16S ribosomal RNA | 16S ribosomal RNA |
| 2861 | CUST_P10036296 | 1282 | 1328 | Ehrlichia ewingii | 16S ribosomal RNA | 16S ribosomal RNA |
| 2862 | CUST_P10041026 | 540829 | 540888 | Ehrlichia muris | 16S ribosomal RNA | 16S ribosomal RNA |
| 2863 | CUST_P10041027 | 540929 | 540988 | Ehrlichia muris | 16S ribosomal RNA | 16S ribosomal RNA |
| 2864 | CUST_P10041028 | 541043 | 541102 | Ehrlichia muris | 16S ribosomal RNA | 16S ribosomal RNA |
| 2865 | CUST_P10041029 | 541193 | 541252 | Ehrlichia muris | 16S ribosomal RNA | 16S ribosomal RNA |
| 2866 | CUST_P10041030 | 541329 | 541388 | Ehrlichia muris | 16S ribosomal RNA | 16S ribosomal RNA |
| 2867 | CUST_P10041031 | 541437 | 541496 | Ehrlichia muris | 16S ribosomal RNA | 16S ribosomal RNA |
| 2868 | CUST_P10041032 | 541659 | 541718 | Ehrlichia muris | 16S ribosomal RNA | 16S ribosomal RNA |
| 2869 | CUST_P10041033 | 541758 | 541817 | Ehrlichia muris | 16S ribosomal RNA | 16S ribosomal RNA |
| 2870 | CUST_P10038359 | 233191 | 233250 | Ehrlichia muris | 16S ribosomal RNA | 16S ribosomal RNA |
| 2871 | CUST_P10038360 | 233399 | 233458 | Ehrlichia muris | 16S ribosomal RNA | 16S ribosomal RNA |
| 2872 | CUST_P10038361 | 233444 | 233503 | Ehrlichia muris | 16S ribosomal RNA | 16S ribosomal RNA |
| 2873 | CUST_P10041027 | 540929 | 540988 | Ehrlichia muris | 16S ribosomal RNA | 16S ribosomal RNA |
| 2874 | CUST_P10041028 | 541043 | 541102 | Ehrlichia muris | 16S ribosomal RNA | 16S ribosomal RNA |
| 2875 | CUST_P10041029 | 541193 | 541252 | Ehrlichia muris | 16S ribosomal RNA | 16S ribosomal RNA |
| 2876 | CUST_P10041030 | 541329 | 541388 | Ehrlichia muris | 16S ribosomal RNA | 16S ribosomal RNA |
| 2877 | CUST_P10041031 | 541437 | 541496 | Ehrlichia muris | 16S ribosomal RNA | 16S ribosomal RNA |
| 2878 | CUST_P10041032 | 541659 | 541718 | Ehrlichia muris | 16S ribosomal RNA | 16S ribosomal RNA |
| 2879 | CUST_P10041771 | 642662 | 642721 | Ehrlichia muris | 16S ribosomal RNA | 16S ribosomal RNA |
| 2880 | CUST_P10041772 | 642918 | 642977 | Ehrlichia muris | 16S ribosomal RNA | 16S ribosomal RNA |
| 2881 | CUST_P10041773 | 642945 | 643004 | Ehrlichia muris | 16S ribosomal RNA | 16S ribosomal RNA |
| 2882 | CUST_P10041774 | 642970 | 643029 | Ehrlichia muris | 16S ribosomal RNA | 16S ribosomal RNA |
| 2883 | CUST_P10041775 | 642995 | 643054 | Ehrlichia muris | 16S ribosomal RNA | 16S ribosomal RNA |
| 2884 | CUST_P10041776 | 643229 | 643288 | Ehrlichia muris | 16S ribosomal RNA | 16S ribosomal RNA |
| 2885 | CUST_P10041777 | 643324 | 643383 | Ehrlichia muris | 16S ribosomal RNA | 16S ribosomal RNA |
| 2886 | CUST_P10041778 | 643453 | 643512 | Ehrlichia muris | 16S ribosomal RNA | 16S ribosomal RNA |
| 2887 | CUST_P10041779 | 643509 | 643562 | Ehrlichia muris | 16S ribosomal RNA | 16S ribosomal RNA |
| 2888 | CUST_P10041780 | 643629 | 643688 | Ehrlichia muris | 16S ribosomal RNA | 16S ribosomal RNA |
| 2889 | CUST_P10041784 | 644380 | 644439 | Ehrlichia muris | 16S ribosomal RNA | 16S ribosomal RNA |
| 2890 | CUST_P10041785 | 644514 | 644573 | Ehrlichia muris | 16S ribosomal RNA | 16S ribosomal RNA |
| 2891 | CUST_P10041786 | 644749 | 644808 | Ehrlichia muris | 16S ribosomal RNA | 16S ribosomal RNA |
| 2892 | CUST_P10041787 | 644886 | 644945 | Ehrlichia muris | 16S ribosomal RNA | 16S ribosomal RNA |
| 2893 | CUST_P10041788 | 645057 | 645116 | Ehrlichia muris | 16S ribosomal RNA | 16S ribosomal RNA |
| 2894 | CUST_P10041789 | 645158 | 645217 | Ehrlichia muris | 16S ribosomal RNA | 16S ribosomal RNA |
| 2895 | CUST_P10041790 | 645281 | 645340 | Ehrlichia muris | 16S ribosomal RNA | 16S ribosomal RNA |
| 2896 | CUST_P10041791 | 645374 | 645433 | Ehrlichia muris | 16S ribosomal RNA | 16S ribosomal RNA |
| 2897 | CUST_P10041792 | 645397 | 645456 | Ehrlichia muris | 16S ribosomal RNA | 16S ribosomal RNA |
| 2898 | CUST_P10044860 | 996657 | 996716 | Ehrlichia muris | 16S ribosomal RNA | 16S ribosomal RNA |
| 2899 | CUST_P10044861 | 996761 | 996820 | Ehrlichia muris | 16S ribosomal RNA | 16S ribosomal RNA |
| 2900 | CUST_P10044862 | 996859 | 996918 | Ehrlichia muris | 16S ribosomal RNA | 16S ribosomal RNA |
| 2901 | CUST_P10044863 | 996901 | 996960 | Ehrlichia muris | 16S ribosomal RNA | 16S ribosomal RNA |
| 2902 | CUST_P10044864 | 996958 | 997017 | Ehrlichia muris | 16S ribosomal RNA | 16S ribosomal RNA |
| 2903 | CUST_P10044865 | 996983 | 997042 | Ehrlichia muris | 16S ribosomal RNA | 16S ribosomal RNA |
| 2904 | CUST_P10044866 | 997035 | 997094 | Ehrlichia muris | 16S ribosomal RNA | 16S ribosomal RNA |
| 2905 | CUST_P10044867 | 997148 | 997207 | Ehrlichia muris | 16S ribosomal RNA | 16S ribosomal RNA |
| 2906 | CUST_P10044868 | 997264 | 997323 | Ehrlichia muris | 16S ribosomal RNA | 16S ribosomal RNA |
| 2907 | CUST_P10046461 | 1170365 | 1170424 | Ehrlichia muris | 16S ribosomal RNA | 16S ribosomal RNA |
| 2908 | CUST_P10046462 | 1170579 | 1170638 | Ehrlichia muris | 16S ribosomal RNA | 16S ribosomal RNA |
| 2909 | CUST_P10043391 | 833268 | 833320 | Ehrlichia muris | groL | chaperonin GroEL |
| 2910 | CUST_P10043392 | 833417 | 833476 | Ehrlichia muris | groL | chaperonin GroEL |
| 2911 | CUST_P10043393 | 833446 | 833505 | Ehrlichia muris | groL | chaperonin GroEL |
| 2912 | CUST_P10043394 | 833575 | 833634 | Ehrlichia muris | groL | chaperonin GroEL |
| 2913 | CUST_P10043395 | 833777 | 833833 | Ehrlichia muris | groL | chaperonin GroEL |
| 2914 | CUST_P10043396 | 833923 | 833982 | Ehrlichia muris | groL | chaperonin GroEL |
| 2915 | CUST_P10043397 | 834065 | 834124 | Ehrlichia muris | groL | chaperonin GroEL |
| 2916 | CUST_P10043398 | 834287 | 834346 | Ehrlichia muris | groL | chaperonin GroEL |
| 2917 | CUST_P10043399 | 834382 | 834441 | Ehrlichia muris | groL | chaperonin GroEL |
| 2918 | CUST_P10043400 | 834405 | 834464 | Ehrlichia muris | groL | chaperonin GroEL |
| 2919 | CUST_P10043401 | 834509 | 834568 | Ehrlichia muris | groL | chaperonin GroEL |
| 2920 | CUST_P10043402 | 834678 | 834737 | Ehrlichia muris | groL | chaperonin GroEL |
| 2921 | CUST_P10043403 | 834745 | 834804 | Ehrlichia muris | groL | chaperonin GroEL |
| 2922 | CUST_P10043404 | 834891 | 834950 | Ehrlichia muris | groL | chaperonin GroEL |
| 2923 | CUST_P10049214 | 444536 | 444595 | Borrelia burgdorferi | 16s | 16S ribosomal RNA |
| 2924 | CUST_P10049215 | 444623 | 444673 | Borrelia burgdorferi | 16s | 16S ribosomal RNA |
| 2925 | CUST_P10049216 | 444762 | 444821 | Borrelia burgdorferi | 16s | 16S ribosomal RNA |
| 2926 | CUST_P10049217 | 444920 | 444964 | Borrelia burgdorferi | 16s | 16S ribosomal RNA |
| 2927 | CUST_P10049218 | 444963 | 445012 | Borrelia burgdorferi | 16s | 16S ribosomal RNA |
| 2928 | CUST_P10049219 | 445091 | 445150 | Borrelia burgdorferi | 16s | 16S ribosomal RNA |

TABLE 9-continued

Exemplary bacterial and protozoan probes

| SEQ ID NO: | ProbeID | Start | End | Pathogen | Genomic Region | Product |
|---|---|---|---|---|---|---|
| 2929 | CUST_P10049220 | 445133 | 445179 | Borrelia burgdorferi | 16s | 16S ribosomal RNA |
| 2930 | CUST_P10049221 | 445305 | 445355 | Borrelia burgdorferi | 16s | 16S ribosomal RNA |
| 2931 | CUST_P10049222 | 445327 | 445373 | Borrelia burgdorferi | 16s | 16S ribosomal RNA |
| 2932 | CUST_P10049223 | 445379 | 445426 | Borrelia burgdorferi | 16s | 16S ribosomal RNA |
| 2933 | CUST_P10049224 | 445405 | 445464 | Borrelia burgdorferi | 16s | 16S ribosomal RNA |
| 2934 | CUST_P10049225 | 445428 | 445487 | Borrelia burgdorferi | 16s | 16S ribosomal RNA |
| 2935 | CUST_P10049226 | 445547 | 445591 | Borrelia burgdorferi | 16s | 16S ribosomal RNA |
| 2936 | CUST_P10049227 | 445605 | 445664 | Borrelia burgdorferi | 16s | 16S ribosomal RNA |
| 2937 | CUST_P10049228 | 445696 | 445740 | Borrelia burgdorferi | 16s | 16S ribosomal RNA |
| 2938 | CUST_P10049229 | 445821 | 445867 | Borrelia burgdorferi | 16s | 16S ribosomal RNA |
| 2939 | CUST_P10049230 | 445995 | 446040 | Borrelia burgdorferi | 16s | 16S ribosomal RNA |
| 2940 | CUST_P10049231 | 446027 | 446077 | Borrelia burgdorferi | 16s | 16S ribosomal RNA |
| 2941 | CUST_P10049138 | 435304 | 435363 | Borrelia burgdorferi | 23S | 23S ribosomal RNA |
| 2942 | CUST_P10049139 | 435400 | 435453 | Borrelia burgdorferi | 23S | 23S ribosomal RNA |
| 2943 | CUST_P10049140 | 435509 | 435553 | Borrelia burgdorferi | 23S | 23S ribosomal RNA |
| 2944 | CUST_P10049141 | 435580 | 435627 | Borrelia burgdorferi | 23S | 23S ribosomal RNA |
| 2945 | CUST_P10049142 | 435666 | 435710 | Borrelia burgdorferi | 23S | 23S ribosomal RNA |
| 2946 | CUST_P10049143 | 435821 | 435872 | Borrelia burgdorferi | 23S | 23S ribosomal RNA |
| 2947 | CUST_P10049144 | 435909 | 435958 | Borrelia burgdorferi | 23S | 23S ribosomal RNA |
| 2948 | CUST_P10049145 | 435971 | 436030 | Borrelia burgdorferi | 23S | 23S ribosomal RNA |
| 2949 | CUST_P10049146 | 436150 | 436201 | Borrelia burgdorferi | 23S | 23S ribosomal RNA |
| 2950 | CUST_P10049147 | 436235 | 436279 | Borrelia burgdorferi | 23S | 23S ribosomal RNA |
| 2951 | CUST_P10049148 | 436286 | 436334 | Borrelia burgdorferi | 23S | 23S ribosomal RNA |
| 2952 | CUST_P10049149 | 436313 | 436371 | Borrelia burgdorferi | 23S | 23S ribosomal RNA |
| 2953 | CUST_P10049150 | 436369 | 436413 | Borrelia burgdorferi | 23S | 23S ribosomal RNA |
| 2954 | CUST_P10049151 | 436388 | 436446 | Borrelia burgdorferi | 23S | 23S ribosomal RNA |
| 2955 | CUST_P10049152 | 436410 | 436469 | Borrelia burgdorferi | 23S | 23S ribosomal RNA |
| 2956 | CUST_P10049153 | 436512 | 436558 | Borrelia burgdorferi | 23S | 23S ribosomal RNA |
| 2957 | CUST_P10049154 | 436617 | 436676 | Borrelia burgdorferi | 23S | 23S ribosomal RNA |
| 2958 | CUST_P10049155 | 436713 | 436766 | Borrelia burgdorferi | 23S | 23S ribosomal RNA |
| 2959 | CUST_P10049156 | 436847 | 436891 | Borrelia burgdorferi | 23S | 23S ribosomal RNA |
| 2960 | CUST_P10049157 | 436877 | 436926 | Borrelia burgdorferi | 23S | 23S ribosomal RNA |
| 2961 | CUST_P10049158 | 436896 | 436952 | Borrelia burgdorferi | 23S | 23S ribosomal RNA |
| 2962 | CUST_P10049166 | 438226 | 438285 | Borrelia burgdorferi | 23S | 23S ribosomal RNA |
| 2963 | CUST_P10049167 | 438549 | 438608 | Borrelia burgdorferi | 23S | 23S ribosomal RNA |
| 2964 | CUST_P10049168 | 438645 | 438697 | Borrelia burgdorferi | 23S | 23S ribosomal RNA |
| 2965 | CUST_P10049169 | 438825 | 438872 | Borrelia burgdorferi | 23S | 23S ribosomal RNA |
| 2966 | CUST_P10049170 | 438911 | 438955 | Borrelia burgdorferi | 23S | 23S ribosomal RNA |
| 2967 | CUST_P10049171 | 439032 | 439076 | Borrelia burgdorferi | 23S | 23S ribosomal RNA |
| 2968 | CUST_P10049172 | 439154 | 439203 | Borrelia burgdorferi | 23S | 23S ribosomal RNA |
| 2969 | CUST_P10049173 | 439168 | 439212 | Borrelia burgdorferi | 23S | 23S ribosomal RNA |
| 2970 | CUST_P10049174 | 439245 | 439304 | Borrelia burgdorferi | 23S | 23S ribosomal RNA |
| 2971 | CUST_P10049175 | 439395 | 439446 | Borrelia burgdorferi | 23S | 23S ribosomal RNA |
| 2972 | CUST_P10049176 | 439480 | 439524 | Borrelia burgdorferi | 23S | 23S ribosomal RNA |
| 2973 | CUST_P10049177 | 439531 | 439579 | Borrelia burgdorferi | 23S | 23S ribosomal RNA |
| 2974 | CUST_P10049178 | 439558 | 439616 | Borrelia burgdorferi | 23S | 23S ribosomal RNA |
| 2975 | CUST_P10049179 | 439619 | 439664 | Borrelia burgdorferi | 23S | 23S ribosomal RNA |
| 2976 | CUST_P10049180 | 439633 | 439691 | Borrelia burgdorferi | 23S | 23S ribosomal RNA |
| 2977 | CUST_P10049181 | 439655 | 439714 | Borrelia burgdorferi | 23S | 23S ribosomal RNA |
| 2978 | CUST_P10049182 | 439757 | 439803 | Borrelia burgdorferi | 23S | 23S ribosomal RNA |
| 2979 | CUST_P10049183 | 439856 | 439915 | Borrelia burgdorferi | 23S | 23S ribosomal RNA |
| 2980 | CUST_P10049184 | 439958 | 440011 | Borrelia burgdorferi | 23S | 23S ribosomal RNA |
| 2981 | CUST_P10049185 | 440092 | 440136 | Borrelia burgdorferi | 23S | 23S ribosomal RNA |
| 2982 | CUST_P10049186 | 440122 | 440171 | Borrelia burgdorferi | 23S | 23S ribosomal RNA |
| 2983 | CUST_P10049187 | 440141 | 440197 | Borrelia burgdorferi | 23S | 23S ribosomal RNA |
| 2984 | CUST_P10049188 | 440177 | 440233 | Borrelia burgdorferi | 23S | 23S ribosomal RNA |
| 2985 | CUST_P10049189 | 440469 | 440528 | Borrelia burgdorferi | 23S | 23S ribosomal RNA |
| 2986 | CUST_P10049190 | 440564 | 440623 | Borrelia burgdorferi | 23S | 23S ribosomal RNA |
| 2987 | CUST_P10049191 | 440760 | 440811 | Borrelia burgdorferi | 23S | 23S ribosomal RNA |
| 2988 | CUST_P10049192 | 440807 | 440865 | Borrelia burgdorferi | 23S | 23S ribosomal RNA |
| 2989 | CUST_P10049193 | 440843 | 440896 | Borrelia burgdorferi | 23S | 23S ribosomal RNA |
| 2990 | CUST_P10049194 | 440888 | 440945 | Borrelia burgdorferi | 23S | 23S ribosomal RNA |
| 2991 | CUST_P10049195 | 441471 | 441530 | Borrelia burgdorferi | 23S | 23S ribosomal RNA |
| 2992 | CUST_P10047332 | 126269 | 126328 | Borrelia burgdorferi | recA | recombinase A |
| 2993 | CUST_P10047333 | 126457 | 126516 | Borrelia burgdorferi | recA | recombinase A |
| 2994 | CUST_P10047334 | 126609 | 126668 | Borrelia burgdorferi | recA | recombinase A |
| 2995 | CUST_P10047335 | 126748 | 126807 | Borrelia burgdorferi | recA | recombinase A |
| 2996 | CUST_P10047336 | 126867 | 126926 | Borrelia burgdorferi | recA | recombinase A |
| 2997 | CUST_P10047337 | 126934 | 126993 | Borrelia burgdorferi | recA | recombinase A |
| 2998 | CUST_P10047338 | 127133 | 127188 | Borrelia burgdorferi | recA | recombinase A |
| 2999 | CUST_P10047339 | 127173 | 127220 | Borrelia burgdorferi | recA | recombinase A |
| 3000 | CUST_P10047340 | 127196 | 127247 | Borrelia burgdorferi | recA | recombinase A |
| 3001 | CUST_P10047341 | 127219 | 127278 | Borrelia burgdorferi | recA | recombinase A |
| 3002 | CUST_P10051940 | 6651 | 6701 | Coxiella burnetii | IS1111A transposase | IS1111A transposase |

TABLE 9-continued

Exemplary bacterial and protozoan probes

| SEQ ID NO: | ProbeID | Start | End | Pathogen | Genomic Region | Product |
|---|---|---|---|---|---|---|
| 3003 | CUST_P10051941 | 6794 | 6851 | Coxiella burnetii | IS1111A transposase | IS1111A transposase |
| 3004 | CUST_P10051942 | 6831 | 6880 | Coxiella burnetii | IS1111A transposase | IS1111A transposase |
| 3005 | CUST_P10051943 | 6911 | 6955 | Coxiella burnetii | IS1111A transposase | IS1111A transposase |
| 3006 | CUST_P10051944 | 6942 | 6986 | Coxiella burnetii | IS1111A transposase | IS1111A transposase |
| 3007 | CUST_P10051945 | 6981 | 7034 | Coxiella burnetii | IS1111A transposase | IS1111A transposase |
| 3008 | CUST_P10051946 | 7090 | 7139 | Coxiella burnetii | IS1111A transposase | IS1111A transposase |
| 3009 | CUST_P10051947 | 7101 | 7154 | Coxiella burnetii | IS1111A transposase | IS1111A transposase |
| 3010 | CUST_P10051948 | 7164 | 7210 | Coxiella burnetii | IS1111A transposase | IS1111A transposase |
| 3011 | CUST_P10051949 | 7287 | 7337 | Coxiella burnetii | IS1111A transposase | IS1111A transposase |
| 3012 | CUST_P10051950 | 7318 | 7367 | Coxiella burnetii | IS1111A transposase | IS1111A transposase |
| 3013 | CUST_P10051951 | 7437 | 7483 | Coxiella burnetii | IS1111A transposase | IS1111A transposase |
| 3014 | CUST_P10051952 | 7459 | 7506 | Coxiella burnetii | IS1111A transposase | IS1111A transposase |
| 3015 | CUST_P10051953 | 7499 | 7544 | Coxiella burnetii | IS1111A transposase | IS1111A transposase |
| 3016 | CUST_P10051954 | 7516 | 7565 | Coxiella burnetii | IS1111A transposase | IS1111A transposase |
| 3017 | CUST_P10051955 | 7551 | 7603 | Coxiella burnetii | IS1111A transposase | IS1111A transposase |
| 3018 | CUST_P10051956 | 7660 | 7704 | Coxiella burnetii | IS1111A transposase | IS1111A transposase |
| 3019 | CUST_P10051957 | 7712 | 7763 | Coxiella burnetii | IS1111A transposase | IS1111A transposase |
| 3020 | CUST_P10051958 | 7817 | 7867 | Coxiella burnetii | IS1111A transposase | IS1111A transposase |
| 3021 | CUST_P10056626 | 345409 | 345458 | Coxiella burnetii | IS1111A transposase | IS1111A transposase |
| 3022 | CUST_P10056627 | 345420 | 345473 | Coxiella burnetii | IS1111A transposase | IS1111A transposase |
| 3023 | CUST_P10056628 | 345483 | 345529 | Coxiella burnetii | IS1111A transposase | IS1111A transposase |
| 3024 | CUST_P10056629 | 345606 | 345656 | Coxiella burnetii | IS1111A transposase | IS1111A transposase |
| 3025 | CUST_P10056630 | 345637 | 345686 | Coxiella burnetii | IS1111A transposase | IS1111A transposase |
| 3026 | CUST_P10056631 | 345756 | 345802 | Coxiella burnetii | IS1111A transposase | IS1111A transposase |
| 3027 | CUST_P10056632 | 345778 | 345825 | Coxiella burnetii | IS1111A transposase | IS1111A transposase |
| 3028 | CUST_P10056633 | 345818 | 345863 | Coxiella burnetii | IS1111A transposase | IS1111A transposase |
| 3029 | CUST_P10056634 | 345835 | 345884 | Coxiella burnetii | IS1111A transposase | IS1111A transposase |
| 3030 | CUST_P10056635 | 345870 | 345922 | Coxiella burnetii | IS1111A transposase | IS1111A transposase |
| 3031 | CUST_P10056636 | 345979 | 346023 | Coxiella burnetii | IS1111A transposase | IS1111A transposase |
| 3032 | CUST_P10056637 | 346031 | 346082 | Coxiella burnetii | IS1111A transposase | IS1111A transposase |
| 3033 | CUST_P10056638 | 346136 | 346186 | Coxiella burnetii | IS1111A transposase | IS1111A transposase |
| 3034 | CUST_P10058309 | 465895 | 465941 | Coxiella burnetii | IS1111A transposase | IS1111A transposase |
| 3035 | CUST_P10058310 | 465926 | 465970 | Coxiella burnetii | IS1111A transposase | IS1111A transposase |
| 3036 | CUST_P10058311 | 466027 | 466080 | Coxiella burnetii | IS1111A transposase | IS1111A transposase |
| 3037 | CUST_P10058312 | 466064 | 466113 | Coxiella burnetii | IS1111A transposase | IS1111A transposase |
| 3038 | CUST_P10058313 | 466123 | 466170 | Coxiella burnetii | IS1111A transposase | IS1111A transposase |
| 3039 | CUST_P10058314 | 466146 | 466192 | Coxiella burnetii | IS1111A transposase | IS1111A transposase |
| 3040 | CUST_P10058315 | 466263 | 466311 | Coxiella burnetii | IS1111A transposase | IS1111A transposase |
| 3041 | CUST_P10058316 | 466301 | 466354 | Coxiella burnetii | IS1111A transposase | IS1111A transposase |
| 3042 | CUST_P10058317 | 466422 | 466466 | Coxiella burnetii | IS1111A transposase | IS1111A transposase |
| 3043 | CUST_P10058318 | 466457 | 466504 | Coxiella burnetii | IS1111A transposase | IS1111A transposase |
| 3044 | CUST_P10058319 | 466479 | 466530 | Coxiella burnetii | IS1111A transposase | IS1111A transposase |
| 3045 | CUST_P10058320 | 466511 | 466555 | Coxiella burnetii | IS1111A transposase | IS1111A transposase |
| 3046 | CUST_P10058321 | 466595 | 466648 | Coxiella burnetii | IS1111A transposase | IS1111A transposase |
| 3047 | CUST_P10058322 | 466644 | 466688 | Coxiella burnetii | IS1111A transposase | IS1111A transposase |
| 3048 | CUST_P10058323 | 466684 | 466728 | Coxiella burnetii | IS1111A transposase | IS1111A transposase |
| 3049 | CUST_P10058324 | 466749 | 466798 | Coxiella burnetii | IS1111A transposase | IS1111A transposase |
| 3050 | CUST_P10058325 | 466778 | 466835 | Coxiella burnetii | IS1111A transposase | IS1111A transposase |
| 3051 | CUST_P10058326 | 466943 | 466999 | Coxiella burnetii | IS1111A transposase | IS1111A transposase |
| 3052 | CUST_P10058816 | 502390 | 502443 | Coxiella burnetii | IS1111A transposase | IS1111A transposase |
| 3053 | CUST_P10058817 | 502499 | 502548 | Coxiella burnetii | IS1111A transposase | IS1111A transposase |
| 3054 | CUST_P10058818 | 502510 | 502563 | Coxiella burnetii | IS1111A transposase | IS1111A transposase |
| 3055 | CUST_P10058819 | 502573 | 502619 | Coxiella burnetii | IS1111A transposase | IS1111A transposase |
| 3056 | CUST_P10058820 | 502696 | 502746 | Coxiella burnetii | IS1111A transposase | IS1111A transposase |
| 3057 | CUST_P10058821 | 502727 | 502776 | Coxiella burnetii | IS1111A transposase | IS1111A transposase |
| 3058 | CUST_P10058822 | 502846 | 502892 | Coxiella burnetii | IS1111A transposase | IS1111A transposase |
| 3059 | CUST_P10058823 | 502868 | 502915 | Coxiella burnetii | IS1111A transposase | IS1111A transposase |
| 3060 | CUST_P10058824 | 502908 | 502953 | Coxiella burnetii | IS1111A transposase | IS1111A transposase |
| 3061 | CUST_P10058825 | 502925 | 502974 | Coxiella burnetii | IS1111A transposase | IS1111A transposase |
| 3062 | CUST_P10058826 | 502960 | 503012 | Coxiella burnetii | IS1111A transposase | IS1111A transposase |
| 3063 | CUST_P10058827 | 503069 | 503113 | Coxiella burnetii | IS1111A transposase | IS1111A transposase |
| 3064 | CUST_P10058828 | 503121 | 503172 | Coxiella burnetii | IS1111A transposase | IS1111A transposase |
| 3065 | CUST_P10058829 | 503226 | 503276 | Coxiella burnetii | IS1111A transposase | IS1111A transposase |
| 3066 | CUST_P10058830 | 503308 | 503358 | Coxiella burnetii | IS1111A transposase | IS1111A transposase |
| 3067 | CUST_P10058831 | 503329 | 503384 | Coxiella burnetii | IS1111A transposase | IS1111A transposase |
| 3068 | CUST_P10058832 | 503374 | 503433 | Coxiella burnetii | IS1111A transposase | IS1111A transposase |
| 3069 | CUST_P10058833 | 503541 | 503597 | Coxiella burnetii | IS1111A transposase | IS1111A transposase |
| 3070 | CUST_P10058834 | 503609 | 503658 | Coxiella burnetii | IS1111A transposase | IS1111A transposase |
| 3071 | CUST_P10058835 | 503681 | 503725 | Coxiella burnetii | IS1111A transposase | IS1111A transposase |
| 3072 | CUST_P10058836 | 503718 | 503765 | Coxiella burnetii | IS1111A transposase | IS1111A transposase |
| 3073 | CUST_P10058837 | 503745 | 503791 | Coxiella burnetii | IS1111A transposase | IS1111A transposase |
| 3074 | CUST_P10058838 | 503852 | 503911 | Coxiella burnetii | IS1111A transposase | IS1111A transposase |
| 3075 | CUST_P10065644 | 1021442 | 1021488 | Coxiella burnetii | IS1111A transposase | IS1111A transposase |
| 3076 | CUST_P10065645 | 1021559 | 1021607 | Coxiella burnetii | IS1111A transposase | IS1111A transposase |

TABLE 9-continued

Exemplary bacterial and protozoan probes

| SEQ ID NO: | ProbeID | Start | End | Pathogen | Genomic Region | Product |
|---|---|---|---|---|---|---|
| 3077 | CUST_P10065646 | 1021597 | 1021650 | Coxiella burnetii | IS1111A transposase | IS1111A transposase |
| 3078 | CUST_P10065647 | 1021718 | 1021762 | Coxiella burnetii | IS1111A transposase | IS1111A transposase |
| 3079 | CUST_P10065648 | 1021753 | 1021800 | Coxiella burnetii | IS1111A transposase | IS1111A transposase |
| 3080 | CUST_P10065649 | 1021775 | 1021826 | Coxiella burnetii | IS1111A transposase | IS1111A transposase |
| 3081 | CUST_P10065650 | 1021807 | 1021851 | Coxiella burnetii | IS1111A transposase | IS1111A transposase |
| 3082 | CUST_P10065651 | 1021891 | 1021944 | Coxiella burnetii | IS1111A transposase | IS1111A transposase |
| 3083 | CUST_P10065652 | 1021940 | 1021984 | Coxiella burnetii | IS1111A transposase | IS1111A transposase |
| 3084 | CUST_P10065653 | 1021980 | 1022024 | Coxiella burnetii | IS1111A transposase | IS1111A transposase |
| 3085 | CUST_P10065654 | 1022045 | 1022094 | Coxiella burnetii | IS1111A transposase | IS1111A transposase |
| 3086 | CUST_P10079271 | 1019 | 1078 | Trypanosoma brucei | kinetoplast apocy | kinetoplast apocy |
| 3087 | CUST_P10079269 | 471 | 530 | Trypanosoma brucei | kinetoplast apocy | kinetoplast apocy |
| 3088 | CUST_P10079274 | 1363 | 1414 | Trypanosoma brucei | kinetoplast apocy | kinetoplast apocy |
| 3089 | CUST_P10079272 | 1279 | 1334 | Trypanosoma brucei | kinetoplast apocy | kinetoplast apocy |
| 3090 | CUST_P10079270 | 628 | 687 | Trypanosoma brucei | kinetoplast apocy | kinetoplast apocy |
| 3091 | CUST_P10079273 | 1329 | 1373 | Trypanosoma brucei | kinetoplast apocy | kinetoplast apocy |
| 3092 | CUST_P10079280 | 687 | 746 | Trypanosoma brucei | kinetoplast DNA m | kinetoplast DNA m |
| 3093 | CUST_P10079276 | 478 | 526 | Trypanosoma brucei | kinetoplast DNA m | kinetoplast DNA m |
| 3094 | CUST_P10079277 | 547 | 601 | Trypanosoma brucei | kinetoplast DNA m | kinetoplast DNA m |
| 3095 | CUST_P10079275 | 1 | 60 | Trypanosoma brucei | kinetoplast DNA m | kinetoplast DNA m |
| 3096 | CUST_P10079279 | 677 | 736 | Trypanosoma brucei | kinetoplast DNA m | kinetoplast DNA m |
| 3097 | CUST_P10079278 | 554 | 610 | Trypanosoma brucei | kinetoplast DNA m | kinetoplast DNA m |
| 3098 | CUST_P10079281 | 23 | 67 | Trypanosoma Cruzi | Mini satellite | Mini satellite |
| 3099 | CUST_P10079284 | 267 | 312 | Leishmania major | kinetoplast DNA | kinetoplast DNA |
| 3100 | CUST_P10079285 | 319 | 365 | Leishmania major | kinetoplast DNA | kinetoplast DNA |
| 3101 | CUST_P10079286 | 360 | 404 | Leishmania major | kinetoplast DNA | kinetoplast DNA |
| 3102 | CUST_P10079283 | 146 | 205 | Leishmania major | kinetoplast DNA | kinetoplast DNA |
| 3103 | CUST_P10079287 | 382 | 426 | Leishmania major | kinetoplast DNA | kinetoplast DNA |
| 3104 | CUST_P10079282 | 1 | 60 | Leishmania major | kinetoplast DNA | kinetoplast DNA |
| 3105 | CUST_P10079294 | 504 | 548 | Leishmania major | kinetoplast DNA | kinetoplast DNA |
| 3106 | CUST_P10079292 | 333 | 377 | Leishmania major | kinetoplast DNA | kinetoplast DNA |
| 3107 | CUST_P10079296 | 588 | 632 | Leishmania major | kinetoplast DNA | kinetoplast DNA |
| 3108 | CUST_P10079291 | 298 | 342 | Leishmania major | kinetoplast DNA | kinetoplast DNA |
| 3109 | CUST_P10079290 | 257 | 303 | Leishmania major | kinetoplast DNA | kinetoplast DNA |
| 3110 | CUST_P10079295 | 551 | 595 | Leishmania major | kinetoplast DNA | kinetoplast DNA |
| 3111 | CUST_P10079289 | 148 | 200 | Leishmania major | kinetoplast DNA | kinetoplast DNA |
| 3112 | CUST_P10079288 | 116 | 168 | Leishmania major | kinetoplast DNA | kinetoplast DNA |
| 3113 | CUST_P10079293 | 462 | 507 | Leishmania major | kinetoplast DNA | kinetoplast DNA |
| 3114 | CUST_P10079326 | 82 | 141 | Babesia microti | 18S ribosomal RNA | 18S ribosomal RNA |
| 3115 | CUST_P10079327 | 140 | 189 | Babesia microti | 18S ribosomal RNA | 18S ribosomal RNA |
| 3116 | CUST_P10079328 | 168 | 227 | Babesia microti | 18S ribosomal RNA | 18S ribosomal RNA |
| 3117 | CUST_P10079329 | 320 | 364 | Babesia microti | 18S ribosomal RNA | 18S ribosomal RNA |
| 3118 | CUST_P10079330 | 336 | 380 | Babesia microti | 18S ribosomal RNA | 18S ribosomal RNA |
| 3119 | CUST_P10079331 | 368 | 412 | Babesia microti | 18S ribosomal RNA | 18S ribosomal RNA |
| 3120 | CUST_P10079332 | 398 | 450 | Babesia microti | 18S ribosomal RNA | 18S ribosomal RNA |
| 3121 | CUST_P10079333 | 434 | 493 | Babesia microti | 18S ribosomal RNA | 18S ribosomal RNA |
| 3122 | CUST_P10079334 | 699 | 758 | Babesia microti | 18S ribosomal RNA | 18S ribosomal RNA |
| 3123 | CUST_P10079335 | 722 | 781 | Babesia microti | 18S ribosomal RNA | 18S ribosomal RNA |
| 3124 | CUST_P10079336 | 771 | 825 | Babesia microti | 18S ribosomal RNA | 18S ribosomal RNA |
| 3125 | CUST_P10079337 | 801 | 860 | Babesia microti | 18S ribosomal RNA | 18S ribosomal RNA |
| 3126 | CUST_P10079338 | 826 | 885 | Babesia microti | 18S ribosomal RNA | 18S ribosomal RNA |
| 3127 | CUST_P10079339 | 891 | 947 | Babesia microti | 18S ribosomal RNA | 18S ribosomal RNA |
| 3128 | CUST_P10079340 | 933 | 987 | Babesia microti | 18S ribosomal RNA | 18S ribosomal RNA |
| 3129 | CUST_P10079341 | 952 | 1006 | Babesia microti | 18S ribosomal RNA | 18S ribosomal RNA |
| 3130 | CUST_P10079342 | 990 | 1042 | Babesia microti | 18S ribosomal RNA | 18S ribosomal RNA |
| 3131 | CUST_P10079343 | 1016 | 1060 | Babesia microti | 18S ribosomal RNA | 18S ribosomal RNA |
| 3132 | CUST_P10079344 | 1055 | 1101 | Babesia microti | 18S ribosomal RNA | 18S ribosomal RNA |
| 3133 | CUST_P10079345 | 1108 | 1152 | Babesia microti | 18S ribosomal RNA | 18S ribosomal RNA |
| 3134 | CUST_P10079346 | 1239 | 1298 | Babesia microti | 18S ribosomal RNA | 18S ribosomal RNA |
| 3135 | CUST_P10079347 | 1357 | 1405 | Babesia microti | 18S ribosomal RNA | 18S ribosomal RNA |
| 3136 | CUST_P10079348 | 1435 | 1479 | Babesia microti | 18S ribosomal RNA | 18S ribosomal RNA |
| 3137 | CUST_P10079349 | 1458 | 1517 | Babesia microti | 18S ribosomal RNA | 18S ribosomal RNA |
| 3138 | CUST_P10079350 | 1620 | 1675 | Babesia microti | 18S ribosomal RNA | 18S ribosomal RNA |
| 3139 | CUST_P10079351 | 1659 | 1718 | Babesia microti | 18S ribosomal RNA | 18S ribosomal RNA |
| 3140 | CUST_P10079352 | 1736 | 1786 | Babesia microti | 18S ribosomal RNA | 18S ribosomal RNA |
| 3141 | CUST_P10079353 | 1758 | 1802 | Babesia microti | 18S ribosomal RNA | 18S ribosomal RNA |
| 3142 | CUST_P10079354 | 1811 | 1855 | Babesia microti | 18S ribosomal RNA | 18S ribosomal RNA |
| 3143 | CUST_P10079355 | 1845 | 1889 | Babesia microti | 18S ribosomal RNA | 18S ribosomal RNA |
| 3144 | CUST_P10079356 | 1894 | 1938 | Babesia microti | 18S ribosomal RNA | 18S ribosomal RNA |
| 3145 | CUST_P10079357 | 1914 | 1962 | Babesia microti | 18S ribosomal RNA | 18S ribosomal RNA |
| 3146 | CUST_P10079358 | 1947 | 1997 | Babesia microti | 18S ribosomal RNA | 18S ribosomal RNA |
| 3147 | CUST_P10079359 | 1975 | 2019 | Babesia microti | 18S ribosomal RNA | 18S ribosomal RNA |
| 3148 | CUST_P10079360 | 2034 | 2093 | Babesia microti | 18S ribosomal RNA | 18S ribosomal RNA |
| 3149 | CUST_P10079361 | 2056 | 2115 | Babesia microti | 18S ribosomal RNA | 18S ribosomal RNA |
| 3150 | CUST_P10079362 | 2125 | 2174 | Babesia microti | 18S ribosomal RNA | 18S ribosomal RNA |

TABLE 9-continued

Exemplary bacterial and protozoan probes

| SEQ ID NO: | ProbeID | Start | End | Pathogen | Genomic Region | Product |
|---|---|---|---|---|---|---|
| 3151 | CUST_P10079363 | 2266 | 2322 | Babesia microti | 18S ribosomal RNA | 18S ribosomal RNA |
| 3152 | CUST_P10079364 | 2342 | 2392 | Babesia microti | 18S ribosomal RNA | 18S ribosomal RNA |
| 3153 | CUST_P10079365 | 2363 | 2418 | Babesia microti | 18S ribosomal RNA | 18S ribosomal RNA |
| 3154 | CUST_P10079366 | 2389 | 2446 | Babesia microti | 18S ribosomal RNA | 18S ribosomal RNA |
| 3155 | CUST_P10079478 | 328 | 375 | Plasmodium falciparum | 18S ribosomal RNA | 18S ribosomal RNA |
| 3156 | CUST_P10079479 | 433 | 492 | Plasmodium falciparum | 18S ribosomal RNA | 18S ribosomal RNA |
| 3157 | CUST_P10079480 | 517 | 566 | Plasmodium falciparum | 18S ribosomal RNA | 18S ribosomal RNA |
| 3158 | CUST_P10079481 | 612 | 671 | Plasmodium falciparum | 18S ribosomal RNA | 18S ribosomal RNA |
| 3159 | CUST_P10079482 | 820 | 879 | Plasmodium falciparum | 18S ribosomal RNA | 18S ribosomal RNA |
| 3160 | CUST_P10079483 | 945 | 1003 | Plasmodium falciparum | 18S ribosomal RNA | 18S ribosomal RNA |
| 3161 | CUST_P10079484 | 971 | 1030 | Plasmodium falciparum | 18S ribosomal RNA | 18S ribosomal RNA |
| 3162 | CUST_P10079485 | 1018 | 1077 | Plasmodium falciparum | 18S ribosomal RNA | 18S ribosomal RNA |
| 3163 | CUST_P10079486 | 1211 | 1257 | Plasmodium falciparum | 18S ribosomal RNA | 18S ribosomal RNA |
| 3164 | CUST_P10079487 | 1284 | 1343 | Plasmodium falciparum | 18S ribosomal RNA | 18S ribosomal RNA |
| 3165 | CUST_P10079488 | 1386 | 1445 | Plasmodium falciparum | 18S ribosomal RNA | 18S ribosomal RNA |
| 3166 | CUST_P10079489 | 1673 | 1727 | Plasmodium falciparum | 18S ribosomal RNA | 18S ribosomal RNA |
| 3167 | CUST_P10079490 | 1817 | 1876 | Plasmodium falciparum | 18S ribosomal RNA | 18S ribosomal RNA |
| 3168 | CUST_P10079491 | 1852 | 1911 | Plasmodium falciparum | 18S ribosomal RNA | 18S ribosomal RNA |
| 3169 | CUST_P10079492 | 70 | 129 | Plasmodium falciparum | 18S ribosomal RNA | 18S ribosomal RNA |
| 3170 | CUST_P10079493 | 321 | 373 | Plasmodium falciparum | 18S ribosomal RNA | 18S ribosomal RNA |
| 3171 | CUST_P10079494 | 460 | 519 | Plasmodium falciparum | 18S ribosomal RNA | 18S ribosomal RNA |
| 3172 | CUST_P10079495 | 489 | 548 | Plasmodium falciparum | 18S ribosomal RNA | 18S ribosomal RNA |
| 3173 | CUST_P10079496 | 519 | 569 | Plasmodium falciparum | 18S ribosomal RNA | 18S ribosomal RNA |
| 3174 | CUST_P10079497 | 599 | 658 | Plasmodium falciparum | 18S ribosomal RNA | 18S ribosomal RNA |
| 3175 | CUST_P10079498 | 800 | 859 | Plasmodium falciparum | 18S ribosomal RNA | 18S ribosomal RNA |
| 3176 | CUST_P10079499 | 826 | 885 | Plasmodium falciparum | 18S ribosomal RNA | 18S ribosomal RNA |
| 3177 | CUST_P10079500 | 990 | 1046 | Plasmodium falciparum | 18S ribosomal RNA | 18S ribosomal RNA |
| 3178 | CUST_P10079501 | 1014 | 1073 | Plasmodium falciparum | 18S ribosomal RNA | 18S ribosomal RNA |
| 3179 | CUST_P10079502 | 1053 | 1112 | Plasmodium falciparum | 18S ribosomal RNA | 18S ribosomal RNA |
| 3180 | CUST_P10079503 | 1264 | 1310 | Plasmodium falciparum | 18S ribosomal RNA | 18S ribosomal RNA |
| 3181 | CUST_P10079504 | 1332 | 1391 | Plasmodium falciparum | 18S ribosomal RNA | 18S ribosomal RNA |
| 3182 | CUST_P10079505 | 1450 | 1509 | Plasmodium falciparum | 18S ribosomal RNA | 18S ribosomal RNA |
| 3183 | CUST_P10079506 | 1721 | 1770 | Plasmodium falciparum | 18S ribosomal RNA | 18S ribosomal RNA |
| 3184 | CUST_P10079507 | 1742 | 1801 | Plasmodium falciparum | 18S ribosomal RNA | 18S ribosomal RNA |
| 3185 | CUST_P10079508 | 1890 | 1949 | Plasmodium falciparum | 18S ribosomal RNA | 18S ribosomal RNA |
| 3186 | CUST_P10079572 | 2 | 61 | Plasmodium vivax | SSU rRNA | external transcribed spacer |
| 3187 | CUST_P10079573 | 38 | 89 | Plasmodium vivax | SSU rRNA | external transcribed spacer |
| 3188 | CUST_P10079574 | 68 | 127 | Plasmodium vivax | SSU rRNA | external transcribed spacer |
| 3189 | CUST_P10079575 | 112 | 171 | Plasmodium vivax | SSU rRNA | external transcribed spacer |
| 3190 | CUST_P10079576 | 249 | 308 | Plasmodium vivax | SSU rRNA | external transcribed spacer |
| 3191 | CUST_P10079577 | 279 | 338 | Plasmodium vivax | SSU rRNA | external transcribed spacer |
| 3192 | CUST_P10079578 | 319 | 372 | Plasmodium vivax | SSU rRNA | external transcribed spacer |
| 3193 | CUST_P10079579 | 421 | 480 | Plasmodium vivax | SSU rRNA | external transcribed spacer |
| 3194 | CUST_P10079580 | 590 | 645 | Plasmodium vivax | SSU rRNA | external transcribed spacer |
| 3195 | CUST_P10079581 | 671 | 719 | Plasmodium vivax | SSU rRNA | external transcribed spacer |
| 3196 | CUST_P10079582 | 783 | 842 | Plasmodium vivax | SSU rRNA | external transcribed spacer |
| 3197 | CUST_P10079583 | 803 | 862 | Plasmodium vivax | SSU rRNA | external transcribed spacer |
| 3198 | CUST_P10079584 | 829 | 888 | Plasmodium vivax | SSU rRNA | external transcribed spacer |
| 3199 | CUST_P10079585 | 849 | 899 | Plasmodium vivax | SSU rRNA | external transcribed spacer |
| 3200 | CUST_P10079586 | 946 | 1005 | Plasmodium vivax | SSU rRNA | external transcribed spacer |
| 3201 | CUST_P10079587 | 1153 | 1212 | Plasmodium vivax | SSU rRNA | external transcribed spacer |
| 3202 | CUST_P10079588 | 1314 | 1373 | Plasmodium vivax | SSU rRNA | external transcribed spacer |
| 3203 | CUST_P10079589 | 1346 | 1405 | Plasmodium vivax | SSU rRNA | external transcribed spacer |
| 3204 | CUST_P10079590 | 1545 | 1591 | Plasmodium vivax | SSU rRNA | external transcribed spacer |
| 3205 | CUST_P10079591 | 1610 | 1669 | Plasmodium vivax | SSU rRNA | external transcribed spacer |
| 3206 | CUST_P10079592 | 1717 | 1776 | Plasmodium vivax | SSU rRNA | external transcribed spacer |
| 3207 | CUST_P10079593 | 1757 | 1816 | Plasmodium vivax | SSU rRNA | external transcribed spacer |

TABLE 10

Exemplary control probes

| SEQ ID NO: | ProbeID | Start | End | Type | Genomic Region |
|---|---|---|---|---|---|
| 3208 | CUST_P10079594 | 1561 | 1605 | Housekeeping Gene | ACTB |
| 3209 | CUST_P10079595 | 1703 | 1750 | Housekeeping Gene | ACTB |
| 3210 | CUST_P10079596 | 2220 | 2264 | Housekeeping Gene | ACTB |
| 3211 | CUST_P10079597 | 2242 | 2286 | Housekeeping Gene | ACTB |
| 3212 | CUST_P10079598 | 2276 | 2320 | Housekeeping Gene | ACTB |
| 3213 | CUST_P10079599 | 2402 | 2446 | Housekeeping Gene | ACTB |

TABLE 10-continued

Exemplary control probes

| SEQ ID NO: | ProbeID | Start | End | Type | Genomic Region |
|---|---|---|---|---|---|
| 3214 | CUST_P10079600 | 2489 | 2533 | Housekeeping Gene | ACTB |
| 3215 | CUST_P10079601 | 2659 | 2703 | Housekeeping Gene | ACTB |
| 3216 | CUST_P10079602 | 2696 | 2740 | Housekeeping Gene | ACTB |
| 3217 | CUST_P10079603 | 2823 | 2867 | Housekeeping Gene | ACTB |
| 3218 | CUST_P10079604 | 2847 | 2891 | Housekeeping Gene | ACTB |
| 3219 | CUST_P10079605 | 2874 | 2918 | Housekeeping Gene | ACTB |
| 3220 | CUST_P10079606 | 3005 | 3049 | Housekeeping Gene | ACTB |
| 3221 | CUST_P10079607 | 3046 | 3090 | Housekeeping Gene | ACTB |
| 3222 | CUST_P10079608 | 3213 | 3257 | Housekeeping Gene | ACTB |
| 3223 | CUST_P10079609 | 3338 | 3382 | Housekeeping Gene | ACTB |
| 3224 | CUST_P10079610 | 3376 | 3420 | Housekeeping Gene | ACTB |
| 3225 | CUST_P10079611 | 3393 | 3437 | Housekeeping Gene | ACTB |
| 3226 | CUST_P10079612 | 3438 | 3482 | Housekeeping Gene | ACTB |
| 3227 | CUST_P10079613 | 3545 | 3593 | Housekeeping Gene | ACTB |
| 3228 | CUST_P10079614 | 3568 | 3622 | Housekeeping Gene | ACTB |
| 3229 | CUST_P10079615 | 3601 | 3645 | Housekeeping Gene | ACTB |
| 3230 | CUST_P10079616 | 3744 | 3788 | Housekeeping Gene | ACTB |
| 3231 | CUST_P10079617 | 3858 | 3902 | Housekeeping Gene | ACTB |
| 3232 | CUST_P10079618 | 3973 | 4017 | Housekeeping Gene | ACTB |
| 3233 | CUST_P10079619 | 4130 | 4177 | Housekeeping Gene | ACTB |
| 3234 | CUST_P10079620 | 4223 | 4267 | Housekeeping Gene | ACTB |
| 3235 | CUST_P10079621 | 4280 | 4324 | Housekeeping Gene | ACTB |
| 3236 | CUST_P10079622 | 4304 | 4348 | Housekeeping Gene | ACTB |
| 3237 | CUST_P10079623 | 4315 | 4359 | Housekeeping Gene | ACTB |
| 3238 | CUST_P10079624 | 4459 | 4503 | Housekeeping Gene | ACTB |
| 3239 | CUST_P10079625 | 4592 | 4636 | Housekeeping Gene | ACTB |
| 3240 | CUST_P10079626 | 4906 | 4950 | Housekeeping Gene | ACTB |
| 3241 | CUST_P10079627 | 4932 | 4978 | Housekeeping Gene | ACTB |
| 3242 | CUST_P10079628 | 4972 | 5016 | Housekeeping Gene | ACTB |
| 3243 | CUST_P10079629 | 5024 | 5068 | Housekeeping Gene | ACTB |
| 3244 | CUST_P10079630 | 5040 | 5084 | Housekeeping Gene | ACTB |
| 3245 | CUST_P10079631 | 5076 | 5120 | Housekeeping Gene | ACTB |
| 3246 | CUST_P10079632 | 5110 | 5154 | Housekeeping Gene | ACTB |
| 3247 | CUST_P10079633 | 5200 | 5244 | Housekeeping Gene | ACTB |
| 3248 | CUST_P10079634 | 5357 | 5401 | Housekeeping Gene | ACTB |
| 3249 | CUST_P10079635 | 5390 | 5434 | Housekeeping Gene | ACTB |
| 3250 | CUST_P10079636 | 5415 | 5459 | Housekeeping Gene | ACTB |
| 3251 | CUST_P10079637 | 5453 | 5497 | Housekeeping Gene | ACTB |
| 3252 | CUST_P10079638 | 5474 | 5518 | Housekeeping Gene | ACTB |
| 3253 | CUST_P10079639 | 5622 | 5666 | Housekeeping Gene | ACTB |
| 3254 | CUST_P10079640 | 5662 | 5706 | Housekeeping Gene | ACTB |
| 3255 | CUST_P10079641 | 5691 | 5736 | Housekeeping Gene | ACTB |
| 3256 | CUST_P10079642 | 5712 | 5756 | Housekeeping Gene | ACTB |
| 3257 | CUST_P10079643 | 5760 | 5804 | Housekeeping Gene | ACTB |
| 3258 | CUST_P10079644 | 5783 | 5827 | Housekeeping Gene | ACTB |
| 3259 | CUST_P10079645 | 5817 | 5861 | Housekeeping Gene | ACTB |
| 3260 | CUST_P10079646 | 5963 | 6007 | Housekeeping Gene | ACTB |
| 3261 | CUST_P10079647 | 6004 | 6048 | Housekeeping Gene | ACTB |
| 3262 | CUST_P10079648 | 6106 | 6150 | Housekeeping Gene | ACTB |
| 3263 | CUST_P10079649 | 6310 | 6354 | Housekeeping Gene | ACTB |
| 3264 | CUST_P10079650 | 6421 | 6465 | Housekeeping Gene | ACTB |
| 3265 | CUST_P10079651 | 6507 | 6553 | Housekeeping Gene | ACTB |
| 3266 | CUST_P10079652 | 6696 | 6740 | Housekeeping Gene | ACTB |
| 3267 | CUST_P10079653 | 6722 | 6769 | Housekeeping Gene | ACTB |
| 3268 | CUST_P10079654 | 6745 | 6789 | Housekeeping Gene | ACTB |
| 3269 | CUST_P10079655 | 6772 | 6816 | Housekeeping Gene | ACTB |
| 3270 | CUST_P10079656 | 6793 | 6837 | Housekeeping Gene | ACTB |
| 3271 | CUST_P10079657 | 6844 | 6888 | Housekeeping Gene | ACTB |
| 3272 | CUST_P10079658 | 7000 | 7044 | Housekeeping Gene | ACTB |
| 3273 | CUST_P10079659 | 7321 | 7365 | Housekeeping Gene | ACTB |
| 3274 | CUST_P10079660 | 7418 | 7462 | Housekeeping Gene | ACTB |
| 3275 | CUST_P10079661 | 7554 | 7598 | Housekeeping Gene | ACTB |
| 3276 | CUST_P10079662 | 7683 | 7727 | Housekeeping Gene | ACTB |
| 3277 | CUST_P10079663 | 7777 | 7821 | Housekeeping Gene | ACTB |
| 3278 | CUST_P10079664 | 7825 | 7869 | Housekeeping Gene | ACTB |
| 3279 | CUST_P10079665 | 7861 | 7917 | Housekeeping Gene | ACTB |
| 3280 | CUST_P10079666 | 8033 | 8077 | Housekeeping Gene | ACTB |
| 3281 | CUST_P10079667 | 8138 | 8182 | Housekeeping Gene | ACTB |
| 3282 | CUST_P10079668 | 8344 | 8388 | Housekeeping Gene | ACTB |
| 3283 | CUST_P10079669 | 8459 | 8503 | Housekeeping Gene | ACTB |
| 3284 | CUST_P10079670 | 8519 | 8563 | Housekeeping Gene | ACTB |
| 3285 | CUST_P10079671 | 8543 | 8587 | Housekeeping Gene | ACTB |
| 3286 | CUST_P10079672 | 8574 | 8618 | Housekeeping Gene | ACTB |
| 3287 | CUST_P10079673 | 8628 | 8672 | Housekeeping Gene | ACTB |
| 3288 | CUST_P10079674 | 8732 | 8776 | Housekeeping Gene | ACTB |

TABLE 10-continued

Exemplary control probes

| SEQ ID NO: | ProbeID | Start | End | Type | Genomic Region |
|---|---|---|---|---|---|
| 3289 | CUST_P10079675 | 8941 | 8985 | Housekeeping Gene | ACTB |
| 3290 | CUST_P10079676 | 8962 | 9006 | Housekeeping Gene | ACTB |
| 3291 | CUST_P10079677 | 8987 | 9031 | Housekeeping Gene | ACTB |
| 3292 | CUST_P10079678 | 9103 | 9147 | Housekeeping Gene | ACTB |
| 3293 | CUST_P10079679 | 9155 | 9199 | Housekeeping Gene | ACTB |
| 3294 | CUST_P10079680 | 9429 | 9474 | Housekeeping Gene | ACTB |
| 3295 | CUST_P10079681 | 9554 | 9600 | Housekeeping Gene | ACTB |
| 3296 | CUST_P10079682 | 9739 | 9785 | Housekeeping Gene | ACTB |
| 3297 | CUST_P10079683 | 9774 | 9820 | Housekeeping Gene | ACTB |
| 3298 | CUST_P10079684 | 9794 | 9838 | Housekeeping Gene | ACTB |
| 3299 | CUST_P10079685 | 10015 | 10062 | Housekeeping Gene | ACTB |
| 3300 | CUST_P10079686 | 10064 | 10108 | Housekeeping Gene | ACTB |
| 3301 | CUST_P10079687 | 10193 | 10245 | Housekeeping Gene | ACTB |
| 3302 | CUST_P10079715 | 3325 | 3369 | Housekeeping Gene | ARL1 |
| 3303 | CUST_P10079713 | 3255 | 3314 | Housekeeping Gene | ARL1 |
| 3304 | CUST_P10079727 | 5957 | 6016 | Housekeeping Gene | ARL1 |
| 3305 | CUST_P10079741 | 10779 | 10838 | Housekeeping Gene | ARL1 |
| 3306 | CUST_P10079759 | 13558 | 13604 | Housekeeping Gene | ARL1 |
| 3307 | CUST_P10079701 | 934 | 979 | Housekeeping Gene | ARL1 |
| 3308 | CUST_P10079692 | 526 | 570 | Housekeeping Gene | ARL1 |
| 3309 | CUST_P10079750 | 11884 | 11939 | Housekeeping Gene | ARL1 |
| 3310 | CUST_P10079730 | 6728 | 6787 | Housekeeping Gene | ARL1 |
| 3311 | CUST_P10079746 | 11349 | 11397 | Housekeeping Gene | ARL1 |
| 3312 | CUST_P10079744 | 11307 | 11354 | Housekeeping Gene | ARL1 |
| 3313 | CUST_P10079732 | 7235 | 7286 | Housekeeping Gene | ARL1 |
| 3314 | CUST_P10079733 | 7270 | 7314 | Housekeeping Gene | ARL1 |
| 3315 | CUST_P10079760 | 13597 | 13641 | Housekeeping Gene | ARL1 |
| 3316 | CUST_P10079762 | 13648 | 13693 | Housekeeping Gene | ARL1 |
| 3317 | CUST_P10079758 | 13449 | 13508 | Housekeeping Gene | ARL1 |
| 3318 | CUST_P10079728 | 6518 | 6577 | Housekeeping Gene | ARL1 |
| 3319 | CUST_P10079738 | 9891 | 9950 | Housekeeping Gene | ARL1 |
| 3320 | CUST_P10079742 | 10939 | 10998 | Housekeeping Gene | ARL1 |
| 3321 | CUST_P10079696 | 746 | 796 | Housekeeping Gene | ARL1 |
| 3322 | CUST_P10079703 | 1025 | 1079 | Housekeeping Gene | ARL1 |
| 3323 | CUST_P10079688 | 137 | 181 | Housekeeping Gene | ARL1 |
| 3324 | CUST_P10079755 | 12703 | 12762 | Housekeeping Gene | ARL1 |
| 3325 | CUST_P10079748 | 11728 | 11787 | Housekeeping Gene | ARL1 |
| 3326 | CUST_P10079722 | 5055 | 5114 | Housekeeping Gene | ARL1 |
| 3327 | CUST_P10079724 | 5213 | 5268 | Housekeeping Gene | ARL1 |
| 3328 | CUST_P10079736 | 8842 | 8901 | Housekeeping Gene | ARL1 |
| 3329 | CUST_P10079714 | 3291 | 3350 | Housekeeping Gene | ARL1 |
| 3330 | CUST_P10079726 | 5923 | 5982 | Housekeeping Gene | ARL1 |
| 3331 | CUST_P10079735 | 8610 | 8669 | Housekeeping Gene | ARL1 |
| 3332 | CUST_P10079739 | 10525 | 10584 | Housekeeping Gene | ARL1 |
| 3333 | CUST_P10079747 | 11552 | 11599 | Housekeeping Gene | ARL1 |
| 3334 | CUST_P10079753 | 12428 | 12487 | Housekeeping Gene | ARL1 |
| 3335 | CUST_P10079768 | 14112 | 14158 | Housekeeping Gene | ARL1 |
| 3336 | CUST_P10079690 | 310 | 354 | Housekeeping Gene | ARL1 |
| 3337 | CUST_P10079691 | 435 | 483 | Housekeeping Gene | ARL1 |
| 3338 | CUST_P10079702 | 977 | 1028 | Housekeeping Gene | ARL1 |
| 3339 | CUST_P10079689 | 209 | 253 | Housekeeping Gene | ARL1 |
| 3340 | CUST_P10079743 | 11265 | 11317 | Housekeeping Gene | ARL1 |
| 3341 | CUST_P10079745 | 11327 | 11379 | Housekeeping Gene | ARL1 |
| 3342 | CUST_P10079712 | 3205 | 3264 | Housekeeping Gene | ARL1 |
| 3343 | CUST_P10079740 | 10708 | 10767 | Housekeeping Gene | ARL1 |
| 3344 | CUST_P10079710 | 2561 | 2620 | Housekeeping Gene | ARL1 |
| 3345 | CUST_P10079717 | 3630 | 3689 | Housekeeping Gene | ARL1 |
| 3346 | CUST_P10079761 | 13619 | 13672 | Housekeeping Gene | ARL1 |
| 3347 | CUST_P10079707 | 1616 | 1675 | Housekeeping Gene | ARL1 |
| 3348 | CUST_P10079767 | 14091 | 14135 | Housekeeping Gene | ARL1 |
| 3349 | CUST_P10079699 | 861 | 910 | Housekeeping Gene | ARL1 |
| 3350 | CUST_P10079697 | 794 | 838 | Housekeeping Gene | ARL1 |
| 3351 | CUST_P10079694 | 683 | 742 | Housekeeping Gene | ARL1 |
| 3352 | CUST_P10079749 | 11842 | 11901 | Housekeeping Gene | ARL1 |
| 3353 | CUST_P10079716 | 3606 | 3665 | Housekeeping Gene | ARL1 |
| 3354 | CUST_P10079708 | 2224 | 2283 | Housekeeping Gene | ARL1 |
| 3355 | CUST_P10079719 | 4420 | 4479 | Housekeeping Gene | ARL1 |
| 3356 | CUST_P10079763 | 13695 | 13749 | Housekeeping Gene | ARL1 |
| 3357 | CUST_P10079752 | 12271 | 12330 | Housekeeping Gene | ARL1 |
| 3358 | CUST_P10079721 | 4794 | 4853 | Housekeeping Gene | ARL1 |
| 3359 | CUST_P10079766 | 14055 | 14099 | Housekeeping Gene | ARL1 |
| 3360 | CUST_P10079764 | 13860 | 13919 | Housekeeping Gene | ARL1 |
| 3361 | CUST_P10079765 | 13910 | 13963 | Housekeeping Gene | ARL1 |
| 3362 | CUST_P10079706 | 1514 | 1573 | Housekeeping Gene | ARL1 |
| 3363 | CUST_P10079705 | 1462 | 1509 | Housekeeping Gene | ARL1 |

TABLE 10-continued

Exemplary control probes

| SEQ ID NO: | ProbeID | Start | End | Type | Genomic Region |
|---|---|---|---|---|---|
| 3364 | CUST_P10079695 | 715 | 774 | Housekeeping Gene | ARL1 |
| 3365 | CUST_P10079698 | 836 | 884 | Housekeeping Gene | ARL1 |
| 3366 | CUST_P10079693 | 655 | 710 | Housekeeping Gene | ARL1 |
| 3367 | CUST_P10079754 | 12585 | 12644 | Housekeeping Gene | ARL1 |
| 3368 | CUST_P10079731 | 7083 | 7139 | Housekeeping Gene | ARL1 |
| 3369 | CUST_P10079723 | 5093 | 5152 | Housekeeping Gene | ARL1 |
| 3370 | CUST_P10079704 | 1198 | 1257 | Housekeeping Gene | ARL1 |
| 3371 | CUST_P10079756 | 12839 | 12888 | Housekeeping Gene | ARL1 |
| 3372 | CUST_P10079711 | 2977 | 3036 | Housekeeping Gene | ARL1 |
| 3373 | CUST_P10079709 | 2313 | 2369 | Housekeeping Gene | ARL1 |
| 3374 | CUST_P10079770 | 14253 | 14312 | Housekeeping Gene | ARL1 |
| 3375 | CUST_P10079700 | 891 | 939 | Housekeeping Gene | ARL1 |
| 3376 | CUST_P10079734 | 7994 | 8053 | Housekeeping Gene | ARL1 |
| 3377 | CUST_P10079729 | 6688 | 6746 | Housekeeping Gene | ARL1 |
| 3378 | CUST_P10079718 | 4205 | 4249 | Housekeeping Gene | ARL1 |
| 3379 | CUST_P10079751 | 12179 | 12229 | Housekeeping Gene | ARL1 |
| 3380 | CUST_P10079720 | 4653 | 4712 | Housekeeping Gene | ARL1 |
| 3381 | CUST_P10079725 | 5683 | 5733 | Housekeeping Gene | ARL1 |
| 3382 | CUST_P10079769 | 14139 | 14193 | Housekeeping Gene | ARL1 |
| 3383 | CUST_P10079771 | 14283 | 14342 | Housekeeping Gene | ARL1 |
| 3384 | CUST_P10079737 | 8984 | 9043 | Housekeeping Gene | ARL1 |
| 3385 | CUST_P10079757 | 12965 | 13024 | Housekeeping Gene | ARL1 |
| 3386 | CUST_P10079772 | 69 | 113 | Housekeeping Gene | CCDN1 |
| 3387 | CUST_P10079773 | 104 | 148 | Housekeeping Gene | CCDN1 |
| 3388 | CUST_P10079774 | 297 | 341 | Housekeeping Gene | CCDN1 |
| 3389 | CUST_P10079775 | 332 | 376 | Housekeeping Gene | CCDN1 |
| 3390 | CUST_P10079776 | 395 | 439 | Housekeeping Gene | CCDN1 |
| 3391 | CUST_P10079777 | 680 | 724 | Housekeeping Gene | CCDN1 |
| 3392 | CUST_P10079778 | 844 | 903 | Housekeeping Gene | CCDN1 |
| 3393 | CUST_P10079779 | 1049 | 1093 | Housekeeping Gene | CCDN1 |
| 3394 | CUST_P10079780 | 1146 | 1190 | Housekeeping Gene | CCDN1 |
| 3395 | CUST_P10079781 | 1368 | 1412 | Housekeeping Gene | CCDN1 |
| 3396 | CUST_P10079782 | 1513 | 1557 | Housekeeping Gene | CCDN1 |
| 3397 | CUST_P10079783 | 1553 | 1597 | Housekeeping Gene | CCDN1 |
| 3398 | CUST_P10079784 | 1811 | 1855 | Housekeeping Gene | CCDN1 |
| 3399 | CUST_P10079785 | 1936 | 1980 | Housekeeping Gene | CCDN1 |
| 3400 | CUST_P10079786 | 2041 | 2085 | Housekeeping Gene | CCDN1 |
| 3401 | CUST_P10079787 | 2206 | 2250 | Housekeeping Gene | CCDN1 |
| 3402 | CUST_P10079788 | 2233 | 2277 | Housekeeping Gene | CCDN1 |
| 3403 | CUST_P10079789 | 2279 | 2323 | Housekeeping Gene | CCDN1 |
| 3404 | CUST_P10079790 | 2321 | 2365 | Housekeeping Gene | CCDN1 |
| 3405 | CUST_P10079791 | 2346 | 2390 | Housekeeping Gene | CCDN1 |
| 3406 | CUST_P10079792 | 2376 | 2420 | Housekeeping Gene | CCDN1 |
| 3407 | CUST_P10079793 | 2385 | 2429 | Housekeeping Gene | CCDN1 |
| 3408 | CUST_P10079794 | 2413 | 2457 | Housekeeping Gene | CCDN1 |
| 3409 | CUST_P10079795 | 2455 | 2499 | Housekeeping Gene | CCDN1 |
| 3410 | CUST_P10079796 | 2584 | 2628 | Housekeeping Gene | CCDN1 |
| 3411 | CUST_P10079797 | 2794 | 2838 | Housekeeping Gene | CCDN1 |
| 3412 | CUST_P10079798 | 2842 | 2886 | Housekeeping Gene | CCDN1 |
| 3413 | CUST_P10079799 | 2899 | 2943 | Housekeeping Gene | CCDN1 |
| 3414 | CUST_P10079800 | 2953 | 2997 | Housekeeping Gene | CCDN1 |
| 3415 | CUST_P10079801 | 3037 | 3081 | Housekeeping Gene | CCDN1 |
| 3416 | CUST_P10079802 | 3135 | 3179 | Housekeeping Gene | CCDN1 |
| 3417 | CUST_P10079803 | 3194 | 3238 | Housekeeping Gene | CCDN1 |
| 3418 | CUST_P10079804 | 3365 | 3409 | Housekeeping Gene | CCDN1 |
| 3419 | CUST_P10079805 | 3518 | 3562 | Housekeeping Gene | CCDN1 |
| 3420 | CUST_P10079806 | 3675 | 3719 | Housekeeping Gene | CCDN1 |
| 3421 | CUST_P10079807 | 3753 | 3797 | Housekeeping Gene | CCDN1 |
| 3422 | CUST_P10079808 | 3904 | 3948 | Housekeeping Gene | CCDN1 |
| 3423 | CUST_P10079809 | 4120 | 4164 | Housekeeping Gene | CCDN1 |
| 3424 | CUST_P10079810 | 4201 | 4245 | Housekeeping Gene | CCDN1 |
| 3425 | CUST_P10079811 | 4312 | 4356 | Housekeeping Gene | CCDN1 |
| 3426 | CUST_P10079812 | 4419 | 4463 | Housekeeping Gene | CCDN1 |
| 3427 | CUST_P10079813 | 4486 | 4530 | Housekeeping Gene | CCDN1 |
| 3428 | CUST_P10079814 | 4518 | 4562 | Housekeeping Gene | CCDN1 |
| 3429 | CUST_P10079815 | 4542 | 4586 | Housekeeping Gene | CCDN1 |
| 3430 | CUST_P10079816 | 4560 | 4609 | Housekeeping Gene | CCDN1 |
| 3431 | CUST_P10079817 | 4595 | 4639 | Housekeeping Gene | CCDN1 |
| 3432 | CUST_P10079818 | 4633 | 4677 | Housekeeping Gene | CCDN1 |
| 3433 | CUST_P10079819 | 4645 | 4692 | Housekeeping Gene | CCDN1 |
| 3434 | CUST_P10079820 | 4674 | 4720 | Housekeeping Gene | CCDN1 |
| 3435 | CUST_P10079821 | 4726 | 4770 | Housekeeping Gene | CCDN1 |
| 3436 | CUST_P10079822 | 4753 | 4797 | Housekeeping Gene | CCDN1 |
| 3437 | CUST_P10079823 | 4910 | 4956 | Housekeeping Gene | CCDN1 |
| 3438 | CUST_P10079824 | 5081 | 5131 | Housekeeping Gene | CCDN1 |

TABLE 10-continued

Exemplary control probes

| SEQ ID NO: | ProbeID | Start | End | Type | Genomic Region |
|---|---|---|---|---|---|
| 3439 | CUST_P10079825 | 5281 | 5325 | Housekeeping Gene | CCDN1 |
| 3440 | CUST_P10079826 | 5295 | 5345 | Housekeeping Gene | CCDN1 |
| 3441 | CUST_P10079827 | 5319 | 5363 | Housekeeping Gene | CCDN1 |
| 3442 | CUST_P10079828 | 5472 | 5516 | Housekeeping Gene | CCDN1 |
| 3443 | CUST_P10079829 | 5506 | 5550 | Housekeeping Gene | CCDN1 |
| 3444 | CUST_P10079830 | 5654 | 5698 | Housekeeping Gene | CCDN1 |
| 3445 | CUST_P10079831 | 5680 | 5724 | Housekeeping Gene | CCDN1 |
| 3446 | CUST_P10079832 | 5709 | 5753 | Housekeeping Gene | CCDN1 |
| 3447 | CUST_P10079833 | 5736 | 5780 | Housekeeping Gene | CCDN1 |
| 3448 | CUST_P10079834 | 5775 | 5819 | Housekeeping Gene | CCDN1 |
| 3449 | CUST_P10079835 | 5804 | 5848 | Housekeeping Gene | CCDN1 |
| 3450 | CUST_P10079836 | 5828 | 5872 | Housekeeping Gene | CCDN1 |
| 3451 | CUST_P10079837 | 5876 | 5920 | Housekeeping Gene | CCDN1 |
| 3452 | CUST_P10079838 | 6010 | 6054 | Housekeeping Gene | CCDN1 |
| 3453 | CUST_P10079839 | 6083 | 6133 | Housekeeping Gene | CCDN1 |
| 3454 | CUST_P10079840 | 6163 | 6207 | Housekeeping Gene | CCDN1 |
| 3455 | CUST_P10079841 | 6270 | 6314 | Housekeeping Gene | CCDN1 |
| 3456 | CUST_P10079842 | 6395 | 6442 | Housekeeping Gene | CCDN1 |
| 3457 | CUST_P10079843 | 6557 | 6604 | Housekeeping Gene | CCDN1 |
| 3458 | CUST_P10079844 | 6611 | 6656 | Housekeeping Gene | CCDN1 |
| 3459 | CUST_P10079845 | 6635 | 6679 | Housekeeping Gene | CCDN1 |
| 3460 | CUST_P10079846 | 6770 | 6814 | Housekeeping Gene | CCDN1 |
| 3461 | CUST_P10079847 | 6895 | 6939 | Housekeeping Gene | CCDN1 |
| 3462 | CUST_P10079848 | 6976 | 7020 | Housekeeping Gene | CCDN1 |
| 3463 | CUST_P10079849 | 7012 | 7056 | Housekeeping Gene | CCDN1 |
| 3464 | CUST_P10079850 | 7064 | 7108 | Housekeeping Gene | CCDN1 |
| 3465 | CUST_P10079851 | 7224 | 7268 | Housekeeping Gene | CCDN1 |
| 3466 | CUST_P10079852 | 7283 | 7327 | Housekeeping Gene | CCDN1 |
| 3467 | CUST_P10079853 | 7444 | 7488 | Housekeeping Gene | CCDN1 |
| 3468 | CUST_P10079854 | 7649 | 7693 | Housekeeping Gene | CCDN1 |
| 3469 | CUST_P10079855 | 7768 | 7812 | Housekeeping Gene | CCDN1 |
| 3470 | CUST_P10079856 | 7794 | 7838 | Housekeeping Gene | CCDN1 |
| 3471 | CUST_P10079857 | 7858 | 7902 | Housekeeping Gene | CCDN1 |
| 3472 | CUST_P10079858 | 7957 | 8001 | Housekeeping Gene | CCDN1 |
| 3473 | CUST_P10079859 | 8092 | 8136 | Housekeeping Gene | CCDN1 |
| 3474 | CUST_P10079860 | 8120 | 8168 | Housekeeping Gene | CCDN1 |
| 3475 | CUST_P10079861 | 8173 | 8217 | Housekeeping Gene | CCDN1 |
| 3476 | CUST_P10079862 | 8228 | 8272 | Housekeeping Gene | CCDN1 |
| 3477 | CUST_P10079863 | 8422 | 8473 | Housekeeping Gene | CCDN1 |
| 3478 | CUST_P10079864 | 8469 | 8513 | Housekeeping Gene | CCDN1 |
| 3479 | CUST_P10079865 | 8649 | 8693 | Housekeeping Gene | CCDN1 |
| 3480 | CUST_P10079866 | 8842 | 8887 | Housekeeping Gene | CCDN1 |
| 3481 | CUST_P10079867 | 8960 | 9004 | Housekeeping Gene | CCDN1 |
| 3482 | CUST_P10079868 | 8995 | 9039 | Housekeeping Gene | CCDN1 |
| 3483 | CUST_P10079869 | 9060 | 9104 | Housekeeping Gene | CCDN1 |
| 3484 | CUST_P10079870 | 9132 | 9176 | Housekeeping Gene | CCDN1 |
| 3485 | CUST_P10079871 | 9183 | 9227 | Housekeeping Gene | CCDN1 |
| 3486 | CUST_P10079872 | 9196 | 9240 | Housekeeping Gene | CCDN1 |
| 3487 | CUST_P10079873 | 9229 | 9273 | Housekeeping Gene | CCDN1 |
| 3488 | CUST_P10079874 | 9266 | 9310 | Housekeeping Gene | CCDN1 |
| 3489 | CUST_P10079875 | 9309 | 9353 | Housekeeping Gene | CCDN1 |
| 3490 | CUST_P10079876 | 9333 | 9377 | Housekeeping Gene | CCDN1 |
| 3491 | CUST_P10079877 | 9390 | 9434 | Housekeeping Gene | CCDN1 |
| 3492 | CUST_P10079878 | 9430 | 9474 | Housekeeping Gene | CCDN1 |
| 3493 | CUST_P10079879 | 9479 | 9523 | Housekeeping Gene | CCDN1 |
| 3494 | CUST_P10079880 | 9508 | 9552 | Housekeeping Gene | CCDN1 |
| 3495 | CUST_P10079881 | 9519 | 9563 | Housekeeping Gene | CCDN1 |
| 3496 | CUST_P10079882 | 9570 | 9614 | Housekeeping Gene | CCDN1 |
| 3497 | CUST_P10079883 | 9592 | 9639 | Housekeeping Gene | CCDN1 |
| 3498 | CUST_P10079884 | 9705 | 9749 | Housekeeping Gene | CCDN1 |
| 3499 | CUST_P10079885 | 9885 | 9933 | Housekeeping Gene | CCDN1 |
| 3500 | CUST_P10079886 | 10029 | 10073 | Housekeeping Gene | CCDN1 |
| 3501 | CUST_P10079887 | 10165 | 10209 | Housekeeping Gene | CCDN1 |
| 3502 | CUST_P10079888 | 10204 | 10248 | Housekeeping Gene | CCDN1 |
| 3503 | CUST_P10079889 | 10442 | 10501 | Housekeeping Gene | CCDN1 |
| 3504 | CUST_P10079890 | 10526 | 10574 | Housekeeping Gene | CCDN1 |
| 3505 | CUST_P10079891 | 10760 | 10819 | Housekeeping Gene | CCDN1 |
| 3506 | CUST_P10079892 | 10833 | 10877 | Housekeeping Gene | CCDN1 |
| 3507 | CUST_P10079893 | 10868 | 10912 | Housekeeping Gene | CCDN1 |
| 3508 | CUST_P10079894 | 10900 | 10944 | Housekeeping Gene | CCDN1 |
| 3509 | CUST_P10079895 | 10931 | 10975 | Housekeeping Gene | CCDN1 |
| 3510 | CUST_P10079896 | 11055 | 11107 | Housekeeping Gene | CCDN1 |
| 3511 | CUST_P10079897 | 11190 | 11242 | Housekeeping Gene | CCDN1 |
| 3512 | CUST_P10079898 | 11364 | 11410 | Housekeeping Gene | CCDN1 |
| 3513 | CUST_P10079899 | 11472 | 11525 | Housekeeping Gene | CCDN1 |

TABLE 10-continued

Exemplary control probes

| SEQ ID NO: | ProbeID | Start | End | Type | Genomic Region |
|---|---|---|---|---|---|
| 3514 | CUST_P10079900 | 11490 | 11547 | Housekeeping Gene | CCDN1 |
| 3515 | CUST_P10079901 | 11807 | 11852 | Housekeeping Gene | CCDN1 |
| 3516 | CUST_P10079902 | 11887 | 11940 | Housekeeping Gene | CCDN1 |
| 3517 | CUST_P10079903 | 12162 | 12221 | Housekeeping Gene | CCDN1 |
| 3518 | CUST_P10079904 | 12355 | 12412 | Housekeeping Gene | CCDN1 |
| 3519 | CUST_P10079905 | 12402 | 12446 | Housekeeping Gene | CCDN1 |
| 3520 | CUST_P10081361 | 16 | 63 | Negative Control | *Aedes albopictus densovirus 2* |
| 3521 | CUST_P10081362 | 47 | 101 | Negative Control | *Aedes albopictus densovirus 2* |
| 3522 | CUST_P10081363 | 79 | 131 | Negative Control | *Aedes albopictus densovirus 2* |
| 3523 | CUST_P10081364 | 204 | 248 | Negative Control | *Aedes albopictus densovirus 2* |
| 3524 | CUST_P10081365 | 302 | 361 | Negative Control | *Aedes albopictus densovirus 2* |
| 3525 | CUST_P10081366 | 330 | 385 | Negative Control | *Aedes albopictus densovirus 2* |
| 3526 | CUST_P10081367 | 390 | 435 | Negative Control | *Aedes albopictus densovirus 2* |
| 3527 | CUST_P10081368 | 426 | 472 | Negative Control | *Aedes albopictus densovirus 2* |
| 3528 | CUST_P10081369 | 590 | 649 | Negative Control | *Aedes albopictus densovirus 2* |
| 3529 | CUST_P10081370 | 617 | 673 | Negative Control | *Aedes albopictus densovirus 2* |
| 3530 | CUST_P10081371 | 654 | 707 | Negative Control | *Aedes albopictus densovirus 2* |
| 3531 | CUST_P10081372 | 753 | 810 | Negative Control | *Aedes albopictus densovirus 2* |
| 3532 | CUST_P10081373 | 791 | 844 | Negative Control | *Aedes albopictus densovirus 2* |
| 3533 | CUST_P10081374 | 824 | 880 | Negative Control | *Aedes albopictus densovirus 2* |
| 3534 | CUST_P10081375 | 966 | 1015 | Negative Control | *Aedes albopictus densovirus 2* |
| 3535 | CUST_P10081376 | 1174 | 1233 | Negative Control | *Aedes albopictus densovirus 2* |
| 3536 | CUST_P10081377 | 1295 | 1339 | Negative Control | *Aedes albopictus densovirus 2* |
| 3537 | CUST_P10081378 | 1385 | 1433 | Negative Control | *Aedes albopictus densovirus 2* |
| 3538 | CUST_P10081379 | 1538 | 1582 | Negative Control | *Aedes albopictus densovirus 2* |
| 3539 | CUST_P10081380 | 1556 | 1601 | Negative Control | *Aedes albopictus densovirus 2* |
| 3540 | CUST_P10081381 | 1636 | 1689 | Negative Control | *Aedes albopictus densovirus 2* |
| 3541 | CUST_P10081382 | 1752 | 1811 | Negative Control | *Aedes albopictus densovirus 2* |
| 3542 | CUST_P10081383 | 1810 | 1854 | Negative Control | *Aedes albopictus densovirus 2* |
| 3543 | CUST_P10081384 | 1836 | 1893 | Negative Control | *Aedes albopictus densovirus 2* |
| 3544 | CUST_P10081385 | 1858 | 1913 | Negative Control | *Aedes albopictus densovirus 2* |
| 3545 | CUST_P10081386 | 1977 | 2036 | Negative Control | *Aedes albopictus densovirus 2* |
| 3546 | CUST_P10081387 | 2065 | 2124 | Negative Control | *Aedes albopictus densovirus 2* |
| 3547 | CUST_P10081388 | 2093 | 2152 | Negative Control | *Aedes albopictus densovirus 2* |
| 3548 | CUST_P10081389 | 2136 | 2195 | Negative Control | *Aedes albopictus densovirus 2* |
| 3549 | CUST_P10081390 | 2162 | 2221 | Negative Control | *Aedes albopictus densovirus 2* |
| 3550 | CUST_P10081391 | 2209 | 2257 | Negative Control | *Aedes albopictus densovirus 2* |
| 3551 | CUST_P10081392 | 2384 | 2434 | Negative Control | *Aedes albopictus densovirus 2* |
| 3552 | CUST_P10081393 | 2497 | 2546 | Negative Control | *Aedes albopictus densovirus 2* |
| 3553 | CUST_P10081394 | 2530 | 2589 | Negative Control | *Aedes albopictus densovirus 3* |

TABLE 10-continued

Exemplary control probes

| SEQ ID NO: | ProbeID | Start | End | Type | Genomic Region |
|---|---|---|---|---|---|
| 3554 | CUST_P10081395 | 2697 | 2754 | Negative Control | Aedes albopictus densovirus 2 |
| 3555 | CUST_P10081396 | 2766 | 2825 | Negative Control | Aedes albopictus densovirus 2 |
| 3556 | CUST_P10081397 | 281 | 340 | Negative Control | Aedes albopictus densovirus 2 |
| 3557 | CUST_P10081398 | 353 | 404 | Negative Control | Aedes albopictus densovirus 2 |
| 3558 | CUST_P10081399 | 411 | 457 | Negative Control | Maize streak virus |
| 3559 | CUST_P10081400 | 572 | 630 | Negative Control | Maize streak virus |
| 3560 | CUST_P10081401 | 727 | 786 | Negative Control | Maize streak virus |
| 3561 | CUST_P10081402 | 760 | 819 | Negative Control | Maize streak virus |
| 3562 | CUST_P10081403 | 799 | 852 | Negative Control | Maize streak virus |
| 3563 | CUST_P10081404 | 839 | 891 | Negative Control | Maize streak virus |
| 3564 | CUST_P10081405 | 871 | 919 | Negative Control | Maize streak virus |
| 3565 | CUST_P10081406 | 937 | 988 | Negative Control | Maize streak virus |
| 3566 | CUST_P10081407 | 961 | 1011 | Negative Control | Maize streak virus |
| 3567 | CUST_P10081408 | 1177 | 1233 | Negative Control | Maize streak virus |
| 3568 | CUST_P10081409 | 1316 | 1365 | Negative Control | Maize streak virus |
| 3569 | CUST_P10081410 | 1362 | 1420 | Negative Control | Maize streak virus |
| 3570 | CUST_P10081411 | 1391 | 1450 | Negative Control | Maize streak virus |
| 3571 | CUST_P10081412 | 1447 | 1506 | Negative Control | Maize streak virus |
| 3572 | CUST_P10081413 | 1694 | 1753 | Negative Control | Maize streak virus |
| 3573 | CUST_P10081414 | 1837 | 1896 | Negative Control | Maize streak virus |
| 3574 | CUST_P10081415 | 2047 | 2106 | Negative Control | Maize streak virus |
| 3575 | CUST_P10081416 | 2095 | 2147 | Negative Control | Maize streak virus |
| 3576 | CUST_P10081417 | 2362 | 2421 | Negative Control | Maize streak virus |
| 3577 | CUST_P10081418 | 2387 | 2446 | Negative Control | Maize streak virus |
| 3578 | CUST_P10081419 | 2536 | 2595 | Negative Control | Maize streak virus |
| 3579 | CUST_P10081420 | 2666 | 2713 | Negative Control | Maize streak virus |
| 3580 | CUST_P10081421 | 2893 | 2952 | Negative Control | Maize streak virus |
| 3581 | CUST_P10081422 | 2953 | 3012 | Negative Control | Maize streak virus |
| 3582 | CUST_P10081423 | 2987 | 3045 | Negative Control | Maize streak virus |
| 3583 | CUST_P10081424 | 3014 | 3071 | Negative Control | Maize streak virus |
| 3584 | CUST_P10081425 | 3054 | 3105 | Negative Control | Maize streak virus |
| 3585 | CUST_P10081426 | 3093 | 3142 | Negative Control | Maize streak virus |
| 3586 | CUST_P10081427 | 3144 | 3203 | Negative Control | Maize streak virus |
| 3587 | CUST_P10081428 | 3194 | 3253 | Negative Control | Maize streak virus |
| 3588 | CUST_P10081429 | 3330 | 3389 | Negative Control | Maize streak virus |
| 3589 | CUST_P10081430 | 3390 | 3438 | Negative Control | Maize streak virus |
| 3590 | CUST_P10081431 | 3414 | 3469 | Negative Control | Maize streak virus |
| 3591 | CUST_P10081432 | 3441 | 3494 | Negative Control | Maize streak virus |
| 3592 | CUST_P10081433 | 3525 | 3584 | Negative Control | Maize streak virus |
| 3593 | CUST_P10081434 | 3586 | 3645 | Negative Control | Maize streak virus |
| 3594 | CUST_P10081435 | 3727 | 3786 | Negative Control | Maize streak virus |
| 3595 | CUST_P10081436 | 3879 | 3923 | Negative Control | Maize streak virus |
| 3596 | CUST_P10081437 | 3967 | 4011 | Negative Control | Maize streak virus |
| 3597 | CUST_P10081438 | 112 | 169 | Negative Control | Maize streak virus |
| 3598 | CUST_P10081439 | 272 | 316 | Negative Control | Maize streak virus |
| 3599 | CUST_P10081440 | 301 | 345 | Negative Control | Tomato pseudo-curly top virus |
| 3600 | CUST_P10081441 | 341 | 387 | Negative Control | Tomato pseudo-curly top virus |
| 3601 | CUST_P10081442 | 436 | 480 | Negative Control | Tomato pseudo-curly top virus |
| 3602 | CUST_P10081443 | 468 | 515 | Negative Control | Tomato pseudo-curly top virus |
| 3603 | CUST_P10081444 | 490 | 534 | Negative Control | Tomato pseudo-curly top virus |
| 3604 | CUST_P10081446 | 687 | 731 | Negative Control | Tomato pseudo-curly top virus |
| 3605 | CUST_P10081447 | 803 | 847 | Negative Control | Tomato pseudo-curly top virus |
| 3606 | CUST_P10081448 | 813 | 857 | Negative Control | Tomato pseudo-curly top virus |
| 3607 | CUST_P10081449 | 842 | 887 | Negative Control | Tomato pseudo-curly top virus |
| 3608 | CUST_P10081451 | 1031 | 1090 | Negative Control | Tomato pseudo-curly top virus |
| 3609 | CUST_P10081452 | 1120 | 1164 | Negative Control | Tomato pseudo-curly top virus |

TABLE 10-continued

Exemplary control probes

| SEQ ID NO: | ProbeID | Start | End | Type | Genomic Region |
|---|---|---|---|---|---|
| 3610 | CUST_P10081453 | 1166 | 1214 | Negative Control | Tomato pseudo-curly top virus |
| 3611 | CUST_P10081454 | 1187 | 1246 | Negative Control | Tomato pseudo-curly top virus |
| 3612 | CUST_P10081455 | 1216 | 1260 | Negative Control | Tomato pseudo-curly top virus |
| 3613 | CUST_P10081456 | 1332 | 1385 | Negative Control | Tomato pseudo-curly top virus |
| 3614 | CUST_P10081457 | 1370 | 1429 | Negative Control | Tomato pseudo-curly top virus |
| 3615 | CUST_P10081458 | 1407 | 1459 | Negative Control | Tomato pseudo-curly top virus |
| 3616 | CUST_P10081459 | 1440 | 1499 | Negative Control | Tomato pseudo-curly top virus |
| 3617 | CUST_P10081460 | 1600 | 1650 | Negative Control | Tomato pseudo-curly top virus |
| 3618 | CUST_P10081461 | 1615 | 1669 | Negative Control | Tomato pseudo-curly top virus |
| 3619 | CUST_P10081462 | 1648 | 1698 | Negative Control | Tomato pseudo-curly top virus |
| 3620 | CUST_P10081463 | 1740 | 1797 | Negative Control | Tomato pseudo-curly top virus |
| 3621 | CUST_P10081464 | 2072 | 2128 | Negative Control | Tomato pseudo-curly top virus |
| 3622 | CUST_P10081465 | 2114 | 2173 | Negative Control | Tomato pseudo-curly top virus |
| 3623 | CUST_P10081466 | 2158 | 2217 | Negative Control | Tomato pseudo-curly top virus |
| 3624 | CUST_P10081467 | 2296 | 2346 | Negative Control | Tomato pseudo-curly top virus |
| 3625 | CUST_P10081468 | 2446 | 2490 | Negative Control | Tomato pseudo-curly top virus |
| 3626 | CUST_P10081470 | 2548 | 2592 | Negative Control | Tomato pseudo-curly top virus |
| 3627 | CUST_P10081471 | 2596 | 2650 | Negative Control | Tomato pseudo-curly top virus |
| 3628 | CUST_P10081472 | 2633 | 2683 | Negative Control | Tomato pseudo-curly top virus |

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

SEQUENCE LISTING

The patent contains a lengthy sequence listing. A copy of the sequence listing is available in electronic form from the USPTO web site (https://seqdata.uspto.gov/?pageRequest=docDetail&DocID=US12385104B2). An electronic copy of the sequence listing will also be available from the USPTO upon request and payment of the fee set forth in 37 CFR 1.19(b)(3).

We claim:

1. A probe set comprising:
   (a) probes having at least 90% identity with the nucleic acid sequences of SEQ ID NOs: 1-1300, 1391-1570, and 1691-1769;
   (b) probes having at least 95% identity with the nucleic acid sequences of SEQ ID NOs: 1-1300, 1391-1570, and 1691-1769;
   (c) probes comprising the nucleic acid sequence of SEQ ID NOs: 1-1300, 1391-1570, and 1691-1769; or
   (d) probes comprising the nucleic acid sequence of SEQ ID NOs: 1-1769,
   wherein each of the probes is covalently linked to a solid support and each of the probes is 60 nucleotides in length.

2. The probe set of claim 1, wherein the probe set comprises probes for each of Chikungunya virus, Dengue virus type 1, Dengue virus type 2, Dengue virus type 3, Dengue virus type 4, Hepatitis A virus, Hepatitis C virus type 1, Hepatitis C virus type 2, Hepatitis C virus type 3, Hepatitis E virus, Human immunodeficiency virus type 1, Human immunodeficiency virus type 2, Human T-lymphotropic virus type I, Human T-lymphotropic virus type II, West Nile virus, and Zika virus.

3. The probe set of claim 1, further comprising at least one negative control probe and/or further comprising at least one positive control probe.

4. The probe set of claim 3, wherein the at least one negative control probe comprises a set of probes with at least 90% identity with each of the nucleic acid sequences of SEQ ID NOs: 1571-1690 and wherein each of the probes is 60 nucleotides in length.

5. The probe set of claim 1, further comprising:
   (a) probes having at least 90% identity with the nucleic acid sequences of SEQ ID NOs: 1770-2647;
   (b) probes having at least 95% identity with the nucleic acid sequences of SEQ ID NOS: 1770-2647; or
   (c) probes comprising the nucleic acid sequence of SEQ ID NOs: 1770-2647;
   wherein each of the probes is covalently linked to a solid support and each of the probes is 40-60 nucleotides in length.

6. The probe set of claim 5, wherein the probe set comprises probes for each of cytomegalovirus, Epstein Barr virus subtype B95-8, Epstein Barr virus subtype AG876, human herpes virus 8, Hepatitis B virus subtype adw, Hepatitis B virus subtype ayw, Hepatitis B virus subtype adr, Hepatitis B virus subtype ayr, human parvovirus B19, human papillomavirus type 6, human papillomavirus type 11, human papillomavirus type 16, and human papillomavirus type 18.

7. The probe set of claim 5, further comprising at least one negative control probe and/or further comprising at least one positive control probe.

8. The probe set of claim 7, wherein the at least one negative control probe comprises a set of probes with at least 90% identity with the nucleic acid sequences of each of SEQ ID NOs: 3520-3628 and each of the probes is 45-60 nucleotides in length.

9. The probe set of claim 1, further comprising:
   (a) probes having at least 90% identity with the nucleic acid sequences of SEQ ID NOs: 2648-3207;
   (b) probes having at least 95% identity with the nucleic acid sequences of SEQ ID NOs: 2648-3207; or
   (c) probes comprising the nucleic acid sequence of SEQ ID NOs: 2648-3207;
   wherein each of the probes is covalently linked to a solid support and each of the probes is 45-60 nucleotides in length.

10. The probe set of claim 9, wherein the probe set comprises at least one probe for each of *Treponema pallidum, Ehrlichia chaffeensis, Ehrlichia ewingii, Ehrlichia muris, Borrelia burgdorferi, Coxiella burnetii, Trypanosoma brucei, Trypanosoma cruzi Leishmania major, Babesia microti, Plasmodium falciparum*, and *Plasmodium vivax*.

11. The probe set of claim 9, further comprising at least one negative control probe and/or further comprising at least one positive control probe.

12. The probe set of claim 11, wherein the at least one positive control probe comprises a set of probes with at least 90% identity with the nucleic acid sequences of each of SEQ ID NOs: 3208-3519 and each of the probes is 45-60 nucleotides in length.

13. A microarray comprising the probe set of claim 1.

14. The microarray of claim 13, wherein the probe set comprises probes comprising the nucleic acid sequence of each of SEQ ID NOs: 1-1769.

15. A method of detecting one or more pathogen nucleic acids in a sample, comprising:
   contacting the sample with the probe set of claim 1 under conditions sufficient to allow hybridization of pathogen nucleic acids present in the sample to the probes of the probe set; and
   measuring hybridization of the sample to one or more of the probes, thereby detecting one or more pathogen nucleic acids in the sample.

16. The method of claim 15, wherein the sample comprises a blood, serum, or plasma sample or nucleic acids isolated from a blood, serum, or plasma sample.

17. The method of claim 16, further comprising isolating nucleic acids from the sample prior to contacting the sample with the probe set.

18. The method of claim 17, further comprising labeling the isolated nucleic acids from the sample.

19. The method of claim 18, wherein the isolated nucleic acids are isolated DNA, isolated RNA, isolated cDNA, or a combination of two or more thereof.

20. The method of claim 19, wherein labeling the isolated nucleic acids comprises labeling the nucleic acids with one or more fluorescent labels.

21. The method of claim 17, wherein the isolated nucleic acids are cDNA.

22. The method of claim 17, wherein isolating the nucleic acids does not comprise amplifying total RNA from the sample prior to preparing cDNA.

23. The method of claim 15, wherein measuring hybridization comprises detecting ≥50% of the probes for the virus have a log ratio of >1.5 and/or the log ratio between the signal intensity mean for the probe set and the mean of a control group probe set is ≥1.5.

24. The method of claim 15, wherein the pathogen nucleic acids comprise nucleic acids from one or more of Chikungunya virus, Dengue virus types 1, 2, 3, or 4, Hepatitis A virus, Hepatitis C virus types 1, 2, or 3, Hepatitis E virus, Human immunodeficiency virus types 1 or 2, Human T-lymphotropic virus types I or II, West Nile virus, and Zika virus.

* * * * *